United States Patent
Allen et al.

(10) Patent No.: US 9,624,504 B2
(45) Date of Patent: Apr. 18, 2017

(54) DROUGHT TOLERANT PLANTS AND RELATED CONSTRUCTS AND METHODS INVOLVING GENES ENCODING DTP6 POLYPEPTIDES

(75) Inventors: Stephen M Allen, Wilmington, DE (US); Jason L Brothers, Newark, DE (US); Krupa Deshmukh, Hyderabad (IN); Honor Renee Lafitte, Davis, CA (US); Xiao-Yi Li, Wilmington, DE (US); Cheng Lu, Newark, DE (US); Stanley Luck, Wilmington, DE (US); Jeffrey Mullen, Maple Plain, MN (US); Hajime Sakai, Newark, DE (US); James J Saylor, Newark, DE (US); Scott V Tingey, Wilmington, DE (US); Robert Wayne Williams, Hockessin, DE (US)

(73) Assignees: E I DU PONT DE NEMOURS AND COMPANY, Wilmington, DE (US); PIONEER HI-BRED INTERNATIONAL, INC., IA (US)

( * ) Notice: Subject to any disclaimer, the term of this patent is extended or adjusted under 35 U.S.C. 154(b) by 912 days.

(21) Appl. No.: 13/877,814

(22) PCT Filed: Oct. 28, 2011

(86) PCT No.: PCT/US2011/058273
§ 371 (c)(1),
(2), (4) Date: Apr. 4, 2013

(87) PCT Pub. No.: WO2012/058528
PCT Pub. Date: May 3, 2012

(65) Prior Publication Data
US 2014/0223595 A1     Aug. 7, 2014

Related U.S. Application Data

(60) Provisional application No. 61/407,612, filed on Oct. 28, 2010.

(51) Int. Cl.
*C12N 15/29* (2006.01)
*C12N 15/82* (2006.01)
*A01H 5/10* (2006.01)
*G06F 19/20* (2011.01)

(52) U.S. Cl.
CPC ........... *C12N 15/8274* (2013.01); *A01H 5/10* (2013.01); *C12N 15/8273* (2013.01); *G06F 19/20* (2013.01)

(58) Field of Classification Search
None
See application file for complete search history.

(56) References Cited

U.S. PATENT DOCUMENTS

2006/0150283 A1*   7/2006   Alexandrov ......... C07K 14/415
                                                                   800/288

FOREIGN PATENT DOCUMENTS

| WO | 2009134339 A2 | 11/2009 |
|----|---------------|---------|
| WO | 2010089392 A1 | 8/2010  |
| WO | 2011053897 A1 | 5/2011  |

OTHER PUBLICATIONS

Theologis et al. (Nature 408 (6814), 816-820 (2000)).*
Guo et al. (2004, Proc. Natl. Acad. Sci. USA 101: 9205-9210).*
Doerks et al. (TIG 14, No. 6: 248-250, Jun. 1998).*
Brenner (TIG 15, 4:132-133, Apr. 1999).*
Bork (TIG 12, 10:425-427, Oct. 1996).*
Lee, et al, "Accumulation of trehalose within transgenic chloroplasts confers drought tolerance" Molecular Breeding, 2003, vol. 11:1, 1-13.
George, et al, A chloroplast-localized and auxin-induced glutathione S-transferase from phreatophyte prosopsis iuliflora confer drought tolerance on tobacco Journal of Plant Physiology, 2010, vol. 167:4, 0176-1617.
Hu, et al, Multifunctional genes: the cross-talk among the regulation networks of abiotic stress responses Biologia Plantarum, 2010, vol. 54:2, 213-223.
Lawrence, et al, "Superoxide dismutase: an all-purpose gene for agri-biotechnology" Molecular Breeding, 2009, vol. 24:2, 103-115.
Sazzad, et al, "Improved drought tolerance without undesired side effects in transgenic plants producing trehalose" Plant Molecular Biology, 2007, vol. 64:4, 371-386.
Miyagawa, et al, "Evaluation of the defense system in chloroplasts to photooxidative stress caused by paraquat using transgenic tobacco plants expressing catalase from *Escherichia coli*" Plant and Cell Physiology, 2000, vol. 41:3,311-320.
H Du, et al, "Characterization of the carotene hydroxylase gene DSM2 conferring drought and oxidative stress resistance by increasing xanthophylls and abscisic acid synthesis in rice" Plant Physiology, 2010, vol. 154:3, 1304-1318.
International Search Report and Written Opinion for International Application No. PCT/US2011/058273, date mailed Mar. 5, 2012.

* cited by examiner

*Primary Examiner* — Elizabeth McElwain
*Assistant Examiner* — Charles Logsdon
(74) *Attorney, Agent, or Firm* — Pioneer Hi-Bred Intl. Inc.

(57) ABSTRACT

Isolated polynucleotides and polypeptides and recombinant DNA constructs useful for conferring drought tolerance, compositions (such as plants or seeds) comprising these recombinant DNA constructs, and methods utilizing these recombinant DNA constructs. The recombinant DNA construct comprises a polynucleotide operably linked to a promoter that is functional in a plant, wherein said polynucleotide encodes a DTP6 polypeptide.

4 Claims, 41 Drawing Sheets

Motif 3

| | | | | | | | | | | | Majority |
|---|---|---|---|---|---|---|---|---|---|---|---|
| C L | - - - | D R X R | - - - | R | - - G - - - | I P A X A | | | | | |
| | | 210 | | | | 220 | | | | | |
| 169 | C L | - - - | D R D S | - - - | R N C S | - - | I P A L A | | | | 18.pro |
| 161 | C - | - - - | G N S E T | - - - | H Y A V T F | - - | - V A | | | | 20.pro |
| 163 | C - | - - - | G N K E P P H | - - - | - C F | - - | - - A | | | | 22.pro |
| 143 | C L | - - - | D R | - - - | G R G G H G | - - | I T A M A | | | | 24.pro |
| 142 | C L | - - - | D R G R | - - - | G R G G H G | - - | - H T A M A | | | | 26.pro |
| 161 | C - | - - - | G N K E P P H | - - - | - C F | - - | - - A | | | | 28.pro |
| 158 | C L | - - - | D G G R R G | - - - | G R G H G | - - | I T A M A | | | | 30.pro |
| 156 | C L | - - - | D R S R G | - - - | G R G H G | - - | - H T A M A | | | | 32.pro |
| 156 | C L | - - - | S R D C | - - - | Q N S G | - - | I P A V A | | | | 34.pro |
| 161 | C L | - - - | D R D R | - - - | R N C S | - - | I P A L A | | | | 36.pro |
| 139 | V - | - - - | - - - | - - - | - - - | - - | A A C R A | | | | 75.pro |
| 161 | C - | - - - | G N K E P P H | - - - | - C F | - - | - - A | | | | 77.pro |
| 158 | C - | - W Q L G D | D P L R S Y | - - - | A A P C V N R | - - | I A V V A | | | | 79.pro |
| 77 | C - | - - - | G N K E A P N | - - - | R A V T F | - - | - - A | | | | 81.pro |
| 153 | - - | - - - | - - - | - - - | - - - | - - | S S S S S | | | | 83.pro |
| 110 | C S | - - - | T P D | - - - | - A R G | - - | V P T F A | | | | 85.pro |
| 169 | C L | - - - | D R D S | - - - | R N C S | - - | I P A L A | | | | 56.pro |

FIG. 12

Percent identity

| | 1 | 2 | 3 | 4 | 5 | 6 | 7 | 8 | 9 | 10 | 11 | 12 | 13 | 14 | 15 | 16 | 17 | |
|---|---|---|---|---|---|---|---|---|---|---|---|---|---|---|---|---|---|---|
| 1 | | 20.8 | 22.0 | 24.5 | 27.2 | 21.6 | 23.6 | 22.1 | 38.2 | 44.0 | 20.1 | 22.2 | 17.7 | 28.1 | 17.2 | 27.9 | 100.0 | 1 | 18.pro |
| 2 | 162.2 | | 56.6 | 20.8 | 23.4 | 54.4 | 21.4 | 19.8 | 19.4 | 19.7 | 21.5 | 54.4 | 53.8 | 62.9 | 17.8 | 23.8 | 20.8 | 2 | 20.pro |
| 3 | 180.5 | 38.7 | | 17.6 | 21.5 | 78.4 | 19.1 | 18.6 | 19.4 | 21.4 | 22.9 | 78.9 | 36.4 | 77.5 | 17.2 | 24.6 | 22.0 | 3 | 22.pro |
| 4 | 116.8 | 148.2 | 166.3 | | 71.5 | 18.2 | 76.7 | 73.6 | 31.4 | 27.7 | 21.5 | 18.2 | 21.4 | 23.6 | 17.2 | 20.5 | 24.5 | 4 | 24.pro |
| 5 | 129.7 | 142.3 | 148.2 | 12.0 | | 22.8 | 74.1 | 72.2 | 31.0 | 28.5 | 20.1 | 22.8 | 21.5 | 27.0 | 17.2 | 23.0 | 27.2 | 5 | 26.pro |
| 6 | 188.9 | 44.3 | 15.8 | 152.9 | 143.8 | | 19.3 | 19.9 | 18.2 | 21.6 | 20.1 | 19.3 | 36.3 | 82.0 | 20.4 | 23.0 | 21.6 | 6 | 28.pro |
| 7 | 127.6 | 147.4 | 177.0 | 14.7 | 15.1 | 167.3 | | 70.3 | 31.2 | 27.6 | 21.5 | 19.9 | 17.8 | 25.8 | 15.3 | 23.0 | 23.6 | 7 | 30.pro |
| 8 | 125.6 | 140.9 | 153.2 | 13.5 | 18.3 | 144.9 | 17.0 | | 29.4 | 27.9 | 22.2 | 19.9 | 18.0 | 27.0 | 17.8 | 22.1 | 25.0 | 8 | 32.pro |
| 9 | 78.2 | 189.8 | 195.0 | 102.7 | 102.7 | 209.0 | 110.5 | 111.5 | | 37.1 | 18.8 | 18.2 | 18.8 | 25.8 | 15.9 | 22.1 | 38.2 | 9 | 34.pro |
| 10 | 57.1 | 156.9 | 165.8 | 95.0 | 105.6 | 191.5 | 101.9 | 103.2 | 77.3 | | 21.5 | 21.6 | 18.3 | 32.6 | 15.3 | 27.0 | 44.0 | 10 | 36.pro |
| 11 | 207.0 | 167.0 | 173.8 | 134.6 | 128.3 | 170.3 | 142.3 | 146.9 | 158.4 | 171.8 | | 20.1 | 18.1 | 25.8 | 39.6 | 23.0 | 20.1 | 11 | 75.pro |
| 12 | 183.1 | 44.3 | 15.1 | 152.9 | 143.8 | 0.6 | 167.3 | 144.9 | 209.0 | 191.5 | 170.3 | | 36.3 | 82.0 | 19.7 | 23.0 | 22.2 | 12 | 77.pro |
| 13 | 183.4 | 44.3 | 79.9 | 151.2 | 148.1 | 85.1 | 154.2 | 160.4 | 206.0 | 172.3 | 194.5 | 85.1 | | 36.0 | 17.8 | 17.2 | 17.7 | 13 | 79.pro |
| 14 | 173.5 | 29.6 | 12.7 | 140.9 | 129.7 | 15.5 | 154.6 | 128.4 | 135.6 | 132.0 | 131.2 | 15.5 | 91.9 | | 22.5 | 29.2 | 28.1 | 14 | 81.pro |
| 15 | 243.0 | 214.0 | 244.0 | 196.4 | 197.0 | 240.0 | 203.0 | 205.0 | 212.0 | 231.0 | 59.2 | 240.0 | 198.0 | 181.3 | | 19.7 | 17.2 | 15 | 83.pro |
| 16 | 132.0 | 153.8 | 146.4 | 159.3 | 164.9 | 156.7 | 173.8 | 161.1 | 120.4 | 142.4 | 191.1 | 150.4 | 213.0 | 125.2 | 205.0 | | 27.9 | 16 | 85.pro |
| 17 | 0.0 | 162.2 | 180.5 | 116.8 | 129.7 | 188.9 | 127.6 | 125.6 | 78.2 | 57.1 | 207.0 | 183.1 | 183.4 | 173.5 | 243.0 | 132.0 | | 17 | 56.pro |
| | 1 | 2 | 3 | 4 | 5 | 6 | 7 | 8 | 9 | 10 | 11 | 12 | 13 | 14 | 15 | 16 | 17 | | |

Divergence

FIG. 13A

HMM Profile for DTP6 Family

| HMMER3/b [3.0] | | | | | | | | | | | | | | | | | | | | | | | |
|---|---|---|---|---|---|---|---|---|---|---|---|---|---|---|---|---|---|---|---|---|---|---|---|
| NAME | DTP6_100_nr_stk | | | | | | | | | | | | | | | | | | | | | | |
| LENG | 175 | | | | | | | | | | | | | | | | | | | | | | |
| ALPH | amino | | | | | | | | | | | | | | | | | | | | | | |
| RF | no | | | | | | | | | | | | | | | | | | | | | | |
| CS | no | | | | | | | | | | | | | | | | | | | | | | |
| MAP | yes | | | | | | | | | | | | | | | | | | | | | | |
| DATE | Wed Oct 5 13:25:10 2011 | | | | | | | | | | | | | | | | | | | | | | |
| NSEQ | 40 | | | | | | | | | | | | | | | | | | | | | | |
| EFFN | 2.1435 | | | | | | | | | | | | | | | | | | | | | | |
| CKSUM | 810285115 | | | | | | | | | | | | | | | | | | | | | | |
| STATS LOCAL MSV | -10.6248 | 0.70711 | | | | | | | | | | | | | | | | | | | | | |
| STATS LOCAL VITERBI | -11.5399 | 0.70711 | | | | | | | | | | | | | | | | | | | | | |
| STATS LOCAL FORWARD | -4.6353 | 0.70711 | | | | | | | | | | | | | | | | | | | | | |
| HMM | A | C | D | E | F | G | H | I | K | L | M | N | P | Q | R | S | T | V | W | Y | | |
| | m->m | m->i | m->d | i->m | i->i | d->m | d->d | | | | | | | | | | | | | | | |
| COMPO | 2.541319 | 2.68762 | 3.81569 | 2.95099 | 2.71692 | 2.91303 | 2.68682 | 2.66873 | 2.69162 | 2.99272 | 2.76393 | 3.04722 | 2.94552 | 2.77995 | 2.09083 | 3.85731 | | | | | | |
| | 2.68762 | 4.42153 | 2.77645 | 2.73229 | 3.45812 | 3.40658 | 3.72948 | 63.07063 | 3.29292 | 2.67822 | 2.69074 | 2.24331 | 2.90502 | 2.73673 | 2.18232 | 2.89932 | 3.7468 | 2.98604 | 4.58713 | 6.6166 | | |
| | 0.38998 | 1.23194 | 3.46724 | 3.25697 | 0.03927 | 0* | 63.72738 | 3.29293 | 2.67822 | 2.69074 | 2.24331 | 2.90502 | 2.73673 | 2.18232 | 2.89932 | 3.7468 | 52.7764 | 8 | 3 | 5 | | |
| | 1 | 3.03368 | 4.59024 | 4.19436 | 3.64673 | 3.48582 | 4.05364 | 3.64024 | 2.74625 | 3.39702 | 2.02961 | 1.08993 | 9.49947 | 4.42613 | 3.28453 | 3.62393 | 3.36922 | 2.95362 | 6.68265 | 1.65730 | 9.98565 | |
| | 2.68618 | 4.42225 | 2.77519 | 2.73123 | 3.46352 | 2.40513 | 3.72493 | 3.29353 | 2.67742 | 2.69355 | 2.90342 | 2.73733 | 3.18142 | 2.89802 | 3.78882 | 2.77512 | 2.98514 | 4.58473 | 6.1503 | | | |
| | 0.01504 | 4.60071 | 5.32305 | 0.61958 | 0.77250 | 0.53330 | 0.88345 | | | | | | | | | | | | | | 67 |

| | | | | | | | | | | | | | | |
|---|---|---|---|---|---|---|---|---|---|---|---|---|---|---|
| 18 | 2.4344 | 4.9678 | | 2.6531 | 4.2359 | 3.8053 | 3.6445 | 2.3649 | 3.2420 | 2.8139 | 3.1579 | 4.0045 | 2.9572 | 1.6148 | 2.5960 | 3.0245 | 3.3222 | 5.4747 | 4.1586 |
| | 4.4222 | 2.7751 | 3.2187 | | 33.0277 | 2 | 4 | 3 | 1 | 4 | 9 | 1 | 5 | 4 | 5 | 4 | 3 | 1 | 93 |
| 2.68618 | 5 | 9 | 2.73123 | 3.4635 | 2.4051 | 3.7249 | 3.2935 | 2.6774 | 2.6935 | 2.9034 | 2.7373 | 3.1814 | 2.8980 | 2.3788 | 2.3788 | 2.3788 | 4.5847 | 3.6150 | |
| | 4.63151.6440 | | 0.61958 | 4 | 5 | 4 | 1 | | 7 | | 6 | 1 | 7 | 9 | 8 | 7 | | | |
| 0.22681 | 2 | 8 | | 0.77250.5469 | 0.8644 | | | | 54.2469 | | | | | | | | | | |
| | 2.50033.5047 | | | 2.77624.1927 | | 3.6053 | 2.7355 | 3.2328 | | 3.0929 | 3.9187 | 3.0926 | 2.3823 | 1.5583 | 2.9192 | 3.2337 | 5.4851 | 4.1915 | |
| 19 | 9 | 9 | 3.3073 | 5 | 42.53853.9123 | | 3 | 6 | 34.0537 | | 5 | | 6 | 1 | 6 | 5 | 8 | 5 | 3 | 94 |
| 2.68618 | 4.4222 | 2.7751 | 2.73123 | 3.4635 | 2.4051 | 3.7249 | 3.2935 | 2.6774 | 2.6935 | 2.9034 | 2.7373 | 3.1814 | 2.8980 | 2.3788 | 2.3788 | 2.3788 | 4.5847 | 3.6150 | |
| | 5 | 5 | | 4 | 3 | 4 | 4 | 1 | | 7 | 6 | 1 | 7 | 9 | 8 | 7 | 3 | | |
| | | 5.1450 | | | 1.0659 | | | | 54.2469 | | | | | | | | | | |
| | 0.017994.4227 | | 0.61958 | | 50.4222 | 6 | | | | | | | | | | | | | |
| | 2.35585.1423 | | | 2.47274.4650 | 2.0853 | 3.7240 | 3.9252 | 2.4768 | 3.4475 | 3.9973 | 2.6718 | 3.5290 | 2.8353 | 2.3368 | 2.5253 | 2.7994 | 3.5254 | 5.6145 | 4.2286 |
| 20 | 6 | 6 | 2.83304 | 4 | 9 | 6 | 8 | 8 | 7 | 4 | 3 | 6 | 1 | 4 | 3 | 6 | 5 | 2 | 6 | 95 |
| 2.68618 | 4.4222 | 2.7751 | 2.73123 | 3.4635 | 2.4051 | 3.7249 | 3.2935 | 2.6774 | 2.6935 | 2.9034 | 2.7373 | 3.1814 | 2.8980 | 2.3788 | 2.3788 | 2.3788 | 4.5847 | 3.6150 | |
| | 5 | 9 | | 4 | 3 | 4 | 4 | 1 | | 7 | 6 | 1 | 7 | 9 | 8 | 7 | 3 | | |
| | 4.60823.5573 | | | 0.77250.5882 | 0.8103 | | | | 54.2469 | | | | | | | | | | |
| | 0.03924 | 5 | 6 | 0.61958 | 5 | 8 | 1 | | | | | | | | | | | | |
| | 2.29883.5142 | | | 2.9509 | | 3.7672 | 4.0460 | 2.6091 | 3.2253 | | 3.4131 | | 4.1416 | 3.4916 | 2.9315 | 2.9545 | | 4.9027 | 3.6935 |
| 21 | 8 | 1 | 3.40983 | 3 | 11.9976 | 4 | 2 | 5 | 4 | | | | 5 | 83.0397 | | 1 | 82.3439 | 4 | 3 | 96 |
| 2.68618 | 4.4222 | 2.7751 | 2.73123 | 3.4635 | 2.4051 | 3.7249 | 3.2935 | 2.6774 | 2.6935 | 2.9034 | 2.7373 | 3.1814 | 2.8980 | 2.3788 | 2.3788 | 2.3788 | 4.5847 | 3.6150 | |
| | 5 | 9 | | 4 | 3 | 4 | 4 | 1 | | 7 | 6 | 1 | 7 | 9 | 8 | 7 | 3 | | |
| | 4.58421.8716 | | | 0.7725 | | | 0.7626 | | 54.2469 | | | | | | | | | | |
| | 0.17922 | 9 | 7 | 0.61958 | | 50.6282 | 1 | | | | | | | | | | | | |
| | 2.47704.3375 | | | 3.0632 | 3.4663 | 3.6690 | 3.4754 | | | 3.0026 | 2.5449 | 3.1673 | 3.4432 | 4.0465 | 2.9451 | 2.5183 | 2.8995 | 2.0876 | 2.8081 |
| 22 | 7 | 3 | 3.63374 | 5 | 4 | 1 | | | 32.6289 | | 3 | 8 | 4 | | 92.9372 | 6 | 1 | 9 | 3 | 33.7005 | 97 |
| 2.68618 | 4.4222 | 2.7751 | 2.73123 | 3.4635 | 2.4051 | 3.7249 | 3.2935 | 2.6774 | 2.6935 | 2.9034 | 2.7373 | 3.1814 | 2.8980 | 2.3788 | 2.3788 | 2.3788 | 4.5847 | 3.6150 | |
| | 5 | 9 | | 4 | 3 | 4 | 4 | 1 | | 7 | 6 | 1 | 7 | 9 | 8 | 7 | 3 | | |
| | | 4.4230 | | | 0.77250.8435 | 0.5624 | | | 54.2469 | | | | | | | | | | |
| | 0.01798 | 65.1454 | 0.61958 | | 4 | 4 | | | | | | | | | | | | | |
| | 2.4137 | 5.1086 | | 4.4227 | 3.1053 | 3.6528 | 3.5935 | 2.4013 | 3.4008 | 4.1583 | | 3.2869 | | 2.6481 | 2.3572 | 2.9076 | | 5.5609 | 4.1696 |
| 23 | 1 | 6 | 2.70404 | 2.2556 | 5 | 6 | 5 | 4 | 1 | 2 | | 62.9417 | | 8 | 8 | 93.1273 | | 2 | 9 | 98 |
| 2.68618 | 4.4222 | 2.7751 | 2.73123 | 3.4635 | 2.4051 | 3.7249 | 3.2935 | 2.6774 | 2.6935 | 2.9034 | 2.7373 | 3.1814 | 2.8980 | 2.3788 | 2.3788 | 2.3788 | 4.5847 | 3.6150 | |
| | 5 | 9 | | 4 | 3 | 4 | 4 | 1 | | 7 | 6 | 1 | 7 | 9 | 8 | 7 | 3 | | |
| | 4.42302.5328 | | | 0.77250.8435 | 0.5624 | | | | 54.2469 | | | | | | | | | | |
| 0.09588 | 6 | 8 | 0.61958 | | 5 | 4 | | | | | | | | | | | | | |
| | 2.64544.3265 | | | 3.1357 | 2.9014 | 3.6423 | 3.9025 | 2.4125 | 2.9678 | 2.3949 | 2.6893 | 3.4071 | 3.0787 | 3.2618 | 3.3044 | 2.8923 | 2.3412 | 2.3646 | 4.9159 | 3.6887 |
| 24 | 3 | 2 | | 2.9014 | 3 | 2.2506 | 4 | 8 | 1 | 3 | 7 | 4 | 3 | 8 | 2 | 4 | 9 | 1 | 3 | 4 | 5 | 99 |
| | | 4.4223 | | 3.4636 | | 3.7250 | 3.2935 | 2.6774 | 2.6936 | 2.9035 | | 3.1815 | 2.8979 | 2.3789 | | 2.9851 | 4.5848 | 3.6150 | |
| 2.68612 | | 52.7747 | 2.73133 | | 42.4051 | 5 | 7 | 5 | | | | 6 | 6 | | 72.7753 | 6 | 7 | 1 | |
| | | | | | 2.2919 | | | | 54.2457 | | | | | | | | | | |
| 0.80693 | | 32.7871 | 0.10655 | | 42.4051 | 0.5464 | | | | | | | | | | | | | |
| | 2.31144.1021 | | | 2.5740 | 3.8162 | 3.0828 | 3.2394 | 2.0322 | 2.6242 | 2.8651 | 3.7180 | 3.1283 | 3.9115 | 2.9615 | 2.9152 | 2.9155 | 2.8714 | 2.4968 | 5.1723 | 3.7518 |
| 25 | 4 | 5 | 3.20366 | 8 | 7 | 4 | 7 | 4 | 3 | 8 | 3 | 4 | 2 | 7 | 1 | 7 | 6 | 1 | 7 | 1 | 101 |
| 2.68618 | 4.4222 | 2.7751 | 2.73123 | 3.4635 | 2.4051 | 3.7249 | 3.2935 | 2.6774 | 2.6935 | 2.9034 | 2.7373 | 3.1814 | 2.8980 | 2.3788 | 2.3788 | 2.3788 | 4.5847 | 3.6150 | |
| | 5 | 9 | | 4 | 3 | 4 | 4 | 1 | | 7 | 6 | 1 | 7 | 9 | 8 | 7 | 3 | | |
| | 4.3153 | 3.1124 | | 0.77250.6445 | 0.7442 | | | | 54.2469 | | | | | | | | | | |
| 0.0596 | 1 | 2 | 0.61958 | 5 | 7 | 1 | | | | | | | | | | | | | |

FIG. 13E

| | | | | | | | | | | | | | | | | | | |
|---|---|---|---|---|---|---|---|---|---|---|---|---|---|---|---|---|---|---|
| 26 | 2.728 83 | 5.186 94 | 1.85587 | 2.0898 5 | 4.503 35 | 3.460 27 | 3.512 32 | 3.974 9 | 2.447 98 | 2.763 79 | 4.238 95 | 2.934 45 | 3.301 18 | 2.521 66 | 2.845 76 | 2.695 37 | 2.963 6 | 3.563 | 5.632 62 | 4.230 27 | 102 |
| 2.68618 | 4.422 25 | 2.775 19 | 2.73123 | 3.4635 4 | 2.405 13 | 3.724 94 | 3.293 54 | 2.677 41 | 2.693 55 | 4.246 9 | 2.903 47 | 2.737 39 | 3.181 46 | 2.898 01 | 2.378 87 | 2.775 19 | 2.985 18 | 4.584 77 | 3.615 03 | | |
| 0.03649 | 4.425 93 | 3.735 28 | 0.61958 | 0.7725 5 | 0.840 35 | 0.564 86 | | | | | | | | | | | | | | | |
| 27 | 2.708 19 | 5.028 64 | 2.90852 | 2.4692 4 | 4.321 52 | 2.858 56 | 3.688 99 | 3.759 01 | 2.350 39 | 3.189 05 | 4.099 08 | 2.997 75 | 2.271 13 | 2.815 14 | 2.095 38 | 2.660 69 | 2.939 6 | 3.394 55 | 5.501 84 | 3.958 72 | 103 |
| 2.6862 | 4.421 96 | 2.775 32 | 2.73118 | 3.4636 6 | 2.405 16 | 3.725 6 | 3.293 66 | 2.677 53 | 2.693 5 | 4.247 02 | 2.903 59 | 2.736 71 | 3.181 59 | 2.897 92 | 2.378 99 | 2.775 32 | 2.984 97 | 4.584 89 | 3.615 15 | | |
| 0.33756 | 1.345 72 | 3.644 37 | 0.74702 | 0.6420 3 | 0.343 53 | 1.235 33 | | | | | | | | | | | | | | | |
| 28 | 2.468 58 | 5.207 84 | 3.05741 | 2.2704 6 | 4.534 35 | 3.553 37 | 3.727 53 | 3.995 1 | 1.720 63 | 3.497 63 | 4.012 37 | 3.032 56 | 3.943 77 | 2.618 22 | 2.128 93 | 2.547 08 | 3.003 39 | 3.091 81 | 5.645 02 | 4.263 91 | 107 |
| 2.68618 | 4.422 25 | 2.775 19 | 2.73123 | 3.4635 4 | 2.405 13 | 3.724 94 | 3.293 54 | 2.677 41 | 2.693 55 | 4.246 9 | 2.903 47 | 2.737 39 | 3.181 46 | 2.898 01 | 2.378 87 | 2.775 19 | 2.985 18 | 4.584 77 | 3.615 03 | | |
| 0.01446 | 4.639 45 | 5.361 8 | 0.61958 | 0.7725 5 | 0.445 89 | 1.022 36 | | | | | | | | | | | | | | | |
| 29 | 2.623 12 | 5.234 64 | 2.02384 | 1.9626 3 | 4.566 11 | 3.295 74 | 3.722 83 | 3.433 48 | 2.322 81 | 3.534 12 | 4.062 96 | 2.904 95 | 3.926 61 | 2.823 93 | 2.794 | 2.425 55 | 2.609 96 | 3.618 02 | 5.675 5 | 4.272 49 | 108 |
| 2.68618 | 4.422 25 | 2.775 19 | 2.73123 | 3.4635 4 | 2.405 13 | 3.724 94 | 3.293 54 | 2.677 41 | 2.693 55 | 4.246 9 | 2.903 47 | 2.737 39 | 3.181 46 | 2.898 01 | 2.378 87 | 2.775 19 | 2.985 18 | 4.584 77 | 3.615 03 | | |
| 0.01396 | 4.674 22 | 5.396 57 | 0.61958 | 0.7725 5 | 0.485 76 | 0.955 1 | | | | | | | | | | | | | | | |
| 30 | 2.666 97 | 5.155 51 | 2.7685 | 2.0156 6 | 4.455 94 | 3.237 41 | 3.743 67 | 3.911 53 | 2.501 05 | 2.551 95 | 4.209 64 | 3.034 39 | 2.401 1 | 2.599 69 | 2.985 5 | 2.488 88 | 2.908 11 | 3.213 68 | 5.616 95 | 4.234 27 | 109 |
| 2.68618 | 4.422 25 | 2.775 19 | 2.73123 | 3.4635 4 | 2.405 13 | 3.724 94 | 3.293 54 | 2.677 41 | 2.693 55 | 4.246 9 | 2.903 47 | 2.737 39 | 3.181 46 | 2.898 01 | 2.378 87 | 2.775 19 | 2.985 18 | 4.584 77 | 3.615 03 | | |
| 0.01396 | 4.674 22 | 5.396 57 | 0.61958 | 0.7725 5 | 0.485 76 | 0.955 1 | | | | | | | | | | | | | | | |
| 31 | 3.469 59 | 4.735 1 | 5.41955 | 4.8650 4 | 3.008 15 | 4.850 58 | 5.267 41 | 1.987 96 | 4.734 4 | 1.556 69 | 3.259 53 | 4.983 67 | 5.076 23 | 4.830 08 | 4.790 27 | 4.212 93 | 3.704 23 | 0.900 38 | 5.578 2 | 4.458 56 | 110 |
| 2.68618 | 4.422 25 | 2.775 19 | 2.73123 | 3.4635 4 | 2.405 13 | 3.724 94 | 3.293 54 | 2.677 41 | 2.693 55 | 4.246 9 | 2.903 47 | 2.737 39 | 3.181 46 | 2.898 01 | 2.378 87 | 2.775 19 | 2.985 18 | 4.584 77 | 3.615 03 | | |
| 0.01396 | 4.674 22 | 5.396 57 | 0.61958 | 0.7725 5 | 0.485 76 | 0.955 1 | | | | | | | | | | | | | | | |
| 32 | 4.422 25 | 4.501 19 | 5.13414 | 4.5621 9 | 2.618 88 | 4.491 04 | 4.891 72 | 1.539 27 | 4.403 96 | 1.797 37 | 3.471 65 | 4.629 13 | 4.794 95 | 4.548 77 | 4.461 19 | 3.829 63 | 2.941 71 | 1.268 63 | 5.330 35 | 4.164 76 | 111 |
| 2.68618 | 4.422 25 | 2.775 19 | 2.73123 | 3.4635 4 | 2.405 13 | 3.724 94 | 3.293 54 | 2.677 41 | 2.693 55 | 4.246 9 | 2.903 47 | 2.737 39 | 3.181 46 | 2.898 01 | 2.378 87 | 2.775 19 | 2.985 18 | 4.584 77 | 3.615 03 | | |
| 0.01396 | 4.674 22 | 5.396 57 | 0.61958 | 0.7725 5 | 0.485 76 | 0.955 1 | | | | | | | | | | | | | | | |
| 33 | 3.190 33 | 4.501 19 | 5.13414 | 5.3286 9 | 5.269 19 | 4.218 96 | 5.825 64 | 4.660 89 | 5.214 19 | 4.477 51 | 5.640 66 | 5.156 84 | 4.965 47 | 5.522 61 | 5.173 06 | 4.094 6 | 4.358 07 | 4.321 1 | 6.403 57 | 5.529 44 | 112 |
| 2.68618 | 3.828 96 | 0.167 94 | 5.37754 | 3.4635 4 | 2.405 15 | 3.724 97 | 3.293 56 | 2.677 43 | 2.693 57 | 4.246 92 | 2.903 49 | 2.737 42 | 3.181 49 | 2.898 03 | 2.378 89 | 2.775 22 | 2.985 21 | 4.584 79 | 3.615 05 | | |
| 0.09905 | 4.422 25 | 2.775 22 | 2.73125 | 1.3776 5 | 0.485 76 | 0.955 1 | | | | | | | | | | | | | | | |
| | 2.410 45 | 5.396 57 | 0.29058 | | | | | | | | | | | | | | | | | | |

FIG. 13F

| | | | | | | | | | | | | | | | | | |
|---|---|---|---|---|---|---|---|---|---|---|---|---|---|---|---|---|---|
| 34 | 3.3282 | 5.1077 5 | 4.0069 | 4.4735 | 3.9229 7 | | 3.9692 3 | 3.8990 | | 4.7205 6 | 4.2298 1 | 0.4420 8 | 4.3364 9 | 4.1186 8 | 3.5267 6 | 3.7722 5 | 3.7260 8 | 5.9399 7 | 4.6774 8 | 114 |
| | 4.4222 5 | 2.7751 9 | 3.4635 4 | 2.4051 3 | 3.7249 4 | 6 4.9384 4 | 2.6774 1 | 2.6935 5 | 2.7536 5 4.2469 | 2.9034 7 | 2.7373 9 | 3.1814 1 | 2.8980 6 | 2.3788 7 | 2.7751 9 | 2.9851 8 | 4.5847 7 | 3.6150 3 | | |
| | 4.6742 2 | 5.3965 7 | 0.7725 5 | 0.4857 6 | 0.9551 | | | | | | | | | | | | | | | |
| 35 | 2.8277 5 | 5.1823 5 | 2.2988 1 | 4.4930 4 | 3.6101 4 | 3.7665 9 | 1.4561 4 | 2.7661 6 | | 3.6336 6 | 3.1016 5 | 3.9959 4 | 2.5769 4 | 2.4344 1 | 2.8174 3 | 3.0513 7 | 3.5554 5 | 5.6209 1 | 4.2698 2 | 115 |
| | 4.4222 5 | 2.7751 9 | 3.4635 4 | 2.4051 3 | 3.7249 4 | 3.2935 4 | 2.6774 1 | 2.6935 5 | 4.2469 | 2.9034 7 | 2.7373 9 | 3.1814 1 | 2.8980 6 | 2.3788 7 | 2.7751 9 | 2.9851 8 | 4.5847 7 | 3.6150 3 | | |
| | 4.6742 2 | 5.3965 7 | 0.7725 5 | 0.4857 6 | 0.9551 | | | | | | | | | | | | | | | |
| 36 | 4.1264 4 | 5.6722 4 | 4.7992 3 | 5.6306 4.8139 8 | 4.3195 4 | 8 5.7383 4 | 5.4766 5 | 4.9417 8 | 9 4.9638 1 | 6.0862 7 | 5.0059 2 | 0.1381 1 | 5.2945 9 | 5.0321 9 4.3314 1 | | 4.6308 1 | 5.0114 1 | 6.5149 6 | 5.7799 3 | 116 |
| | 4.4222 5 | 2.7751 9 | 3.4635 4 | 2.4051 3 | 3.7249 4 | 3.2935 4 | 2.6774 1 | 2.6935 5 | 4.2469 | 2.9034 7 | 2.7373 9 | 3.1814 1 | 2.8980 6 | 2.3788 7 | 2.7751 9 | 2.9851 8 | 4.5847 7 | 3.6150 3 | | |
| | 4.6742 2 | 5.3965 7 | 0.7725 5 | 0.4857 6 | 0.9551 | | | | | | | | | | | | | | | |
| 37 | 2.9718 9 | 3.8746 6 | 2.8097 3 | 4.4260 3.7297 3 | | 3.2595 6 | 3.8682 5 | 2.4628 8 | 3.4283 3 | 4.2587 3 | 3.2879 6 | 4.1322 1 | 3.0321 8 | 1.0285 8 | 3.0008 1 | 3.1974 9 3.5394 | | 5.5873 9 | 4.2899 8 | 117 |
| | 4.4222 5 | 2.7751 9 | 3.11028 | 3.4635 4 | 2.4051 3 | 3.7249 4 | 3.2935 4 | 2.6774 1 | 2.6935 5 | 4.2469 | 2.9034 7 | 2.7373 9 | 3.1814 1 | 2.8980 6 | 2.3788 7 | 2.7751 9 | 2.9851 8 | 4.5847 7 | 3.6150 3 | |
| | 4.6742 2 | 5.3965 7 | 0.7725 5 | 0.4857 6 | 0.9551 | | | | | | | | | | | | | | | |
| 38 | 3.5885 7 | 5.5699 5 | 3.3936 1 | 5.0082 | 4.3195 8 4.1711 | 3.9954 | 4 4.3309 6 | 2.0274 8 | 3.0433 6 | 4.6736 8 | 3.7173 6 | 4.5066 7 | 3.1375 3 | 0.6574 7 | 3.5995 4 | 3.7184 5 | 4.0570 6 | 5.7900 4 | 4.6738 5 | 118 |
| | 4.4222 5 | 2.7751 9 | 3.4635 4 | 2.4051 3 | 3.7249 4 | 3.2935 4 | 2.6774 1 | 2.6935 5 | 4.2469 | 2.9034 7 | 2.7373 9 | 3.1814 1 | 2.8980 6 | 2.3788 7 | 2.7751 9 | 2.9851 8 | 4.5847 7 | 3.6150 3 | | |
| | 4.6742 2 | 2.1983 2 | 0.1282 | 0.61958 6 | | | | | | | 2.9583 | | 3.5464 5 3.6871 | | 3.6555 7 | 3.1214 8 | 2.9719 3 | | | | |
| 39 | 2.2482 2 | 4.2270 8 | 3.5674 4 | 3.2271 4 | 3.8368 9 | 4.1427 7 | 2.5373 3 | 3.4566 5 | 2.0326 | 3.7724 1 | 2.9375 8 | 3.5106 9 | 2.6151 5 | 2.9717 2 | 2.4998 5 | 2.6304 8 | 3.4053 1 | 5.5294 8 | 4.1635 4 | 119 |
| | 4.4222 5 | 2.7751 9 | 4.15038 | 3.4635 4 | 2.4051 3 | 3.7249 4 | 3.2935 4 | 2.6774 1 | 2.6935 5 | 4.2469 | 2.9034 7 | 2.7373 9 | 3.1814 1 | 2.8980 6 | 2.3788 7 | 2.7751 9 | 2.9851 8 | 4.5847 7 | 3.6150 3 | |
| | 4.5616 4 | 3.7983 7 | 0.0334 | 0.61958 3 | | | | | | | | | | | | | | | | |
| 40 | 2.5140 1 | 5.0410 5 | 2.4881 3 | 4.3310 6 | 1.9244 1 | 3.7223 7 | 3.7724 1 | 2.4938 7 | 3.2237 6 | 3.7077 3 | 2.9835 8 | 3.5106 9 | 2.6151 5 | 2.9717 2 | 2.4998 5 | 2.6304 8 | 3.4053 1 | 5.5294 8 | 4.1635 4 | 120 |
| | 4.4222 5 | 2.7751 9 | 2.77728 | 3.4635 4 | 2.4051 3 | 3.7249 4 | 3.2935 4 | 2.6774 1 | 2.6935 5 | 4.2469 | 2.9034 7 | 2.7373 9 | 3.1814 1 | 2.8980 6 | 2.3788 7 | 2.7751 9 | 2.9851 8 | 4.5847 7 | 3.6150 3 | |
| | 4.5441 5 | 5.2665 3 | 0.01592 | 0.61958 | | | | | | | | | | | | | | | | |
| 41 | 2.4909 8 | 4.3476 4 | 3.1683 9 | 3.2867 2 | 3.7272 9 | 3.9938 | 2.375 4 | 2.6774 1 | 2.6935 5 | 3.0090 5 | 1.7427 3.4546 | | 2.9832 1 | 2.3788 7 | 2.9428 6 | 2.7751 9 | 2.9851 8 | 2.7884 3 | 2.5502 4 | 3.3807 8 | 4.1037 4 | 2.9832 1 | 2.9428 6 | 2.9851 8 | 2.4189 6 | 4.9405 1 | 3.7217 4 | 121 |
| | 4.4222 5 | 2.7751 9 | 3.74069 | 3.4635 4 | 2.4051 3 | 3.7249 4 | 3.2935 4 | 2.6774 1 | 2.6935 5 | 4.2469 | 2.9034 7 | 2.7373 9 | 3.1814 1 | 2.8980 6 | 2.3788 7 | 2.7751 9 | 2.9851 8 | 4.5847 7 | 3.6150 3 | |
| | 4.5441 8 | 4.0114 2 | 0.02916 | 0.61958 | 0.7725 5 | 0.7075 1 | 0.6789 9 | | | | | | | | | | | | | |

FIG. 13G

| | | | | | | | | | | | | |
|---|---|---|---|---|---|---|---|---|---|---|---|---|
| 42 | 2.6034 5 | 3.416 | 4.44434 | 3.8441 1 | 2.8563 2 | 3.8511 3 | 4.1742 4 | 2.2662 5 | 3.6767 6 | 1.5197 7 | 3.2372 8 | 3.9033 4 | 2.8504 6 | 3.5516 8 | 2.7981 9 | 2.8660 8 | 0.0084 9 | 4.7423 | 122 |
| | 4.4222 5 | 2.7751 9 | 2.73123 | 3.4635 2 | 2.4051 3 | 3.7249 4 | 3.2935 3 | 2.6774 4 | 2.6935 1 | | 54.2469 7 | | 2.9034 2 | 2.7373 7 | 3.1814 9 | 2.8980 6 | 2.3788 1 | 2.7751 7 | 2.9851 9 | 4.5847 8 | 3.6150 3 | |
| | 4.5311 | | 0.61958 | 0.7725 5 | 0.7258 8 | 0.6614 5 | | | | | | | | | | | | | | | |
| | 0.01613 | 55.2535 | | | | | | | | | | | | | | | | | | | |
| 43 | 2.0683 6 | 5.0843 4 | 2.83241 | 2.4597 | 3.2649 4 | 3.2275 4 | 3.579 | | 2.4676 3 | 3.1813 8 | 4.1429 9 | 2.1434 2 | 2.8368 | 32.7494 | | 2.9494 2 | 2.7055 6 | 2.9469 8 | 3.4474 6 | 5.5531 5 | 4.1768 4 | 123 |
| | 4.4222 6 | 2.7751 9 | 2.73123 | 3.4635 4 | 2.4051 3 | 3.7249 4 | 3.2935 3 | 2.6774 4 | 2.6935 1 | | 54.2469 7 | | 2.9034 2 | 2.7373 7 | 3.1814 9 | 2.8980 6 | 2.3788 1 | 2.7751 7 | 2.9851 9 | 4.5847 8 | 3.6150 3 | |
| | 4.5311 3 | 3.9893 5 | 0.61958 | 0.7725 5 | 0.7258 8 | 0.6614 5 | | | | | | | | | | | | | | | |
| | 0.02972 | | | | | | | | | | | | | | | | | | | | |
| 44 | 2.6511 7 | 4.9176 2 | 3.0207 | 2.4693 | 3.5303 3 | 3.3330 | | 23.2768 | | 2.5294 2 | 2.8171 9 | 3.9872 6 | 1.1052 2 | 2.1095 9 | 2.9799 8 | 2.8803 6 | 2.7481 8 | 2.4752 2 | 2.9339 5 | 3.2517 1 | 5.4172 4 | 4.0787 9 | 124 |
| | 4.4222 5 | 2.7751 9 | 2.73123 | 3.4635 4 | 2.4051 3 | 3.7249 4 | 3.2935 3 | 2.6774 4 | 2.6935 1 | | 54.2469 7 | | 2.9034 2 | 2.7373 7 | 3.1814 9 | 2.8980 6 | 2.3788 1 | 2.7751 7 | 2.9851 9 | 4.5847 8 | 3.6150 3 | |
| | 4.5177 2 | 83.7924 | 0.61958 | 0.7725 5 | 0.7441 4 | 0.6446 3 | | | | | | | | | | | | | | | |
| | 0.03403 | | | | | | | | | | | | | | | | | | | | |
| 45 | 2.4016 3 | 3.4560 3 | 3.00165 | 2.5683 5 | 4.0794 4 | 3.5367 1 | 3.2581 4 | 3.4891 8 | 2.5600 5 | | 92.7077 | | 3.9281 5 | 2.2302 | 3.1866 2 | 2.9072 3 | 0.0179 5 | 2.4084 5 | 2.7544 4 | 3.1780 7 | 5.3651 5 | 3.8848 2 | 125 |
| | 4.4222 6 | 2.7749 2 | 2.73091 | 3.4636 2 | 2.4053 3 | 3.7245 4 | 3.2931 | | 2.6933 2 | 2.4267 6 | 2.9035 2 | 2.7376 3 | 3.1818 4 | 2.8983 | | 2.7753 2 | 2.9845 4 | 4.5851 7 | 3.6152 | |
| | 1.02315 4 | 2.2227 3 | 0.29200 2 | 0.4327 | 41.0462 | | | 62.6776 | | | 82.3788 | | | | | | |
| | 0.4539 | 1.37338 | | | | | | | | | | | | | | | | | | | |
| 46 | 2.7389 3 | 3.7819 4 | 3.28699 | 2.7285 3 | 3.9456 5 | 3.0336 3 | 3.4652 7 | 3.3353 8 | 2.7116 7 | 2.8924 9 | 3.8411 6 | 2.5693 3 | | 2.9672 9 | 3.1451 | | 62.3099 | | 12.5606 | 2.8243 4 | 2.2832 3 | 5.2936 5 | 4.0022 6 | 132 |
| | 4.4222 5 | 2.7751 9 | 2.73123 | 3.4635 4 | 2.4051 3 | 3.7249 4 | 3.2935 3 | 2.6774 4 | 2.6935 1 | | 54.2469 7 | | 2.9034 2 | 2.7373 7 | 3.1814 9 | 2.8980 6 | 2.3788 1 | 2.7751 7 | 2.9851 9 | 4.5847 8 | 3.6150 3 | |
| | 4.6338 5 | 5.3561 7 | 0.61958 | 0.7725 5 | 0.5632 9 | 0.8424 2 | | | | | | | | | | | | | | | |
| | 0.01454 | | | | | | | | | | | | | | | | | | | | |
| 47 | 2.4342 3 | 3.5716 5 | 3.84643 | 3.2725 3 | 3.3443 5 | 3.7752 4 | 4.0496 6 | 1.9399 | 12.5538 | | 2.4883 5 | 3.2668 9 | 3.6094 4 | 3.5899 | 3.4751 | | 52.9588 2 | 2.7337 | | 2.6819 5 | 2.5844 2 | 4.9399 | 13.7271 | 133 |
| | 4.4222 5 | 2.7751 9 | 2.73123 | 3.4635 4 | 2.4051 3 | 3.7249 4 | 3.2935 3 | 2.6774 4 | 2.6935 1 | | 54.2469 7 | | 2.9034 2 | 2.7373 7 | 3.1814 9 | 2.8980 6 | 2.3788 1 | 2.7751 7 | 2.9851 9 | 4.5847 8 | 3.6150 3 | |
| | 4.6338 5 | 5.3561 7 | 0.61958 | 0.7725 5 | 0.5632 9 | 0.8424 2 | | | | | | | | | | | | | | | |
| | 0.01454 | | | | | | | | | | | | | | | | | | | | |
| 48 | 2.0631 5 | 5.0951 1 | 3.20766 | 2.6648 3 | 4.4852 6 | 3.6002 2 | 3.8325 | | 93.9109 | | 2.4250 3 | 3.4574 4 | 2.5503 7 | 0.5252 | 2.9992 5 | 2.9642 1 | 4.5987 2 | 2.6669 6 | 3.0831 5 | 3.5378 8 | 5.6339 | 4.3082 | 134 |
| | 4.4222 5 | 2.7751 9 | 2.73123 | 3.4635 4 | 2.4051 3 | 3.7249 4 | 3.2935 3 | 2.6774 4 | 2.6935 1 | | 54.2469 7 | | 2.9034 2 | 2.7373 7 | 3.1814 9 | 2.8980 6 | 2.3788 1 | 2.7751 7 | 2.9851 9 | 4.5847 8 | 3.6150 3 | |
| | 4.6338 5 | 5.3561 7 | 0.61958 | 0.7725 5 | 0.5632 9 | 0.8424 2 | | | | | | | | | | | | | | | |
| | 0.01454 | | | | | | | | | | | | | | | | | | | | |
| 49 | 2.7579 4 | 4.8348 9 | 3.25009 | 2.7097 4 | 4.0963 3 | 3.2664 5 | 4.6185 6 | 2.8991 2 | 6.6700 | | 83.1318 | | 3.9677 3 | 3.2006 4 | | | 51.7299 | | | 3.0359 2 | 2.7725 1 | 2.1659 3 | 3.0044 7 | 3.1945 6 | 14.0998 | 135 |
| | 4.4222 5 | 2.7751 9 | 2.73123 | 3.4635 4 | 2.4051 3 | 3.7249 4 | 3.2935 3 | 2.6774 4 | 2.6935 1 | | 54.2469 7 | | 2.9034 2 | 2.7373 7 | 3.1814 9 | 2.8980 6 | 2.3788 1 | 2.7751 7 | 2.9851 9 | 4.5847 8 | 3.6150 3 | |
| | 4.6338 5 | 5.3561 7 | 0.61958 | 0.7725 5 | 0.5632 9 | 0.8424 2 | | | | | | | | | | | | | | | |
| | 0.01454 | | | | | | | | | | | | | | | | | | | | |

FIG. 13H

| | | | | | | | | | | | | | | | | | | |
|---|---|---|---|---|---|---|---|---|---|---|---|---|---|---|---|---|---|---|
| 50 | 2.7476 | 4.2902 | | 3.4192 | 2.8099 | | 3.1373 | 2.4936 | 3.3254 | 1.5340 | 3.4004 | 3.7054 | 2.7140 | 3.5808 | 3.2451 | 2.9599 | 2.9795 | 2.5484 | 4.8824 | | 43.4505 | 136- |
| | 4.4222 | 2.7751 | 3.99787 | 3.4635 | 2.4051 | 3.811 | 3.7249 | 3.2935 | 2.6774 | 2.6935 | | 2.9034 | 2.7373 | 3.1814 | 2.8980 | 2.3788 | 2.7751 | 2.9851 | 4.5847 | 3.6150 | | |
| 2.68618 | 4.6385 | 5.3561 | 2.73123 | 0.7725 | 0.5632 | 0.8424 | | | | 54.2469 | | | | | | | | | | | | |
| 0.01454 | | | 0.61958 | | | | | | | | | | | | | | | | | | | |
| 51 | 3.0889 | 5.3473 | | 2.8335 | 4.0962 | 3.8054 | 3.8321 | 4.1223 | 1.8113 | 3.5963 | 4.4144 | 3.3027 | 3.3237 | 2.8164 | 1.1220 | 3.0772 | 3.2817 | 3.7702 | 5.6918 | 4.4358 | | 137- |
| | 4.4222 | 2.7751 | 3.47291 | 3.4635 | 2.4051 | 3.7249 | 3.2935 | 2.6774 | 2.6935 | | 2.9034 | 2.7373 | 3.1814 | 2.8980 | 2.3788 | 2.7751 | 2.9851 | 4.5847 | 3.6150 | | |
| 2.68618 | 4.6338 | | 2.73123 | 0.7725 | 0.5632 | 0.8424 | | | | 54.2469 | | | | | | | | | | | | |
| 0.05521 | | 23.1236 | 0.61958 | | | | | | | | | | | | | | | | | | | |
| 52 | 2.7263 | 3.0156 | | 3.7147 | 2.9686 | | 4.1578 | | | 3.5742 | 1.5829 | 3.1104 | 3.8738 | 3.7759 | 3.7753 | 3.1787 | 2.4817 | 2.8858 | 2.4247 | 3.1059 | 3.5996 | 138- |
| | 4.4222 | 2.7751 | 4.30747 | 3.4635 | 2.4051 | 53.8469 | 3.7249 | 3.2935 | 2.6774 | 2.6935 | | 2.9034 | 2.7373 | 3.1814 | 2.8980 | 2.3788 | 2.7751 | 2.9851 | 4.5847 | 3.6150 | | |
| 2.68618 | | | 2.73123 | 0.7725 | 0.6319 | 0.7583 | | | | 54.2469 | | | | | | | | | | | | |
| 0.01514 | 4.5937 | 55.3161 | 0.61958 | | | | | | | | | | | | | | | | | | | |
| 53 | 2.7385 | 5.0868 | | 2.4972 | 4.3712 | 3.5351 | 2.0198 | 3.8171 | | | 3.8447 | 2.2779 | 3.5427 | 2.5824 | | 2.9520 | 2.5975 | 2.9690 | 3.4458 | 5.5533 | 3.5852 | 139- |
| | 4.4252 | 2.7754 | 3.0514 | 3.4634 | 2.4054 | 3.7248 | | | 42.3723 | 3.2214 | | 3.1807 | 2.8981 | 2.3781 | | 2.9852 | 4.5850 | 3.6153 | | |
| 2.68639 | | | 2.73123 | 0.7725 | 0.4836 | 0.5088 | | | 63.2934 | 4.2444 | 2.9031 | | | | 32.7755 | | | | | | | |
| 0.67803 | 2.6877 | 0.8572 | 0.95851 | | | 20.9193 | | | | | | | 22.7377 | | | | | | | | | |
| 54 | 2.1104 | 3.5995 | | 2.5521 | 4.0377 | 2.8458 | 2.4361 | 3.4396 | 2.6136 | | 3.9036 | 3.1340 | 3.9636 | 2.5305 | 2.9464 | 2.7846 | 2.9527 | 2.8491 | 5.3459 | 3.6532 | 145- |
| | 4.4222 | 2.7751 | 3.18664 | 3.4635 | 2.4051 | 3.7249 | 3.2935 | 2.6774 | 2.6935 | 53.0717 | 2.9034 | 2.7373 | 3.1814 | 2.8980 | 2.3788 | 2.7751 | 2.9851 | 4.5847 | 3.6150 | | |
| 2.68618 | | | 2.73123 | 0.7725 | | 1.0568 | | | | 54.2469 | | | | | | | | | | | | |
| 0.01546 | 4.5735 | 2.2956 | 0.61958 | | 0.427 | | | | | | | | | | | | | | | | | |
| 55 | 1.7978 | 5.2315 | | 2.4039 | 4.5528 | 3.5361 | 3.5929 | 4.0227 | 2.5049 | 5.2874 | 4.2856 | 2.5529 | 3.9442 | 2.1358 | 2.9957 | 2.3071 | 2.8154 | 3.6108 | 5.6832 | 4.2844 | 146- |
| | 4.4222 | 2.7751 | 2.81709 | 3.4635 | 2.4051 | 3.7249 | 3.2935 | 2.6774 | 2.6935 | | 2.9034 | 2.7373 | 3.1814 | 2.8980 | 2.3788 | 2.7751 | 2.9851 | 4.5847 | 3.6150 | | |
| 2.68618 | | | 2.73123 | 0.7725 | 0.5159 | 0.9086 | | | | 54.2469 | | | | | | | | | | | | |
| 0.01418 | 4.6590 | 5.3813 | 0.61958 | | | | | | | | | | | | | | | | | | | |
| 56 | 1.9856 | 4.3479 | | 3.2935 | 3.1771 | 3.3881 | 4.0639 | 2.8194 | 3.2221 | 1.9877 | 2.8138 | 3.6265 | 3.5829 | 3.4936 | 3.5102 | 2.3944 | 2.8418 | 2.2741 | 4.9471 | 3.7351 | 147- |
| | 4.4222 | 2.7751 | 3.67162 | 3.4635 | 2.4051 | 3.7249 | 3.2935 | 2.6774 | 2.6935 | | 2.9034 | 2.7373 | 3.1814 | 2.8980 | 2.3788 | 2.7751 | 2.9851 | 4.5847 | 3.6150 | | |
| 2.68618 | | | 2.73123 | 0.7725 | 0.5159 | 0.9086 | | | | 54.2469 | | | | | | | | | | | | |
| 0.01418 | 4.6590 | 5.3813 | 0.61958 | | | | | | | | | | | | | | | | | | | |

FIG. 13I

| | | | | | | | | | | | | | | | | |
|---|---|---|---|---|---|---|---|---|---|---|---|---|---|---|---|---|
| 57 | 2.5240 3 | 5.2581 5 | | 1.8516 3 | 4.5940 4 | 3.2390 2 | 3.2688 3 | 4.0752 7 | 2.3117 6 | 3.5594 9 | 3.7775 5 | 2.8977 9 | 2.5658 6 | 2.8252 7 | 2.9617 7 | 2.7279 7 | 2.9962 7 | 3.6440 5 | 5.6955 1 | 4.2872 1 | 148 |
| | 4.4222 5 | 2.7751 9 | 2.28954 | 3.4635 4 | 2.4051 3 | 3.7249 5 | 3.2935 4 | 2.6774 1 | 2.6935 5 | | 2.9034 7 | 2.7373 3 | 3.1814 6 | 2.8980 1 | 2.3788 7 | 2.7751 7 | 2.9851 9 | 4.5847 8 | 3.6150 3 | |
| 2.68618 | 4.6590 5 | 5.3813 9 | 2.73123 | 0.7725 5 | 0.5159 7 | 0.9086 3 | | | 5 4.2469 | | | | | | | | | | | |
| 0.01418 | | | 0.61958 | | | | | | | | | | | | | | | | | |
| 58 | 2.5609 5 | 4.3976 8 | 3.53708 | 3.1187 5 | 3.2049 4 | 3.7578 7 | 2.7695 8 | 3.1284 4 | 1.8259 7 | | 3.5551 6 | 2.6122 4 | 3.1393 4 | 3.1642 8 | 3.0171 | | 2.3447 3 | 4.9890 5 | 3.3991 3 | 149 |
| | 4.4222 5 | 2.7751 9 | | 3.1876 | | | | | 2 3.1885 | | | | | | 3 2.9823 | | | | |
| 2.68618 | 4.6590 5 | 5.3813 9 | 2.73123 | 3.4635 4 | 2.4051 3 | 3.7249 5 | 3.2935 4 | 2.6774 1 | 2.6935 | | 2.9034 7 | 2.7373 3 | 3.1814 6 | 2.8980 1 | 2.3788 7 | 2.7751 7 | 2.9851 9 | 4.5847 8 | 3.6150 3 | |
| 0.01418 | | | 0.61958 | 0.7725 5 | 0.5159 7 | 0.9086 3 | | | 5 4.2469 | | | | | | | | | | | |
| 59 | 2.6813 6 | 2.0767 7 | 3.73475 | 3.1673 7 | 3.5591 3 | 3.4821 | 2.9167 2 | 3.1112 2 | 2.5130 4 | 3.5368 | | 3.4698 9 | 3.4013 3 | 3.4380 5 | 2.5130 8 | 2.7945 2 | 2.5507 9 | 5.0194 2 | 2.5137 7 | 150 |
| | 4.4222 5 | 2.7751 9 | 2.73123 | 3.4635 4 | 2.4051 3 | 4.0293 4 | 3.2935 4 | 2.6774 1 | 2.6935 | 9 2.9938 | | 2.9034 7 | 2.7373 3 | 3.1814 6 | 2.8980 1 | 2.3788 7 | 2.7751 7 | 2.9851 9 | 4.5847 8 | 3.6150 3 | |
| 2.68618 | 4.6590 5 | 5.3813 9 | 0.61958 | 0.7725 5 | 0.5159 7 | 0.9086 3 | | | 5 4.2469 | | | | | | | | | | | |
| 0.01418 | | | | | | | | | | | | | | | | | | | | |
| 60 | 2.8507 | 9.5703 | 1.73452 | 1.8638 8 | 3.1123 2 | 3.7863 1 | 4.1948 6 | 2.3749 7 | 3.6706 | 4.4208 2 | 3.0027 9 | 3.9746 2 | 2.8932 5 | 2.4078 9 | 4.5452 9 | 3.0885 2 | 3.7572 3 | 5.8027 3 | 4.3803 4 | 151 |
| | 4.4222 5 | 2.7751 9 | 2.73123 | 3.4635 4 | 2.4051 3 | 3.7249 5 | 3.2935 4 | 2.6774 1 | 2.6935 | | 2.9034 7 | 2.7373 3 | 3.1814 6 | 2.8980 1 | 2.3788 7 | 2.7751 7 | 2.9851 9 | 4.5847 8 | 3.6150 3 | |
| 2.68618 | 4.6590 5 | | | 4.7058 | | | | | 5 4.2469 | | | | | | | | | | | |
| 0.04329 | | | 0.61958 | 0.7725 5 | 0.5159 7 | 0.9086 3 | | | | | | | | | | | | | | |
| 61 | 2.2853 7 | 4.8963 7 | 2.87931 | 2.6239 5 | 4.1580 6 | 3.0675 2 | 3.8080 7 | 3.5704 2 | 2.6214 7 | 3.2702 5 | 4.0041 5 | 3.1335 3 | 3.3886 5 | 2.9674 8 | 3.0794 2 | 1.5916 4 | 2.9787 3 | 3.2502 3 | 4.9186 1 | 4.1130 5 | 152 |
| | 4.4222 5 | 2.7751 9 | 2.73123 | 3.4635 4 | 2.4051 3 | 3.7249 5 | 3.2935 4 | 2.6774 1 | 2.6934 4 | 2.6934 1 | 2.9034 5 | 2.9034 7 | 2.7373 3 | 3.1814 6 | 2.8980 1 | 2.3788 7 | 2.7751 7 | 2.9851 9 | 4.5847 8 | 3.6150 3 | |
| 2.68618 | 4.6303 5 | 3.3526 9 | 0.61958 | 0.7725 5 | 0.5695 7 | 0.8342 3 | | | 5 4.2469 | | | | | | | | | | | |
| 0.01459 | | | | | | | | | | | | | | | | | | | | |
| 62 | 2.5491 6 | 5.2306 8 | 2.44532 | 4.5665 5 | 3.5174 4 | 3.5689 3 | 3.5927 3 | 2.6663 6 | 2.8436 4 | 3.9923 6 | 2.9679 4 | 3.0134 5 | 3.1127 7 | 2.1636 8 | 2.9934 4 | 3.2233 4 | 5.4288 5 | 4.1140 5 | 153 |
| | 4.4222 | | 2.2105 3 | | | 4 | | | 1 | 5 | | | | 8 | | 1 | | | | | |
| 2.68619 | 62.7752 | 2.73124 | 3.4635 4 | 2.4051 3 | 3.7249 5 | 3.2935 4 | 2.6774 1 | 2.6935 | | 2.9034 7 | 2.7373 3 | 3.1814 6 | 2.8980 1 | 2.3788 7 | 2.7751 7 | 2.9851 9 | 4.5847 8 | 3.6150 3 | |
| 0.11797 | 3.0447 9 | 2.7539 6 | 0.40949 | 1.0906 2 | 0.4367 8 | 1.0388 | | | | | | | | 3.1814 7 | | 4 2.7752 | | | | | |
| 63 | 1.5473 4 | 4.8568 9 | 3.1908 | 2.5454 6 | 4.1303 1 | 3.5689 5 | 3.5927 3 | 2.9275 8 | 2.638 | 2.6901 1 | 3.7821 6 | 3.2679 7 | 4.0341 8 | 3.1027 4 | 3.0978 | | 2.5687 2 | 2.9873 6 | 5.2414 2 | 3.9640 2 | 155 |
| | 4.4222 5 | 2.7751 9 | 2.73123 | 3.4635 4 | 2.4051 3 | 3.7249 5 | 3.2935 4 | 2.6774 1 | 2.6935 | | 2.9034 7 | 2.7373 3 | 3.1814 6 | 2.8980 1 | 2.3788 7 | 2.7751 7 | 2.9851 9 | 4.5847 8 | 3.6150 3 | |
| 2.68618 | 4.6161 6 | 5.3385 1 | 0.61958 | 0.7725 5 | 0.4768 4 | 0.9695 5 | | | 5 4.2469 | | | | | | | | 12.7346 | | | |
| 0.0148 | | | | | | | | | | | | | | | | | | | | |
| 64 | 2.4173 8 | 3.5418 5 | 3.20461 | 2.7194 6 | 3.8679 8 | 1.8578 9 | 3.8771 | | | | | | | | | | | | | 156 |
| | 4.4222 5 | 2.7751 9 | 2.73123 | 3.4635 4 | 2.4051 3 | 3.7249 5 | 3.2935 4 | 2.6774 1 | 2.6935 | | 2.9034 7 | 2.7373 3 | 3.1814 6 | 2.8980 1 | 2.3788 7 | 2.7751 7 | 2.9851 9 | 4.5847 8 | 3.6150 3 | |
| 2.68618 | 4.6553 6 | 5.3777 1 | 0.61958 | 0.7725 | 0.8981 6 | 0.5231 5 | | | | | | | | | | | | | | |
| 0.01423 | | | | | | | | | | | | | | | | | | | | |

FIG. 13J

| | | | | | | | | | | | | | | | | |
|---|---|---|---|---|---|---|---|---|---|---|---|---|---|---|---|---|
| 65 | 1.9419 | | 3.1129 3 | | 3.2097 5 | 2.9434 7 | 3.4627 8 | 3.4395 7 | 2.7970 | | 2.3498 2 | 3.0118 4 | | 3.413 3 | 4.1683 8 | 3.5186 7 | 3.2209 3 | 2.7328 4 | 2.6718 | 2.3952 5 | 4.9289 | 3.2014 3 | 157 |
| | 2.68618 | 4.4222 5 | 2.7751 9 | | 3.4635 4 | 2.4051 3 | 3.7249 4 | 3.2935 4 | 2.6774 1 | | | 2.9034 7 | 2.7373 9 | | 2.8980 1 | 2.3788 7 | 2.9851 9 | 4.5847 8 | 3.6150 3 | | |
| | 0.01423 | 4.6553 6 | 5.3777 1 | 0.7725 5 | 0.61958 0 | | 0.8981 6 | | | | 5 | 4.2469 9 | | | | | | | | | |
| 66 | | 2.8067 2 | 5.6064 5 | | 1.3703 2 | 4.9249 6 | 3.0140 3 | 3.9230 9 | 4.4329 8 | 2.7872 | | 4.6787 9 | 2.5870 3 | 4.0688 6 | 3.0491 9 | 3.0524 7 | 2.9553 3 | 3.2902 9 | 3.9874 5 | 6.0399 | 4.5765 | 158 |
| | 2.68618 | 4.4222 5 | 2.7751 9 | | 3.4635 4 | 2.4051 3 | 3.7249 4 | 3.2935 4 | 2.6774 1 | | 3.9026 | 2.9034 7 | 2.7373 9 | | 2.8980 1 | 2.3788 7 | 2.9851 9 | 4.5847 8 | 3.6150 3 | | | |
| | 0.01423 | 4.6553 6 | 5.3777 1 | 0.7725 5 | 0.61958 0 | | 0.8981 6 | | | | 5 | 4.2469 9 | | | | | | | | | |
| 67 | | 3.0241 7 | 4.4071 7 | 4.75521 | 4.1678 5 | 3.1627 6 | 4.2126 1 | 4.5531 1 | 1.4767 1 | 4.0147 1 | 1.3009 3 | 3.3172 5 | 4.2913 3 | | 4.1763 3 | 4.1123 3 | 3.5262 3 | 3.0027 4 | 2.2540 6 | 5.0703 3 | 3.9115 3 | 159 |
| | 2.68618 | 4.4222 5 | 2.7751 9 | | 3.4635 4 | 2.4051 3 | 3.7249 4 | 3.2935 4 | 2.6774 1 | | | 2.9034 7 | 2.7373 9 | | 2.8980 1 | 2.3788 7 | 2.9851 9 | 4.5847 8 | 3.6150 3 | | | |
| | 0.01423 | 4.6553 6 | 5.3777 1 | 0.7725 5 | 0.61958 0 | | 0.8981 6 | | | | 5 | 4.2469 9 | | | | | | | | | |
| 68 | | 2.8292 5 | 4.3771 2 | 4.08254 | 3.5273 5 | 3.1627 6 | 3.8696 1 | 3.6540 | 2.7727 4 | | 1.0586 6 | 3.4413 3 | 3.8003 5 | | | 3.6766 3 | 3.6179 5 | 3.1668 8 | 2.8768 1 | 2.3669 2 | 4.9875 3 | 3.7829 2 | 160 |
| | | | | 23.4507 | | | | | | | | | | 63.4391 | | | | | | | | |
| | 2.68618 | 4.4222 5 | 2.7751 9 | | 3.4635 4 | 2.4051 3 | 3.7249 4 | 3.2935 4 | 2.6774 1 | | | 2.9034 7 | 2.7373 9 | | 2.8980 1 | 2.3788 7 | 2.9851 9 | 4.5847 8 | 3.6150 3 | | | |
| | 0.01423 | 4.6553 6 | 5.3777 1 | 0.7725 5 | 0.61958 0 | | 0.8981 6 | | | | 5 | 4.2469 9 | | | | | | | | | |
| 69 | | 3.1735 2 | 5.7816 6 | 1.09723 | 1.7746 5 | 5.0870 5 | 3.5637 7 | 4.0225 | | | 2.9652 | 74.0766 1 | 4.8798 | | 2.6435 1 | 2.9347 4 | 3.1648 9 | 3.5434 6 | 3.0692 7 | 3.1031 2 | 4.1595 5 | 6.2202 7 | 4.7227 4 | 161 |
| | 2.68618 | 4.4222 5 | 2.7751 9 | | 3.4635 4 | 2.4051 3 | 3.7249 4 | 3.2935 4 | 2.6774 1 | | 74.6099 5 | 2.9034 7 | 2.7373 9 | | 2.8980 1 | 2.3788 7 | 2.9851 9 | 4.5847 8 | 3.6150 3 | | | |
| | 0.01423 | 4.6553 6 | 5.3777 1 | 0.7725 5 | 0.61958 0 | | 0.8981 6 | | | | 5 | 4.2469 9 | | | | | | | | | |
| 70 | | 2.8066 4 | 4.2295 7 | 4.47109 | 3.8773 3 | 2.7864 5 | 3.9460 8 | 4.2660 4 | 1.4193 5 | 3.7178 9 | 1.7752 2 | 3.3128 6 | 4.0042 | 84.3088 | | 3.9084 5 | 3.4632 6 | 2.7210 8 | 2.9334 | 7 | 2.4031 5 | 4.8533 3 | 3.6679 1 | 162 |
| | 2.68618 | 4.4222 5 | 2.7751 9 | | 3.4635 4 | 2.4051 3 | 3.7249 4 | 3.2935 4 | 2.6774 1 | | | 2.9034 7 | 2.7373 9 | | 2.8980 1 | 2.3788 7 | 2.9851 9 | 4.5847 8 | 3.6150 3 | | | |
| | 0.01423 | 4.6553 6 | 5.3777 1 | 0.7725 5 | 0.61958 0 | | 0.8981 6 | | | | 5 | 4.2469 9 | | | | | | | | | |
| 71 | | 3.2216 3 | 4.5632 8 | 5.03289 | 4.4530 7 | 2.2951 4 | 4.4467 3 | 4.7534 6 | 1.0753 1 | 4.2899 1 | 1.6634 3 | 4.2916 2 | 4.5494 | 63.8601 | | 4.4044 4 | 4.3490 3 | 3.7752 9 | 3.4520 4 | 2.3768 6 | 5.1559 | 83.9709 3 | | 163 |
| | 2.68618 | 4.4222 5 | 2.7751 9 | | 3.4635 4 | 2.4051 3 | 3.7249 4 | 3.2935 4 | 2.6774 1 | | | 2.9034 7 | 2.7373 9 | | 2.8980 1 | 2.3788 7 | 2.9851 9 | 4.5847 8 | 3.6150 3 | | | |
| | 0.01423 | 4.6553 6 | 5.3777 1 | 0.7725 5 | 0.61958 0 | | 0.8981 6 | | | | 5 | 4.2469 9 | | | | | | | | | |

FIG. 13K

| | | | | | | | | | | | | | | |
|---|---|---|---|---|---|---|---|---|---|---|---|---|---|---|
| 72 | 2.6914 | | | | | | | 3.1443 | 3.0844 | 2.6814 | 5.0304 | 3.8174 | | |
| | 84.4516 | 3.95407 | 3.3790 | 3.1719 | 3.8657 | 4.1395 | 2.8484 | 3.2095 | 1.1677 | 3.4799 | 3.7087 | 3.6879 | 3.5491 | |
| | 4.4222 | | 9 | 1 | 8 | 7 | 3 | 1 | | 5 | 6 | 9 | | 164 |
| | 2.7751 | | 3.4635 | 2.4051 | 3.7249 | 3.2935 | 2.6774 | 2.6935 | | 2.9034 | 2.7373 | 3.1814 | 2.8980 | 32.4745 |
| 2.68618 | 5 | 2.73123 | 4 | 3 | 4 | 4 | 4 | 1 | 54.2469 | 7 | 9 | 6 | 1 | |
| | 4.6553 | | | 0.9924 | | | | | | | | | | |
| 0.01423 | 5.3777 | 0.61958 | 0.7725 | 4 | | | | | 50.4631 | | | | | |
| | 6 | | | | | | | | | | | | | |
| 73 | 2.5583 | | 2.9965 | 4.2317 | 3.5824 | 3.7917 | 3.6510 | 2.5796 | 3.0480 | 3.2434 | 2.5211 | 3.9766 | 2.9375 | 2.2804 | 1.9116 | 2.4420 | 3.3200 | 5.4832 | 4.1454 |
| | 4.9758 | 3.15391 | 5 | 7 | 5 | 2 | 2 | 4 | 2 | 2 | 3 | 1 | 4 | 3 | | 3 | 3 | 6 | 6 | 4 |
| | 7 | | | | | | | | | | | | | | | | | | | 165 |
| | 4.4222 | | 3.4635 | 2.4051 | 3.7249 | 3.2935 | 2.6774 | 2.6935 | | 2.9034 | 2.7373 | 3.1814 | 2.8980 | | | | | | | |
| 2.68618 | 2.7751 | 2.73123 | 4 | 3 | 4 | 4 | 4 | 1 | 54.2469 | 7 | 9 | 6 | 1 | | | | | | | |
| | 5 | | | | | | | | | | | | | | | | | | | |
| | 4.6742 | | 0.7725 | 0.4857 | | | | | | | | | | |
| 0.01396 | 5.3965 | 0.61958 | 5 | | 60.9551 | | | | | | | | | |
| | 2 | | | | | | | | | | | | | |
| 74 | 3.0252 | | 2.7967 | 5.0677 | 3.9672 | 3.9271 | 4.4063 | | | | 3.8149 | 4.6621 | 3.4642 | 4.3408 | 3.0509 | 2.2344 | 3.3331 | 3.5301 | 4.0597 | 5.8417 | 4.6568 |
| | 5.5739 | 3.64457 | 6 | 3 | 2 | 8 | | 70.7369 | | | 4 | 2 | 3 | 9 | 5 | 4 | 3 | 7 | 3 | 1 | 2 |
| | 8 | | | | | | | | | | | | | | | | | | | | 166 |
| | 4.4222 | | 3.4635 | 2.4049 | 3.7249 | 3.2935 | 2.6774 | 2.6935 | 4.2469 | | | 2.8980 | 2.7373 | 3.1814 | | | | 3.6150 | | | |
| 2.68611 | 2.7751 | 2.73118 | 7 | 8 | 4 | 4 | 4 | 8 | | | 32.9035 | 4 | 2.7374 | 33.1815 | | | | 24.5848 | | | 7 |
| | 9 | | | | | | | | | | | | | | | | | | | | |
| | 2.0144 | | 1.5977 | 0.4857 | | | | | | | | | | |
| 0.20643 | 2.9351 | 0.22609 | 0 | | 60.9551 | | | | | | | | | |
| | 2 | | | | | | | | | | | | | |
| | 5 | | | | | | | | | | | | | |
| 75 | 3.0123 | | 1.6671 | 4.8992 | 2.1243 | 3.9069 | 4.4061 | 2.7711 | 3.8783 | 4.6543 | 2.2021 | 4.0508 | 3.0331 | 3.1141 | | 3.2682 | 3.9609 | 6.0173 | 4.5558 |
| | 5.5747 | 2.15659 | 4 | 1 | 8 | 4 | 2 | 1 | 4 | 2 | 7 | 3 | 2 | | | 3 | 6 | 9 | 4 |
| | 5 | | | | | | | | | | | | | 72.2264 | | | | | | 168 |
| | 4.4222 | | 3.4635 | 2.4051 | 3.7249 | 3.2935 | 2.6774 | 2.6935 | | 2.9034 | 2.7373 | 3.1814 | 2.8980 | | | | | | |
| 2.68618 | 2.7751 | 2.73123 | 4 | 3 | 4 | 4 | 4 | 1 | 54.2469 | 7 | 9 | 6 | 1 | | | | | | |
| | 5 | | | | | | | | | | | | | | | | | | |
| | 4.6244 | | 0.7725 | 0.5800 | 0.8206 | | | | | | | | | |
| 0.01468 | 5.3467 | 0.61958 | 5 | 9 | 3 | | | | | | | | | |
| | 1 | | | | | | | | | | | | | |
| | 6 | | | | | | | | | | | | | |
| 76 | 2.8132 | | 2.2374 | 4.5866 | 2.2832 | 3.7742 | 4.0584 | 2.5068 | 3.5664 | 4.3299 | 3.0062 | 3.9576 | 2.7395 | 3.0509 | | 2.4055 | 3.0521 | 3.6468 | 5.7243 | 4.3193 |
| | 3.9941 | 1.72091 | 3 | 5 | 6 | 1 | 1 | 7 | 4 | 9 | 8 | 3 | 6 | 1 | | 3 | 5 | 2 | 8 | 9 |
| | 8 | | | | | | | | | | | | | | | | | | | 169 |
| | 3 | | | | | | | | | | | | | | | | | | | |
| | 4.4222 | | 3.4635 | 2.4051 | 3.7249 | 3.2935 | 2.6774 | 2.6935 | | 2.9034 | 2.7373 | 3.1814 | 2.8980 | | | | | | |
| 2.68618 | 2.7751 | 2.73123 | 4 | 3 | 4 | 4 | 4 | 1 | 54.2469 | 7 | 9 | 6 | 1 | | | | | | |
| | 5 | | | | | | | | | | | | | | | | | | |
| | 4.6244 | | 0.7725 | 0.5800 | 0.8206 | | | | | | | | | |
| 0.01468 | 5.3467 | 0.61958 | 5 | 9 | 3 | | | | | | | | | |
| | 1 | | | | | | | | | | | | | |
| | 6 | | | | | | | | | | | | | |
| 77 | 2.7370 | | | 3.4230 | 3.5325 | 2.9812 | 2.5787 | 2.6369 | 3.7259 | 2.4580 | 3.2247 | 3.1248 | | | | 2.5418 | 2.9686 | 2.9240 | 5.1893 | 2.4075 |
| | 3.9276 | 3.38554 | 2.8231 | 2 | 6 | 8 | 2 | 9 | 7 | 1 | 2 | 3 | 83.0476 | | | 2 | 4 | 3 | 8 | 8 |
| | 8 | | | | | | | | | | | | | | | | | | | 170 |
| | 5 | | | | | | | | | | | | | | | | | | | |
| | 4.4222 | | 3.4635 | 2.4051 | 3.7249 | 3.2935 | 2.6774 | 2.6935 | | 2.9034 | 2.7373 | 3.1814 | 2.8980 | | | | | | 3.6150 | |
| 2.68618 | 2.7751 | 2.73123 | 4 | 3 | 4 | 4 | 4 | 1 | 54.2469 | 7 | 9 | 6 | 1 | | | | 9 | | 7 | |
| | 5 | | | | | | | | | | | | | | | | | | | |
| | 4.6244 | | 0.7725 | 0.5800 | 0.8206 | | | | | | | | | |
| 0.01468 | 5.3467 | 0.61958 | 5 | 9 | 3 | | | | | | | | | |
| | 1 | | | | | | | | | | | | | |
| | 6 | | | | | | | | | | | | | |
| 78 | 2.8474 | | 2.0114 | 4.7454 | 1.7399 | 3.8294 | | 2.5237 | | | 2.9962 | 3.9994 | 2.9461 | 2.9007 | 2.5190 | | 3.1496 | 3.8037 | 5.8622 | 4.4310 |
| | 5.4203 | 2.02938 | 4 | 1 | 3 | 6 | 4.235 | 3 | 93.7197 | 4.4841 | 3 | 9 | 4 | 2 | 3 | | 3 | 9 | 1 | 6 |
| | 1 | | | | | | | | | | | | | | | | | | | 171 |
| | 2 | | | | | | | | | | | | | | | | | | | |
| | 4.4222 | | 3.4635 | 2.4051 | 3.7249 | 3.2935 | 2.6774 | 2.6935 | | 2.9034 | 2.7373 | 3.1814 | 2.8980 | | | | | | 3.6150 | |
| 2.68618 | 2.7751 | 2.73123 | 4 | 3 | 4 | 4 | 4 | 1 | 54.2469 | 7 | 9 | 6 | 1 | | | | 9 | | 7 | |
| | 5 | | | | | | | | | | | | | | | | | | | |
| | 4.6244 | | 0.7725 | 0.5800 | 0.8206 | | | | | | | | | |
| 0.04485 | 3.3798 | 0.61958 | 5 | 9 | 3 | | | | | | | | | |
| | 1 | | | | | | | | | | | | | |
| | 7 | | | | | | | | | | | | | |

FIG. 13L

| | | | | | | | | | | | | | | | | |
|---|---|---|---|---|---|---|---|---|---|---|---|---|---|---|---|---|
| 79 | 2.6176 6 | | | | 2.7655 4 | 3.7981 4 | 3.4258 3 | 2.6329 7 | 2.8892 6 | 3.7424 4 | 3.1483 1 | 3.8295 6 | 2.9759 5 | 2.9870 2 | 2.6642 7 | 2.2015 3 | 2.4195 8 | 5.3412 1 | 3.4522 | 172 |
| | 4.8158 1 | 2.41706 | 2.6443 | 4.0261 | | | | | | 2.9034 7 | 2.7373 9 | 3.1814 6 | 2.8980 1 | 2.3788 7 | 2.7751 9 | 2.9851 8 | 4.5847 7 | 3.6150 3 | | |
| 2.68618 | 4.4222 5 | 2.7751 9 | 2.73123 | 3.4635 4 | 2.4051 3 | 3.7249 4 | 3.2935 4 | 2.6774 1 | 2.6935 5 | | | | | | | | | | | |
| 0.03073 | 4.5946 9 | 3.9040 4 | 0.61958 | 0.7725 5 | 0.6304 3 | 0.7600 | | 4.2469 | | | | | | | | | | | | |
| 80 | 2.7271 8 | 5.1537 9 | 2.29005 | 2.1233 8 | 4.4651 1 | 2.6643 3 | 3.7040 4 | 2.8423 | | 3.4445 4 | 4.2041 2 | 2.9917 3 | 3.9049 5 | 2.5592 9 | 2.6207 8 | 2.8378 4 | 3.2471 6 | 5.6071 9 | 4.2171 | 173 |
| 2.68595 | 4.4219 3 | 2.7754 5 | 2.73139 | 3.4632 6 | 2.4054 4 | 3.7251 9 | 2.9336 | 2.6775 6 | 2.6936 3 | | 2.9034 8 | 2.7373 | 4.2469 | 3.1808 1 | 2.8975 6 | 2.3787 2 | 2.7751 6 | 2.9851 1 | 4.5851 | 3.6152 9 |
| 0.51408 | 1.1925 1 | 2.3177 6 | 1.36728 | 0.2941 | 0.4319 | 8 1.0476 | | | | | | | | | | | | | | |
| 81 | 2.3312 7 | 4.8795 3 | 2.96964 | 2.3633 2 | 3.2115 6 | 3.7657 2 | 3.5172 6 | 2.4837 5 | 2.4574 9 | 3.9536 2 | 2.9661 | | 2.9251 2 | 3.0367 3 | 2.6852 6 | 3.2052 1 | 5.3901 9 | 3.8739 8 | | 182 |
| 2.68618 | 4.4222 5 | 2.7751 9 | 2.73123 | 3.4635 4 | 2.4051 3 | 3.7249 4 | 3.2935 4 | 2.6774 1 | 2.6935 5 | 2.9034 7 | 2.7373 9 | 3.394 3.1814 6 | 2.8980 1 | 2.3788 7 | 2.7751 9 | 2.9851 8 | 4.5847 7 | 3.6150 3 | | |
| 0.01553 | 4.5687 5 | 5.2910 9 | 0.61958 | 0.7725 5 | 0.4693 8 | 0.9818 6 | | 4.2469 | | | | | | | | | | | | |
| 82 | 2.7706 5 | 5.2781 | 2.52113 | 2.0599 2 | 4.6177 7 | 3.4157 2 | 3.7261 9 | 4.1030 | 3.5811 | 4.4322 4 | 2.5160 5 | 3.7226 9 | 2.0257 4 | 2.8510 7 | 2.2280 5 | 2.6473 6 | 3.6662 4 | 5.7126 9 | 4.2996 3 | 183 |
| 2.68618 | 4.4222 5 | 2.7751 9 | 2.73123 | 3.4635 4 | 2.4051 3 | 3.7249 4 | 3.2935 4 | 2.6774 1 | 2.6935 5 | | 2.9034 7 | 2.7373 9 | 2.4728 3.1814 6 | 2.8980 1 | 2.3788 7 | 2.7751 9 | 2.9851 8 | 4.5847 7 | 3.6150 3 |
| 0.01443 | 4.6411 7 | 5.3635 2 | 0.61958 | 0.7725 5 | 0.5498 5 | 0.8604 7 | | 4.2469 | | | | | | | | | | | | |
| 83 | 2.5526 5 | 4.5606 4 | 2.34742 | 2.6752 8 | 3.1971 2 | 3.6877 7 | 3.9288 4 | 3.0741 7 | 2.8914 2 | 2.1841 7 | 3.4610 6 | 3.3656 1 | 4.0702 7 | 3.2082 7 | 2.6737 9 | 2.8530 4 | 2.0176 2 | 5.1312 3 | 3.8786 1 | 184 |
| 2.68618 | 4.4222 5 | 2.7751 9 | 2.73123 | 3.4635 4 | 2.4051 3 | 3.7249 4 | 3.2935 4 | 2.6774 1 | 2.6935 5 | 2.9034 7 | 2.7373 9 | | 3.1814 6 | 2.8980 1 | 2.3788 7 | 2.7751 9 | 2.9851 8 | 4.5847 7 | 3.6150 3 | |
| 0.01443 | 4.6411 7 | 5.3635 2 | 0.61958 | 0.7725 5 | 0.4937 5 | 0.9425 2 | | 4.2469 | | | | | | | | | | | | |
| 84 | 2.2855 4 | 5.1425 9 | 2.63406 | 2.3327 8 | 4.4418 4 | 2.9118 7 | 3.7356 9 | 3.7029 1 | 2.4039 2 | 2.6603 5 | 4.1963 1 | 2.6509 4 | 3.7749 1 | 2.8495 5 | 2.9760 2 | 2.0923 4 | 2.9813 8 | 5.6043 5 | 4.2229 3 | 185 |
| 2.68618 | 4.4222 5 | 2.7751 9 | 2.73123 | 3.4635 4 | 2.4051 3 | 3.7249 4 | 3.2935 4 | 2.6774 1 | 2.6935 5 | 2.9034 7 | 2.7373 9 | | 3.1814 6 | 2.8980 1 | 2.3788 7 | 2.7751 9 | 2.9851 8 | 4.5847 7 | 3.6150 3 | |
| 0.01418 | 4.6590 5 | 5.3813 9 | 0.61958 | 0.7725 5 | 0.5159 7 | 0.9086 | | 4.2469 | | | | | | | | | | | | |
| 85 | 2.5375 4 | 3.5395 2 | 2.77466 | 2.6288 2 | 4.2149 3 | 3.5682 5 | 3.8232 1 | 3.6312 5 | 2.6304 | 3.2383 1 | 3.7253 7 | 2.9621 3.9821 | 2.8129 1 | 3.0905 9 | 1.3941 8 | 2.9951 1 | 3.3004 1 | 5.4836 4 | 4.1525 1 | 186 |
| 2.68618 | 4.4222 5 | 2.7751 9 | 2.73123 | 3.4635 4 | 2.4051 3 | 3.7249 4 | 3.2935 4 | 2.6774 1 | 2.6935 5 | 2.9034 7 | 2.7373 9 | | 3.1814 6 | 2.8980 1 | 2.3788 7 | 2.7751 9 | 2.9851 8 | 4.5847 7 | 3.6150 3 | |
| 0.01418 | 4.6590 5 | 5.3813 9 | 0.61958 | 0.7725 5 | 0.4673 3 | 0.9853 | | | | | | | | | | | | | | |

FIG. 13M

| | | | | | | | | | | | | | | | |
|---|---|---|---|---|---|---|---|---|---|---|---|---|---|---|---|
| 86 | 2.63585 | 3.33793 | 3.3034 | 3.47420 | 2.23707 | 4.35958 | 3.89174 | 3.27548 | 3.54737 | 4.36737 | 3.57816 | 3.36717 | 3.58806 | 3.40913 | | 2.69190 | 3.43476 | 5.80648 | 4.56344 | 187 |
| | 4.42225 | 2.77519 | | 3.46354 | 3.72494 | 3.29354 | 2.67741 | 2.69351 | | 2.90347 | 2.73739 | 3.18146 | 2.89806 | 2.37881 | 1.10043 | 2.97517 | 2.98519 | 4.58478 | 3.61503 | |
| 2.68618 | | 3.79092 | | | | | | | | | | | | | | | | | |
| 0.2476 | 4.67422 | 1.56068 | 0.77253 | 0.48575 | 0.95516 | | | | | 4.24695 | | | | | | | | | | |
| 87 | 2.68586 | 3.82321 | 3.02752 | 2.31063 | 4.25453 | 3.49371 | 3.69074 | 3.68887 | 2.45964 | 4.04803 | 3.25694 | 3.00169 | 2.94318 | 2.14213 | 2.67472 | | 2.18071 | 2.91707 | 3.33468 | 5.46578 | 3.48248 | 188 |
| | 4.42225 | 2.77519 | | 3.46354 | 3.72494 | 3.29354 | 2.67741 | 2.69351 | | 2.90347 | 2.73739 | 3.18146 | 2.89806 | | | 2.97517 | 2.98519 | 4.58478 | 3.61503 | |
| 2.68618 | | 2.73123 | | | | | | | | | | | | | | | | | |
| 0.0176 | 4.44425 | 5.16653 | 0.61958 | 0.77253 | 0.31645 | 1.30459 | | | | | 4.24695 | | | | | | | | | |
| 88 | 2.58612 | 4.45476 | 3.67478 | 2.81616 | 3.58747 | 3.62041 | 2.94736 | 3.05318 | 2.52672 | 3.14563 | 3.50064 | 1.82156 | 3.35293 | | 3.39533 | | 2.90263 | 2.98974 | 2.28469 | 3.80916 | 189 |
| | 4.42225 | 2.77519 | | 3.46354 | 3.72494 | 3.29354 | 2.67741 | 2.69351 | | 2.90347 | 2.73739 | 3.18146 | 2.89806 | | | 2.97517 | 2.98519 | 4.58478 | 3.61503 | |
| 2.68618 | | 2.73123 | | | | | | | | | | | | | | | | | |
| 0.01396 | 4.67425 | 5.39652 | 0.61958 | 0.77253 | 0.48576 | 0.95516 | | | | | 4.24695 | | | | | | | | | |
| 89 | 1.94972 | 4.62101 | 3.75205 | 3.31876 | 2.14765 | 4.39666 | 3.91363 | 3.22213 | 2.54182 | 4.40985 | 2.00479 | 3.39792 | 3.63048 | 3.69208 | | 2.81265 | 2.64662 | | 5.84823 | 4.60697 | 190 |
| | 4.42225 | 2.77519 | | 3.46354 | 3.72494 | 3.29354 | 2.67741 | 2.69351 | | 2.90347 | 2.73739 | 3.18146 | 2.89806 | | | 2.97517 | 2.98519 | 4.58478 | 3.61503 | |
| 2.68618 | | 2.73123 | | | | | | | | | | | | | | | | | |
| 0.01396 | 4.67425 | 5.39652 | 0.61958 | 0.77253 | 0.48576 | 0.95516 | | | | | 4.24695 | | | | | | | | | |
| 90 | 2.58033 | 4.29183 | 4.46313 | 3.88453 | 1.65618 | 3.97703 | 4.17248 | 3.73518 | 3.39799 | | 3.48999 | | | | 3.85527 | | 3.09665 | 3.27621 | 3.32886 | 4.68929 | 2.11039 | 191 |
| | 4.42225 | 2.77519 | | 3.46354 | 3.72494 | 3.29354 | 2.67741 | 2.69351 | | 2.90347 | 2.73739 | 3.18146 | 2.89806 | | | 2.97517 | 2.98519 | 4.58478 | 3.61503 | |
| 2.68618 | | 2.73123 | | | | | | | | | | | | | | | | | |
| 0.055 | 4.67425 | 3.11945 | 0.61958 | 0.77253 | 0.48576 | 0.95516 | | | | | 4.24695 | | | | | | | | | |
| 91 | 4.07624 | 5.26019 | 5.33257 | 5.01346 | 0.62169 | 4.94716 | 4.06569 | 8.33739 | 4.81709 | 1.99223 | 3.94039 | 5.19883 | 4.70569 | 4.76816 | 4.32157 | 4.28941 | 3.43378 | 4.17808 | 2.30184 | 192 |
| | 4.42225 | 2.77519 | | 3.46354 | 3.72494 | 3.29354 | 2.67741 | 2.69351 | | 2.90347 | 2.73739 | 3.18146 | 2.89806 | | | 2.97517 | 2.98519 | 4.58478 | 3.61503 | |
| 2.68618 | | 2.73123 | | | | | | | | | | | | | | | | | |
| 0.01454 | 4.63371 | 5.35617 | 0.61958 | 0.77253 | 0.56335 | 0.84229 | | | | | 4.24695 | | | | | | | | | |
| 92 | 2.73318 | 1.89661 | 3.66788 | 3.40488 | 3.10486 | 2.85818 | 4.00796 | 2.96672 | 3.05563 | 2.61693 | 3.29029 | 2.80307 | 3.35355 | 1.33992 | | 2.60736 | 2.84494 | 2.73895 | 5.05425 | 3.29421 | 193 |
| | 4.42225 | 2.77519 | | 3.46354 | 3.72494 | 3.29354 | 2.67741 | 2.69351 | | 2.90347 | 2.73739 | 3.18146 | 2.89806 | | | 2.97517 | 2.98519 | 4.58478 | 3.61503 | |
| 2.68618 | | 2.73123 | | | | | | | | | | | | | | | | | |
| 0.01454 | 4.63371 | 5.35617 | 0.61958 | 0.77253 | 0.56335 | 0.84229 | | | | | 4.24695 | | | | | | | | | |

FIG. 13N

| | | | | | | | | | | | | | | | | |
|---|---|---|---|---|---|---|---|---|---|---|---|---|---|---|---|---|
| 93 | 2.8759 | 3.0574 | | 5.1192 | 0.3874 | 5.3153 | 4.5829 | 4.5278 | 4.3282 | 5.1956 | | 4.7608 | 4.6267 | 3.0966 | 3.4336 | 3.9383 | 6.3680 | 5.3629 |
| | 5 | 9 | 4.72319 | 4.5785 | 8 | 1 | 5 | 7 | 9 | 1 | 4.3079 | 4.3544 | 5 | 8 | 4 | 3 | 6 | 5 | 194 |
| | 4.4222 | 2.7751 | | 3.4635 | 2.4051 | 3.7249 | 3.2935 | 2.6774 | 2.6935 | | 2.9034 | 2.7373 | 3.1814 | 2.8980 | 2.3788 | 2.7751 | 4.5847 | 3.6150 |
| 2.68618 | 5 | 9 | 2.73123 | 4 | 3 | 4 | 1 | | 5 | 4.2469 | 7 | 9 | 6 | 1 | 7 | 8 | 7 | 3 |
| | 4.6337 | 5.3561 | | 0.7725 | 0.4401 | 1.0327 | | | | | | | | | | | | |
| 0.01454 | 7 | 1 | 0.61958 | 5 | 1 | 3 | | | | | | | | | | | | |
| 94 | 2.9278 | 4.8257 | | 4.0860 | 5.0424 | 3.5525 | 5.1215 | 4.7184 | 4.2248 | 4.3888 | 5.2775 | 4.1083 | 4.3639 | 4.5044 | 0.3343 | 3.4751 | | 6.3447 |
| | 2 | 8 | 4.16141 | 2 | 4 | 7 | 3 | 1 | 9 | 7 | 1 | 2 | 4.4248 | 1 | 4 | | 3.4093 | 4 | 5.1564 | 195 |
| | 4.4222 | 2.7751 | | 3.4635 | 2.4051 | 3.7249 | 3.2935 | 2.6774 | 2.6935 | | 2.9034 | 2.7373 | 3.1814 | 2.8980 | 2.3788 | 2.7751 | 4.5847 | 3.6150 |
| 2.68618 | 5 | 9 | 2.73123 | 4 | 3 | 4 | 1 | | 5 | 4.2469 | 7 | 9 | 6 | 1 | 7 | 8 | 7 | 3 |
| | 4.6742 | 5.3965 | | 0.7725 | 0.4857 | | | | | | | | | | | | | |
| 0.01396 | 2 | 7 | 0.61958 | 5 | 6 | 0.9551 | | | | | | | | | | | | |
| 95 | 4.1264 | 5.6722 | | 4.7992 | 5.6306 | 4.3195 | 5.4766 | 4.9417 | | | 6.0862 | 5.0059 | 0.1381 | 5.2945 | 5.0321 | | 4.6308 | 5.0114 | 6.5149 | 5.7799 |
| | 7 | 4 | 4.81398 | 4 | 4 | | 8 | | 85.7383 | 94.9638 | 7 | 2 | 1 | 9 | | 94.3314 | 1 | 8 | 6 | 3 | 196 |
| | 4.4222 | 2.7751 | | 3.4635 | 2.4051 | 3.7249 | 3.2935 | 2.6774 | 2.6935 | | 2.9034 | 2.7373 | 3.1814 | 2.8980 | 2.3788 | 2.7751 | 4.5847 | 3.6150 |
| 2.68618 | 5 | 9 | 2.73123 | 4 | 3 | 4 | 1 | | 5 | 4.2469 | 7 | 9 | 6 | 1 | 7 | 8 | 7 | 3 |
| | 4.6742 | 5.3965 | | 0.7725 | 0.4857 | | | | | | | | | | | | | |
| 0.01396 | 2 | 7 | 0.61958 | 5 | 6 | 0.9551 | | | | | | | | | | | | |
| 96 | 4.1264 | 5.6722 | | 4.7992 | 5.6306 | 4.3195 | 5.4766 | 4.9417 | | | 6.0862 | 5.0059 | 0.1381 | 5.2945 | 5.0321 | | 4.6308 | 5.0114 | 6.5149 | 5.7799 |
| | 7 | 4 | 4.81398 | 4 | 4 | | 8 | | 85.7383 | 94.9638 | 7 | 2 | 1 | 9 | | 94.3314 | 1 | 8 | 6 | 3 | 197 |
| | 4.4222 | 2.7751 | | 3.4635 | 2.4051 | 3.7249 | 3.2935 | 2.6774 | 2.6935 | | 2.9034 | 2.7373 | 3.1814 | 2.8980 | 2.3788 | 2.7751 | 4.5847 | 3.6150 |
| 2.68618 | 5 | 9 | 2.73123 | 4 | 3 | 4 | 1 | | 5 | 4.2469 | 7 | 9 | 6 | 1 | 7 | 8 | 7 | 3 |
| | 4.6742 | 5.3965 | | 0.7725 | 0.4857 | | | | | | | | | | | | | |
| 0.01396 | 2 | 7 | 0.61958 | 5 | 6 | 0.9551 | | | | | | | | | | | | |
| 97 | 2.0921 | 4.7410 | | 3.9937 | 3.6157 | 3.9052 | 3.1950 | 3.0407 | 3.0630 | | | 84.0341 | 3.1118 | 2.6965 | 1.6370 | 2.8876 | 2.4556 | 5.3430 | 4.0572 |
| | 2 | 2 | 3.35204 | 2.7975 | 9 | 2 | 3 | 3 | 2 | 6 | 4 | | 7 | 1 | 5 | 4 | 6 | 7 | 2 | 1 | 198 |
| | 4.4222 | 2.7751 | | 3.4635 | 2.4051 | 3.7249 | 3.2935 | 2.6774 | 2.6935 | | 2.9034 | 2.7373 | 3.1814 | 2.8980 | 2.3788 | 2.7751 | 4.5847 | 3.6150 |
| 2.68618 | 5 | 9 | 2.73123 | 4 | 3 | 4 | 1 | | 5 | 4.2469 | 7 | 9 | 6 | 1 | 7 | 8 | 7 | 3 |
| | 4.6742 | 5.3965 | | 0.7725 | 0.4857 | | | | | | | | | | | | | |
| 0.01396 | 2 | 7 | 0.61958 | 5 | 6 | 0.9551 | | | | | | | | | | | | |
| 98 | 4.1778 | 5.8177 | | 4.1837 | 5.3994 | | 4.7529 | 5.0706 | 3.0099 | 4.4357 | 5.4654 | | 4.9241 | 3.9816 | 0.2467 | 4.4197 | 4.7684 | | 5.2222 |
| | 4 | 2 | 4.76375 | 7 | | 54.4129 | 8 | 7 | 2 | 6 | 8 | 44.4563 | 7 | 3 | 2 | 1 | 5 | 46.1802 | 7 | 199 |
| | 4.4222 | 2.7751 | | 3.4635 | 2.4051 | 3.7249 | 3.2935 | 2.6774 | 2.6935 | | 2.9034 | 2.7373 | 3.1814 | 2.8980 | 2.3788 | 2.7751 | 4.5847 | 3.6150 |
| 2.68618 | 5 | 9 | 2.73123 | 4 | 3 | 4 | 1 | | 5 | 4.2469 | 7 | 9 | 6 | 1 | 7 | 8 | 7 | 3 |
| | 4.6742 | 5.3965 | | 0.7725 | 0.4857 | | | | | | | | | | | | | |
| 0.01396 | 2 | 7 | 0.61958 | 5 | 6 | 0.9551 | | | | | | | | | | | | |
| 99 | 0.9933 | 4.4697 | | 3.7107 | 4.2127 | 3.4687 | 4.5602 | 3.4488 | 3.6516 | 3.2785 | 4.1649 | 3.8207 | 4.1495 | 3.9176 | 2.4305 | 2.2556 | 2.0734 | 6.6550 | 4.4612 |
| | 9 | 6 | 4.16455 | 2 | 4 | 6 | 7 | 2 | 3 | 4 | 7 | 6 | 3 | 7 | 6 | 3 | 1 | 1 | 5 | 4 | 200 |
| | 4.4222 | 2.7751 | | 3.4635 | 2.4051 | 3.7249 | 3.2935 | 2.6774 | 2.6935 | | 2.9034 | 2.7373 | 3.1814 | 2.8980 | 2.3788 | 2.7751 | 4.5847 | 3.6150 |
| 2.68618 | 5 | 9 | 2.73123 | 4 | 3 | 4 | 1 | | 5 | 4.2469 | 7 | 9 | 6 | 1 | 7 | 8 | 7 | 3 |
| | 4.6742 | 5.3965 | | 0.7725 | 0.4857 | | | | | | | | | | | | | |
| 0.01396 | 2 | 7 | 0.61958 | 5 | 6 | 0.9551 | | | | | | | | | | | | |

| | | | | | | | | | | | | | | | | |
|---|---|---|---|---|---|---|---|---|---|---|---|---|---|---|---|---|
| 107 | 1.5908 | 4.5603 | | 3.1430 | 3.9661 | 3.5726 | 4.1402 | 3.1057 | 3.1080 | | 3.9033 | | 2.1328 | 3.4182 | 3.4800 | 2.1986 | 2.8217 | 5.3737 | 4.1312 | 208 |
| | 4.4222 | 2.7751 | 3.6776 | 3.4635 | 2.4051 | 3.7249 | 3.2935 | 2.6774 | 2.6935 | | 3 | 3.5043 | 2 | 2 | 5 | 8 | 2 | 2.3732 | 4 | 8 | |
| 2.68618 | 4.6742 | 5.3965 | 2.73123 | 4 | 3 | 4 | 4 | 1 | 5 | 4.2469 | 2.9034 | 2.7373 | 3.1814 | 2.8980 | 2.3788 | 2.7751 | 2.9851 | 4.5847 | 3.6150 | |
| 0.01396 | 2 | 7 | 0.61958 | 0.7725 | 0.4857 | | | | | | 7 | 9 | 6 | 1 | 7 | 9 | 8 | 7 | 3 | |
| | 3.1532 | 5.4752 | | 2.8578 | 4.9135 | 3.8481 | 3.1846 | 4.3018 | 1.8790 | 3.4090 | 4.5289 | 3.1166 | 4.2069 | 1.8406 | 1.3681 | 3.1212 | 3.3372 | 3.9245 | 5.7724 | 4.5230 | 209 |
| 108 | 4 | 9 | 3.51777 | 5 | 7 | 4 | 7 | 8 | 2 | 9 | 3 | 4 | 4 | 4 | 6 | 8 | 1 | 6 | 5 | |
| | 4.4222 | 2.7751 | | 3.4635 | 2.4051 | 3.7249 | 3.2935 | 2.6774 | 2.6935 | | 2.9034 | 2.7373 | 3.1814 | 2.8980 | 2.3788 | 2.7751 | 2.9851 | 4.5847 | 3.6150 | |
| 2.68618 | 5 | 9 | 2.73123 | 4 | 3 | 4 | 4 | 1 | 5 | 4.2469 | 7 | 9 | 6 | 1 | 7 | 9 | 8 | 7 | 3 | |
| 0.01396 | 4.6742 | 5.3965 | 0.61958 | 0.7725 | 0.4857 | | | | | | | | | | | | | | | |
| | 4.4718 | 5.6450 | | 5.2826 | 0.2751 | 4.8423 | 4.5023 | 3.9909 | 5.1960 | | 4.6222 | 5.0318 | 5.3209 | 5.1565 | 5.1170 | 4.6548 | 4.7915 | | | 4.6191 | 2.9306 | 210 |
| 109 | 6 | 1 | 5.37109 | 4 | 9 | 6 | 4 | 7 | 2 | 2.3192 | 2 | 7 | 6 | 8 | 3 | 3 | 8 | 4.0286 | 8 | 5 | |
| | 4.4222 | 2.7751 | | 3.4635 | 2.4051 | 3.7249 | 3.2935 | 2.6774 | 2.6935 | | 2.9034 | 2.7373 | 3.1814 | 2.8980 | 2.3788 | 2.7751 | 2.9851 | 4.5847 | 3.6150 | |
| 2.68618 | 5 | 9 | 2.73123 | 4 | 3 | 4 | 4 | 1 | 5 | 4.2469 | 7 | 9 | 6 | 1 | 7 | 9 | 8 | 7 | 3 | |
| 0.01396 | 4.6742 | 5.3965 | 0.61958 | 0.7725 | 0.4857 | | | | | | | | | | | | | | | |
| | 2.8302 | 4.5690 | | 3.1285 | 3.7192 | 1.7347 | 4.0397 | 2.3130 | 2.9551 | 2.2052 | 3.6728 | 3.5257 | 4.1721 | 3.3494 | 2.3293 | | | | 3.0688 | 2.8075 | 5.1625 | 3.9290 | 211 |
| 110 | 2 | 9 | 3.69862 | 9 | 8 | 1 | 5 | 5 | 1 | 3 | 5 | 1 | 2 | 2 | | 2.3.0451 | | 1 | 1 | 2 | 2 | |
| | 4.4222 | 2.7752 | | 3.4635 | 2.4051 | 3.7249 | 3.2935 | 2.6774 | 2.6932 | 4.2463 | | 2.7374 | 3.1814 | 2.8980 | | 2.7752 | 2.9852 | | | 3.6150 | |
| 2.68618 | 8 | 3 | 2.73126 | 7 | 6 | 8 | 7 | 4 | 3 | 52.9035 | | 3 | 9 | | 42.3789 | 3 | | 14.5848 | 6 | |
| 0.3513 | 2.1560 | 1.7123 | 0.24832 | 1.5146 | 0.4857 | | | | | | | | | | | | | | | |
| | 2.7930 | 5.3082 | | 2.2613 | 4.6425 | 3.4761 | 3.0560 | 4.1296 | 2.3553 | 3.6059 | 4.3587 | 2.3344 | 3.9133 | 2.6495 | 2.6778 | 2.7432 | 3.0302 | 3.6945 | 5.7379 | 4.3183 | 213 |
| 111 | 5 | 3 | 1.7105 | 8 | 6 | 4 | 1 | 9 | 9 | 5 | 2 | 8 | 5 | 4 | 1 | 7 | 9 | 2 | 7 | 2 | |
| | 4.4222 | 2.7751 | | 3.4635 | 2.4051 | 3.7249 | 3.2935 | 2.6774 | 2.6935 | | 2.9034 | 2.7373 | 3.1814 | 2.8980 | 2.3788 | 2.7751 | 2.9851 | 4.5847 | 3.6150 | |
| 2.68618 | 5 | 9 | 2.73123 | 4 | 3 | 4 | 4 | 1 | 5 | 4.2469 | 7 | 9 | 6 | 1 | 7 | 9 | 8 | 7 | 3 | |
| 0.01697 | 4.4807 | 5.2031 | 0.61958 | 0.7725 | 0.5289 | 0.8896 | | | | | | | | | | | | | | |
| | 2.7359 | 3.5309 | | 1.7215 | 4.5626 | 3.5051 | 3.3172 | 4.0420 | 2.1930 | 3.5262 | 4.2692 | 2.7238 | 3.9015 | 2.2707 | 2.7828 | 2.7011 | 2.9671 | 3.6121 | 5.6615 | 4.2566 | 214 |
| 112 | 4 | 2 | 2.75373 | 6 | 5 | 7 | 2 | 4 | 4 | 9 | 6 | 9 | 4 | 9 | 9 | 2 | 4 | 1 | 8 | 9 | |
| | 4.4222 | 2.7751 | | 3.4635 | 2.4051 | 3.7249 | 3.2935 | 2.6774 | 2.6935 | | 2.9034 | 2.7373 | 3.1814 | 2.8980 | 2.3788 | 2.7751 | 2.9851 | 4.5847 | 3.6150 | |
| 2.68618 | 5 | 9 | 2.73123 | 4 | 3 | 4 | 4 | 1 | 5 | 4.2469 | 7 | 9 | 6 | 1 | 7 | 9 | 8 | 7 | 3 | |
| 0.01527 | 4.5853 | 5.3076 | 0.61958 | 0.7725 | 0.3974 | 1.1147 | | | | | | | | | | | | | | |
| | 2.8333 | 5.3040 | | 2.3189 | 4.6618 | 3.5907 | | 4.1280 | 1.5387 | 3.3785 | 4.3484 | 4.5621 | 3.1242 | | | 2.4193 | 2.7975 | 3.0572 | 3.7030 | 5.7125 | 4.3342 | 215 |
| 113 | 5 | 1 | 3.08877 | 4 | 7 | 9 | 3.7463 | 6 | 6 | 7 | 4 | 8 | | 42.3567 | | 4 | 2 | 4 | 9 | 2 | 4 | |
| | 4.4222 | 2.7751 | | 3.4635 | 2.4051 | 3.7249 | 3.2935 | 2.6774 | 2.6935 | | 2.9034 | 2.7373 | 3.1814 | 2.8980 | 2.3788 | 2.7751 | 2.9851 | 4.5847 | 3.6150 | |
| 2.68618 | 5 | 9 | 2.73123 | 4 | 3 | 4 | 4 | 1 | 5 | 4.2469 | 7 | 9 | 6 | 1 | 7 | 9 | 8 | 7 | 3 | |
| 0.01396 | 4.6742 | 5.3965 | 0.61958 | 0.7725 | 0.4857 | | | | | | | | | | | | | | | |

| | | | | | | | | | | | | | | |
|---|---|---|---|---|---|---|---|---|---|---|---|---|---|---|
| 121 | 2.4884 2 | | 3.2140 3 | 3.5214 5 | 3.2754 8 | 4.0425 5 | 2.6152 | 3.1527 | 3.1944 3 | 2.6529 6 | 3.9476 4 | 3.4361 1 | 3.4660 6 | 2.4793 | 2.2981 | 3.7706 1 | 223 |
| | 4.4222 5 | 3.7851 | | 3.4635 4 | 2.4051 3 | 3.7249 1 | 3.2935 4 | 2.6774 | 2.6935 | 2.9034 7 | 2.7373 9 | 3.1814 6 | 2.8980 1 | 2.3788 7 | 2.7751 9 | 2.9851 8 | 72.7204 | 34.9898 | 4.5847 7 | 3.6150 3 | |
| 2.68618 | | 2.73123 | | | | | | | 54.2469 | | | | | | | | | |
| 0.01396 | 4.6742 2 | 5.3965 7 | 0.61958 | 0.7725 5 | 0.4857 | 60.9551 | | | | | | | | | |
| 122 | 2.7492 3 | 4.9841 3 | 3.14811 | 2.5989 7 | 4.0158 8 | 2.4595 2 | 3.8063 5 | 3.7126 9 | 2.5966 5 | 3.3002 3 | 3.9077 7 | 2.7108 7 | 2.3375 4 | 2.8816 9 | 3.0636 6 | 1.9411 1 | 2.7716 | 3.2408 6 | 5.5265 1 | 4.1824 1 | 224 |
| 2.68555 | 4.4228 5 | 2.7757 | 2.73147 | 3.4635 6 | 2.4055 3 | 3.2940 5 | 2.6779 9 | 2.6930 6 | 4.2472 8 | 2.9040 2 | 2.7357 7 | 3.1812 1 | 2.8985 4 | 2.3789 6 | 2.7751 7 | 2.9847 5 | 4.5853 8 | 3.6143 2 | |
| 1.09946 | 1.0282 8 | 1.1733 5 | 1.58671 | 0.2289 1 | 0.4857 | 60.9551 | | | | | | | | | |
| 123 | 2.3879 1 | 4.6951 | 3.15265 | 2.6077 5 | 3.9872 8 | 2.0956 2 | 3.7552 5 | 3.2666 | 3.0242 1 | 2.8579 | 3.6928 9 | 2.8339 6 | 2.7530 1 | 3.2205 6 | 2.8776 8 | 2.7516 8 | 5.2988 | 23.9953 | 236 |
| 2.68618 | 4.4222 5 | 2.7751 9 | 2.73123 | 3.4635 4 | 2.4051 3 | 3.7249 4 | 3.2935 4 | 2.6774 1 | 2.6935 | 2.9034 7 | 2.7373 9 | 3.1814 6 | 2.8980 1 | 2.3788 7 | 2.7751 9 | 2.9851 8 | 4.5847 7 | 3.6150 3 | |
| 0.02015 | 4.3106 7 | 5.0330 2 | 0.61958 | 0.7725 5 | 0.5289 | 50.8897 | | | | | | | | | |
| 124 | 2.3613 5 | 4.2462 6 | 3.9502 | 3.3723 7 | 3.3272 5 | 3.5597 2 | 4.0537 8 | 2.4949 5 | 3.2838 6 | 2.2079 2 | 3.3600 3 | 3.6599 6 | 3.4361 6 | 3.4066 6 | 2.5324 4 | 2.1865 9 | 2.9338 2 | 2.2054 7 | 4.8525 3 | 3.6493 5 | 237 |
| 2.68618 | 4.4222 5 | 2.7751 9 | 2.73123 | 3.4635 4 | 2.4051 3 | 3.7249 4 | 3.2935 4 | 2.6774 1 | 2.6935 | 2.9034 7 | 2.7373 9 | 3.1814 6 | 2.8980 1 | 2.3788 7 | 2.7751 9 | 2.9851 8 | 4.5847 7 | 3.6150 3 | |
| 0.01621 | 4.5257 | 55.2481 | 0.61958 | 0.7725 5 | 0.7333 2 | 0.6545 | | | | | | | | | |
| 125 | 2.7021 3 | 3.8534 1 | 3.42096 | 2.8573 9 | 3.2055 5 | 3.2789 2 | 3.3196 8 | 2.9304 2 | 2.8262 1 | 2.5203 3 | 3.6350 4 | 3.3053 3 | 2.5329 2 | 2.9178 3 | 3.2201 2 | 0.0823 2 | 2.8106 6 | 2.7255 4 | 5.1040 2 | 3.8477 1 | 238 |
| 2.68618 | 4.4222 5 | 2.7751 9 | 2.73123 | 3.4635 4 | 2.4051 3 | 3.7249 4 | 3.2935 4 | 2.6774 1 | 2.6935 | 2.9034 7 | 2.7373 9 | 3.1814 6 | 2.8980 1 | 2.3788 7 | 2.7751 9 | 2.9851 8 | 4.5847 7 | 3.6150 3 | |
| 0.01621 | 4.5257 | 55.2481 | 0.61958 | 0.7725 5 | 0.6065 5 | 0.7879 7 | | | | | | | | | |
| 126 | 2.6935 6 | 5.0072 9 | 2.80177 | 2.5131 5 | 3.513 1 | 3.2494 3 | 4.7312 2 | 3.7034 6 | 2.3149 | 93.0716 | 4.0706 8 | 3.0425 8 | 3.3880 | 2.5934 9 | 1.8722 8 | 2.9035 9 | 3.3535 8 | 5.4920 7 | 3.2236 4 | 239 |
| 2.68618 | 4.4222 5 | 2.7751 9 | 2.73123 | 3.4635 4 | 2.4051 3 | 3.7249 4 | 3.2935 4 | 2.6774 1 | 2.6935 | 2.9034 7 | 2.7373 9 | 3.1814 6 | 2.8980 1 | 2.3788 7 | 2.7751 9 | 2.9851 8 | 22.8634 | 4.5847 7 | 3.6150 3 | |
| 0.01548 | 4.5720 5 | 5.2943 9 | 0.61958 | 0.7725 5 | 0.6310 3 | 0.7593 8 | | | | | | | | | |
| 127 | 2.8074 6 | 4.8933 2 | 3.13843 | 2.8718 4 | 4.5590 3 | 2.0944 2 | 3.1842 3 | 4.0543 | 3.6569 | 64.4856 | 3.3117 3 | 1.1837 3 | 3.3581 2 | 3.4305 3 | 2.7838 | 3.178 | 3.6168 1 | 5.8381 7 | 4.5099 1 | 240 |
| 2.68618 | 4.4222 5 | 2.7751 9 | 2.73123 | 3.4635 4 | 2.4051 3 | 3.7249 4 | 3.2935 4 | 2.6774 1 | 2.6935 | 2.9034 7 | 2.7373 9 | 3.1814 6 | 2.8980 1 | 2.3788 7 | 2.7751 9 | 2.9851 8 | 4.5847 7 | 3.6150 3 | |
| 0.01529 | 4.5839 | 65.3063 | 0.61958 | 0.7725 5 | 0.6476 4 | 0.7408 2 | 13.0212 | | 54.2469 | | | | | | |

FIG. 13S

| | | | | | | | | | | | | | | | | | | | | | |
|---|---|---|---|---|---|---|---|---|---|---|---|---|---|---|---|---|---|---|---|---|---|
| 128 | | 2.731 81 | 5.155 05 | 3.01283 | 2.458 28 | 4.062 35 | 3.406 09 | 3.706 04 | 3.931 41 | 1.951 4 | 3.446 12 | 4.206 83 | 2.741 94 | 3.512 75 | 2.666 82 | 2.692 11 | 1.874 67 | 2.545 7 | 3.529 96 | 5.607 74 | 4.220 72 | 241 |
| | 2.68618 | | 4.422 25 | 2.775 19 | 2.73123 | 3.463 54 | 2.405 13 | 3.293 94 | 2.677 41 | 2.693 55 | 4.246 9 | 2.903 47 | 2.737 39 | 3.181 46 | 2.898 01 | 2.378 87 | 2.775 19 | 2.985 18 | 4.584 77 | 3.615 03 | |
| | 0.01529 | | 4.583 96 | 5.306 3 | | 0.647 64 | 0.740 82 | | | | | | | | | | | | | | | |
| 129 | | 2.563 27 | 4.740 2 | 3.25945 | 2.700 3 | 3.935 78 | 3.326 23 | 3.289 02 | 3.204 41 | 2.599 1 | 2.722 56 | 3.073 59 | 3.191 04 | 2.340 83 | 3.021 25 | 3.115 13 | 1.999 35 | 2.956 79 | 3.048 59 | 5.279 88 | 3.986 53 | 242 |
| | 2.68618 | | 4.422 25 | 2.775 19 | 2.73123 | 3.463 54 | 2.405 13 | 3.293 94 | 2.677 41 | 2.693 55 | 4.246 9 | 2.903 47 | 2.737 39 | 3.181 46 | 2.898 01 | 2.378 87 | 2.775 19 | 2.985 18 | 4.584 77 | 3.615 03 | |
| | 0.03107 | | 4.583 96 | 3.893 31 | | 0.530 01 | 0.888 19 | | | | | | | | | | | | | | | |
| 130 | | 2.574 04 | 5.053 29 | 2.94423 | 2.509 55 | 3.958 28 | 3.539 15 | 3.735 5 | 3.767 76 | 2.345 25 | 3.124 86 | 4.113 9 | 3.042 82 | 3.098 2 | 2.861 5 | 2.239 24 | 1.882 46 | 2.790 34 | 3.405 84 | 5.530 84 | 3.692 35 | 243 |
| | 2.68618 | | 4.422 47 | 2.775 42 | 2.73145 | 3.463 62 | 2.405 35 | 3.293 68 | 2.677 76 | 2.693 7 | 4.247 12 | 2.903 69 | 2.737 31 | 3.181 68 | 2.898 01 | 2.378 37 | 2.775 23 | 2.984 78 | 4.584 99 | 3.614 81 | |
| | 0.6096 | | 1.128 65 | 2.017 7 | 0.89297 | 0.526 68 | 0.605 85 | 0.788 8 | | | | | | | | | | | | | | |
| 131 | | 2.289 3 | 4.715 33 | 3.23485 | 2.682 46 | 3.987 4 | 3.525 34 | 3.813 73 | 3.382 08 | 2.657 15 | 3.028 44 | 2.927 18 | 3.163 49 | 2.717 71 | 3.004 05 | 2.766 05 | 1.880 54 | 2.752 1 | 3.083 03 | 5.314 71 | 4.018 2 | 250 |
| | 2.68618 | | 4.422 25 | 2.775 19 | 2.73123 | 3.463 54 | 2.405 13 | 3.293 94 | 2.677 41 | 2.693 55 | 4.246 9 | 2.903 47 | 2.737 39 | 3.181 46 | 2.898 01 | 2.378 87 | 2.775 19 | 2.985 18 | 4.584 77 | 3.615 03 | |
| | 0.01711 | | 4.472 39 | 5.194 73 | | 0.750 15 | 0.639 22 | | | | | | | | | | | | | | | |
| 132 | | 2.463 86 | 4.580 28 | 3.50115 | 3.006 3 | 4.349 44 | 2.620 68 | 4.122 58 | 3.767 32 | 3.000 37 | 3.407 59 | 4.221 98 | 3.360 27 | 2.174 89 | 3.321 95 | 3.408 59 | 1.587 82 | 2.189 24 | 2.944 59 | 5.657 12 | 4.385 49 | 251 |
| | 2.68618 | | 4.422 25 | 2.775 19 | 2.73123 | 3.463 54 | 2.405 13 | 3.293 94 | 2.677 41 | 2.693 55 | 4.246 9 | 2.903 47 | 2.737 39 | 3.181 46 | 2.898 01 | 2.378 87 | 2.775 19 | 2.985 18 | 4.584 77 | 3.615 03 | |
| | 0.05402 | | 4.491 91 | 3.184 74 | 0.61958 | 0.772 55 | 0.777 9 | 0.615 02 | | | | | | | | | | | | | | |
| 133 | | 2.682 96 | 4.861 75 | 2.82059 | 2.539 48 | 4.095 36 | 3.518 47 | 3.725 02 | 3.508 61 | 2.530 46 | 3.118 77 | 3.100 79 | 3.056 1 | 3.408 93 | 2.880 07 | 2.492 94 | 1.985 79 | 2.584 81 | 3.052 14 | 5.369 81 | 3.420 65 | 252 |
| | 2.68618 | | 4.422 25 | 2.775 19 | 2.73123 | 3.463 54 | 2.405 13 | 3.293 94 | 2.677 41 | 2.693 55 | 4.246 9 | 2.903 47 | 2.737 39 | 3.181 46 | 2.898 01 | 2.378 87 | 2.775 19 | 2.985 18 | 4.584 77 | 3.615 03 | |
| | 0.16485 | | 4.455 3 | 1.963 5 | 0.61958 | 0.772 55 | 0.699 15 | 0.687 18 | | | | | | | | | | | | | | |
| 134 | | 2.370 14 | 3.959 79 | 3.52696 | 2.962 6 | 3.528 38 | 3.611 97 | 3.296 35 | 2.889 78 | 2.915 46 | 2.603 68 | 3.494 66 | 4.003 98 | 3.364 1 | 3.219 8 | 3.269 87 | 1.994 62 | 2.706 34 | 2.149 74 | 4.971 32 | 3.174 49 | 253 |
| | 2.68618 | | 4.422 25 | 2.775 19 | 2.73123 | 3.463 54 | 2.405 13 | 3.293 94 | 2.677 41 | 2.693 55 | 4.246 9 | 2.903 47 | 2.737 39 | 3.181 46 | 2.898 01 | 2.378 87 | 2.775 19 | 2.985 18 | 4.584 77 | 3.615 03 | |
| | 0.01905 | | 4.366 06 | 5.088 41 | 0.61958 | 0.772 55 | 0.833 29 | 0.570 26 | | | | | | | | | | | | | | |

FIG. 13T

| | | | | | | | | | | | | | | | | | | | |
|---|---|---|---|---|---|---|---|---|---|---|---|---|---|---|---|---|---|---|---|
| 135 | 2.514 99 | 5.082 19 | 2.90826 | | | | | | | | | | 2.946 89 | 1.896 53 | 2.824 07 | 3.471 67 | 5.573 43 | 4.189 54 | 254 |
| | 4.422 25 | 2.775 19 | 2.73123 | 3.463 54 | 2.405 13 | 3.724 94 | 3.293 54 | 2.677 41 | 2.693 55 | 4.246 9 | 2.903 47 | 2.737 39 | 3.181 46 | 2.898 01 | 2.378 87 | 2.775 19 | 2.985 18 | 4.584 77 | 3.615 03 | |
| 2.68618 | 4.401 55 | 5.123 9 | 0.61958 | 0.772 55 | 0.811 34 | 0.587 46 | | | | | | | | | | | | | |
| 0.01838 | 2.560 12 | 4.533 71 | 3.37294 | 2.812 02 | 3.718 83 | 3.585 44 | 3.848 12 | 2.949 99 | 2.776 28 | 3.651 53 | 3.261 87 | 2.934 6 | 3.172 79 | 3.104 33 | 2.816 6 | 1.945 41 | 2.721 37 | 2.193 22 | 5.118 21 | 3.857 46 | 255 |
| 136 | 4.422 25 | 2.775 19 | 2.73123 | 3.463 54 | 2.405 13 | 3.724 94 | 3.293 54 | 2.677 41 | 2.693 55 | 4.246 9 | 2.903 47 | 2.737 39 | 3.181 46 | 2.898 01 | 2.378 87 | 2.775 19 | 2.985 18 | 4.584 77 | 3.615 03 | |
| 2.68618 | 4.430 1 | 5.152 44 | 0.61958 | 0.772 55 | 0.783 43 | 0.610 34 | | | | | | | | | | | | | |
| 0.01786 | 2.582 67 | 4.544 03 | 3.09259 | 2.538 83 | 4.197 27 | 2.022 81 | 3.734 68 | 3.620 03 | 2.469 22 | 3.211 16 | 3.721 29 | 2.934 35 | 3.611 46 | 2.878 89 | 2.421 99 | 2.255 84 | 2.924 23 | 3.277 55 | 5.440 28 | 4.102 32 | 256 |
| 137 | 4.422 25 | 2.775 19 | 2.73123 | 3.463 54 | 2.405 13 | 3.724 94 | 3.293 54 | 2.677 41 | 2.693 55 | 4.246 9 | 2.903 47 | 2.737 39 | 3.181 46 | 2.898 01 | 2.378 87 | 2.775 19 | 2.985 18 | 4.584 77 | 3.615 03 | |
| 2.68618 | 4.456 74 | 5.179 09 | 0.61958 | 0.772 55 | 0.385 64 | 1.139 47 | | | | | | | | | | | | | |
| 0.01738 | 2.758 95 | 5.111 02 | 3.07113 | 2.519 7 | 4.413 96 | 2.489 14 | 3.750 09 | 3.859 55 | 2.418 84 | 3.402 82 | 4.180 57 | 2.945 3 | 3.947 44 | 2.599 47 | 2.459 69 | 1.783 6 | 2.816 68 | 3.025 62 | 5.587 48 | 4.219 11 | 257 |
| 138 | 4.422 25 | 2.775 19 | 2.73123 | 3.463 54 | 2.405 13 | 3.724 94 | 3.293 54 | 2.677 41 | 2.693 55 | 4.246 9 | 2.903 47 | 2.737 39 | 3.181 46 | 2.898 01 | 2.378 87 | 2.775 19 | 2.985 18 | 4.584 77 | 3.615 03 | |
| 2.68618 | 4.643 02 | 5.365 37 | 0.61958 | 0.772 55 | 0.546 43 | 0.865 16 | | | | | | | | | | | | | |
| 0.01441 | 2.616 03 | 5.246 5 | 2.72309 | 2.448 68 | 4.581 66 | 2.986 3 | 3.392 99 | 4.060 31 | 1.894 74 | 3.549 08 | 4.294 98 | 2.745 87 | 2.742 94 | 2.827 72 | 2.962 65 | 2.023 21 | 2.995 83 | 3.632 92 | 5.688 71 | 4.282 9 | 258 |
| 139 | 4.422 25 | 2.775 19 | 2.73123 | 3.463 54 | 2.405 13 | 3.724 94 | 3.293 54 | 2.677 41 | 2.693 55 | 4.246 9 | 2.903 47 | 2.737 39 | 3.181 46 | 2.898 01 | 2.378 87 | 2.775 19 | 2.985 18 | 4.584 77 | 3.615 03 | |
| 2.68618 | 4.643 02 | 2.108 31 | 0.61958 | 0.772 55 | 0.546 43 | 0.865 16 | | | | | | | | | | | | | |
| 0.1405 | 2.701 33 | 4.882 76 | 3.15539 | 2.641 49 | 4.297 7 | 1.729 68 | 3.831 81 | 3.720 54 | 2.605 73 | 3.312 82 | 4.118 08 | 2.782 27 | 3.947 54 | 2.981 61 | 2.327 09 | 2.444 49 | 2.794 31 | 2.950 96 | 5.535 29 | 4.208 55 | 259 |
| 140 | 4.422 25 | 2.775 19 | 2.73123 | 3.463 54 | 2.405 13 | 3.724 94 | 3.293 54 | 2.677 41 | 2.693 55 | 4.246 9 | 2.903 47 | 2.737 39 | 3.181 46 | 2.898 01 | 2.378 87 | 2.775 19 | 2.985 18 | 4.584 77 | 3.615 03 | |
| 2.68618 | 4.518 85 | 5.241 2 | 0.61958 | 0.772 55 | 0.424 59 | 1.061 42 | | | | | | | | | | | | | |
| 0.01633 | 2.664 47 | 4.693 2 | 3.53378 | 3.243 1 | 4.848 43 | 1.279 15 | 4.463 37 | 4.311 65 | 3.391 48 | 3.927 62 | 4.716 08 | 2.860 27 | 4.077 19 | 3.671 24 | 3.784 75 | 1.380 78 | 2.637 74 | 3.714 32 | 6.119 37 | 4.856 44 | 260 |
| 141 | 4.422 25 | 2.775 19 | 2.73123 | 3.463 54 | 2.405 13 | 3.724 94 | 3.293 54 | 2.677 41 | 2.693 55 | 4.246 9 | 2.903 47 | 2.737 39 | 3.181 46 | 2.898 01 | 2.378 87 | 2.775 19 | 2.985 18 | 4.584 77 | 3.615 03 | |
| 0.01441 | 4.643 02 | 5.365 37 | 0.61958 | 0.772 55 | 0.500 87 | 0.931 41 | | | | | | | | | | | | | |

FIG. 13U

| | | | | | | | | | | | | | | |
|---|---|---|---|---|---|---|---|---|---|---|---|---|---|---|
| 142 | 2.4795 5 | 1.0937 3 | | 3.6474 9 | 3.7926 8 | 2.9692 1 | 4.3700 1 | 3.1458 2 | 3.5471 6 | 2.7315 5 | 3.7948 9 | 3.8013 3 | 4.1630 3 | 3.8143 |
| | | | | | | | | | | | | | | 2.5922 7 | 3.0411 2 | 2.8730 2 | 5.2673 | 93.6347 | 261 |
| | | 2.7752 5 | 4.14379 | | 2.4050 | 3.2935 9 | 2.6774 | | | 4.2469 | 2.7374 5 | 3.1815 2 | 2.8980 6 | 2.3789 2 | 2.7750 6 | 2.9851 2 | 4.5848 2 | 3.6150 8 | |
| 2.68623 | 4.4223 5 | | 2.73128 | 3.4632 | | 2 | 3.725 | | | 62.6936 | | 52.9033 | | 53.7852 | | | | | |
| 0.49409 | 1.64451.6257 | | 1.8255 0.4654 | | | | | | | | | | | | | | | | |
| | | 3 | 0.1757 | 4 | 90.9884 | | | | | | | | | | | | | | |
| 143 | 4.3913 1 | 1.8023 | | 3.2269 1 | 3.7494 6 | 3.1014 1 | 4.1370 8 | 2.9829 9 | 3.1868 2 | 2.7194 6 | 3.7115 7 | 2.9631 2 | 4.0634 5 | 3.4840 5 | 3.5084 1 | 2.8779 7 | 1.4677 6 | 5.2051 8 | 3.9819 6 | 263 |
| | | | 3.72012 | | | | | | | | | | | 52.9621 | | | | | |
| 2.68618 | 4.4222 5 | 2.7751 9 | | 3.4635 4 | 2.4051 3 | 3.7249 4 | 2.6774 4 | 2.9352 4 | 2.6774 4 | | 2.9034 1 | 2.7373 7 | 3.1814 6 | 2.8980 1 | 2.3788 7 | 2.7751 9 | 2.9851 8 | 4.5847 7 | 3.6150 3 | |
| 0.13624 | 4.4647 8 | 2.1553 5 | | 0.7725 5 | 0.8112 | 0.5875 | | | | 54.2469 | | | | | | | | | |
| | | | 0.61958 | | | | | | | | | | | | | | | | |
| 144 | 2.8238 3 | 4.9081 | | 2.7793 6 | 4.2893 8 | 3.5863 6 | 3.7918 9 | 3.6799 2 | 3.4093 2 | 3.2594 8 | 3.6204 6 | 3.2230 7 | | 2.9527 9 | 1.2465 1 | 2.5363 5 | 3.0697 5 | 3.3567 7 | 5.4556 1 | 4.1948 9 | 264 |
| | | | 3.36486 | | | | | | | 33.6239 | | | | | | | |
| 2.68618 | 4.4222 5 | 2.7751 9 | | 3.4635 4 | 2.4051 3 | 3.7249 4 | 2.6774 4 | 2.9352 4 | 2.6774 1 | | 2.9034 7 | 2.7373 9 | 3.1814 6 | 2.8980 1 | 2.3788 7 | 2.7751 9 | 2.9851 8 | 4.5847 7 | 3.6150 3 | |
| | 4.3479 4 | 5.0702 | | 0.7725 5 | 0.81171 | 0.5828 4 | | | | 54.2469 | | | | | | | | | |
| 0.0194 | | 9 | 0.61958 | | | | | | | | | | | | | | | | |
| 145 | 2.0939 6 | 4.4659 8 | | 2.8677 7 | 3.6324 4 | 3.4178 6 | 3.2901 6 | 3.0006 9 | 2.8259 2 | 2.6996 4 | 2.1910 5 | 3.3002 7 | | 3.0157 3 | 3.2049 9 | 2.4481 1 | 2.8982 7 | 2.5743 7 | 3.8018 1 | | 265 |
| | | | 3.4255 | | | | | | | | 93.9911 | | | | | 5.051 | |
| 2.68596 | 4.4222 8 | 2.7752 5 | | 3.4631 9 | 2.4051 6 | 3.7249 8 | 2.6774 4 | 2.9352 4 | 2.6774 1 | | 2.7374 | 2.8980 | | 2.8980 4 | | 2.7751 4 | 2.9852 | | 3.6150 6 | |
| 0.09834 | 2.4339 4 | | 0.65878 | 0.72870.4129 9 3 | | 1.0838 7 | | | | 32.9035 | | 33.1815 | | 42.3789 | | | 24.5848 | | |
| 146 | 2.7626 7 | 5.2137 7 | | 3.0178 4 | 2.4726 4 | 4.5574 | 2.6930 7 | 3.7232 5 | 4.0261 8 | 1.8086 1 | 4.2740 5 | 2.6459 8 | 3.3730 5 | 2.8279 7 | 2.5379 9 | 2.0474 2 | 2.9252 3 | 3.6078 6 | 6.6627 4 | 4.2722 1 | 268 |
| | | | | | | | | | 3.521 | | | | | | | | | |
| 2.68618 | 4.4222 5 | 2.7751 9 | | 3.4635 4 | 2.4051 3 | 3.7249 4 | 2.6774 4 | 2.9352 4 | 2.6774 1 | | 2.9034 7 | 2.7373 9 | 3.1814 6 | 2.8980 1 | 2.3788 7 | 2.7751 9 | 2.9851 8 | 4.5847 7 | 3.6150 3 | |
| 0.01484 | 4.6138 6 | 5.3362 1 | | 0.7725 5 | 0.5367 3 | 0.8786 5 | | | | 54.2469 | | | | | | | | | |
| | | | 0.61958 | | | | | | | | | | | | | | | | |
| 147 | 2.7540 4 | 2.2193 4 | | 3.6685 9 | 1.6935 | 4.1565 2 | 2.6615 3 | 3.5394 | | 22.1496 | 3.3283 8 | 3.8571 4 | 4.2301 5 | 3.7534 9 | 3.4210 2 | 2.5678 6 | 2.7129 7 | 2.1851 7 | 4.8091 9 | 2.9036 | 269 |
| | | | 4.25596 | | 93.8609 | | | | | | | | | | | | | | |
| 2.68618 | 4.4222 5 | 2.7751 9 | | 3.4635 4 | 2.4051 3 | 3.7249 4 | 2.6774 4 | 2.9352 4 | 2.6774 1 | | 2.9034 7 | 2.7373 9 | 3.1814 6 | 2.8980 1 | 2.3788 7 | 2.7751 9 | 2.9851 8 | 4.5847 7 | 3.6150 3 | |
| 0.01454 | 4.6340 8 | 5.3564 3 | | 0.7725 5 | 0.4404 5 | 1.0321 6 | | | | 54.2469 | | | | | | | | | |
| | | | 0.61958 | | | | | | | | | | | | | | | | |
| 148 | 4.8145 5 | 2.2138 | | 3.0779 4 | 4.8673 5 | 1.1492 9 | 4.3893 5 | 4.3311 2 | 3.3287 4 | 3.9345 1 | 4.7272 6 | 3.4512 4 | 4.1014 6 | 3.5829 5 | 3.7659 9 | 1.6382 3 | 3.1806 9 | 3.7644 3 | 6.1280 4 | 4.8279 | 270 |
| | | | 2.92333 | | | | | | | | | | | | | | | | |
| 2.68618 | 4.4222 5 | 2.7751 9 | | 3.4635 4 | 2.4051 3 | 3.7249 4 | 2.6774 4 | 2.9352 4 | 2.6774 1 | | 2.9034 7 | 2.7373 9 | 3.1814 6 | 2.8980 1 | 2.3788 7 | 2.7751 9 | 2.9851 8 | 4.5847 7 | 3.6150 3 | |
| 0.01396 | 4.6742 2 | 5.3965 7 | | 0.7725 5 | 0.4857 | 60.9551 | | | | | | | | | | | | | |
| | | | 0.61958 | | | | | | | | | | | | | | | | |

FIG. 13V

| | | | | | | | | | | | | | |
|---|---|---|---|---|---|---|---|---|---|---|---|---|---|
| 149 | 2.24284.6328 6 9 | | | 2.64182.5608 1 7 | 3.67573.74203.0489 5 9 | | 2.13563.7772 2 7 | 2.74783.75323.1597 8 9 | | 2.31422.98722.8464 3 7 | 75.1925 9 | 3.9276 | 271- |
| 2.68618 5 | 4.42222.7751 5 9 | | | | 3.46513.72493.29352.67742.6935 4 3 4 9 1 | 62.8352 | | | 2.90342.73733.18142.89802.37882.77512.98514.58473.6150 7 9 6 4 1 7 8 7 3 | | | | |
| 0.01396 2 | 4.67425.3965 7 | | | 0.77250.4857 5 | | 54.2469 | | | | | | | |
| | 1502.4002 5 | 5.2512 | 3.02221 | 2.32454.58933.54173.72584.06561.87943.55054.0515 5 2 5 3 4 5 9 | | | 3.93542.49492.70082.26632.99933.63845.6854 3 3 5 3 8 | | | | 84.2855 | 272- |
| 2.68618 5 | 4.42222.7751 5 9 | | 2.73123 4 | | 3.46513.72493.29352.67742.6935 4 3 4 9 1 | | | | 2.90342.73733.18142.89802.37882.77512.98514.58473.6150 7 9 6 4 1 7 8 7 3 | | | | |
| 0.01396 2 | 4.67425.3965 7 | | 0.61958 5 | 60.9551 | | 54.2469 | | | | | | | |
| | 2.70395.0843 2 | | 3.10854 | 2.62994.47443.56763.86693.91032.4186 7 7 2 9 4 | | | 4.26653.14371.57882.61243.06412.09982.85563.53135.6674 6 4 9 8 4 1 8 5 | | | | 4.319 | 273- |
| 2.68618 5 | 4.42222.7751 5 9 | | 2.73123 4 | | 3.46513.72493.29352.67742.6935 4 3 4 9 1 | | | | 2.90342.73733.18142.89802.37882.77512.98514.58473.6150 7 9 6 4 1 7 8 7 3 | | | | |
| 0.01396 2 | 4.67425.3965 7 | | 0.61958 5 | 60.9551 | | 54.2469 | | | | | | | |
| | 1.74484.8938 2 8 | | 3.20658 | 2.65354.13493.42513.82363.54132.37482.98803.98863.16092.43932.74563.08612.66302.99592.7248 7 7 9 5 1 2 8 6 3 | | | | | | | 75.4255 6 | 4.1066 | 274- |
| 2.68618 5 | 4.42222.7751 5 9 | | 2.73123 4 | | 3.46513.72493.29352.67742.6935 4 3 4 9 1 | | | | 2.90342.73733.18142.89802.37882.77512.98514.58473.6150 7 9 6 4 1 7 8 7 3 | | | | |
| 0.39241 2 | 4.67421.1544 5 1 | | 0.61958 5 | 60.9551 | | 54.2469 | | | | | | | |
| | 1.7546 | 14.8089 | 3.06058 | 2.29514.06713.47173.70323.47052.31453.08853.75473.03063.60122.86212.94912.69452.56733.05005.34184.0178 5 2 8 3 4 6 8 4 9 5 9 5 8 6 2 | | | | | | | | | 275- |
| 2.68618 5 | 4.42222.7751 5 9 | | 2.73123 4 | | 3.46513.72493.29352.67742.6935 4 3 4 9 1 | | | | 2.90342.73733.18142.89802.37882.77512.98514.58473.6150 7 9 6 4 1 7 8 7 3 | | | | |
| 0.02032 3 | 4.30215.0244 8 4 | | 0.61958 5 | 60.9551 | | 54.2469 | | | | | | | |
| | 3.19464.5471 4 8 | | 4.96009 | 4.42233.80134.46704.97141.90784.29162.54343.3295 3 8 7 5 2 6 | | | 4.82174.52804.44733.12513.45450.73665.53994.3373 9 2 6 2 7 1 6 6 | | | | | | 276- |
| 2.68618 5 | 4.42222.7750 5 8 | | 2.73108 6 | | 3.46513.72493.29352.67742.6935 7 8 4 9 1 | 34.5722 | | 2.7374 | 2.8978 | 2.7752 2.9852 3 | 33.1815 32.3789 | 3.6150 6 | |
| 0.0553.0163 7 | 5.3965 | | 0.85517 | 0.55370.4857 5 | | | | | | | | | |
| | 4.17785.8177 4 2 | | 4.76375 | 4.18375.3994 5 | 4.75295.07063.00994.43575.4654 2 8 5 8 | | 4.92413.98160.24674.25984.41974.7684 7 3 2 1 5 | | | | 46.1802 7 | 5.2222 | 280- |
| 2.68618 5 | 4.42222.7751 5 9 | | 2.73123 4 | | 3.46513.72493.29352.67742.6935 4 3 4 9 1 | | 44.4563 | | 2.90342.73733.18142.89802.37882.77512.98514.58473.6150 7 9 6 4 1 7 8 7 3 | | | | |
| 0.01396 2 | 4.67425.3965 7 | | 0.61958 5 | 60.9551 | | | | | | | | | |

FIG. 13W

| | | | | | | | | | | | | | |
|---|---|---|---|---|---|---|---|---|---|---|---|---|---|
| 156 | 3.5955 | 4.7894 | | 5.2030 | 4.0972 | 5.2194 | 5.9346 | 1.0608 | 5.1437 | 2.2433 | 3.8296 | 5.3688 | 5.4221 | 5.3777 | 5.3013 | 4.6526 | 3.8527 | 0.9344 | 2.2535 | 5.0234 | 281 |
| | | | 5.673 | 3 | 6 | 1 | 3 | 4 | 4 | 7 | 9 | 9 | 2 | 1 | 1 | 1 | 5 | 1 | 3 | | |
| | 4.4222 | 2.7751 | | 3.4635 | 2.4051 | 3.7249 | 3.2935 | 2.6774 | 2.6935 | | 2.9034 | 2.7373 | 3.1814 | 2.8980 | 2.3788 | 2.7751 | 2.9851 | 4.5847 | 3.6150 | | |
| 2.68618 | 5 | 9 | 2.73123 | 4 | 3 | 4 | 4 | 1 | | 54.2469 | 7 | 9 | 6 | 1 | 7 | 9 | 8 | 7 | 3 | | |
| | 4.6742 | 5.3965 | | 0.7725 | 0.4857 | | | | | | | | | | | | | | | | |
| 0.01396 | 2 | 7 | 0.61958 | 5 | | 60.9551 | | | | | | | | | | | | | | | |
| | 2.8429 | 3.7961 | | 1.1474 | 4.4402 | 3.5906 | 3.8430 | 3.8570 | 2.5994 | 3.4334 | 4.2408 | 3.1212 | 4.0206 | 2.4718 | 3.0484 | 2.8487 | 3.0866 | 3.2825 | 5.6438 | 4.2869 | 282 |
| 157 | 2 | 6 | 3.06547 | 6 | 7 | 1 | 2 | 7 | 3 | | 8 | 4 | 1 | 4 | 5 | 1 | 9 | 3 | 3 | 6 | |
| | 4.4222 | 2.7751 | | 3.4635 | 2.4051 | 3.7249 | 3.2935 | 2.6774 | 2.6935 | | 2.9034 | 2.7373 | 3.1814 | 2.8980 | 2.3788 | 2.7751 | 2.9851 | 4.5847 | 3.6150 | | |
| 2.68618 | 5 | 9 | 2.73123 | 4 | 3 | 4 | 4 | 1 | | 54.2469 | 7 | 9 | 6 | 1 | 7 | 9 | 8 | 7 | 3 | | |
| | 4.6742 | 5.3965 | | 0.7725 | 0.4857 | | | | | | | | | | | | | | | | |
| 0.01396 | 2 | 7 | 0.61958 | 5 | | 60.9551 | | | | | | | | | | | | | | | |
| | 3.0498 | 5.1187 | | 2.9443 | 4.7038 | 0.7302 | 4.3617 | 4.1751 | 3.3456 | 3.0022 | | 3.4171 | 4.2503 | 3.5877 | 3.7945 | 3.1199 | | 3.7764 | 6.0205 | 4.6781 | 283 |
| 158 | 9 | 6 | 2.62045 | 8 | 6 | 9 | 1 | 6 | 1 | | 64.7181 | 1 | 7 | 4 | 3 | | 43.4289 | 8 | 5 | 8 | |
| | 4.4222 | 2.7751 | | 3.4635 | 2.4051 | 3.7249 | 3.2935 | 2.6774 | 2.6935 | | 2.9034 | 2.7373 | 3.1814 | 2.8980 | 2.3788 | 2.7751 | 2.9851 | 4.5847 | 3.6150 | | |
| 2.68618 | 5 | 9 | 2.73123 | 4 | 3 | 4 | 4 | 1 | | 54.2469 | 7 | 9 | 6 | 1 | 7 | 9 | 8 | 7 | 3 | | |
| | 4.6742 | 5.3965 | | 0.7725 | 0.4857 | | | | | | | | | | | | | | | | |
| 0.01396 | 2 | 7 | 0.61958 | 5 | | 60.9551 | | | | | | | | | | | | | | | |
| | 4.5485 | 5.5755 | | 5.3767 | 0.4118 | 5.1127 | | 4.0553 | 5.1459 | 3.2116 | 4.5857 | | | 5.3969 | 4.9014 | 4.9976 | 4.5627 | 4.7617 | 4.0550 | 2.9804 | 2.2895 | 284 |
| 159 | 1 | 6 | 5.51098 | 3 | 1 | | 73.9498 | 6 | 5 | 4 | 1 | 4 | 4.77 | 6 | 7 | 5 | 2 | 2 | 5 | 6 | 9 | |
| | 4.4222 | 2.7751 | | 3.4635 | 2.4051 | 3.7249 | 3.2935 | 2.6774 | 2.6935 | | 2.9034 | 2.7373 | 3.1814 | 2.8980 | 2.3788 | 2.7751 | 2.9851 | 4.5847 | 3.6150 | | |
| 2.68618 | 5 | 9 | 2.73123 | 4 | 3 | 4 | 4 | 1 | | 54.2469 | 7 | 9 | 6 | 1 | 7 | 9 | 8 | 7 | 3 | | |
| | 4.6742 | 5.3965 | | 0.7725 | 0.4857 | | | | | | | | | | | | | | | | |
| 0.01396 | 2 | 7 | 0.61958 | 5 | | 60.9551 | | | | | | | | | | | | | | | |
| | 2.2794 | 5.3070 | | 2.4933 | 3.8414 | 3.2163 | 3.8515 | 4.0846 | 2.6646 | 3.6116 | 4.3927 | | 4.0163 | 2.6851 | 3.1690 | 2.8575 | 3.1357 | 3.6874 | 5.7861 | 4.3820 | 285 |
| 160 | 6 | 4 | 1.30566 | 3 | 3 | 8 | 4 | 8 | 4 | | 8 | 9 | 2.802 | 2 | 6 | 8 | 9 | 3 | 5 | 1 | |
| | 4.4223 | 2.7752 | | | 3.7250 | 3.2936 | 2.6936 | 2.9035 | 2.7434 | 2.9052 | 2.7743 | 3.1815 | 2.8980 | 2.3789 | 2.7752 | 2.9847 | 4.5848 | | | | |
| 2.68555 | 2 | 7 | 2.7313 | 3.4636 | 2 | 1 | 8 | | 2 | 7 | 4 | | | 3 | 8 | 4 | 7 | 8 | 43.6151 | | |
| | 2.4104 | 5.3965 | | | 0.4857 | | | | | | | | | | | | | | | | |
| 0.09905 | 5 | 7 | 0.93661 | 0.4975 | | 60.9551 | | | | | | | | | | | | | | | |
| | | | | 4.1524 | 4.1273 | 3.5129 | 4.7633 | | | 2.6904 | 4.1867 | | | 4.2344 | 4.2404 | 4.1207 | 2.1783 | 3.1584 | 3.0577 | 5.6400 | 4.4142 | 289 |
| 161 | 2.6969 | 30.8334 | 4.53643 | 6 | 6 | 9 | 3.3767 | 6 | 63.9639 | 9 | | 24.0468 | | 4 | 2 | 8 | 4 | 2 | 1 | 9 | 4 | 2 | |
| | 4.4222 | 2.7751 | | 3.4635 | 2.4051 | 3.7249 | 3.2935 | 2.6774 | 2.6935 | | 2.9034 | 2.7373 | 3.1814 | 2.8980 | 2.3789 | 2.7751 | 2.9851 | 4.5847 | 3.6150 | | |
| 2.68618 | 5 | 9 | 2.73123 | 4 | 3 | 4 | 4 | 1 | | 54.2469 | 7 | 9 | 6 | 1 | 7 | 9 | 8 | 7 | 3 | | |
| | 4.6742 | 2.9514 | | 0.7725 | 0.4857 | | | | | | | | | | | | | | | | |
| 0.06358 | 2 | 2 | 0.61958 | 5 | | 60.9551 | | | | | | | | | | | | | | | |

FIG. 13X

| | | | | | | | | | | | | | | | | | |
|---|---|---|---|---|---|---|---|---|---|---|---|---|---|---|---|---|---|
| 162 | 2.7579 9 | 4.5733 4 | | 2.9380 1 | 3.3661 1 | 2.4111 1 | 3.9307 1 | 3.1026 5 | 2.7155 | 3.6780 5 | 3.3744 4 | 4.0770 3 | 3.2081 4 | 2.5766 3 | 2.6525 4 | 2.9911 2 | 2.8627 3 | 5.1421 9 | 3.8914 1 | 290 |
| | 4.4222 5 | 2.7751 9 | 3.50107 | 3.4635 4 | 2.4051 3 | 3.7249 4 | 3.2935 1 | 2.6774 | 2.6935 | | 2.9034 7 | 2.7373 9 | 3.1814 6 | 2.8980 1 | 2.3788 7 | 2.3788 7 | 2.9851 8 | 4.5847 7 | 3.6150 3 | |
| 2.68618 | 4.6253 1 | 5.3476 6 | 0.7725 5 | 0.5217 1 | 0.9001 9 | | | | 91.6547 | | | | | | | | | | |
| 0.01467 | | | 0.61958 | | | | | | 54.2469 | | | | | | | | | | |
| | 2.6224 6 | 5.4411 6 | | 2.4800 3 | 4.8585 3 | 2.8513 1 | 3.9396 8 | 4.3545 2 | 2.8011 8 | 3.8477 | 1.6774 7 | 4.0546 6 | 3.0697 7 | 3.3192 5 | 2.1786 9 | 3.2452 3 | 2.9050 3 | 5.9973 2 | 4.5573 4 | 291 |
| 163 | 4.4222 5 | 2.7751 9 | 1.72599 | 3.4635 4 | 2.4051 3 | 3.7249 4 | 3.2935 1 | 2.6774 | 2.6935 | | | 2.9034 7 | 2.7373 9 | 3.1814 6 | 2.8980 1 | 2.3788 7 | 2.9851 7 | 4.5847 8 | 3.6150 3 | |
| 2.68618 | 4.6006 6 | 5.3230 1 | 0.7725 5 | 0.5451 | 0.8668 7 | | | | 4.626 8 | | | | | | | | | | |
| 0.01504 | | | 0.61958 | | | | | | 54.2469 | | | | | | | | | | |
| 164 | 2.8388 | 75.2281 | 3.11841 | 2.5611 8 | 4.5806 8 | 3.1310 5 | 3.7527 2 | 4.0253 8 | 2.1581 2 | 3.5225 4 | 2.9643 1 | 3.0846 4 | 3.5302 9 | 2.7158 | 2.0809 | 3.0637 | 3.6293 2 | 5.6587 2 | 4.3068 2 | 292 |
| | 4.4222 5 | 2.7751 9 | | 3.4635 4 | 2.4051 3 | 3.7249 4 | 3.2935 1 | 2.6774 | 2.6935 | | | 2.9034 7 | 2.7373 9 | 3.1814 6 | 2.8980 1 | 2.3788 7 | 2.9851 7 | 4.5847 8 | 3.6150 3 | |
| 2.68618 | 4.6006 6 | 5.3230 1 | 0.7725 5 | 0.5451 | 0.8668 7 | | | | 1.615 | | | | | | | | | | |
| 0.01504 | | | 0.61958 | | | | | | 54.2469 | | | | | | | | | | |
| 165 | 2.7780 5 | 5.2702 4 | 1.69955 | 2.0347 6 | 4.6011 3 | 3.1065 3 | 5.2403 4 | 4.0818 8 | 2.3255 6 | 3.1376 4 | 4.3177 8 | 2.9818 4 | 3.9272 6 | 2.8352 1 | 2.8554 5 | 2.5859 9 | 3.0122 5 | 3.6538 | 4.2975 7 | 293 |
| | 4.4222 5 | 2.7751 9 | | 3.4635 4 | 2.4051 3 | 3.7249 4 | 3.2935 1 | 2.6774 | 2.6935 | | | 2.9034 7 | 2.7373 9 | 3.1814 6 | 2.8980 1 | 2.3788 7 | 2.9851 7 | 4.5847 8 | 3.6150 3 | |
| 2.68618 | 4.6006 6 | 5.3230 1 | 0.7725 5 | 0.4957 | 10.9394 | | | | | 55.7081 | | | | | | | | | | |
| 0.01504 | | | 0.61958 | | | | | | 54.2469 | | | | | | | | | | |
| 166 | 2.7549 8 | 4.3409 1 | 3.13216 | 2.5704 6 | 4.2752 5 | 3.5681 7 | 3.7647 | | 2.4057 3 | 0.0469 | | 3.0912 8 | 3.1988 8 | 2.8319 7 | 1.7593 3 | 2.2361 9 | 2.5271 7 | 3.3578 3 | 5.4983 7 | 4.1570 7 | 294 |
| | 4.4223 2 | 2.7752 7 | | 3.4636 2 | 2.4046 3 | 3.7250 3 | 3.2936 2 | 2.6936 1 | 2.6936 | 23.6993 | | 2.9034 7 | 2.7374 3 | 3.1815 2 | 2.8980 2 | 2.3789 7 | 2.9852 7 | 4.5847 8 | 3.6151 3 | |
| 2.68625 | 1.8167 9 | 1.8244 2 | 0.8322 4 | 0.5153 4 | 0.9095 6 | | | | 2 | | | | | | | 54.0813 | 43.6151 | | | |
| 0.39135 | | | 0.57106 | | | | | | 54.2469 | | | | | | | | | | |
| 167 | 2.6927 9 | 3.8245 8 | 3.04455 | 2.4897 2 | 4.3144 1 | 2.9471 7 | 3.7043 3 | 3.7521 5 | 2.4521 4 | 3.3089 1 | 4.0952 9 | 3.0142 6 | 3.1660 2 | 2.0854 | 2.4063 6 | 2.9310 4 | 3.3837 | 4.1481 9 | | 297 |
| | 4.4222 5 | 2.7751 9 | | 3.4635 4 | 2.4051 3 | 3.7249 4 | 3.2935 1 | 2.6774 | 2.6935 | | | 2.9034 7 | 2.7373 9 | 3.1814 6 | 2.8980 1 | 2.3788 7 | 12.1725 | 2.9851 7 | 95.5044 | 3.6150 3 | |
| 2.68618 | 4.4468 5 | 5.1691 6 | 2.73123 | 0.7725 5 | 0.3412 2 | 1.2409 8 | | | | | | | | | | | | | | |
| 0.01756 | | | 0.61958 | | | | | | | | | | | | | | | | |
| 168 | 2.7463 5 | 4.4657 6 | 3.06942 | 2.5163 6 | 4.3600 2 | 2.7157 3 | 2.8038 2 | 3.5089 7 | 4.1419 3 | 1.9155 7 | 3.9405 6 | 2.8691 1 | 2.6659 3 | 2.3950 | | 3.4371 9 | 5.5541 1 | 3.5291 2 | | 298 |
| | 4.4222 2 | 2.7752 7 | 2.73123 | 3.4635 4 | 2.4051 3 | 3.7249 4 | 3.2935 1 | 2.6774 | 2.6935 | | | 2.9034 7 | 2.7373 9 | 3.1814 6 | 2.8980 1 | 2.3788 7 | 92.9785 | 2.9851 7 | 4.5847 8 | 3.6150 3 | |
| 2.68618 | 4.6325 2 | 5.3548 7 | 0.61958 | 0.7725 5 | 0.4857 | 60.9551 | | | | | | | | | | | | | | |
| 0.01456 | | | | | | | | | | | | | | | | | | | | |

FIG. 13Y

| | | | | | | | | | | | | |
|---|---|---|---|---|---|---|---|---|---|---|---|---|
| 169 | 2.5294 5 | 2.1441 7 | | 3.4213 6 | 2.8606 8 | 3.8199 5 | 53.6542 | 3.0687 1 | 3.2026 3 | 2.8084 7 | 2.8835 6 | 3.7521 | | 4.0504 | 93.1523 | 2.7623 3 | 1.9614 3 | 2.9864 4 | 2.9466 2 | 5.2081 3 | 3.5109 5 | 299 |
| 2.68618 | 4.4222 5 | 2.7751 9 | | | 3.4635 4 | 2.4051 3 | 3.7249 4 | 3.2935 1 | 2.6774 4 | 2.6935 | | 2.9034 7 | 2.7373 9 | 3.1814 | 2.8980 1 | 2.3788 | 2.7751 7 | 2.9851 8 | 4.5847 7 | 3.6150 3 | | |
| 0.01456 | 4.6325 2 | 5.3548 7 | | 0.61958 | 0.7725 5 | 0.4857 | | | | | 54.2469 | | | 6 | 1 | | | | | | | |
| 170 | 2.3038 7 | 4.7805 5 | | 3.2584 2 | 2.7016 2 | 3.5092 2 | 2.7714 7 | 3.8364 9 | | 2.6876 1 | 3.0366 3 | 3.8790 7 | 3.0116 | | 2.6244 | 73.9988 | | 83.1276 1 | 1.7466 9 | 2.9741 1 | 2.8172 9 | 5.3277 | 4.0284 2 | 300 |
| 2.68618 | 4.4222 5 | 2.7751 9 | | | 3.4635 4 | 2.4051 3 | 3.7249 4 | 3.2935 1 | 2.6774 4 | 2.6935 | | 2.9034 7 | 2.7373 9 | 3.1814 | 2.8980 1 | 2.3788 | 2.7751 7 | 2.9851 8 | 4.5847 7 | 3.6150 3 | | |
| 0.01456 | 4.6325 2 | 5.3548 7 | | 0.61958 | 0.7725 5 | 0.4857 | | | | | 54.2469 | | | 6 | 1 | | | | | | | |
| 171 | 2.7875 3 | 4.4547 | | 4.85935 | 4.2984 4 | 3.6420 | 4.3590 8 | 4.7784 2 | 1.0603 5 | 4.1658 1 | | | 3.5486 4 | 4.4401 5 | 3.4912 8 | 4.3774 4 | 4.2993 5 | 3.6902 8 | 3.3456 1 | 1.6211 5 | | 4.1441 4 | 5.332 4 | 301 |
| 2.68618 | 4.4222 5 | 2.7751 9 | | | 3.4635 4 | 2.4051 3 | 3.7249 4 | 3.2935 1 | 2.6774 4 | 2.6935 | | 2.9034 7 | 2.7373 9 | 3.1814 | 2.8980 1 | 2.3788 | 2.7751 7 | 2.9851 8 | 4.5847 7 | 3.6150 3 | | |
| 0.04763 2 | 4.6325 2 | 3.3028 2 | | 0.61958 | 0.7725 5 | 0.4857 | | | | | 54.2469 | | | 6 | 1 | | | | | | | |
| 172 | 2.4733 3 | 2.2819 4 | | 3.83563 | 3.3523 4 | 4.4140 6 | 2.8101 7 | 4.3742 9 | 3.8265 3 | 3.3226 7 | 3.4944 1 | 4.3197 | 3.5853 | | 81.6663 | 3.6219 1 | 3.6828 6 | 1.6745 2 | 2.0333 7 | 3.3689 3 | 5.7639 7 | 4.5343 3 | 302 |
| 2.68618 | 4.4222 5 | 2.7751 9 | | | 3.4635 4 | 2.4051 3 | 3.7249 4 | 3.2935 1 | 2.6774 4 | 2.6935 | | 2.9034 7 | 2.7373 9 | 3.1814 | 2.8980 1 | 2.3788 | 2.7751 7 | 2.9851 8 | 4.5847 7 | 3.6150 3 | | |
| 0.01505 | 4.5999 4 | 5.3222 9 | | 0.61958 | 0.7725 5 | 0.54640 | .8650 | | | | 54.2469 | | | 6 | 1 | | | | | | | |
| 173 | 1.0632 4 | 4.4032 1 | | 4.08673 | 3.5682 9 | 2.9065 6 | 3.6696 5 | 4.3392 4 | 2.8660 5 | 3.4934 8 | 2.7330 3 | 3.7016 5 | 3.7905 1 | 4.2038 3 | 3.7597 8 | 3.7616 3 | | 73.0217 | 2.5526 4 | 2.3701 9 | 5.2423 1 | 4.0277 8 | 303 |
| 2.68618 | 4.4222 5 | 2.7751 9 | | | 3.4635 4 | 2.4051 3 | 3.7249 4 | 3.2935 1 | 2.6774 4 | 2.6935 | | 2.9034 7 | 2.7373 9 | 3.1814 | 2.8980 1 | 2.3788 | 2.7751 7 | 2.9851 8 | 4.5847 7 | 3.6150 3 | | |
| 0.01505 | 4.5999 4 | 5.3222 9 | | 0.61958 | 0.7725 5 | 0.54640 | .8650 | | | | 54.2469 | | | 6 | 1 | | | | | | | |
| 174 | 2.5704 9 | 4.2905 9 | | 3.95253 | 3.3750 8 | 3.4057 3 | 3.7893 4 | 4.0762 2 | 2.7466 3 | 2.2793 | | 2.0192 3 | 3.1738 4 | 4.1644 | 83.5452 | 3.0883 9 | 2.7731 4 | 2.9670 5 | 2.1448 6 | 4.8960 1 | 3.6914 7 | 304 |
| 2.68618 | 4.4222 5 | 2.7751 9 | | | 3.4635 4 | 2.4051 3 | 3.7249 4 | 3.2935 1 | 2.6774 4 | 2.6935 | | 2.9034 7 | 2.7373 9 | 3.1814 | 2.8980 1 | 2.3788 | 2.7751 7 | 2.9851 8 | 4.5847 7 | 3.6150 3 | | |
| 0.07625 | 4.5999 4 | 2.7588 1 | | 0.61958 | 0.7725 5 | 0.54640 | .8650 | | | | 54.2469 | | | 6 | 1 | | | | | | | |
| 175 | 0.9954 9 | 4.8649 9 | | 3.35841 | 2.9193 4 | 4.3673 3 | 2.5651 5 | 4.0148 1 | 3.7625 7 | 2.6846 3 | 3.7844 4 | 4.2368 5 | 3.3428 3 | 4.0883 2 | 2.7593 6 | 2.6116 9 | 2.9272 7 | 3.1444 2 | 3.4158 4 | 5.6127 3 | 4.3456 4 | 305 |
| 2.68618 | 4.4223 1 | 2.7752 5 | | 2.73129 | 3.4636 8 | 2.4051 | 3.725 | 3.2932 8 | 2.6774 4 | 2.6936 6 | | 2.9035 2 | 2.7374 3 | 3.1815 2 | 2.8980 5 | 2.3788 7 | 2.7752 7 | 2.9847 7 | 4.5848 3 | 3.6150 9 | | |
| 0.06139 | 2.8210 5* | | | 1.16825 | 0.3723 8 | 0* | | | | | | | | | | | | | | | | |

DROUGHT TOLERANT PLANTS AND RELATED CONSTRUCTS AND METHODS INVOLVING GENES ENCODING DTP6 POLYPEPTIDES

CROSS REFERENCE TO RELATED APPLICATIONS

This application claims the benefit of U.S. Provisional Application No. 61/407,612, filed Oct. 28, 2010, the entire content of which is herein incorporated by reference.

REFERENCE TO SEQUENCE LISTING SUBMITTED ELECTRONICALLY

The official copy of the sequence listing is submitted electronically via EFS-Web as an ASCII formatted sequence listing with a file named "20140407_BB1677USPCT_AmendedSequenceListing.txt" created on Apr. 7, 2014, and having a size of 400 kilobytes. The sequence listing contained in this ASCII formatted document is part of the specification and is herein incorporated by reference in its entirety.

FIELD OF THE INVENTION

The field of invention relates to plant breeding and genetics and, in particular, relates to recombinant DNA constructs useful in plants for conferring tolerance to drought.

BACKGROUND OF THE INVENTION

Abiotic stress is the primary cause of crop loss worldwide, causing average yield losses of more than 50% for major crops (Boyer, J. S. (1982) *Science* 218:443-448; Bray, E. A. et al. (2000) In Biochemistry and Molecular Biology of Plants, Edited by Buchannan, B. B. et al., Amer. Soc. Plant Biol., pp. 1158-1203). Among the various abiotic stresses, drought is the major factor that limits crop productivity worldwide. Exposure of plants to a water-limiting environment during various developmental stages appears to activate various physiological and developmental changes. Understanding of the basic biochemical and molecular mechanism for drought stress perception, transduction and tolerance is a major challenge in biology. Reviews on the molecular mechanisms of abiotic stress responses and the genetic regulatory networks of drought stress tolerance have been published (Valliyodan, B., and Nguyen, H. T., (2006) *Curr. Opin. Plant Biol.* 9:189-195; Wang, W., et al. (2003) *Planta* 218:1-14); Vinocur, B., and Altman, A. (2005) *Curr. Opin. Biotechnol.* 16:123-132; Chaves, M. M., and Oliveira, M. M. (2004) *J. Exp. Bot.* 55:2365-2384; Shinozaki, K., et al. (2003) *Curr. Opin. Plant Biol.* 6:410-417; Yamaguchi-Shinozaki, K., and Shinozaki, K. (2005) *Trends Plant Sci.* 10:88-94).

Earlier work on molecular aspects of abiotic stress responses was accomplished by differential and/or subtractive analysis (Bray, E. A. (1993) Plant Physiol. 103:1035-1040; Shinozaki, K., and Yamaguchi-Shinozaki, K. (1997) Plant Physiol. 115:327-334; Zhu, J.-K. et al. (1997) *Crit. Rev. Plant Sci.* 16:253-277;

Thomashow, M. F. (1999) *Annu. Rev. Plant Physiol. Plant Mol. Biol.* 50:571-599). Other methods include selection of candidate genes and analyzing expression of such a gene or its active product under stresses, or by functional complementation in a stressor system that is well defined (Xiong, L., and Zhu, J.-K. (2001) Physiologia Plantarum 112:152-166). Additionally, forward and reverse genetic studies involving the identification and isolation of mutations in regulatory genes have also been used to provide evidence for observed changes in gene expression under stress or exposure (Xiong, L., and Zhu, J.-K. (2001) *Physiologia Plantarum* 112:152-166).

Activation tagging can be utilized to identify genes with the ability to affect a trait. This approach has been used in the model plant species *Arabidopsis thaliana* (Weigel, D., et al. (2000) *Plant Physiol.* 122:1003-1013). Insertions of transcriptional enhancer elements can dominantly activate and/or elevate the expression of nearby endogenous genes. This method can be used to select genes involved in agronomically important phenotypes, including stress tolerance.

SUMMARY OF THE INVENTION

The present invention includes:

In one embodiment, a plant comprising in its genome a recombinant DNA construct comprising a polynucleotide operably linked to at least one regulatory element, wherein said polynucleotide encodes a polypeptide having an amino acid sequence of at least 50% sequence identity, based on the Clustal V method of alignment, when compared to SEQ ID NOS: 18, 20, 22, 24, 26, 28, 30, 32, 34, 36, 38-70, 75, 77, 79, 81, 83, 85, 87, 89, 91, 92-102 or 103, and wherein said plant exhibits increased drought tolerance when compared to a control plant not comprising said recombinant DNA construct.

In one embodiment, a plant comprising in its genome a recombinant DNA construct comprising a polynucleotide operably linked to at least one regulatory element, wherein said polynucleotide encodes a polypeptide having an amino acid sequence of at least 50% sequence identity, based on the Clustal V method of alignment, when compared to SEQ ID NOS: 18, 20, 22, 24, 26, 28, 30, 32, 34, 36, 38-70, 75, 77, 79, 81, 83, 85, 87, 89, 91, 92-102 or 103, and wherein said plant exhibits increased tolerance to triple stress, or Paraquat, or both, when compared to a control plant not comprising said recombinant DNA construct.

Another embodiment is a plant comprising in its genome a recombinant DNA construct comprising a first polynucleotide operably linked to a second polynucleotide, wherein said first polynucleotide encodes a polypeptide comprising the amino acid sequence of SEQ ID NO: 90, and the second polynucleotide encodes a polypeptide comprising: (a) an amino acid sequence of at least 50% sequence identity, based on the Clustal V method of alignment, when compared to SEQ ID NOS: 18, 22, 24, 26, 28, 30, 32, 34, 36, 38-70, 75, 77, 79, 81, 83, 85, 87, 89, 91, 92-102 or 103; or (b) a mature DTP6 polypeptide with the HMM profile given in FIG. 13A-FIG. 13Y, and wherein said plant exhibits an increase in at least one trait selected from the group consisting of: drought tolerance, triple stress tolerance, Paraquat tolerance, when compared to a control plant not comprising said recombinant DNA construct.

In another embodiment, a plant comprising in its genome a recombinant DNA construct comprising a polynucleotide operably linked to at least one regulatory element, wherein said polynucleotide encodes a polypeptide having an amino acid sequence of at least 50% sequence identity, based on the Clustal V method of alignment, when compared to SEQ ID NOS: 18, 20, 22, 24, 26, 28, 30, 32, 34, 36, 38-70, 75, 77, 79, 81, 83, 85, 87, 89, 91, 92-102 or 103, and wherein said plant exhibits an alteration of at least one agronomic characteristic when compared to a control plant not comprising said recombinant DNA construct. Optionally, the plant exhibits said alteration of said at least one agronomic characteristic when compared, under water limiting conditions, to said control plant not comprising said recombinant DNA construct. The at least one agronomic trait may be yield, biomass, or both and the alteration may be an increase. The at least one agronomic characteristic may also be an increase in at least trait selected from the group consisting of drought tolerance, triple stress tolerance and Paraquat tolerance. The increase in one or more of these traits maybe under one or more of the following stress conditions: drought stress, triple stress or Paraquat stress conditions.

In another embodiment, a plant comprising in its genome a polynucleotide operably linked to at least one recombinant regulatory element, wherein said polynucleotide encodes a polypeptide having an amino acid sequence of at least 50% sequence identity, based on the Clustal V method of alignment, when compared to SEQ ID NOS: 18, 20, 22, 24, 26, 28, 30, 32, 34, 36, 38-70, 75, 77, 79, 81, 83, 85, 87, 89, 91, 92-102 or 103, and wherein said plant exhibits increased drought tolerance when compared to a control plant not comprising the recombinant regulatory element.

In another embodiment, the present invention includes any of the plants of the present invention wherein the plant is selected from the group consisting of: maize, soybean, sunflower, sorghum, canola, wheat, alfalfa, cotton, rice, barley, millet, sugar cane and switchgrass.

In another embodiment, the present invention includes seed of any of the plants of the present invention, wherein said seed comprises in its genome a recombinant DNA construct comprising a polynucleotide operably linked to at least one regulatory element, wherein said polynucleotide encodes a polypeptide having an amino acid sequence of at least 50% sequence identity, based on the Clustal V method of alignment, when compared to SEQ ID NOS: 18, 20, 22, 24, 26, 28, 30, 32, 34, 36, 38-70, 75, 77, 79, 81, 83, 85, 87, 89, 91, 92-102 or 103, and wherein a plant produced from said seed exhibits an increase in at least one trait selected from the group consisting of drought tolerance, triple stress tolerance, Paraquat tolerance, yield and biomass, when compared to a control plant not comprising said recombinant DNA construct.

Another embodiment of this invention is a method of identifying a DTP6 protein, the method comprising the steps of: (a) use the profile of FIG. 13A-FIG. 13Y to identify at least one candidate sequence in an amino acid sequence database; (b) determine an e-value score for the at least one candidate sequence from step (a); (c) select the at least one candidate sequence from step (b), wherein the e-value score is $<10^{-3}$; and (d) further select the at least one candidate sequence from step (c), wherein the at least one candidate sequence matches the profile of FIG. 13A-FIG. 13Y by at least 80% over the entire length of the profile.

In another embodiment, a method of increasing drought tolerance in a plant, comprising: (a) introducing into a regenerable plant cell a recombinant DNA construct comprising a polynucleotide operably linked to at least one regulatory sequence, wherein the polynucleotide encodes a polypeptide having an amino acid sequence of at least 50% sequence identity, based on the Clustal V method of alignment, when compared to SEQ ID NOS: 18, 20, 22, 24, 26, 28, 30, 32, 34, 36, 38-70, 75, 77, 79, 81, 83, 85, 87, 89, 91, 92-102 or 103; (b) regenerating a transgenic plant from the regenerable plant cell after step (a), wherein the transgenic plant comprises in its genome the recombinant DNA construct; and (c) obtaining a progeny plant derived from the transgenic plant of step (b), wherein said progeny plant comprises in its genome the recombinant DNA construct and exhibits increased drought tolerance when compared to a control plant not comprising the recombinant DNA construct.

In another embodiment, a method of evaluating drought tolerance in a plant, comprising: (a) obtaining a transgenic plant, wherein the transgenic plant comprises in its genome a recombinant DNA construct comprising a polynucleotide operably linked to at least one regulatory element, wherein said polynucleotide encodes a polypeptide having an amino acid sequence of at least 50% sequence identity, based on the Clustal V method of alignment, when compared to SEQ ID NOS: 18, 20, 22, 24, 26, 28, 30, 32, 34, 36, 38-70, 75, 77, 79, 81, 83, 85, 87, 89, 91, 92-102 or 103; (b) obtaining a progeny plant derived from the transgenic plant, wherein the progeny plant comprises in its genome the recombinant DNA construct; and (c) evaluating the progeny plant for drought tolerance compared to a control plant not comprising the recombinant DNA construct.

In another embodiment, a method of determining an alteration of at least one agronomic characteristic in a plant, comprising: (a) obtaining a transgenic plant, wherein the transgenic plant comprises in its genome a recombinant DNA construct comprising a polynucleotide operably linked to at least one regulatory element, wherein said polynucleotide encodes a polypeptide having an amino acid sequence of at least 50% sequence identity, based on the Clustal V method of alignment, when compared to SEQ ID NOS: 18, 20, 22, 24, 26, 28, 30, 32, 34, 36, 38-70, 75, 77, 79, 81, 83, 85, 87, 89, 91, 92-102 or 103, wherein the transgenic plant comprises in its genome the recombinant DNA construct; (c) obtaining a progeny plant derived from the transgenic plant, wherein the progeny plant comprises in its genome the recombinant DNA construct; and (d) determining whether the progeny plant exhibits an alteration of at least one agronomic characteristic when compared to a control plant not comprising the recombinant DNA construct. Optionally, said determining step (d) comprises determining whether the transgenic plant exhibits an alteration of at least one agronomic characteristic when compared, under water limiting conditions, to a control plant not comprising the recombinant DNA construct. The at least one agronomic trait may be yield, biomass, or both and the alteration may be an increase.

In another embodiment, a method of increasing tolerance to triple stress in a plant, comprising: (a) introducing into a regenerable plant cell a recombinant DNA construct comprising a polynucleotide operably linked to at least one regulatory sequence, wherein the polynucleotide encodes a polypeptide having an amino acid sequence of at least 50% sequence identity, based on the Clustal V method of alignment, when compared to SEQ ID NOS: 18, 20, 22, 24, 26, 28, 30, 32, 34, 36, 38-70, 75, 77, 79, 81, 83, 85, 87, 89, 91, 92-102 or 103; (b) regenerating a transgenic plant from the regenerable plant cell after step (a), wherein the transgenic plant comprises in its genome the recombinant DNA construct; and (c) obtaining a progeny plant derived from the transgenic plant of step (b), wherein said progeny plant comprises in its genome the recombinant DNA construct and exhibits increased tolerance to triple stress when compared to a control plant not comprising the recombinant DNA construct.

In another embodiment, a method of increasing Paraquat tolerance in a plant, comprising: (a) introducing into a regenerable plant cell a recombinant DNA construct comprising a polynucleotide operably linked to at least one regulatory sequence, wherein the polynucleotide encodes a polypeptide having an amino acid sequence of at least 50% sequence identity, based on the Clustal V method of alignment, when compared to SEQ ID NOS: 18, 20, 22, 24, 26, 28, 30, 32, 34, 36, 38-70, 75, 77, 79, 81, 83, 85, 87, 89, 91, 92-102 or 103; (b) regenerating a transgenic plant from the regenerable plant cell after step (a), wherein the transgenic plant comprises in its genome the recombinant DNA construct; and (c) obtaining a progeny plant derived from the transgenic plant of step (b), wherein said progeny plant comprises in its genome the recombinant DNA construct and exhibits increased tolerance to Paraquat when compared to a control plant not comprising the recombinant DNA construct.

A method of increasing stress tolerance in a plant, wherein the stress is selected from a group consisting of drought stress, triple stress and Paraquat stress, comprising: (a) introducing into a regenerable plant cell a recombinant DNA construct comprising a polynucleotide operably linked to at least one regulatory sequence, wherein the polynucleotide encodes a polypeptide comprising a mature DTP6 polypeptide with the HMM profile given in FIG. 13A-FIG. 13Y; (b) regenerating a transgenic plant from the regenerable plant cell after step (a), wherein the transgenic plant comprises in its genome the recombinant DNA construct; and (c) obtaining a progeny plant derived from the transgenic plant of step (b), wherein said progeny plant comprises in its genome the recombinant DNA construct and exhibits increased tolerance at least one stress selected from the group consisting of drought stress, triple stress and Paraquat stress, when compared to a control plant not comprising the recombinant DNA construct.

In another embodiment, the present invention includes any of the methods of the present invention wherein the plant is selected from the group consisting of: maize, soybean, sunflower, sorghum, canola, wheat, alfalfa, cotton, rice, barley, millet, sugar cane and switchgrass.

In another embodiment, the present invention includes an isolated polynucleotide comprising: (a) a nucleotide sequence encoding a polypeptide with drought tolerance activity, wherein the polypeptide has an amino acid sequence of at least 90% sequence identity when compared to SEQ ID NOS: 18, 20, 22, 24, 26, 28, 30, 32, 34, 36, 38-70, 75, 77, 79, 81, 83, 85, 87, 89, 91, 92-102 or 103, (b) a nucleotide sequence encoding a polypeptide with drought tolerance activity, wherein, the polypeptide has an amino acid sequence comprising a mature DTP6 polypeptide with the HMM profile given in FIG. 3; or (c) a full complement of the nucleotide sequence, wherein the full complement and the nucleotide sequence consist of the same number of nucleotides and are 100% complementary. The polypeptide may comprise the amino acid sequence of SEQ ID NOS: 18, 20, 22, 24, 26, 28, 30, 32, 34, 36, 38-70, 75, 77, 79, 81, 83, 85, 87, 89, 91, 92-102 or 103. The nucleotide sequence may comprise the nucleotide sequence of SEQ ID NO: 17, 19, 21, 23, 25, 27, 29, 31, 33, 35, 37, 74, 76, 78, 80, 82, 84, 86 and 88.

In another embodiment, the present invention concerns a recombinant DNA construct comprising any of the isolated polynucleotides of the present invention operably linked to at least one regulatory sequence, and a cell, a plant, and a seed comprising the recombinant DNA construct. The cell may be eukaryotic, e.g., a yeast, insect or plant cell, or prokaryotic, e.g., a bacterial cell.

BRIEF DESCRIPTION OF THE DRAWINGS AND SEQUENCE LISTING

The invention can be more fully understood from the following detailed description and the accompanying drawings and Sequence Listing which form a part of this application.

Figure 11D:
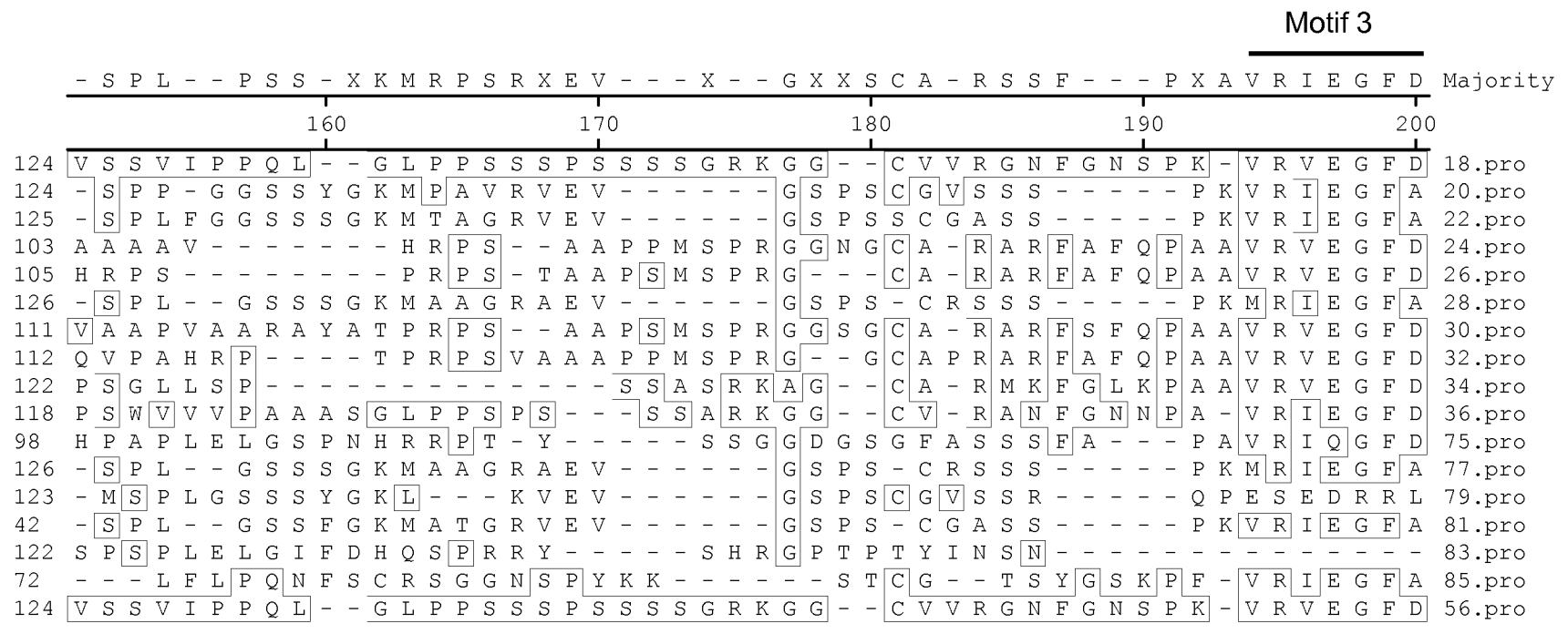
Figure 1:
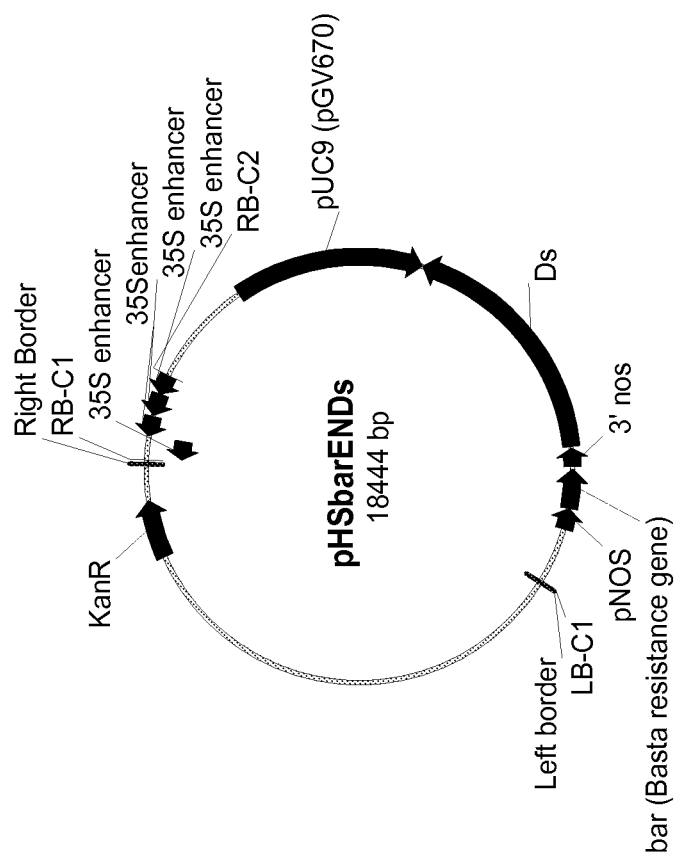
FIG. 1 shows a schematic of the pHSbarENDs activation tagging construct (SEQ ID NO:1) used to make the *Arabidopsis* populations.

FIGS. 11A-11E show the multiple alignment of the amino acid sequences of the DTP6 polypeptides of SEQ ID NOS: 18, 20, 22, 24, 26, 28, 30, 32, 34, 36, 75, 77, 79, 81, 83, 85 and 56. A majority consensus sequence (SEQ ID NO:105) is presented above the aligned amino acid sequences. Residues that are identical to the residues of the majority consensus at a given position at a given position are enclosed in a box. Three conserved amino acid motifs are present in the DTP6 polypeptides.

FIG. 12 shows the percent sequence identity and the divergence values for each pair of amino acids sequences of DTP6 polypeptides displayed in FIGS. 11A-11E.

Figure 13B:
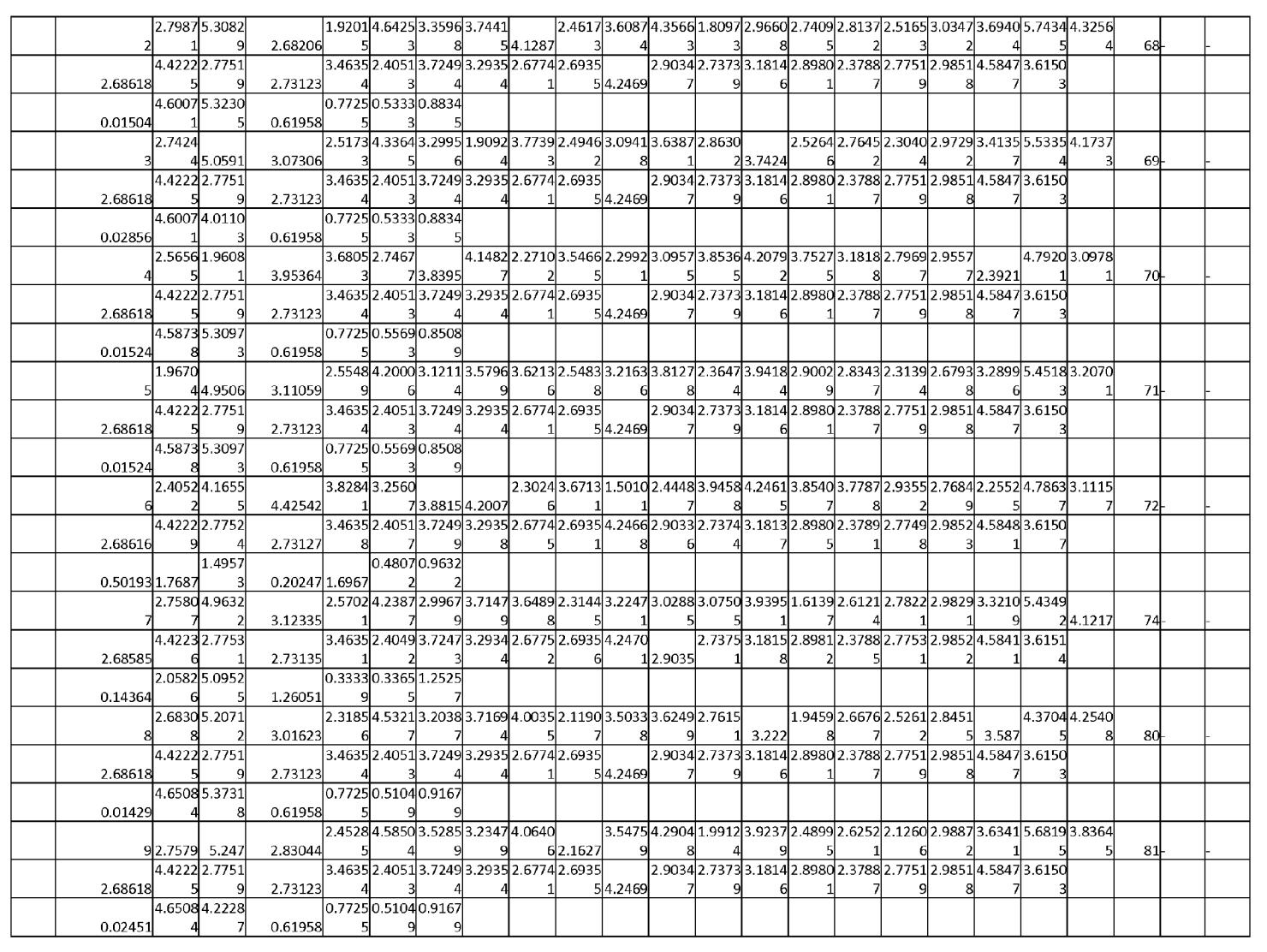
Figure 13C:
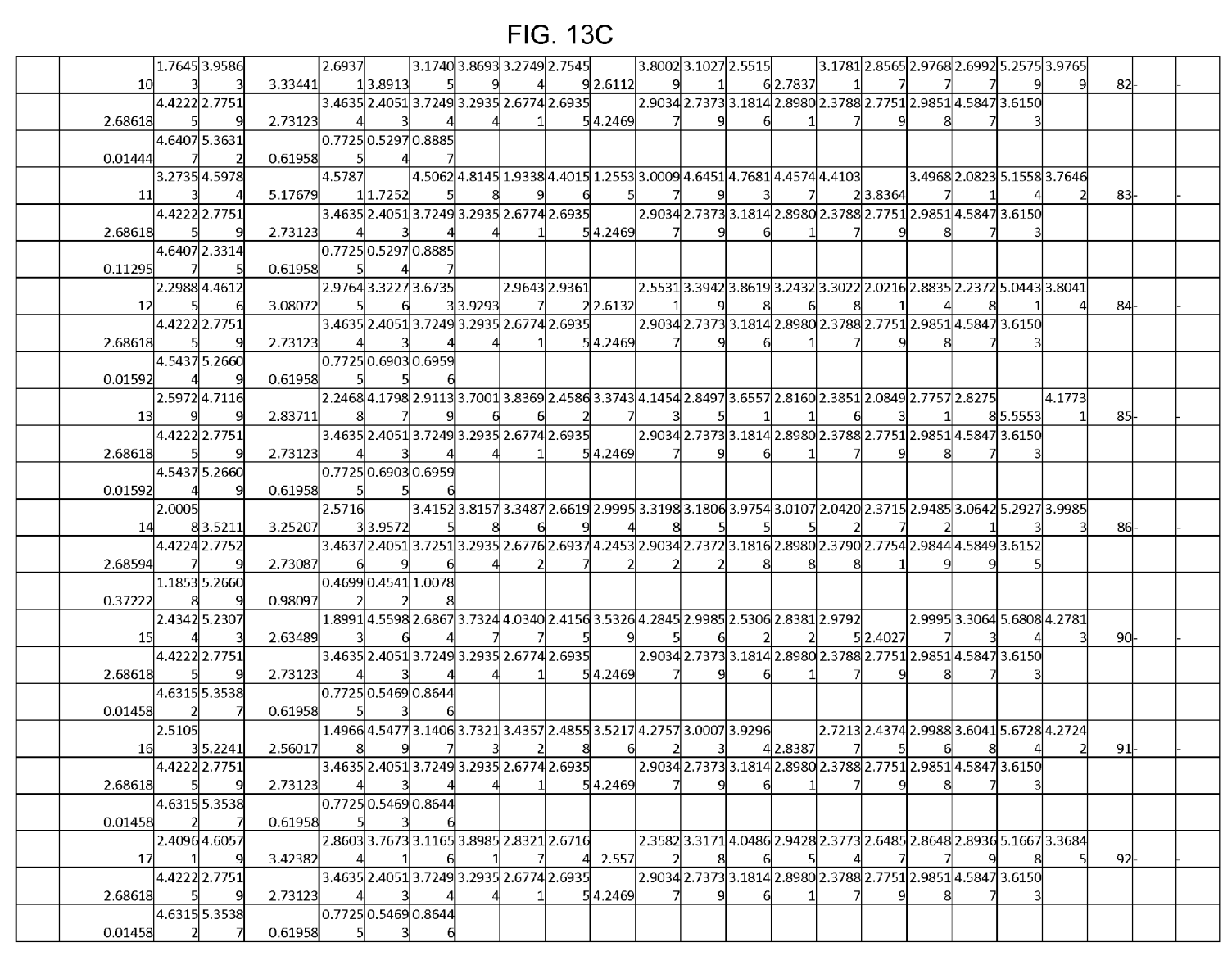
Figure 13O:
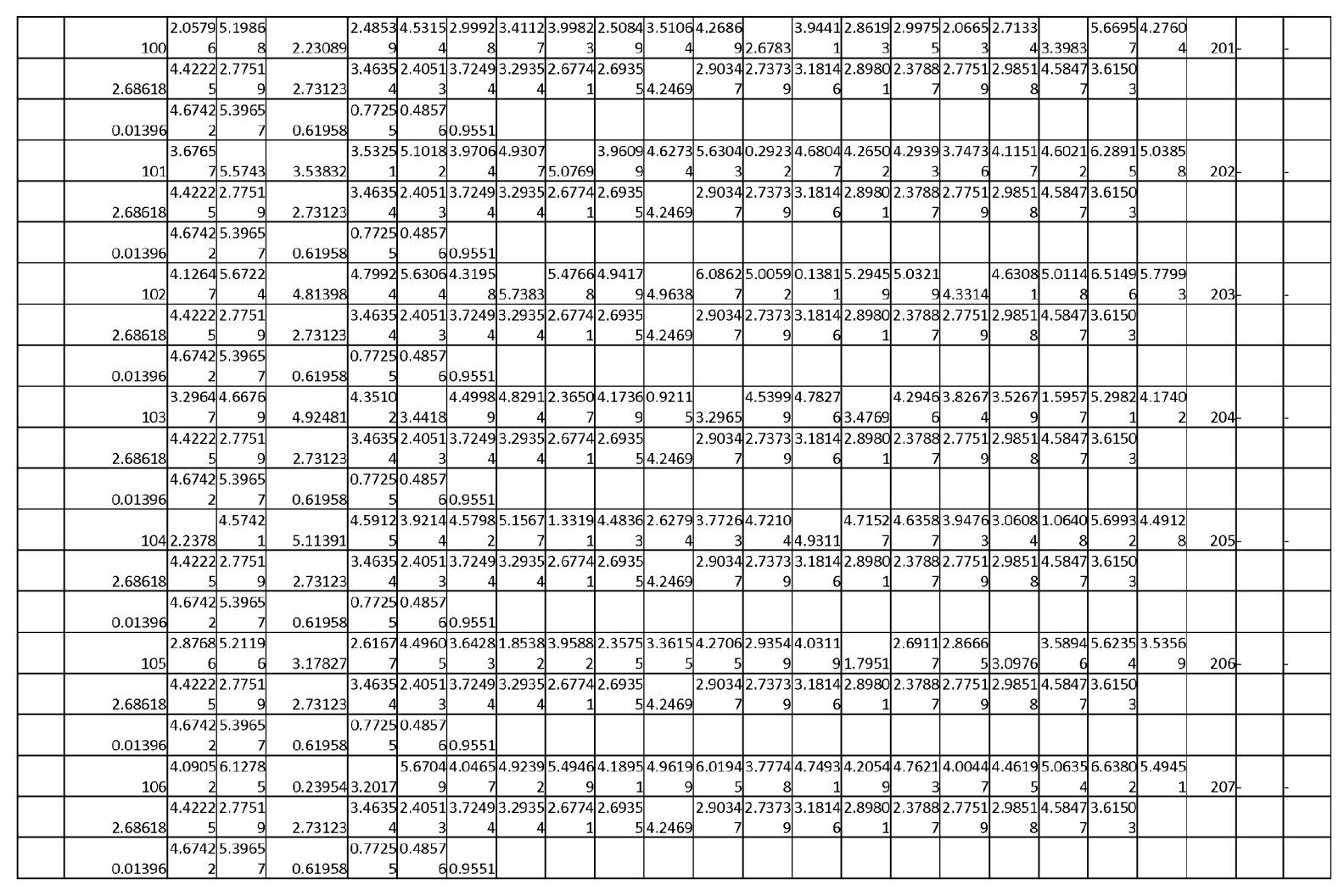
Figure 13Q:
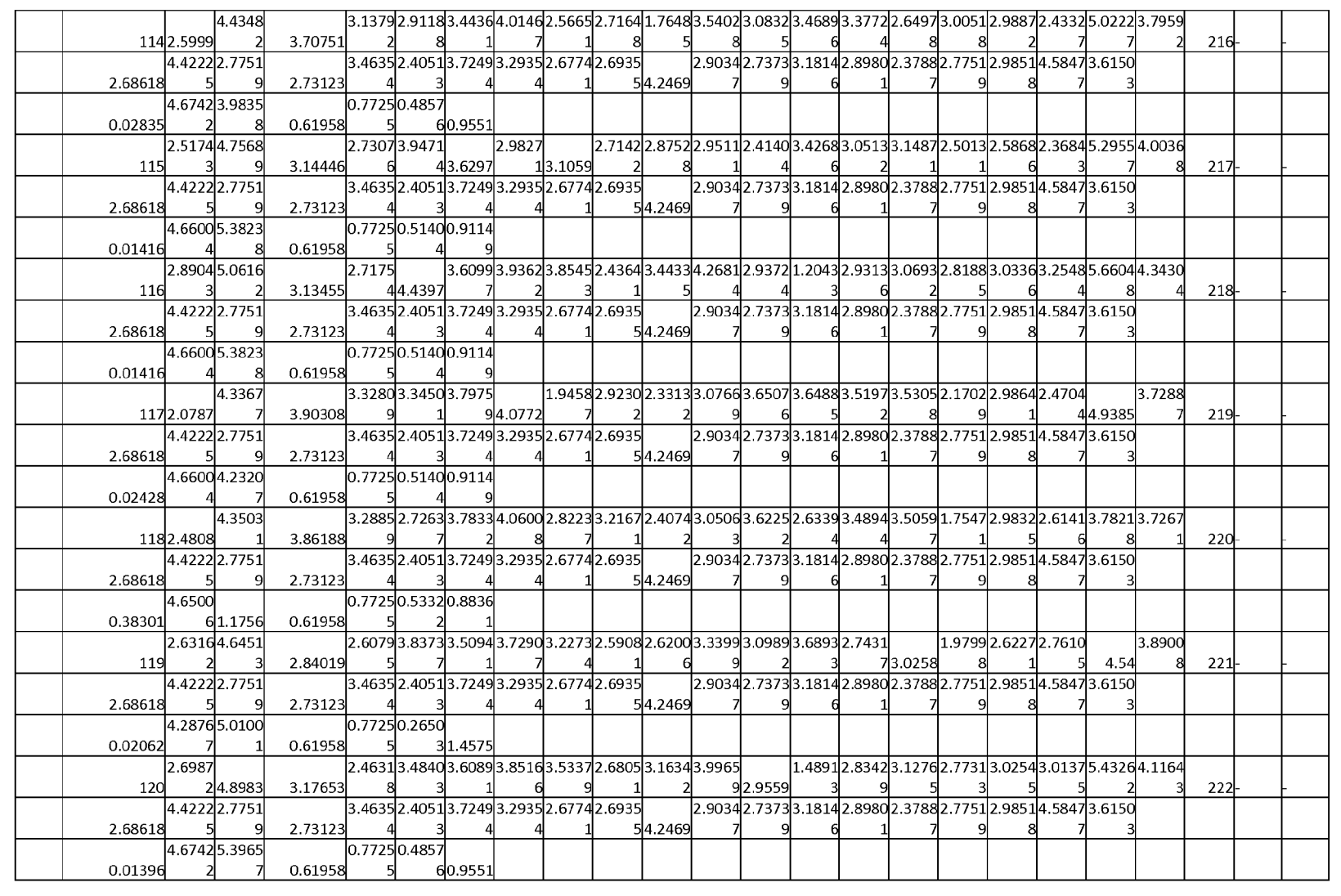

FIG. 13A-FIG. 13Y show the HMM profile for DTP6 polypeptides.

SEQ ID NO:1 is the nucleotide sequence of the pHSbarENDs activation tagging vector.

SEQ ID NO:2 is the nucleotide sequence of the GATEWAY® donor vector pDONR™/Zeo.

SEQ ID NO:3 is the nucleotide sequence of the GATEWAY® donor vector pDONR™221.

SEQ ID NO:4 is the nucleotide sequence of pBC-yellow, a destination vector for use with *Arabidopsis*.

SEQ ID NO:5 is the nucleotide sequence of PHP27840, a destination vector for use with soybean.

SEQ ID NO:6 is the nucleotide sequence of PHP23236, a destination vector for use with Gaspe Flint derived maize lines.

SEQ ID NO:7 is the nucleotide sequence of PHP10523 (Komari et al., *Plant J.* 10:165-174 (1996); NCBI General Identifier No. 59797027).

SEQ ID NO:8 is the nucleotide sequence of PHP23235, a destination vector for use with Gaspe Flint derived lines.

SEQ ID NO:9 is the nucleotide sequence of PHP28647, a destination vector for use with maize inbred-derived lines.

SEQ ID NO:10 is the nucleotide sequence of the attB1 site.

SEQ ID NO:11 is the nucleotide sequence of the attB2 site.

SEQ ID NO:12 is the nucleotide sequence of the At1g68490-5'attB forward primer, containing the attB1 sequence, used to amplify the At1g68490 protein-coding region.

SEQ ID NO:13 is the nucleotide sequence of the At1g68490-3'attB reverse primer, containing the attB2 sequence, used to amplify the At1g68490 protein-coding region.

SEQ ID NO: 14 is the nucleotide sequence of the VC062 primer, containing the T3 promoter and attB1 site, useful to amplify cDNA inserts cloned into a BLUESCRIPT® II SK(+) vector (Stratagene).

SEQ ID NO: 15 is the nucleotide sequence of the VC063 primer, containing the T7 promoter and attB2 site, useful to amplify cDNA inserts cloned into a BLUESCRIPT® II SK(+) vector (Stratagene).

SEQ ID NO: 16 is the nucleotide sequence of PHP29634 (also called DV11), a destination vector for use with Gaspe Flint derived maize lines.

SEQ ID NO: 17 corresponds to NCBI GI No. 29028823, which is the nucleotide sequence from locus At1g68490.

SEQ ID NO: 18 corresponds to the amino acid sequence of At1g68490 encoded by SEQ ID NO: 17.

Table 1 presents SEQ ID NOs for the nucleotide sequences obtained from cDNA clones from maize, soybean, Bahia grass, resurrection grass and hay fern. The SEQ ID NOs for the corresponding amino acid sequences encoded by the cDNAs are also presented.

TABLE 1 cDNAs Encoding DTP6 Polypeptides

| Plant | Clone Designation* | SEQ ID NO: (Nucleotide) | SEQ ID NO: (Amino Acid) |
|---|---|---|---|
| Corn | cfp5n.pk061.k20 (FIS) | 19 | 20 |
| Corn | cie3s.pk008.j21 (FIS) | 21 | 22 |
| Corn | cfp7n.pk001.j9 (FIS) | 23 | 24 |
| Corn | cds3f.pk005.m8 | 25 | 26 |
| Corn | my.cco1n.pk088.j17 | 27 | 28 |
| Resurrection grass | En_NODE_47983 | 29 | 30 |
| Bahia grass | Pn_NODE_10482 | 31 | 32 |
| Soybean | sdp4c.pk004.f4 (FIS) | 33 | 34 |
| Soybean | sfp1n.pk034.b12 | 35 | 36 |
| Corn | pco599449 (contig) | 74 | 75 |
| Corn | pco592873 (contig) | 76 | 77 |
| Corn | pco596845 (contig) | 78 | 79 |
| Bahia grass | epn2n.pk019.o1 | 80 | 81 |
| Bahia grass | Pn_NODE_38377 | 82 | 83 |
| Hay fern | ehsf2n.pk006.d22 | 84 | 85 |

*The "Full-Insert Sequence" ("FIS") is the sequence of the entire cDNA insert.

SEQ ID NO: 37 is the nucleic acid sequence corresponding to a predicted CDS from BAC ZMMBBc0382C02 (AC200490) (*Zea mays*).

SEQ ID NO: 38 is the amino acid sequence a predicted protein from BAC ZMMBBc0382C02, and is the amino acid sequence encoded by SEQ ID NO: 37 (*Zea mays*).

SEQ ID NO: 39 is the amino acid sequence corresponding to a peptide homolog of At1g64890 from Phytozome database (*Manihot esculenta*).

SEQ ID NO: 40 is the amino acid sequence corresponding to NCBI GI No. 255581637 (*Ricinus communis*).

SEQ ID NO: 41 is the amino acid sequence corresponding to NCBI GI No. 224108468 (*Populus trichocarpa*).

SEQ ID NO: 42 is the amino acid sequence corresponding to NCBI GI No. 224101735 (*Populus trichocarpa*).

SEQ ID NO: 43 is the amino acid sequence corresponding to NCBI GI No. 158564576 (*Paeonia suffruticosa*).

SEQ ID NO: 44 is the amino acid sequence corresponding to Glyma20g24980.1, a soybean (*Glycine max*) predicted protein from predicted coding sequences from Soybean JGI Glyma1.01 genomic sequence from the US Department of energy Joint Genome Institute.

SEQ ID NO: 45 is the amino acid sequence corresponding to Glyma07g10220.1, a soybean (*Glycine max*) predicted protein from predicted coding sequences from Soybean JGI Glyma1.01 genomic sequence from the US Department of energy Joint Genome Institute.

SEQ ID NO: 46 is the amino acid sequence corresponding to Glyma09g31670.1, a soybean (*Glycine max*) predicted protein from predicted coding sequences from Soybean JGI Glyma1.01 genomic sequence from the US Department of energy Joint Genome Institute.

SEQ ID NO: 47 is the amino acid sequence corresponding to NCBI GI No. 225423987 (*Vitis vinifera*).

SEQ ID NO: 48 is the amino acid sequence corresponding to NCBI GI No. 225452037 (*Vitis vinifera*).

SEQ ID NO: 49 is the amino acid sequence corresponding to NCBI GI No. 224127662 (*Populus trichocarpa*).

SEQ ID NO: 50 is the amino acid sequence corresponding to NCBI GI No. 255560420 (*Ricinus communis*).

SEQ ID NO: 51 is the amino acid sequence corresponding to NCBI GI No. 90657583 (*Cleome spinosa*).

SEQ ID NO: 52 is the amino acid sequence corresponding to NCBI GI No. 90657618 (*Cleome spinosa*).

SEQ ID NO: 53 is the amino acid sequence corresponding to NCBI GI No. 217071284 (*Medicago truncatula*).

SEQ ID NO: 54 is the amino acid sequence corresponding to NCBI GI No. 30683268 (*Arabidopsis thaliana*).

SEQ ID NO: 55 is the amino acid sequence presented in SEQ ID NO: 7047 of US Publication No. US20090019601 (*Brassica napus*).

SEQ ID NO: 56 is the amino acid sequence presented in SEQ ID NO: 23781 of US Publication No. US20070214517 (*Arabidopsis thaliana*).

SEQ ID NO: 57 is the amino acid sequence corresponding to NCBI GI No. 226502893 (*Zea mays*).

SEQ ID NO: 58 is the amino acid sequence presented in SEQ ID NO: 51344 of US Publication No. US20070271633 (*Sorghum bicolor*).

SEQ ID NO: 59 is the amino acid sequence corresponding to NCBI GI No. 226510375 (*Zea mays*).

SEQ ID NO: 60 is the amino acid sequence presented in SEQ ID NO: 291825 of US Publication No. US20090087878 (*Zea mays*).

SEQ ID NO: 61 is the amino acid sequence corresponding to NCBI GI No. 242086136 (*Sorghum bicolor*).

SEQ ID NO: 62 is the amino acid sequence presented in SEQ ID NO: 305885 of US Publication No. US20090087878 (*Zea mays*).

SEQ ID NO: 63 is the amino acid sequence presented in SEQ ID NO: 322258 of US Publication No. US20090087878 (*Zea mays*).

SEQ ID NO: 64 is the amino acid sequence corresponding to NCBI GI No. 226510044 (*Zea mays*).

SEQ ID NO: 65 is the amino acid sequence presented in SEQ ID NO: 292701 of US Publication No. US20090087878 (*Zea mays*).

SEQ ID NO: 66 is the amino acid sequence presented in SEQ ID NO: 64538 of PCT International Patent Publication No WO2009134339 (*Triticum aestivum*).

SEQ ID NO: 67 is the amino acid sequence corresponding to NCBI GI No. 255640685 (*Glycine max*).

SEQ ID NO: 68 is the amino acid sequence presented in SEQ ID NO: 52070 of US Publication No. US20070214517 (*Glycine max*).

SEQ ID NO: 69 is the amino acid sequence corresponding to NCBI GI No. 255632129 (*Glycine max*).

SEQ ID NO: 70 is the amino acid sequence presented in SEQ ID NO: 58426 of PCT International Patent Publication No WO2009134339 (*Glycine max*).

SEQ ID NO: 71 is the sequence of a conserved motif (motif 1) present near the amino-terminus of the DTP6 polypeptides of the present invention.

SEQ ID NO: 72 is the sequence of a conserved motif (motif 2) present in DTP6 polypeptides of the present invention.

SEQ ID NO: 73 is the sequence of a conserved motif (motif 3) present near the carboxyl-terminus of the DTP6 polypeptides of the present invention.

SEQ ID NO: 86 is the nucleotide sequence corresponding to GI No. 39569725 (*Triticum aestivum*).

SEQ ID NO: 87 is the polypeptide sequence encoded by the nucleotide sequence presented in SEQ ID NO: 86 (*Triticum aestivum*).

SEQ ID NO: 88 is the nucleotide sequence corresponding to GI No. 16321621 (*Hordeum vulgare*).

SEQ ID NO: 89 is the polypeptide sequence encoded by the nucleotide sequence presented in SEQ ID NO: 88 (*Hordeum vulgare*).

SEQ ID NO: 90 is the amino acid sequence of the predicted chloroplast transit peptide for AT-DTP6 protein (SEQ ID NO: 18).

SEQ ID NO: 91 is the amino acid sequence of the predicted mature AT-DTP6 protein.

SEQ ID NO: 92 is the amino acid sequence presented in SEQ ID NO: 333737 of US Publication No. US20110214206 (*Zea mays*).

SEQ ID NO: 93 is the amino acid sequence corresponding to NCBI GI No. 195612706 (*Zea mays*).

SEQ ID NO: 94 is the amino acid sequence presented in SEQ ID NO: 292701 of US Publication No US20110214206 (*Zea mays*).

SEQ ID NO: 95 is the amino acid sequence corresponding to NCBI GI No. 223949655 (*Zea mays*).

SEQ ID NO: 96 is the amino acid sequence presented in SEQ ID NO: 43585 of PCT International Patent Publication No WO2010083178 (*Zea mays*).

SEQ ID NO: 97 is the amino acid sequence corresponding to NCBI GI No. 238006286 (*Zea mays*).

SEQ ID NO: 98 is the amino acid sequence presented in SEQ ID NO: 77016 of US Publication No US20110214205 (*Setaria italica*).

SEQ ID NO: 99 is the amino acid sequence corresponding to NCBI GI No. 194703114 (*Zea mays*).

SEQ ID NO: 100 is the amino acid sequence presented in SEQ ID NO: 85465 of US Publication No US20110214205 (*Setaria italica*).

SEQ ID NO: 101 is the amino acid sequence corresponding to NCBI GI No. 57900114 (*Oryza sativa*).

SEQ ID NO: 102 is the amino acid sequence presented in SEQ ID NO: 67537 of EP2336332 (*Picea sitchensis*).

SEQ ID NO: 103 is the amino acid sequence corresponding to NCBI GI No. 116790833 (*Picea sitchensis*).

The sequence descriptions and Sequence Listing attached hereto comply with the rules governing nucleotide and/or amino acid sequence disclosures in patent applications as set forth in 37 C.F.R. §1.821-1.825.

The Sequence Listing contains the one letter code for nucleotide sequence characters and the three letter codes for amino acids as defined in conformity with the IUPAC-IUBMB standards described in *Nucleic Acids Res.* 13:3021-3030 (1985) and in the *Biochemical J.* 219 (No. 2):345-373 (1984) which are herein incorporated by reference. The symbols and format used for nucleotide and amino acid sequence data comply with the rules set forth in 37 C.F.R. §1.822.

DETAILED DESCRIPTION

The disclosure of each reference set forth herein is hereby incorporated by reference in its entirety.

As used herein and in the appended claims, the singular forms "a", "an", and "the" include plural reference unless the context clearly dictates otherwise. Thus, for example, reference to "a plant" includes a plurality of such plants, reference to "a cell" includes one or more cells and equivalents thereof known to those skilled in the art, and so forth.

As used herein:

The term "AT-DTP6" refers to an *Arabidopsis thaliana* protein that confers a drought tolerance (DT) phenotype and is encoded by the *Arabidopsis thaliana* locus At1g68490. The terms "DTP" and "Drought Tolerant Phenotype" are used interchangeably herein. "DTP6 polypeptide" refers to a protein with a Drought Tolerance Phenotype and refers herein to the AT-DTP6 polypeptide and its homologs from other organisms. The terms Zm-DTP6 and Gm-DTP6 refer respectively to *Zea mays* and *Glycine max* proteins that are homologous to AT-DTP6.

The AT-DTP6 polypeptide (SEQ ID NO: 18) encoded by the nucleotide sequence (SEQ ID NO: 17) at locus At1g68490, has been reported to be upregulated by cytokinin treatment (Brenner et al *Plant Journal* (2005) 44, 314-333). It is downregulated in the seedling-lethal dpa1 (deficiency of plastid ATP synthase 1) *Arabidopsis* mutants (Bosco et al *J. Biol. Chem.* (2004) 279 (2): 1060-1069). This protein does not have any prior assigned function or annotation. The DTP6 sequences presented herein have three conserved motifs, shown as motif 1, motif 2 and motif 3 (SEQ ID NOS: 71, 72 and 73, respectively).

As disclosed herein, The AT-DTP6 protein is predicted to be localized in the chloroplast, and has a predicted chloroplast transit peptide (SEQ ID NO: 90) at the N-terminus.

As disclosed herein, AT-DTP6 protein also confers tolerance to the combined triple stress of high heat, high light and drought. AT-DTP6 overexpressing plants also exhibit resistance to Paraquat, which indicates greater tolerance to oxidative stress.

The terms "monocot" and "monocotyledonous plant" are used interchangeably herein. A monocot of the current invention includes the Gramineae.

The terms "dicot" and "dicotyledonous plant" are used interchangeably herein. A dicot of the current invention includes the following families: Brassicaceae, Leguminosae, and Solanaceae.

The terms "full complement" and "full-length complement" are used interchangeably herein, and refer to a complement of a given nucleotide sequence, wherein the complement and the nucleotide sequence consist of the same number of nucleotides and are 100% complementary.

An "Expressed Sequence Tag" ("EST") is a DNA sequence derived from a cDNA library and therefore is a sequence which has been transcribed. An EST is typically obtained by a single sequencing pass of a cDNA insert. The sequence of an entire cDNA insert is termed the "Full-Insert Sequence" ("FIS"). A "Contig" sequence is a sequence assembled from two or more sequences that can be selected from, but not limited to, the group consisting of an EST, FIS and PCR sequence. A sequence encoding an entire or functional protein is termed a "Complete Gene Sequence" ("CGS") and can be derived from an FIS or a contig.

A "trait" refers to a physiological, morphological, biochemical, or physical characteristic of a plant or particular plant material or cell. In some instances, this characteristic is visible to the human eye, such as seed or plant size, or can be measured by biochemical techniques, such as detecting the protein, starch, or oil content of seed or leaves, or by observation of a metabolic or physiological process, e.g. by measuring tolerance to water deprivation or particular salt or sugar concentrations, or by the observation of the expression level of a gene or genes, or by agricultural observations such as osmotic stress tolerance or yield.

"Agronomic characteristic" is a measurable parameter including but not limited to, greenness, yield, growth rate, biomass, fresh weight at maturation, dry weight at maturation, fruit yield, seed yield, total plant nitrogen content, fruit nitrogen content, seed nitrogen content, nitrogen content in a vegetative tissue, total plant free amino acid content, fruit free amino acid content, seed free amino acid content, free amino acid content in a vegetative tissue, total plant protein content, fruit protein content, seed protein content, protein content in a vegetative tissue, drought tolerance, nitrogen uptake, root lodging, harvest index, stalk lodging, plant height, ear height, ear length, salt tolerance, early seedling vigor and seedling emergence under low temperature stress.

Increased biomass can be measured, for example, as an increase in plant height, plant total leaf area, plant fresh weight, plant dry weight or plant seed yield, as compared with control plants.

The ability to increase the biomass or size of a plant would have several important commercial applications. Crop species may be generated that produce larger cultivars, generating higher yield in, for example, plants in which the vegetative portion of the plant is useful as food, biofuel or both.

Increased leaf size may be of particular interest. Increasing leaf biomass can be used to increase production of plant-derived pharmaceutical or industrial products. An increase in total plant photosynthesis is typically achieved by increasing leaf area of the plant. Additional photosynthetic capacity may be used to increase the yield derived from particular plant tissue, including the leaves, roots, fruits or seed, or permit the growth of a plant under decreased light intensity or under high light intensity.

Modification of the biomass of another tissue, such as root tissue, may be useful to improve a plant's ability to grow under harsh environmental conditions, including drought or nutrient deprivation, because larger roots may better reach water or nutrients or take up water or nutrients.

For some ornamental plants, the ability to provide larger varieties would be highly desirable. For many plants, including fruit-bearing trees, trees that are used for lumber production, or trees and shrubs that serve as view or wind screens, increased stature provides improved benefits in the forms of greater yield or improved screening.

The growth and emergence of maize silks has a considerable importance in the determination of yield under drought (Fuad-Hassan et al. 2008 *Plant Cell Environ.* 31:1349-1360). When soil water deficit occurs before flowering, silk emergence out of the husks is delayed while anthesis is largely unaffected, resulting in an increased anthesis-silking interval (ASI) (Edmeades et al. 2000 *Physiology and Modeling Kernel set in Maize* (eds M. E. Westgate & K. Boote; CSSA (*Crop Science Society of America*) *Special Publication No.* 29. Madison, Wis.: CSSA, 43-73). Selection for reduced ASI has been used successfully to increase drought tolerance of maize (Edmeades et al. 1993 *Crop Science* 33: 1029-1035; Bolanos & Edmeades 1996 *Field Crops Research* 48:65-80; Bruce et al. 2002 *J. Exp. Botany* 53:13-25).

Terms used herein to describe thermal time include "growing degree days" (GDD), "growing degree units" (GDU) and "heat units" (HU).

"Transgenic" refers to any cell, cell line, callus, tissue, plant part or plant, the genome of which has been altered by the presence of a heterologous nucleic acid, such as a recombinant DNA construct, including those initial transgenic events as well as those created by sexual crosses or asexual propagation from the initial transgenic event. The term "transgenic" as used herein does not encompass the alteration of the genome (chromosomal or extra-chromosomal) by conventional plant breeding methods or by naturally occurring events such as random cross-fertilization, non-recombinant viral infection, non-recombinant bacterial transformation, non-recombinant transposition, or spontaneous mutation.

"Genome" as it applies to plant cells encompasses not only chromosomal DNA found within the nucleus, but organelle DNA found within subcellular components (e.g., mitochondrial, plastid) of the cell.

"Plant" includes reference to whole plants, plant organs, plant tissues, seeds and plant cells and progeny of same. Plant cells include, without limitation, cells from seeds, suspension cultures, embryos, meristematic regions, callus tissue, leaves, roots, shoots, gametophytes, sporophytes, pollen, and microspores.

"Progeny" comprises any subsequent generation of a plant.

"Transgenic plant" includes reference to a plant which comprises within its genome a heterologous polynucleotide. For example, the heterologous polynucleotide is stably integrated within the genome such that the polynucleotide is passed on to successive generations. The heterologous polynucleotide may be integrated into the genome alone or as part of a recombinant DNA construct.

The commercial development of genetically improved germplasm has also advanced to the stage of introducing multiple traits into crop plants, often referred to as a gene stacking approach. In this approach, multiple genes conferring different characteristics of interest can be introduced into a plant. Gene stacking can be accomplished by many means including but not limited to co-transformation, retransformation, and crossing lines with different transgenes.

"Transgenic plant" also includes reference to plants which comprise more than one heterologous polynucleotide within their genome. Each heterologous polynucleotide may confer a different trait to the transgenic plant.

"Heterologous" with respect to sequence means a sequence that originates from a foreign species, or, if from the same species, is substantially modified from its native form in composition and/or genomic locus by deliberate human intervention.

"Polynucleotide", "nucleic acid sequence", "nucleotide sequence", or "nucleic acid fragment" are used interchangeably and is a polymer of RNA or DNA that is single- or double-stranded, optionally containing synthetic, non-natural or altered nucleotide bases. Nucleotides (usually found in their 5'-monophosphate form) are referred to by their single letter designation as follows: "A" for adenylate or deoxyadenylate (for RNA or DNA, respectively), "C" for cytidylate or deoxycytidylate, "G" for guanylate or deoxyguanylate, "U" for uridylate, "T" for deoxythymidylate, "R" for purines (A or G), "Y" for pyrimidines (C or T), "K" for G or T, "H" for A or C or T, "I" for inosine, and "N" for any nucleotide.

"Polypeptide", "peptide", "amino acid sequence" and "protein" are used interchangeably herein to refer to a polymer of amino acid residues. The terms apply to amino acid polymers in which one or more amino acid residue is an artificial chemical analogue of a corresponding naturally occurring amino acid, as well as to naturally occurring amino acid polymers. The terms "polypeptide", "peptide", "amino acid sequence", and "protein" are also inclusive of modifications including, but not limited to, glycosylation, lipid attachment, sulfation, gamma-carboxylation of glutamic acid residues, hydroxylation and ADP-ribosylation.

"Messenger RNA (mRNA)" refers to the RNA that is without introns and that can be translated into protein by the cell.

"cDNA" refers to a DNA that is complementary to and synthesized from a mRNA template using the enzyme reverse transcriptase. The cDNA can be single-stranded or converted into the double-stranded form using the Klenow fragment of DNA polymerase I.

"Mature" protein refers to a post-translationally processed polypeptide; i.e., one from which any pre- or pro-peptides present in the primary translation product have been removed.

"Precursor" protein refers to the primary product of translation of mRNA; i.e., with pre- and pro-peptides still present. Pre- and pro-peptides may be and are not limited to intracellular localization signals.

"Isolated" refers to materials, such as nucleic acid molecules and/or proteins, which are substantially free or otherwise removed from components that normally accompany or interact with the materials in a naturally occurring environment. Isolated polynucleotides may be purified from a host cell in which they naturally occur. Conventional nucleic acid purification methods known to skilled artisans may be used to obtain isolated polynucleotides. The term also embraces recombinant polynucleotides and chemically synthesized polynucleotides.

"Recombinant" refers to an artificial combination of two otherwise separated segments of sequence, e.g., by chemical synthesis or by the manipulation of isolated segments of nucleic acids by genetic engineering techniques. "Recombinant" also includes reference to a cell or vector, that has been modified by the introduction of a heterologous nucleic acid or a cell derived from a cell so modified, but does not encompass the alteration of the cell or vector by naturally occurring events (e.g., spontaneous mutation, natural transformation/transduction/transposition) such as those occurring without deliberate human intervention.

"Recombinant DNA construct" refers to a combination of nucleic acid fragments that are not normally found together in nature. Accordingly, a recombinant DNA construct may comprise regulatory sequences and coding sequences that are derived from different sources, or regulatory sequences and coding sequences derived from the same source, but arranged in a manner different than that normally found in nature.

The terms "entry clone" and "entry vector" are used interchangeably herein.

"Regulatory sequences" refer to nucleotide sequences located upstream (5' non-coding sequences), within, or downstream (3' non-coding sequences) of a coding sequence, and which influence the transcription, RNA processing or stability, or translation of the associated coding sequence. Regulatory sequences may include, but are not limited to, promoters, translation leader sequences, introns, and polyadenylation recognition sequences. The terms "regulatory sequence" and "regulatory element" are used interchangeably herein.

"Promoter" refers to a nucleic acid fragment capable of controlling transcription of another nucleic acid fragment.

"Promoter functional in a plant" is a promoter capable of controlling transcription in plant cells whether or not its origin is from a plant cell.

"Tissue-specific promoter" and "tissue-preferred promoter" are used interchangeably, and refer to a promoter that is expressed predominantly but not necessarily exclusively in one tissue or organ, but that may also be expressed in one specific cell.

"Developmentally regulated promoter" refers to a promoter whose activity is determined by developmental events.

"Operably linked" refers to the association of nucleic acid fragments in a single fragment so that the function of one is regulated by the other. For example, a promoter is operably linked with a nucleic acid fragment when it is capable of regulating the transcription of that nucleic acid fragment.

"Expression" refers to the production of a functional product. For example, expression of a nucleic acid fragment may refer to transcription of the nucleic acid fragment (e.g., transcription resulting in mRNA or functional RNA) and/or translation of mRNA into a precursor or mature protein.

"Phenotype" means the detectable characteristics of a cell or organism.

"Introduced" in the context of inserting a nucleic acid fragment (e.g., a recombinant DNA construct) into a cell, means "transfection" or "transformation" or "transduction" and includes reference to the incorporation of a nucleic acid fragment into a eukaryotic or prokaryotic cell where the nucleic acid fragment may be incorporated into the genome of the cell (e.g., chromosome, plasmid, plastid or mitochondrial DNA), converted into an autonomous replicon, or transiently expressed (e.g., transfected mRNA).

A "transformed cell" is any cell into which a nucleic acid fragment (e.g., a recombinant DNA construct) has been introduced.

"Transformation" as used herein refers to both stable transformation and transient transformation.

"Stable transformation" refers to the introduction of a nucleic acid fragment into a genome of a host organism resulting in genetically stable inheritance. Once stably transformed, the nucleic acid fragment is stably integrated in the genome of the host organism and any subsequent generation.

"Transient transformation" refers to the introduction of a nucleic acid fragment into the nucleus, or DNA-containing organelle, of a host organism resulting in gene expression without genetically stable inheritance.

"Allele" is one of several alternative forms of a gene occupying a given locus on a chromosome. When the alleles present at a given locus on a pair of homologous chromosomes in a diploid plant are the same that plant is homozygous at that locus. If the alleles present at a given locus on a pair of homologous chromosomes in a diploid plant differ that plant is heterozygous at that locus. If a transgene is present on one of a pair of homologous chromosomes in a diploid plant that plant is hemizygous at that locus.

A "chloroplast transit peptide" is an amino acid sequence which is translated in conjunction with a protein and directs the protein to the chloroplast or other plastid types present in the cell in which the protein is made (Lee et al. (2008) *Plant Cell* 20:1603-1622). The terms "chloroplast transit peptide" and "plastid transit peptide" are used interchangeably herein. "Chloroplast transit sequence" refers to a nucleotide sequence that encodes a chloroplast transit peptide. A "signal peptide" is an amino acid sequence which is translated in conjunction with a protein and directs the protein to the secretory system (Chrispeels (1991) *Ann. Rev. Plant Phys. Plant Mol. Biol.* 42:21-53). If the protein is to be directed to a vacuole, a vacuolar targeting signal (supra) can further be added, or if to the endoplasmic reticulum, an endoplasmic reticulum retention signal (supra) may be added. If the protein is to be directed to the nucleus, any signal peptide present should be removed and instead a nuclear localization signal included (Raikhel (1992) *Plant Phys.* 100:1627-1632). A "mitochondrial signal peptide" is an amino acid sequence which directs a precursor protein into the mitochondria (Zhang and Glaser (2002) *Trends Plant Sci* 7:14-21).

The terms "Expressologs" or "expression homologs" are used interchangeably herein and refer to homologous sets of genes occurring across two or more distinct species that share similarity in gene expression patterns under specific conditions. The best expressologs are not necessarily the most similar at the level of sequence.

The terms "Profile HMMs" or "HMM profile" are used interchangeably herein as used herein are statistical models of multiple sequence alignments, or even of single sequences. They capture position-specific information about how conserved each column of the alignment is, and which residues are likely.

Sequence alignments and percent identity calculations may be determined using a variety of comparison methods designed to detect homologous sequences including, but not limited to, the Megalign® program of the LASERGENE® bioinformatics computing suite (DNASTAR® Inc., Madison, Wis.). Unless stated otherwise, multiple alignment of the sequences provided herein were performed using the Clustal V method of alignment (Higgins and Sharp (1989) CABIOS. 5:151-153) with the default parameters (GAP PENALTY=10, GAP LENGTH PENALTY=10). Default parameters for pairwise alignments and calculation of percent identity of protein sequences using the Clustal V method are KTUPLE=1, GAP PENALTY=3, WINDOW=5 and DIAGONALS SAVED=5. For nucleic acids these parameters are KTUPLE=2, GAP PENALTY=5, WINDOW=4 and DIAGONALS SAVED=4. After alignment of the sequences, using the Clustal V program, it is possible to obtain "percent identity" and "divergence" values by viewing the "sequence distances" table on the same program; unless stated otherwise, percent identities and divergences provided and claimed herein were calculated in this manner.

Standard recombinant DNA and molecular cloning techniques used herein are well known in the art and are described more fully in Sambrook, J., Fritsch, E. F. and Maniatis, T. *Molecular Cloning: A Laboratory Manual*; Cold Spring Harbor Laboratory Press Cold Spring Harbor, 1989 (hereinafter "Sambrook").

Turning now to the embodiments:

The present invention encompasses all protein sequences that match DTP6 profile HMM given FIG. 13A-FIG. 13Y.

In one embodiment of the invention the AT-DTP6 polypeptide has a chloroplast transit peptide at the N-terminus.

In one embodiment, the mature AT-DTP6 polypeptide can be operably linked to any chloroplast transit peptide sequence. In one embodiment the chloroplast transit peptide sequence comprises the amino acid sequence of SEQ ID NO: 90.

In one embodiment, any of the DTP6 proteins disclosed in the current invention can be operably linked to a chloroplast transit peptide sequence.

In one embodiment, the predicted chloroplast transit peptide disclosed in SEQ ID NO: 90 can be operably linked to another DTP6 polypeptide.

Embodiments include isolated polynucleotides and polypeptides, recombinant DNA constructs useful for conferring drought tolerance, compositions (such as plants or seeds) comprising these recombinant DNA constructs, and methods utilizing these recombinant DNA constructs.

Isolated Polynucleotides and Polypeptides:

The present invention includes the following isolated polynucleotides and polypeptides:

An isolated polynucleotide comprising: (i) a nucleic acid sequence encoding a polypeptide having an amino acid sequence of at least 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or 100% sequence identity, based on the Clustal V method of alignment, when compared to SEQ ID NOS: 18, 20, 22, 24, 26, 28, 30, 32, 34, 36, 38-70, 75, 77, 79, 81, 83, 85, 87, 89, 91, 92-102 or 103 or (ii) a full complement of the nucleic acid sequence of (i), wherein the full complement and the nucleic acid sequence of (i) consist of the same number of nucleotides and are 100% complementary. Any of the foregoing isolated polynucleotides may be utilized in any recombinant DNA constructs (including suppression DNA constructs) of the present invention. The polypeptide is preferably a DTP6 polypeptide. The polypeptide preferably has either one or more than one of the following: drought tolerance activity, triple stress tolerance activity or Paraquat tolerance activity.

An isolated polypeptide having an amino acid sequence of at least 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or 100% sequence identity, based on the Clustal V method of alignment, when compared to SEQ ID NOS: 18, 20, 22, 24, 26, 28, 30, 32, 34, 36, 38-70, 75, 77, 79, 81, 83, 85, 87, 89, 91, 92-102 or 103. The polypeptide is preferably a DTP6 polypeptide. The polypeptide preferably has either one or more than one of the following: drought tolerance activity, triple stress tolerance activity or Paraquat tolerance activity.

An isolated polynucleotide comprising (i) a nucleic acid sequence of at least 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or 100% sequence identity, based on the Clustal V method of alignment, when compared to SEQ ID NOS: 18, 20, 22, 24, 26, 28, 30, 32, 34, 36, 38-70, 75, 77, 79, 81, 83, 85, 87, 89, 91, 92-102 or 103; or (ii) a full complement of the nucleic acid sequence of (i). Any of the foregoing isolated polynucleotides may be utilized in any recombinant DNA constructs (including suppression DNA constructs) of the present invention. The isolated polynucleotide preferably encodes a DTP6 polypeptide. The DTP6 polypeptide preferably has either one or more than one of the following: drought tolerance activity, triple stress tolerance activity or Paraquat tolerance activity.

An isolated polynucleotide comprising: (i) a nucleic acid sequence encoding a polypeptide having an amino acid sequence comprising at least one, or at least two, or at least three of the sequences selected from the group consisting of SEQ ID NO:71, 72 and 73 or (ii) a full complement of the nucleic acid sequence of (i), wherein the full complement and the nucleic acid sequence of (i) consist of the same number of nucleotides and are 100% complementary. The polypeptide is preferably a DTP6 polypeptide. The polypeptide preferably has either one or more than one of the following: drought tolerance activity, triple stress tolerance activity or Paraquat tolerance activity.

An isolated polypeptide having an amino acid sequence comprising at least one, or at least two, or at least three of the sequences selected from the group consisting of SEQ ID NO: 71, 72 and 73. The polypeptide is preferably a DTP6 polypeptide. The polypeptide preferably has either one or more than one of the following: drought tolerance activity, triple stress tolerance activity or Paraquat tolerance activity.

An isolated polynucleotide comprising a nucleotide sequence encoding a polypeptide with one or more than one of the following: drought tolerance activity, triple stress tolerance activity or Paraquat tolerance activity, wherein the nucleotide sequence is hybridizable under stringent conditions with a DNA molecule comprising the full complement of SEQ ID NOS: 18, 20, 22, 24, 26, 28, 30, 32, 34, 36, 38-70, 75, 77, 79, 81, 83, 85, 87, 89, 91, 92-102 or 103;

An isolated polynucleotide comprising a nucleotide sequence encoding a polypeptide with one or more than one of the following: drought tolerance activity, triple stress tolerance activity or Paraquat tolerance activity, wherein the nucleotide sequence is derived from SEQ ID NOS: 18, 20, 22, 24, 26, 28, 30, 32, 34, 36, 38-70, 75, 77, 79, 81, 83, 85, 87, 89, 91, 92-102 or 103 by alteration of one or more nucleotides by at least one method selected from the group consisting of: deletion, substitution, addition and insertion.

It is understood, as those skilled in the art will appreciate, that the invention encompasses more than the specific exemplary sequences. Alterations in a nucleic acid fragment which result in the production of a chemically equivalent amino acid at a given site, but do not affect the functional properties of the encoded polypeptide, are well known in the art. For example, a codon for the amino acid alanine, a hydrophobic amino acid, may be substituted by a codon encoding another less hydrophobic residue, such as glycine, or a more hydrophobic residue, such as valine, leucine, or isoleucine. Similarly, changes which result in substitution of one negatively charged residue for another, such as aspartic acid for glutamic acid, or one positively charged residue for another, such as lysine for arginine, can also be expected to produce a functionally equivalent product. Nucleotide changes which result in alteration of the N-terminal and C-terminal portions of the polypeptide molecule would also not be expected to alter the activity of the polypeptide. Each of the proposed modifications is well within the routine skill in the art, as is determination of retention of biological activity of the encoded products.

The protein of the current invention may also be a protein which comprises an amino acid sequence comprising deletion, substitution, insertion and/or addition of one or more amino acids in an amino acid sequence selected from the group consisting of SEQ ID NO:27, 32, 41, 42, 45, 46, 52, 54, 56, 58, 60, 62, 64 and 66. The substitution may be conservative, which means the replacement of a certain amino acid residue by another residue having similar physical and chemical characteristics. Non-limiting examples of conservative substitution include replacement between aliphatic group-containing amino acid residues such as Ile, Val, Leu or Ala, and replacement between polar residues such as Lys-Arg, Glu-Asp or Gln-Asn replacement.

Proteins derived by amino acid deletion, substitution, insertion and/or addition can be prepared when DNAs encoding their wild-type proteins are subjected to, for example, well-known site-directed mutagenesis (see, e.g., Nucleic Acid Research, Vol. 10, No. 20, p. 6487-6500, 1982, which is hereby incorporated by reference in its entirety). As used herein, the term "one or more amino acids" is intended to mean a possible number of amino acids which may be deleted, substituted, inserted and/or added by site-directed mutagenesis.

Site-directed mutagenesis may be accomplished, for example, as follows using a synthetic oligonucleotide primer that is complementary to single-stranded phage DNA to be mutated, except for having a specific mismatch (i.e., a desired mutation). Namely, the above synthetic oligonucleotide is used as a primer to cause synthesis of a complementary strand by phages, and the resulting duplex DNA is then used to transform host cells. The transformed bacterial culture is plated on agar, whereby plaques are allowed to form from phage-containing single cells. As a result, in theory, 50% of new colonies contain phages with the mutation as a single strand, while the remaining 50% have the original sequence. At a temperature which allows hybridization with DNA completely identical to one having the above desired mutation, but not with DNA having the original strand, the resulting plaques are allowed to hybridize with a synthetic probe labeled by kinase treatment. Subsequently, plaques hybridized with the probe are picked up and cultured for collection of their DNA.

Techniques for allowing deletion, substitution, insertion and/or addition of one or more amino acids in the amino acid sequences of biologically active peptides such as enzymes while retaining their activity include site-directed mutagenesis mentioned above, as well as other techniques such as those for treating a gene with a mutagen, and those in which a gene is selectively cleaved to remove, substitute, insert or add a selected nucleotide or nucleotides, and then ligated.

The protein of the present invention may also be a protein which is encoded by a nucleic acid comprising a nucleotide sequence comprising deletion, substitution, insertion and/or addition of one or more nucleotides in a nucleotide sequence selected from the group consisting of SEQ ID NO:26, 31, 39, 40, 43, 44, 51, 53, 55, 57, 59, 60, 63 and 65. Nucleotide deletion, substitution, insertion and/or addition may be accomplished by site-directed mutagenesis or other techniques as mentioned above.

The protein of the present invention may also be a protein which is encoded by a nucleic acid comprising a nucleotide sequence hybridizable under stringent conditions with the complementary strand of a nucleotide sequence selected from the group consisting of SEQ ID NO:26, 31, 39, 40, 43, 44, 51, 53, 55, 57, 59, 60, 63 and 65.

The term "under stringent conditions" means that two sequences hybridize under moderately or highly stringent conditions. More specifically, moderately stringent conditions can be readily determined by those having ordinary skill in the art, e.g., depending on the length of DNA. The basic conditions are set forth by Sambrook et al., Molecular Cloning: A Laboratory Manual, third edition, chapters 6 and 7, Cold Spring Harbor Laboratory Press, 2001 and include the use of a prewashing solution for nitrocellulose filters 5×SSC, 0.5% SDS, 1.0 mM EDTA (pH 8.0), hybridization conditions of about 50% formamide, 2×SSC to 6×SSC at about 40-50° C. (or other similar hybridization solutions, such as Stark's solution, in about 50% formamide at about 42° C.) and washing conditions of, for example, about 40-60° C., 0.5-6×SSC, 0.1% SDS. Preferably, moderately stringent conditions include hybridization (and washing) at about 50° C. and 6×SSC. Highly stringent conditions can also be readily determined by those skilled in the art, e.g., depending on the length of DNA.

Generally, such conditions include hybridization and/or washing at higher temperature and/or lower salt concentration (such as hybridization at about 65° C., 6×SSC to 0.2×SSC, preferably 6×SSC, more preferably 2×SSC, most preferably 0.2×SSC), compared to the moderately stringent conditions. For example, highly stringent conditions may include hybridization as defined above, and washing at approximately 65-68° C., 0.2×SSC, 0.1% SDS. SSPE (1×SSPE is 0.15 M NaCl, 10 mM NaH2PO4, and 1.25 mM EDTA, pH 7.4) can be substituted for SSC (1×SSC is 0.15 M NaCl and 15 mM sodium citrate) in the hybridization and washing buffers; washing is performed for 15 minutes after hybridization is completed.

It is also possible to use a commercially available hybridization kit which uses no radioactive substance as a probe. Specific examples include hybridization with an ECL direct labeling & detection system (Amersham). Stringent conditions include, for example, hybridization at 42° C. for 4 hours using the hybridization buffer included in the kit, which is supplemented with 5% (w/v) Blocking reagent and 0.5 M NaCl, and washing twice in 0.4% SDS, 0.5×SSC at 55° C. for 20 minutes and once in 2×SSC at room temperature for 5 minutes.

Recombinant DNA Constructs and Suppression DNA Constructs:

In one aspect, the present invention includes recombinant DNA constructs (including suppression DNA constructs).

In one embodiment, a recombinant DNA construct comprises a polynucleotide operably linked to at least one regulatory sequence (e.g., a promoter functional in a plant), wherein the polynucleotide comprises (i) a nucleic acid sequence encoding an amino acid sequence of at least 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or 100% sequence identity, based on the Clustal V method of alignment, when compared to SEQ ID NOS: 18, 20, 22, 24, 26, 28, 30, 32, 34, 36, 38-70, 75, 77, 79, 81, 83, 85, 87, 89, 91, 92-102 or 103; or (ii) a full complement of the nucleic acid sequence of (i).

In another embodiment, a recombinant DNA construct comprises a polynucleotide operably linked to at least one regulatory sequence (e.g., a promoter functional in a plant), wherein said polynucleotide comprises (i) a nucleic acid sequence of at least 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or 100% sequence identity, based on the Clustal V method of alignment, when compared to SEQ ID NOS: 17, 19, 21, 23, 25, 27, 29, 31, 33, 35, 37, 74, 76, 78, 80, 82, 84, 86 and 88; or (ii) a full complement of the nucleic acid sequence of (i).

In another embodiment, a recombinant DNA construct comprises a polynucleotide operably linked to at least one regulatory sequence (e.g., a promoter functional in a plant), wherein said polynucleotide encodes a DTP6 polypeptide. The DTP6 polypeptide preferably has either one or more than one of the following: drought tolerance activity, triple stress tolerance activity or Paraquat tolerance activity.

The DTP6 polypeptide may be from *Arabidopsis thaliana*, *Zea mays*, *Glycine max*, *Glycine tabacina*, *Glycine soja*, *Glycine tomentella*, *Populus trichocarpa*, *Vitis vinifera*, *Ricinus communis*, *Paeonia suffruticosa*, *Manihot esculenta*, *Cleome spinosa*, *Brassica napus*, *Sorghum bicolor*, *Triticum aestivum*, *Paspalum notatum*, *Dennstaedtia punctilobuia* and *Eragrostis nindensis*.

In another aspect, the present invention includes suppression DNA constructs.

A suppression DNA construct may comprise at least one regulatory sequence (e.g., a promoter functional in a plant) operably linked to (a) all or part of: (i) a nucleic acid sequence encoding a polypeptide having an amino acid sequence of at least 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or 100% sequence identity, based on the Clustal V method of alignment, when compared to SEQ ID NOS: 18, 20, 22, 24, 26, 28, 30, 32, 34, 36, 38-70, 75, 77, 79, 81, 83, 85, 87, 89, 91, 92-102 or 103, or (ii) a full complement of the nucleic acid sequence of (a)(i); or (b) a region derived from all or part of a sense strand or antisense strand of a target gene of interest, said region having a nucleic acid sequence of at least 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or 100% sequence identity, based on the Clustal V method of alignment, when compared to said all or part of a sense strand or antisense strand from which said region is derived, and wherein said target gene of interest encodes a DTP6 polypeptide; or (c) all or part of: (i) a nucleic acid sequence of at least 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or 100% sequence identity, based on the Clustal V method of alignment, when compared to SEQ ID NOS: 17, 19, 21, 23, 25, 27, 29, 31, 33, 35, 37, 74, 76, 78, 80, 82, 84, 86 and 88, or (ii) a full complement of the nucleic acid sequence of (c)(i). The suppression DNA construct may comprise a cosuppression construct, antisense construct, viral-suppression construct, hairpin suppression construct, stem-loop suppression construct, double-stranded RNA-producing construct, RNAi construct, or small RNA construct (e.g., an siRNA construct or an miRNA construct).

It is understood, as those skilled in the art will appreciate, that the invention encompasses more than the specific exemplary sequences. Alterations in a nucleic acid fragment which result in the production of a chemically equivalent amino acid at a given site, but do not affect the functional properties of the encoded polypeptide, are well known in the art. For example, a codon for the amino acid alanine, a hydrophobic amino acid, may be substituted by a codon encoding another less hydrophobic residue, such as glycine, or a more hydrophobic residue, such as valine, leucine, or isoleucine. Similarly, changes which result in substitution of one negatively charged residue for another, such as aspartic acid for glutamic acid, or one positively charged residue for another, such as lysine for arginine, can also be expected to produce a functionally equivalent product. Nucleotide changes which result in alteration of the N-terminal and C-terminal portions of the polypeptide molecule would also not be expected to alter the activity of the polypeptide. Each of the proposed modifications is well within the routine skill in the art, as is determination of retention of biological activity of the encoded products.

"Suppression DNA construct" is a recombinant DNA construct which when transformed or stably integrated into the genome of the plant, results in "silencing" of a target gene in the plant. The target gene may be endogenous or transgenic to the plant. "Silencing," as used herein with respect to the target gene, refers generally to the suppression of levels of mRNA or protein/enzyme expressed by the target gene, and/or the level of the enzyme activity or protein functionality. The terms "suppression", "suppressing" and "silencing", used interchangeably herein, include lowering, reducing, declining, decreasing, inhibiting, eliminating or preventing. "Silencing" or "gene silencing" does not specify mechanism and is inclusive, and not limited to, anti-sense, cosuppression, viral-suppression, hairpin suppression, stem-loop suppression, RNAi-based approaches, and small RNA-based approaches.

A suppression DNA construct may comprise a region derived from a target gene of interest and may comprise all or part of the nucleic acid sequence of the sense strand (or antisense strand) of the target gene of interest. Depending upon the approach to be utilized, the region may be 100% identical or less than 100% identical (e.g., at least 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, or 99% identical) to all or part of the sense strand (or antisense strand) of the gene of interest.

Suppression DNA constructs are well-known in the art, are readily constructed once the target gene of interest is selected, and include, without limitation, cosuppression constructs, antisense constructs, viral-suppression constructs, hairpin suppression constructs, stem-loop suppression constructs, double-stranded RNA-producing constructs, and more generally, RNAi (RNA interference) constructs and small RNA constructs such as siRNA (short interfering RNA) constructs and miRNA (microRNA) constructs.

"Antisense inhibition" refers to the production of antisense RNA transcripts capable of suppressing the expression of the target gene or gene product. "Antisense RNA" refers to an RNA transcript that is complementary to all or part of a target primary transcript or mRNA and that blocks the expression of a target isolated nucleic acid fragment (U.S. Pat. No. 5,107,065). The complementarity of an antisense RNA may be with any part of the specific gene transcript, i.e., at the 5' non-coding sequence, 3' non-coding sequence, introns, or the coding sequence.

"Cosuppression" refers to the production of sense RNA transcripts capable of suppressing the expression of the target gene or gene product. "Sense" RNA refers to RNA transcript that includes the mRNA and can be translated into protein within a cell or in vitro. Cosuppression constructs in plants have been previously designed by focusing on overexpression of a nucleic acid sequence having homology to a native mRNA, in the sense orientation, which results in the reduction of all RNA having homology to the overexpressed sequence (see Vaucheret et al., *Plant J.* 16:651-659 (1998); and Gura, *Nature* 404:804-808 (2000)).

Another variation describes the use of plant viral sequences to direct the suppression of proximal mRNA encoding sequences (PCT Publication No. WO 98/36083 published on Aug. 20, 1998).

RNA interference refers to the process of sequence-specific post-transcriptional gene silencing in animals mediated by short interfering RNAs (siRNAs) (Fire et al., *Nature* 391:806 (1998)). The corresponding process in plants is commonly referred to as post-transcriptional gene silencing (PTGS) or RNA silencing and is also referred to as quelling in fungi. The process of post-transcriptional gene silencing is thought to be an evolutionarily-conserved cellular defense mechanism used to prevent the expression of foreign genes and is commonly shared by diverse flora and phyla (Fire et al., *Trends Genet.* 15:358 (1999)).

Small RNAs play an important role in controlling gene expression. Regulation of many developmental processes, including flowering, is controlled by small RNAs. It is now possible to engineer changes in gene expression of plant genes by using transgenic constructs which produce small RNAs in the plant.

Small RNAs appear to function by base-pairing to complementary RNA or DNA target sequences. When bound to RNA, small RNAs trigger either RNA cleavage or translational inhibition of the target sequence. When bound to DNA target sequences, it is thought that small RNAs can mediate DNA methylation of the target sequence. The consequence of these events, regardless of the specific mechanism, is that gene expression is inhibited.

MicroRNAs (miRNAs) are noncoding RNAs of about 19 to about 24 nucleotides (nt) in length that have been identified in both animals and plants (Lagos-Quintana et al., *Science* 294:853-858 (2001), Lagos-Quintana et al., *Curr. Biol.* 12:735-739 (2002); Lau et al., *Science* 294:858-862 (2001); Lee and Ambros, *Science* 294:862-864 (2001); Llave et al., *Plant Cell* 14:1605-1619 (2002); Mourelatos et al., *Genes Dev.* 16:720-728 (2002); Park et al., Curr. Biol. 12:1484-1495 (2002); Reinhart et al., *Genes. Dev.* 16:1616-1626 (2002)). They are processed from longer precursor transcripts that range in size from approximately 70 to 200 nt, and these precursor transcripts have the ability to form stable hairpin structures.

MicroRNAs (miRNAs) appear to regulate target genes by binding to complementary sequences located in the transcripts produced by these genes. It seems likely that miRNAs can enter at least two pathways of target gene regulation: (1) translational inhibition; and (2) RNA cleavage. MicroRNAs entering the RNA cleavage pathway are analogous to the 21-25 nt short interfering RNAs (siRNAs) generated during RNA interference (RNAi) in animals and posttranscriptional gene silencing (PTGS) in plants, and likely are incorporated into an RNA-induced silencing complex (RISC) that is similar or identical to that seen for RNAi.

Regulatory Sequences:

A recombinant DNA construct (including a suppression DNA construct) of the present invention may comprise at least one regulatory sequence.

A regulatory sequence may be a promoter.

A number of promoters can be used in recombinant DNA constructs of the present invention. The promoters can be selected based on the desired outcome, and may include constitutive, tissue-specific, inducible, or other promoters for expression in the host organism.

Promoters that cause a gene to be expressed in most cell types at most times are commonly referred to as "constitutive promoters".

High level, constitutive expression of the candidate gene under control of the 35S or UBI promoter may have pleiotropic effects, although candidate gene efficacy may be estimated when driven by a constitutive promoter. Use of tissue-specific and/or stress-specific promoters may eliminate undesirable effects but retain the ability to enhance drought tolerance. This effect has been observed in *Arabidopsis* (Kasuga et al. (1999) *Nature Biotechnol.* 17:287-91).

Suitable constitutive promoters for use in a plant host cell include, for example, the core promoter of the Rsyn7 promoter and other constitutive promoters disclosed in WO 99/43838 and U.S. Pat. No. 6,072,050; the core CaMV 35S promoter (Odell et al., Nature 313:810-812 (1985)); rice actin (McElroy et al., Plant Cell 2:163-171 (1990)); ubiquitin (Christensen et al., Plant Mol. Biol. 12:619-632 (1989) and Christensen et al., Plant Mol. Biol. 18:675-689 (1992)); pEMU (Last et al., Theor. Appl. Genet. 81:581-588 (1991)); MAS (Velten et al., EMBO J. 3:2723-2730 (1984)); ALS promoter (U.S. Pat. No. 5,659,026), and the like. Other constitutive promoters include, for example, those discussed in U.S. Pat. Nos. 5,608,149; 5,608,144; 5,604,121; 5,569,597; 5,466,785; 5,399,680; 5,268,463; 5,608,142; and 6,177,611.

In choosing a promoter to use in the methods of the invention, it may be desirable to use a tissue-specific or developmentally regulated promoter.

A tissue-specific or developmentally regulated promoter is a DNA sequence which regulates the expression of a DNA sequence selectively in the cells/tissues of a plant critical to tassel development, seed set, or both, and limits the expression of such a DNA sequence to the period of tassel development or seed maturation in the plant. Any identifiable promoter may be used in the methods of the present invention which causes the desired temporal and spatial expression.

Promoters which are seed or embryo-specific and may be useful in the invention include soybean Kunitz trypsin inhibitor (Kti3, Jofuku and Goldberg, Plant Cell 1:1079-1093 (1989)), patatin (potato tubers) (Rocha-Sosa, M., et al. (1989) EMBO J. 8:23-29), convicilin, vicilin, and legumin (pea cotyledons) (Rerie, W. G., et al. (1991) Mol. Gen. Genet. 259:149-157; Newbigin, E. J., et al. (1990) Planta 180:461-470; Higgins, T. J. V., et al. (1988) Plant. Mol. Biol. 11:683-695), zein (maize endosperm) (Schemthaner, J. P., et al. (1988) EMBO J. 7:1249-1255), phaseolin (bean cotyledon) (Segupta-Gopalan, C., et al. (1985) Proc. Natl. Acad. Sci. U.S.A. 82:3320-3324), phytohemagglutinin (bean cotyledon) (Voelker, T. et al. (1987) EMBO J. 6:3571-3577), B-conglycinin and glycinin (soybean cotyledon) (Chen, Z-L, et al. (1988) EMBO J. 7:297-302), glutelin (rice endosperm), hordein (barley endosperm) (Marris, C., et al. (1988) Plant Mol. Biol. 10:359-366), glutenin and gliadin (wheat endosperm) (Colot, V., et al. (1987) EMBO J. 6:3559-3564), and sporamin (sweet potato tuberous root) (Hattori, T., et al. (1990) Plant Mol. Biol. 14:595-604). Promoters of seed-specific genes operably linked to heterologous coding regions in chimeric gene constructions maintain their temporal and spatial expression pattern in transgenic plants. Such examples include *Arabidopsis thaliana* 2S seed storage protein gene promoter to express enkephalin peptides in *Arabidopsis* and *Brassica napus* seeds (Vanderkerckhove et al., Bio/Technology 7:L929-932 (1989)), bean lectin and bean beta-phaseolin promoters to express luciferase (Riggs et al., Plant Sci. 63:47-57 (1989)), and wheat glutenin promoters to express chloramphenicol acetyl transferase (Colot et al., EMBO J 6:3559-3564 (1987)).

Inducible promoters selectively express an operably linked DNA sequence in response to the presence of an endogenous or exogenous stimulus, for example by chemical compounds (chemical inducers) or in response to environmental, hormonal, chemical, and/or developmental signals. Inducible or regulated promoters include, for example, promoters regulated by light, heat, stress, flooding or drought, phytohormones, wounding, or chemicals such as ethanol, jasmonate, salicylic acid, or safeners.

Promoters for use in the current invention include the following: 1) the stress-inducible RD29A promoter (Kasuga et al. (1999) Nature Biotechnol. 17:287-91); 2) the barley promoter, B22E; expression of B22E is specific to the pedicel in developing maize kernels ("Primary Structure of a Novel Barley Gene Differentially Expressed in Immature Aleurone Layers". Klemsdal, S. S. et al., Mol. Gen. Genet. 228(1/2):9-16 (1991)); and 3) maize promoter, Zag2 ("Identification and molecular characterization of ZAG1, the maize homolog of the *Arabidopsis* floral homeotic gene AGAMOUS", Schmidt, R. J. et al., Plant Cell 5(7):729-737 (1993); "Structural characterization, chromosomal localization and phylogenetic evaluation of two pairs of AGAMOUS-like MADS-box genes from maize", Theissen et al. Gene 156(2):155-166 (1995); NCBI GenBank Accession No. X80206)). Zag2 transcripts can be detected 5 days prior to pollination to 7 to 8 days after pollination ("DAP"), and directs expression in the carpel of developing female inflorescences and Ciml which is specific to the nucleus of developing maize kernels. Ciml transcript is detected 4 to 5 days before pollination to 6 to 8 DAP. Other useful promoters include any promoter which can be derived from a gene whose expression is maternally associated with developing female florets.

Additional promoters for regulating the expression of the nucleotide sequences of the present invention in plants are stalk-specific promoters. Such stalk-specific promoters include the alfalfa S2A promoter (GenBank Accession No. EF030816; Abrahams et al., Plant Mol. Biol. 27:513-528 (1995)) and S2B promoter (GenBank Accession No. EF030817) and the like, herein incorporated by reference.

Promoters may be derived in their entirety from a native gene, or be composed of different elements derived from different promoters found in nature, or even comprise synthetic DNA segments.

Promoters for use in the current invention may include: RIP2, mLIP15, ZmCOR1, Rab17, CaMV 35S, RD29A, B22E, Zag2, SAM synthetase, ubiquitin, CaMV 19S, nos, Adh, sucrose synthase, R-allele, the vascular tissue preferred promoters S2A (Genbank accession number EF030816) and S2B (Genbank accession number EF030817), and the constitutive promoter GOS2 from *Zea mays*. Other promoters include root preferred promoters, such as the maize NAS2 promoter, the maize Cyclo promoter (US 2006/0156439, published Jul. 13, 2006), the maize ROOTMET2 promoter (WO05063998, published Jul. 14, 2005), the CR1BIO promoter (WO06055487, published May 26, 2006), the CRWAQ81 (WO05035770, published Apr. 21, 2005) and the maize ZRP2.47 promoter (NCBI accession number: U38790; GI No. 1063664), Recombinant DNA constructs of the present invention may also include other regulatory sequences, including but not limited to, translation leader sequences, introns, and polyadenylation recognition sequences. In another embodiment of the present invention, a recombinant DNA construct of the present invention further comprises an enhancer or silencer.

An intron sequence can be added to the 5' untranslated region, the protein-coding region or the 3' untranslated region to increase the amount of the mature message that accumulates in the cytosol. Inclusion of a spliceable intron in the transcription unit in both plant and animal expression constructs has been shown to increase gene expression at both the mRNA and protein levels up to 1000-fold. Buchman and Berg, *Mol. Cell Biol.* 8:4395-4405 (1988); Callis et al., *Genes Dev.* 1:1183-1200 (1987).

Any plant can be selected for the identification of regulatory sequences and DTP6 polypeptide genes to be used in recombinant DNA constructs of the present invention. Examples of suitable plant targets for the isolation of genes and regulatory sequences would include but are not limited to alfalfa, apple, apricot, *Arabidopsis*, artichoke, arugula, asparagus, avocado, banana, barley, beans, beet, blackberry, blueberry, broccoli, brussels sprouts, cabbage, canola, cantaloupe, carrot, cassava, castorbean, cauliflower, celery, cherry, chicory, cilantro, citrus, clementines, clover, coconut, coffee, corn, cotton, cranberry, cucumber, Douglas fir, eggplant, endive, escarole, eucalyptus, fennel, figs, garlic, gourd, grape, grapefruit, honey dew, jicama, kiwifruit, lettuce, leeks, lemon, lime, Loblolly pine, linseed, mango, melon, mushroom, nectarine, nut, oat, oil palm, oil seed rape, okra, olive, onion, orange, an ornamental plant, palm, papaya, parsley, parsnip, pea, peach, peanut, pear, pepper, persimmon, pine, pineapple, plantain, plum, pomegranate, poplar, potato, pumpkin, quince, radiata pine, radicchio, radish, rapeseed, raspberry, rice, rye, sorghum, Southern pine, soybean, spinach, squash, strawberry, sugarbeet, sugarcane, sunflower, sweet potato, sweetgum, switchgrass, tangerine, tea, tobacco, tomato, triticale, turf, turnip, a vine, watermelon, wheat, yams, and zucchini.

Compositions:

A composition of the present invention is a plant comprising in its genome any of the recombinant DNA constructs (including any of the suppression DNA constructs) of the present invention (such as any of the constructs discussed above). Compositions also include any progeny of the plant, and any seed obtained from the plant or its progeny, wherein the progeny or seed comprises within its genome the recombinant DNA construct (or suppression DNA construct). Progeny includes subsequent generations obtained by self-pollination or out-crossing of a plant. Progeny also includes hybrids and inbreds.

In hybrid seed propagated crops, mature transgenic plants can be self-pollinated to produce a homozygous inbred plant. The inbred plant produces seed containing the newly introduced recombinant DNA construct (or suppression DNA construct). These seeds can be grown to produce plants that would exhibit an altered agronomic characteristic (e.g., an increased agronomic characteristic optionally under water limiting conditions), or used in a breeding program to produce hybrid seed, which can be grown to produce plants that would exhibit such an altered agronomic characteristic. The seeds may be maize seeds.

The plant may be a monocotyledonous or dicotyledonous plant, for example, a maize or soybean plant, such as a maize hybrid plant or a maize inbred plant. The plant may also be sunflower, sorghum, canola, wheat, alfalfa, cotton, rice, barley, millet, sugar cane or switchgrass.

The recombinant DNA construct may be stably integrated into the genome of the plant.

Particular embodiments include but are not limited to the following:

1. A plant (for example, a maize, rice or soybean plant) comprising in its genome a recombinant DNA construct comprising a polynucleotide operably linked to at least one regulatory sequence, wherein said polynucleotide encodes a polypeptide having an amino acid sequence of at least 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or 100% sequence identity, based on the Clustal V method of alignment, when compared to SEQ ID NOS: 18, 20, 22, 24, 26, 28, 30, 32, 34, 36, 38-70, 75, 77, 79, 81, 83, 85, 87, 89, 91, 92-102 or 103, and wherein said plant exhibits increased tolerance to one or more of the following stresses: drought stress, triple stress and Paraquat stress, when compared to a control plant not comprising said recombinant DNA construct. The plant may further exhibit an alteration of at least one agronomic characteristic when compared to the control plant.

2. A plant (for example, a maize, rice or soybean plant) comprising in its genome a recombinant DNA construct comprising a polynucleotide operably linked to at least one regulatory sequence, wherein said polynucleotide encodes a DTP6 polypeptide, and wherein said plant exhibits increased tolerance to one or more of the following stresses: drought stress, triple stress and Paraquat stress, when compared to a control plant not comprising said recombinant DNA construct. The plant may further exhibit an alteration of at least one agronomic characteristic when compared to the control plant.

3. A plant (for example, a maize, rice or soybean plant) comprising in its genome a recombinant DNA construct comprising a polynucleotide operably linked to at least one regulatory sequence, wherein said polynucleotide encodes a DTP6 polypeptide, and wherein said plant exhibits an alteration of at least one agronomic characteristic when compared to a control plant not comprising said recombinant DNA construct.

4. A plant (for example, a maize, rice or soybean plant) comprising in its genome a recombinant DNA construct comprising a polynucleotide operably linked to at least one regulatory element, wherein said polynucleotide comprises a nucleotide sequence encoding a polypeptide with drought tolerance activity, wherein the nucleotide sequence is: (a) hybridizable under stringent conditions with a DNA molecule comprising the full complement of SEQ ID NOS: 18, 20, 22, 24, 26, 28, 30, 32, 34, 36, 38-70, 75, 77, 79, 81, 83, 85, 87, 89, 91, 92-102 or 103; or (b) derived from SEQ ID NOS: 18, 20, 22, 24, 26, 28, 30, 32, 34, 36, 38-70, 75, 77, 79, 81, 83, 85, 87, 89, 91, 92-102 or 103 by alteration of one or more nucleotides by at least one method selected from the group consisting of: deletion, substitution, addition and insertion; and wherein said plant exhibits increased tolerance to one or more of the following stresses: drought stress, triple stress and Paraquat stress, when compared to a control plant not comprising said recombinant DNA construct.

5. A plant (for example, a maize, rice or soybean plant) comprising in its genome a recombinant DNA construct comprising a polynucleotide operably linked to at least one regulatory element, wherein said polynucleotide encodes a polypeptide having an amino acid sequence of at least 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or 100% sequence identity, based on the Clustal V method of alignment, when compared to SEQ ID NOS: 18, 20, 22, 24, 26, 28, 30, 32, 34, 36, 38-70, 75, 77, 79, 81, 83, 85, 87, 89, 91, 92-102 or 103, and wherein said plant exhibits an alteration of at least one agronomic characteristic when compared to a control plant not comprising said recombinant DNA construct.

6. A plant (for example, a maize, rice or soybean plant) comprising in its genome a recombinant DNA construct comprising a polynucleotide operably linked to at least one regulatory element, wherein said polynucleotide comprises a nucleotide sequence encoding a polypeptide with drought tolerance activity, wherein the nucleotide sequence is: (a) hybridizable under stringent conditions with a DNA molecule comprising the full complement of SEQ ID NOS: 18, 20, 22, 24, 26, 28, 30, 32, 34, 36, 38-70, 75, 77, 79, 81, 83, 85, 87, 89, 91, 92-102 or 103; or (b) derived from SEQ ID NOS: 18, 20, 22, 24, 26, 28, 30, 32, 34, 36, 38-70, 75, 77, 79, 81, 83, 85, 87, 89, 91, 92-102 or 103 by alteration of one or more nucleotides by at least one method selected from the group consisting of: deletion, substitution, addition and insertion; and wherein said plant exhibits an alteration of at least one agronomic characteristic when compared to a control plant not comprising said recombinant DNA construct.

7. A plant (for example, a maize, rice or soybean plant) comprising in its genome a suppression DNA construct comprising at least one regulatory element operably linked to a region derived from all or part of a sense strand or antisense strand of a target gene of interest, said region having a nucleic acid sequence of at least 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or 100% sequence identity, based on the Clustal V method of alignment, when compared to said all or part of a sense strand or antisense strand from which said region is derived, and wherein said target gene of interest encodes a DTP6 polypeptide, and wherein said plant exhibits an alteration of at least one agronomic characteristic when compared to a control plant not comprising said suppression DNA construct.

8. A plant (for example, a maize, rice or soybean plant) comprising in its genome a suppression DNA construct comprising at least one regulatory element operably linked to all or part of (a) a nucleic acid sequence encoding a polypeptide having an amino acid sequence of at least 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or 100% sequence identity, based on the Clustal V method of alignment, when compared to SEQ ID NOS: 18, 20, 22, 24, 26, 28, 30, 32, 34, 36, 38-70, 75, 77, 79, 81, 83, 85, 87, 89, 91, 92-102 or 103, or (b) a full complement of the nucleic acid sequence of (a), and wherein said plant exhibits an alteration of at least one agronomic characteristic when compared to a control plant not comprising said suppression DNA construct.

9. In another embodiment, a plant comprising in its genome a polynucleotide operably linked to at least one recombinant regulatory element, wherein said polynucleotide encodes a polypeptide having an amino acid sequence of at least 50% sequence identity, based on the Clustal V method of alignment, when compared to SEQ ID NOS: 18, 20, 22, 24, 26, 28, 30, 32, 34, 36, 38-70, 75, 77, 79, 81, 83, 85, 87, 89, 91, 92-102 or 103, and wherein said plant exhibits increased drought tolerance when compared to a control plant not comprising the recombinant regulatory element. The at least one recombinant regulatory element may comprise a promoter, an enhancer, or both, wherein the promoter and the enhancer are functional in a plant cell. The promoter and the enhancer may be constitutive or may have at least one property selected from the group consisting of: tissue-specific, developmentally specific and inducible.

10. Any progeny of the above plants in embodiments 1-9, any seeds of the above plants in embodiments 1-9, any seeds of progeny of the above plants in embodiments 1-9, and cells from any of the above plants in embodiments 1-9 and progeny thereof.

In any of the foregoing embodiments 1-10 or any other embodiments of the present invention, the DTP6 polypeptide may be from *Arabidopsis thaliana, Zea mays, Glycine max, Glycine tabacina, Glycine soja, Glycine tomentella, Populus trichocarpa, Vitis vinifera, Ricinus communis, Paeonia suffruticosa, Manihot esculenta, Cleome spinosa, Brassica napus, Sorghum bicolor, Triticum aestivum, Paspalum notatum, Dennstaedtia punctilobula* and *Eragrostis nindensis*.

In any of the foregoing embodiments 1-10 or any other embodiments of the present invention, the recombinant DNA construct (or suppression DNA construct) may comprise at least a promoter functional in a plant as a regulatory sequence.

In any of the foregoing embodiments 1-10 or any other embodiments of the present invention, the alteration of at least one agronomic characteristic is either an increase or decrease.

In any of the foregoing embodiments 1-10 or any other embodiments of the present invention, the at least one agronomic characteristic may be selected from the group consisting of greenness, yield, growth rate, biomass, fresh weight at maturation, dry weight at maturation, fruit yield, seed yield, total plant nitrogen content, fruit nitrogen content, seed nitrogen content, nitrogen content in a vegetative tissue, total plant free amino acid content, fruit free amino acid content, seed free amino acid content, free amino acid content in a vegetative tissue, total plant protein content, fruit protein content, seed protein content, protein content in a vegetative tissue, drought tolerance, nitrogen uptake, root lodging, harvest index, stalk lodging, plant height, ear height, ear length, salt tolerance, early seedling vigor and seedling emergence under low temperature stress. For example, the alteration of at least one agronomic characteristic may be an increase in yield, greenness or biomass.

In any of the foregoing embodiments 1-10 or any other embodiments of the present invention, the plant may exhibit the alteration of at least one agronomic characteristic when compared, under water limiting conditions, to a control plant not comprising said recombinant DNA construct (or said suppression DNA construct).

In any of the foregoing embodiments 1-10 or any other embodiments of the present invention, the plant may exhibit the alteration of at least one agronomic characteristic when compared, under triple stress conditions, to a control plant not comprising said recombinant DNA construct (or said suppression DNA construct).

In any of the foregoing embodiments 1-10 or any other embodiments of the present invention, the plant may exhibit the alteration of at least one agronomic characteristic when compared, under Paraquat stress, to a control plant not comprising said recombinant DNA construct (or said suppression DNA construct).

"Drought" refers to a decrease in water availability to a plant that, especially when prolonged, can cause damage to the plant or prevent its successful growth (e.g., limiting plant growth or seed yield).

The terms "drought", "drought stress", "low water availability", "water stress" and "reduced water availability" are used interchangeably herein, and refer to less water availability to the plant than what is required for optimal growth and productivity.

"Drought tolerance" is a trait of a plant to survive under drought conditions over prolonged periods of time without exhibiting substantial physiological or physical deterioration.

"Drought tolerance activity" of a polypeptide indicates that over-expression of the polypeptide in a transgenic plant confers increased drought tolerance to the transgenic plant relative to a reference or control plant.

"Increased drought tolerance" of a plant is measured relative to a reference or control plant, and is a trait of the plant to survive under drought conditions over prolonged periods of time, without exhibiting the same degree of physiological or physical deterioration relative to the reference or control plant grown under similar drought conditions. Typically, when a transgenic plant comprising a recombinant DNA construct or suppression DNA construct in its genome exhibits increased drought tolerance relative to a reference or control plant, the reference or control plant does not comprise in its genome the recombinant DNA construct or suppression DNA construct.

"Triple stress" as used herein refers to the abiotic stress exerted on the plant by the combination of drought stress, high temperature stress and high light stress.

The terms "heat stress" and "high temperature stress" are used interchangeably herein, and are defined as where ambient temperatures are hot enough for sufficient time that they cause damage to plant function or development, which might be reversible or irreversible in damage. "High temperature" can be either "high air temperature" or "high soil temperature", "high day temperature" or "high night temperature, or a combination of more than one of these.

In one embodiment of the invention, the ambient temperature can be in the range of 30° C. to 36° C. In one embodiment of the invention, the duration for the high temperature stress could be in the range of 1-16 hours.

"High light intensity" and "high irradiance" and "light stress" are used interchangeably herein, and refer to the stress exerted by subjecting plants to light intensities that are high enough for sufficient time that they cause photoinhibition damage to the plant.

In one embodiment of the invention, the light intensity can be in the range of 250 µE to 450 µE. In one embodiment of the invention, the duration for the high light intensity stress could be in the range of 12-16 hours.

"Triple stress tolerance" is a trait of a plant to survive under the combined stress conditions of drought, high temperature and high light intensity over prolonged periods of time without exhibiting substantial physiological or physical deterioration.

"Paraquat" is an herbicide that exerts oxidative stress on the plants. Paraquat, a bipyridylium herbicide, acts by intercepting electrons from the electron transport chain at PSI. This reaction results in the production of bipyridyl radicals that readily react with dioxygen thereby producing superoxide. Paraquat tolerance in a plant has been associated with the scavenging capacity for oxyradicals (Lannelli, M. A. et al (1999) *J Exp Botany*, Vol. 50, No. 333, pp. 523-532). Paraquat resistant plants have been reported to have higher tolerance to other oxidative stresses as well.

"Paraquat stress" is defined as stress exerted on the plants by subjecting them to Paraquat concentrations ranging from 0.03 to 0.3 µM.

Many adverse environmental conditions such as drought, salt stress, and use of herbicide promote the overproduction of reactive oxygen species (ROS) in plant cells. ROS such as singlet oxygen, superoxide radicals, hydrogen peroxide ($H_2O_2$), and hydroxyl radicals are believed to be the major factor responsible for rapid cellular damage due to their high reactivity with membrane lipids, proteins, and DNA (Mittler, R. (2002) *Trends Plant Sci* Vol. 7 No. 9).

"Increased stress tolerance" of a plant is measured relative to a reference or control plant, and is a trait of the plant to survive under stress conditions over prolonged periods of time, without exhibiting the same degree of physiological or physical deterioration relative to the reference or control plant grown under similar stress conditions.

A plant with "increased stress tolerance" can exhibit increased tolerance to one or more different stress conditions. Examples of stress include, but are not limited to sub-optimal conditions associated with salinity, drought, temperature, pathogens, metal, chemical, and oxidative stresses.

"Stress tolerance activity" of a polypeptide indicates that over-expression of the polypeptide in a transgenic plant confers increased stress tolerance to the transgenic plant relative to a reference or control plant. A polypeptide with "triple stress tolerance activity" indicates that over-expression of the polypeptide in a transgenic plant confers increased triple stress tolerance to the transgenic plant relative to a reference or control plant. A polypeptide with "paraquat stress tolerance activity" indicates that over-expression of the polypeptide in a transgenic plant confers increased Paraquat stress tolerance to the transgenic plant relative to a reference or control plant.

Typically, when a transgenic plant comprising a recombinant DNA construct or suppression DNA construct in its genome exhibits increased stress tolerance relative to a reference or control plant, the reference or control plant does not comprise in its genome the recombinant DNA construct or suppression DNA construct.

One of ordinary skill in the art is familiar with protocols for simulating drought conditions and for evaluating drought tolerance of plants that have been subjected to simulated or naturally-occurring drought conditions. For example, one can simulate drought conditions by giving plants less water than normally required or no water over a period of time, and one can evaluate drought tolerance by looking for differences in physiological and/or physical condition, including (but not limited to) vigor, growth, size, or root length, or in particular, leaf color or leaf area size. Other techniques for evaluating drought tolerance include measuring chlorophyll fluorescence, photosynthetic rates and gas exchange rates.

A drought stress experiment may involve a chronic stress (i.e., slow dry down) and/or may involve two acute stresses (i.e., abrupt removal of water) separated by a day or two of recovery. Chronic stress may last 8-10 days. Acute stress may last 3-5 days. The following variables may be measured during drought stress and well watered treatments of transgenic plants and relevant control plants:

The variable "% area chg_start chronic—acute2" is a measure of the percent change in total area determined by remote visible spectrum imaging between the first day of chronic stress and the day of the second acute stress.

The variable "% area chg_start chronic—end chronic" is a measure of the percent change in total area determined by remote visible spectrum imaging between the first day of chronic stress and the last day of chronic stress.

The variable "% area chg_start chronic—harvest" is a measure of the percent change in total area determined by remote visible spectrum imaging between the first day of chronic stress and the day of harvest.

The variable "% area chg_start chronic—recovery24hr" is a measure of the percent change in total area determined by remote visible spectrum imaging between the first day of chronic stress and 24 hrs into the recovery (24 hrs after acute stress 2).

The variable "psii_acute1" is a measure of Photosystem II (PSII) efficiency at the end of the first acute stress period. It provides an estimate of the efficiency at which light is absorbed by PSII antennae and is directly related to carbon dioxide assimilation within the leaf.

The variable "psii_acute2" is a measure of Photosystem II (PSII) efficiency at the end of the second acute stress period. It provides an estimate of the efficiency at which light is absorbed by PSII antennae and is directly related to carbon dioxide assimilation within the leaf.

The variable "fv/fm_acute1" is a measure of the optimum quantum yield (Fv/Fm) at the end of the first acute stress—(variable fluorescence difference between the maximum and minimum fluorescence/maximum fluorescence)

The variable "fv/fm_acute2" is a measure of the optimum quantum yield (Fv/Fm) at the end of the second acute stress—(variable fluorescence difference between the maximum and minimum fluorescence/maximum fluorescence).

The variable "leaf rolling_harvest" is a measure of the ratio of top image to side image on the day of harvest.

The variable "leaf rolling_recovery24hr" is a measure of the ratio of top image to side image 24 hours into the recovery.

The variable "Specific Growth Rate (SGR)" represents the change in total plant surface area (as measured by Lemna Tec Instrument) over a single day ($Y(t)=Y0*e^{r*t}$). $Y(t)=Y0*e^{r*t}$ is equivalent to % change in $Y/\Delta t$ where the individual terms are as follows: Y(t)=Total surface area at t; Y0=Initial total surface area (estimated); r=Specific Growth Rate day$^{-1}$, and t=Days After Planting ("DAP").

The variable "shoot dry weight" is a measure of the shoot weight 96 hours after being placed into a 104° C. oven.

The variable "shoot fresh weight" is a measure of the shoot weight immediately after being cut from the plant.

The Examples below describe some representative protocols and techniques for simulating drought conditions and/or evaluating drought tolerance.

One can also evaluate drought tolerance by the ability of a plant to maintain sufficient yield (at least 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or 100% yield) in field testing under simulated or naturally-occurring drought conditions (e.g., by measuring for substantially equivalent yield under drought conditions compared to non-drought conditions, or by measuring for less yield loss under drought conditions compared to a control or reference plant).

One of ordinary skill in the art would readily recognize a suitable control or reference plant to be utilized when assessing or measuring an agronomic characteristic or phenotype of a transgenic plant in any embodiment of the present invention in which a control plant is utilized (e.g., compositions or methods as described herein). For example, by way of non-limiting illustrations:

1. Progeny of a transformed plant which is hemizygous with respect to a recombinant DNA construct (or suppression DNA construct), such that the progeny are segregating into plants either comprising or not comprising the recombinant DNA construct (or suppression DNA construct): the progeny comprising the recombinant DNA construct (or suppression DNA construct) would be typically measured relative to the progeny not comprising the recombinant DNA construct (or suppression DNA construct) (i.e., the progeny not comprising the recombinant DNA construct (or the suppression DNA construct) is the control or reference plant).

2. Introgression of a recombinant DNA construct (or suppression DNA construct) into an inbred line, such as in maize, or into a variety, such as in soybean: the introgressed line would typically be measured relative to the parent inbred or variety line (i.e., the parent inbred or variety line is the control or reference plant).

3. Two hybrid lines, where the first hybrid line is produced from two parent inbred lines, and the second hybrid line is produced from the same two parent inbred lines except that one of the parent inbred lines contains a recombinant DNA construct (or suppression DNA construct): the second hybrid line would typically be measured relative to the first hybrid line (i.e., the first hybrid line is the control or reference plant).

4. A plant comprising a recombinant DNA construct (or suppression DNA construct): the plant may be assessed or measured relative to a control plant not comprising the recombinant DNA construct (or suppression DNA construct) but otherwise having a comparable genetic background to the plant (e.g., sharing at least 90%, 91%, 92%, 93%, 94%, 95%, 96%, 97%, 98%, 99%, or 100% sequence identity of nuclear genetic material compared to the plant comprising the recombinant DNA construct (or suppression DNA construct)). There are many laboratory-based techniques available for the analysis, comparison and characterization of plant genetic backgrounds; among these are Isozyme Electrophoresis, Restriction Fragment Length Polymorphisms (RFLPs), Randomly Amplified Polymorphic DNAs (RAPDs), Arbitrarily Primed Polymerase Chain Reaction (AP-PCR), DNA Amplification Fingerprinting (DAF), Sequence Characterized Amplified Regions (SCARs), Amplified Fragment Length Polymorphisms (AFLP®s), and Simple Sequence Repeats (SSRs) which are also referred to as Microsatellites.

Furthermore, one of ordinary skill in the art would readily recognize that a suitable control or reference plant to be utilized when assessing or measuring an agronomic characteristic or phenotype of a transgenic plant would not include a plant that had been previously selected, via mutagenesis or transformation, for the desired agronomic characteristic or phenotype.

Methods:

Methods include but are not limited to methods for increasing drought tolerance, triple stress tolerance and Paraquat tolerance in a plant, methods for evaluating drought tolerance, triple stress tolerance and Paraquat tolerance in a plant, methods for altering an agronomic characteristic in a plant, methods for determining an alteration of an agronomic characteristic in a plant, and methods for producing seed. The plant may be a monocotyledonous or dicotyledonous plant, for example, a maize or soybean plant. The plant may also be sunflower, sorghum, canola, wheat, alfalfa, cotton, rice, barley, millet, sugar cane or sorghum. The seed may be a maize or soybean seed, for example, a maize hybrid seed or maize inbred seed.

Methods include but are not limited to the following:

A method for transforming a cell comprising transforming a cell with any of the isolated polynucleotides of the present invention. The cell transformed by this method is also included. In particular embodiments, the cell is eukaryotic cell, e.g., a yeast, insect or plant cell, or prokaryotic, e.g., a bacterial cell.

A method for producing a transgenic plant comprising transforming a plant cell with any of the isolated polynucleotides or recombinant DNA constructs (including suppression DNA constructs) of the present invention and regenerating a transgenic plant from the transformed plant cell. The invention is also directed to the transgenic plant produced by this method, and transgenic seed obtained from this transgenic plant. The transgenic plant obtained by this method may be used in other methods of the present invention.

A method for isolating a polypeptide of the invention from a cell or culture medium of the cell, wherein the cell comprises a recombinant DNA construct comprising a polynucleotide of the invention operably linked to at least one regulatory sequence, and wherein the transformed host cell is grown under conditions that are suitable for expression of the recombinant DNA construct.

A method of altering the level of expression of a polypeptide of the invention in a host cell comprising: (a) transforming a host cell with a recombinant DNA construct of the present invention; and (b) growing the transformed host cell under conditions that are suitable for expression of the recombinant DNA construct wherein expression of the recombinant DNA construct results in production of altered levels of the polypeptide of the invention in the transformed host cell. In one embodiment, a plant comprising in its genome a recombinant DNA construct comprising a polynucleotide operably linked to at least one regulatory element, wherein said polynucleotide encodes a polypeptide having an amino acid sequence of at least 50% sequence identity, based on the Clustal V method of alignment, when compared to SEQ ID NOS: 18, 20, 22, 24, 26, 28, 30, 32, 34, 36, 38-70, 75, 77, 79, 81, 83, 85, 87, 89, 91, 92-102 or 103, and wherein said plant exhibits increased tolerance to triple stress, or Paraquat, or both, when compared to a control plant not comprising said recombinant DNA construct.

A method of identifying a DTP6 protein, the method comprising the steps of: (a) use the profile of FIG. 13A-FIG. 13Y to identify at least one candidate sequence in an amino acid sequence database; (b) determine an e-value score for the at least one candidate sequence from step (a); (c) select the at least one candidate sequence from step (b), wherein the e-value score is $<10^{-3}$; and (d) further select the at least one candidate sequence from step (c), wherein the at least one candidate sequence matches the profile of FIG. 13A-FIG. 13Y by at least 80% over the entire length of the profile. A polynucleotide encoding the DTP6 polypeptide obtained by this method may be used in other methods of the present invention.

Another embodiment of this invention is a method of identifying a DTP6 protein, the method comprising the steps of: (a) develop an HMM profile by use of at least one sequence selected from the group consisting of: SEQ ID NOS: 18, 20, 22, 24, 26, 28, 30, 32, 34, 36, 38-70, 75, 77, 79, 81, 83, 85, 87, 89, 91, 92-102, 103 and the sequences presented in Table 5; (b) use the profile of step (a) to identify at least one candidate sequence in an amino acid sequence database; (c) determine an e-value score for the at least one candidate sequence from step (b); (d) select the at least one candidate sequence from step (c), wherein the e-value score is $<10^{-3}$; and (e) further select the at least one candidate sequence from step (d), wherein the at least one candidate sequence matches the profile of step (a) by at least 80% over the entire length of the profile. A polynucleotide encoding the DTP6 polypeptide obtained by this method may be used in other methods of the present invention.

A method of increasing tolerance to either one or more of the following stresses in a plant: drought stress, triple stress and Paraquat stress; the method comprising: (a) introducing into a regenerable plant cell a recombinant DNA construct comprising a polynucleotide operably linked to at least one regulatory sequence (for example, a promoter functional in a plant), wherein the polynucleotide encodes a polypeptide having an amino acid sequence of at least 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or 100% sequence identity, based on the Clustal V method of alignment, when compared to SEQ ID NOS: 18, 20, 22, 24, 26, 28, 30, 32, 34, 36, 38-70, 75, 77, 79, 81, 83, 85, 87, 89, 91, 92-102 or 103; and (b) regenerating a transgenic plant from the regenerable plant cell after step (a), wherein the transgenic plant comprises in its genome the recombinant DNA construct and exhibits increased tolerance to one or more of the following stresses: drought stress, triple stress and Paraquat stress, when compared to a control plant not comprising the recombinant DNA construct. The method may further comprise (c) obtaining a progeny plant derived from the transgenic plant, wherein said progeny plant comprises in its genome the recombinant DNA construct and exhibits increased drought tolerance when compared to a control plant not comprising the recombinant DNA construct.

A method of increasing tolerance to either one or more of the following stresses in a plant: drought stress, triple stress and Paraquat stress; the method comprising: (a) introducing into a regenerable plant cell a recombinant DNA construct comprising a polynucleotide operably linked to at least one regulatory element, wherein said polynucleotide comprises a nucleotide sequence encoding a polypeptide with drought tolerance activity, wherein the nucleotide sequence is: (a) hybridizable under stringent conditions with a DNA molecule comprising the full complement of SEQ ID NOS: 18, 20, 22, 24, 26, 28, 30, 32, 34, 36, 38-70, 75, 77, 79, 81, 83, 85, 87, 89, 91, 92-102 or 103; or (b) derived from SEQ ID NOS: 18, 20, 22, 24, 26, 28, 30, 32, 34, 36, 38-70, 75, 77, 79, 81, 83, 85, 87, 89, 91, 92-102 or 103 by alteration of one or more nucleotides by at least one method selected from the group consisting of: deletion, substitution, addition and insertion; and (b) regenerating a transgenic plant from the regenerable plant cell after step (a), wherein the transgenic plant comprises in its genome the recombinant DNA construct and -exhibits increased drought tolerance when compared to a control plant not comprising the recombinant DNA construct. The method may further comprise (c) obtaining a progeny plant derived from the transgenic plant, wherein said progeny plant comprises in its genome the recombinant DNA construct and exhibits increased tolerance to one or more of the following stresses: drought stress, triple stress and Paraquat stress, when compared to a control plant not comprising the recombinant DNA construct.

A method of increasing tolerance to either one or more of the following stresses in a plant: drought stress, triple stress and Paraquat stress; the method, comprising: (a) introducing into a regenerable plant cell a suppression DNA construct comprising at least one regulatory sequence (for example, a promoter functional in a plant) operably linked to all or part of (i) a nucleic acid sequence encoding a polypeptide having an amino acid sequence of at least 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or 100% sequence identity, based on the Clustal V method of alignment, when compared to SEQ ID NOS: 18, 20, 22, 24, 26, 28, 30, 32, 34, 36, 38-70, 75, 77, 79, 81, 83, 85, 87, 89, 91, 92-102 or 103, or (ii) a full complement of the nucleic acid sequence of (a)(i); and (b) regenerating a transgenic plant from the regenerable plant cell after step (a), wherein the transgenic plant comprises in its genome the suppression DNA construct and exhibits increased drought tolerance when compared to a control plant not comprising the suppression DNA construct. The method may further comprise (c) obtaining a progeny plant derived from the transgenic plant, wherein said progeny plant comprises in its genome the suppression DNA construct and exhibits increased tolerance to one or more of the following stresses: drought stress, triple stress and Paraquat stress, when compared to a control plant not comprising the suppression DNA construct.

A method of increasing tolerance to either one or more of the following stresses in a plant: drought stress, triple stress and Paraquat stress; the method, comprising: (a) introducing into a regenerable plant cell a suppression DNA construct comprising at least one regulatory sequence (for example, a promoter functional in a plant) operably linked to a region derived from all or part of a sense strand or antisense strand of a target gene of interest, said region having a nucleic acid sequence of at least 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or 100% sequence identity, based on the Clustal V method of alignment, when compared to said all or part of a sense strand or antisense strand from which said region is derived, and wherein said target gene of interest encodes a DTP6 polypeptide; and (b) regenerating a transgenic plant from the regenerable plant cell after step (a), wherein the transgenic plant comprises in its genome the suppression DNA construct and exhibits increased tolerance to one or more of the following stresses: drought stress, triple stress and Paraquat stress, when compared to a control plant not comprising the suppression DNA construct. The method may further comprise (c) obtaining a progeny plant derived from the transgenic plant, wherein said progeny plant comprises in its genome the suppression DNA construct and exhibits increased drought tolerance when compared to a control plant not comprising the suppression DNA construct.

A method of evaluating tolerance to either one or more of the following stresses in a plant: drought stress, triple stress and Paraquat stress; the method, comprising (a) obtaining a transgenic plant, wherein the transgenic plant comprises in its genome a recombinant DNA construct comprising a polynucleotide operably linked to at least one regulatory sequence (for example, a promoter functional in a plant), wherein said polynucleotide encodes a polypeptide having an amino acid sequence of at least 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or 100% sequence identity, based on the Clustal V method of alignment, when compared to SEQ ID NOS: 18, 20, 22, 24, 26, 28, 30, 32, 34, 36, 38-70, 75, 77, 79, 81, 83, 85, 87, 89, 91, 92-102 or 103; (b) obtaining a progeny plant derived from said transgenic plant, wherein the progeny plant comprises in its genome the recombinant DNA construct; and (c) evaluating the progeny plant for increased tolerance to one or more of the following stresses: drought stress, triple stress and Paraquat stress, compared to a control plant not comprising the recombinant DNA construct.

A method of evaluating tolerance to either one or more of the following stresses in a plant: drought stress, triple stress and Paraquat stress; the method, comprising: (a) obtaining a transgenic plant, wherein the transgenic plant comprises in its genome a recombinant DNA construct comprising a polynucleotide operably linked to at least one regulatory element, wherein said polynucleotide comprises a nucleotide sequence encoding a polypeptide with drought tolerance activity, wherein the nucleotide sequence is: (a) hybridizable under stringent conditions with a DNA molecule comprising the full complement of SEQ ID NOS: 18, 20, 22, 24, 26, 28, 30, 32, 34, 36, 38-70, 75, 77, 79, 81, 83, 85, 87, 89, 91, 92-102 or 103; or (b) derived from SEQ ID NOS: 18, 20, 22, 24, 26, 28, 30, 32, 34, 36, 38-70, 75, 77, 79, 81, 83, 85, 87, 89, 91, 92-102 or 103 by alteration of one or more nucleotides by at least one method selected from the group consisting of: deletion, substitution, addition and insertion; (b) obtaining a progeny plant derived from said transgenic plant, wherein the progeny plant comprises in its genome the recombinant DNA construct; and (c) evaluating the progeny plant for increased tolerance to one or more of the following stresses: drought stress, triple stress and Paraquat stress, compared to a control plant not comprising the recombinant DNA construct.

A method of evaluating drought tolerance in a plant, comprising (a) obtaining a transgenic plant, wherein the transgenic plant comprises in its genome a suppression DNA construct comprising at least one regulatory sequence (for example, a promoter functional in a plant) operably linked to all or part of (i) a nucleic acid sequence encoding a polypeptide having an amino acid sequence of at least 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or 100% sequence identity, based on the Clustal V method of alignment, when compared to SEQ ID NOS: 18, 20, 22, 24, 26, 28, 30, 32, 34, 36, 38-70, 75, 77, 79, 81, 83, 85, 87, 89, 91, 92-102 or 103, or (ii) a full complement of the nucleic acid sequence of (a)(i); (b) obtaining a progeny plant derived from said transgenic plant, wherein the progeny plant comprises in its genome the suppression DNA construct; and (c) evaluating the progeny plant for increased tolerance to one or more of the following stresses: drought stress, triple stress and Paraquat stress, compared to a control plant not comprising the suppression DNA construct.

A method of evaluating drought tolerance in a plant, comprising (a) obtaining a transgenic plant, wherein the transgenic plant comprises in its genome a suppression DNA construct comprising at least one regulatory sequence (for example, a promoter functional in a plant) operably linked to a region derived from all or part of a sense strand or antisense strand of a target gene of interest, said region having a nucleic acid sequence of at least 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or 100% sequence identity, based on the Clustal V method of alignment, when compared to said all or part of a sense strand or antisense strand from which said region is derived, and wherein said target gene of interest encodes a DTP6 polypeptide; (b) obtaining a progeny plant derived from the transgenic plant, wherein the progeny plant comprises in its genome the suppression DNA construct; and (c) evaluating the progeny plant for increased tolerance to one or more of the following stresses: drought stress, triple stress and Paraquat stress, compared to a control plant not comprising the suppression DNA construct.

A method of determining an alteration of an agronomic characteristic in a plant, comprising (a) obtaining a transgenic plant, wherein the transgenic plant comprises in its genome a recombinant DNA construct comprising a polynucleotide operably linked to at least one regulatory sequence (for example, a promoter functional in a plant), wherein said polynucleotide encodes a polypeptide having an amino acid sequence of at least 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or 100% sequence identity, based on the Clustal V method of alignment, when compared to SEQ ID NOS: 18, 20, 22, 24, 26, 28, 30, 32, 34, 36, 38-70, 75, 77, 79, 81, 83, 85, 87, 89, 91, 92-102 or 103; (b) obtaining a progeny plant derived from said transgenic plant, wherein the progeny plant comprises in its genome the recombinant DNA construct; and (c) determining whether the progeny plant exhibits an alteration in at least one agronomic characteristic when compared, optionally under water limiting conditions, to a control plant not comprising the recombinant DNA construct.

A method of determining an alteration of an agronomic characteristic in a plant, comprising (a) obtaining a transgenic plant, wherein the transgenic plant comprises in its genome a recombinant DNA construct comprising a polynucleotide operably linked to at least one regulatory element, wherein said polynucleotide comprises a nucleotide sequence encoding a polypeptide with drought tolerance activity, wherein the nucleotide sequence is: (a) hybridizable under stringent conditions with a DNA molecule comprising the full complement of SEQ ID NOS: 18, 20, 22, 24, 26, 28, 30, 32, 34, 36, 38-70, 75, 77, 79, 81, 83, 85, 87, 89, 91, 92-102 or 103; or (b) derived from SEQ ID NOS: 18, 20, 22, 24, 26, 28, 30, 32, 34, 36, 38-70, 75, 77, 79, 81, 83, 85, 87, 89, 91, 92-102 or 103 by alteration of one or more nucleotides by at least one method selected from the group consisting of: deletion, substitution, addition and insertion; (b) obtaining a progeny plant derived from said transgenic plant, wherein the progeny plant comprises in its genome the recombinant DNA construct; and (c) determining whether the progeny plant exhibits an alteration in at least one agronomic characteristic when compared, optionally under water limiting conditions, to a control plant not comprising the recombinant DNA construct.

A method of determining an alteration of an agronomic characteristic in a plant, comprising (a) obtaining a transgenic plant, wherein the transgenic plant comprises in its genome a suppression DNA construct comprising at least one regulatory sequence (for example, a promoter functional in a plant) operably linked to all or part of (i) a nucleic acid sequence encoding a polypeptide having an amino acid sequence of at least 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or 100% sequence identity, based on the Clustal V method of alignment, when compared to SEQ ID NOS: 18, 20, 22, 24, 26, 28, 30, 32, 34, 36, 38-70, 75, 77, 79, 81, 83, 85, 87, 89, 91, 92-102 or 103, or (ii) a full complement of the nucleic acid sequence of (i); (b) obtaining a progeny plant derived from said transgenic plant, wherein the progeny plant comprises in its genome the suppression DNA construct; and (c) determining whether the progeny plant exhibits an alteration in at least one agronomic characteristic when compared, optionally under water limiting conditions, to a control plant not comprising the suppression DNA construct.

A method of determining an alteration of an agronomic characteristic in a plant, comprising (a) obtaining a transgenic plant, wherein the transgenic plant comprises in its genome a suppression DNA construct comprising at least one regulatory sequence (for example, a promoter functional in a plant) operably linked to a region derived from all or part of a sense strand or antisense strand of a target gene of interest, said region having a nucleic acid sequence of at least 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or 100% sequence identity, based on the Clustal V method of alignment, when compared to said all or part of a sense strand or antisense strand from which said region is derived, and wherein said target gene of interest encodes a DTP6 polypeptide; (b) obtaining a progeny plant derived from said transgenic plant, wherein the progeny plant comprises in its genome the suppression DNA construct; and (c) determining whether the progeny plant exhibits an alteration in at least one agronomic characteristic when compared, optionally under water limiting conditions, to a control plant not comprising the suppression DNA construct.

A method of producing seed (for example, seed that can be sold as a drought tolerant product offering) comprising any of the preceding methods, and further comprising obtaining seeds from said progeny plant, wherein said seeds comprise in their genome said recombinant DNA construct (or suppression DNA construct).

In any of the preceding methods or any other embodiments of methods of the present invention, in said introducing step said regenerable plant cell may comprise a callus cell, an embryogenic callus cell, a gametic cell, a meristematic cell, or a cell of an immature embryo. The regenerable plant cells may derive from an inbred maize plant.

In any of the preceding methods or any other embodiments of methods of the present invention, said regenerating step may comprise the following: (i) culturing said transformed plant cells in a media comprising an embryogenic promoting hormone until callus organization is observed; (ii) transferring said transformed plant cells of step (i) to a first media which includes a tissue organization promoting hormone; and (iii) subculturing said transformed plant cells after step (ii) onto a second media, to allow for shoot elongation, root development or both.

In any of the preceding methods or any other embodiments of methods of the present invention, the at least one agronomic characteristic may be selected from the group consisting of greenness, yield, growth rate, biomass, fresh weight at maturation, dry weight at maturation, fruit yield, seed yield, total plant nitrogen content, fruit nitrogen content, seed nitrogen content, nitrogen content in a vegetative tissue, total plant free amino acid content, fruit free amino acid content, seed free amino acid content, amino acid content in a vegetative tissue, total plant protein content, fruit protein content, seed protein content, protein content in a vegetative tissue, drought tolerance, nitrogen uptake, root lodging, harvest index, stalk lodging, plant height, ear height, ear length, salt tolerance, early seedling vigor and seedling emergence under low temperature stress. The alteration of at least one agronomic characteristic may be an increase in yield, greenness or biomass.

In any of the preceding methods or any other embodiments of methods of the present invention, the plant may exhibit the alteration of at least one agronomic characteristic when compared, under water limiting conditions, to a control plant not comprising said recombinant DNA construct (or said suppression DNA construct).

In any of the preceding methods or any other embodiments of methods of the present invention, alternatives exist for introducing into a regenerable plant cell a recombinant DNA construct comprising a polynucleotide operably linked to at least one regulatory sequence. For example, one may introduce into a regenerable plant cell a regulatory sequence (such as one or more enhancers, optionally as part of a transposable element), and then screen for an event in which the regulatory sequence is operably linked to an endogenous gene encoding a polypeptide of the instant invention.

The introduction of recombinant DNA constructs of the present invention into plants may be carried out by any suitable technique, including but not limited to direct DNA uptake, chemical treatment, electroporation, microinjection, cell fusion, infection, vector-mediated DNA transfer, bombardment, or *Agrobacterium*-mediated transformation. Techniques for plant transformation and regeneration have been described in International Patent Publication WO 2009/006276, the contents of which are herein incorporated by reference.

The development or regeneration of plants containing the foreign, exogenous isolated nucleic acid fragment that encodes a protein of interest is well known in the art. The regenerated plants may be self-pollinated to provide homozygous transgenic plants. Otherwise, pollen obtained from the regenerated plants is crossed to seed-grown plants of agronomically important lines. Conversely, pollen from plants of these important lines is used to pollinate regenerated plants. A transgenic plant of the present invention containing a desired polypeptide is cultivated using methods well known to one skilled in the art.

EXAMPLES

The present invention is further illustrated in the following Examples, in which parts and percentages are by weight and degrees are Celsius, unless otherwise stated. It should be understood that these Examples, while indicating embodiments of the invention, are given by way of illustration only. From the above discussion and these Examples, one skilled in the art can ascertain the essential characteristics of this invention, and without departing from the spirit and scope thereof, can make various changes and modifications of the invention to adapt it to various usages and conditions. Thus, various modifications of the invention in addition to those shown and described herein will be apparent to those skilled in the art from the foregoing description. Such modifications are also intended to fall within the scope of the appended claims.

Example 1

Creation of an *Arabidopsis* Population with Activation-Tagged Genes

An 18.4 kb T-DNA based binary construct, pHSbarENDs (SEQ ID NO:1), was made that contains four multimerized enhancer elements derived from the Cauliflower Mosaic Virus 35S promoter, corresponding to sequences −341 to −64, as defined by Odell et al. (1985) *Nature* 313:810-812. The construct also contains vector sequences (pUC9) to allow plasmid rescue, transposon sequences (Ds) to remobilize the T-DNA, and the bar gene to allow for glufosinate selection of transgenic plants. In principle, only the 10.8 kb segment from the right border (RB) to left border (LB) inclusive will be transferred into the host plant genome. Since the enhancer elements are located near the RB, they can induce cis-activation of genomic loci following T-DNA integration.

Two *Arabidopsis* activation-tagged populations were created by whole plant *Agrobacterium* transformation: Population 1 and Population 2.

For Population 1, the pHSbarENDs construct (FIG. 1) was transformed into *Agrobacterium tumefaciens* strain C58, grown in LB at 25° C. to OD600 ~1.0. Cells were then pelleted by centrifugation and resuspended in an equal volume of 5% sucrose/0.05% Silwet L-77 (OSI Specialties, Inc). At early bolting, soil grown *Arabidopsis thaliana* ecotype Col-0 were top watered with the *Agrobacterium* suspension. A week later, the same plants were top watered again with the same *Agrobacterium* strain in sucrose/Silwet. The plants were then allowed to set seed as normal. The resulting $T_1$ seed were sown on soil, and transgenic seedlings were selected by spraying with glufosinate (Finale®; AgrEvo; Bayer Environmental Science). $T_2$ seed was collected from approximately 35,000 individual glufosinate resistant $T_1$ plants. $T_2$ plants were grown and equal volumes of $T_3$ seed from 96 separate $T_2$ lines were pooled. This constituted 360 sub-populations.

For Population 2, the pHSbarENDs construct was slightly modified.

The PacI restriction site at position 5775 was substituted with the following poly-linker:

(SEQ ID NO: 104)
GATCACTAGTGGCGCGCCTAGGAGATCTCGA

GTAGGGATAACAGGGTAAT that adds BclI, SpeI, AscI, BlnI, BglII, XhoI and I-SceI restriction sites. This modified plasmid was designated pHS-barENDs2.

The *Agrobacterium* strain and whole plant transformation was performed as described for Population 1.

A total of 100,000 glufosinate resistant $T_1$ seedlings were selected. $T_2$ seed from each line was kept separate.

Example 2A

Screens to Identify Lines with Enhanced Drought Tolerance (Population 1)

Seedling Vigor/Drought Screen (Population 1):

Approximately 1000 seed from each of the 360 bulked sub-populations (96 lines each) were imbibed for 4 days at 4° C., then sown evenly on the surface of a fungicide-treated, 10×25 inch flat filled with standard soil. This represents an approximately 10× sampling of each sub-population (1000 seeds @ 96 lines/sub-population).

When plants were approximately at a 3-4 leaf rosette stage (~2.5 weeks after planting), flats were saturated with water, and then water was withheld to identify *Arabidopsis* mutants showing tolerance to a progressive increase in drought stress (i.e., over ~14 day period).

For purposes of this screen, we assessed drought tolerance by visually inspecting the plants at least once a day. The relative degree of anthocyanin accumulation, leaf size, leaf yellowing and amount of leaf wilting were compared to control plants in each flat. Individual plants that showed a delay in anthocyanin production, leaf yellowing, and/or leaf wilting relative to all other plants in the flat were noted as drought tolerant.

Individual plants showing tolerance to progressive drought stress conditions, compared to susceptible neighboring plants, were numbered, carefully re-watered in the flat for 2-3 days while minimizing re-hydration of surrounding plants, and then subsequently transferred to individual pots for seed production. Re-watering of plants in the flat prior to transferring to individual pots was a better approach, since this allowed plants to recover in part to the drought stress, before being subjected to additional stresses imposed prior to transfer.

Plants showing enhanced seedling growth or morphological changes were numbered when differences were first visible.

402 individual plants were identified as potentially drought tolerant or drought sensitive relative to the rest of the plants in each flat. A total of 104 sub-populations (flats) produced plants selected for their potential drought tolerance phenotype.

T4 seed from each of the lines was grown and re-screened under similar conditions. The drought stress was initiated at approximately 15 to 20 days after germination. Unlike the initial screen though, the plants were grown at a much lower density (32 plants/flat) with each flat containing 24 "mutant" plants and 8 untransformed control plants.

Positive hits were defined visually as having a delayed wilting and/or stay green. A total of 37 lines from 10 subpopulations had enhanced drought tolerance. In addition, 8 lines from a single subpopulation had "enhanced seedling growth/vigor", and one line was described as drought hypersensitive based on its rapid wilting during drought stress.

Example 2B

Screens to Identify Lines with Enhanced Drought Tolerance (Population 2)

Quantitative Drought Screen:

From each of 96,000 separate T1 activation-tagged lines, nine glufosinate resistant T2 plants are sown, each in a single pot on Scotts® Metro-Mix® 200 soil. Flats are configured with 8 square pots each. Each of the square pots is filled to the top with soil. Each pot (or cell) is sown to produce 9 glufosinate resistant seedlings in a 3×3 array.

The soil is watered to saturation and then plants are grown under standard conditions (i.e., 16 hour light, 8 hour dark cycle; 22° C.; ~60% relative humidity). No additional water is given.

Digital images of the plants are taken at the onset of visible drought stress symptoms. Images are taken once a day (at the same time of day), until the plants appear dessicated. Typically, four consecutive days of data is captured.

Color analysis is employed for identifying potential drought tolerant lines. Color analysis can be used to measure the increase in the percentage of leaf area that falls into a yellow color bin. Using hue, saturation and intensity data ("HSI"), the yellow color bin consists of hues 35 to 45.

Maintenance of leaf area is also used as another criterion for identifying potential drought tolerant lines, since *Arabidopsis* leaves wilt during drought stress. Maintenance of leaf area can be measured as reduction of rosette leaf area over time.

Leaf area is measured in terms of the number of green pixels obtained using the LemnaTec imaging system. Activation-tagged and control (e.g., wild-type) plants are grown side by side in flats that contain 72 plants (9 plants/pot). When wilting begins, images are measured for a number of days to monitor the wilting process. From these data wilting profiles are determined based on the green pixel counts obtained over four consecutive days for activation-tagged and accompanying control plants. The profile is selected from a series of measurements over the four day period that gives the largest degree of wilting. The ability to withstand drought is measured by the tendency of activation-tagged plants to resist wilting compared to control plants.

LemnaTec HTSBonitUV software is used to analyze CCD images. Estimates of the leaf area of the *Arabidopsis* plants are obtained in terms of the number of green pixels. The data for each image is averaged to obtain estimates of mean and standard deviation for the green pixel counts for activation-tagged and wild-type plants. Parameters for a noise function are obtained by straight line regression of the squared deviation versus the mean pixel count using data for all images in a batch. Error estimates for the mean pixel count data are calculated using the fit parameters for the noise function. The mean pixel counts for activation-tagged and wild-type plants are summed to obtain an assessment of the overall leaf area for each image. The four-day interval with maximal wilting is obtained by selecting the interval that corresponds to the maximum difference in plant growth. The individual wilting responses of the activation-tagged and wild-type plants are obtained by normalization of the data using the value of the green pixel count of the first day in the interval. The drought tolerance of the activation-tagged plant compared to the wild-type plant is scored by summing the weighted difference between the wilting response of activation-tagged plants and wild-type plants over day two to day four; the weights are estimated by propagating the error in the data. A positive drought tolerance score corresponds to an activation-tagged plant with slower wilting compared to the wild-type plant. Significance of the difference in wilting response between activation-tagged and wild-type plants is obtained from the weighted sum of the squared deviations.

Lines with a significant delay in yellow color accumulation and/or with significant maintenance of rosette leaf area, when compared to the average of the whole flat, are designated as Phase 1 hits. Phase 1 hits are re-screened in duplicate under the same assay conditions. When either or both of the Phase 2 replicates show a significant difference (score of greater than 0.9) from the whole flat mean, the line is then considered a validated drought tolerant line.

Example 3A

Identification of Activation-Tagged Genes

Genes flanking the T-DNA insert in drought tolerant lines are identified using one, or both, of the following two standard procedures: (1) thermal asymmetric interlaced (TAIL) PCR (Liu et al., (1995), Plant J. 8:457-63); and (2) SAIFF PCR (Siebert et al., (1995) Nucleic Acids Res. 23:1087-1088). In lines with complex multimerized T-DNA inserts, TAIL PCR and SAIFF PCR may both prove insufficient to identify candidate genes. In these cases, other procedures, including inverse PCR, plasmid rescue and/or genomic library construction, can be employed.

A successful result is one where a single TAIL or SAIFF PCR fragment contains a T-DNA border sequence and Arabidopsis genomic sequence.

Once a tag of genomic sequence flanking a T-DNA insert is obtained, candidate genes are identified by alignment to publicly available Arabidopsis genome sequence.

Specifically, the annotated gene nearest the 35S enhancer elements/T-DNA RB are candidates for genes that are activated.

To verify that an identified gene is truly near a T-DNA and to rule out the possibility that the TAIL/SAIFF fragment is a chimeric cloning artifact, a diagnostic PCR on genomic DNA is done with one oligo in the T-DNA and one oligo specific for the candidate gene. Genomic DNA samples that give a PCR product are interpreted as representing a T-DNA insertion. This analysis also verifies a situation in which more than one insertion event occurs in the same line, e.g., if multiple differing genomic fragments are identified in TAIL and/or SAIFF PCR analyses.

Example 3B

Identification of Activation-Tagged Genes

With respect to Population 1 in Example 2A, initially, candidate genes were only cloned from a single line from each of the subpopulations. Using the same oligos to validate the genomic insertion of the T-DNA, PCR analysis showed that all lines from the same subpopulation had the same T-DNA insertion event. We therefore independently isolated siblings of the same insertion event as being drought tolerant from among the 37 lines from the 10 subpopulations.

Therefore, we identified eleven candidate lines from the Population 1 screen: 10 enhanced drought tolerance candidate lines and 1 drought sensitive candidate line.

Example 4A

Identification of Activation-Tagged AT-DTP6 Polypeptide Gene

An activation-tagged line (No. 900067) showing drought tolerance was further analyzed. DNA from the line was extracted, and genes flanking the T-DNA insert in the mutant line were identified using SAIFF PCR (Siebert et al., Nucleic Acids Res. 23:1087-1088 (1995)). A PCR amplified fragment was identified that contained T-DNA border sequence and Arabidopsis genomic sequence. Genomic sequence flanking the T-DNA insert was obtained, and the candidate gene was identified by alignment to the completed Arabidopsis genome. For a given T-DNA integration event, the annotated gene nearest the 35S enhancer elements/T-DNA RB was the candidate for gene that is activated in the line. In the case of line 900067, the 35S enhancer is present in the 3' UTR of the gene At1g68490 (SEQ ID NO: 17; NCBI GI No. 30697690) encoding a DTP6 polypeptide (SEQ ID NO: 18; NCBI GI NO. 18409044).

Example 4B

Assay for Expression Level of Candidate Drought Tolerance Genes

A functional activation-tagged allele should result in either up-regulation of the candidate gene in tissues where it is normally expressed, ectopic expression in tissues that do not normally express that gene, or both.

Expression levels of the candidate genes in the cognate mutant line vs. wild-type are compared. A standard RT-PCR procedure, such as the QuantiTect® Reverse Transcription Kit from QIAGEN®, is used. RT-PCR of the actin gene is used as a control to show that the amplification and loading of samples from the mutant line and wild-type are similar.

Assay conditions are optimized for each gene. Expression levels are checked in mature rosette leaves. If the activation-tagged allele results in ectopic expression in other tissues (e.g., roots), it is not detected by this assay. As such, a positive result is useful but a negative result does not eliminate a gene from further analysis.

Example 5

Validation of Arabidopsis Candidate Gene At1g68490 (AT-DTP6 Polypeptide) Via Transformation into Arabidopsis Candidate genes can be transformed into Arabidopsis and overexpressed under the 35S promoter. If the same or similar phenotype is observed in the transgenic line as in the parent activation-tagged line, then the candidate gene is considered to be a validated "lead gene" in Arabidopsis.

The candidate Arabidopsis DTP6 polypeptide gene (At1g68490; SEQ ID NO: 17; NCBI GI No. 30697690) was tested for its ability to confer drought tolerance in the following manner.

Figure 4:
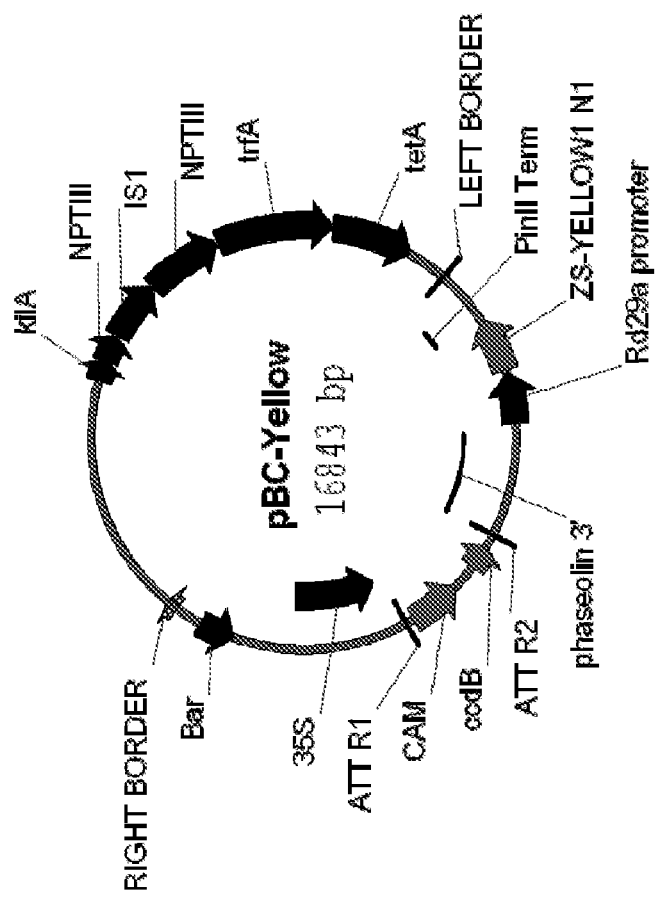
FIG. 4 shows a map of the vector pBC-yellow (SEQ ID NO:4), a destination vector for use in construction of expression vectors for *Arabidopsis*. The attR1 site is at nucleotides 11276-11399 (complementary strand); the attR2 site is at nucleotides 9695-9819 (complementary strand).

A 16.8-kb T-DNA based binary vector, called pBC-yellow (SEQ ID NO:4; FIG. 4), was constructed with a 1.3-kb 35S promoter immediately upstream of the INVITROGEN™ GATEWAY® C1 conversion insert. The vector also contains the RD29a promoter driving expression of the gene for ZS-Yellow (INVITROGEN™), which confers yellow fluorescence to transformed seed.

The At1g68490 cDNA protein-coding region was amplified by RT-PCR with the following primers:

```
(1) At1g68490-5'attB forward primer
(SEQ ID NO: 12):
GGGGACAAGTTTGTACAAAAAAGCAGGCTCGAAGAAAAGATGAATC

ACTTTGCGG
```

-continued (2) At1g68490-3'attB reverse primer
(SEQ ID NO: 13):
GGGGACCACTTTGTACAAGAAAGCTGGGTCCAAAAGGGTTCGTTTC

GGGTTTCG

The forward primer contains the attB1 sequence (ACAAGTTTGTACAAAAAAGCAGGCT; SEQ ID NO: 10) adjacent to 10 nucleotides from 5' UTR and 16 nucleotides from the protein coding region of At1g68490.

The reverse primer contains the attB2 sequence (ACCACTTTGTACAAGAAAGCTGGGT; SEQ ID NO:11) adjacent to the reverse complement of 23 nucleotides from the 3'UTR of At1g68490.

Figure 2:
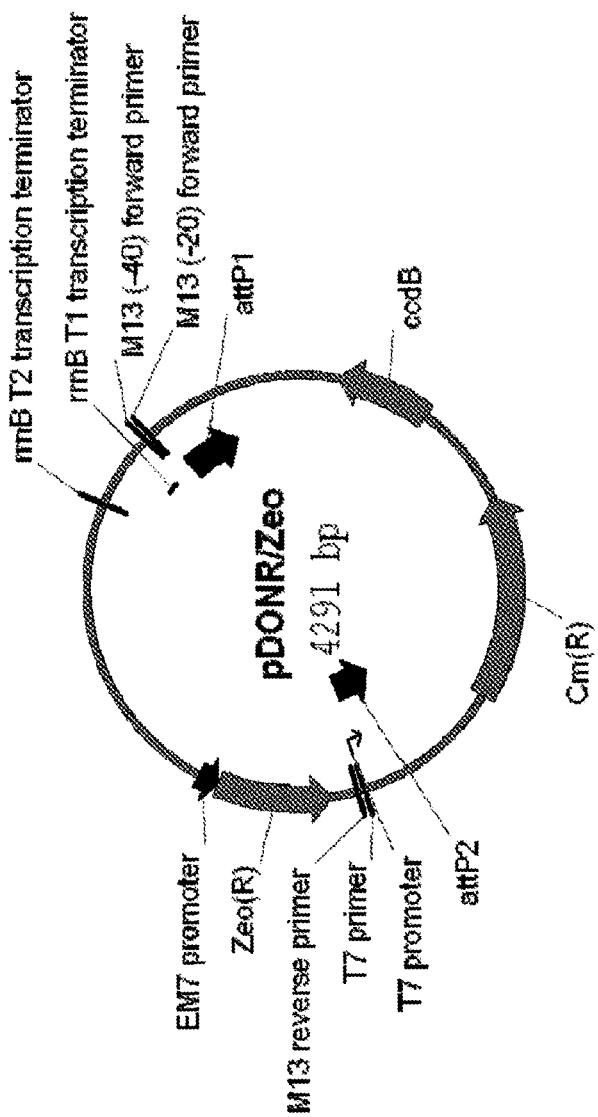
FIG. 2 shows a map of the vector pDONR™/Zeo (SEQ ID NO:2). The attP1 site is at nucleotides 570-801; the attP2 site is at nucleotides 2754-2985 (complementary strand).

Using the INVITROGEN™ GATEWAY® CLONASE™ technology, a BP Recombination Reaction was performed with pDONR™/Zeo (SEQ ID NO:2; FIG. 2). This process removed the bacteria lethal ccdB gene, as well as the chloramphenicol resistance gene (CAM) from pDONR™/Zeo and directionally cloned the PCR product with flanking attB1 and attB2 sites creating an entry clone, PHP31329. This entry clone was used for a subsequent LR Recombination Reaction with a destination vector, as follows.

A 16.8-kb T-DNA based binary vector (destination vector), called pBC-yellow (SEQ ID NO:4; FIG. 4), was constructed with a 1.3-kb 35S promoter immediately upstream of the INVITROGEN™ GATEWAY® C1 conversion insert, which contains the bacterial lethal ccdB gene as well as the chloramphenicol resistance gene (CAM) flanked by attR1 and attR2 sequences. The vector also contains the RD29a promoter driving expression of the gene for ZS-Yellow (INVITROGEN™), which confers yellow fluorescence to transformed seed. Using the INVITROGEN™ GATEWAY® technology, an LR Recombination Reaction was performed on the PHP31329 entry clone, containing the directionally cloned PCR product, and pBC-yellow. This allowed for rapid and directional cloning of the candidate gene behind the 35S promoter in pBC-yellow to create the 35S promoter::At1g68490 expression construct, pBC-Yellow-At1g68490.

Applicants then introduced the 35S promoter::At1g68490 expression construct into wild-type Arabidopsis ecotype Col-0, using the same Agrobacterium-mediated transformation procedure described in Example 1. Transgenic T1 seeds were selected by yellow fluorescence, and T1 seeds were plated next to wild-type seeds and grown under water limiting conditions. Growth conditions and imaging analysis were as described in Example 2. It was found that the original drought tolerance phenotype from activation tagging could be recapitulated in wild-type Arabidopsis plants that were transformed with a construct where At1g68490 was directly expressed by the 35S promoter. The drought tolerance score, as determined by the method of Example 2, was 1.264.

Example 6

Preparation of cDNA Libraries and Isolation and Sequencing of cDNA Clones cDNA libraries may be prepared by any one of many methods available. For example, the cDNAs may be introduced into plasmid vectors by first preparing the cDNA libraries in UNI-ZAP™ XR vectors according to the manufacturer's protocol (Stratagene Cloning Systems, La Jolla, Calif.). The UNI-ZAP™ XR libraries are converted into plasmid libraries according to the protocol provided by Stratagene. Upon conversion, cDNA inserts will be contained in the plasmid vector pBLUESCRIPT®. In addition, the cDNAs may be introduced directly into precut BLUE-SCRIPT® II SK(+) vectors (Stratagene) using T4 DNA ligase (New England Biolabs), followed by transfection into DH10B cells according to the manufacturer's protocol (GIBCO BRL Products). Once the cDNA inserts are in plasmid vectors, plasmid DNAs are prepared from randomly picked bacterial colonies containing recombinant pBLUE-SCRIPT® plasmids, or the insert cDNA sequences are amplified via polymerase chain reaction using primers specific for vector sequences flanking the inserted cDNA sequences. Amplified insert DNAs or plasmid DNAs are sequenced in dye-primer sequencing reactions to generate partial cDNA sequences (expressed sequence tags or "ESTs"; see Adams et al., (1991) Science 252:1651-1656). The resulting ESTs are analyzed using a Perkin Elmer Model 377 fluorescent sequencer.

Full-insert sequence (FIS) data is generated utilizing a modified transposition protocol. Clones identified for FIS are recovered from archived glycerol stocks as single colonies, and plasmid DNAs are isolated via alkaline lysis. Isolated DNA templates are reacted with vector primed M13 forward and reverse oligonucleotides in a PCR-based sequencing reaction and loaded onto automated sequencers. Confirmation of clone identification is performed by sequence alignment to the original EST sequence from which the FIS request is made.

Confirmed templates are transposed via the Primer Island transposition kit (PE Applied Biosystems, Foster City, Calif.) which is based upon the Saccharomyces cerevisiae Ty1 transposable element (Devine and Boeke (1994) Nucleic Acids Res. 22:3765-3772). The in vitro transposition system places unique binding sites randomly throughout a population of large DNA molecules. The transposed DNA is then used to transform DH10B electro-competent cells (GIBCO BRL/Life Technologies, Rockville, Md.) via electroporation. The transposable element contains an additional selectable marker (named DHFR; Fling and Richards (1983) Nucleic Acids Res. 11:5147-5158), allowing for dual selection on agar plates of only those subclones containing the integrated transposon. Multiple subclones are randomly selected from each transposition reaction, plasmid DNAs are prepared via alkaline lysis, and templates are sequenced (ABI PRISM® dye-terminator ReadyReaction mix) outward from the transposition event site, utilizing unique primers specific to the binding sites within the transposon.

Sequence data is collected (ABI PRISM® Collections) and assembled using Phred and Phrap (Ewing et al. (1998) Genome Res. 8:175-185; Ewing and Green (1998) Genome Res. 8:186-194). Phred is a public domain software program which re-reads the ABI sequence data, re-calls the bases, assigns quality values, and writes the base calls and quality values into editable output files. The Phrap sequence assembly program uses these quality values to increase the accuracy of the assembled sequence contigs. Assemblies are viewed by the Consed sequence editor (Gordon et al. (1998) Genome Res. 8:195-202).

In some of the clones the cDNA fragment may correspond to a portion of the 3'-terminus of the gene and does not cover the entire open reading frame. In order to obtain the upstream information one of two different protocols is used. The first of these methods results in the production of a fragment of DNA containing a portion of the desired gene sequence while the second method results in the production of a fragment containing the entire open reading frame. Both of these methods use two rounds of PCR amplification to obtain fragments from one or more libraries. The libraries some times are chosen based on previous knowledge that the specific gene should be found in a certain tissue and some times are randomly-chosen. Reactions to obtain the same gene may be performed on several libraries in parallel or on a pool of libraries. Library pools are normally prepared using from 3 to 5 different libraries and normalized to a uniform dilution. In the first round of amplification both methods use a vector-specific (forward) primer corresponding to a portion of the vector located at the 5'-terminus of the clone coupled with a gene-specific (reverse) primer. The first method uses a sequence that is complementary to a portion of the already known gene sequence while the second method uses a gene-specific primer complementary to a portion of the 3'-untranslated region (also referred to as UTR). In the second round of amplification a nested set of primers is used for both methods. The resulting DNA fragment is ligated into a pBLUESCRIPT® vector using a commercial kit and following the manufacturer's protocol. This kit is selected from many available from several vendors including INVITROGEN™ (Carlsbad, Calif.), Promega Biotech (Madison, Wis.), and GIBCO-BRL (Gaithersburg, Md.). The plasmid DNA is isolated by alkaline lysis method and submitted for sequencing and assembly using Phred/Phrap, as above.

An alternative method for preparation of cDNA Libraries and obtainment of sequences can be the following. mRNAs can be isolated using the Qiagen® RNA isolation kit for total RNA isolation, followed by mRNA isolation via attachment to oligo(dT) Dynabeads from Invitrogen (Life Technologies, Carlsbad, Calif.), and sequencing libraries can be prepared using the standard mRNA-Seq kit and protocol from Illumina, Inc. (San Diego, Calif.). In this method, mRNAs are fragmented using a ZnCl2 solution, reverse transcribed into cDNA using random primers, end repaired to create blunt end fragments, 3' A-tailed, and ligated with Illumina paired-end library adaptors. Ligated cDNA fragments can then be PCR amplified using Illumina paired-end library primers, and purified PCR products can be checked for quality and quantity on the Agilent Bioanalyzer DNA 1000 chip prior to sequencing on the Genome Analyzer II equipped with a paired end module.

Reads from the sequencing runs can be soft-trimmed prior to assembly such that the first base pair of each read with an observed FASTQ quality score lower than 15 and all subsequent bases are clipped using a Python script. The Velvet assembler (Zerbino et al. Genome Research 18:821-9 (2008)) can be run under varying kmer and coverage cutoff parameters to produce several putative assemblies along a range of stringency. The contiguous sequences (contigs) within those assemblies can be combined into clusters using Vmatch software (available on the Vmatch website) such that contigs which are identified as substrings of longer contigs are grouped and eliminated, leaving a non-redundant set of longest "sentinel" contigs. These non-redundant sets can be used in alignments to homologous sequences from known model plant species.

Example 7

Identification of cDNA Clones cDNA clones encoding DTP6 polypeptides can be identified by conducting BLAST® (Basic Local Alignment Search Tool; Altschul et al. (1993) J. Mol. Biol. 215:403-410; see also the explanation of the BLAST algorithm on the world wide web site for the National Center for Biotechnology Information at the National Library of Medicine of the National Institutes of Health) searches for similarity to amino acid sequences contained in the BLAST® "nr" database (comprising all non-redundant GenBank CDS translations, sequences derived from the 3-dimensional structure Brookhaven Protein Data Bank, the last major release of the SWISS-PROT protein sequence database, EMBL, and DDBJ databases). The DNA sequences from clones can be translated in all reading frames and compared for similarity to all publicly available protein sequences contained in the "nr" database using the BLASTX algorithm (Gish and States (1993) Nat. Genet. 3:266-272) provided by the NCBI. The polypeptides encoded by the cDNA sequences can be analyzed for similarity to all publicly available amino acid sequences contained in the "nr" database using the BLASTP algorithm provided by the National Center for Biotechnology Information (NCBI). For convenience, the P-value (probability) or the E-value (expectation) of observing a match of a cDNA-encoded sequence to a sequence contained in the searched databases merely by chance as calculated by BLAST® are reported herein as "p Log" values, which represent the negative of the logarithm of the reported P-value or E-value. Accordingly, the greater the p Log value, the greater the likelihood that the cDNA-encoded sequence and the BLAST® "hit" represent homologous proteins.

ESTs sequences can be compared to the Genbank database as described above. ESTs that contain sequences more 5- or 3-prime can be found by using the BLASTN algorithm (Altschul et al (1997) Nucleic Acids Res. 25:3389-3402.) against the DUPONT™ proprietary database comparing nucleotide sequences that share common or overlapping regions of sequence homology. Where common or overlapping sequences exist between two or more nucleic acid fragments, the sequences can be assembled into a single contiguous nucleotide sequence, thus extending the original fragment in either the 5 or 3 prime direction. Once the most 5-prime EST is identified, its complete sequence can be determined by Full Insert Sequencing as described above. Homologous genes belonging to different species can be found by comparing the amino acid sequence of a known gene (from either a proprietary source or a public database) against an EST database using the TBLASTN algorithm. The TBLASTN algorithm searches an amino acid query against a nucleotide database that is translated in all 6 reading frames. This search allows for differences in nucleotide codon usage between different species, and for codon degeneracy.

In cases where the sequence assemblies are in fragments, the percent identity to other homologous genes can be used to infer which fragments represent a single gene. The fragments that appear to belong together can be computationally assembled such that a translation of the resulting nucleotide sequence will return the amino acid sequence of the homologous protein in a single open-reading frame. These computer-generated assemblies can then be aligned with other polypeptides of the invention.

Example 8

Characterization of cDNA Clones Encoding DTP6 Polypeptides cDNA libraries representing mRNAs from various tissues of maize, soybean, Bahia grass and resurrection grass were prepared and cDNA clones encoding DTP6 polypeptides were identified.

DTP6 polypeptides were also identified from two exotic plant species, *Paspalum notatum*, commonly called Bahia grass and *Eragrostis nindensis*, also called resurrection grass. These are included in Table 1. One DTP6 homolog, En_NODE_47983 (SEQ ID NO: 29) was identified from resurrection grass and three homologs, Pn_NODE_10482, epn2n.pk019.o1 and Pn_NODE_38377 were identified from Bahia grass (SEQ ID NOS: 31, 80 and 82). Mining of homologs from resurrection and Bahia grass was performed by performing a TblastN of the *Arabidopsis* DTP6 genes, and the identified maize DTP6 homologs against the Bahia and resurrection grass assemblies. The resulting hits were translated based on the blast alignments; and the translations were aligned with the other known DTP6 polypeptides.

The characteristics of the maize and soybean libraries are described below. The cDNA assemblies used for identifying the exotic grass homologs are described in example 6B.

TABLE 2 cDNA Libraries from Maize, Soybean and Scented Hay Fern

| Library | Description | Clone |
|---|---|---|
| cfp5n | Maize Kernel, pooled stages, Full-length enriched, normalized | cfp5n.pk061.k20:fis |
| cie3s | Defined meristem types from the developing ear- 15-20 mm B73 ear, 3 mm tip tissue includes late stage inflorescence and spikelet pair meristems | cie3s.pk008.j21:fis |
| cfp7n | Maize Root, Pooled stages, Full-length enriched, normalized | cfp7n.pk001.j9:fis |
| cds3f | Corn (*Zea mays*, B73) 1-5 day seedlings. | cds3f.pk005.m8 |
| ccoln | Corn (*Zea mays* L.) cob of 67 day old plants grown in green house (normalized) | my.cco1n.pk088.j17 |
| sdp4c | Soybean (*Glycine max* L.) developing pods 10-12 mm | sdp4c.pk004.f4:fis |
| sfp1n | Soy cDNA full-insert enriched normalized library, mixed tissue (flower and pod) | sfp1n.pk034.b12:fis |
| ehsf2n | Normalized cDNA library of scented hay fern from Total RNA | ehsf2n.pk006.d22 |

*These libraries were normalized essentially as described in U.S. Pat. No. 5,482,845

The BLAST search using the sequences from clones listed in Table 2 revealed similarity of the polypeptides encoded by the cDNAs to the DTP6 polypeptides from various organisms. As shown in Table 3 and FIGS. 11A-11E, certain cDNAs encoded polypeptides similar to AT-DTP6 polypeptide from *Arabidopsis* (GI No. 18409044; SEQ ID NO: 18).

BLAST analyses were performed on one or more of the following: individual Expressed Sequence Tag ("EST"), the sequences of the entire cDNA inserts comprising the indicated cDNA clones ("Full-Insert Sequence" or "FIS"), the sequences of contigs assembled from two or more EST, FIS or PCR sequences ("Contig"), or sequences encoding an entire or functional protein derived from an FIS or a contig ("Complete Gene Sequence" or "CGS"). Shown in Table 3 (non-patent literature) and Table 4 (patent literature) are the BLAST results for CGS sequences of various DTP6 polypeptides. Also shown in Tables 3 and 4 are the percent sequence identity values for each pair of amino acid sequences using the Clustal V method of alignment with default parameters.

TABLE 3

BLASTP Results for DTP6 Polypeptides

| Sequence (SEQ ID NO) | NCBI GI No. (SEQ ID NO) | BLASTP pLog of E-value | Percent Sequence Identity |
|---|---|---|---|
| cfp5n.pk061.k20 (FIS) (SEQ ID NO: 20) | 226502893 (SEQ ID NO: 57) | >180 | 99.4 |
| cie3s.pk008.j21(FIS) (SEQ ID NO: 22) | 226510375 (SEQ ID NO: 59) | >180 | 100 |
| cfp7n.pk001.j9:fis(FIS) (SEQ ID NO: 24) | 242086136 (SEQ ID NO: 61) | 152 | 75.5 |
| cds3f.pk005.m8(FIS) (SEQ ID NO: 26) | 242086136 (SEQ ID NO: 61) | 164 | 81.6 |
| my.cco1n.pk088.j17(FIS) (SEQ ID NO: 28) | 226510044 (SEQ ID NO: 64) | >180 | 100 |
| En_NODE_47983(FIS) (SEQ ID NO: 30) | 242086136 (SEQ ID NO: 61) | 169 | 76.4 |
| Pn_NODE_10482(FIS) (SEQ ID NO: 32) | 242086136 (SEQ ID NO: 61) | 165 | 76.2 |
| sdp4c.pk004.f4:fis(FIS) (SEQ ID NO: 34) | 255640685 (SEQ ID NO: 67) | >180 | 91.2 |
| sfp1n.pk034.b12 (FIS) (SEQ ID NO: 36) | 255632129 (SEQ ID NO: 69) | >180 | 99.4 |
| pco599449 (contig) (SEQ ID NO: 75) | 195612706 (SEQ ID NO: 93) | >180 | 100 |
| pco592873 (SEQ ID NO: 77) | 223949655 (SEQ ID NO: 95) | >180 | 100 |
| pco596845 (SEQ ID NO: 79) | 238006286 (SEQ ID NO: 97) | 114 | 54.3 |
| epn2n.pk019.o1 (SEQ ID NO: 81) | 194703114 (SEQ ID NO: 99) | 78 | 77.5 |
| Pn_NODE_38377 (SEQ ID NO: 83) | 57900114 (SEQ ID NO: 101) | 84 | 44.6 |
| ehsf2n.pk006.d22 (SEQ ID NO: 85) | 116790833 (SEQ ID NO: 103) | 39 | 39.3 |

TABLE 4

BLASTP Results for DTP6 Polypeptides

| Sequence (SEQ ID NO) | Reference (SEQ ID NO) | BLASTP pLog of E-value | Percent Sequence Identity |
|---|---|---|---|
| At1g68490 (SEQ ID NO: 18) | SEQ ID NO: 23781 of US20070214517 (SEQ ID NO: 56) | >180 | 100 |
| cfp5n.pk061.k20 (FIS) (SEQ ID NO: 20) | SEQ ID NO: 51344 of US20070271633 (SEQ ID NO: 58) | >180 | 86.1 |
| cie3s.pk008.j21(FIS) (SEQ ID NO: 22) | SEQ ID NO: 291825 of US20090087878 (SEQ ID NO: 60) | >180 | 100 |
| cfp7n.pk001.j9:fis(FIS) (SEQ ID NO: 24) | SEQ ID NO: 305885 of US20090087878 (SEQ ID NO: 62) | >180 | 100 |
| cds3f.pk005.m8(FIS) (SEQ ID NO: 26) | SEQ ID NO: 322258 of US20090087878 (SEQ ID NO: 63) | 179 | 94 |
| my.cco1n.pk088.j17(FIS) (SEQ ID NO: 28) | SEQ ID NO: 292701 of US20090087878 (SEQ ID NO: 65) | >180 | 99.4 |
| En_NODE_47983(FIS) (SEQ ID NO: 30) | SEQ ID NO: 64538 of WO2009134339 (SEQ ID NO: 66) | 146 | 66.9 |
| Pn_NODE_10482(FIS) (SEQ ID NO: 32) | SEQ ID NO: 64538 of WO2009134339 (SEQ ID NO: 66) | 139 | 66.9 |
| sdp4c.pk004.f4:fis(FIS) (SEQ ID NO: 34) | SEQ ID NO: 52070 of US20070214517 (SEQ ID NO: 68) | >180 | 90.6 |
| sfp1n.pk034.b12 (FIS) (SEQ ID NO: 36) | SEQ ID NO: 58426 of WO2009134339 (SEQ ID NO: 70) | >180 | 96.6 |

TABLE 4-continued

BLASTP Results for DTP6 Polypeptides

| Sequence (SEQ ID NO) | Reference (SEQ ID NO) | BLASTP pLog of E-value | Percent Sequence Identity |
|---|---|---|---|
| pco599449 (contig) (SEQ ID NO: 75) | SEQ ID NO: 333737 of US20110214206 (SEQ ID NO: 92) | >180 | 100 |
| pco592873 (SEQ ID NO: 77) | SEQ ID NO: 292701 of US20110214206 (SEQ ID NO: 94) | >180 | 100 |
| pco596845 (SEQ ID NO: 79) | SEQ ID NO: 43585 of WO2010083178 (SEQ ID NO: 96) | 163 | 74 |
| epn2n.pk019.o1 (SEQ ID NO: 81) | SEQ ID NO: 77016 of US20110214205 (SEQ ID NO: 98) | 86 | 86.5 |
| Pn_NODE_38377 (SEQ ID NO: 83) | SEQ ID NO: 85465 of US20110214205 (SEQ ID NO: 100) | 137 | 70.1 |
| ehsf2n.pk006.d22 (SEQ ID NO: 85) | SEQ ID NO: 67537 of EP2336332 (SEQ ID NO: 102) | 39 | 39.3 |

FIGS. 11A-11E present an alignment of the amino acid sequences of DTP6 polypeptides set forth in SEQ ID NOs: 18, 20, 22, 24, 26, 28, 30, 32, 34, 36, 75, 77, 79, 81, 83, 85 and 56. FIG. 12 presents the percent sequence identities and divergence values for each sequence pair presented in FIGS. 11A-11E.

Sequence alignments and percent identity calculations were performed using the Megalign® program of the LASERGENE® bioinformatics computing suite (DNAS-TAR® Inc., Madison, Wis.). Multiple alignment of the sequences was performed using the Clustal V method of alignment (Higgins and Sharp (1989) *CABIOS*. 5:151-153) with the default parameters (GAP PENALTY=10, GAP LENGTH PENALTY=10). Default parameters for pairwise alignments using the Clustal method were KTUPLE=1, GAP PENALTY=3, WINDOW=5 and DIAGONALS SAVED=5.

Sequence alignments and BLAST scores and probabilities indicate that the nucleic acid fragments comprising the instant cDNA clones encode DTP6 polypeptides.

Table 5 lists other DTP6 polypeptides identified from different plant species.

TABLE 5

| No. | NCGI GI No. | Species |
|---|---|---|
| 1. | 255632093 | *Glycine max* |
| 2. | 255625985 | *Glycine max* |
| 3. | 255628125 | *Glycine max* |
| 4. | 255635949 | *Glycine max* |
| 5. | 222629869 | *Oryza sativa* |
| 6. | 297729369 | *Oryza sativa* |
| 7. | 125537294 | *Oryza sativa* |
| 8. | 116784705 | *Picea sitchensis* |
| 9. | 116780176 | *Picea sitchensis* |
| 10. | 116780009 | *Picea sitchensis* |
| 11. | 116790833 | *Picea sitchensis* |
| 12. | 148907503 | *Picea sitchensis* |
| 13. | 300432704 | *Hevea brasiliensis* |
| 14. | 300432708 | *Hevea brasiliensis* |
| 15. | 300432706 | *Hevea brasiliensis* |
| 16. | 296082245 | *Vitis vinifera* |
| 17. | 224118822 | *Populus trichocarpa* |
| 18. | 224079302 | *Populus trichocarpa* |
| 19. | 242089131 | *Sorghum bicolor* |
| 20. | 242055493 | *Sorghum bicolor* |
| 21. | 242056783 | *Sorghum bicolor* |
| 22. | 297849730 | *Arabidopsis lyrata* |
| 23. | 297811749 | *Arabidopsis lyrata* |
| 24. | 297832892 | *Arabidopsis lyrata* |
| 25. | 297838603 | *Arabidopsis lyrata* |
| 26. | 255582747 | *Ricinus communis* |
| 27. | 255581637 | *Ricinus communis* |
| 28. | 255543485 | *Ricinus communis* |
| 29. | 302783579 | *Selaginella moellendorffii* |
| 30. | 302798118 | *Selaginella moellendorffii* |
| 31. | 168009810 | *Physcomitrella patens* subsp. *patens* |
| 32. | 82621168 | *Solanum tuberosum* |
| 33. | 77745460 | *Solanum tuberosum* |
| 34. | 11762168 | *Arabidopsis thaliana* |
| 35. | 110741233 | *Arabidopsis thaliana* |
| 36. | 15222278 | *Arabidopsis thaliana* |
| 37. | 30685676 | *Arabidopsis thaliana* |
| 38. | 18396232 | *Arabidopsis thaliana* |

Example 9

Preparation of a Plant Expression Vector Containing a Homolog to the *Arabidopsis* Lead Gene Sequences homologous to the *Arabidopsis* AT-DTP6 polypeptide can be identified using sequence comparison algorithms such as BLAST (Basic Local Alignment Search Tool; Altschul et al., *J. Mol. Biol.* 215:403-410 (1993); see also the explanation of the BLAST algorithm on the world wide web site for the National Center for Biotechnology Information at the National Library of Medicine of the National Institutes of Health). Sequences encoding homologous DTP6 polypeptides can be PCR-amplified by either of the following methods.

Method 1 (RNA-based): If the 5' and 3' sequence information for the protein-coding region or the 5' and 3' UTR of a gene encoding a DTP6 polypeptide homolog is available, gene-specific primers can be designed as outlined in Example 5. RT-PCR can be used with plant RNA to obtain a nucleic acid fragment containing the protein-coding region flanked by attB1 (SEQ ID NO: 10) and attB2 (SEQ ID NO:11) sequences. The primer may contain a consensus Kozak sequence (CAACA) upstream of the start codon.

Method 2 (DNA-based): Alternatively, if a cDNA clone is available for a gene encoding a DTP6 polypeptide homolog, the entire cDNA insert (containing 5' and 3' non-coding regions) can be PCR amplified. Forward and reverse primers can be designed that contain either the attB1 sequence and vector-specific sequence that precedes the cDNA insert or the attB2 sequence and vector-specific sequence that follows the cDNA insert, respectively. For a cDNA insert cloned into the vector pBluescript® SK+, the forward primer VC062 (SEQ ID NO:14) and the reverse primer VC063 (SEQ ID NO:15) can be used.

Methods 1 and 2 can be modified according to procedures known by one skilled in the art. For example, the primers of Method 1 may contain restriction sites instead of attB1 and attB2 sites, for subsequent cloning of the PCR product into a vector containing attB1 and attB2 sites. Additionally, Method 2 can involve amplification from a cDNA clone, a lambda clone, a BAC clone or genomic DNA.

Figure 3:
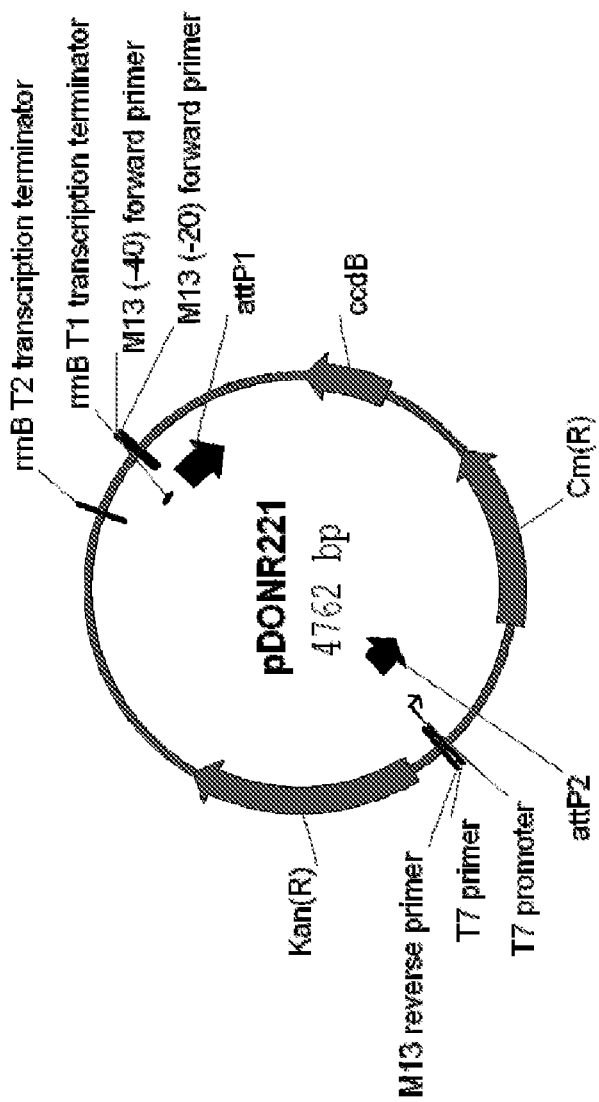
FIG. 3 shows a map of the vector pDONR™221 (SEQ ID NO:3). The attP1 site is at nucleotides 570-801; the attP2 site is at nucleotides 2754-2985 (complementary strand).

A PCR product obtained by either method above can be combined with the GATEWAY® donor vector, such as pDONR™/Zeo (INVITROGEN™; FIG. 2; SEQ ID NO:2)

or pDONR™221 (INVITROGEN™; FIG. 3; SEQ ID NO:3), using a BP Recombination Reaction. This process removes the bacteria lethal ccdB gene, as well as the chloramphenicol resistance gene (CAM) from pDONR™221 and directionally clones the PCR product with flanking attB1 and attB2 sites to create an entry clone. Using the INVITROGEN™ GATEWAY® CLONASE™ technology, the sequence encoding the homologous DTP6 polypeptide from the entry clone can then be transferred to a suitable destination vector, such as pBC-Yellow (FIG. 4; SEQ ID NO:4), PHP27840 (FIG. 5; SEQ ID NO:5) or PHP23236 (FIG. 6; SEQ ID NO:6), to obtain a plant expression vector for use with Arabidopsis, soybean and corn, respectively.

Figure 5:
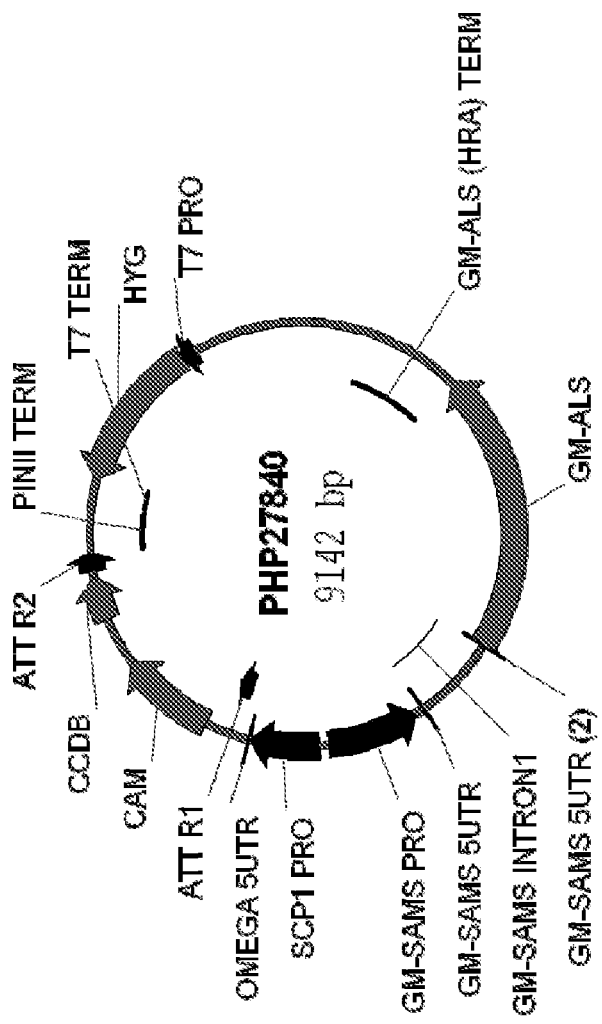
FIG. 5 shows a map of PHP27840 (SEQ ID NO:5), a destination vector for use in construction of expression vectors for soybean. The attR1 site is at nucleotides 7310-7434; the attR2 site is at nucleotides 8890-9014.
Figure 6:
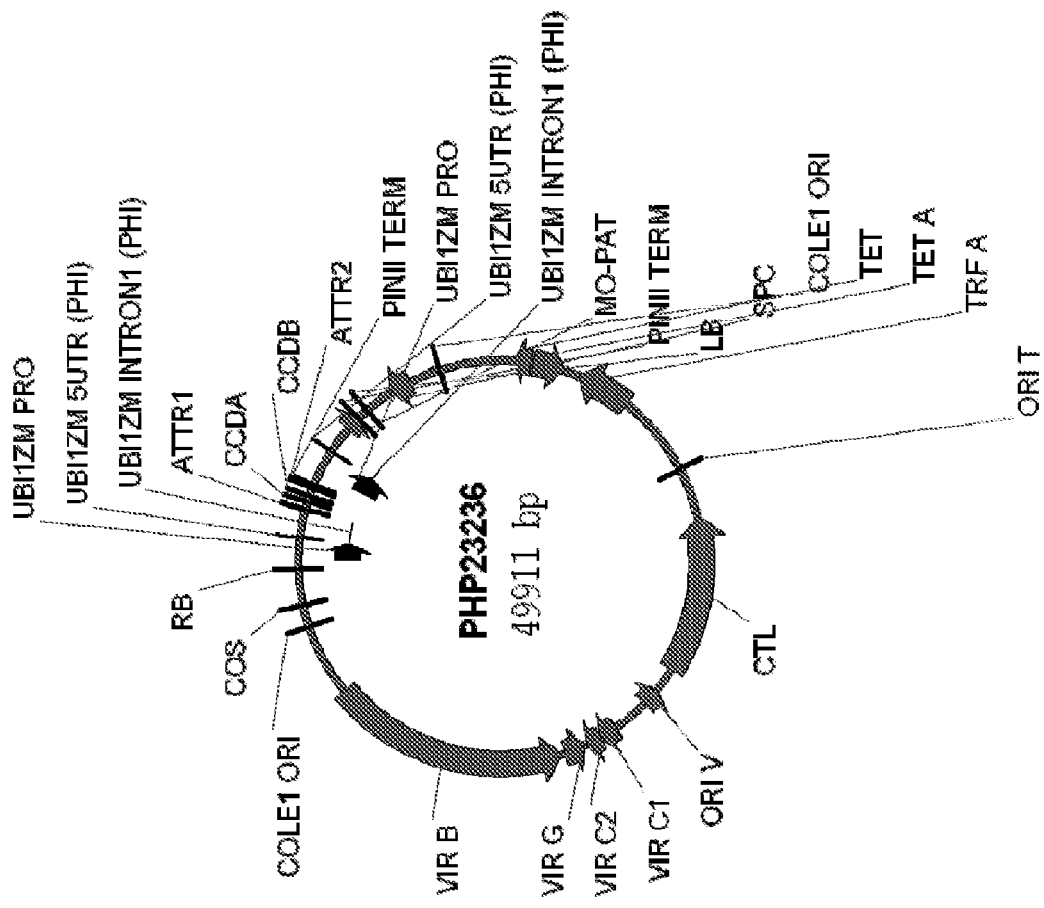
FIG. 6 shows a map of PHP23236 (SEQ ID NO:6), a destination vector for use in construction of expression vectors for Gaspe Flint derived maize lines. The attR1 site is at nucleotides 2006-2130; the attR2 site is at nucleotides 2899-3023.

The attP1 and attP2 sites of donor vectors pDONR™/Zeo or pDONR™221 are shown in FIGS. 2 and 3, respectively. The attR1 and attR2 sites of destination vectors pBC-Yellow, PHP27840 and PHP23236 are shown in FIGS. 4, 5 and 6, respectively.

Alternatively a MultiSite GATEWAY® LR recombination reaction between multiple entry clones and a suitable destination vector can be performed to create an expression vector.

Example 10

Preparation of Soybean Expression Vectors and Transformation of Soybean with Validated Arabidopsis Lead Genes Soybean plants can be transformed to overexpress a validated Arabidopsis lead gene or the corresponding homologs from various species in order to examine the resulting phenotype.

The same GATEWAY® entry clone described in Example 5 can be used to directionally clone each gene into the PHP27840 vector (SEQ ID NO:5; FIG. 5) such that expression of the gene is under control of the SCP1 promoter (International Publication No. 03/033651).

Using the INVITROGEN™ GATEWAY® technology, an LR Recombination Reaction was performed on the PHP31329 entry clone, containing the directionally cloned PCR product, and PHP27840. This allowed for rapid and directional cloning of the candidate gene behind the SCP1 promoter in PHP27840 to create the SCP1 promoter:: At1g68490 expression construct, PHP28053.

Soybean embryos may then be transformed with the SCP1 promoter::At1g68490 expression vector comprising sequences encoding the DTP6 polypeptides. Techniques for soybean transformation and regeneration have been described in International Patent Publication WO 2009/006276, the contents of which are herein incorporated by reference.

T1 plants can be subjected to a soil-based drought stress. Using image analysis, plant area, volume, growth rate and color analysis can be taken at multiple times before and during drought stress. Overexpression constructs that result in a significant delay in wilting or leaf area reduction, yellow color accumulation and/or increased growth rate during drought stress will be considered evidence that the Arabidopsis gene functions in soybean to enhance drought tolerance.

Soybean plants transformed with validated genes can then be assayed under more vigorous field-based studies to study yield enhancement and/or stability under well-watered and water-limiting conditions.

Example 11

Transformation of Maize with Validated Arabidopsis Lead Genes Using Particle Bombardment Maize plants can be transformed to overexpress a validated Arabidopsis lead gene or the corresponding homologs from various species in order to examine the resulting phenotype.

The same GATEWAY® entry clone described in Example 5 can be used to directionally clone each gene into a maize transformation vector. Expression of the gene in the maize transformation vector can be under control of a constitutive promoter such as the maize ubiquitin promoter (Christensen et al., (1989) Plant Mol. Biol. 12:619-632 and Christensen et al., (1992) Plant Mol. Biol. 18:675-689)

The recombinant DNA construct described above can then be introduced into corn cells by particle bombardment. Techniques for corn transformation by particle bombardment have been described in International Patent Publication WO 2009/006276, the contents of which are herein incorporated by reference.

T1 plants can be subjected to a soil-based drought stress. Using image analysis, plant area, volume, growth rate and color analysis can be taken at multiple times before and during drought stress. Overexpression constructs that result in a significant delay in wilting or leaf area reduction, yellow color accumulation and/or increased growth rate during drought stress will be considered evidence that the Arabidopsis gene functions in maize to enhance drought tolerance.

Example 12

Electroporation of Agrobacterium tumefaciens LBA4404

Figure 7:
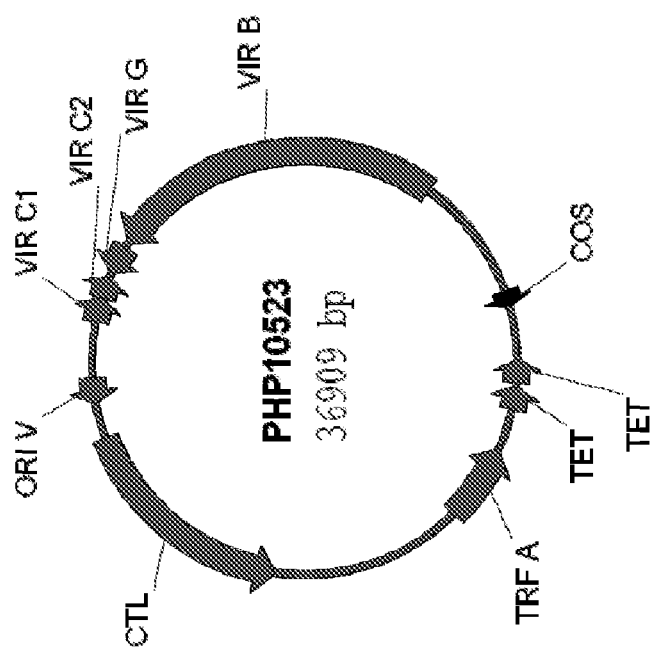
FIG. 7 shows a map of PHP10523 (SEQ ID NO:7), a plasmid DNA present in *Agrobacterium* strain LBA4404 (Komari et al., *Plant J.* 10:165-174 (1996); NCBI General Identifier No. 59797027).

Electroporation competent cells (40 µL), such as Agrobacterium tumefaciens LBA4404 containing PHP10523 (FIG. 7; SEQ ID NO:7), are thawed on ice (20-30 min). PHP10523 contains VIR genes for T-DNA transfer, an Agrobacterium low copy number plasmid origin of replication, a tetracycline resistance gene, and a Cos site for in vivo DNA bimolecular recombination. Meanwhile the electroporation cuvette is chilled on ice. The electroporator settings are adjusted to 2.1 kV. A DNA aliquot (0.5 µL parental DNA at a concentration of 0.2 µg-1.0 µg in low salt buffer or twice distilled $H_2O$) is mixed with the thawed Agrobacterium tumefaciens LBA4404 cells while still on ice. The mixture is transferred to the bottom of electroporation cuvette and kept at rest on ice for 1-2 min. The cells are electroporated (Eppendorf electroporator 2510) by pushing the "pulse" button twice (ideally achieving a 4.0 millisecond pulse). Subsequently, 0.5 mL of room temperature 2×YT medium (or SOC medium) are added to the cuvette and transferred to a 15 mL snap-cap tube (e.g., FALCON™ tube). The cells are incubated at 28-30° C., 200-250 rpm for 3 h.

Aliquots of 250 µL are spread onto plates containing YM medium and 50 µg/mL spectinomycin and incubated three days at 28-30° C. To increase the number of transformants one of two optional steps can be performed:

Option 1: Overlay plates with 30 µL of 15 mg/mL rifampicin. LBA4404 has a chromosomal resistance gene for rifampicin. This additional selection eliminates some contaminating colonies observed when using poorer preparations of LBA4404 competent cells.

Option 2: Perform two replicates of the electroporation to compensate for poorer electrocompetent cells.

Identification of Transformants:

Four independent colonies are picked and streaked on plates containing AB minimal medium and 50 µg/mL spectinomycin for isolation of single colonies. The plates are incubated at 28° C. for two to three days. A single colony for each putative co-integrate is picked and inoculated with 4 mL of 10 g/L bactopeptone, 10 g/L yeast extract, 5 g/L sodium chloride and 50 mg/L spectinomycin. The mixture is incubated for 24 h at 28° C. with shaking. Plasmid DNA from 4 mL of culture is isolated using Qiagen® Miniprep and an optional Buffer PB wash. The DNA is eluted in 30 µL. Aliquots of 2 µL are used to electroplate 20 µL of DH10b+20 µL of twice distilled H$_2$O as per above. Optionally a 15 µL aliquot can be used to transform 75-100 µL of INVITROGEN™ Library Efficiency DH5α. The cells are spread on plates containing LB medium and 50 µg/mL spectinomycin and incubated at 37° C. overnight.

Three to four independent colonies are picked for each putative co-integrate and inoculated 4 mL of 2×YT medium (10 g/L bactopeptone, 10 g/L yeast extract, 5 g/L sodium chloride) with 50 µg/mL spectinomycin. The cells are incubated at 37° C. overnight with shaking. Next, isolate the plasmid DNA from 4 mL of culture using QIAprep® Miniprep with optional Buffer PB wash (elute in 50 µL). Use 8 µL for digestion with SalI (using parental DNA and PHP10523 as controls). Three more digestions using restriction enzymes BamHI, EcoRI, and HindIII are performed for 4 plasmids that represent 2 putative co-integrates with correct SalI digestion pattern (using parental DNA and PHP10523 as controls). Electronic gels are recommended for comparison.

Example 13

Transformation of Maize Using *Agrobacterium*

Maize plants can be transformed to overexpress a validated *Arabidopsis* lead gene or the corresponding homologs from various species in order to examine the resulting phenotype.

*Agrobacterium*-mediated transformation of maize is performed essentially as described by Zhao et al. in *Meth. Mol. Biol.* 318:315-323 (2006) (see also Zhao et al., *Mol. Breed.* 8:323-333 (2001) and U.S. Pat. No. 5,981,840 issued Nov. 9, 1999, incorporated herein by reference). The transformation process involves bacterium innoculation, co-cultivation, resting, selection and plant regeneration.

1. Immature Embryo Preparation:

Immature maize embryos are dissected from caryopses and placed in a 2 mL microtube containing 2 mL PHI-A medium.

2. *Agrobacterium* Infection and Co-Cultivation of Immature Embryos:

2.1 Infection Step:

PHI-A medium of (1) is removed with 1 mL micropipettor, and 1 mL of *Agrobacterium* suspension is added. The tube is gently inverted to mix. The mixture is incubated for 5 min at room temperature.

2.2 Co-Culture Step:

The *Agrobacterium* suspension is removed from the infection step with a 1 mL micropipettor. Using a sterile spatula the embryos are scraped from the tube and transferred to a plate of PHI-B medium in a 100×15 mm Petri dish. The embryos are oriented with the embryonic axis down on the surface of the medium. Plates with the embryos are cultured at 20° C., in darkness, for three days. L-Cysteine can be used in the co-cultivation phase. With the standard binary vector, the co-cultivation medium supplied with 100-400 mg/L L-cysteine is critical for recovering stable transgenic events.

3. Selection of Putative Transgenic Events:

To each plate of PHI-D medium in a 100×15 mm Petri dish, 10 embryos are transferred, maintaining orientation and the dishes are sealed with parafilm. The plates are incubated in darkness at 28° C. Actively growing putative events, as pale yellow embryonic tissue, are expected to be visible in six to eight weeks. Embryos that produce no events may be brown and necrotic, and little friable tissue growth is evident. Putative transgenic embryonic tissue is subcultured to fresh PHI-D plates at two-three week intervals, depending on growth rate. The events are recorded.

4. Regeneration of T0 plants:

Embryonic tissue propagated on PHI-D medium is subcultured to PHI-E medium (somatic embryo maturation medium), in 100×25 mm Petri dishes and incubated at 28° C., in darkness, until somatic embryos mature, for about ten to eighteen days. Individual, matured somatic embryos with well-defined scutellum and coleoptile are transferred to PHI-F embryo germination medium and incubated at 28° C. in the light (about 80 µE from cool white or equivalent fluorescent lamps). In seven to ten days, regenerated plants, about 10 cm tall, are potted in horticultural mix and hardened-off using standard horticultural methods.

Media for Plant Transformation:

1. PHI-A: 4 g/L CHU basal salts, 1.0 mL/L 1000× Eriksson's vitamin mix, 0.5 mg/L thiamin HCl, 1.5 mg/L 2,4-D, 0.69 g/L L-proline, 68.5 g/L sucrose, 36 g/L glucose, pH 5.2. Add 100 µM acetosyringone (filter-sterilized).
2. PHI-B: PHI-A without glucose, increase 2,4-D to 2 mg/L, reduce sucrose to 30 g/L and supplemented with 0.85 mg/L silver nitrate (filter-sterilized), 3.0 g/L Gelrite®, 100 µM acetosyringone (filter-sterilized), pH 5.8.
3. PHI-C: PHI-B without Gelrite® and acetosyringone, reduce 2,4-D to 1.5 mg/L and supplemented with 8.0 g/L agar, 0.5 g/L 2-[N-morpholino]ethane-sulfonic acid (MES) buffer, 100 mg/L carbenicillin (filter-sterilized).
4. PHI-D: PHI-C supplemented with 3 mg/L bialaphos (filter-sterilized).
5. PHI-E: 4.3 g/L of Murashige and Skoog (MS) salts, (Gibco, BRL 11117-074), 0.5 mg/L nicotinic acid, 0.1 mg/L thiamine HCl, 0.5 mg/L pyridoxine HCl, 2.0 mg/L glycine, 0.1 g/L myo-inositol, 0.5 mg/L zeatin (Sigma, Cat. No. Z-0164), 1 mg/L indole acetic acid (IAA), 26.4 µg/L abscisic acid (ABA), 60 g/L sucrose, 3 mg/L bialaphos (filter-sterilized), 100 mg/L carbenicillin (filter-sterilized), 8 g/L agar, pH 5.6.
6. PHI-F: PHI-E without zeatin, IAA, ABA; reduce sucrose to 40 g/L; replacing agar with 1.5 g/L Gelrite®; pH 5.6.

Plants can be regenerated from the transgenic callus by first transferring clusters of tissue to N6 medium supplemented with 0.2 mg per liter of 2,4-D. After two weeks the tissue can be transferred to regeneration medium (Fromm et al., *Bio/Technology* 8:833-839 (1990)).

Transgenic T0 plants can be regenerated and their phenotype determined. T1 seed can be collected.

Furthermore, a recombinant DNA construct containing a validated *Arabidopsis* gene can be introduced into an elite maize inbred line either by direct transformation or introgression from a separately transformed line.

Transgenic plants, either inbred or hybrid, can undergo more vigorous field-based experiments to study yield enhancement and/or stability under water limiting and water non-limiting conditions.

Subsequent yield analysis can be done to determine whether plants that contain the validated *Arabidopsis* lead gene have an improvement in yield performance (under water limiting or non-limiting conditions), when compared to the control (or reference) plants that do not contain the validated *Arabidopsis* lead gene. Specifically, water limiting conditions can be imposed during the flowering and/or grain fill period for plants that contain the validated *Arabidopsis* lead gene and the control plants. Plants containing the validated *Arabidopsis* lead gene would have less yield loss relative to the control plants, for example, at least 25%, 20%, 15%, 10% or 5% less yield loss, under water limiting conditions, or would have increased yield, for example, at least 5%, 10%, 15%, 20% or 25% increased yield, relative to the control plants under water non-limiting conditions.

Example 14A

Preparation of *Arabidopsis* Lead Gene (At1g68490) Expression Vector for Transformation of Maize Using INVITROGEN™ GATEWAY® technology, an LR Recombination Reaction was performed with an entry clone (PHP31329) and a destination vector (PHP28647) to create the precursor plasmid PHP31368. The vector PHP31368 contains the following expression cassettes:
1. Ubiquitin promoter::moPAT::PinII terminator; cassette expressing the PAT herbicide resistance gene used for selection during the transformation process.
2. LTP2 promoter::DS-RED2::PinII terminator; cassette expressing the DS-RED color marker gene used for seed sorting.
3. Ubiquitin promoter::At1g68490::PinII terminator; cassette overexpressing the gene of interest, *Arabidopsis* AT-DTP6 polypeptide.

Example 14B

Transformation of Maize with the *Arabidopsis* Lead Gene (At1g68490) Using *Agrobacterium*

The AT-DTP6 polypeptide expression cassette present in vector PHP31368 can be introduced into a maize inbred line, or a transformable maize line derived from an elite maize inbred line, using *Agrobacterium*-mediated transformation as described in Examples 12 and 13.

Vector PHP31368 can be electroporated into the LBA4404 *Agrobacterium* strain containing vector PHP10523 (FIG. 7; SEQ ID NO:7) to create the co-integrate vector PHP31378. The co-integrate vector is formed by recombination of the 2 plasmids, and PHP10523, through the COS recombination sites contained on each vector. The co-integrate vector PHP31378 contains the same 3 expression cassettes as above (Example 14A) in addition to other genes (TET, TET, TRFA, ORI terminator, CTL, ORI V, VIR C1, VIR C2, VIR G, VIR B) needed for the *Agrobacterium* strain and the *Agrobacterium*-mediated transformation.

Example 15

Figure 8:
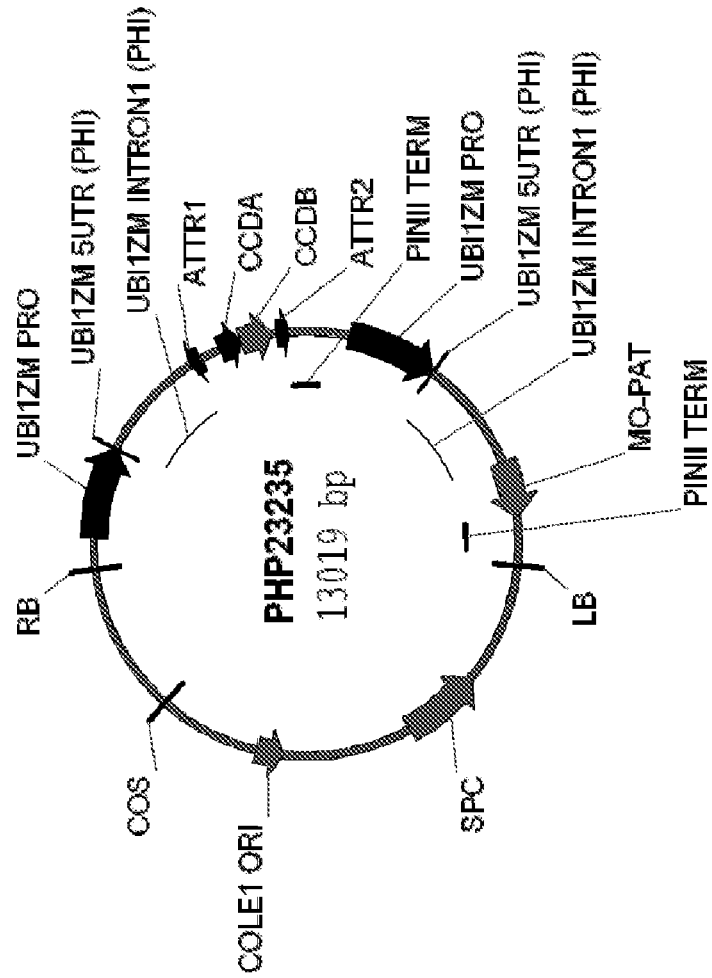
FIG. 8 shows a map of PHP23235 (SEQ ID NO:8), a vector used to construct the destination vector PHP23236.
Figure 9:
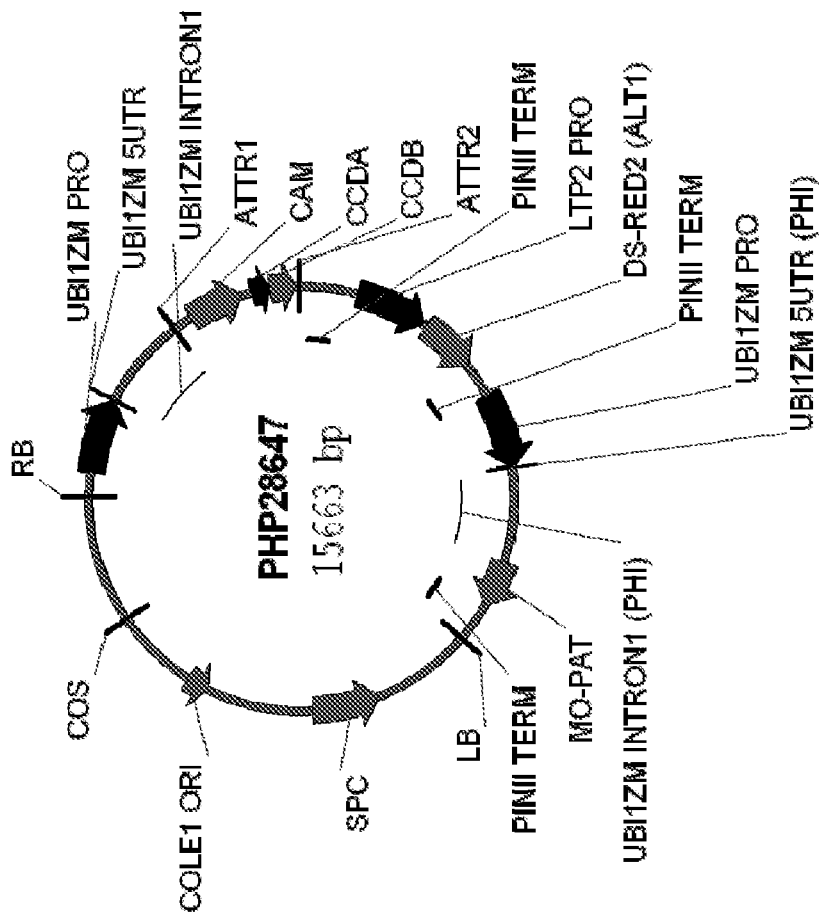
FIG. 9 shows a map of PHP28647 (SEQ ID NO:9), a destination vector for use with maize inbred-derived lines. The attR1 site is at nucleotides 2289-2413; the attR2 site is at nucleotides 3869-3993.
Figure 10:
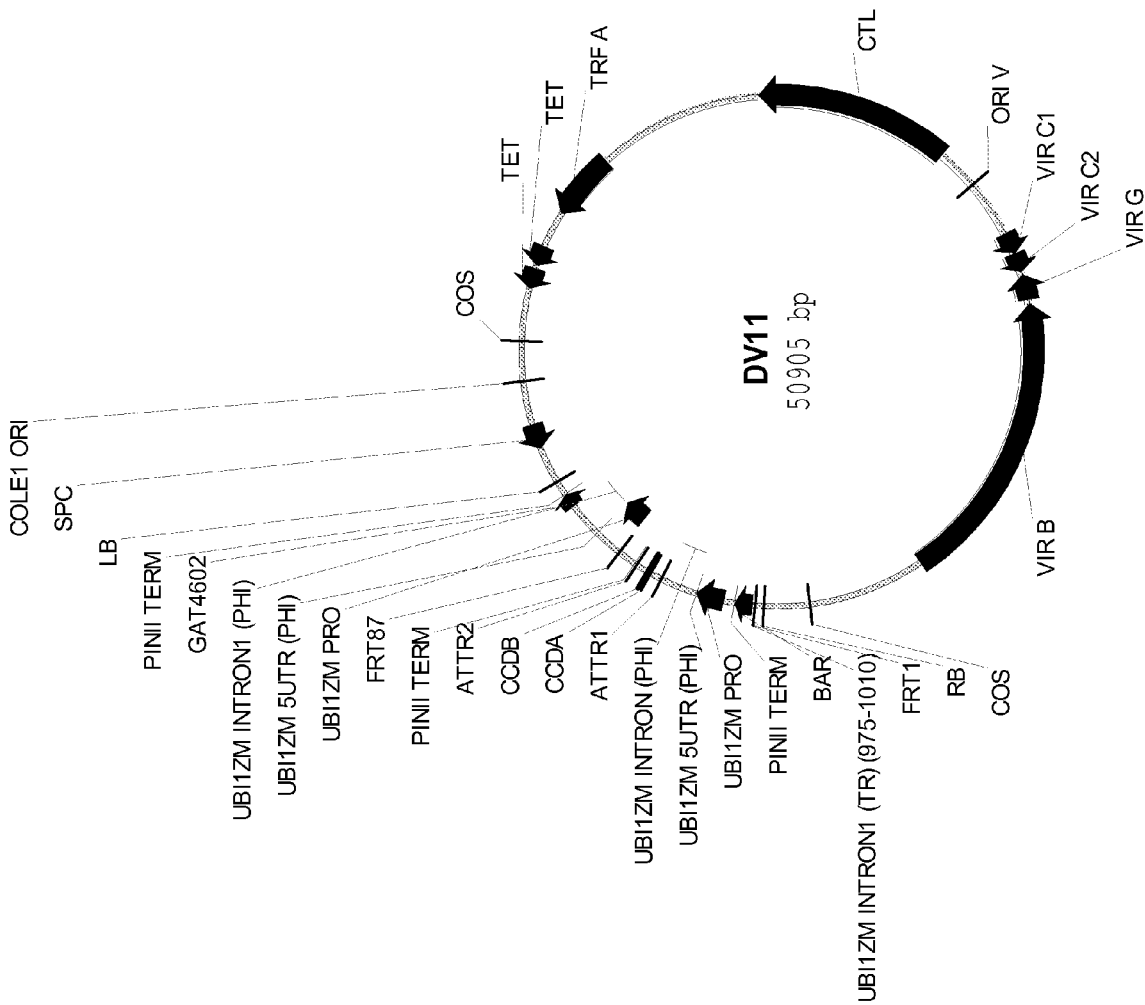
FIG. 10 shows a map of PHP29634 (also called DV11), a destination vector for use with Gaspe Flint derived maize lines.
Figure 11A:
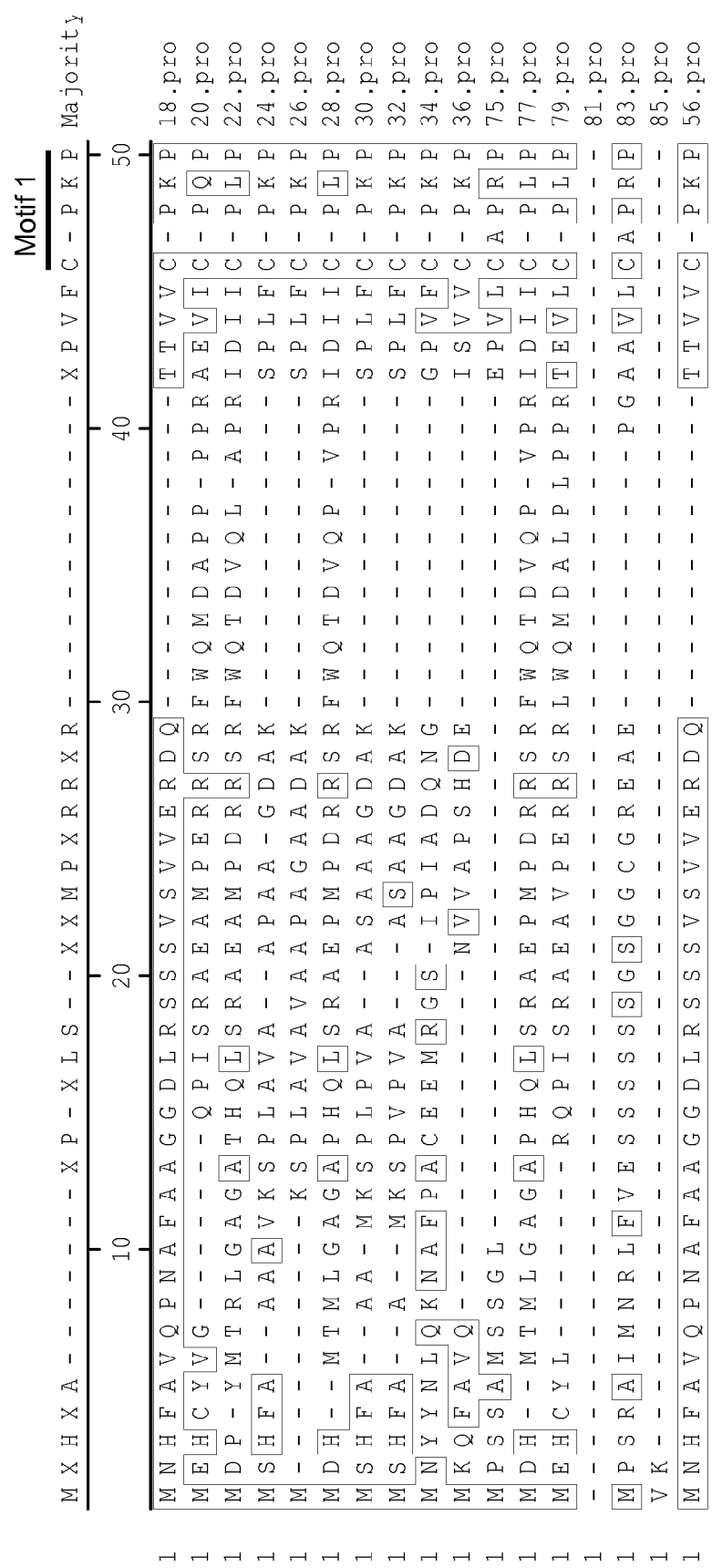
Figure 11B:
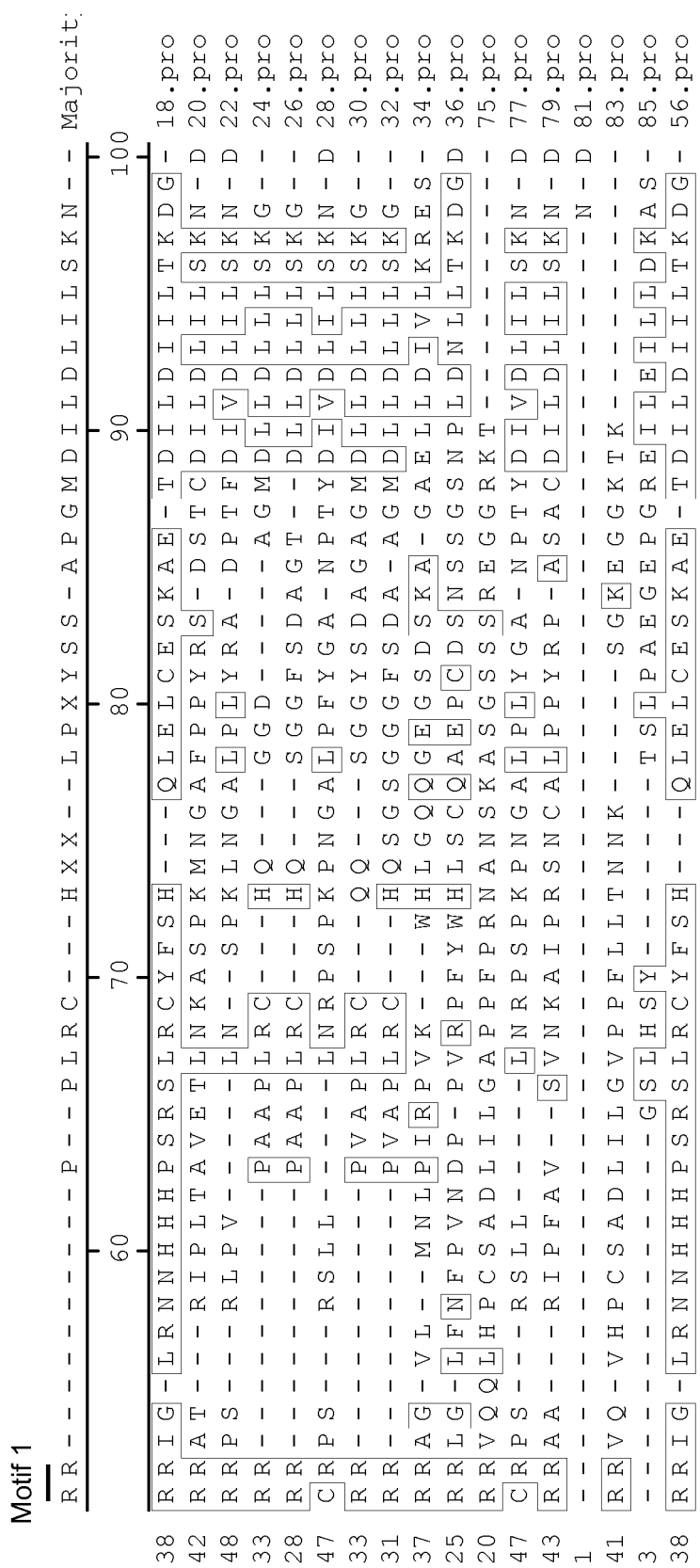
Figure 11C:
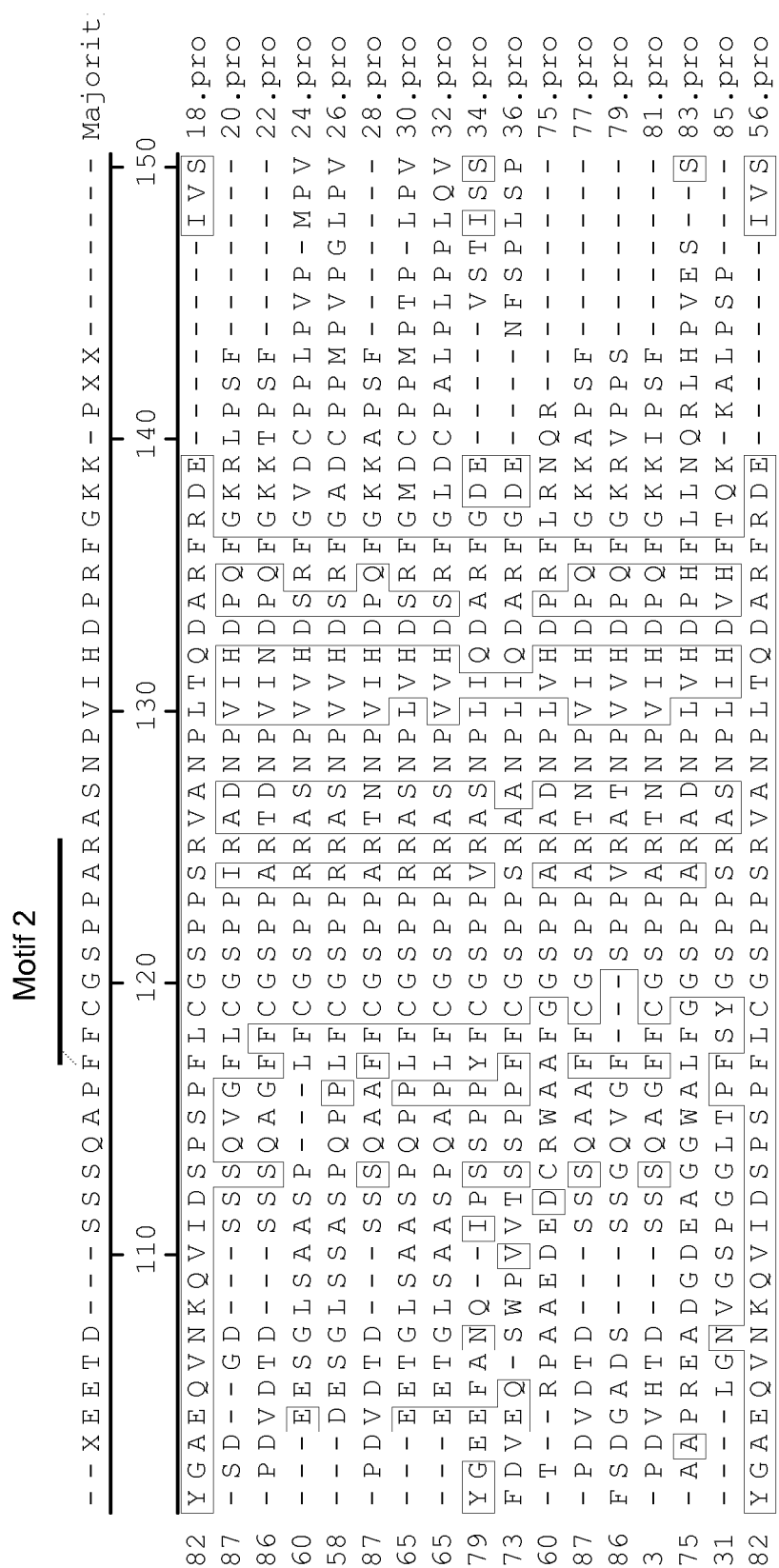

Preparation of the Destination Vector PHP23236 for Transformation into Gaspe Flint Derived Maize Lines Destination vector PHP23236 (FIG. 6, SEQ ID NO:6) was obtained by transformation of *Agrobacterium* strain LBA4404 containing plasmid PHP10523 (FIG. 7, SEQ ID NO:7) with plasmid PHP23235 (FIG. 8, SEQ ID NO:8) and isolation of the resulting co-integration product. Destination vector PHP23236, can be used in a recombination reaction with an entry clone as described in Example 16 to create a maize expression vector for transformation of Gaspe Flint-derived maize lines.

Example 16

Preparation of Plasmids for Transformation into Gaspe Flint Derived Maize Lines

Using the INVITROGEN™ GATEWAY® LR Recombination technology, the protein-coding region of the candidate gene described in Example 5, PHP31329, was directionally cloned into the destination vector PHP23236 (SEQ ID NO:6; FIG. 6) to create an expression vector, PHP27927. This expression vector contains the protein-coding region of interest, encoding the AT-DTP6 polypeptide, under control of the UBI promoter and is a T-DNA binary vector for *Agrobacterium*-mediated transformation into corn as described, but not limited to, the examples described herein.

Example 17

Transformation of Gaspe Flint Derived Maize Lines with a Validated *Arabidopsis* Lead Gene Maize plants can be transformed to overexpress the *Arabidopsis* lead gene or the corresponding homologs from other species in order to examine the resulting phenotype.

Recipient Plants:

Recipient plant cells can be from a uniform maize line having a short life cycle ("fast cycling"), a reduced size, and high transformation potential. Typical of these plant cells for maize are plant cells from any of the publicly available Gaspe Flint (GBF) line varieties. One possible candidate plant line variety is the F1 hybrid of GBFxQTM (Quick Turnaround Maize, a publicly available form of Gaspe Flint selected for growth under greenhouse conditions) disclosed in Tomes et al. U.S. Patent Application Publication No. 2003/0221212. Transgenic plants obtained from this line are of such a reduced size that they can be grown in four inch pots (¼ the space needed for a normal sized maize plant) and mature in less than 2.5 months. (Traditionally 3.5 months is required to obtain transgenic T0 seed once the transgenic plants are acclimated to the greenhouse.) Another suitable line is a double haploid line of GS3 (a highly transformable line)×Gaspe Flint. Yet another suitable line is a transformable elite inbred line carrying a transgene which causes early flowering, reduced stature, or both.

Transformation Protocol:

Any suitable method may be used to introduce the transgenes into the maize cells, including but not limited to inoculation type procedures using *Agrobacterium* based vectors. Transformation may be performed on immature embryos of the recipient (target) plant.

Precision Growth and Plant Tracking:

The event population of transgenic (T0) plants resulting from the transformed maize embryos is grown in a controlled greenhouse environment using a modified randomized block design to reduce or eliminate environmental error. A randomized block design is a plant layout in which the experimental plants are divided into groups (e.g., thirty plants per group), referred to as blocks, and each plant is randomly assigned a location with the block.

For a group of thirty plants, twenty-four transformed, experimental plants and six control plants (plants with a set phenotype) (collectively, a "replicate group") are placed in pots which are arranged in an array (a.k.a. a replicate group or block) on a table located inside a greenhouse. Each plant, control or experimental, is randomly assigned to a location with the block which is mapped to a unique, physical greenhouse location as well as to the replicate group. Multiple replicate groups of thirty plants each may be grown in the same greenhouse in a single experiment. The layout (arrangement) of the replicate groups should be determined to minimize space requirements as well as environmental effects within the greenhouse. Such a layout may be referred to as a compressed greenhouse layout.

An alternative to the addition of a specific control group is to identify those transgenic plants that do not express the gene of interest. A variety of techniques such as RT-PCR can be applied to quantitatively assess the expression level of the introduced gene. T0 plants that do not express the transgene can be compared to those which do.

Each plant in the event population is identified and tracked throughout the evaluation process, and the data gathered from that plant is automatically associated with that plant so that the gathered data can be associated with the transgene carried by the plant. For example, each plant container can have a machine readable label (such as a Universal Product Code (UPC) bar code) which includes information about the plant identity, which in turn is correlated to a greenhouse location so that data obtained from the plant can be automatically associated with that plant.

Alternatively any efficient, machine readable, plant identification system can be used, such as two-dimensional matrix codes or even radio frequency identification tags (RFID) in which the data is received and interpreted by a radio frequency receiver/processor. See U.S. Published Patent Application No. 2004/0122592, incorporated herein by reference.

Phenotypic Analysis Using Three-Dimensional Imaging:

Each greenhouse plant in the T0 event population, including any control plants, is analyzed for agronomic characteristics of interest, and the agronomic data for each plant is recorded or stored in a manner so that it is associated with the identifying data (see above) for that plant. Confirmation of a phenotype (gene effect) can be accomplished in the T1 generation with a similar experimental design to that described above.

The T0 plants are analyzed at the phenotypic level using quantitative, non-destructive imaging technology throughout the plant's entire greenhouse life cycle to assess the traits of interest. A digital imaging analyzer may be used for automatic multi-dimensional analyzing of total plants. The imaging may be done inside the greenhouse. Two camera systems, located at the top and side, and an apparatus to rotate the plant, are used to view and image plants from all sides. Images are acquired from the top, front and side of each plant. All three images together provide sufficient information to evaluate the biomass, size and morphology of each plant.

Due to the change in size of the plants from the time the first leaf appears from the soil to the time the plants are at the end of their development, the early stages of plant development are best documented with a higher magnification from the top. This may be accomplished by using a motorized zoom lens system that is fully controlled by the imaging software.

In a single imaging analysis operation, the following events occur: (1) the plant is conveyed inside the analyzer area, rotated 360 degrees so its machine readable label can be read, and left at rest until its leaves stop moving; (2) the side image is taken and entered into a database; (3) the plant is rotated 90 degrees and again left at rest until its leaves stop moving, and (4) the plant is transported out of the analyzer.

Plants are allowed at least six hours of darkness per twenty four hour period in order to have a normal day/night cycle.

Imaging Instrumentation:

Any suitable imaging instrumentation may be used, including but not limited to light spectrum digital imaging instrumentation commercially available from LemnaTec GmbH of Wurselen, Germany. The images are taken and analyzed with a LemnaTec Scanalyzer HTS LT-0001-2 having a ½" IT Progressive Scan IEE CCD imaging device. The imaging cameras may be equipped with a motor zoom, motor aperture and motor focus. All camera settings may be made using LemnaTec software. For example, the instrumental variance of the imaging analyzer is less than about 5% for major components and less than about 10% for minor components.

Software:

The imaging analysis system comprises a LemnaTec HTS Bonit software program for color and architecture analysis and a server database for storing data from about 500,000 analyses, including the analysis dates. The original images and the analyzed images are stored together to allow the user to do as much reanalyzing as desired. The database can be connected to the imaging hardware for automatic data collection and storage. A variety of commercially available software systems (e.g. Matlab, others) can be used for quantitative interpretation of the imaging data, and any of these software systems can be applied to the image data set.

Conveyor System:

A conveyor system with a plant rotating device may be used to transport the plants to the imaging area and rotate them during imaging. For example, up to four plants, each with a maximum height of 1.5 m, are loaded onto cars that travel over the circulating conveyor system and through the imaging measurement area. In this case the total footprint of the unit (imaging analyzer and conveyor loop) is about 5 m×5 m.

The conveyor system can be enlarged to accommodate more plants at a time. The plants are transported along the conveyor loop to the imaging area and are analyzed for up to 50 seconds per plant. Three views of the plant are taken. The conveyor system, as well as the imaging equipment, should be capable of being used in greenhouse environmental conditions.

Illumination:

Any suitable mode of illumination may be used for the image acquisition. For example, a top light above a black background can be used. Alternatively, a combination of top- and backlight using a white background can be used. The illuminated area should be housed to ensure constant illumination conditions. The housing should be longer than the measurement area so that constant light conditions prevail without requiring the opening and closing or doors. Alternatively, the illumination can be varied to cause excitation of either transgene (e.g., green fluorescent protein (GFP), red fluorescent protein (RFP)) or endogenous (e.g. Chlorophyll) fluorophores.

Biomass Estimation Based on Three-Dimensional Imaging:

For best estimation of biomass the plant images should be taken from at least three axes, for example, the top and two side (sides 1 and 2) views. These images are then analyzed to separate the plant from the background, pot and pollen control bag (if applicable). The volume of the plant can be estimated by the calculation:

$$\text{Volume(voxels)} = \sqrt{\text{TopArea(pixels)}} \times \sqrt{\text{Side1Area(pixels)}} \times \sqrt{\text{Side2Area(pixels)}}$$

In the equation above the units of volume and area are "arbitrary units". Arbitrary units are entirely sufficient to detect gene effects on plant size and growth in this system because what is desired is to detect differences (both positive-larger and negative-smaller) from the experimental mean, or control mean. The arbitrary units of size (e.g. area) may be trivially converted to physical measurements by the addition of a physical reference to the imaging process. For instance, a physical reference of known area can be included in both top and side imaging processes. Based on the area of these physical references a conversion factor can be determined to allow conversion from pixels to a unit of area such as square centimeters ($cm^2$). The physical reference may or may not be an independent sample. For instance, the pot, with a known diameter and height, could serve as an adequate physical reference.

Color Classification:

The imaging technology may also be used to determine plant color and to assign plant colors to various color classes. The assignment of image colors to color classes is an inherent feature of the LemnaTec software. With other image analysis software systems color classification may be determined by a variety of computational approaches.

For the determination of plant size and growth parameters, a useful classification scheme is to define a simple color scheme including two or three shades of green and, in addition, a color class for chlorosis, necrosis and bleaching, should these conditions occur. A background color class which includes non plant colors in the image (for example pot and soil colors) is also used and these pixels are specifically excluded from the determination of size. The plants are analyzed under controlled constant illumination so that any change within one plant over time, or between plants or different batches of plants (e.g. seasonal differences) can be quantified.

In addition to its usefulness in determining plant size growth, color classification can be used to assess other yield component traits. For these other yield component traits additional color classification schemes may be used. For instance, the trait known as "staygreen", which has been associated with improvements in yield, may be assessed by a color classification that separates shades of green from shades of yellow and brown (which are indicative of senescing tissues). By applying this color classification to images taken toward the end of the T0 or T1 plants' life cycle, plants that have increased amounts of green colors relative to yellow and brown colors (expressed, for instance, as Green/Yellow Ratio) may be identified. Plants with a significant difference in this Green/Yellow ratio can be identified as carrying transgenes which impact this important agronomic trait.

The skilled plant biologist will recognize that other plant colors arise which can indicate plant health or stress response (for instance anthocyanins), and that other color classification schemes can provide further measures of gene action in traits related to these responses.

Plant Architecture Analysis:

Transgenes which modify plant architecture parameters may also be identified using the present invention, including such parameters as maximum height and width, internodal distances, angle between leaves and stem, number of leaves starting at nodes and leaf length. The LemnaTec system software may be used to determine plant architecture as follows. The plant is reduced to its main geometric architecture in a first imaging step and then, based on this image, parameterized identification of the different architecture parameters can be performed. Transgenes that modify any of these architecture parameters either singly or in combination can be identified by applying the statistical approaches previously described.

Pollen Shed Date:

Pollen shed date is an important parameter to be analyzed in a transformed plant, and may be determined by the first appearance on the plant of an active male flower. To find the male flower object, the upper end of the stem is classified by color to detect yellow or violet anthers. This color classification analysis is then used to define an active flower, which in turn can be used to calculate pollen shed date.

Alternatively, pollen shed date and other easily visually detected plant attributes (e.g. pollination date, first silk date) can be recorded by the personnel responsible for performing plant care. To maximize data integrity and process efficiency this data is tracked by utilizing the same barcodes utilized by the LemnaTec light spectrum digital analyzing device. A computer with a barcode reader, a palm device, or a notebook PC may be used for ease of data capture recording time of observation, plant identifier, and the operator who captured the data.

Orientation of the Plants:

Mature maize plants grown at densities approximating commercial planting often have a planar architecture. That is, the plant has a clearly discernable broad side, and a narrow side. The image of the plant from the broadside is determined. To each plant a well defined basic orientation is assigned to obtain the maximum difference between the broadside and edgewise images. The top image is used to determine the main axis of the plant, and an additional rotating device is used to turn the plant to the appropriate orientation prior to starting the main image acquisition.

Example 18

Evaluation of Gaspe Flint Derived Maize Lines for Drought Tolerance

Transgenic Gaspe Flint derived maize lines containing the candidate gene can be screened for tolerance to drought stress in the following manner.

Transgenic maize plants are subjected to well-watered conditions (control) and to drought-stressed conditions. Transgenic maize plants are screened at the T1 stage or later.

For plant growth, the soil mixture consists of ⅓ TURFACE®, ⅓ SB300 and ⅓ sand. All pots are filled with the same amount of soil±10 grams. Pots are brought up to 100% field capacity ("FC") by hand watering. All plants are maintained at 60% FC using a 20-10-20 (N-P-K) 125 ppm N nutrient solution. Throughout the experiment pH is monitored at least three times weekly for each table. Starting at 13 days after planting (DAP), the experiment can be divided into two treatment groups, well watered and reduce watered. All plants comprising the reduced watered treatment are maintained at 40% FC while plants in the well watered treatment are maintained at 80% FC. Reduced watered plants are grown for 10 days under chronic drought stress conditions (40% FC). All plants are imaged daily throughout chronic stress period. Plants are sampled for metabolic profiling analyses at the end of chronic drought period, 22 DAP. At the conclusion of the chronic stress period all plants are imaged and measured for chlorophyll fluorescence. Reduced watered plants are subjected to a severe drought stress period followed by a recovery period, 23-31 DAP and 32-34 DAP respectively. During the severe drought stress, water and nutrients are withheld until the plants reached 8% FC. At the conclusion of severe stress and recovery periods all plants are again imaged and measured for chlorophyll fluorescence. The probability of a greater Student's t Test is calculated for each transgenic mean compared to the appropriate null mean (either segregant null or construct null). A minimum (P<t) of 0.1 is used as a cut off for a statistically significant result.

Example 19A

Yield Analysis of Maize Lines with the *Arabidopsis* Lead Gene

A recombinant DNA construct containing a validated *Arabidopsis* gene can be introduced into an elite maize inbred line either by direct transformation or introgression from a separately transformed line.

Transgenic plants, either inbred or hybrid, can undergo more vigorous field-based experiments to study yield enhancement and/or stability under well-watered and water-limiting conditions.

Subsequent yield analysis can be done to determine whether plants that contain the validated *Arabidopsis* lead gene have an improvement in yield performance under water-limiting conditions, when compared to the control plants that do not contain the validated *Arabidopsis* lead gene. Specifically, drought conditions can be imposed during the flowering and/or grain fill period for plants that contain the validated *Arabidopsis* lead gene and the control plants. Reduction in yield can be measured for both. Plants containing the validated *Arabidopsis* lead gene have less yield loss relative to the control plants, for example, at least 25%, 20%, 15%, 10% or 5% less yield loss.

The above method may be used to select transgenic plants with increased yield, under water-limiting conditions and/or well-watered conditions, when compared to a control plant not comprising said recombinant DNA construct.

Example 19B

Yield Analysis of Maize Lines Transformed with PHP31378 Encoding the *Arabidopsis* Lead Gene At1g68490

The DTP6 polypeptide present in the cointegrated vector PHP31378 was introduced into a transformable maize line derived from an elite maize inbred line as described in Examples 14A and 14B.

Seven transgenic events were field tested in 2009 at Johnston, Iowa ("JH"), York, Nebr. ("YK"), and Woodland, Calif. ("WO"). At the Woodland, Calif., location, drought conditions were imposed during flowering ("FS"; flowering stress) and during the grain fill period ("GFS"; grain fill stress). The JH location was well-watered, and the YK location experienced mild drought during the grain-filling period.

Yield data were collected in 4 locations in 2010 (York, Johnston, Woodland-2 water treatments), with 4-8 replicates per location.

Yield data (bushel/acre; bu/ac) for 2009 and 2010 for the 7 transgenic events are shown in Table 6 and Table 7 together with the bulk null control (BN). Yield analysis was by ASREML (VSN International Ltd), and the values are BLUPs (Best Linear Unbiased Prediction) (Cullis, B. R et al (1998) *Biometrics* 54: 1-18, Gilmour, A. R. et al (2009). ASRemI User Guide 3.0, Gilmour, A. R., et al (1995) *Biometrics* 51: 1440-50).

To analyze the yield data, a mixed model framework was used to perform the single and multi location analysis.

In the single location analysis, main effect of construct is considered as a fixed effect. (However, construct effect might be considered as random in other circumstances). The main effect of event is considered as random. The blocking factors such as replicates and incblock (incomplete block design) within replicates are considered as random.

There are 3 components of spatial effects including x_adj, y_adj and autoregressive correlation as AR1*AR1 to remove the noise caused by spatial variation in the field.

In the multi-location analysis, main effect of loc_id, construct and their interaction are considered as fixed effects in this analysis. The main effect of event and its interaction with loc_id are considered as random effects. The blocking factors such as replicates and incblock within replicates are considered as random.

We performed single_loc analyses in each year, and across_loc analysis over the two years (last column), in Table 5 and calculated blup (Best Linear Unbiased Prediction) for each event. The significance test between the event and BN was performed using a p-value of 0.1 in a two-tailed test, and the results are shown in Table 6 and Table 7. The significant values (with p-value less than or equal to 0.1 with a 2-tailed test) are shown in bold.

As shown in Table 6 and Table 7, the effect of the transgene on yield was significant for at least three events in three of the four locations in 2009 and in one of the locations in 2010. These four locations represented yield levels ranging from 55 to 170 bu/acre, and the yield advantage attributed to the transgene ranged from 4 to 10 bu/acre. In the across-location analysis, the overall effect of the transgene was positive, with two events reaching statistical significance. JH and York were wet environments in 2010, and there was no significant effect of the gene on yield. No significant differences were observed in plant or ear height or flowering date. There was a tendency for slightly higher grain moisture at harvest; this difference was significant for 1 event in York and for 2 events in Johnston. The data are shown in Table 7. The significant values (with p-value less than or equal to 0.1 with a 2-tailed test) are shown in bold.

TABLE 6

2009 Field Test of Maize Transformed with PHP31378

| | | | 2009 | | | |
|---|---|---|---|---|---|---|
| DNA | Event | ** | JH YIB205 Pred value | WO RL0909 Pred value | WO RLSEGN Pred value | YK RLJ20R Pred value |
| 1* | BN_YSPNTIBA | BN | 188.65 | 94.51 | 55.06 | 170.10 |
| 2* | BN_YSPNTIDA | BN | — | — | — | — |
| 3* | E7899.54.1.3 | BN | (+−)189 | (++)104 | (++)68 | (−−)170 |
| | E7899.54.5.1 | BN | (+−)189 | (+−)96 | (++)65 | (++)177 |
| | E7899.54.5.2 | BN | (+−)189 | (+−)95 | (++)63 | (+−)174 |
| | E7899.54.5.4 | BN | (+−)193 | (++)101 | (++)64 | (++)177 |
| | E7899.54.6.3 | BN | (+−)184 | (+−)97 | (+−)60 | (+−)174 |
| | E7899.54.8.10 | BN | (+−)191 | (++)102 | (++)66 | (++)177 |
| | E7899.54.8.5 | BN | (+−)185 | (−−)93 | (++)65 | (+−)171 |

*DNA "1" is BN_YSPNTIBA; DNA "2" is BN_YSPNTIDA; DNA "3" is PHP31378.
** Comp_Factor_Entry_Type

TABLE 7

2010 Field Test of Maize Transformed with PHP31378

| DNA | Event | ** | WO RF2015 Pred value | WO RG2012 Pred value | JH YIB106 Pred value | YK RLP20R Pred value | Across All Four Sites Pred value |
|---|---|---|---|---|---|---|---|
| 1* | BN_YSPNTIBA | BN | — | — | — | — | 151.21 |
| 2* | BN_YSPNTIDA | BN | 123.93 | 141.27 | 167.36 | 172.46 | |
| 3* | E7899.54.1.3 | BN | (++)128 | (+−)144 | (−−)167 | (+−)173 | (+−)154 |
| | E7899.54.5.1 | BN | (++)128 | (+−)145 | (−−)166 | (+−)173 | (++)154 |
| | E7899.54.5.2 | BN | (+−)127 | (−−)139 | (+−)167 | (+−)173 | (+−)153 |
| | E7899.54.5.4 | BN | (++)128 | (+−)145 | (−−)167 | (+−)173 | (++)154 |
| | E7899.54.6.3 | BN | (+−)127 | (+−)145 | (−−)167 | (+−)173 | (+−)153 |
| | E7899.54.8.10 | BN | (+−)126 | (+−)143 | (−−)167 | (+−)173 | (+−)153 |
| | E7899.54.8.5 | BN | (+−)127 | (−−)140 | (−−)166 | (+−)173 | (+−)153 |

*DNA "1" is BN_YSPNTIBA; DNA "2" is BN_YSPNTIDA; DNA "3" is PHP31378.
** Comp_Factor_Entry_Type Table 8 shows data from a 2009 field test of maize transformed with PHP31378. The WO_ASI column shows silk delay in the WO gradual stress treatment. Two out of seven events show positive effect as indicated by significantly lower ASI as compared to the BN control. None of the events show a negative effect.

TABLE 8

2009 Field Test - Measure of Delay in Silking

| Event ID | WO_ASI (GDU) |
|---|---|
| E7899.54.1.3 | 40 |
| E7899.54.5.1 | 40 |
| E7899.54.5.2 | 60 |
| E7899.54.5.4 | 14 * |
| E7899.54.6.3 | 27 * |
| E7899.54.8.10 | 41 |
| E7899.54.8.5 | 40 |
| WT | 50 |
| BN | 70 |

* significantly superior to null at p < 0.1

Example 20A

Preparation of Maize DTP6 Polypeptide Lead Gene Expression Vector for Transformation of Maize Clones cfp5n.pk061.k20, cie3s.pk008.j21, cfp7n.pk001.j9, cds3f.pk005.m8 and my.cco1n.pk088.j17 encode complete DTP6 polypeptides and are designated as Zm-DTP6-1, Zm-DTP6-2, Zm-DTP6-3, Zm-DTP6-4 and Zm-DTP6-5 (presented in SEQ ID NOS: 19, 21, 23, 25 and 27, respectively). The protein-coding region of these clones containing these sequences can be introduced into the INVITROGEN™ vector pENTR/D-TOPO® to create entry clones.

Using INVITROGEN™ GATEWAY® technology, an LR Recombination Reaction can be performed with an entry clone and a destination vector to create the precursor plasmid. The precursor plasmid contains the following expression cassettes:

1. Ubiquitin promoter::moPAT::PinII terminator; cassette expressing the PAT herbicide resistance gene used for selection during the transformation process.

2. LTP2 promoter::DS-RED2::PinII terminator; cassette expressing the DS-RED color marker gene used for seed sorting.

3. Ubiquitin promoter::Zm-DTP6-Polypeptide::PinII terminator; cassette overexpressing the gene of interest, maize DTP6 polypeptide.

Example 20B

Transformation of Maize with Maize DTP6 Polypeptide Lead Gene Using Agrobacterium The maize DTP6 polypeptide expression cassette present in the precursor plasmids can be introduced into a maize inbred line, or a transformable maize line derived from an elite maize inbred line, using Agrobacterium-mediated transformation as described in Examples 12 and 13.

The precursor plasmid can be electroporated into the LBA4404 Agrobacterium strain containing vector PHP10523 (FIG. 7; SEQ ID NO:7) to create a co-integrate vector. The co-integrate vector is formed by recombination of the 2 plasmids, precursor plasmid and PHP10523, through the COS recombination sites contained on each vector. The co-integrate vector contains the same 3 expression cassettes as above (Example 20A) in addition to other genes (TET, TET, TRFA, ORI terminator, CTL, ORI V, VIR C1, VIR C2, VIR G, VIR B) needed for the Agrobacterium strain and the Agrobacterium-mediated transformation.

Example 21

Preparation of Maize Expression Plasmids for Transformation into Gaspe Flint Derived Maize Lines Clones cfp5n.pk061.k20, cie3s.pk008.j21, cfp7n.pk001.j9, cds3f.pk005.m8 and my.cco1n.pk088.j17 encode complete DTP6 polypeptides and are designated as Zm-DTP6-1, Zm-DTP6-2, Zm-DTP6-3, Zm-DTP6-4 and Zm-DTP6-5 respectively (presented in SEQ ID NOS: 19, 21, 23, 25 and 27, respectively).

Using the INVITROGEN™ GATEWAY® Recombination technology described in Example 9, the clones encoding maize Zm-DTP6-1, Zm-DTP6-2 and Zm-DTP6-3 polypeptide homologs were directionally cloned into the destination vector PHP23236 (SEQ ID NO:6; FIG. 6) to create the expression vectors listed in Table 6. Each expression vector contains the cDNA of interest under control of the UBI promoter and is a T-DNA binary vector for Agrobacterium-mediated transformation into corn as described, but not limited to, the examples described herein.

TABLE 9

Maize DTP6 Polypeptide Expression Vectors

| Protein | Clone Origin | SEQ ID NO: (Amino Acid) | Expression Vector |
|---|---|---|---|
| Zm-DTP6-1 | cfp5n.pk061.k20 (FIS) | 20 | PHP30760 |
| Zm-DTP6-2 | cie3s.pk008.j21 (FIS) | 22 | PHP30841 |
| Zm-DTP6-3 | cfp7n.pk001.j9 (FIS) | 24 | PHP30854 |

Example 22

Transformation and Evaluation of Soybean with Soybean Homologs of Validated Lead Genes Based on homology searches, several candidate soybean homologs of validated *Arabidopsis* lead genes have been identified. Clones sdp4c.pk004.f4 and sfp1n.pk034.b12 encode complete DTP6 polypeptides and are designated as Gm-DTP6-1 and Gm-DTP6-2, respectively (presented in SEQ ID NOS: 33 and 35, respectively). These clones can also be assessed for their ability to enhance drought tolerance in soybean. Vector construction, plant transformation and phenotypic analysis can be similar to that in previously described Examples.

Example 23

Transformation of *Arabidopsis* with Maize and Soybean Homologs of Validated Lead Genes Soybean and maize homologs to validated *Arabidopsis* lead genes can be transformed into *Arabidopsis* under control of the 35S promoter and assessed for their ability to enhance drought tolerance in *Arabidopsis*. Vector construction, plant transformation and phenotypic analysis can be similar to that in previously described Examples.

Example 24

Creation of HMM Profile for DTP6 Proteins Profile HMM Specific to DTP6

Profile HMMs are statistical models of multiple sequence alignments, or even of single sequences. They capture position-specific information about how conserved each column of the alignment is, and which residues are likely.
Description:
HMMER® (biosequence analysis using profile hidden Markov models) is used to search sequence databases for homologs of protein sequences, and to make protein sequence alignments. HMMER® can be used to search sequence databases with single query sequences, but it becomes particularly powerful when the query is a multiple sequence alignment of a sequence family. HMMER® makes a profile of the query that assigns a position-specific scoring system for substitutions, insertions, and deletions. HMMER® profiles are probabilistic models called "profile hidden Markov models" (profile HMMs) (Krogh et al., 1994, *J. Mol. Biol.*, 235:1501-1531; Eddy, 1998, *Curr. Opin. Struct. Biol.*, 6:361-365.; Durbin et al., *Probabilistic Models of Proteins and Nucleic Acids*. Cambridge University Press, Cambridge UK. 1998, Eddy, Sean R., March 2010, HMMER User's Guide Version 3.0, Howard Hughes Medical Institute, Janelia Farm Research Campus, Ashburn Va., USA; US patent publication No. US20100293118).Compared to BLAST, FASTA, and other sequence alignment and database search tools based on older scoring methodology, HMMER® aims to be significantly more accurate and more able to detect remote homologs, because of the strength of its underlying probability models.
Method for Creating Profile HMMs Specific to DTP6 Gene Family
Step 1: Identification of Homologs of DTP6:
Homologs for AtDTP6 were identified by querying protein sequence of AtDTP6 using PSI-BLAST (Altschul et al, 1997; *Nucleic Acids Research* 25: 3389-3402) within an in house database of protein sequences generated by compilation of protein sequences from UniProt and translated ORFs from various plant genomes that were retrieved from NCBI. Hits retrieved from the search were shortlisted further to identify homologs on the basis of E-value (Altschul et al, 1997; *Nucleic Acids Research* 25: 3389-3402) cut off less than 0.001 in the third iteration of PSI-BLAST and matching the query sequence with significant coverage. Homologs thus identified were aligned using the software MUSCLE (Edgar, Robert C. (2004), *Nucleic Acids Research* 19; 32(5): 1792-7). All the homologs of DTP6 identified correspond to plant species and no significant homologs could be identified in other organisms, suggesting DTP6 as a plant specific gene family.
Step 2: Creating Profile HMM for DTP6
We have used HMMbuild module of HMMER® 3.0 to create a profile HMM for DTP6 based on Multiple Sequence Aliignment (MSA) of homologs of DTP6.
Step 3: Using Profile to Search Protein Database
Profile HMM created was queried in a database of protein sequences described in Step 1. Hits retrieved were further examined as described in Step 4.
Step 4: Determining Specificity of Profile to Identify DTP6 Related Protein Sequences
All protein sequences that matched the profile HMM of DTP6 with an E-value of less than 0.001 over at least 80% length of the HMM profile were regarded as statistically significant and corresponding to gene family. Since all statistically significant protein hits obtained are members of DTP6 gene family, it is suggested that profile HMM for DTP6 described here is specific to identify any member of DTP6 family. The HMM profile for DTP6 family is shown in FIGS. 13A-13Y.

Example 25

Identification of DTP6 Expressologs

Identification of AtDTP6 Expressologs in Maize:
Protein sequences homologous to AT-DTP6 (SEQ ID NO: 18) were identified by searching through protein database comprising of sequences from various organisms including several plant genomes such as *Arabidopsis*, rice, maize and sorghum. Phylogenetic tree generated based on sequence similarity between homologs has been used as an evolutionary framework to overlay stress and hormone dependent changes in gene expression. Gene expression data used in the current analysis for *Arabidopsis* and rice has been retrieved from [Nottingham *Arabidopsis* Stock Centre's Microarray database (NASCARRAYS) and Gene Expression Omnibus database (GEO) and proprietary data. The maize gene expression data analysis is completely based on proprietary gene expression data.

Comparison of stress related gene expression changes in various homologs and their subcellular localization identified pco599449 (SEQ ID NO: 74) as maize expressolog of AT-DTP6. Based on computational prediction using (Target P software; Emanuelsson O et al, (2000) *J Mol Bio*, July 21; 300(4):1005-16) pco599449 polypeptide (SEQ ID NO: 75) has been suggested to localize in chloroplast. Gene expression analysis suggested upregulation of pco599449 transcripts in shoot (~6 fold) and seedlings (~2 fold) under cold treatment and upregulation in leaves (~4-fold) under drought treatment. This gene expression profile is similar to that of AT-DTP6, which was also found to be upregulated in shoots (~4 fold) under cold treatment. AT-DTP6 was also found to be also upregulated in drought (~2.0 fold) and other drought related conditions such as osmotic stress (~2 fold) and heat stress (~2.5 fold). Taken together, similarity in subcellular localization and gene expression under stress conditions, pco599449 is predicted to be an expressolog of AtDTP6. Expressologs have been recently used in comparative genomics to identify functional homologs across species (Patel et al. 2011, Expressolog Identification in Plant Species, Poster Abstract No. 209, 22$^{nd}$ International Conference on *Arabidopsis* Research, University of Wisconsin, Madison, Wis., USA). Relevant bioinformatic tools are available at the Bio-Array Resource for Plant Biology at the University of Toronto, Canada.

Example 26

Chloroplast Localization Prediction for AT-DTP6 Polypeptide

Amino acid sequence of AT-DTP6 polypeptide was analyzed for potential chloroplast transit peptides by using TargetP software (Emanuelsson O et al, (2000) *J Mol Bio*, July 21; 300(4):1005-16. The sequence of the predicted chloroplast transit peptide based on the cleavage site prediction by the Target P software is given in SEQ ID NO: 90 and the sequence of the predicted mature AT-DTP6 polypeptide is given is SEQ ID NO: 91.

Example 27

Paraquat Tolerance Assay for AT-DTP6 Polypeptide

Col-0 and 35S-DTP6 transgenic T2 seeds were sterilized and then stratified at 4° C. for 4 days. 18 seeds of each were planted on ½×MS medium supplemented with 0.03 µM Paraquat (FIG. 1). After 7 days grown in a chamber programmed for 16 h of light at 22° C. temperature, 150 µE light intensity and 50% relative humidity, transgenic lines plants had bigger and greener cotyledons.

In another experiment setting, we planted ~50 Col-0 seeds on ½×MS medium supplemented with 0.03 or 0.06 µM paraquat and then put five 35S-DTP6 T2 seeds on the same plate. After 7-day-incubation at growth chamber, transgenic plants are easily distinguished from control seeds. The transgenic seedlings have bigger and greener cotyledons (pointed by red arrows) on both paraquat concentrations (FIG. 2).

Example 28A

Triple Stress Assay

*Arabidopsis* plants grown in a combination of three abiotic stresses is presented. Specifically, plants are grown in conditions of simultaneous drought stress, heat stress and high light stress. Mutants with positive growth and/or positive decay parameters can then be identified.

Materials:

*Arabidopsis* lines over-expressing a transgene and their non-transgenic siblings.

Methods:

Phase 1 Screen:

Seeds are soaked in water and incubated at 4° C. for 3 days in the dark. Cold shocked seeds are lines are planted in controlled density and spacing on soil. Specifically, 9 plants in a 3×3 grid are grown per 5.5 inch square pot with 8 pots per flat. For DTP6 testing, one flat consists of 4 pots transgenics and 4 pots of non-transgenic siblings. Thus 36 mutant plants are directly compared to 36 wild type plants.

For 14 days, plants are grown under non-stressed conditions involving: (a) Soil: Metromix 360; (b) Fertilizer: Osmocote and Peter's; (c) Light Regime: 16 hours light/8 hours dark; (d) Light Intensity: 150 µE; (e) Temperature Regime: 22 C day/20 C night; and (f) Humidity: 50% Relative Humidity. On the last day of non-stressed growth, flats are brought to 100% soil water capacity and imaged and analyzed to get total green area pixel count using a LemnaTec Scanalyzer The flats are then transferred to "triple stress" conditions consisting of: (a) no additional watering, (b) Light Regime: 16 hours light/8 hours dark; (c) Light Intensity: 350 µE (d) Temperature Regime: 22 C day with a 32 C pulse for 4 hours in the middle of the day/20 C night; and (f) Humidity: 50% Relative Humidity. In these conditions, flats are imaged daily for 14 days.

From the LemnaTec data, p-values are determined for growth area, growth slope and maximum day area, decay area and decay slope. Lines with a P-value of <0.05 for one or more of the parameters are considered positive Example 28B Triple Stress Assay with AT-DTP6 Protein Plants over-expressing DTP6 were assayed for the triple stress assay essentially as described in Example 28A. Below is the performance of 35S::DTP6 compared to non-transgenic sibs for the five triple stress parameters.

TABLE 10

Performance of 35S::DTP6 Line

| Parameter | Value |
|---|---|
| gro_comp | — |
| gro_area_p | 0.095 |
| slope_gro_comp | — |
| gro_slope_p | 0.086 |
| max_comp | — |
| max_p | 0.381 |
| decay_comp | + |
| decay_area_p | 0.225 |
| slope_dec_comp | + |
| decay_slope_p | 0.031 |

Comparison ("Comp") values of "+" indicate that 35S::DTP6 line had a positive value as compared to non-transgenic sibs. The p-value is also with respect to the difference between 35S::DTP6 and control sibs. This shows that over-expression of DTP6 reduces of the slope of leaf area loss with a p-value of 0.03.

What is claimed is:

1. A plant comprising in its genome a recombinant DNA construct comprising a polynucleotide operably linked to at least one regulatory element, wherein said polynucleotide encodes a polypeptide having an amino acid sequence of at least 90% sequence identity, based on the Clustal V method of alignment, when compared to SEQ ID NO: 18, and wherein said plant exhibits increased drought tolerance when compared to a control plant not comprising said recombinant DNA construct.

2. The plant of claim 1, wherein said plant is selected from the group consisting of: maize, soybean, sunflower, sorghum, canola, wheat, alfalfa, cotton, rice, barley, millet, sugar cane and switchgrass.

3. Seed of the plant of claim 1, wherein said seed comprises in its genome a recombinant DNA construct comprising a polynucleotide operably linked to at least one regulatory element, wherein said polynucleotide encodes a polypeptide having an amino acid sequence of at least 90% sequence identity, based on the Clustal V method of alignment, when compared to SEQ ID NO: 18, and wherein a plant produced from said seed exhibits an increase in at least one trait selected from the group consisting of: drought tolerance, triple stress tolerance, Paraquat tolerance, yield and biomass, when compared to a control plant not comprising said recombinant DNA construct.

4. A plant comprising in its genome a polynucleotide operably linked to at least one recombinant regulatory element, wherein said polynucleotide encodes a polypeptide having an amino acid sequence of at least 90% sequence identity, based on the Clustal V method of alignment, when compared to SEQ ID NO: 18, and wherein said plant exhibits increased drought tolerance when compared to a control plant not comprising the recombinant regulatory element.

* * * * *

SEQUENCE LISTING

<160> NUMBER OF SEQ ID NOS: 105

<210> SEQ ID NO 1
<211> LENGTH: 18444
<212> TYPE: DNA
<213> ORGANISM: Artificial Sequence
<220> FEATURE:
<223> OTHER INFORMATION: pHSbarENDs activation tagging vector for Population-1

<400> SEQUENCE: 1

| | | | | | |
|---|---|---|---|---|---|
| catgaatcaa | acaaacatac | acagcgactt | attcacacga | gctcaaatta | caacggtata |   60 |
| tatcctgccg | tcgacaacca | tggtctagac | aggatccccg | ggtaccgagc | tcgaatttgc |  120 |
| aggtcgactg | cgtcatccct | tacgtcagtg | gagatatcac | atcaatccac | ttgctttgaa |  180 |
| gacgtggttg | gaacgtcttc | ttttccacg | atgctcctcg | tgggtggggg | tccatctttg |  240 |
| ggaccactgt | cggcagaggc | atcttgaacg | atagcctttc | ctttatcgca | atgatggcat |  300 |
| ttgtaggtgc | caccttcctt | ttctactgtc | cttttgatga | agtgacagat | agctgggcaa |  360 |
| tggaatccga | ggaggtttcc | cgatattacc | ctttgttgaa | aagtctcaat | tgccctttgg |  420 |
| tcttctgaga | ctgttgcgtc | atcccttacg | tcagtggaga | tatcacatca | atccacttgc |  480 |
| tttgaagacg | tggttggaac | gtcttctttt | tccacgatgc | tcctcgtggg | tggggtcca |  540 |
| tctttgggac | cactgtcggc | agaggcatct | tgaacgatag | cctttccttt | atcgcaatga |  600 |
| tggcatttgt | aggtgccacc | ttccttttct | actgtccttt | tgatgaagtg | acagatagct |  660 |
| gggcaatgga | atccgaggag | gtttcccgat | attaccctt | gttgaaaagt | ctcagttaac |  720 |
| ccgcgatcct | gcgtcatccc | ttacgtcagt | ggagatatca | catcaatcca | cttgctttga |  780 |
| agacgtggtt | ggaacgtctt | ctttttccac | gatgctcctc | gtgggtgggg | gtccatcttt |  840 |
| gggaccactg | tcggcagagg | catcttgaac | gatagccttt | cctttatcgc | aatgatggca |  900 |
| tttgtaggtg | ccaccttcct | tttctactgt | ccttttgatg | aagtgacaga | tagctgggca |  960 |
| atggaatccg | aggaggtttc | ccgatattac | cctttgttga | aaagtctcaa | ttgccctttg | 1020 |
| gtcttctgag | actgttgcgt | catcccttac | gtcagtggag | atatcacatc | aatccacttg | 1080 |
| ctttgaagac | gtggttggaa | cgtcttcttt | ttccacgatg | ctcctcgtgg | gtgggggtcc | 1140 |
| atctttggga | ccactgtcgg | cagaggcatc | ttgaacgata | gcctttcctt | tatcgcaatg | 1200 |
| atggcatttg | taggtgccac | cttcctttc | tactgtcctt | ttgatgaagt | gacagatagc | 1260 |
| tgggcaatgg | aatccgagga | ggtttcccga | tattacccttt | tgttgaaaag | tctcagttaa | 1320 |
| cccgcaattc | actggccgtc | gttttacaac | gtcgtgactg | ggaaaaccct | ggcgttaccc | 1380 |
| aacttaatcg | ccttgcagca | catccccctt | tcgccagctg | gcgtaatagc | gaagaggccc | 1440 |
| gcaccgatcg | cccttcccaa | cagttgcgca | gcctgaatgg | cgaatggatc | gatccgtcga | 1500 |
| tcgaccaaag | cggccatcgt | gcctcccac | tcctgcagtt | cggggcatg | gatgcgcgga | 1560 |
| tagccgctgc | tggtttcctg | gatgccgacg | gatttgcact | gccggtagaa | ctccgcgagg | 1620 |
| tcgtccagcc | tcaggcagca | gctgaaccaa | ctcgcgaggg | gatcgagccc | ctgctgagcc | 1680 |
| tcgacatgtt | gtcgcaaaat | cgccctgga | cccgcccaac | gatttgtcgt | cactgtcaag | 1740 |
| gtttgacctg | cacttcattt | ggggcccaca | tacaccaaaa | aaatgctgca | taattctcgg | 1800 |
| ggcagcaagt | cggttacccg | ccgccgtgc | tggaccgggt | tgaatggtgc | ccgtaacttt | 1860 |
| cggtagagcg | gacggccaat | actcaacttc | aaggaatctc | acccatgcgc | gccggcgggg | 1920 |
| aaccggagtt | cccttcagtg | aacgttatta | gttcgccgct | cggtgtgtcg | tagatactag | 1980 |

```
cccctggggc cttttgaaat tgaataaga tttatgtaat cagtctttta ggtttgaccg    2040
gttctgccgc ttttttaaa attggatttg taataataaa acgcaattgt ttgttattgt    2100
ggcgctctat catagatgtc gctataaacc tattcagcac aatatattgt tttcatttta    2160
atattgtaca tataagtagt agggtacaat cagtaaattg aacggagaat attattcata    2220
aaaatacgat agtaacgggt gatatattca ttagaatgaa ccgaaaccgg cggtaaggat    2280
ctgagctaca catgctcagg ttttttacaa cgtgcacaac agaattgaaa gcaaatatca    2340
tgcgatcata ggcgtctcgc atatctcatt aaagcagggg gtgggcgaag aactccagca    2400
tgagatcccc cgcgctggag gatcatccag cggcgtcccg gaaaacgatt ccgaagccca    2460
acctttcata gaaggcggcg gtggaatcga aatctcgtga tggcaggttg ggcgtcgctt    2520
ggtcggtcat ttcgaacccc agagtcccgc tcagaagaac tcgtcaagaa ggcgatagaa    2580
ggcgatgcgc tgcgaatcgg gagcggcgat accgtaaagc acgaggaagc ggtcagccca    2640
ttcgccgcca agctcttcag caatatcacg ggtagccaac gctatgtcct gatagcggtc    2700
cgccacaccc agccggccac agtcgatgaa tccagaaaag cggccatttt ccaccatgat    2760
attcggcaag caggcatcgc catgggtcac gacgagatcc tcgccgtcgg gcatgccccc    2820
caattcactg gccgtcgttt tacaacgtcg tgactgggaa aaccctggcg ttacccaact    2880
taatcgcctt gcagcacatc cccctttcgc cagctggcgt aatagcgaag aggcccgcac    2940
cgatcgccct tcccaacagt tgcgcagcct gaatggcgaa tggcgcctga tgcggtattt    3000
tctccttacg catctgtgcg gtatttcaca ccgcatatgg tgcactctca gtacaatctg    3060
ctctgatgcc gcatagttaa gccagccccg acacccgcca cacccgctg acgcgccctg     3120 acgggcttgt ctgctcccgg catccgctta cagacaagct gtgaccgtct ccgggagctg    3180
catgtgtcag aggttttcac cgtcatcacc gaaacgcgcg agacgaaagg cctcgtgat    3240 acgcctattt ttataggtta atgtcatgat aataatggtt tcttagacgt caggtggcac    3300
ttttcgggga aatgtgcgcg gaacccctat ttgtttattt ttctaaatac attcaaatat    3360
gtatccgctc atgagacaat aaccctgata aatgcttcaa taatattgaa aaaggaagag    3420
tatgagtatt caacatttcc gtgtcgccct tattcccttt tttgcggcat ttgccttcc     3480 tgttttgct cacccagaaa cgctggtgaa agtaaaagat gctgaagatc agttgggtgc     3540 acgagtggg tacatcgaac tggatctcaa cagcggtaag atccttgaga gttttcgccc     3600
cgaagaacgt tttccaatga tgagcacttt taaagttctg ctatgtggcg cggtattatc    3660
ccgtattgac gccgggcaag agcaactcgg tcgccgcata cactattctc agaatgactt    3720
ggttgagtac tcaccagtca cagaaaagca tcttacggat ggcatgacag taagagaatt    3780
atgcagtgct gccataacca tgagtgataa cactgcggcc aacttacttc tgacaacgat    3840
cggaggaccg aaggagctaa ccgcttttt gcacaacatg ggggatcatg taactcgcct    3900
tgatcgttgg gaaccggagc tgaatgaagc cataccaaac gacgagcgtg acaccacgat    3960
gcctgtagca atggcaacaa cgttgcgcaa actattaact ggcgaactac ttactctagc    4020
ttcccggcaa caattaatag actggatgga ggcggataaa gttgcaggac cacttctgcg    4080
ctcggccctt ccggctggct ggtttattgc tgataaatct ggagccggtg agcgtgggtc    4140
tcgcggtatc attgcagcac tggggccaga tggtaagccc tcccgtatcg tagttatcta    4200
cacgacgggg agtcaggcaa ctatggatga acgaaataga cagatcgctg agataggtgc    4260
ctcactgatt aagcattggt aactgtcaga ccaagtttac tcatatatac tttagattga    4320
tttaaaactt cattttaat ttaaaggat ctaggtgaag atcctttttg ataatctcat     4380
```

```
gaccaaaatc ccttaacgtg agttttcgtt ccactgagcg tcagaccccg tagaaaagat   4440
caaaggatct tcttgagatc ctttttttct gcgcgtaatc tgctgcttgc aaacaaaaaa   4500
accaccgcta ccagcggtgg tttgtttgcc ggatcaagag ctaccaactc ttttttccgaa  4560 ggtaactggc ttcagcagag cgcagatacc aaatactgtc cttctagtgt agccgtagtt   4620
aggccaccac ttcaagaact ctgtagcacc gcctacatac ctcgctctgc taatcctgtt   4680
accagtggct gctgccagtg gcgataagtc gtgtcttacc gggttggact caagacgata   4740
gttaccggat aaggcgcagc ggtcgggctg aacggggggt tcgtgcacac agcccagctt   4800
ggagcgaacg acctacaccg aactgagata cctacagcgt gagcattgag aaagcgccac   4860
gcttcccgaa gggagaaagg cggacaggta tccggtaagc ggcagggtcg aacaggaga   4920 gcgcacgagg gagcttccag ggggaaacgc ctggtatctt tatagtcctg tcgggtttcg   4980
ccacctctga cttgagcgtc gatttttgtg atgctcgtca gggggcgga gcctatggaa    5040 aaacgccagc aacgcggcct ttttacggtt cctggccttt tgctggcctt ttgctcacat   5100
gttctttcct gcgttatccc ctgattctgt ggataaccgt attaccgcct tgagtgagc    5160 tgataccgct cgccgcagcc gaacgaccga gcgcagcgag tcagtgagcg aggaagcgga   5220
agagcgccca atacgcaaac cgcctctccc cgcgcgttgg ccgattcatt aatgcagctg   5280
gcacgacagg tttcccgact ggaaagcggg cagtgagcgc aacgcaatta atgtgagtta   5340
gctcactcat taggcacccc aggctttaca ctttatgctt ccggctcgta tgttgtgtgg   5400
aattgtgagc ggataacaat ttcacacagg aaacagctat gaccatgatt acgccaagct   5460
ttctaggggg ggggtaccga tctgagatcg gtaacgaaaa cgaacgggta gggatgaaaa   5520
cggtcggtaa cggtcggtaa aatacctcta ccgttttcat tttcatattt aacttgcggg   5580
acggaaacga aaacgggata taccggtaac gaaaacgaac gggataaata cggtaatcga   5640
aaaccgatac gatccggtcg ggttaaagtc gaaatcggac gggaaccggt atttttgttc   5700
ggtaaaatca cacatgaaaa catatattca aaacttaaaa acaaatataa aaaattgtaa   5760
acacaagtct taattaaaca tagataaaat ccatataaat ctggagcaca catagtttaa   5820
tgtagcacat aagtgataag tcttgggctc ttggctaaca taagaagcca tataagtcta   5880
ctagcacaca tgacacaata taaagtttaa aacacatatt cataatcact tgctcacatc   5940
tggatcactt agcatgctac agctagtgca atattagaca ctttccaata tttctcaaac   6000
ttttcactca ttgcaacggc cattctccta atgacaaatt tttcatgaac acaccattgg   6060
tcaatcaaat cctttatctc acagaaacct ttgtaaaata aatttgcagt ggaatattga   6120
gtaccagata ggagttcagt gagatcaaaa aacttcttca aacacttaaa aagagttaat   6180
gccatcttcc actcctcggc tttaggacaa attgcatcgt acctacaata attgacattt   6240
gattaattga gaatttataa tgatgacatg tacaacaatt gagacaaaca tacctgcgag   6300
gatcacttgt tttaagccgt gttagtgcag gcttataata taaggcatcc ctcaacatca   6360
aataggttga attccatcta gttgagacat catatgagat cccttagat ttatccaagt     6420 cacattcact agcacacttc attagttctt cccactgcaa aggagaagat tttacagcaa   6480
gaacaatcgc tttgattttc tcaattgttc ctgcaattac agccaagcca tcctttgcaa   6540
ccaagttcag tatgtgacaa gcacacctca catgaaagaa agcaccatca caaactagat   6600
ttgaatcagt gtcctgcaaa tcctcaatta tatcgtgcac agctacttca tttgcactag   6660
cattatccaa agacaaggca aacaattttt tctcaatgtt ccacttaacc atgattgcag   6720
```

```
tgaaggtttg tgataacctt tggccagtgt ggcgcccttc aacatgaaaa aagccaacaa    6780
ttcttttttg agacaccaa tcatcatcaa tccaatggat ggtgacacac atgtatgact    6840
tattttgaca agatgtccac atatccatag ttgtactgaa gcgagactga acatctttta    6900
gttttccata caacttttct ttttcttcca aatacaaatc catgatatat tttctagcag    6960
tgacacggga ctttattgga aagtgagggc gcagagactt aacaaactca acaaagtact    7020
catgttctac aatattgaaa ggatattcat gcatgattat tgccaaatga agcttcttta    7080
ggctaaccac ttcatcgtac ttataaggct caatgagatt tatgtctttg ccatgatcct    7140
tttcactttt tagacacaac tgacctttaa ctaaactatg tgatgttctc aagtgatttc    7200
gaaatccgct tgttccatga tgaccctcag ccctatactt agccttgcaa ttaggaaagt    7260
tgcaatgtcc ccatacctga acgtatttct ttccatcgac ctccacttca atttccttct    7320
tggtgaaatg ctgccataca tccgatgtgc acttctttgc cctcttctgt ggtgcttctt    7380
cttcgggttc aggttgtggc tgtggttgtg gttctggttg tggttgtggt tgtggttgtg    7440
gttcatgaac aatagccata tcatcttgac tcggatctgt agctgtacca tttgcattac    7500
tactgcttac actctgaata aaatgcctct cggcctcagc tgttgatgat gatggtgatg    7560
tgcggccaca tccatgccca cgcgcacgtg cacgtacatt ctgaatccga ctagaagagg    7620
cttcagcttt tcttttcaac cctgttataa acagattttt cgtattattc tacagtcaat    7680
atgatgcttc ccaatctaca accaattagt aatgctaatg ctattgctac tgttttccta    7740
atatatacct tgagcatatg cagagaatac ggaatttgtt ttgcgagtag aaggcgctct    7800
tgtggtagac atcaacttgg ccaatcttat ggctgagcct gagggaggat tatttccaac    7860
cggaggcgtc atctgaggaa tggagtcgta gccggctagc cgaagtggag agcagagccc    7920
tggacagcag gtgttcagca atcagcttgg tgctgtactg ctgtgacttg tgagcacctg    7980
gacggctgga cagcaatcag caggtgttgc agagcccctg gacagcacac aaatgacaca    8040
acagcttggt gcaatggtgc tgacgtgctg tactgctaag tgctgtgagc ctgtgagcag    8100
ccgtggagac agggagaccg cggatggccg gatgggcgag cgccgagcag tggaggtctg    8160
gaggaccgct gaccgcagat ggcggatggc ggatgggcgg accgcggatg ggcgagcagt    8220
ggagtggagg tctgggcgga tgggcggacc gcggcgcgga tgggcgagtc gcgagcagtg    8280
gagtggaggg cggaccgtgg atggcggcgt ctgcgtccgg cgtgccgcgt cacggccgtc    8340
accgcgtgtg gtgcctggtg cagcccagcg gccggccggc tgggagacag ggagagtcgg    8400
agagagcagg cgagagcgag acgcgtcgcc ggcgtcggcg tgcggctggc ggcgtccgga    8460
ctccggcgtg ggcgcgtggc ggcgtgtgaa tgtgtgatgc tgttactcgt gtggtgcctg    8520
gccgcctggg agagaggcag agcagcgttc gctaggtatt tcttacatgg gctgggcctc    8580
agtggttatg gatgggagtt ggagctggcc atattgcagt catcccgaat tagaaaatac    8640
ggtaacgaaa cgggatcatc ccgattaaaa acgggatccc ggtgaaacgg tcgggaaact    8700
agctctaccg tttccgtttc cgtttaccgt tttgtatatc ccgtttccgt tccgttttcg    8760
tttttttacct cgggttcgaa atcgatcggg ataaaactaa caaaatcggt tatacgataa    8820
cggtcggtac gggatttttcc catcctactt tcatccctga gattattgtc gtttctttcg    8880
cagatcggta ccccccccct agagtcgaca tcgatctagt aacatagatg acaccgcgcg    8940
cgataattta tcctagtttg cgcgctatat tttgttttct atcgcgtatt aaatgtataa    9000
ttgcgggact ctaatcataa aaacccatct cataaataac gtcatgcatt acatgttaat    9060
tattacatgc ttaacgtaat tcaacagaaa ttatatgata atcatcgcaa gaccggcaac    9120
```

```
aggattcaat cttaagaaac tttattgcca aatgtttgaa cgatctgctt cgacgcactc    9180
cttctttagg tacggactag atctcggtga cgggcaggac cggacggggc ggtaccggca    9240
ggctgaagtc cagctgccag aaacccacgt catgccagtt cccgtgcttg aagccggccg    9300
cccgcagcat gccgcggggg gcatatccga gcgcctcgtg catgcgcacg ctcgggtcgt    9360
tgggcagccc gatgacagcg accacgctct gaagccctg tgcctccagg gacttcagca     9420
ggtgggtgta gagcgtggag cccagtcccg tccgctggtg gcgggggggag acgtacacgg   9480 tcgactcggc cgtccagtcg taggcgttgc gtgccttcca ggggcccgcg taggcgatgc    9540
cggcgacctc gccgtccacc tcggcgacga gccaggata gcgctcccgc agacggacga     9600
ggtcgtccgt ccactcctgc ggttcctgcg gctcggtacg gaagttgacc gtgcttgtct    9660
cgatgtagtg gttgacgatg gtgcagaccg ccggcatgtc cgcctcggtg gcacggcgga   9720
tgtcggccgg gcgtcgttct gggctcatgg atctggattg agagtgaata tgagactcta   9780
attggatacc gaggggaatt tatgaacgt cagtggagca ttttgacaa gaaatatttg      9840 ctagctgata gtgaccttag gcgactttg aacgcgcaat aatggtttct gacgtatgtg    9900
cttagctcat taaactccag aaacccgcgc ctgagtggct ccttcaatcg ttgcggttct    9960
gtcagttcca aacgtaaaac ggcttgtccc gcgtcatcgg cggggggtcat aacgtgactc  10020 ccttaattct ccgctcatga tccccgggta ccgagctcga attgcggctg agtggctcct   10080
tcaatcgttg cggttctgtc agttccaaac gtaaaacggc ttgtcccgcg tcatcggcgg   10140
gggtcataac gtgactccct taattctccg ctcatgatct tgatccctg cgccatcaga    10200 tccttggcgg caagaaagcc atccagttta ctttgcaggg cttcccaacc ttaccagagg   10260
gcgccccagc tggcaattcc ggttcgcttg ctgtatcgat atggtggatt tatcacaaat   10320
gggacccgcc gccgacagag gtgtgatgtt aggccaggac tttgaaaatt tgcgcaacta   10380
tcgtatagtg gccgacaaat tgacgccgag ttgacagact gcctagcatt tgagtgaatt   10440
atgtgaggta atgggctaca ctgaattggt agctcaaact gtcagtattt atgtatatga   10500
gtgtatattt tcgcataatc tcagaccaat ctgaagatga aatgggtatc tgggaatggc   10560
gaaatcaagg catcgatcgt gaagtttctc atctaagccc ccatttggac gtgaatgtag   10620
acacgtcgaa ataaagattt ccgaattaga ataatttgtt tattgctttc gcctataaat   10680
acgacggatc gtaatttgtc gttttatcaa aatgtacttt cattttataa taacgctgcg   10740
gacatctaca tttttgaatt gaaaaaaaat tggtaattac tctttctttt tctccatatt   10800
gaccatcata ctcattgctg atccatgtag atttcccgga catgaagcca tttacaattg   10860
aatatatcct gccgccgctg ccgctttgca cccggtggag cttgcatgtt ggtttctacg   10920
cagaactgag ccggttaggc agataatttc cattgagaac tgagccatgt gcaccttccc   10980
cccaacacgg tgagcgacgg ggcaacggag tgatccacat gggactttta aacatcatcc   11040
gtcggatggc gttgcgagag aagcagtcga tccgtgagat cagccgacgc accgggcagg   11100
cgcgcaacac gatcgcaaag tatttgaacg caggtacaat cgagccgacg ttcaccgtca   11160
ccctggatgt gtaggcata ggcttggtta tgccggtact gccgggcctc ttgcgggata    11220
tcgtccattc cgacagcatc gccagtcact atggcgtgct gctagcgcta tatgcgttga   11280
tgcaatttct atgcgcaccc gttctcggag cactgtccga ccgctttggc cgccgcccag   11340
tcctgctcgc ttcgctactt ggagccacta tcgactacgc gatcatggcg accacacccg   11400
tcctgtggtc caacccctcc gctgctatag tgcagtcggc ttctgacgtt cagtgcagcc   11460
```

-continued

```
gtcttctgaa aacgacatgt cgcacaagtc ctaagttacg cgacaggctg ccgccctgcc   11520
cttttcctgg cgtttcttg tcgcgtgttt tagtcgcata aagtagaata cttgcgacta    11580
gaaccggaga cattacgcca tgaacaagag cgccgccgct ggcctgctgg gctatgcccg    11640
cgtcagcacc gacgaccagg acttgaccaa ccaacgggcc gaactgcacg cggccggctg    11700
caccaagctg ttttccgaga agatcaccgg caccaggcgc gaccgcccgg agctggccag    11760
gatgcttgac cacctacgcc ctggcgacgt tgtgacagtg accaggctag accgcctggc    11820
ccgcagcacc cgcgacctac tggacattgc cgagcgcatc caggaggccg cgcgggcct    11880 gcgtagcctg gcagagccgt gggccgacac caccacgccg gccggccgca tggtgttgac    11940
cgtgttcgcc ggcattgccg agttcgagcg ttccctaatc atcgaccgca cccggagcgg    12000
gcgcgaggcc gccaaggccc gaggcgtgaa gtttggcccc cgccctaccc tcaccccggc    12060
acagatcgcg cacgcccgcg agctgatcga ccaggaaggc cgcaccgtga agaggcggc    12120 tgcactgctt ggcgtgcatc gctcgaccct gtaccgcgca cttgagcgca gcgaggaagt    12180
gacgcccacc gaggccaggc ggcgcggtgc cttccgtgag gacgcattga ccgaggccga    12240
cgccctggcg ccgccgaga atgaacgcca agaggaacaa gcatgaaacc gcaccaggac    12300
ggccaggacg aaccgttttt cattaccgaa gagatcgagg cggagatgat cgcggccggg    12360
tacgtgttcg agccgccgc gcacgtctca accgtgcggc tgcatgaaat cctggccggt    12420
ttgtctgatg ccaagctggc ggcctggccg gcagcttggg ccgctgaaga aaccgagcgc    12480
cgccgtctaa aaggtgatg tgtatttgag taaaacagct tgcgtcatgc ggtcgctgcg    12540
tatatgatgc gatgagtaaa taaacaaata cgcaagggaa cgcatgaagt tatcgctgta    12600
cttaaccaga aggcgggtc aggcaagacg accatcgcaa cccatctagc ccgcgccctg    12660
caactcgccg gggccgatgt tctgttagtc gattccgatc cccagggcag tgcccgcgat    12720
tgggcggccg tgcgggaaga tcaaccgcta accgttgtcg gcatcgaccg cccgacgatt    12780
gaccgcgacg tgaaggccat cggcggcgc gacttcgtag tgatcgacgg agcgcccag     12840 gcggcggact tggctgtgtc cgcgatcaag gcagccgact tcgtgctgat tccggtgcag    12900
ccaagccctt acgacatatg ggccaccgcc gacctggtgg agctggttaa gcagcgcatt    12960
gaggtcacgg atggaaggct acaagcggcc tttgtcgtgt cgcgggcgat caaaggcacg    13020
cgcatcggcg gtgaggttgc cgaggcgctg gccgggtacg agctgcccat tcttgagtcc    13080
cgtatcacgc agcgcgtgag ctacccaggc actgccgccg ccggcacaac cgttcttgaa    13140
tcagaacccg agggcgacgc tgcccgcgag gtccaggcgc tggccgctga aattaaatca    13200
aaactcattt gagttaatga ggtaaagaga aaatgagcaa agcacaaac acgctaagtg    13260 ccggccgtcc gagcgcacgc agcagcaagg ctgcaacgtt ggccagcctg cagacacgc    13320 cagccatgaa gcgggtcaac tttcagttgc cggcggagga tcacaccaag ctgaagatgt    13380
acgcggtacg ccaaggcaag accattaccg agctgctatc tgaatacatc gcgcagctac    13440
cagagtaaat gagcaaatga ataaatgagt agatgaattt tagcggctaa aggaggcggc    13500
atggaaaatc aagaacaacc aggcaccgac gccgtggaat gccccatgtg tggaggaacg    13560
ggcggttggc caggcgtaag cggctgggtt gtctgccggc cctgcaatgg cactggaacc    13620
cccaagcccg aggaatcggc gtgagcggtc gcaaaccatc cggcccggta caaatcggcg    13680
cggcgctggg tgatgacctg gtggagaagt tgaaggccgc gcaggccgcc cagcggcaac    13740 gcatcgagc agaagcacgc cccggtgaat cgtggcaagc ggccgctgat cgaatccgca    13800
aagaatcccg gcaaccgccg gcagccggtg cgccgtcgat taggaagccg cccaagggcg    13860
```

```
acgagcaacc agatttttc gttccgatgc tctatgacgt gggcaccgc gatagtcgca    13920
gcatcatgga cgtggccgtt ttccgtctgt cgaagcgtga ccgacgagct ggcgaggtga    13980
tccgctacga gcttccagac gggcacgtag aggtttccgc agggccggcc ggcatggcca    14040
gtgtgtggga ttacgacctg gtactgatgg cggtttccca tctaaccgaa tccatgaacc    14100
gataccggga agggaaggga gacaagcccg gccgcgtgtt ccgtccacac gttgcggacg    14160
tactcaagtt ctgccggcga gccgatggcg gaaagcagaa agacgacctg gtagaaacct    14220
gcattcggtt aaacaccacg cacgttgcca tgcagcgtac gaagaaggcc aagaacggcc    14280
gcctggtgac ggtatccgag ggtgaagcct tgattagccg ctacaagatc gtaaagagcg    14340
aaaccgggcg gccggagtac atcgagatcg agctagctga ttggatgtac cgcgagatca    14400
cagaaggcaa gaaccggac gtgctgacgg ttcaccccga ttacttttg atcgatcccg    14460
gcatcggccg ttttctctac cgcctggcac gccgcgccgc aggcaaggca gaagccagat    14520
ggttgttcaa gacgatctac gaacgcagtg gcagcgccgg agagttcaag aagttctgtt    14580
tcaccgtgcg caagctgatc gggtcaaatg acctgccgga gtacgatttg aaggaggagg    14640
cggggcaggc tggcccgatc ctagtcatgc gctaccgcaa cctgatcgag ggcgaagcat    14700
ccgccggttc ctaatgtacg gagcagatgc tagggcaaat tgccctagca ggggaaaaag    14760
gtcgaaaagg tctcttttcct gtggatagca cgtacattgg gaacccaaag ccgtacattg    14820
ggaaccggaa cccgtacatt gggaacccaa agccgtacat tgggaaccgg tcacacatgt    14880
aagtgactga tataaaagag aaaaaaggcg attttccgc ctaaaactct ttaaaactta    14940
ttaaaactct taaacccgc ctggcctgtg cataactgtc tggccagcgc acagccgaag    15000
agctgcaaaa agcgcctacc cttcggtcgc tgcgctccct acgccccgcc gcttcgcgtc    15060
ggcctatcgc ggccgctggc cgctcaaaaa tggctggcct acggccaggc aatctaccag    15120
ggcgcggaca agccgcgccg tcgccactcg accgccggcg cccacatcaa ggcaccctgc    15180
ctcgcgcgtt tcggtgatga cggtgaaaac ctctgacaca tgcagctccc ggagacggtc    15240
acagcttgtc tgtaagcgga tgccgggagc agacaagccc gtcagggcgc gtcagcgggt    15300
gttggcgggt gtcggggcgc agccatgacc cagtcacgta gcgatagcgg agtgtatact    15360
ggcttaacta tgcggcatca gagcagattg tactgagagt gcaccatatg cggtgtgaaa    15420
taccgcacag atgcgtaagg agaaaatacc gcatcaggcg ctcttccgct tcctcgctca    15480
ctgactcgct gcgctcggtc gttcggctgc ggcgagcggt atcagctcac tcaaaggcgg    15540
taatacggtt atccacagaa tcaggggata acgcaggaaa gaacatgtga gcaaaaggcc    15600
agcaaaaggc caggaaccgt aaaaaggccg cgttgctggc gttttccat aggctccgcc    15660
ccctgacga gcatcacaaa aatcgacgct caagtcagag gtggcgaaac ccgacaggac    15720
tataagata ccaggcgttt ccccctggaa gctccctcgt gcgctctcct gttccgaccc    15780
tgccgcttac cggatacctg tccgcctttc tcccttcggg aagcgtggcg ctttctcata    15840
gctcacgctg taggtatctc agttcggtgt aggtcgttcg ctccaagctg ggctgtgtgc    15900
acgaacccccc cgttcagccc gaccgctgcg ccttatccgg taactatcgt cttgagtcca    15960
acccggtaag acacgactta tcgccactgg cagcagccac tggtaacagg attagcagag    16020
cgaggtatgt aggcggtgct acagagttct tgaagtggtg gcctaactac ggctacacta    16080
gaaggacagt atttggtatc tgcgctctgc tgaagccagt taccttcgga aaaagagttg    16140
gtagctcttg atccggcaaa caaaccaccg ctggtagcgg tggttttttt gtttgcaagc    16200
```

```
agcagattac gcgcagaaaa aaaggatctc aagaagatcc tttgatcttt tctacggggt    16260
ctgacgctca gtggaacgaa aactcacgtt aagggatttt ggtcatgaga ttatcaaaaa    16320
ggatcttcac ctagatcctt ttaaattaaa aatgaagttt taaatcaatc taaagtatat    16380
atgagtaaac ttggtctgac agttaccaat gcttaatcag tgaggcacct atctcagcga    16440
tctgtctatt tcgttcatcc atagttgcct gactcccgt cgtgtagata actacgatac     16500
gggagggctt accatctggc cccagtgctg caatgatacc gcgagaccca cgctcaccgg    16560
ctccagattt atcagcaata accagccag ccggaagggc cgagcgcaga agtggtcctg     16620
caactttatc cgcctccatc cagtctatta attgttgccg ggaagctaga gtaagtagtt    16680
cgccagttaa tagtttgcgc aacgttgttg ccattgctac aggcatcgtg gtgtcacgct    16740
cgtcgtttgg tatggcttca ttcagctccg gttcccaacg atcaaggcga gttacatgat    16800
cccccatgtt gtgcaaaaaa gcggttagct ccttcggtcc tccgatcgtt gtcagaagta    16860
agttggccgc agtgttatca ctcatggtta tggcagcact gcataattct cttactgtca    16920
tgccatccgt aagatgcttt tctgtgactg gtgagtactc aaccaagtca ttctgagaat    16980
agtgtatgcg gcgaccgagt tgctcttgcc cggcgtcaac acgggataat accgcgccac    17040
atagcagaac tttaaaagtg ctcatcattg gaaaagacct gcagggggg ggggaaagc     17100 cacgttgtgt ctcaaaatct ctgatgttac attgcacaag ataaaatat atcatcatga     17160 acaataaaac tgtctgctta cataaacagt aatacaaggg gtgttatgag ccatattcaa    17220
cgggaaacgt cttgctcgag gccgcgatta aattccaaca tggatgctga tttatatggg    17280
tataaatggg ctcgcgataa tgtcgggcaa tcaggtgcga caatctatcg attgtatggg    17340
aagcccgatg cgccagagtt gtttctgaaa catggcaaag gtagcgttgc caatgatgtt    17400
acagatgaga tggtcagact aaactggctg acggaattta tgcctcttcc gaccatcaag    17460
cattttatcc gtactcctga tgatgcatgg ttactcacca ctgcgatccc cgggaaaaca    17520
gcattccagg tattagaaga atatcctgat tcaggtgaaa atattgttga tgcgctggca    17580
gtgttcctgc gccggttgca ttcgattcct gtttgtaatt gtccttttaa cagcgatcgc    17640
gtatttcgtc tcgctcaggc gcaatcacga atgaataacg gtttggttga tgcgagtgat    17700
tttgatgacg agcgtaatgg ctggcctgtt gaacaagtct ggaaagaaat gcataagctt    17760
ttgccattct caccggattc agtcgtcact catggtgatt tctcacttga taaccttatt    17820
tttgacgagg ggaaattaat aggttgtatt gatgttggac gagtcggaat cgcagaccga    17880
taccaggatc ttgccatcct atggaactgc ctcggtgagt tttctccttc attacagaaa    17940
cggctttttc aaaaatatgg tattgataat cctgatatga ataaattgca gtttcatttg    18000
atgctcgatg agttttttcta atcagaattg gttaattggt tgtaacactg gcagagcatt    18060
acgctgactt gacgggacgg cggctttgtt gaataaatcg aacttttgct gagttgaagg    18120
atcagatcac gcatcttccc gacaacgcag accgttccgt ggcaaagcaa aagttcaaaa    18180
tcaccaactg gtccacctac aacaaagctc tcatcaaccg tggctccctc actttctggc    18240
tggatgatgg ggcgattcag gcctggtatg agtcagcaac accttcttca cgaggcagac    18300
ctcagcgccc ccccccccct gcaggtcaat tcggtcgata tggctattac gaagaaggct    18360
cgtgcgcgga gtcccgtgaa ctttcccacg caacaagtga accgcaccgg gtttgccgga    18420
ggccatttcg ttaaaatgcg cagc                                           18444

<210> SEQ ID NO 2
<211> LENGTH: 4291
```

```
<212> TYPE: DNA
<213> ORGANISM: artificial sequence
<220> FEATURE:
<223> OTHER INFORMATION: Gateway donor vector pDONR-Zeo

<400> SEQUENCE: 2
ctttcctgcg ttatcccctg attctgtgga taaccgtatt accgcctttg agtgagctga      60
taccgctcgc cgcagccgaa cgaccgagcg cagcgagtca gtgagcgagg aagcggaaga     120
gcgcccaata cgcaaaccgc ctctccccgc gcgttggccg attcattaat gcagctggca     180
cgacaggttt cccgactgga aagcgggcag tgagcgcaac gcaattaata cgcgtaccgc     240
tagccaggaa gagtttgtag aaacgcaaaa aggccatccg tcaggatggc cttctgctta     300
gtttgatgcc tggcagttta tggcgggcgt cctgcccgcc accctccggg ccgttgcttc     360
acaacgttca atccgctccc ggcggattt gtcctactca ggagagcgtt caccgacaaa      420
caacagataa aacgaaaggc ccagtcttcc gactgagcct ttcgttttat ttgatgcctg     480
gcagttccct actctcgcgt taacgctagc atggatgttt tcccagtcac gacgttgtaa     540
aacgacggcc agtcttaagc tcgggcccca ataatgatt ttattttgac tgatagtgac      600
ctgttcgttg caacacattg atgagcaatg ctttttttata atgccaactt tgtacaaaaa     660
agctgaacga gaaacgtaaa atgatataaa tatcaatata ttaaattaga ttttgcataa     720
aaaacagact acataatact gtaaaacaca acatatccag tcactatgaa tcaactactt     780
agatggtatt agtgacctgt agtcgaccga cagccttcca aatgttcttc gggtgatgct     840
gccaacttag tcgaccgaca gccttccaaa tgttcttctc aaacggaatc gtcgtatcca     900
gcctactcgc tattgtcctc aatgccgtat taaatcataa aagaaataa gaaaaagagg      960 tgcgagcctc ttttttgtgt gacaaaataa aaacatctac ctattcatat acgctagtgt    1020
catagtcctg aaaatcatct gcatcaagaa caatttcaca actcttatac ttttctctta    1080
caagtcgttc ggcttcatct ggattttcag cctctatact tactaaacgt gataaagttt    1140
ctgtaatttc tactgtatcg acctgcagac tggctgtgta agggagcc tgacatttat      1200 attccccaga acatcaggtt aatgcgtttt ttgatgtcat tttcgcggtg gctgagatca    1260
gccacttctt ccccgataac ggagaccggc acactggcca tatcggtggt catcatgcgc    1320
cagctttcat ccccgatatg caccaccggg taaagttcac gggagacttt atctgacagc    1380
agacgtgcac tggccagggg gatcaccatc cgtcgcccgg gcgtgtcaat aatatcactc    1440
tgtacatcca caaacagacg ataacggctc tctcttttat aggtgtaaac cttaaactgc    1500
atttcaccag cccctgttct cgtcagcaaa agagccgttc atttcaataa accgggcgac    1560
ctcagccatc ccttcctgat tttccgcttt ccagcgttcg gcacgcagac gacgggcttc    1620
attctgcatg gttgtgctta ccagaccgga gatattgaca tcatatatgc cttgagcaac    1680
tgatagctgt cgctgtcaac tgtcactgta atacgctgct tcatagcata cctcttttg     1740 acatacttcg ggtatacata tcagtatata ttcttatacc gcaaaaatca gcgcgcaaat    1800
acgcatactg ttatctggct tttagtaagc cggatccacg cggcgtttac gccccgccct    1860
gccactcatc gcagtactgt tgtaattcat taagcattct gccgacatgg aagccatcac    1920
agacggcatg atgaacctga atcgccagcg gcatcagcac cttgtcgcct tgcgtataat    1980
atttgcccat ggtgaaaacg ggggcgaaga agttgtccat attggccacg tttaaatcaa    2040
aactggtgaa actcacccag ggattggctg agacgaaaaa catattctca ataaacccct    2100
tagggaaata ggccaggttt tcaccgtaac acgccacatc ttgcgaatat atgtgtagaa    2160
```

```
actgccggaa atcgtcgtgg tattcactcc agagcgatga aaacgtttca gtttgctcat    2220
ggaaaacggt gtaacaaggg tgaacactat cccatatcac cagctcaccg tctttcattg    2280
ccatacggaa ttccggatga gcattcatca ggcgggcaag aatgtgaata aaggccggat    2340
aaaacttgtg cttatttttc tttacggtct taaaaaggc cgtaatatcc agctgaacgg     2400
tctggttata ggtacattga gcaactgact gaaatgcctc aaaatgttct ttacgatgcc    2460
attgggatat atcaacggtg gtatatccag tgatttttt ctccatttta gcttccttag     2520
ctcctgaaaa tctcgataac tcaaaaaata cgcccggtag tgatcttatt tcattatggt    2580
gaaagttgga acctcttacg tgccgatcaa cgtctcattt tcgccaaaag ttgggcccagg   2640
gcttcccggt atcaacaggg acaccaggat ttatttattc tgcgaagtga tcttccgtca    2700
caggtattta ttcggcgcaa agtgcgtcgg gtgatgctgc caacttagtc gactacaggt    2760
cactaatacc atctaagtag ttgattcata gtgactggat atgttgtgtt ttacagtatt    2820
atgtagtctg tttttatgc aaaatctaat ttaatatatt gatatttata tcattttacg     2880
tttctcgttc agctttcttg tacaaagttg gcattataag aaagcattgc ttatcaattt    2940
gttgcaacga acaggtcact atcagtcaaa ataaaatcat tatttgccat ccagctgata    3000
tcccctatag tgagtcgtat tacatggtca tagctgtttc ctggcagctc tggcccgtgt    3060
ctcaaaatct ctgatgttac attgcacaag ataaaataat atcatcatga tcagtcctgc    3120
tcctcggcca cgaagtgcac gcagttgccg gccgggtcgc gcagggcgaa ctcccgcccc    3180
cacggctgct cgccgatctc ggtcatggcc ggcccggagg cgtcccggaa gttcgtggac    3240
acgacctccg accactcggc gtacagctcg tccaggccgc gcacccacac ccaggccagg    3300
gtgttgtccg gcaccacctg gtcctggacc gcgctgatga acagggtcac gtcgtcccgg    3360
accacaccgg cgaagtcgtc ctccacgaag tcccgggaga acccgagccg gtcggtccag    3420
aactcgaccg ctccggcgac gtcgcgcgcg gtgagcaccg gaacggcact ggtcaacttg    3480
gccatggttt agttcctcac cttgtcgtat tatactatgc cgatatacta tgccgatgat    3540
taattgtcaa cacgtgctga tcatgaccaa aatcccttaa cgtgagttac gcgtcgttcc    3600
actgagcgtc agaccccgta gaaaagatca aaggatcttc ttgagatcct ttttttctgc    3660
gcgtaatctg ctgcttgcaa acaaaaaaac caccgctacc agcggtggtt tgtttgccgg    3720
atcaagagct accaactctt tttccgaagg taactggctt cagcagagcg cagataccaa    3780
atactgttct tctagtgtag ccgtagttag gccaccactt caagaactct gtagcaccgc    3840
ctacatacct cgctctgcta atcctgttac cagtggctgc tgccagtggc gataagtcgt    3900
gtcttaccgg gttggactca agacgatagt taccggataa ggcgcagcgg tcgggctgaa    3960
cggggggttc gtgcacacag cccagcttgg agcgaacgac ctacaccgaa ctgagatacc    4020
tacagcgtga gctatgagaa agcgccacgc ttcccgaagg gagaaaggcg gacaggtatc    4080
cggtaagcgg cagggtcgga acaggagagc gcacgaggga gcttccaggg ggaaacgcct    4140
ggtatcttta tagtcctgtc gggtttcgcc acctctgact tgagcgtcga ttttttgtgat   4200
gctcgtcagg ggggcggagc ctatggaaaa acgccagcaa cgcggccttt ttacggttcc    4260
tggccttttg ctggccttttt gctcacatgt t                                  4291
```

<210> SEQ ID NO 3
<211> LENGTH: 4762
<212> TYPE: DNA
<213> ORGANISM: Artificial Sequence
<220> FEATURE:
<223> OTHER INFORMATION: gateway donor vector pDONR221

<400> SEQUENCE: 3

```
ctttcctgcg ttatcccctg attctgtgga taaccgtatt accgcctttg agtgagctga    60
taccgctcgc cgcagccgaa cgaccgagcg cagcgagtca gtgagcgagg aagcggaaga   120
gcgcccaata cgcaaaccgc ctctccccgc gcgttggccg attcattaat gcagctggca   180
cgacaggttt cccgactgga aagcgggcag tgagcgcaac gcaattaata cgcgtaccgc   240
tagccaggaa gagtttgtag aaacgcaaaa aggccatccg tcaggatggc cttctgctta   300
gtttgatgcc tggcagttta tggcgggcgt cctgcccgcc accctccggg ccgttgcttc   360
acaacgttca aatccgctcc cggcggattt gtcctactca ggagagcgtt caccgacaaa   420
caacagataa aacgaaaggc ccagtcttcc gactgagcct ttcgttttat ttgatgcctg   480
gcagttccct actctcgcgt taacgctagc atggatgttt cccagtcac gacgttgtaa    540
aacgacggcc agtcttaagc tcgggcccca ataatgatt ttattttgac tgatagtgac   600
ctgttcgttg caacacattg atgagcaatg ctttttata tgccaactt tgtacaaaaa    660
agctgaacga gaaacgtaaa atgatataaa tatcaatata ttaaattaga ttttgcataa   720
aaaacagact acataatact gtaaaacaca acatatccag tcactatgaa tcaactactt   780
agatggtatt agtgacctgt agtcgaccga cagccttcca aatgttcttc gggtgatgct   840
gccaacttag tcgaccgaca gccttccaaa tgttcttctc aaacggaatc gtcgtatcca   900
gcctactcgc tattgtcctc aatgccgtat taaatcataa aagaaataa gaaaagagg    960
tgcgagcctc tttttgtgt gacaaaataa aaacatctac ctattcatat acgctagtgt  1020
catagtcctg aaaatcatct gcatcaagaa caatttcaca actcttatac ttttctctta  1080
caagtcgttc ggcttcatct ggattttcag cctctatact tactaaacgt gataaagttt  1140
ctgtaatttc tactgtatcg acctgcagac tggctgtgta taagggagcc tgacatttat  1200
attccccaga acatcaggtt aatggcgttt ttgatgtcat tttcgcggtg gctgagatca  1260
gccacttctt ccccgataac ggagaccggc acactggcca tatcggtggt catcatgcgc  1320
cagctttcat ccccgatatg caccaccggg taaagttcac gggagacttt atctgacagc  1380
agacgtgcac tggccagggg gatcaccatc cgtcgcccgg gcgtgtcaat aatatcactc  1440
tgtacatcca caaacagacg ataacggctc tctctttat aggtgtaaac cttaaactgc  1500
atttcaccag cccctgttct cgtcagcaaa agagccgttc atttcaataa accgggcgac  1560
ctcagccatc ccttcctgat tttccgcttt ccagcgttcg gcacgcagac gacgggcttc  1620
attctgcatg gttgtgctta ccagaccgga gatattgaca tcatatatgc cttgagcaac  1680
tgatagctgt cgctgtcaac tgtcactgta atacgctgct tcatagcata cctcttttg   1740
acatacttcg ggtatacata tcagtatata ttcttatacc gcaaaaatca gcgcgcaaat  1800
acgcatactg ttatctggct tttagtaagc cggatccacg cggcgtttac gccccgccct  1860
gccactcatc gcagtactgt tgtaattcat taagcattct gccgacatgg aagccatcac  1920
agacggcatg atgaacctga atcgccagcg gcatcagcac cttgtcgcct tgcgtataat  1980
atttgcccat ggtgaaaacg ggggcgaaga agttgtccat attggccacg tttaaatcaa  2040
aactggtgaa actcacccag ggattggctg agacgaaaaa catattctca ataaaccctt  2100
tagggaaata ggccaggttt tcaccgtaac acgccacatc ttgcgaatat atgtgtagaa  2160
actgccggaa atcgtcgtgg tattcactcc agagcgatga aaacgtttca gtttgctcat  2220
ggaaaacggt gtaacaaggg tgaacactat cccatatcac cagctcaccg tctttcattg  2280
```

```
ccatacggaa ttccggatga gcattcatca ggcgggcaag aatgtgaata aaggccggat    2340
aaaacttgtg cttattttc tttacggtct ttaaaaaggc cgtaatatcc agctgaacgg    2400
tctggttata ggtacattga gcaactgact gaaatgcctc aaaatgttct ttacgatgcc   2460
attgggatat atcaacggtg gtatatccag tgattttttt ctccatttta gcttccttag   2520
ctcctgaaaa tctcgataac tcaaaaaata cgcccggtag tgatcttatt tcattatggt   2580
gaaagttgga acctcttacg tgccgatcaa cgtctcattt cgccaaaag ttgggcccagg   2640 gcttcccggt atcaacaggg acaccaggat ttatttattc tgcgaagtga tcttccgtca   2700
caggtattta ttcggcgcaa agtgcgtcgg gtgatgctgc caacttagtc gactacaggt   2760
cactaatacc atctaagtag ttgattcata gtgactggat atgttgtgtt ttacagtatt   2820
atgtagtctg ttttttatgc aaaatctaat ttaatatatt gatatttata tcattttacg   2880
tttctcgttc agctttcttg tacaaagttg gcattataag aaagcattgc ttatcaattt   2940
gttgcaacga acaggtcact atcagtcaaa ataaaatcat tatttgccat ccagctgata   3000 tccctatag tgagtcgtat tacatggtca tagctgtttc ctggcagctc tggcccgtgt    3060
ctcaaaatct ctgatgttac attgcacaag ataaaataat atcatcatga acaataaaac   3120
tgtctgctta cataaacagt aatacaaggg gtgttatgag ccatattcaa cgggaaacgt   3180
cgaggccgcg attaaattcc aacatggatg ctgatttata tgggtataaa tgggctcgcg   3240
ataatgtcgg gcaatcaggt gcgacaatct atcgcttgta tgggaagccc gatgcgccag   3300
agttgtttct gaaacatggc aaaggtagcg ttgccaatga tgttacagat gagatggtca   3360
gactaaactg gctgacggaa tttatgcctc ttccgaccat caagcatttt atccgtactc   3420
ctgatgatgc atggttactc accactgcga tccccggaaa acagcattc caggtattag    3480 aagaatatcc tgattcaggt gaaaatattg ttgatgcgct ggcagtgttc ctgcgccggt   3540
tgcattcgat tcctgtttgt aattgtcctt ttaacagcga tcgcgtattt cgtctcgctc   3600
aggcgcaatc acgaatgaat aacggtttgg ttgatgcgag tgattttgat gacgagcgta   3660
atggctggcc tgttgaacaa gtctggaaag aaatgcataa acttttgcca ttctcaccgg   3720
attcagtcgt cactcatggt gatttctcac ttgataacct tattttgac gaggggaat    3780 taataggttg tattgatgtt ggacgagtcg gaatcgcaga ccgataccag gatcttgcca   3840
tcctatggaa ctgcctcggt gagttttctc cttcattaca gaaacggctt tttcaaaaat   3900
atggtattga taatcctgat atgaataaat tgcagtttca tttgatgctc gatgagtttt   3960
tctaatcaga attggttaat tggttgtaac actggcagag cattacgctg acttgacggg   4020
acggcgcaag ctcatgacca aaatcccctta acgtgagtta cgcgtcgttc cactgagcgt   4080
cagaccccgt agaaaagatc aaaggatctt cttgagatcc ttttttttctg cgcgtaatct   4140 gctgcttgca acaaaaaaa ccaccgctac cagcggtggt ttgtttgccg gatcaagagc    4200
taccaactct ttttccgaag gtaactggct tcagcagagc gcagatacca aatactgttc   4260
ttctagtgta gccgtagtta ggccaccact tcaagaactc tgtagcaccg cctacatacc   4320
tcgctctgct aatcctgtta ccagtggctg ctgccagtgg cgataagtcg tgtcttaccg   4380
ggttggactc aagacgatag ttaccggata aggcgcagcg gtcgggctga acggggggtt   4440
cgtgcacaca gcccagcttg gagcgaacga cctacaccga actgagatac ctacagcgtg   4500
agctatgaga aagcgccacg cttcccgaag ggagaaaggc ggacaggtat ccggtaagcg   4560
gcagggtcgg aacaggagag cgcacagggg agcttccagg gggaaacgcc tggtatcttt   4620
atagtcctgt cgggtttcgc cacctctgac ttgagcgtcg attttttgtga tgctcgtcag   4680
```

```
ggggcggag cctatggaaa aacgccagca acgcggcctt tttacggttc ctggccttt      4740 gctggccttt tgctcacatg tt                                              4762

<210> SEQ ID NO 4
<211> LENGTH: 16843
<212> TYPE: DNA
<213> ORGANISM: artificial sequence
<220> FEATURE:
<223> OTHER INFORMATION: destination vector for use with arabidopsis

<400> SEQUENCE: 4
ccgggctggt tgccctcgcc gctgggctgg cggccgtcta tggccctgca acgcgccag        60 aaacgccgtc gaagccgtgt gcgagacacc gcggccgccg gcgttgtgga tacctcgcgg      120
aaaacttggc cctcactgac agatgagggg cggacgttga cacttgaggg gccgactcac      180
ccggcgcggc gttgacagat gaggggcagg ctcgatttcg gccggcgacg tggagctggc      240
cagcctcgca aatcggcgaa aacgcctgat tttacgcgag tttcccacag atgatgtgga      300
caagcctggg gataagtgcc ctgcggtatt gacacttgag gggcgcgact actgacagat      360
gaggggcgcg atccttgaca cttgaggggc agagtgctga cagatgaggg gcgcaccctat     420 tgacatttga ggggctgtcc acaggcagaa aatccagcat ttgcaagggt ttccgcccgt      480
ttttcggcca ccgctaacct gtctttaac ctgcttttaa accaatattt ataaaccttg       540
tttttaacca gggctgcgcc ctgtgcgcgt gaccgcgcac gccgaagggg ggtgccccc       600 cttctcgaac cctcccggcc cgctaacgcg ggcctccat cccccagggg gctgcgcccc       660
tcggccgcga acggcctcac cccaaaaatg gcagcgctgg cagtccttgc cattgccggg      720
atcggggcag taacgggatg ggcgatcagc ccgagcgcga cgcccggaag cattgacgtg      780
ccgcaggtgc tggcatcgac attcagcgac caggtgccgg gcagtgaggg cggcggcctg      840
ggtggcggcc tgcccttcac ttcggccgtc ggggcattca cggacttcat ggcggggccg      900
gcaattttta ccttgggcat tcttggcata gtggtcgcgg gtgccgtgct cgtgttcggg      960
ggtgcgataa acccagcgaa ccatttgagg tgataggtaa gattataccg aggtatgaaa     1020
acgagaattg gacctttaca gaattactct atgaagcgcc atatttaaaa agctaccaag     1080
acgaagagga tgaagaggat gaggaggcag attgccttga atatattgac aatactgata     1140
agataatata tcttttatat agaagatatc gccgtatgta aggatttcag ggggcaaggc     1200
ataggcagcg cgcttatcaa tatatctata gaatgggcaa agcataaaaa cttgcatgga     1260
ctaatgcttg aaacccagga caataacctt atagcttgta aattctatca taattgggta     1320
atgactccaa cttattgata gtgttttatg ttcagataat gcccgatgac tttgtcatgc     1380
agctccaccg atttgagaa cgacagcgac ttccgtccca gccgtgccag gtgctgcctc      1440
agattcaggt tatgccgctc aattcgctgc gtatatcgct tgctgattac gtgcagcttt     1500
cccttcaggc gggattcata cagcggccag ccatccgtca tccatatcac cacgtcaaag     1560
ggtgacagca ggctcataag acgccccagc gtcgccatag tgcgttcacc gaatacgtgc     1620
gcaacaaccg tcttccggag actgtcatac gcgtaaaaca gccagcgctg gcgcgattta     1680
gccccgacat agccccactg ttcgtccatt tccgcgcaga cgatgacgtc actgcccggc     1740
tgtatgcgcg aggttaccga ctgcggcctg agtttttaa gtgacgtaaa atcgtgttga     1800
ggccaacgcc cataatgcgg gctgttgccc ggcatccaac gccattcatg gccatatcaa     1860
tgattttctg gtgcgtaccg ggttgagaag cggtgtaagt gaactgcagt tgccatgttt     1920
```

```
tacggcagtg agagcagaga tagcgctgat gtccggcggt gcttttgccg ttacgcacca   1980
ccccgtcagt agctgaacag gagggacagc tgatagacac agaagccact ggagcacctc   2040
aaaaacacca tcatacacta aatcagtaag ttggcagcat cacccataat tgtggtttca   2100
aaatcggctc cgtcgatact atgttatacg ccaactttga aaacaacttt gaaaaagctg   2160
ttttctggta tttaaggttt tagaatgcaa ggaacagtga attggagttc gtcttgttat   2220
aattagcttc ttggggtatc tttaaatact gtagaaaaga ggaaggaaat aataaatggc   2280
taaaatgaga atatcaccgg aattgaaaaa actgatcgaa aaataccgct gcgtaaaaga   2340
tacggaagga atgtctcctg ctaaggtata taagctggtg ggagaaaatg aaaacctata   2400
tttaaaaatg acggacagcc ggtataaagg gaccacctat gatgtggaac gggaaaagga   2460
catgatgcta tggctggaag gaaagctgcc tgttccaaag gtcctgcact ttgaacggca   2520
tgatggctgg agcaatctgc tcatgagtga ggccgatggc gtcctttgct cggaagagta   2580
tgaagatgaa caaagccctg aaaagattat cgagctgtat gcggagtgca tcaggctctt   2640
tcactccatc gacatatcgg attgtcccta tacgaatagc ttagacagcc gcttagccga   2700
attggattac ttactgaata cgatctggc cgatgtggat tgcgaaaact gggaagaaga   2760
cactccattt aaagatccgc gcgagctgta tgattttta aagacggaaa agcccgaaga   2820
ggaacttgtc ttttcccacg gcgacctggg agacagcaac atctttgtga agatggcaa   2880
agtaagtggc tttattgatc ttgggagaag cggcagggcg acaagtggt atgacattgc   2940
cttctgcgtc cggtcgatca gggaggatat cggggaagaa cagtatgtcg agctatttt   3000
tgacttactg gggatcaagc ctgattggga gaaaataaaa tattatattt tactggatga   3060
attgttttag tacctagatg tggcgcaacg atgccggcga caagcaggag cgcaccgact   3120
tcttccgcat caagtgtttt ggctctcagg ccgaggccca cggcaagtat ttgggcaagg   3180
ggtcgctggt attcgtgcag ggcaagattc ggaataccaa gtacgagaag gacggccaga   3240
cggtctacgg gaccgacttc attgccgata aggtggatta tctggacacc aaggcaccag   3300
gcgggtcaaa tcaggaataa gggcacattg ccccggcgtg agtcggggca atcccgcaag   3360
gagggtgaat gaatcggacg tttgaccgga aggcatacag gcaagaactg atcgacgcgg   3420
ggttttccgc cgaggatgcc gaaaccatcg caagccgcac cgtcatgcgt gcgccccgcg   3480
aaaccttcca gtccgtcggc tcgatggtcc agcaagctac ggccaagatc gagcgcgaca   3540
gcgtgcaact ggctccccct gccctgcccg cgccatcggc cgccgtggag cgttcgcgtc   3600
gtctcgaaca ggaggcggca ggtttggcga agtcgatgac catcgacacg cgaggaacta   3660
tgacgaccaa gaagcgaaaa accgccggcg aggacctggc aaaacaggtc agcgaggcca   3720
agcaggccgc gttgctgaaa cacacgaagc agcagatcaa ggaaatgcag cttttccttgt   3780
tcgatattgc gccgtggccg gacacgatgc gagcgatgcc aaacgacacg gcccgctctg   3840
ccctgttcac cacgcgcaac aagaaaatcc cgcgcgaggc gctgcaaaac aaggtcatt   3900
tccacgtcaa caaggacgtg aagatcacct acaccggcgt cgagctgcgg gccgacgatg   3960
acgaactggt gtggcagcag gtgttggagt acgcgaagcg caccectatc ggcgagccga   4020
tcaccttcac gttctacgag cttttgccagg acctgggctg gtcgatcaat ggccggtatt   4080
acacgaaggc cgaggaatgc ctgtcgcgcc tacaggcgac ggcgatgggc ttcacgtccg   4140
accgcgttgg gcacctggaa tcggtgtcgc tgctgcaccg cttccgcgtc ctggaccgtg   4200
gcaagaaaac gtcccgttgc caggtcctga tcgacgagga atcgtcgtg ctgtttgctg   4260
gcgaccacta cacgaaattc atatgggaga agtaccgcaa gctgtcgccg acggcccgac   4320
```

```
ggatgttcga ctatttcagc tcgcaccggg agccgtaccc gctcaagctg gaaaccttcc    4380
gcctcatgtg cggatcggat tccacccgcg tgaagaagtg gcgcgagcag gtcggcgaag    4440
cctgcgaaga gttgcgaggc agcggcctgg tggaacacgc ctgggtcaat gatgacctgg    4500
tgcattgcaa acgctagggc cttgtggggt cagttccggc tgggggttca gcagccagcg    4560
ctttactggc atttcaggaa caagcgggca ctgctcgacg cacttgcttc gctcagtatc    4620
gctcgggacg cacggcgcgc tctacgaact gccgataaac agaggattaa aattgacaat    4680
tgtgattaag gctcagattc gacggcttgg agcggccgac gtgcaggatt ccgcgagat     4740 ccgattgtcg gccctgaaga agctccagat gatgttcggg tccgtttacg agcacgagga    4800
gaaaaagccc atggaggcgt tcgctgaacg gttgcgagat gccgtggcat tcggcgccta    4860
catcgacggc gagatcattg gctgtcggt cttcaaacag gaggacggcc ccaaggacgc     4920
tcacaaggcg catctgtccg gcgttttcgt ggagcccgaa cagcgaggcc gagggggtcgc   4980 cggtatgctg ctgcgggcgt tgccggcggg tttattgctc gtgatgatcg tccgacagat    5040
tccaacggga atctggtgga tgcgcatctt catcctcggc gcacttaata tttcgctatt    5100
ctggagcttg ttgtttattt cggtctaccg cctgccgggc ggggtcgcgg cgacggtagg    5160
cgctgtgcag ccgctgatgg tcgtgttcat ctctgccgct ctgctaggta gcccgatacg    5220
attgatggcg gtcctggggg ctatttgcgg aactgcgggc gtggcgctgt tggtgttgac    5280
accaaacgca gcgctagatc ctgtcggcgt cgcagcgggc ctggcggggg cggtttccat    5340
ggcgttcgga accgtgctga cccgcaagtg gcaacctccc gtgcctctgc tcacctttac    5400
cgcctggcaa ctggcggccg gaggacttct gctcgttcca gtagctttag tgtttgatcc    5460
gccaatcccg atgcctacag gaaccaatgt tctcggcctg gcgtggctcg gcctgatcgg    5520
agcgggttta acctacttcc tttggttccg ggggatctcg cgactcgaac ctacagttgt    5580
ttccttactg ggctttctca gccccagatc tggggtcgat cagccgggga tgcatcaggc    5640
cgacagtcgg aacttcgggt ccccgacctg taccattcgg tgagcaatgg ataggggagt    5700
tgatatcgtc aacgttcact tctaaagaaa tagcgccact cagcttcctc agcggcttta    5760
tccagcgatt tcctattatg tcggcatagt tctcaagatc gacagcctgt cacggttaag    5820
cgagaaatga ataagaaggc tgataattcg gatctctgcg agggagatga tatttgatca    5880
caggcagcaa cgctctgtca tcgttacaat caacatgcta ccctccgcga gatcatccgt    5940
gtttcaaacc cggcagctta gttgccgttc ttccgaatag catcggtaac atgagcaaag    6000
tctgccgcct tacaacggct ctcccgctga cgccgtcccg gactgatggg ctgcctgtat    6060
cgagtggtga ttttgtgccg agctgccggt cggggagctg ttggctggct ggtggcagga    6120
tatattgtgt tgtaaacaaa ttgacgctta gacaacttaa taacacattg cggacgtttt    6180
taatgtactg gggtggtttt tcttttcacc agtgagacgg gcaacagctg attgcccttc    6240
accgcctggc cctgagagag ttgcagcaag cggtccacgc tggtttgccc cagcaggcga    6300
aaatcctgtt tgatggtggt tccgaaatcg gcaaaatccc ttataaatca aaagaatagc    6360
ccgagatagg gttgagtgtt gttccagttt ggaacaagag tccactatta agaacgtgg     6420 actccaacgt caaagggcga aaaccgtctc atcagggcga tgggccacta cctgtatggc    6480
cgcattcgca aaacacacct agactagatt tgttttgcta acccaattga tattaattat    6540
atatgattaa tatttatatg tatatggatt tggttaatga aatgcatctg gttcatcaaa    6600
gaattataaa gacacgtgac attcatttag gataagaaat atggatgatc tctttctctt    6660
```

```
ttattcagat aactagtaat tacacataac acacaacttt gatgcccaca ttatagtgat    6720
tagcatgtca ctatgtgtgc atccttttat ttcatacatt aattaagttg gccaatccag    6780
aagatggaca agtctaggtt aaccatgtgg tacctacgcg ttcgaatatc catgggccgc    6840
ttcaggccag ggcgctgggg aaggcgatgg cgtgctcggt cagctgccac ttctggttct    6900
tggcgtcgct ccggtcctcc cgcagcagct tgtgctggat gaagtgccac tcgggcatct    6960
tgctgggcac gctcttggcc ttgtacacgg tgtcgaactg gcaccggtac cggccgccgt    7020
ccttcagcag caggtacatg ctcacgtcgc ccttcaggat gccctgctta ggcacgggca    7080
tgatcttctc gcagctggcc tcccagttgg tggtcatctt cttcatcacg gggccgtcgg    7140
cggggaagtt cacgccgttg aagatgctct tgtggtagat gcagttctcc ttcacgctca    7200
cggtgatgtc cacgttacag atgcacacgg cgccgtcctc gaacaggaag ctccggcccc    7260
aggtgtagcc ggcggggcag ctgttcttga agtagtccac gatgtcctgg gggtactcgg    7320
tgaagatccg gtcgccgtac ttgaagccgg cgctcaggat gtcctcgctg aagggcaggg    7380
ggccgccctc gatcacgcac aggttgatgg tctgcttgcc cttgaagggg tagccgatgc    7440
cctcgccggt gatcacgaac ttgtggccgt tcacgcagcc ctccatgtgg tacttcatgg    7500
tcatctcctc cttcaggccg tgcttgctgt gggccatggt ggcgaccggt gaattcgagc    7560
tcggtacccg ggatcctga gtaaaacaga ggagggtctc actaagttta tagagagact    7620
gagagagata aagggacacg tatgaagcgt ctgttttcgt ggtgtgacgt caaagtcatt    7680
ttgctctcta cgcgtgtctg tgtcggcttg atcttttttt ttgcttttg gaactcatgt     7740 cggtagtata tcttttattt attttttctt ttttccctt ttctttcaaa ctgatgtcgg     7800
tatgatattt attccatcct aaaatgtaac ttactattat tagtagtcgg tccatgtcta    7860
ttggcccatc atgtggtcat tttacgttta cgtcgtgtgg ctgtttatta taacaaacgg    7920
cacatccttc tcattcgaat tgtatttctc cttaatcgtt ctaataggta tgatctttta    7980
ttttatacgt aaaattaaaa ttgaatgatg tcaagaacga aaattaattt gtatttacaa    8040
aggagctaaa tattgtttat tcctctactg gtagaagata aagaagtag atgaaataat     8100 gatcttacta gagaatattc ctcatttaca ctagtcaaat ggaaatcttg taaactttta    8160
caataattta tcctgaaaat atgaaaaaat agaagaaaat gtttacctcc tctctcctct    8220
taattcacct acgatcggtg cgggcctctt cgctattacg ccagctggcg aaaggggat    8280 gtgctgcaag gcgattaagt tgggtaacgc cagggttttc ccagtcacga cgttgtaaaa    8340
cgacggccag tgaattcgag ctcggtaccc ggggatcctc tagagtcgac ctgcaggcat    8400
gcaagcttgt tgaaacatcc ctgaagtgtc tcattttatt ttatttattc tttgctgata    8460
aaaaaataaa ataaagaag ctaagcacac ggtcaaccat tgctctactg ctaaagggt     8520 tatgtgtagt gttttactgc ataaattatg cagcaaacaa gacaactcaa attaaaaaat    8580
ttcctttgct tgttttttg ttgtctctga cttgacttc ttgtggaagt tggttgtata     8640
aggattggga cacaccattg tccttcttaa tttaatttta tttctttgct gataaaaaaa    8700
aaaaatttca tatagtgtta aataataatt tgttaaataa ccaaaaagtc aaatatgttt    8760
actctcgttt aaataattga gagtcgtcca gcaaggctaa acgattgtat agatttatga    8820
caatatttac tttttttatag ataaatgtta tattataata aatttatata catatattat   8880 atgttatttta ttatttatta ttattttaaa tccttcaata tttatcaaa ccaactcata    8940 atttttttt tatctgtaag aagcaataaa attaaataga cccactttaa ggatgatcca    9000
acctttatac agagtaagag agttcaaata gtacccttc atatacatat caactaaaat     9060
```

-continued

```
attagaaata tcatggatca aaccttataa agacattaaa taagtggata agtataatat   9120
ataaatgggt agtatataat atataaatgg atacaaactt ctctctttat aattgttatg   9180
tctccttaac atcctaatat aatacataag tgggtaatat ataatatata aatggagaca   9240
aacttcttcc attataattg ttatgtcttc ttaacactta tgtctcgttc acaatgctaa   9300
agttagaatt gtttagaaag tcttatagta cacatttgtt tttgtactat ttgaagcatt   9360
ccataagccg tcacgattca gatgatttat aataataaga ggaaatttat catagaacaa   9420
taaggtgcat agatagagtg ttaatatatc ataacatcct tgtttattc atagaagaag    9480
tgagatggag ctcagttatt atactgttac atggtcggat acaatattcc atgctctcca   9540
tgagctctta cacctacatg cattttagtt catacttcat gcacgtggcc atcacagcta   9600
gctgcagcta catatttaca ttttacaaca ccaggagaac tgccctgtta gtgcataaca   9660
atcagaagat ggccgtggct actcgagtta tcgaaccact ttgtacaaga aagctgaacg   9720
agaaacgtaa aatgatataa atatcaatat attaaattag attttgcata aaaaacagac   9780
tacataatac tgtaaaacac aacatatcca gtcactatgg tcgacctgca gactggctgt   9840
gtataaggga gcctgacatt tatattcccc agaacatcag gttaatggcg ttttgatgt    9900
cattttcgcg gtggctgaga tcagccactt cttccccgat aacggagacc ggcacactgg   9960
ccatatcggt ggtcatcatg cgccagcttt catcccgat atgcaccacc gggtaaagtt    10020
cacgggagac tttatctgac agcagacgtg cactggccag ggggatcacc atccgtcgcc   10080
cgggcgtgtc aataatatca ctctgtacat ccacaaacag acgataacgg ctctctcttt   10140
tataggtgta aaccttaaac tgcatttcac cagtccctgt tctcgtcagc aaaagagccg   10200
ttcatttcaa taaccgggc gacctcagcc atcccttcct gattttccgc tttccagcgt    10260
tcggcacgca gacgacgggc ttcattctgc atggttgtgc ttaccagacc ggagatattg   10320
acatcatata tgccttgagc aactgatagc tgtcgctgtc aactgtcact gtaatacgct   10380
gcttcatagc acacctcttt ttgacatact tcgggtatac atatcagtat atattcttat   10440
accgcaaaaa tcagcgcgca aatacgcata ctgttatctg ctttttagta agccggatcc   10500
tctagattac gccccgccct gccactcatc gcagtactgt tgtaattcat taagcattct   10560
gccgacatgg aagccatcac agacggcatg atgaacctga atcgccagcg gcatcagcac   10620
cttgtcgcct tgcgtataat atttgcccat ggtgaaaacg ggggcgaaga agttgtccat   10680
attggccacg tttaaatcaa aactggtgaa actcacccag ggattggctg agacgaaaaa   10740
catattctca ataaacccttt tagggaaata ggccaggttt tcaccgtaac acgccacatc   10800
ttgcgaatat atgtgtagaa actgccggaa atcgtcgtgg tattcactcc agagcgatga   10860
aaacgtttca gtttgctcat ggaaaacggt gtaacaaggg tgaacactat cccatatcac   10920
cagctcaccg tctttcattg ccatacggaa ttccggatga gcattcatca ggcgggcaag   10980
aatgtgaata aaggccggat aaaacttgtg cttatttttc tttacggtct ttaaaaggc    11040
cgtaatatcc agctgaacgg tctggttata ggtacattga gcaactgact gaaatgcctc   11100
aaaatgttct ttacgatgcc attgggatat atcaacggtg gtatatccag tgattttttt   11160
ctccatttta gcttccttag ctcctgaaaa tctcgccgga tcctaactca aaatccacac   11220
attatacgag ccggaagcat aaagtgtaaa gcctggggtg cctaatgcgg ccgccatagt   11280
gactggatat gttgtgtttt acagtattat gtagtctgtt ttttatgcaa aatctaattt   11340
aatatattga tatttatatc attttacgtt tctcgttcag cttttttgta caaacttgtt   11400
```

```
tgataaccgg tactagtgtg cacgtcgagc gtgtcctctc caaatgaaat gaacttcctt    11460
atatagagga agggtcttgc gaaggatagt gggattgtgc gtcatccctt acgtcagtgg    11520
agatgtcaca tcaatccact tgctttgaag acgtggttgg aacgtcttct ttttccacga    11580
tgctcctcgt gggtgggggt ccatctttgg gaccactgtc ggcagaggca tcttgaatga    11640
tagcctttcc tttatcgcaa tgatggcatt tgtaggagcc accttccttt tctactgtcc    11700
tttcgatgaa gtgacagata gctgggcaat ggaatccgag gaggtttccc gaaattatcc    11760
tttgttgaaa agtctcaata gccctttggt cttctgagac tgtatctttg acattttggg    11820
agtagaccag agtgtcgtgc tccaccatgt tgacgaagat tttcttcttg tcattgagtc    11880
gtaaaagact ctgtatgaac tgttcgccag tcttcacggc gagttctgtt agatcctcga    11940
tttgaatctt agactccatg catggcctta gattcagtag gaactacctt tttagagact    12000
ccaatctcta ttacttgcct tggtttatga agcaagcctt gaatcgtcca tactggaata    12060
gtacttctga tcttgagaaa tatgtctttc tctgtgttct tgatgcaatt agtcctgaat    12120
cttttgactg catctttaac cttcttggga aggtatttga tctcctggag attgttactc    12180
gggtagatcg tcttgatgag acctgctgcg taggcctctc taaccatctg tgggtcagca    12240
ttctttctga aattgaagag gctaaccttc tcattatcag tggtgaacat agtgtcgtca    12300
ccttcacctt cgaacttcct tcctagatcg taaagataga ggaaatcgtc cattgtaatc    12360
tccggggcaa aggagatctc ttttggggct ggatcactgc tgggcctttt ggttcctagc    12420
gtgagccagt gggctttttg ctttggtggg cttgttaggg ccttagcaaa gctcttgggc    12480
ttgagttgag cttctccttt ggggatgaag ttcaacctgt ctgtttgctg acttgttgtg    12540
tacgcgtcag ctgctgctct tgcctctgta atagtggcaa atttcttgtg tgcaactccg    12600
ggaacgccgt ttgttgccgc cttttgtacaa ccccagtcat cgtatatacc ggcatgtgga    12660
ccgttataca caacgtagta gttgatatga gggtgttgaa tacccgattc tgctctgaga    12720
ggagcaactg tgctgttaag ctcagatttt tgtgggattg gaattggatc ctctagagca    12780
aagcttggcg taatcatggt catagctgtt tcctgtgtga aattgttatc cgctcacaat    12840
tccacacaac atacgagccg gaagcataaa gtgtaaagcc tggggtgcct aatgagtgag    12900
ctaactcaca ttaattgcgt tgcgctcact gcccgctttc cagtcgggaa acctgtcgtg    12960
ccagctgcat taatgaatcg gccaacgcgc ggggagaggc ggtttgcgta ttgggccaaa    13020
gacaaagggg cgacattcaa ccgattgagg gagggaaggt aaatattgac ggaaattatt    13080
cattaaaggt gaattatcac cgtcaccgac ttgagccatt tgggaattag agccagcaaa    13140
atcaccagta gcaccattac cattagcaag gccggaaacg tcaccaatga aaccatcatc    13200
tagtaacata gatgacaccg cgcgcgataa tttatcctag tttgcgcgct atattttgtt    13260
ttctatcgcg tattaaatgt ataattgcgg gactctaatc ataaaaaccc atctcataaa    13320
taacgtcatg cattacatgt taattattac atgcttaacg taattcaaca gaaattatat    13380
gataatcatc gcaagaccgg caacaggatt caatcttaag aaactttatt gccaaatgtt    13440
tgaacgatct gcttcgacgc actccttctt taggtacgga ctagatctcg gtgacgggca    13500
ggaccggacg gggcggtacc ggcaggctga agtccagctg ccagaaaccc acgtcatgcc    13560
agttcccgtg cttgaagccg gccgcccgca gcatgccgcg gggggcatat ccgagcgcct    13620
cgtgcatgcg cacgctcggg tcgttgggca gcccgatgac agcgaccacg ctcttgaagc    13680
cctgtgcctc cagggacttc agcaggtggg tgtagagcgt ggagcccagt cccgtccgct    13740
ggtggcgggg ggagacgtac acggtcgact cggccgtcca gtcgtaggcg ttgcgtgcct    13800
```

```
tccaggggcc cgcgtaggcg atgccggcga cctcgccgtc cacctcggcg acgagccagg    13860
gatagcgctc ccgcagacgg acgaggtcgt ccgtccactc ctgcggttcc tgcggctcgg    13920
tacggaagtt gaccgtgctt gtctcgatgt agtggttgac gatggtgcag accgccggca    13980
tgtccgcctc ggtggcacgg cggatgtcgg ccgggcgtcg ttctgggctc atggatctgg    14040
attgagagtg aatatgagac tctaattgga taccgagggg aatttatgga acgtcagtgg    14100
agcattttg acaagaaata tttgctagct gatagtgacc ttaggcgact tttgaacgcg     14160
caataatggt ttctgacgta tgtgcttagc tcattaaact ccagaaaccc gcggctgagt    14220
ggctccttca acgttgcggt tctgtcagtt ccaaacgtaa aacggcttgt cccgcgtcat    14280
cggcggggggt cataacgtga ctcccttaat tctccgctca tgatcagatt gtcgtttccc   14340
gccttcagtt taaactatca gtgtttgaca ggatatattg gcgggtaaac ctaagagaaa    14400
agagcgttta ttagaataat cggatattta aagggcgtg aaaaggttta tccgttcgtc     14460
catttgtatg tgcatgccaa ccacagggtt ccccagatct ggcgccggcc agcgagacga    14520
gcaagattgg ccgccgcccg aaacgatccg acagcgcgcc cagcacaggt gcgcaggcaa    14580
attgcaccaa cgcatacagc gccagcagaa tgccatagtg ggcggtgacg tcgttcgagt    14640
gaaccagatc gcgcaggagg cccggcagca ccggcataat caggccgatg ccgacagcgt    14700
cgagcgcgac agtgctcaga attacgatca ggggtatgtt gggtttcacg tctgcctcc    14760
ggaccagcct ccgctggtcc gattgaacgc gcggattctt tatcactgat aagttggtgg    14820
acatattatg tttatcagtg ataaagtgtc aagcatgaca aagttgcagc cgaatacagt    14880
gatccgtgcc gccctggacc tgttgaacga ggtcggcgta gacggtctga cgacacgcaa    14940
actggcggaa cggttggggg ttcagcagcc ggcgctttac tggcacttca ggaacaagcg    15000
ggcgctgctc gacgcactgg ccgaagccat gctggcggag aatcatacgc attcggtgcc    15060
gagagccgac gacgactggc gctcatttct gatcgggaat gcccgcagct tcaggcaggc    15120
gctgctcgcc taccgcgatg gcgcgcgcat ccatgccggc acgcgaccgg gcgcaccgca    15180
gatggaaacg gccgacgcgc agcttcgctt cctctgcgag gcgggttttt cggccgggga    15240
cgccgtcaat gcgctgatga caatcagcta cttcactgtt ggggccgtgc ttgaggagca    15300
ggccggcgac agcgatgccg gcgagcgcgg cggcaccgtt gaacaggctc cgctctcgcc    15360
gctgttgcgg gccgcgatag acgccttcga cgaagccggt ccggacgcag cgttcgagca    15420
gggactcgcg gtgattgtcg atggattggc gaaaaggagg ctcgttgtca ggaacgttga    15480
aggaccgaga aagggtgacg attgatcagg accgctgccg gagcgcaacc cactcactac    15540
agcagagcca tgtagacaac atcccctccc cctttccacc gcgtcagacg cccgtagcag    15600
cccgctacgg gcttttttcat gccctgccct agcgtccaag cctcacggcc gcgctcggcc    15660
tctctggcgg ccttctggcg ctcttccgct tcctcgctca ctgactcgct gcgctcggtc    15720
gttcggctgc ggcgagcggt atcagctcac tcaaaggcgg taatacggtt atccacagaa    15780
tcaggggata acgcaggaaa gaacatgtga gcaaaaggcc agcaaaaggc caggaaccgt    15840
aaaaaggccg cgttgctggc gttttttccat aggctccgcc ccctgacga gcatcacaaa    15900
aatcgacgct caagtcagag gtggcgaaac ccgacaggac tataaagata ccaggcgttt    15960
ccccctggaa gctccctcgt gcgctctcct gttccgaccc tgccgcttac cggatacctg    16020
tccgccttc tcccttcggg aagcgtggcg cttttccgct gcataaccct gcttcggggt     16080
cattatagcg attttttcgg tatatccatc cttttcgca cgatatacag gattttgcca     16140
```

```
aagggttcgt gtagactttc cttggtgtat ccaacggcgt cagccgggca ggataggtga    16200
agtaggccca cccgcgagcg ggtgttcctt cttcactgtc ccttattcgc acctggcggt    16260
gctcaacggg aatcctgctc tgcgaggctg gccggctacc gccggcgtaa cagatgaggg    16320
caagcggatg gctgatgaaa ccaagccaac caggaagggc agcccaccta tcaaggtgta    16380
ctgccttcca gacgaacgaa gagcgattga ggaaaaggcg gcggcggccg gcatgagcct    16440
gtcggcctac ctgctggccg tcggccaggg ctacaaaatc acgggcgtcg tggactatga    16500
gcacgtccgc gagctggccc gcatcaatgg cgacctgggc cgcctgggcg gcctgctgaa    16560
actctggctc accgacgacc cgcgcacggc gcggttcggt gatgccacga tcctcgccct    16620
gctggcgaag atcgaagaga agcaggacga gcttggcaag gtcatgatgg gcgtggtccg    16680
cccgagggca gagccatgac ttttttagcc gctaaaacgg ccggggggtg cgcgtgattg    16740
ccaagcacgt ccccatgcgc tccatcaaga agagcgactt cgcggagctg gtgaagtaca    16800
tcaccgacga gcaaggcaag accgagcgcc tttgcgacgc tca                      16843

<210> SEQ ID NO 5
<211> LENGTH: 9142
<212> TYPE: DNA
<213> ORGANISM: artificial sequence
<220> FEATURE:
<223> OTHER INFORMATION: destination vector for use with soybean

<400> SEQUENCE: 5
ctagttatct gaataaaaga gaaagagatc atccatattt cttatcctaa atgaatgtca      60
cgtgtcttta taattctttg atgaaccaga tgcatttcat taaccaaatc catatacata    120
taaatattaa tcatatataa ttaatatcaa ttgggttagc aaaacaaatc tagtctaggt    180
gtgttttgcg aattcgatat caagcttgat gggtaccggc gcgccgatc  atccggatat    240 agttcctcct ttcagcaaaa aaccccctcaa gacccgttta gaggccccaa ggggttatgc    300
tagttattgc tcagcggtgg cagcagccaa ctcagcttcc tttcgggctt tgttagcagc    360
cggatcgatc caagctgtac ctcactattc ctttgccctc ggacgagtgc tggggcgtcg    420
gtttccacta tcggcgagta cttctacaca gccatcggtc cagacggccg cgcttctgcg    480
ggcgatttgt gtacgcccga cagtcccggc tccggatcgg acgattgcgt cgcatcgacc    540
ctgcgcccaa gctgcatcat cgaaattgcc gtcaaccaag ctctgataga gttggtcaag    600
accaatgcgg agcatatacg cccggagccg cggcgatcct gcaagctccg gatgcctccg    660
ctcgaagtag cgcgtctgct gctccataca agccaaccac ggcctccaga agaagatgtt    720
ggcgacctcg tattgggaat ccccgaacat cgcctcgctc cagtcaatga ccgctgttat    780
gcggccattg tccgtcagga cattgttgga gccgaaatcc gcgtgcacga ggtgccggac    840
ttcggggcag tcctcggccc aaagcatcag ctcatcgaga gcctgcgcga cggacgcact    900
gacggtgtcg tccatcacag tttgccagtg atacacatgg ggatcagcaa tcgcgcatat    960
gaaatcacgc catgtagtgt attgaccgat tccttgcggt ccgaatgggc cgaacccgct   1020
cgtctggcta agatcggccg cagcgatcgc atccatagcc tccgcgaccg gctgcagaac   1080
agcgggcagt tcggtttcag gcaggtcttg caacgtgaca ccctgtgcac ggcgggagat   1140
gcaataggtc aggctctcgc tgaattcccc aatgtcaagc acttccggaa tcgggagcgc   1200
ggccgatgca agtgccgata aacataacg  atctttgtag aaaccatcgg cgcagctatt   1260
tacccgcagg acatatccac gccctcctac atcgaagctg aaagcacgag attcttcgcc   1320
ctccgagagc tgcatcaggt cggagacgct gtcgaacttt tcgatcagaa acttctcgac   1380
```

```
agacgtcgcg gtgagttcag gcttttccat gggtatatct ccttcttaaa gttaaacaaa    1440
attatttcta gagggaaacc gttgtggtct ccctatagtg agtcgtatta atttcgcggg    1500
atcgagatct gatcaacctg cattaatgaa tcggccaacg cgcggggaga ggcggtttgc    1560
gtattgggcg ctcttccgct tcctcgctca ctgactcgct gcgctcggtc gttcggctgc    1620
ggcgagcggt atcagctcac tcaaaggcgg taatacggtt atccacagaa tcagggggata   1680 acgcaggaaa gaacatgtga gcaaaaggcc agcaaaaggc caggaaccgt aaaaaggccg    1740
cgttgctggc gtttttccat aggctccgcc cccctgacga gcatcacaaa aatcgacgct    1800
caagtcagag gtggcgaaac ccgacaggac tataaagata ccaggcgttt ccccctggaa    1860
gctccctcgt gcgctctcct gttccgaccc tgccgcttac cggatacctg tccgcctttc    1920
tcccttcggg aagcgtggcg ctttctcaat gctcacgctg taggtatctc agttcggtgt    1980
aggtcgttcg ctccaagctg gctgtgtgc acgaaccccc cgttcagccc gaccgctgcg     2040
ccttatccgg taactatcgt cttgagtcca acccggtaag acacgactta tcgccactgg    2100
cagcagccac tggtaacagg attagcagag cgaggtatgt aggcggtgct acagagttct    2160
tgaagtggtg gcctaactac ggctacacta aggacagt atttggtatc tgcgctctgc      2220
tgaagccagt taccttcgga aaaagagttg gtagctcttg atccggcaaa caaaccaccg    2280
ctggtagcgg tggttttttt gtttgcaagc agcagattac gcgcagaaaa aaggatctc     2340 aagaagatcc tttgatcttt tctacggggt ctgacgctca gtggaacgaa aactcacgtt    2400
aagggatttt ggtcatgaca ttaacctata aaaataggcg tatcacgagg ccctttcgtc    2460
tcgcgcgttt cggtgatgac ggtgaaaacc tctgacacat gcagctcccg gagacggtca    2520
cagcttgtct gtaagcggat gccgggagca gacaagcccg tcaggcgcg tcagcgggtg     2580 ttggcgggtg tcgggctgg cttaactatg cggcatcaga gcagattgta ctgagagtgc     2640
accatatgga catattgtcg ttagaacgcg gctacaatta atacataacc ttatgtatca    2700
tacacatacg atttaggtga cactatagaa cggcgcgcca agctgggtct agaactagaa    2760
acgtgatgcc acttgttatt gaagtcgatt acagcatcta ttctgtttta ctatttataa    2820 cttttgccatt tctgactttt gaaaactatc tctggatttc ggtatcgctt tgtgaagatc    2880
gagcaaaaga gacgttttgt ggacgcaatg gtccaaatcc gttctacatg aacaaattgg    2940
tcacaatttc cactaaaagt aaataaatgg caagttaaaa aaggaatatg cattttactg    3000
attgcctagg tgagctccaa gagaagttga atctacacgt ctaccaaccg ctaaaaaaag    3060
aaaaacattg aatatgtaac ctgattccat tagcttttga cttcttcaac agattctcta    3120
cttagatttc taacagaaat attattacta gcacatcatt ttcagtctca ctacagcaaa    3180
aaatccaacg gcacaataca gacaacagga gatatcagac tacagagata gatagatgct    3240
actgcatgta gtaagttaaa taaaaggaaa ataaaatgtc ttgctaccaa aactactaca    3300
gactatgatg ctcaccacag gccaaatcct gcaactagga cagcattatc ttatatatat    3360
tgtacaaaac aagcatcaag gaacatttgg tctaggcaat cagtacctcg ttctaccatc    3420
accctcagtt atcacatcct tgaaggatcc attactggga atcatcggca acacatgctc    3480
ctgatggggc acaatgacat caagaaggta ggggccaggg gtgtccaaca ttctctgaat    3540
tgccgctcta agctcttcct tcttcgtcac tcgcgctgcc ggtatcccac aagcatcagc    3600
aaacttgagc atgtttggga atatctcgct ctcgctagac ggatctccaa gataggtgtg    3660
agctctattg gacttgtaga acctatcctc caactgaacc accatacccc aatgctgatt    3720
```

```
gttcaacaac aatatcttaa ctgggagatt ctccactctt atagtggcca actcctgaac   3780
attcatgatg aaactaccat ccccatcaat gtcaaccaca acagcccag ggttagcaac    3840 agcagcacca atagccgcag gcaatccaaa acccatggct ccaagacccc ctgaggtcaa   3900
ccactgcctc ggtctcttgt acttgtaaaa ctgcgcagcc cacatttgat gctgcccaac   3960
cccagtacta acaatagcat ctccattagt caactcatca agaacctcga tagcatgctg   4020
cggagaaatc gcgtcctgga atgtcttgta acccaatgga aacttgtgtt tctgcacatt   4080
aatctcttct ctccaacctc caagatcaaa cttaccctcc actcctttct cctccaaaat   4140
catattaatt cccttcaagg ccaacttcaa atccgcgcaa accgacacgt gcgcctgctt   4200
gttcttccca atctcggcag aatcaatatc aatgtgaaca atcttagccc tactagcaaa   4260
agcctcaagc ttcccagtaa cacggtcatc aaaccttacc ccaaaggcaa gcaacaaatc   4320
actattgtca acagcatagt tagcataaac agtaccatgc atacccagca tctgaaggga   4380
atattcatca ccaataggaa aagttccaag acccattaaa gtgctagcaa cgggaatacc   4440
agtgagttca acaaagcgcc tcaattcagc actggaattc aaactgccac cgccgacgta   4500
gagaacgggc ttttgggcct ccatgatgag tctgacaatg tgttccaatt gggcctcggc   4560 gggggggcctg gcagcctgg cgaggtaacc ggggaggtta acgggctcgt cccaattagg   4620
cacggcgagt tgctgctgaa cgtctttggg aatgtcgatg aggaccggac cggggcggcc   4680
ggaggtggcg acgaagaaag cctcggcgac gacgcgggg atgtcgtcga cgtcgaggat   4740
gaggtagttg tgcttcgtga tggatctgct cacctccacg atcggggttt cttggaaggc   4800
gtcggtgccg atcatccggc gggcgacctg gccggtgatg gcgacgactg ggacgctgtc   4860
cattaaagcg tcggcgaggc cgctcacgag gttggtggcg ccggggccgg aggtggcaat   4920
gcagacgccg gggaggccgg aggaacgcgc gtagccttcg gcggcgaaga cgccgccctg   4980
ctcgtggcgc gggagcacgt tgcggatggc ggcggagcgc gtgagcgcct ggtggatctc   5040
catcgacgca ccgccggggt acgcgaacac cgtcgtcacg ccctgcctct ccagcgcctc   5100
cacaaggatg tccgcgccct tgcgaggttc gccggaggcg aaccgtgaca cgaagggctc   5160
cgtggtcggc gcttccttgg tgaagggcgc cgccgtgggg ggtttggaga tggaacattt   5220
gattttgaga gcgtggttgg gtttggtgag ggtttgatga gagagaggga gggtggatct   5280
agtaatgcgt ttggggaagg tggggtgtga agaggaagaa gagaatcggg tggttctgga   5340
agcggtggcc gccattgtgt tgtgtggcat ggttatactt caaaaactgc acaacaagcc   5400
tagagttagt acctaaacag taaatttaca acagagagca aagacacatg caaaaatttc   5460
agccataaaa aaagttataa tagaatttaa agcaaaagtt tcattttta aacatatata   5520 caaacaaact ggatttgaag gaagggatta attcccctgc tcaaagtttg aattcctatt   5580
gtgacctata ctcgaataaa attgaagcct aaggaatgta tgagaaacaa gaaaacaaaa   5640
caaaactaca gacaaacaag tacaattaca aaattcgcta aaattctgta atcaccaaac   5700
cccatctcag tcagcacaag gcccaaggtt tattttgaaa taaaaaaaaa gtgattttat   5760
ttctcataag ctaaagaaa gaaaggcaat tatgaaatga tttcgactag atctgaaagt   5820
caaacgcgta ttccgcagat attaaagaaa gagtagagtt tcacatggat cctagatgga   5880
cccagttgag gaaaaagcaa ggcaaagcaa accagaagtg caagatccga aattgaacca   5940
cggaatctag gatttggtag agggagaaga aaagtacctt gagaggtaga agagaagaga   6000
agagcagaga gatatatgaa cgagtgtgtc ttggtctcaa ctctgaagcg atacgagttt   6060
agaggggagc attgagttcc aatttatagg gaaaccgggt ggcaggggtg agttaatgac   6120
```

-continued

```
ggaaaagccc ctaagtaacg agattggatt gtgggttaga ttcaaccgtt tgcatccgcg    6180
gcttagattg gggaagtcag agtgaatctc aaccgttgac tgagttgaaa attgaatgta    6240
gcaaccaatt gagccaaccc cagcctttgc cctttgattt tgatttgttt gttgcatact    6300
ttttatttgt cttctggttc tgactctctt tctctcgttt caatgccagg ttgcctactc    6360
ccacaccact cacaagaaga ttctactgtt agtattaaat attttttaat gtattaaatg    6420
atgaatgctt ttgtaaacag aacaagacta tgtctaataa gtgtcttgca acatttttta    6480
agaaattaaa aaaatatat ttattatcaa aatcaaatgt atgaaaaatc atgaataata     6540
taattttata cattttttta aaaatctttt taatttctta attaatatct taaaaataat    6600
gattaatatt taacccaaaa taattagtat gattggtaag gaagatatcc atgttatgtt    6660
tggatgtgag tttgatctag agcaaagctt actagagtcg acctgcagcc cctccaccgc    6720
ggtggcggcc gctctagaga tccgtcaaca tggtggagca cgacactctc gtctactcca    6780
agaatatcaa agatacagtc tcagaagacc aaagggctat tgagactttt caacaaaggg    6840
taatatcggg aaacctcctc ggattccatt gcccagctat ctgtcacttc atcaaaagga    6900
cagtagaaaa ggaaggtggc acctacaaat gccatcattg cgataaagga aaggctatcg    6960
ttcaagatgc ctctgccgac agtggtccca agatggaccc ccacccacg aggagcatcg     7020 tggaaaaaga agacgttcca accacgtctt caaagcaagt ggattgatgt gatgatccta    7080
tgcgtatggt atgacgtgtg ttcaagatga tgacttcaaa cctacctatg acgtatggta    7140
tgacgtgtgt cgactgatga cttagatcca ctcgagcggc tataaatacg tacctacgca    7200
ccctgcgcta ccatccctag agctgcagct tattttttaca acaattacca acaacaacaa    7260
acaacaaaca acattacaat tactatttac aattacagtc gacccatcaa caagtttgta    7320
caaaaaagct gaacgagaaa cgtaaaatga tataaatatc aatatattaa attagatttt    7380
gcataaaaaa cagactacat aatactgtaa aacacaacat atccagtcat attggcggcc    7440
gcattaggca ccccaggctt tacactttat gcttccggct cgtataatgt gtggattttg    7500
agttaggatc cgtcgagatt ttcaggagct aaggaagcta aaatggagaa aaaaatcact    7560
ggatatacca ccgttgatat atcccaatgg catcgtaaag aacattttga ggcatttcag    7620
tcagttgctc aatgtaccta taaccagacc gttcagctgg atattacggc cttttaaag    7680 accgtaaaga aaaataagca caagttttat ccggccttta ttcacattct tgcccgcctg    7740
atgaatgctc atccggaatt ccgtatggca atgaaagacg gtgagctggt gatatgggat    7800
agtgttcacc cttgttacac cgttttccat gagcaaactg aaacgttttc atcgctctgg    7860
agtgaatacc acgacgattt ccggcagttt ctacacatat attcgcaaga tgtggcgtgt    7920
tacggtgaaa acctggccta tttccctaaa gggtttattg agaatatgtt tttcgtctca    7980
gccaatccct gggtgagttt caccagtttt gatttaaacg tggccaatat ggacaacttc    8040 ttcgccccg ttttcaccat gggcaaatat tatacgcaag cgacaaggt gctgatgccg      8100 ctggcgattc aggttcatca tgccgtttgt gatggcttcc atgtcggcag aatgcttaat    8160
gaattacaac agtactgcga tgagtggcag ggcggggcgt aaagatctgg atccggctta    8220
ctaaaagcca gataacagta tgcgtatttg cgcgctgatt tttgcggtat aagaatatat    8280
actgatatgt atacccgaag tatgtcaaaa agaggtatgc tatgaagcag cgtattacag    8340
tgacagttga cagcgacagc tatcagttgc tcaaggcata tatgatgtca atatctccgg    8400
tctggtaagc acaaccatgc agaatgaagc ccgtcgtctg cgtgccgaac gctggaaagc    8460
```

```
ggaaaatcag gaagggatgg ctgaggtcgc ccggtttatt gaaatgaacg gctctttttgc    8520 tgacgagaac aggggctggt gaaatgcagt ttaaggttta cacctataaa agagagagcc    8580
gttatcgtct gtttgtggat gtacagagtg atattattga cacgcccggg cgacggatgg    8640
tgatccccct ggccagtgca cgtctgctgt cagataaagt ctcccgtgaa ctttacccgg    8700
tggtgcatat cggggatgaa agctggcgca tgatgaccac cgatatggcc agtgtgccgg    8760
tctccgttat cggggaagaa gtggctgatc tcagccaccg cgaaaatgac atcaaaaacg    8820
ccattaacct gatgttctgg ggaatataaa tgtcaggctc ccttatacac agccagtctg    8880
caggtcgacc atagtgactg gatatgttgt gttttacagt attatgtagt ctgttttttta   8940 tgcaaaatct aatttaatat attgatattt atatcatttt acgtttctcg ttcagctttc    9000
ttgtacaaag tggttgataa cctagacttg tccatcttct ggattggcca acttaattaa    9060
tgtatgaaat aaaaggatgc acacatagtg acatgctaat cactataatg tgggcatcaa    9120
agttgtgtgt tatgtgtaat ta    9142
```

<210> SEQ ID NO 6
<211> LENGTH: 49911
<212> TYPE: DNA
<213> ORGANISM: artificial sequence
<220> FEATURE:
<223> OTHER INFORMATION: destination vector for use with Gaspe-Flint derived maize lines

<400> SEQUENCE: 6

```
gtgcagcgtg acccggtcgt gcccctctct agagataatg agcattgcat gtctaagtta      60
taaaaaatta ccacatattt tttttgtcac acttgtttga agtgcagttt atctatcttt     120
atacatatat ttaaacttta ctctacgaat aatataatct atagtactac aataatatca     180
gtgttttaga gaatcatata aatgaacagt tagacatggt ctaaaggaca attgagtatt     240
ttgacaacag gactctacag ttttatcttt ttagtgtgca tgtgttctcc tttttttttg     300
caaatagctt cacctatata atacttcatc cattttatta gtacatccat ttagggttta     360
gggttaatgg ttttttataga ctaattttttt tagtacatct atttttattct attttagcct   420 ctaaattaag aaaactaaaa ctctatttta gtttttttat ttaataattt agatataaaa     480
tagaataaaa taaagtgact aaaaattaaa caaataccct ttaagaaatt aaaaaaacta    540
aggaaacatt tttcttgttt cgagtagata atgccagcct gttaaacgcc gtcgacgagt    600
ctaacggaca ccaaccagcg aaccagcagc gtcgcgtcgg gccaagcgaa gcagacggca    660
cggcatctct gtcgctgcct ctggacccct ctcgagagtt ccgctccacc gttggacttg    720
ctccgctgtc ggcatccaga aattgcgtgg cggagcggca gacgtgagcc ggcacggcag    780
gcggcctcct cctcctctca cggcacggca gctacggggg attcctttcc caccgctcct    840
tcgctttccc ttcctcgccc gccgtaataa atagacaccc cctccacacc ctctttcccc    900
aacctcgtgt tgttcggagc gcacacacac acaaccagat ctcccccaaa tccacccgtc    960
ggcacctccg cttcaaggta cgccgctcgt cctcccccccc ccccctctc taccttctct    1020 agatcggcgt tccggtccat ggttagggcc cggtagttct acttctgttc atgtttgtgt    1080
tagatccgtg tttgtgttag atccgtgctg ctagcgttcg tacacggatg cgacctgtac    1140
gtcagacacg ttctgattgc taacttgcca gtgtttctct ttggggaatc ctgggatggc    1200
tctagccgtt ccgcagacgg gatcgatttc atgattttttt ttgtttcgtt gcatagggtt    1260
tggtttgccc ttttcctttta tttcaatata tgccgtgcac ttgtttgtcg ggtcatcttt    1320
```

```
tcatgcttttt ttttgtcttg gttgtgatga tgtggtctgg ttgggcggtc gttctagatc    1380
ggagtagaat tctgtttcaa actacctggt ggatttatta attttggatc tgtatgtgtg    1440
tgccatacat attcatagtt acgaattgaa gatgatggat ggaaatatcg atctaggata    1500
ggtatacatg ttgatgcggg ttttactgat gcatatacag agatgctttt tgttcgcttg    1560
gttgtgatga tgtggtgtgg ttgggcggtc gttcattcgt tctagatcgg agtagaatac    1620
tgtttcaaac tacctggtgt atttattaat tttggaactg tatgtgtgtg tcatacatct    1680
tcatagttac gagtttaaga tggatggaaa tatcgatcta ggataggtat acatgttgat    1740
gtgggtttta ctgatgcata tacatgatgg catatgcagc atctattcat atgctctaac    1800
cttgagtacc tatctattat aataaacaag tatgttttat aattattttg atcttgatat    1860
acttggatga tggcatatgc agcagctata tgtggatttt tttagccctg ccttcatacg    1920
ctatttattt gcttggtact gtttcttttg tcgatgctca ccctgttgtt tggtgttact    1980
tctgcaggtc gactctagag gatccacaag tttgtacaaa aaagctgaac gagaaacgta    2040
aaatgatata aatatcaata tattaaatta gattttgcat aaaaaacaga ctacataata    2100
ctgtaaaaca caacatatcc agtcactatg gcggccgcat taggcacccc aggctttaca    2160
ctttatgctt ccggctcgta taatgtgtgg attttgagtt aggatttaaa tacgcgttga    2220
tccggcttac taaaagccag ataacagtat gcgtatttgc gcgctgattt ttgcggtata    2280
agaatatata ctgatatgta tacccgaagt atgtcaaaaa gaggtatgct atgaagcagc    2340
gtattacagt gacagttgac agcgacagct atcagttgct caaggcatat atgatgtcaa    2400
tatctccggt ctggtaagca caaccatgca gaatgaagcc cgtcgtctgc gtgccgaacg    2460
ctggaaagcg gaaaatcagg aagggatggc tgaggtcgcc cggtttattg aaatgaacgg    2520
ctcttttgct gacgagaaca ggggctggtg aaatgcagtt taaggtttac acctataaaa    2580
gagagagccg ttatcgtctg tttgtggatg tacagagtga tatcattgac acgcccggtc    2640
gacggatggt gatcccccctg gccagtgcac gtctgctgtc agataaagtc tcccgtgaac    2700
tttacccggt ggtgcatatc ggggatgaaa gctggcgcat gatgaccacc gatatggcca    2760
gtgtgccggt ctccgttatc ggggaagaag tggctgatct cagccaccgc gaaaatgaca    2820
tcaaaaacgc cattaacctg atgttctggg aatataaat gtcaggctcc cttatacaca    2880
gccagtctgc aggtcgacca tagtgactgg atatgttgtg ttttacagta ttatgtagtc    2940
tgttttttat gcaaaatcta atttaatata ttgatattta tatcattttta cgtttctcgt    3000 tcagctttct tgtacaaagt ggtgttaacc tagacttgtc catcttctgg attggccaac    3060
ttaattaatg tatgaaataa aaggatgcac acatagtgac atgctaatca ctataatgtg    3120
ggcatcaaag ttgtgtgtta tgtgtaatta ctagttatct gaataaaaga gaaagagatc    3180
atccatattt cttatcctaa atgaatgtca cgtgtcttta taattctttg atgaaccaga    3240
tgcatttcat taaccaaatc catatacata taaatattaa tcatatataa ttaatatcaa    3300
ttgggttagc aaaacaaatc tagtctaggt gtgttttgcg aattgcggcc gccaccgcgg    3360
tggagctcga attccggtcc gggtcacctt tgtccaccaa gatggaactg cggccgctca    3420
ttaattaagt caggcgcgcc tctagttgaa gacacgttca tgtcttcatc gtaagaagac    3480
actcagtagt cttcggccag aatggccatc tggattcagc aggcctagaa ggccatttaa    3540
atcctgagga tctggtcttc ctaaggaccc gggatatcgg accgattaaa ctttaattcg    3600
gtccgaagct tgcatgcctg cagtgcagcg tgacccggtc gtgcccctct ctagagataa    3660
tgagcattgc atgtctaagt tataaaaaat taccacatat ttttttttgtc acacttgttt    3720
```

| | |
|---|---|
| gaagtgcagt ttatctatct ttatacatat atttaaactt tactctacga ataatataat | 3780 |
| ctatagtact acaataatat cagtgtttta gagaatcata taaatgaaca gttagacatg | 3840 |
| gtctaaagga caattgagta ttttgacaac aggactctac agttttatct ttttagtgtg | 3900 |
| catgtgttct ccttttttt tgcaaatagc ttcacctata taatacttca tccattttat | 3960 |
| tagtacatcc atttagggtt tagggttaat ggttttttata gactaatttt tttagtacat | 4020 |
| ctattttatt ctattttagc ctctaaatta agaaaactaa aactctatttt tagttttttt | 4080 |
| atttaataat ttagatataa aatagaataa aataaagtga ctaaaaatta aacaaatacc | 4140 |
| ctttaagaaa ttaaaaaaac taaggaaaca ttttttcttgt ttcgagtaga taatgccagc | 4200 |
| ctgttaaacg ccgtcgacga gtctaacgga caccaaccag cgaaccagca gcgtcgcgtc | 4260 |
| gggccaagcg aagcagacgg cacggcatct ctgtcgctgc ctctggaccc ctctcgagag | 4320 |
| ttccgctcca ccgttggact tgctccgctg tcggcatcca gaaattgcgt ggcggagcgg | 4380 |
| cagacgtgag ccggcacggc aggcggcctc ctcctcctct cacggcaccg gcagctacgg | 4440 |
| gggattcctt tcccaccgct ccttcgcttt cccttcctcg cccgccgtaa taaatagaca | 4500 |
| cccctccac accctctttc cccaacctcg tgttgttcgg agcgcacaca cacacaacca | 4560 |
| gatctccccc aaatccaccc gtcggcacct ccgcttcaag gtacgccgct cgtcctcccc | 4620 |
| cccccccctc tctaccttct ctagatcggc gttccggtcc atgcatggtt agggcccggt | 4680 |
| agttctactt ctgttcatgt ttgtgttaga tccgtgtttg tgttagatcc gtgctgctag | 4740 |
| cgttcgtaca cggatgcgac ctgtacgtca gacacgttct gattgctaac ttgccagtgt | 4800 |
| ttctctttgg ggaatcctgg gatggctcta gccgttccgc agacgggatc gatttcatga | 4860 |
| ttttttttgt ttcgttgcat agggtttggt ttgccctttt cctttatttc aatatatgcc | 4920 |
| gtgcacttgt ttgtcgggtc atcttttcat gcttttttt gtcttggttg tgatgatgtg | 4980 |
| gtctggttgg gcggtcgttc tagatcggag tagaattctg tttcaaacta cctggtggat | 5040 |
| ttattaattt tggatctgta tgtgtgtgcc atacatattc atagttacga attgaagatg | 5100 |
| atggatggaa atatcgatct aggataggta tacatgttga tgcgggtttt actgatgcat | 5160 |
| atacagagat gcttttttgtt cgcttggttg tgatgatgtg gtgtggttgg gcggtcgttc | 5220 |
| attcgttcta gatcggagta gaatactgtt tcaaactacc tggtgtattt attaattttg | 5280 |
| gaactgtatg tgtgtgtcat acatcttcat agttacgagt ttaagatgga tggaaatatc | 5340 |
| gatctaggat aggtatacat gttgatgtgg gttttactga tgcatataca tgatggcata | 5400 |
| tgcagcatct attcatatgc tctaaccttg agtacctatc tattataata aacaagtatg | 5460 |
| tttataatt attttgatct tgatatactt ggatgatggc atatgcagca gctatatgtg | 5520 |
| gattttttta gccctgcctt catacgctat ttatttgctt ggtactgttt cttttgtcga | 5580 |
| tgctcaccct gttgtttggt gttacttctg caggtcgact ttaacttagc ctaggatcca | 5640 |
| cacgacacca tgtcccccga gcgccgcccc gtcgagatcc gccggccac cgccgccgac | 5700 |
| atggccgccg tgtgcgacat cgtgaaccac tacatcgaga cctccaccgt gaacttccgc | 5760 |
| accgagccgc agaccccgca ggagtggatc gacgacctgg agcgcctcca ggaccgctac | 5820 |
| ccgtggctcg tggccgaggt ggagggcgtg gtggccggca tcgcctacgc cggccgtgg | 5880 |
| aaggcccgca acgcctacga ctggaccgtg gagtccaccg tgtacgtgtc ccaccgccac | 5940 |
| cagcgcctcg gcctcggctc caccctctac acccacctcc tcaagagcat ggaggcccag | 6000 |
| ggcttcaagt ccgtggtggc cgtgatcggc ctcccgaacg acccgtccgt gcgcctccac | 6060 |

```
gaggccctcg gctacaccgc ccgcggcacc ctccgcgccg ccggctacaa gcacggcggc    6120
tggcacgacg tcggcttctg gcagcgcgac ttcgagctgc cggccccgcc gcgcccggtg    6180
cgcccggtga cgcagatctg agtcgaaacc tagacttgtc catcttctgg attggccaac    6240
ttaattaatg tatgaaataa aaggatgcac acatagtgac atgctaatca ctataatgtg    6300
ggcatcaaag ttgtgtgtta tgtgtaatta ctagttatct gaataaaaga gaaagagatc    6360
atccatattt cttatcctaa atgaatgtca cgtgtcttta taattctttg atgaaccaga    6420
tgcatttcat taaccaaatc catatacata taaatattaa tcatatataa ttaatatcaa    6480
ttgggttagc aaaacaaatc tagtctaggt gtgttttgcg aattgcggcc gccaccgcgg    6540
tggagctcga attcattccg attaatcgtg gcctcttgct cttcaggatg aagagctatg    6600
tttaaacgtg caagcgctac tagacaattc agtacattaa aaacgtccgc aatgtgttat    6660
taagttgtct aagcgtcaat ttggtttaca ccacaatata tcctgccacc agccagccaa    6720 cagctcccg accggcagct cggcacaaaa tcaccactcg atacaggcag cccatcagtc      6780
cgggacggcg tcagcgggag agccgttgta aggcggcaga cttt gctcat gttaccgatg    6840 ctattcggaa gaacggcaac taagctgccg ggtttgaaac acggatgatc tcgcggaggg    6900
tagcatgttg attgtaacga tgacagagcg ttgctgcctg tgatcaaata tcatctccct    6960
cgcagagatc cgaattatca gccttcttat tcatttctcg cttaaccgtg acaggctgtc    7020
gatcttgaga actatgccga cataatagga aatcgctgga taaagccgct gaggaagctg    7080
agtggcgcta tttctttaga agtgaacgtt gacgatcgtc gaccgtaccc cgatgaatta    7140
attcggacgt acgttctgaa cacagctgga tacttacttg ggcgattgtc atacatgaca    7200
tcaacaatgt acccgtttgt gtaaccgtct cttggaggtt cgtatgacac tagtggttcc    7260
cctcagcttg cgactagatg ttgaggccta acattttatt agagagcagg ctagttgctt    7320
agatacatga tcttcaggcc gttatctgtc agggcaagcg aaaattggcc atttatgacg    7380
accaatgccc cgcagaagct cccatctttg ccgccataga cgccgcgccc ccttttgggg    7440
gtgtagaaca tccttttgcc agatgtggaa aagaagttcg ttgtcccatt gttggcaatg    7500
acgtagtagc cggcgaaagt gcgagaccca tttgcgctat atataagcct acgatttccg    7560
ttgcgactat tgtcgtaatt ggatgaacta ttatcgtagt tgctctcaga gttgtcgtaa    7620
tttgatggac tattgtcgta attgcttatg gagttgtcgt agttgcttgg agaaatgtcg    7680
tagttggatg gggagtagtc atagggaaga cgagcttcat ccactaaaac aattggcagg    7740
tcagcaagtg cctgccccga tgccatcgca agtacgaggc ttagaaccac cttcaacaga    7800
tcgcgcatag tcttccccag ctctctaacg cttgagttaa gccgcgccgc gaagcggcgt    7860
cggcttgaac gaattgttag acattatttg ccgactacct tggtgatctc gcctttcacg    7920
tagtgaacaa attcttccaa ctgatctgcg cgcgaggcca agcgatcttc ttgtccaaga    7980
taagcctgcc tagcttcaag tatgacgggc tgatactggg ccggcaggcg ctccattgcc    8040
cagtcggcag cgacatcctt cggcgcgatt ttgccggtta ctgcgctgta ccaaatgcgg    8100
gacaacgtaa gcactacatt tcgctcatcg ccagcccagt cgggcggcga gttccatagc    8160
gttaaggttt catttagcgc ctcaaataga tcctgttcag gaaccggatc aaagagttcc    8220
tccgccgctg gacctaccaa ggcaacgcta tgttctcttg cttttgtcag caagatagcc    8280
agatcaatgt cgatcgtggc tggctcgaag atacctgcaa gaatgtcatt gcgctgccat    8340
tctccaaatt gcagttcgcg cttagctgga taacgccacg gaatgatgtc gtcgtgcaca    8400
acaatggtga cttctacagc gcggagaatc tcgctctctc caggggaagc cgaagtttcc    8460
```

-continued

```
aaaaggtcgt tgatcaaagc tcgccgcgtt gtttcatcaa gccttacagt caccgtaacc    8520
agcaaatcaa tatcactgtg tggcttcagg ccgccatcca ctgcggagcc gtacaaatgt    8580
acggccagca acgtcggttc gagatggcgc tcgatgacgc caactacctc tgatagttga    8640
gtcgatactt cggcgatcac cgcttccctc atgatgttta actcctgaat taagccgcgc    8700
cgcgaagcgg tgtcggcttg aatgaattgt taggcgtcat cctgtgctcc cgagaaccag    8760
taccagtaca tcgctgtttc gttcgagact tgaggtctag ttttatacgt gaacaggtca    8820
atgccgccga gagtaaagcc acattttgcg tacaaattgc aggcaggtac attgttcgtt    8880
tgtgtctcta atcgtatgcc aaggagctgt ctgcttagtg cccactttt cgcaaattcg     8940
atgagactgt gcgcgactcc tttgcctcgg tgcgtgtgcg acacaacaat gtgttcgata    9000
gaggctagat cgttccatgt tgagttgagt tcaatcttcc cgacaagctc ttggtcgatg    9060
aatgcgccat agcaagcaga gtcttcatca gagtcatcat ccgagatgta atccttccgg    9120
taggggctca cacttctggt agatagttca aagccttggt cggataggtg cacatcgaac    9180
acttcacgaa caatgaaatg gttctcagca tccaatgttt ccgccacctg ctcagggatc    9240
accgaaatct tcatatgacg cctaacgcct ggcacagcgg atcgcaaacc tggcgcggct    9300
tttggcacaa aaggcgtgac aggtttgcga atccgttgct gccacttgtt aaccctttg     9360
ccagatttgg taactataat ttatgttaga ggcgaagtct tgggtaaaaa ctggcctaaa    9420
attgctgggg atttcaggaa agtaaacatc accttccggc tcgatgtcta ttgtagatat    9480
atgtagtgta tctacttgat cgggggatct gctgcctcgc gcgtttcggt gatgacggtg    9540
aaaacctctg acacatgcag ctcccggaga cggtcacagc ttgtctgtaa gcggatgccg    9600
ggagcagaca agcccgtcag ggcgcgtcag cgggtgttgg cgggtgtcgg ggcgcagcca    9660
tgacccagtc acgtagcgat agcggagtgt atactggctt aactatgcgg catcagagca    9720
gattgtactg agagtgcacc atatgcggtg tgaaataccg cacagatgcg taaggagaaa    9780
ataccgcatc aggcgctctt ccgcttcctc gctcactgac tcgctgcgct cggtcgttcg    9840
gctgcggcga gcggtatcag ctcactcaaa ggcggtaata cggttatcca cagaatcagg    9900
ggataacgca ggaaagaaca tgtgagcaaa aggccagcaa aaggccagga accgtaaaaa    9960
ggccgcgttg ctggcgtttt tccataggct ccgcccccct gacgagcatc acaaaaatcg   10020
acgctcaagt cagaggtggc gaaacccgac aggactataa agataccagg cgtttccccc   10080
tggaagctcc ctcgtgcgct ctcctgttcc gaccctgccg cttaccggat acctgtccgc   10140
ctttctccct tcgggaagcg tggcgctttc tcatagctca cgctgtaggt atctcagttc   10200
ggtgtaggtc gttcgctcca agctgggctg tgtgcacgaa ccccccgttc agcccgaccg   10260
ctgcgcctta tccggtaact atcgtcttga gtccaacccg gtaagacacg acttatcgcc   10320
actggcagca gccactggta acaggattag cagagcgagg tatgtaggcg gtgctacaga   10380
gttcttgaag tggtggccta actacggcta cactagaagg acagtatttg gtatctgcgc   10440
tctgctgaag ccagttacct tcggaaaaag agttggtagc tcttgatccg gcaaacaaac   10500
caccgctggt agcggtggtt tttttgtttg caagcagcag attacgcgca gaaaaaaagg   10560
atctcaagaa gatcctttga tcttttctac ggggtctgac gctcagtgga acgaaaactc   10620
acgttaaggg attttggtca tgagattatc aaaaaggatc ttcacctaga tccttttaaa   10680
ttaaaaatga agttttaaat caatctaaag tatatatgag taaacttggt ctgacagtta   10740
ccaatgctta atcagtgagg cacctatctc agcgatctgt ctatttcgtt catccatagt   10800
```

```
tgcctgactc cccgtcgtgt agataactac gatacgggag ggcttaccat ctggccccag   10860
tgctgcaatg ataccgcgag acccacgctc accggctcca gatttatcag caataaacca   10920
gccagccgga agggccgagc gcagaagtgg tcctgcaact ttatccgcct ccatccagtc   10980
tattaattgt tgccgggaag ctagagtaag tagttcgcca gttaatagtt tgcgcaacgt   11040
tgttgccatt gctgcagggg ggggggggg ggggacttc cattgttcat tccacggaca    11100
aaaacagaga aaggaaacga cagaggccaa aaagcctcgc tttcagcacc tgtcgtttcc   11160
tttcttttca gagggtattt taaataaaaa cattaagtta tgacgaagaa gaacggaaac   11220
gccttaaacc ggaaaatttt cataaatagc gaaaacccgc gaggtcgccg ccccgtaacc   11280
tacctgtcgg atcaccggaa aggacccgta aagtgataat gattatcatc tacatatcac   11340
aacgtgcgtg gaggccatca aaccacgtca aataatcaat tatgacgcag gtatcgtatt   11400
aattgatctg catcaactta acgtaaaaac aacttcagac aatacaaatc agcgacactg   11460 aatacgggc aacctcatgt ccccccccc cccccctg caggcatcgt ggtgtcacgc      11520
tcgtcgtttg gtatggcttc attcagctcc ggttcccaac gatcaaggcg agttacatga   11580
tcccccatgt tgtgcaaaaa agcggttagc tccttcggtc ctccgatcgt tgtcagaagt   11640
aagttggccg cagtgttatc actcatggtt atggcagcac tgcataattc tcttactgtc   11700
atgccatccg taagatgctt ttctgtgact ggtgagtact caaccaagtc attctgagaa   11760
tagtgtatgc ggcgaccgag ttgctcttgc ccggcgtcaa cacgggataa taccgcgcca   11820
catagcagaa ctttaaaagt gctcatcatt ggaaaacgtt cttcggggcg aaaactctca   11880
aggatcttac cgctgttgag atccagttcg atgtaaccca ctcgtgcacc caactgatct   11940
tcagcatctt ttactttcac cagcgtttct gggtgagcaa aaacaggaag gcaaaatgcc   12000
gcaaaaaagg gaataagggc gacacggaaa tgttgaatac tcatactctt cctttttcaa   12060
tattattgaa gcatttatca gggttattgt ctcatgagcg gatacatatt tgaatgtatt   12120
tagaaaaata aacaaatagg ggttccgcgc acatttcccc gaaaagtgcc acctgacgtc   12180
taagaaacca ttattatcat gacattaacc tataaaaata ggcgtatcac gaggcccttt   12240
cgtcttcaag aattcggagc ttttgccatt ctcaccggat tcagtcgtca ctcatggtga   12300
tttctcactt gataaccttta tttttgacga ggggaaatta ataggttgta ttgatgttgg   12360
acgagtcgga atcgcagacc gataccagga tcttgccatc ctatggaact gcctcggtga   12420
gttttctcct tcattacaga aacggctttt tcaaaaatat ggtattgata atcctgatat   12480
gaataaattg cagtttcatt tgatgctcga tgagttttc taatcagaat tggttaattg    12540
gttgtaacac tggcagagca ttacgctgac ttgacgggac ggcggctttg ttgaataaat   12600
cgaacttttg ctgagttgaa ggatcagatc acgcatcttc ccgacaacgc agaccgttcc   12660
gtggcaaagc aaaagttcaa aatcaccaac tggtccacct acaacaaagc tctcatcaac   12720
cgtggctccc tcactttctg gctggatgat ggggcgattc aggcctggta tgagtcagca   12780
acaccttctt cacgaggcag acctcagcgc cagaaggccg ccagagaggc cgagcgcggc   12840
cgtgaggctt ggacgctagg gcagggcatg aaaaagcccg tagcgggctg ctacgggcgt   12900 ctgacgcgt ggaagggg agggatgtt gtctacatgg ctctgctgta gtgagtgggt       12960
tgcgctccgg cagcggtcct gatcaatcgt caccctttct cggtccttca acgttcctga   13020
caacgagcct cctttcgcc aatccatcga caatcaccgc gagtccctgc tcgaacgctg    13080
cgtccggacc ggcttcgtcg aaggcgtcta tcgcggcccg caacagcggc gagagcgag    13140 cctgttcaac ggtgccgccg cgctcgccgg catcgctgtc gccggcctgc tcctcaagca   13200
```

```
cggccccaac agtgaagtag ctgattgtca tcagcgcatt gacgcgtcc ccggccgaaa    13260 aacccgcctc gcagaggaag cgaagctgcg cgtcggccgt ttccatctgc ggtgcgcccg    13320
gtcgcgtgcc ggcatggatg cgcgcgccat cgcggtaggc gagcagcgcc tgcctgaagc    13380
tgcgggcatt cccgatcaga aatgagcgcc agtcgtcgtc ggctctcggc accgaatgcg    13440
tatgattctc cgccagcatg gcttcggcca gtgcgtcgag cagcgcccgc ttgttcctga    13500
agtgccagta aagcgccggc tgctgaaccc ccaaccgttc cgccagtttg cgtgtcgtca    13560
gaccgtctac gccgacctcg ttcaacaggt ccagggcggc acggatcact gtattcggct    13620
gcaactttgt catgcttgac actttatcac tgataaacat aatatgtcca ccaacttatc    13680
agtgataaag aatccgcgcg ttcaatcgga ccagcggagg ctggtccgga ggccagacgt    13740
gaaacccaac atacccctga tcgtaattct gagcactgtc gcgctcgacg ctgtcggcat    13800
cggcctgatt atgccggtgc tgccgggcct cctgcgcgat ctggttcact cgaacgacgt    13860
caccgcccac tatggcattc tgctggcgct gtatgcgttg gtgcaatttg cctgcgcacc    13920
tgtgctgggc gcgctgtcgg atcgtttcgg gcggcggcca atcttgctcg tctcgctggc    13980
cggcgccact gtcgactacg ccatcatggc gacagcgcct ttcctttggg ttctctatat    14040
cgggcggatc gtggccggca tcaccggggc gactggggcg gtagccggcg cttatattgc    14100
cgatatcact gatggcgatg agcgcgcgcg gcacttcggc ttcatgagcg cctgtttcgg    14160
gttcgggatg gtcgcgggac ctgtgctcgg tgggctgatg ggcggtttct cccccacgc    14220 tccgttcttc gccgcggcag ccttgaacgg cctcaatttc ctgacgggct gtttccttttt  14280 gccggagtcg cacaaaggcg aacgccggcc gttacgccgg gaggctctca acccgctcgc    14340
ttcgttccgg tgggcccggg gcatgaccgt cgtcgccgcc ctgatggcgg tcttcttcat    14400
catgcaactt gtcggacagg tgccggccgc gctttgggtc attttcggcg aggatcgctt    14460
tcactgggac gcgaccacga tcggcatttc gcttgccgca tttggcattc tgcattcact    14520
cgcccaggca atgatcaccg gccctgtagc cgcccggctc ggcgaaaggc gggcactcat    14580
gctcggaatg attgccgacg gcacaggcta catcctgctt gccttcgcga cacggggatg    14640
gatggcgttc ccgatcatgg tcctgcttgc ttcgggtggc atcggaatgc cggcgctgca    14700
agcaatgttg tccaggcagg tggatgagga acgtcagggg cagctgcaag gctcactggc    14760
ggcgctcacc agcctgacct cgatcgtcgg acccctcctc ttcacggcga tctatgcggc    14820
ttctataaca acgtggaacg ggtgggcatg gattgcaggc gctgccctct acttgctctg    14880
cctgccggcg ctgcgtcgcg ggcttttggag cggcgcaggg caacgagccg atcgctgatc    14940
gtggaaacga taggcctatg ccatgcgggt caaggcgact tccggcaagc tatacgcgcc    15000
ctaggagtgc ggttggaacg ttggcccagc cagatactcc cgatcacgag caggacgccg    15060
atgatttgaa gcgcactcag cgtctgatcc aagaacaacc atcctagcaa cacggcggtc    15120
cccgggctga gaaagcccag taaggaaaca actgtaggtt cgagtcgcga gatccccgg    15180 aaccaaagga agtaggttaa acccgctccg atcaggccga gccacgccag gccgagaaca    15240
ttggttcctg taggcatcgg gattggcgga tcaaacacta aagctactgg aacgagcaga    15300
agtcctccgg ccgccagttg ccaggcggta aaggtgagca gaggcacggg aggttgccac    15360
ttgcgggtca gcacggttcc gaacgccatg gaaaccgccc ccgcccaggcc cgctgcgacg    15420 ccgacaggat ctagcgctgc gtttggtgtc aacaccaaca gcgccacgcc cgcagttccg    15480
caaatagccc ccaggaccgc catcaatcgt atcgggctac ctagcagagc ggcagagatg    15540
```

```
aacacgacca tcagcggctg cacagcgcct accgtcgccg cgaccccgcc cggcaggcgg    15600
tagaccgaaa taaacaacaa gctccagaat agcgaaatat taagtgcgcc gaggatgaag    15660
atgcgcatcc accagattcc cgttggaatc tgtcggacga tcatcacgag caataaaccc    15720
gccggcaacg cccgcagcag cataccggcg acccctcggc ctcgctgttc gggctccacg    15780
aaaacgccgg acagatgcgc cttgtgagcg tccttgggc cgtcctcctg tttgaagacc    15840
gacagcccaa tgatctcgcc gtcgatgtag gcgccgaatg ccacggcatc tcgcaaccgt    15900
tcagcgaacg cctccatggg cttttttctcc tcgtgctcgt aaacggaccc gaacatctct    15960
ggagctttct tcagggccga caatcggatc tcgcggaaat cctgcacgtc ggccgctcca    16020
agccgtcgaa tctgagcctt aatcacaatt gtcaatttta atcctctgtt tatcggcagt    16080
tcgtagagcg cgccgtgcgt cccgagcgat actgagcgaa gcaagtgcgt cgagcagtgc    16140
ccgcttgttc ctgaaatgcc agtaaagcgc tggctgctga accccagcc ggaactgacc    16200 ccacaaggcc ctagcgtttg caatgccacca ggtcatcatt gacccaggcg tgttccacca    16260
ggccgctgcc tcgcaactct tcgcaggctt cgccgacctg ctcgcgccac ttcttcacgc    16320
gggtggaatc cgatccgcac atgaggcgga aggtttccag cttgagcggg tacggctccc    16380
ggtgcgagct gaaatagtcg aacatccgtc gggccgtcgg cgacagcttg cggtacttct    16440
cccatatgaa tttcgtgtag tggtcgccag caaacagcac gacgatttcc tcgtcgatca    16500
ggacctggca acgggacgtt ttcttgccac ggtccaggac gcggaagcgg tgcagcagcg    16560
acaccgattc caggtgccca acgcggtcgg acgtgaagcc catcgccgtc gcctgtaggc    16620
gcgacaggca ttcctcggcc ttcgtgtaat accggccatt gatcgaccag cccaggtcct    16680
ggcaaagctc gtagaacgtg aaggtgatcg gctcgccgat aggggtgcgc ttcgcgtact    16740
ccaacacctg ctgccacacc agttcgtcat cgtcggcccg cagctcgacg ccggtgtagg    16800
tgatcttcac gtccttgttg acgtggaaaa tgaccttgtt ttgcagcgcc tcgcgcggga    16860
ttttcttgtt gcgcgtggtg aacagggcag agcgggccgt gtcgtttggc atcgctcgca    16920
tcgtgtccgg ccacggcgca atatcgaaca aggaaagctg catttccttg atctgctgct    16980
tcgtgtgttt cagcaacgcg gcctgcttgg cctcgctgac ctgttttgcc aggtcctcgc    17040
cggcggtttt tcgcttcttg gtcgtcatag ttcctcgcgt gtcgatggtc atcgacttcg    17100
ccaaacctgc cgcctcctgt tcgagacgac gcgaacgctc cacggcggcc gatgcgcgg    17160 gcagggcagg gggagccagt tgcacgctgt cgcgctcgat cttggccgta gcttgctgga    17220
ccatcgagcc gacggactgg aaggtttcgc ggggcgcacg catgacggtg cggcttgcga    17280
tggtttcggc atcctcggcg gaaaacccg cgtcgatcag ttcttgcctg tatgccttcc    17340
ggtcaaacgt ccgattcatt caccctcctt gcgggattgc cccgactcac gccggggcaa    17400
tgtgccctta ttcctgatt gacccgcctg gtgccttggt gtccagataa tccaccttat    17460
cggcaatgaa gtcggtcccg tagaccgtct ggccgtcctt tcgtacttg gtattccgaa    17520 tcttgccctg cacgaatacc agcgaccct tgcccaaata cttgccgtgg gcctcggcct    17580
gagagccaaa acacttgatg cggaagaagt cggtgcgctc ctgcttgtcg ccggcatcgt    17640
tgcgccactc ttcattaacc gctatatcga aaattgcttg cggcttgtta gaattgccat    17700
gacgtacctc ggtgtcacgg gtaagattac cgataaactg gaactgatta tggctcatat    17760
cgaaagtctc cttgagaaag gagactctag tttagctaaa cattggttcc gctgtcaaga    17820
actttagcgg ctaaaatttt gcgggccgcg accaaaggtg cgaggggcgg cttccgctgt    17880
gtacaaccag atattttttca ccaacatcct tcgtctgctc gatgagcggg gcatgacgaa    17940
```

```
acatgagctg tcggagaggg cagggg tttc aatttcgttt ttatcagact taaccaacgg   18000
taaggccaac ccctcgttga aggtgatgga ggccattgcc gacgccctgg aaactcccct   18060
acctcttctc ctggagtcca ccgaccttga ccgcgaggca ctcgcggaga ttgcgggtca   18120
tcctttcaag agcagcgtgc cgcccggata cgaacgcatc agtgtggttt tgccgtcaca   18180
taaggcgttt atcgtaaaga aatggggcga cgacacccga aaaagctgc gtggaaggct    18240 ctgacgccaa gggttagggc ttgcacttcc ttctttagcc gctaaaacgg ccccttctct   18300
gcgggccgtc ggctcgcgca tcatatcgac atcctcaacg aagccgtgc cgcgaatggc    18360 atcgggcggg tgcgctttga cagttgtttt ctatcagaac ccctacgtcg tgcggttcga   18420
ttagctgttt gtcttgcagg ctaaacactt tcggtatatc gtttgcctgt gcgataatgt   18480
tgctaatgat ttgttgcgta ggggttactg aaaagtgagc gggaaagaag agtttcagac   18540
catcaaggag cgggccaagc gcaagctgga acgcgacatg ggtgcggacc tgttggccgc   18600
gctcaacgac ccgaaaaccg ttgaagtcat gctcaacgcg gacggcaagg tgtggcacga   18660
acgccttggc gagccgatgc ggtacatctg cgacatgcgg cccagccagt cgcaggcgat   18720
tatagaaacg gtgccggat tccacggcaa agaggtcacg cggcattcgc ccatcctgga    18780
aggcgagttc cccttggatg gcagccgctt tgccggccaa ttgccgccgg tcgtggccgc   18840
gccaaccttt gcgatccgca agcgcgcggt cgccatcttc acgctggaac agtacgtcga   18900
ggcgggcatc atgacccgcg agcaatacga ggtcattaaa agcgccgtcg cggcgcatcg   18960
aaacatcctc gtcattggcg gtactggctc gggcaagacc acgctcgtca acgcgatcat   19020
caatgaaatg gtcgccttca acccgtctga gcgcgtcgtc atcatcgagg acaccggcga   19080
aatccagtgc gccgcagaga acgccgtcca ataccacacc agcatcgacg tctcgatgac   19140
gctgctgctc aagacaacgc tgcgtatgcg ccccgaccgc atcctggtcg gtgaggtacg   19200 tggcccccgaa gcccttgatc tgttgatggc ctggaacacc gggcatgaag gaggtgccgc   19260
caccctgcac gcaaacaacc ccaaagcggg cctgagccgg ctcgccatgc ttatcagcat   19320
gcacccggat tcaccgaaac ccattgagcg gctgattggc gaggcggttc atgtggtcgt   19380
ccatatcgcc aggacccta gcggccgtcg agtgcaagaa attctcgaag ttcttggtta    19440
cgagaacggc cagtacatca ccaaaaccct gtaaggagta tttccaatga caacggctgt   19500
tccgttccgt ctgaccatga atcgcggcat tttgttctac cttgccgtgt tcttcgttct   19560
cgctctcgcg ttatccgcgc atccggcgat ggcctcggaa ggcaccggcg gcagcttgcc   19620
atatgagagc tggctgacga acctgcgcaa ctccgtaacc ggcccggtgg ccttcgcgct   19680
gtccatcatc ggcatcgtcg tcgccggcgg cgtgctgatc ttcggcggcg aactcaacgc   19740
cttcttccga accctgatct tcctggttct ggtgatggcg ctgctggtcg gcgcgcagaa   19800
cgtgatgagc accttcttcg gtcgtggtgc cgaaatcgcg gccctcggca acggggcgct   19860
gcaccaggtg caagtcgcgg cggcggatgc cgtgcgtgcg gtagcggctg gacggctcgc   19920
ctaatcatgg ctctgcgcac gatccccatc cgtcgcgcag gcaaccgaga aaacctgttc   19980
atgggtggtg atcgtgaact ggtgatgttc tcgggcctga tggcgtttgc gctgattttc   20040
agcgcccaag agctgcgggc caccgtggtc ggtctgatcc tgtggttcgg ggcgctctat   20100
gcgttccgaa tcatggcgaa ggccgatccg aagatgcggt tcgtgtacct gcgtcaccgc   20160
cggtacaagc cgtattaccc ggcccgctcg accccgttcc gcgagaacac caatagccaa   20220
gggaagcaat accgatgatc caagcaattg cgattgcaat cgcgggcctc ggcgcgcttc   20280
```

```
tgttgttcat cctctttgcc cgcatccgcg cggtcgatgc cgaactgaaa ctgaaaaagc    20340
atcgttccaa ggacgccggc ctggccgatc tgctcaacta cgccgctgtc gtcgatgacg    20400
gcgtaatcgt gggcaagaac ggcagcttta tggctgcctg gctgtacaag ggcgatgaca    20460
acgcaagcag caccgaccag cagcgcgaag tagtgtccgc ccgcatcaac caggccctcg    20520
cgggcctggg aagtgggtgg atgatccatg tggacgccgt gcggcgtcct gctccgaact    20580
acgcggagcg gggcctgtcg gcgttccctg accgtctgac ggcagcgatt gaagaagagc    20640
gctcggtctt gccttgctcg tcggtgatgt acttcaccag ctccgcgaag tcgctcttct    20700
tgatggagcg catggggacg tgcttggcaa tcacgcgcac ccccggccg ttttagcggc    20760
taaaaaagtc atggctctgc cctcgggcgg accacgccca tcatgacctt gccaagctcg    20820
tcctgcttct cttcgatctt cgccagcagg gcgaggatcg tggcatcacc gaaccgcgcc    20880
gtgcgcgggt cgtcggtgag ccagagtttc agcaggccgc ccaggcggcc caggtcgcca    20940
ttgatgcggg ccagctcgcg gacgtgctca tagtccacga cgcccgtgat tttgtagccc    21000
tggccgacgg ccagcaggta ggccgacagg ctcatgccgg ccgccgccgc cttttcctca    21060
atcgctcttc gttcgtctgg aaggcagtac accttgatag gtgggctgcc cttcctggtt    21120
ggcttggttt catcagccat ccgcttgccc tcatctgtta cgccggcggt agccggccag    21180
cctcgcagag caggattccc gttgagcacc gccaggtgcg aataagggac agtgaagaag    21240
gaacaccgc tcgcgggtgg gcctacttca cctatcctgc ccggctgacg ccgttggata    21300
caccaaggaa agtctacacg aacccttgg caaaatcctg tatatcgtgc gaaaaaggat    21360
ggatataccg aaaaaatcgc tataatgacc ccgaagcagg gttatgcagc ggaaaagcgc    21420
tgcttccctg ctgttttgtg gaatatctac cgactggaaa caggcaaatg caggaaatta    21480
ctgaactgag gggacaggcg agagacgatg ccaaagagct acaccgacga gctggccgag    21540
tgggttgaat cccgcgcggc caagaagcgc cggcgtgatg aggctgcggt tgcgttcctg    21600
gcggtgaggc cggatgtcga ggcggcgtta gcgtccggct atgcgctcgt caccatttgg    21660
gagcacatgc gggaaacggg gaaggtcaag ttctcctacg agacgttccg ctcgcacgcc    21720
aggcggcaca tcaaggccaa gcccgccgat gtgcccgcac cgcaggccaa ggctgcggaa    21780
cccgcgccgg cacccaagac gccggagcca cggcggccga agcaggggg caaggctgaa    21840
aagccggccc ccgctgcggc cccgaccggc ttcaccttca acccaacacc ggacaaaaag    21900
gatctactgt aatggcgaaa attcacatgg ttttgcaggg caagggcggg gtcggcaagt    21960
cggccatcgc cgcgatcatt gcgcagtaca agatggacaa ggggcagaca cccttgtgca    22020
tcgacaccga cccggtgaac gcgacgttcg agggctacaa ggccctgaac gtccgccggc    22080
tgaacatcat ggccggcgac gaaattaact cgcgcaactt cgacaccctg gtcgagctga    22140
ttgcgccgac caaggatgac gtggtgatcg acaacggtgc cagctcgttc gtgcctctgt    22200
cgcattacct catcagcaac caggtgccgg ctctgctgca agaaatgggg catgagctgg    22260
tcatccatac cgtcgtcacc ggcggccagg ctctcctgga cacggtgagc ggcttcgccc    22320
agctcgccag ccagttcccg gccgaagcgc ttttcgtggt ctggctgaac ccgtattggg    22380
ggcctatcga gcatgagggc aagagctttg agcagatgaa ggcgtacacg gccaacaagg    22440
cccgcgtgtc gtccatcatc cagattccgg ccctcaagga agaaacctac ggccgcgatt    22500
tcagcgacat gctgcaagag cggctgacgt tcgaccagc gctggccgat gaatcgctca    22560
cgatcatgac gcgcaacgc ctcaagatcg tgcggcgcgg cctgtttgaa cagctcgacg    22620
cggcggccgt gctatgagcg accagattga agagctgatc cgggagattg cggccaagca    22680
```

```
cggcatcgcc gtcggccgcg acgacccggt gctgatcctg cataccatca acgcccggct   22740
catggccgac agtgcggcca agcaagagga aatccttgcc gcgttcaagg aagagctgga   22800
agggatcgcc catcgttggg gcgaggacgc caaggccaaa gcggagcgga tgctgaacgc   22860
ggccctggcg gccagcaagg acgcaatggc gaaggtaatg aaggacagcg ccgcgcaggc   22920
ggccgaagcg atccgcaggg aaatcgacga cggccttggc cgccagctcg cggccaaggt   22980
cgcggacgcg cggcgcgtgg cgatgatgaa catgatcgcc ggcggcatgg tgttgttcgc   23040
ggccgccctg gtggtgtggg cctcgttatg aatcgcagag gcgcagatga aaaagcccgg   23100
cgttgccggg ctttgttttt gcgttagctg ggcttgtttg acaggcccaa gctctgactg   23160
cgcccgcgct cgcgctcctg ggcctgtttc ttctcctgct cctgcttgcg catcagggcc   23220
tggtgccgtc gggctgcttc acgcatcgaa tcccagtcgc cggccagctc gggatgctcc   23280
gcgcgcatct tgcgcgtcgc cagttcctcg atcttgggcg cgtgaatgcc catgccttcc   23340
ttgatttcgc gcaccatgtc cagccgcgtg tgcagggtct gcaagcgggc ttgctgttgg   23400
gcctgctgct gctgccaggc ggcctttgta cgcggcaggg acagcaagcc ggggggcattg   23460 gactgtagct gctgcaaacg cgcctgctga cggtctacga gctgttctag gcggtcctcg   23520
atgcgctcca cctggtcatg cttttgcctgc acgtagagcg caagggtctg ctggtaggtc   23580
tgctcgatgg gcgcggattc taagagggcc tgctgttccg tctcggcctc ctgggccgcc   23640
tgtagcaaat cctcgccgct gttgccgctg gactgcttta ctgccgggga ctgctgttgc   23700
cctgctcgcg ccgtcgtcgc agttcggctt gcccccactc gattgactgc ttcatttcga   23760
gccgcagcga tgcgatctcg gattgcgtca acggacgggg cagcgcggag gtgtccggct   23820
tctccttggg tgagtcggtc gatgccatag ccaaaggttt ccttccaaaa tgcgtccatt   23880
gctggaccgt gtttctcatt gatgcccgca agcatcttcg gcttgaccgc caggtcaagc   23940
gcgccttcat gggcggtcat gacggacgcc gccatgacct tgccgccgtt gttctcgatg   24000
tagccgcgta atgaggcaat ggtgccgccc atcgtcagcg tgtcatcgac aacgatgtac   24060
ttctggccgg ggatcacctc cccctcgaaa gtcgggttga acgccaggcg atgatctgaa   24120
ccggctccgg ttcgggcgac cttctcccgc tgcacaatgt ccgtttcgac ctcaaggcca   24180
aggcggtcgg ccagaacgac cgccatcatg gccggaatct tgttgttccc cgccgcctcg   24240
acggcgagga ctgaacgat gcggggcttg tcgtcgccga tcagcgtctt gagctgggca   24300
acagtgtcgt ccgaaatcag gcgctcgacc aaattaagcg ccgcttccgc gtcgccctgc   24360
ttcgcagcct ggtattcagg ctcgttggtc aaagaaccaa ggtcgccgtt gcgaaccacc   24420 tcgggaagt ctccccacgg tgcgcgctcg gctctgctgt agctgctcaa gacgcctccc   24480
tttttagccg ctaaaactct aacgagtgcg cccgcgactc aacttgacgc tttcggcact   24540
tacctgtgcc ttgccacttg cgtcataggt gatgcttttc gcactcccga tttcaggtac   24600
tttatcgaaa tctgaccggg cgtgcattac aaagttcttc cccacctgtt ggtaaatgct   24660
gccgctatct gcgtggacga tgctgccgtc gtggcgctgc gacttatcgg ccttttgggc   24720
catatagatg ttgtaaatgc caggtttcag ggccccggct ttatctacct tctggttcgt   24780
ccatgcgcct tggttctcgg tctggacaat tctttgccca ttcatgacca ggaggcggtg   24840
tttcattggg tgactcctga cggttgcctc tggtgttaaa cgtgtcctgg tcgcttgccg   24900
gctaaaaaaa agccgacctc ggcagttcga ggccggcttt ccctagagcc gggcgcgtca   24960
aggttgttcc atctattta gtgaactgcg ttcgatttat cagttacttt cctcccgctt   25020
```

| | |
|---|---|
| tgtgtttcct cccactcgtt tccgcgtcta gccgacccct caacatagcg gcctcttctt | 25080 |
| gggctgcctt tgcctcttgc cgcgcttcgt cacgctcggc ttgcaccgtc gtaaagcgct | 25140 |
| cggcctgcct ggccgcctct tgcgccgcca acttcctttg ctcctggtgg gcctcggcgt | 25200 |
| cggcctgcgc cttcgctttc accgctgcca actccgtgcg caaactctcc gcttcgcgcc | 25260 |
| tggtggcgtc gcgctcgccg cgaagcgcct gcatttcctg gttggccgcg tccagggtct | 25320 |
| tgcggctctc ttctttgaat gcgcgggcgt cctggtgagc gtagtccagc tcggcgcgca | 25380 |
| gctcctgcgc tcgacgctcc acctcgtcgg cccgctgcgt cgccagcgcg gcccgctgct | 25440 |
| cggctcctgc cagggcggtg cgtgcttcgg ccagggcttg ccgctggcgt gcggccagct | 25500 |
| cggccgcctc ggcggcctgc tgctctagca atgtaacgcg cgcctgggct tcttccagct | 25560 |
| cgcgggcctg cgcctcgaag gcgtcggcca gctccccgcg cacggcttcc aactcgttgc | 25620 |
| gctcacgatc ccagccggct tgcgctgcct gcaacgattc attggcaagg gcctgggcgg | 25680 |
| cttgccagag ggcggccacg gcctggttgc cggcctgctg caccgcgtcc ggcacctgga | 25740 |
| ctgccagcgg ggcggcctgc gccgtgcgct ggcgtcgcca ttcgcgcatg ccggcgctgg | 25800 |
| cgtcgttcat gttgacgcgg gcggccttac gcactgcatc cacggtcggg aagttctccc | 25860 |
| ggtcgccttg ctcgaacagc tcgtccgcag ccgcaaaaat gcggtcgcgc gtctctttgt | 25920 |
| tcagttccat gttggctccg gtaattggta agaataataa tactcttacc taccttatca | 25980 |
| gcgcaagagt ttagctgaac agttctcgac ttaacggcag gtttttagc ggctgaaggg | 26040 |
| caggcaaaaa aagccccgca cggtcggcgg gggcaaaggg tcagcgggaa ggggattagc | 26100 |
| gggcgtcggg cttcttcatg cgtcggggcc gcgcttcttg ggatggagca cgacgaagcg | 26160 |
| cgcacgcgca tcgtcctcgg ccctatcggc ccgcgtcgcg gtcaggaact tgtcgcgcgc | 26220 |
| taggtcctcc ctggtgggca ccaggggcat gaactcggcc tgctcgatgt aggtccactc | 26280 |
| catgaccgca tcgcagtcga ggccgcgttc cttcaccgtc tcttgcaggt cgcggtacgc | 26340 |
| ccgctcgttg agcggctggt aacgggccaa ttggtcgtaa atggctgtcg gccatgagcg | 26400 |
| gcctttcctg ttgagccagc agccgacgac gaagccggca atgcaggccc ctggcacaac | 26460 |
| caggccgacg ccggggggcag gggatggcag cagctcgcca accaggaacc ccgccgcgat | 26520 |
| gatgccgatg ccggtcaacc agcccttgaa actatccggc cccgaaacac ccctgcgcat | 26580 |
| tgcctggatg ctgcgccgga tagcttgcaa catcaggagc cgtttctttt gttcgtcagt | 26640 |
| catggtccgc cctcaccagt tgttcgtatc ggtgtcggac gaactgaaat cgcaagagct | 26700 |
| gccggtatcg gtccagccgc tgtccgtgtc gctgctgccg aagcacggcg aggggtccgc | 26760 |
| gaacgccgca gacggcgtat ccggccgcag cgcatcgccc agcatggccc cggtcagcga | 26820 |
| gccgccggcc aggtagccca gcatggtgct gttggtcgcc ccggccacca gggccgacgt | 26880 |
| gacgaaatcg ccgtcattcc ctctggattg ttcgctgctc ggcggggcag tgcgccgcgc | 26940 |
| cggcggcgtc gtggatggct cgggttggct ggcctgcgac ggccggcgaa aggtgcgcag | 27000 |
| cagctcgtta tcgaccggct gcggcgtcgg ggccgccgcc ttgcgctgcg gtcggtgttc | 27060 |
| cttcttcggc tcgcgcagct tgaacagcat gatcgcggaa accagcagca acgccgcgcc | 27120 |
| tacgcctccc gcgatgtaga acagcatcgg attcattctt cggtcctcct tgtagcggaa | 27180 |
| ccgttgtctg tgcggcgcgg gtggcccgcg ccgctgtctt tggggatcag ccctcgatga | 27240 |
| gcgcgaccag tttcacgtcg gcaaggttcg cctcgaactc ctggccgtcg tcctcgtact | 27300 |
| tcaaccaggc atagccttcc gccggcggcc gacggttgag gataaggcgg gcagggcgct | 27360 |
| cgtcgtgctc gacctggacg atggcctttt tcagcttgtc cgggtccggc tccttcgcgc | 27420 |

```
ccttttcctt ggcgtcctta ccgtcctggt cgccgtcctc gccgtcctgg ccgtcgccgg   27480
cctccgcgtc acgctcggca tcagtctggc cgttgaaggc atcgacggtg ttgggatcgc   27540
ggcccttctc gtccaggaac tcgcgcagca gcttgaccgt gccgcgcgtg atttcctggg   27600
tgtcgtcgtc aagccacgcc tcgacttcct ccgggcgctt cttgaaggcc gtcaccagct   27660
cgttcaccac ggtcacgtcg cgcacgcggc cggtgttgaa cgcatcggcg atcttctccg   27720
gcaggtccag cagcgtgacg tgctgggtga tgaacgccgg cgacttgccg atttccttgg   27780
cgatatcgcc tttcttcttg cccttcgcca gctcgcggcc aatgaagtcg gcaatttcgc   27840
gcggggtcag ctcgttgcgt tgcaggttct cgataacctg gtcggcttcg ttgtagtcgt   27900
tgtcgatgaa cgccgggatg gacttcttgc cggcccactt cgagccacgg tagcggcggg   27960
cgccgtgatt gatgatatag cggcccggct gctcctggtt ctcgcgcacc gaaatgggtg   28020
acttcacccc gcgctctttg atcgtggcac cgatttccgc gatgctctcc ggggaaaagc   28080
cggggttgtc ggccgtccgc ggctgatgcg gatcttcgtc gatcaggtcc aggtccagct   28140
cgatagggcc ggaaccgccc tgagacgccg caggagcgtc caggaggctc gacaggtcgc   28200
cgatgctatc caaccccagg ccggacggct gcgccgcgcc tgcggcttcc tgagcggccg   28260
cagcggtgtt tttcttggtg gtcttggctt gagccgcagt cattgggaaa tctccatctt   28320
cgtgaacacg taatcagcca gggcgcgaac ctctttcgat gccttgcgcg cggccgtttt   28380
cttgatcttc cagaccggca caccggatgc gagggcatcg gcgatgctgc tgcgcaggcc   28440
aacggtggcc ggaatcatca tcttggggta cgcggccagc agctcggctt ggtggcgcgc   28500
gtggcgcgga ttccgcgcat cgaccttgct gggcaccatg ccaaggaatt gcagcttggc   28560
gttcttctgg cgcacgttcg caatggtcgt gaccatcttc ttgatgccct ggatgctgta   28620
cgcctcaagc tcgatggggg acagcacata gtcgccgcg aagagggcgg ccgccaggcc   28680
gacgccaagg gtcggggccg tgtcgatcag gcacacgtcg aagccttggt tcgccagggc   28740
cttgatgttc gccccgaaca gctcgcgggc gtcgtccagc gacagccgtt cggcgttcgc   28800
cagtaccggg ttggactcga tgagggcgag gcgcgcggcc tggccgtcgc cggctgcggg   28860
tgcggtttcg gtccagccgc cggcaggac agcgccgaac agcttgcttg catgcaggcc   28920
ggtagcaaag tccttgagcg tgtaggacgc attgccctgg gggtccaggt cgatcacggc   28980
aacccgcaag ccgcgctcga aaagtcgaa ggcaagatgc acaagggtcg aagtcttgcc   29040
gacgccgcct ttctggttgg ccgtgaccaa agttttcatc gtttggtttc ctgttttttc   29100
ttggcgtccg cttcccactt ccggacgatg tacgcctgat gttccggcag aaccgccgtt   29160
acccgcgcgt acccctcggg caagttcttg tcctcgaacg cggcccacac gcgatgcacc   29220
gcttgcgaca ctgcgcccct ggtcagtccc agcgacgttg cgaacgtcgc ctgtggcttc   29280
ccatcgacta agacgccccg cgctatctcg atggtctgct gccccacttc cagcccctgg   29340
atcgcctcct ggaactggct ttcggtaagc cgtttcttca tggataacac ccataatttg   29400
ctccgcgcct tggttgaaca tagcggtgac agccgccagc acatgagaga agtttagcta   29460
aacatttctc gcacgtcaac acctttagcc gctaaaactc gtccttggcg taacaaaaca   29520
aaagcccgga aacgggcttt tcgtctcttg ccgcttatgg ctctgcaccc ggctccatca   29580
ccaacaggtc gcgcacgcgc ttcactcggt tgcggatcga cactgccagc ccaacaaagc   29640
cggttgccgc cgccgccagg atcgcgccga tgatgccggc cacaccggcc atcgcccacc   29700
aggtcgccgc cttccggttc cattcctgct ggtactgctt cgcaatgctg gacctcggct   29760
```

| | |
|---|---|
| caccataggc tgaccgctcg atggcgtatg ccgcttctcc ccttggcgta aaacccagcg | 29820 |
| ccgcaggcgg cattgccatg ctgcccgccg ctttcccgac cacgacgcgc gcaccaggct | 29880 |
| tgcggtccag accttcggcc acggcgagct gcgcaaggac ataatcagcc gccgacttgg | 29940 |
| ctccacgcgc ctcgatcagc tcttgcactc gcgcgaaatc cttggcctcc acggccgcca | 30000 |
| tgaatcgcgc acgcggcgaa ggctccgcag ggccggcgtc gtgatcgccg ccgagaatgc | 30060 |
| ccttcaccaa gttcgacgac acgaaaatca tgctgacggc tatcaccatc atgcagacgg | 30120 |
| atcgcacgaa cccgctgaat tgaacacgag cacggcaccc gcgaccacta tgccaagaat | 30180 |
| gcccaaggta aaaattgccg gccccgccat gaagtccgtg aatgcccga cggccgaagt | 30240 |
| gaagggcagg ccgccaccca ggccgccgcc ctcactgccc ggcacctggt cgctgaatgt | 30300 |
| cgatgccagc acctgcggca cgtcaatgct tccgggcgtc gcgctcgggc tgatcgccca | 30360 |
| tcccgttact gccccgatcc cggcaatggc aaggactgcc agcgctgcca tttttgggt | 30420 |
| gaggccgttc gcggccgagg ggcgcagccc ctgggggat gggaggcccg cgttagcggg | 30480 |
| ccgggagggt tcgagaaggg ggggcacccc ccttcggcgt gcgcggtcac gcgcacaggg | 30540 |
| cgcagccctg gttaaaaaca aggtttataa atattggttt aaaagcaggt taaaagacag | 30600 |
| gttagcggtg gccgaaaaac gggcggaaac ccttgcaaat gctggatttt ctgcctgtgg | 30660 |
| acagcccctc aaatgtcaat aggtgcgccc ctcatctgtc agcactctgc ccctcaagtg | 30720 |
| tcaaggatcg cgcccctcat ctgtcagtag tcgcgcccct caagtgtcaa taccgcaggg | 30780 |
| cacttatccc caggcttgtc cacatcatct gtgggaaact cgcgtaaaat caggcgtttt | 30840 |
| cgccgatttg cgaggctggc cagctccacg tcgccggccg aaatcgagcc tgcccctcat | 30900 |
| ctgtcaacgc cgcgccgggt gagtcggccc ctcaagtgtc aacgtccgcc cctcatctgt | 30960 |
| cagtgagggc caagttttcc gcgaggtatc cacaacgccg gcggccgcgg tgtctcgcac | 31020 |
| acggcttcga cggcgtttct ggcgcgtttg cagggccata gacggccgcc agcccagcgg | 31080 |
| cgagggcaac cagcccggtg agcgtcggaa aggcgctgga agccccgtag cgacgcggag | 31140 |
| aggggcgaga caagccaagg gcgcaggctc gatgcgcagc acgacatagc cggttctcgc | 31200 |
| aaggacgaga atttccctgc ggtgcccctc aagtgtcaat gaaagtttcc aacgcgagcc | 31260 |
| attcgcgaga gccttgagtc cacgctagat gagagctttg ttgtaggtgg accagttggt | 31320 |
| gattttgaac ttttgctttg ccacggaacg gtctgcgttg tcgggaagat gcgtgatctg | 31380 |
| atccttcaac tcagcaaaag ttcgatttat tcaacaaagc cacgttgtgt ctcaaaatct | 31440 |
| ctgatgttac attgcacaag ataaaaatat atcatcatga acaataaaac tgtctgctta | 31500 |
| cataaacagt aatacaaggg gtgttatgag ccatattcaa cgggaaacgt cttgctcgac | 31560 |
| tctagagctc gttcctcgag gaacggtacc tgcggggaag cttacaataa tgtgtgttgt | 31620 |
| taagtcttgt tgcctgtcat cgtctgactg actttcgtca taaatcccgg cctccgtaac | 31680 |
| ccagctttgg gcaagctcac ggatttgatc cggcggaacg ggaatatcga gatgccgggc | 31740 |
| tgaacgctgc agttccagct ttccctttcg ggacaggtac tccagctgat tgattatctg | 31800 |
| ctgaagggtc ttggttccac ctcctggcac aatgcgaatg attacttgag cgcgatcggg | 31860 |
| catccaattt tctcccgtca ggtgcgtggt caagtgctac aaggcacctt tcagtaacga | 31920 |
| gcgaccgtcg atccgtcgcc gggatacgga caaaatggag cgcagtagtc catcgagggc | 31980 |
| ggcgaaagcc tcgccaaaag caatacgttc atctcgcaca gcctccagat ccgatcgagg | 32040 |
| gtcttcggca taggcagata gaagcatgga tacattgctt gagagtattc cgatggactg | 32100 |
| aagtatggct tccatctttt ctcgtgtgtc tgcatctatt tcgagaaagc ccccgatgcg | 32160 |

```
gcgcaccgca acgcgaattg ccatactatc cgaaagtccc agcaggcgcg cttgatagga   32220
aaaggtttca tactcggccg atcgcagacg ggcactcacg accttgaacc cttcaacttt   32280
cagggatcga tgctggttga tggtagtctc actcgacgtg gctctggtgt gttttgacat   32340
agcttcctcc aaagaaagcg gaaggtctgg atactccagc acgaaatgtg cccgggtaga   32400
cggatggaag tctagccctg ctcaatatga aatcaacagt acatttacag tcaatactga   32460
atatacttgc tacatttgca attgtcttat aacgaatgtg aaataaaaat agtgtaacaa   32520
cgcttttact catcgataat cacaaaaaca tttatacgaa caaaaataca aatgcactcc   32580
ggtttcacag dataggcggg atcagaatat gcaacttttg acgttttgtt ctttcaaagg   32640
gggtgctggc aaaaccaccg cactcatggg cctttgcgct gctttggcaa atgacggtaa   32700
acgagtggcc ctctttgatg ccgacgaaaa ccggcctctg acgcgatgga gagaaaacgc   32760
cttacaaagc agtactggga tcctcgctgt gaagtctatt ccgccgacga aatgcccctt   32820
cttgaagcag cctatgaaaa tgccgagctc gaaggatttg attatgcgtt ggccgatacg   32880
cgtggcggct cgagcgagct caacaacaca atcatcgcta gctcaaacct gcttctgatc   32940
cccaccatgc taacgccgct cgacatcgat gaggcactat ctacctaccg ctacgtcatc   33000
gagctgctgt tgagtgaaaa tttggcaatt cctacagctg ttttgcgcca acgcgtcccg   33060
gtcggccgat tgacaacatc gcaacgcagg atgtcagaga cgctagagag ccttccagtt   33120
gtaccgtctc ccatgcatga aagagatgca tttgccgcga tgaaagaacg cggcatgttg   33180
catcttacat tactaaacac gggaactgat ccgacgatgc gcctcataga gaggaatctt   33240
cggattgcga tggaggaagt cgtggtcatt tcgaaactga tcagcaaaat cttggaggct   33300
tgaagatggc aattcgcaag cccgcattgt cggtcggcga agcacggcgg cttgctggtg   33360
ctcgacccga gatccaccat cccaacccga cacttgttcc ccagaagctg gacctccagc   33420
acttgcctga aaaagccgac gagaaagacc agcaacgtga gcctctcgtc gccgatcaca   33480
tttacagtcc cgatcgacaa cttaagctaa ctgtggatgc ccttagtcca cctccgtccc   33540
cgaaaaagct ccaggttttt ctttcagcgc gaccgcccgc gcctcaagtg tcgaaaacat   33600
atgacaacct cgttcggcaa tacagtccct cgaagtcgct acaaatgatt ttaaggcgcg   33660
cgttggacga tttcgaaagc atgctggcag atggatcatt tcgcgtggcc ccgaaaagtt   33720
atccgatccc ttcaactaca gaaaaatccg ttctcgttca gacctcacgc atgttcccgg   33780
ttgcgttgct cgaggtcgct cgaagtcatt ttgatccgtt ggggttggag accgctcgag   33840
ctttcggcca caagctggct accgccgcgc tcgcgtcatt ctttgctgga gagaagccat   33900
cgagcaattg gtgaagaggg acctatcgga accctcacc aaatattgag tgtaggtttg   33960
aggccgctgg ccgcgtcctc agtcacctttt gagccagat aattaagagc caaatgcaat   34020
tggctcaggc tgccatcgtc ccccgtgcg aaacctgcac gtccgcgtca aagaaataac   34080
cggcacctct tgctgttttt atcagttgag ggcttgacgg atccgcctca gtttgcggc   34140 gcagccgcaa aatgagaaca tctatactcc tgtcgtaaac ctcctcgtcg cgtactcgac   34200
tggcaatgag aagttgctcg cgcgatagaa cgtcgcgggg tttctctaaa aacgcgagga   34260
gaagattgaa ctcacctgcc gtaagtttca cctcaccgcc agcttcggac atcaagcgac   34320
gttgcctgag attaagtgtc cagtcagtaa aacaaaaaga ccgtcggtct ttggagcgga   34380
caacgttggg gcgcacgcgc aaggcaaccc gaatgcgtgc aagaaactct ctcgtactaa   34440
acggcttagc gataaaatca cttgctccta gctcgagtgc aacaacttta tccgtctcct   34500
```

```
caaggcggtc gccactgata attatgattg aatatcaga ctttgccgcc agatttcgaa    34560
cgatctcaag cccatcttca cgacctaaat ttagatcaac aaccacgaca tcgaccgtcg    34620
cggaagagag tactctagtg aactgggtgc tgtcggctac cgcggtcact ttgaaggcgt    34680
ggatcgtaag gtattcgata taagatgcc gcatagcgac atcgtcatcg ataagaagaa    34740
cgtgtttcaa cggctcacct ttcaatctaa aatctgaacc cttgttcaca gcgcttgaga    34800
aattttcacg tgaaggatgt acaatcatct ccagctaaat gggcagttcg tcagaattgc    34860
ggctgaccgc ggatgacgaa aatgcgaacc aagtatttca attttatgac aaaagttctc    34920
aatcgttgtt acaagtgaaa cgcttcgagg ttacagctac tattgattaa ggagatcgcc    34980
tatggtctcg ccccggcgtc gtgcgtccgc cgcgagccag atctcgccta cttcataaac    35040
gtcctcatag gcacggaatg gaatgatgac atcgatcgcc gtagagagca tgtcaatcag    35100
tgtgcgatct tccaagctag caccttgggc gctacttttg acaagggaaa acagtttctt    35160
gaatccttgg attggattcg cgccgtgtat tgttgaaatc gatcccggat gtcccgagac    35220
gacttcactc agataagccc atgctgcatc gtcgcgcatc tcgccaagca atatccggtc    35280
cggccgcata cgcagacttg cttggagcaa gtgctcggcg ctcacagcac ccagcccagc    35340
accgttcttg gagtagagta gtctaacatg attatcgtgt ggaatgacga gttcgagcgt    35400
atcttctatg gtgattagcc tttcctgggg ggggatggcg ctgatcaagg tcttgctcat    35460
tgttgtcttg ccgcttccgg tagggccaca tagcaacatc gtcagtcggc tgacgacgca    35520
tgcgtgcaga aacgcttcca aatccccgtt gtcaaaatgc tgaaggatag cttcatcatc    35580
ctgattttgg cgtttccttc gtgtctgcca ctggttccac ctcgaagcat cataacggga    35640
ggagacttct ttaagaccag aaacacgcga gcttggccgt cgaatggtca agctgacggt    35700
gcccgaggga acggtcggcg gcagacagat ttgtagtcgt tcaccaccag gaagttcagt    35760
ggcgcagagg gggttacgtg gtccgacatc ctgctttctc agcgcgcccg ctaaaatagc    35820
gatatcttca agatcatcat aagagacggg caaaggcatc ttggtaaaaa tgccggcttg    35880
gcgcacaaat gcctctccag gtcgattgat cgcaatttct tcagtcttcg ggtcatcgag    35940
ccattccaaa atcggcttca gaagaaagcg tagttgcgga tccacttcca tttacaatgt    36000
atcctatctc taagcggaaa tttgaattca ttaagagcgg cggttcctcc cccgcgtggc    36060
gccgccagtc aggcggagct ggtaaacacc aaagaaatcg aggtcccgtg ctacgaaaat    36120
ggaaacggtg tcaccctgat tcttcttcag ggttggcggt atgttgatgg ttgccttaag    36180
ggctgtctca gttgtctgct caccgttatt ttgaaagctg ttgaagctca tcccgccacc    36240
cgagctgccg gcgtaggtgc tagctgcctg gaaggcgcct tgaacaacac tcaagagcat    36300
agctccgcta aaacgctgcc agaagtggct gtcgaccgag cccggcaatc ctgagcgacc    36360
gagttcgtcc gcgcttggcg atgttaacga gatcatcgca tggtcaggtg tctcggcgcg    36420
atcccacaac acaaaaacgc gcccatctcc ctgttgcaag ccacgctgta tttcgccaac    36480
aacggtggtg ccacgatcaa gaagcacgat attgttcgtt gttccacgaa tatcctgagg    36540
caagacacac tttacatagc ctgccaaatt tgtgtcgatt gcggtttgca agatgcacgg    36600
aattattgtc ccttgcgtta ccataaaatc ggggtgcggc aagagcgtgg cgctgctggg    36660
ctgcagctcg gtgggtttca tacgtatcga caaatcgttc tcgccggaca cttcgccatt    36720
cggcaaggag ttgtcgtcac gcttgccttc ttgtcttcgg cccgtgtcgc cctgaatggc    36780
gcgtttgctc acccttgat cgccgctgct atatgcaaaa atcggtgttt cttccggccg    36840
tggctcatgc cgctccggtt cgcccctcgg cggtagagga gcagcaggct gaacagcctc    36900
```

```
ttgaaccgct ggaggatccg gcggcacctc aatcggagct ggatgaaatg gcttggtgtt    36960
tgttgcgatc aaagttgacg gcgatgcgtt ctcattcacc ttcttttggc gcccacctag    37020
ccaaatgagg cttaatgata acgcgagaac gacacctccg acgatcaatt tctgagaccc    37080
cgaaagacgc cggcgatgtt tgtcggagac cagggatcca gatgcatcaa cctcatgtgc    37140
cgcttgctga ctatcgttat tcatcccttc gccccttca ggacgcgttt cacatcgggc    37200
ctcaccgtgc ccgtttgcgg cctttggcca acgggatcgt aagcggtgtt ccagatacat    37260
agtactgtgt ggccatccct cagacgccaa cctcgggaaa ccgaagaaat ctcgacatcg    37320
ctccctttaa ctgaatagtt ggcaacagct tccttgccat caggattgat ggtgtagatg    37380
gagggtatgc gtacattgcc cggaaagtgg aataccgtcg taaatccatt gtcgaagact    37440
tcgagtggca acagcgaacg atcgccttgg gcgacgtagt gccaattact gtccgccgca    37500
ccaagggctg tgacaggctg atccaataaa ttctcagctt tccgttgata ttgtgcttcc    37560
gcgtgtagtc tgtccacaac agccttctgt tgtgcctccc ttcgccgagc cgccgcatcg    37620 tcggcgggt aggcgaattg gacgctgtaa tagagatcgg gctgctcttt atcgaggtgg    37680
gacagagtct tggaacttat actgaaaaca taacggcgca tcccggagtc gcttgcggtt    37740
agcacgatta ctggctgagg cgtgaggacc tggcttgcct tgaaaaatag ataatttccc    37800
cgcggtaggg ctgctagatc tttgctattt gaaacggcaa ccgctgtcac cgtttcgttc    37860
gtggcgaatg ttacgaccaa agtagctcca accgccgtcg agaggcgcac cacttgatcg    37920
ggattgtaag ccaaataacg catgcgcgga tctagcttgc ccgccattgg agtgtcttca    37980
gcctccgcac cagtcgcagc ggcaaataaa catgctaaaa tgaaaagtgc ttttctgatc    38040
atggttcgct gtggcctacg tttgaaacgg tatcttccga tgtctgatag gaggtgacaa    38100
ccagacctgc cgggttggtt agtctcaatc tgccgggcaa gctggtcacc ttttcgtagc    38160
gaactgtcgc ggtccacgta ctcaccacag gcattttgcc gtcaacgacg agggtccttt    38220 tatacgaat ttgctgcgtg cttggagtta catcatttga agcgatgtgc tcgacctcca    38280
ccctgccgcg tttgccaaga atgacttgag gcgaactggg attgggatag ttgaagaatt    38340
gctggtaatc ctggcgcact gttggggcac tgaagttcga taccaggtcg taggcgtact    38400
gagcggtgtc ggcatcataa ctctcgcgca ggcgaacgta ctcccacaat gaggcgttaa    38460
cgacggcctc ctcttgagtt gcaggcaatc gcgagacaga cacctcgctg tcaacggtgc    38520
cgtccggccg tatccataga tatacgggca caagcctgct caacggcacc attgtggcta    38580
tagcgaacgc ttgagcaaca tttcccaaaa tcgcgatagc tgcgacagct gcaatgagtt    38640
tggagagacg tcgcgccgat ttcgctcgcg cggtttgaaa ggcttctact tccttatagt    38700
gctcggcaag gctttcgcgc gccactagca tggcatattc aggccccgtc atagcgtcca    38760
cccgaattgc cgagctgaag atctgacgga gtaggctgcc atcgcccac attcagcggg    38820 aagatcgggc ctttgcagct cgctaatgtg tcgtttgtct ggcagccgct caaagcgaca    38880
actaggcaca gcaggcaata cttcatagaa ttctccattg aggcgaattt tgcgcgacc    38940 tagcctcgct caacctgagc gaagcgacgg tacaagctgc tggcagattg ggttgcgccg    39000
ctccagtaac tgcctccaat gttgccgcg atcgccggca aagcgacaat gagcgcatcc    39060
cctgtcagaa aaaacatatc gagttcgtaa agaccaatga tcttggccgc ggtcgtaccg    39120
gcgaaggtga ttcaccaag cataagggtg agcgcagtcg cttcggttag gatgacgatc    39180
gttgccacga ggtttaagag gagaagcaag agaccgtagg tgataagttg cccgatccac    39240
```

```
ttagctgcga tgtcccgcgt gcgatcaaaa atatatccga cgaggatcag aggcccgatc   39300
gcgagaagca ctttcgtgag aattccaacg gcgtcgtaaa ctccgaaggc agaccagagc   39360
gtgccgtaaa ggacccactg tgccccttgg aaagcaagga tgtcctggtc gttcatcgga   39420
ccgatttcgg atgcgatttt ctgaaaaacg gcctgggtca cggcgaacat tgtatccaac   39480
tgtgccggaa cagtctgcag aggcaagccg gttacactaa actgctgaac aaagtttggg   39540
accgtctttt cgaagatgga aaccacatag tcttggtagt tagcctgccc aacaattaga   39600
gcaacaacga tggtgaccgt gatcacccga gtgataccgc tacgggtatc gacttcgccg   39660
cgtatgacta aaatacccctg aacaataatc caaagagtga cacaggcgat caatggcgca   39720
ctcaccgcct cctggatagt ctcaagcatc gagtccaagc ctgtcgtgaa ggctacatcg   39780
aagatcgtat gaatgccgt aaacggcgcc ggaatcgtga aattcatcga ttggacctga   39840
acttgactgg tttgtcgcat aatgttggat aaaatgagct cgcattcggc gaggatgcgg   39900
gcggatgaac aaatcgccca gccttagggg agggcaccaa agatgacagc ggtcttttga   39960
tgctccttgc gttgagcggc cgcctcttcc gcctcgtgaa ggccggcctg cgcggtagtc   40020
atcgttaata ggcttgtcgc ctgtacattt tgaatcattg cgtcatggat ctgcttgaga   40080
agcaaaccat tggtcacggt tgcctgcatg atattgcgag atcgggaaag ctgagcagac   40140
gtatcagcat tcgccgtcaa gcgtttgtcc atcgtttcca gattgtcagc cgcaatgcca   40200
gcgctgtttg cggaaccggt gatctgcgat cgcaacaggt ccgcttcagc atcactaccc   40260
acgactgcac gatctgtatc gctggtgatc gcacgtgccg tggtcgacat tggcattcgc   40320
ggcgaaaaca tttcattgtc taggtccttc gtcgaaggat actgatttt ctggttgagc   40380
gaagtcagta gtccagtaac gccgtaggcc gacgtcaaca tcgtaaccat cgctatagtc   40440
tgagtgagat tctccgcagt cgcgagcgca gtcgcgagcg tctcagcctc cgttgccggg   40500
tcgctaacaa caaactgcgc ccgcgcgggc tgaatatata gaaagctgca ggtcaaaact   40560
gttgcaataa gttgcgtcgt cttcatcgtt tcctaccta tcaatcttct gcctcgtggt   40620
gacgggccat gaattcgctg agccagccag atgagttgcc ttcttgtgcc tcgcgtagtc   40680
gagttgcaaa gcgcaccgtg ttggcacgcc ccgaaagcac ggcgacatat tcacgcatat   40740
cccgcagatc aaattcgcag atgacgcttc cactttctcg tttaagaaga aacttacggc   40800
tgccgaccgt catgtcttca cggatcgcct gaaattcctt ttcggtacat ttcagtccat   40860
cgacataagc cgatcgatct gcggttggtg atggatagaa aatcttcgtc atacattgcg   40920
caaccaagct ggctcctagc ggcgattcca gaacatgctc tggttgctgc gttgccagta   40980
ttagcatccc gttgttttt cgaacggtca ggaggaattt gtcgacgaca gtcgaaaatt   41040
tagggtttaa caaataggcg cgaaactcat cgcagctcat cacaaaacgg cggccgtcga   41100
tcatggctcc aatccgatgc aggagatatg ctgcagcggg agcgcatact tcctcgtatt   41160
cgagaagatg cgtcatgtcg aagccggtaa tcgacggatc taactttact tcgtcaactt   41220
cgccgtcaaa tgcccagcca agcgcatggc cccggcacca gcgttggagc cgcgctcctg   41280
cgccttcggc gggcccatgc aacaaaaatt cacgtaaccc cgcgattgaa cgcatttgtg   41340
gatcaaacga gagctgacga tggataccac ggaccgacg gcggttctct tccggagaaa   41400
tcccaccccg accatcactc tcgatgagag ccacgatcca ttcgcgcaga aaatcgtgtg   41460
aggctgctgt gttttctagg ccacgcaacg gcgccaaccc gctgggtgtg cctctgtgaa   41520
gtgccaaata tgttcctcct gtggcgcgaa ccagcaattc gccaccccgg tccttgtcaa   41580
agaacacgac cgtacctgca cggtcgacca tgctctgttc gagcatggct agaacaaaca   41640
```

```
tcatgagcgt cgtcttaccc ctcccgatag gcccgaatat tgccgtcatg ccaacatcgt    41700
gctcatgcgg gatatagtcg aaaggcgttc cgccattggt acgaaatcgg gcaatcgcgt    41760
tgccccagtg gcctgagctg gcgccctctg gaaagttttc gaaagagaca aaccctgcga    41820
aattgcgtga agtgattgcg ccagggcgtg tgcgccactt aaaattcccc ggcaattggg    41880
accaataggc cgcttccata ccaataccct cttggacaac cacggcacct gcatccgcca    41940
ttcgtgtccg agcccgcgcg cccctgtccc caagactatt gagatcgtct gcatagacgc    42000
aaaggctcaa atgatgtgag cccataacga attcgttgct cgcaagtgcg tcctcagcct    42060
cggataattt gccgatttga gtcacggctt tatcgccgga actcagcatc tggctcgatt    42120
tgaggctaag tttcgcgtgc gcttgcgggc gagtcaggaa cgaaaaactc tgcgtgagaa    42180
caagtggaaa atcgagggat agcagcgcgt tgagcatgcc cggccgtgtt tttgcaggg    42240 attcgcgaaa cgaatagatg gatccaacgt aactgtcttt tggcgttctg atctcgagtc    42300
ctcgcttgcc gcaaatgact ctgtcggtat aaatcgaagc gccgagtgag ccgctgacga    42360
ccggaaccgg tgtgaaccga ccagtcatga tcaaccgtag cgcttcgcca atttcggtga    42420
agagcacacc ctgcttctcg cggatgccaa gacgatgcag gccatacgct ttaagagagc    42480
cagcgacaac atgccaaaga tcttccatgt tcctgatctg gcccgtgaga tcgttttccc    42540 ttttccgct tagcttggtg aacctcctct ttaccttccc taaagccgcc tgtgggtaga    42600
caatcaacgt aaggaagtgt tcattgcgga ggagttggcc ggagagcacg cgctgttcaa    42660
aagcttcgtt caggctagcg gcgaaaacac tacggaagtg tcgcggcgcc gatgatggca    42720
cgtcggcatg acgtacgagg tgagcatata ttgacacatg atcatcagcg atattgcgca    42780
acagcgtgtt gaacgcacga caacgcgcat tgcgcatttc agtttcctca agctcgaatg    42840
caacgccatc aattctcgca atggtcatga tcgatccgtc ttcaagaagg acgatatggt    42900
cgctgaggtg gccaatataa gggagataga tctcaccgga tctttcggtc gttccactcg    42960
cgccgagcat cacaccattc ctctccctcg tgggggaacc ctaattggat ttgggctaac    43020
agtagcgccc ccccaaactg cactatcaat gcttcttccc gcggtccgca aaaatagcag    43080
gacgacgctc gccgcattgt agtctcgctc cacgatgagc cgggctgcaa accataacgg    43140
cacgagaacg acttcgtaga gcgggttctg aacgataacg atgacaaagc cggcgaacat    43200
catgaataac cctgccaatg tcagtggcac cccaagaaac aatgcgggcc gtgtggctgc    43260
gaggtaaagg gtcgattctt ccaaacgatc agccatcaac taccgccagt gagcgtttgg    43320
ccgaggaagc tcgccccaaa catgataaca atgccgccga cgacgccggc aaccagccca    43380
agcgaagccc gcccgaacat ccaggagatc ccgatagcga caatgccgag aacagcgagt    43440
gactggccga acgaccaag gataaacgtg catatattgt taaccattgt ggcggggtca    43500
gtgccgccac ccgcagattg cgctgcggcg ggtccggatg aggaaatgct ccatgcaatt    43560
gcaccgcaca agcttggggc gcagctcgat atcacgcgca tcatcgcatt cgagagcgag    43620
aggcgattta gatgtaaacg gtatctctca aagcatcgca tcaatgcgca cctccttagt    43680
ataagtcgaa taagacttga ttgtcgtctg cggatttgcc gttgtcctgg tgtggcggtg    43740
gcggagcgat taaccgcca gcgccatcct cctgcgagcg gcgctgatat gaccccccaaa   43800 catcccacgt ctcttcggat tttagcgcct cgtgatcgtc ttttggaggc tcgattaacg    43860
cgggcaccag cgattgagca gctgtttcaa ctttttcgcac gtagccgttt gcaaaaccgc    43920
cgatgaaatt accggtgttg taagcggaga tcgcccgacg aagcgcaaat tgcttctcgt    43980
```

```
caatcgtttc gccgcctgca taacgacttt tcagcatgtt tgcagcggca gataatgatg    44040
tgcacgcctg gagcgcaccg tcaggtgtca gaccgagcat agaaaaattt cgagagttta    44100
tttgcatgag gccaacatcc agcgaatgcc gtgcatcgag acggtgcctg acgacttggg    44160
ttgcttggct gtgatcttgc cagtgaagcg tttcgccggt cgtgttgtca tgaatcgcta    44220
aaggatcaaa gcgactctcc accttagcta tcgccgcaag cgtagatgtc gcaactgatg    44280
gggcacactt gcgagcaaca tggtcaaact cagcagatga gagtggcgtg gcaaggctcg    44340
acgaacagaa ggagaccatc aaggcaagag aaagcgaccc cgatctctta agcataccttt   44400 atctccttag ctcgcaacta acaccgcctc tcccgttgga agaagtgcgt tgttttatgt    44460
tgaagattat cgggagggtc ggttactcga aaattttcaa ttgcttcttt atgatttcaa    44520
ttgaagcgag aaacctcgcc cggcgtcttg aacgcaaca tggaccgaga accgcgcatc     44580
catgactaag caaccggatc gacctattca ggccgcagtt ggtcaggtca ggctcagaac    44640
gaaaatgctc ggcgaggtta cgctgtctgt aaacccattc gatgaacggg aagcttcctt    44700
ccgattgctc ttggcaggaa tattggccca tgcctgcttg cgcttgcaa atgctcttat     44760 cgcgttggta tcatatgcct tgtccgccag cagaaacgca ctctaagcga ttatttgtaa    44820
aaatgtttcg gtcatgcggc ggtcatgggc ttgacccgct gtcagcgcaa gacggatcgg    44880
tcaaccgtcg gcatcgacaa cagcgtgaat cttggtggtc aaaccgccac gggaacgtcc    44940
catacagcca tcgtcttgat cccgctgttt cccgtcgccg catgttggtg gacgcggaca    45000
caggaactgt caatcatgac gacattctat cgaaagcctt ggaaatcaca ctcagaatat    45060
gatcccagac gtctgcctca cgccatcgta caaagcgatt gtagcaggtt gtacaggaac    45120
cgtatcgatc aggaacgtct gcccagggcg ggcccgtccg gaagcgccac aagatgacat    45180
tgatcacccg cgtcaacgcg cggcacgcga cgcggcttat ttgggaacaa aggactgaac    45240
aacagtccat tcgaaatcgg tgacatcaaa gcggggacgg ttatcagtg gcctccaagt     45300 caagcctcaa tgaatcaaaa tcagaccgat ttgcaaacct gatttatgag tgtgcggcct    45360
aaatgatgaa atcgtccttc tagatcgcct ccgtggtgta gcaacacctc gcagtatcgc    45420
cgtgctgacc ttggccaggg aattgactgg caagggtgct ttcacatgac cgctctttg     45480 gccgcgatag atgatttcgt tgctgctttg ggcacgtaga aggagagaag tcatatcgga    45540
gaaattcctc ctggcgcgag agcctgctct atcgcgacgg catcccactg tcgggaacag    45600
accggatcat tcacgaggcg aaagtcgtca acacatgcgt tataggcatc ttcccttgaa    45660
ggatgatctt gttgctgcca atctggaggt gcggcagccg caggcagatg cgatctcagc    45720
gcaacttgcg gcaaaacatc tcactcacct gaaaaccact agcgagtctc gcgatcagac    45780
gaaggccttt tacttaacga cacaatatcc gatgtctgca tcacaggcgt cgctatccca    45840
gtcaatacta aagcggtgca ggaactaaag attactgatg acttaggcgt gccacgaggc    45900
ctgagacgac gcgcgtagac agtttttga aatcattatc aaagtgatgg cctccgctga     45960
agcctatcac ctctgcgccg gtctgtcgga gagatgggca agcattatta cggtcttcgc    46020
gcccgtacat gcattggacg attgcagggt caatggatct gagatcatcc agaggattgc    46080
cgcccttacc ttccgtttcg agttggagcc agccctaaa tgagacgaca tagtcgactt     46140
gatgtgacaa tgccaagaga gagatttgct taacccgatt ttttgctca agcgtaagcc     46200 tattgaagct tgccggcatg acgtccgcgc cgaaagaata tcctacaagt aaaacattct    46260
gcacaccgaa atgcttggtg tagacatcga ttatgtgacc aagatcctta gcagtttcgc    46320
ttggggaccg ctccgaccag aaataccgaa gtgaactgac gccaatgaca ggaatccctt    46380
```

```
ccgtctgcag ataggtacca tcgatagatc tgctgcctcg cgcgtttcgg tgatgacggt    46440
gaaaacctct gacacatgca gctcccggag acggtcacag cttgtctgta agcggatgcc    46500
gggagcagac aagcccgtca gggcgcgtca gcgggtgttg gcgggtgtcg gggcgcagcc    46560
atgacccagt cacgtagcga tagcggagtg tatactggct taactatgcg gcatcagagc    46620
agattgtact gagagtgcac catatgcggt gtgaaatacc gcacagatgc gtaaggagaa    46680
aataccgcat caggcgctct tccgcttcct cgctcactga ctcgctgcgc tcggtcgttc    46740
ggctgcggcg agcggtatca gctcactcaa aggcggtaat acggttatcc acagaatcag    46800
gggataacgc aggaaagaac atgtgagcaa aaggccagca aaaggccagg aaccgtaaaa    46860
aggccgcgtt gctggcgttt ttccataggc tccgcccccc tgacgagcat cacaaaaatc    46920
gacgctcaag tcagaggtgg cgaaacccga caggactata aagataccag gcgtttcccc    46980
ctggaagctc cctcgtgcgc tctcctgttc cgaccctgcc gcttaccgga tacctgtccg    47040
cctttctccc ttcgggaagc gtggcgcttt ctcatagctc acgctgtagg tatctcagtt    47100
cggtgtaggt cgttcgctcc aagctgggct gtgtgcacga accccccgtt cagcccgacc    47160
gctgcgcctt atccggtaac tatcgtcttg agtccaaccc ggtaagacac gacttatcgc    47220
cactggcagc agccactggt aacaggatta gcagagcgag gtatgtaggc ggtgctacag    47280
agttcttgaa gtggtggcct aactacggct acactagaag gacagtattt ggtatctgcg    47340
ctctgctgaa gccagttacc ttcggaaaaa gagttggtag ctcttgatcc ggcaaacaaa    47400
ccaccgctgg tagcggtggt ttttttgttt gcaagcagca gattacgcgc agaaaaaaag    47460
gatctcaaga agatcctttg atcttttcta cggggtctga cgctcagtgg aacgaaaact    47520
cacgttaagg gattttggtc atgagattat caaaaaggat cttcacctag atccttttaa    47580
attaaaaatg aagttttaaa tcaatctaaa gtatatatga gtaaacttgg tctgacagtt    47640
accaatgctt aatcagtgag gcacctatct cagcgatctg tctatttcgt tcatccatag    47700
ttgcctgact ccccgtcgtg tagataacta cgatacggga gggcttacca tctggcccca    47760
gtgctgcaat gataccgcga gacccacgct caccggctcc agatttatca gcaataaacc    47820
agccagccgg aagggccgag cgcagaagtg gtcctgcaac tttatccgcc tccatccagt    47880
ctattaattg ttgccgggaa gctagagtaa gtagttcgcc agttaatagt ttgcgcaacg    47940
ttgttgccat tgctgcaggg ggggggggg gggggactt ccattgttca ttccacggac    48000
aaaaacagag aaaggaaacg acagaggcca aaaagcctcg ctttcagcac ctgtcgtttc    48060
ctttcttttc agagggtatt ttaaataaaa acattaagtt atgacgaaga agaacggaaa    48120
cgccttaaac cggaaaattt tcataaatag cgaaacccg cgaggtcgcc gccccgtagt    48180
cggatcaccg gaaaggaccc gtaaagtgat aatgattatc atctacatat cacaacgtgc    48240
gtggaggcca tcaaaccacg tcaaataatc aattatgacg caggtatcgt attaattgat    48300
ctgcatcaac ttaacgtaaa aacaacttca gacaatacaa atcagcgaca ctgaatacgg    48360
ggcaacctca tgtcccccc cccccccccc ctgcaggcat cgtggtgtca cgctcgtcgt    48420
ttggtatggc ttcattcagc tccggttccc aacgatcaag gcgagttaca tgatccccca    48480
tgttgtgcaa aaaagcggtt agctccttcg gtcctccgat cgttgtcaga agtaagttgg    48540
ccgcagtgtt atcactcatg gttatggcag cactgcataa ttctcttact gtcatgccat    48600
ccgtaagatg cttttctgtg actggtgagt actcaaccaa gtcattctga gaatagtgta    48660
tgcggcgacc gagttgctct tgcccggcgt caacacggga taataccgcg ccacatagca    48720
```

| | |
|---|---|
| gaactttaaa agtgctcatc attggaaaac gttcttcggg gcgaaaactc tcaaggatct | 48780 |
| taccgctgtt gagatccagt tcgatgtaac ccactcgtgc acccaactga tcttcagcat | 48840 |
| cttttacttt caccagcgtt tctgggtgag caaaaacagg aaggcaaaat gccgcaaaaa | 48900 |
| agggaataag ggcgacacgg aaatgttgaa tactcatact cttccttttt caatattatt | 48960 |
| gaagcattta tcagggttat tgtctcatga gcggatacat atttgaatgt atttagaaaa | 49020 |
| ataaacaaat aggggttccg cgcacatttc cccgaaaagt gccacctgac gtctaagaaa | 49080 |
| ccattattat catgacatta acctataaaa ataggcgtat cacgaggccc tttcgtcttc | 49140 |
| aagaattggt cgacgatctt gctgcgttcg gatattttcg tggagttccc gccacagacc | 49200 |
| cggattgaag gcgagatcca gcaactcgcg ccagatcatc ctgtgacgga actttggcgc | 49260 |
| gtgatgactg gccaggacgt cggccgaaag agcgacaagc agatcacgct tttcgacagc | 49320 |
| gtcggatttg cgatcgagga tttttcggcg ctgcgctacg tccgcgaccg cgttgaggga | 49380 |
| tcaagccaca gcagcccact cgaccttcta gccgacccag acgagccaag ggatcttttt | 49440 |
| ggaatgctgc tccgtcgtca ggcttttccga cgtttgggtg gttgaacaga agtcattatc | 49500 |
| gtacggaatg ccaagcactc ccgagggggaa ccctgtggtt ggcatgcaca tacaaatgga | 49560 |
| cgaacggata aaccttttca cgccctttta aatatccgtt attctaataa acgctctttt | 49620 |
| ctcttaggtt tacccgccaa tatatcctgt caaacactga tagtttaaac tgaaggcggg | 49680 |
| aaacgacaat ctgatcatga gcggagaatt aagggagtca cgttatgacc cccgccgatg | 49740 |
| acgcgggaca agccgtttta cgtttggaac tgacagaacc gcaacgttga aggagccact | 49800 |
| cagcaagctg gtacgattgt aatacgactc actatagggc gaattgagcg ctgtttaaac | 49860 |
| gctcttcaac tggaagagcg gttacccgga ccgaagcttg catgcctgca g | 49911 |

<210> SEQ ID NO 7
<211> LENGTH: 36909
<212> TYPE: DNA
<213> ORGANISM: artificial sequence
<220> FEATURE:
<223> OTHER INFORMATION: NCBI General Identifier No. 59797027

<400> SEQUENCE: 7

| | |
|---|---|
| tctagagctc gttcctcgag gcctcgaggc ctcgaggaac ggtacctgcg gggaagctta | 60 |
| caataatgtg tgttgttaag tcttgttgcc tgtcatcgtc tgactgactt tcgtcataaa | 120 |
| tcccggcctc cgtaacccag cttttgggcaa gctcacggat ttgatccggc ggaacgggaa | 180 |
| tatcgagatg ccgggctgaa cgctgcagtt ccagctttcc ctttcgggac aggtactcca | 240 |
| gctgattgat tatctgctga agggtcttgg ttccacctcc tggcacaatg cgaatgatta | 300 |
| cttgagcgcg atcgggcatc caattttctc ccgtcaggtg cgtggtcaag tgctacaagg | 360 |
| caccttcag taacgagcga ccgtcgatcc gtcgccggga tacggacaaa atggagcgca | 420 |
| gtagtccatc gagggcggcg aaagcctcgc caaaagcaat acgttcatct cgcacagcct | 480 |
| ccagatccga tcgagggtct tcggcgtagg cagatagaag catggataca ttgcttgaga | 540 |
| gtattccgat ggactgaagt atggcttcca tcttttctcg tgtgtctgca tctatttcga | 600 |
| gaaagcccccc gatgcggcgc accgcaacgc gaattgccat actatccgaa agtcccagca | 660 |
| ggcgcgcttg ataggaaaag gtttcatact cggccgatcg cagacgggca ctcacgacct | 720 |
| tgaacccttc aactttcagg gatcgatgct ggttgatggt agtctcactc gacgtggctc | 780 |
| tggtgtgttt tgacatagct tcctccaaag aaagcggaag gtctggatac tccagcacga | 840 |
| aatgtgcccg ggtagacgga tggaagtcta gccctgctca atatgaaatc aacagtacat | 900 |

```
ttacagtcaa tactgaatat acttgctaca tttgcaattg tcttataacg aatgtgaaat    960
aaaaatagtg taacaacgct tttactcatc gataatcaca aaaacattta tacgaacaaa   1020
aatacaaatg cactccggtt tcacaggata ggcgggatca gaatatgcaa cttttgacgt   1080
tttgttcttt caaaggggt gctggcaaaa ccaccgcact catgggcctt tgcgctgctt    1140
tggcaaatga cggtaaacga gtggccctct tgatgccga cgaaaaccgg cctctgacgc    1200
gatggagaga aaacgcctta caaagcagta ctgggatcct cgctgtgaag tctattccgc   1260
cgacgaaatg ccccttcttg aagcagccta tgaaaatgcc gagctcgaag gatttgatta   1320
tgcgttggcc gatacgcgtg gcggctcgag cgagctcaac aacacaatca tcgctagctc   1380
aaacctgctt ctgatcccca ccatgctaac gccgctcgac atcgatgagg cactatctac   1440
ctaccgctac gtcatcgagc tgctgttgag tgaaaatttg gcaattccta cagctgtttt   1500
gcgccaacgc gtcccggtcg gccgattgac aacatcgcaa cgcaggatgt cagagacgct   1560
agagagcctt ccagttgtac cgtctcccat gcatgaaaga gatgcatttg ccgcgatgaa   1620
agaacgcggc atgttgcatc ttacattact aaacacggga actgatccga cgatgcgcct   1680
catagagagg aatcttcgga ttgcgatgga ggaagtcgtg gtcatttcga aactgatcag   1740
caaaatcttg gaggcttgaa gatggcaatt cgcaagcccg cattgtcggt cggcgaagca   1800
cggcggcttg ctggtgctcg acccgagatc caccatccca acccgacact tgttccccag   1860
aagctggacc tccagcactt gcctgaaaaa gccgacgaga aagaccagca acgtgagcct   1920
ctcgtcgccg atcacattta cagtcccgat cgacaactta agctaactgt ggatgccctt   1980
agtccacctc cgtccccgaa aaagctccag ttttttcttt cagcgcgacc gccgcgcct    2040
caagtgtcga aaacatatga caacctcgtt cggcaataca gtccctcgaa gtcgctacaa   2100
atgattttaa ggcgcgcgtt ggacgatttc gaaagcatgc tggcagatgg atcatttcgc   2160
gtggccccga aaagttatcc gatcccttca actacagaaa aatccgttct cgttcagacc   2220
tcacgcatgt tcccggttgc gttgctcgag gtcgctcgaa gtcattttga tccgttgggg   2280
ttggagaccg ctcgagcttt cggccacaag ctggctaccg ccgcgctcgc gtcattcttt   2340
gctggagaga agccatcgag caattggtga agagggacct atcggaaccc ctcaccaaat   2400
attgagtgta ggtttgaggc cgctggccgc gtcctcagtc acctttgag ccagataatt    2460
aagagccaaa tgcaattggc tcaggctgcc atcgtccccc cgtgcgaaac ctgcacgtcc   2520
gcgtcaaaga aataaccggc acctcttgct gttttatca gttgagggct tgacggatcc    2580
gcctcaagtt tgcggcgcag ccgcaaaatg agaacatcta tactcctgtc gtaaacctcc   2640
tcgtcgcgta ctcgactggc aatgagaagt tgctcgcgcg atagaacgtc gcggggtttc   2700
tctaaaaacg cgaggagaag attgaactca cctgccgtaa gtttcacctc accgccagct   2760
tcggacatca agcgacgttg cctgagatta agtgtccagt cagtaaaaca aaaagaccgt   2820
cggtcttttg gagcggacaac gttggggcgc acgcgcaagg caacccgaat gcgtgcaaga   2880
aactctctcg tactaaacgg cttagcgata aaatcacttg ctcctagctc gagtgcaaca   2940
actttatccg tctcctcaag gcggtcgcca ctgataatta tgattggaat atcagacttt   3000
gccgccagat ttcgaacgat ctcaagccca tcttcacgac ctaaatttag atcaacaacc   3060
acgacatcga ccgtcgcgga agagagtact ctagtgaact gggtgctgtc ggctaccgcg   3120
gtcactttga aggcgtggat cgtaaggtat tcgataataa gatgccgcat agcgacatcg   3180
tcatcgataa gaagaacgtg tttcaacggc tcacctttca atctaaaatc tgaacccttg   3240
```

```
ttcacagcgc ttgagaaatt ttcacgtgaa ggatgtacaa tcatctccag ctaaatgggc    3300
agttcgtcag aattgcggct gaccgcggat gacgaaaatg cgaaccaagt atttcaattt    3360
tatgacaaaa gttctcaatc gttgttacaa gtgaaacgct tcgaggttac agctactatt    3420
gattaaggag atcgcctatg gtctcgcccc ggcgtcgtgc gtccgccgcg agccagatct    3480
cgcctacttc ataaacgtcc tcataggcac ggaatggaat gatgacatcg atcgccgtag    3540
agagcatgtc aatcagtgtg cgatcttcca agctagcacc ttgggcgcta cttttgacaa    3600
gggaaaacag tttcttgaat ccttggattg gattcgcgcc gtgtattgtt gaaatcgatc    3660
ccggatgtcc cgagacgact tcactcagat aagcccatgc tgcatcgtcg cgcatctcgc    3720
caagcaatat ccggtccggc cgcatacgca gacttgcttg gagcaagtgc tcggcgctca    3780
cagcacccag cccagcaccg ttcttggagt agagtagtct aacatgatta tcgtgtggaa    3840
tgacgagttc gagcgtatct tctatggtga ttagcctttc ctgggggggg atggcgctga    3900
tcaaggtctt gctcattgtt gtcttgccgc ttccggtagg gccacatagc aacatcgtca    3960
gtcggctgac gacgcatgcg tgcagaaacg cttccaaatc cccgttgtca aaatgctgaa    4020
ggatagcttc atcatcctga ttttggcgtt tccttcgtgt ctgccactgg ttccacctcg    4080
aagcatcata acgggaggag acttctttaa gaccagaaac acgcgagctt ggccgtcgaa    4140
tggtcaagct gacggtgccc gagggaacgg tcggcggcag acagatttgt agtcgttcac    4200
caccaggaag ttcagtggcg cagaggggt tacgtggtcc gacatcctgc tttctcagcg    4260
cgcccgctaa aatagcgata tcttcaagat catcataaga gacgggcaaa ggcatcttgg    4320
taaaaatgcc ggcttggcgc acaaatgcct ctccaggtcg attgatcgca atttcttcag    4380
tcttcgggtc atcgagccat tccaaaatcg gcttcagaag aaagcgtagt gcggatcca    4440 cttccattta caatgtatcc tatctctaag cggaaatttg aattcattaa gagcggcggt    4500
tcctcccccg cgtggcgccg ccagtcaggc ggagctggta acaccaaag aaatcgaggt    4560 cccgtgctac gaaaatggaa acggtgtcac cctgattctt cttcagggtt ggcggtatgt    4620
tgatggttgc cttaagggct gtctcagttg tctgctcacc gttatttga aagctgttga    4680 agctcatccc gccaccccgag ctgccggcgt aggtgctagc tgcctggaag gcgccttgaa    4740
caacactcaa gagcatagct ccgctaaaac gctgccagaa gtggctgtcg accgagcccg    4800
gcaatcctga cgaccgagt tcgtccgcgc ttggcgatgt taacgagatc atcgcatggt    4860
caggtgtctc ggcgcgatcc cacaacacaa aaacgcgccc atctccctgt tgcaagccac    4920
gctgtatttc gccaacaacg gtggtgccac gatcaagaag cacgatattg ttcgttgttc    4980
cacgaatatc ctgaggcaag acacacttta catagcctgc caatttgtg tcgattgcgg    5040 tttgcaagat gcacggaatt attgtccctt gcgttaccat aaaatcgggg tgcggcaaga    5100
gcgtggcgct gctgggctgc agctcggtgg gtttcatacg tatcgacaaa tcgttctcgc    5160
cggacacttc gccattcggc aaggagttgt cgtcacgctt gccttcttgt cttcggcccg    5220
tgtcgccctg aatggcgcgt ttgctgaccc cttgatcgcc gctgctatat gcaaaaatcg    5280
gtgtttcttc cggccgtggc tcatgccgct ccggttcgcc cctcggcggt agaggagcag    5340
caggctgaac agcctcttga accgctggag gatccggcgg cacctcaatc ggagctggat    5400
gaaatggctt ggtgtttgtt gcgatcaaag ttgacggcga tgcgttctca ttcacccttct    5460 tttggcgccc acctagccaa atgaggctta atgataacgc gagaacgaca cctccgacga    5520
tcaatttctg agaccccgaa agacgccggc gatgtttgtc ggagaccagg gatccagatg    5580
catcaacctc atgtgccgct tgctgactat cgttattcat cccttcgccc ccttcaggac    5640
```

```
gcgtttcaca tcgggcctca ccgtgcccgt tgcggccctt tggccaacgg gatcgtaagc    5700
ggtgttccag atacatagta ctgtgtggcc atccctcaga cgccaacctc gggaaaccga    5760
agaaatctcg acatcgctcc ctttaactga atagttggca acagcttcct tgccatcagg    5820
attgatggtg tagatggagg gtatgcgtac attgcccgaa aagtggaata ccgtcgtaaa    5880
tccattgtcg aagacttcga gtggcaacag cgaacgatcg ccttgggcga cgtagtgcca    5940
attactgtcc gccgcaccaa gggctgtgac aggctgatcc aataaattct cagctttccg    6000
ttgatattgt gcttccgcgt gtagtctgtc cacaacagcc ttctgttgtg cctcccttcg    6060
ccgagccgcc gcatcgtcgg cggggtaggc gaattggacg ctgtaataga gatcgggctg    6120
ctctttatcg aggtgggaca gagtcttgga acttatactg aaaacataac ggcgcatccc    6180
ggagtcgctt gcggttagca cgattactgg ctgaggcgtg aggacctggc ttgccttgaa    6240
aaatagataa tttccccgcg gtagggctgc tagatctttg ctatttgaaa cggcaaccgc    6300
tgtcaccgtt tcgttcgtgg cgaatgttac gaccaaagta gctccaaccg ccgtcgagag    6360
gcgcaccact tgatcgggat tgtaagccaa ataacgcatg cgcggatcta gcttgcccgc    6420
cattggagtg tcttcagcct ccgcaccagt cgcagcggca aataaacatg ctaaaatgaa    6480
aagtgctttt ctgatcatgg ttcgctgtgg cctacgtttg aaacggtatc ttccgatgtc    6540
tgataggagg tgacaaccag acctgccggg ttggttagtc tcaatctgcc gggcaagctg    6600
gtcacctttt cgtagcgaac tgtcgcggtc cacgtactca ccacaggcat tttgccgtca    6660
acgacgaggg tccttttata gcgaatttgc tgcgtgcttg gagttacatc atttgaagcg    6720
atgtgctcga cctccaccct gccgcgtttg ccaagaatga cttgaggcga actgggattg    6780
ggatagttga agaattgctg gtaatcctgg cgcactgttg gggcactgaa gttcgatacc    6840
aggtcgtagg cgtactgagc ggtgtcggca tcataactct cgcgcaggcg aacgtactcc    6900
cacaatgagg cgttaacgac ggcctcctct tgagttgcag gcaatcgcga gacagacacc    6960
tcgctgtcaa cggtgccgtc cggccgtatc catagatata cgggcacaag cctgctcaac    7020
ggcaccattg tggctatagc gaacgcttga gcaacatttc ccaaaatcgc gatagctgcg    7080
acagctgcaa tgagtttgga gagacgtcgc gccgatttcg ctcgcgcggt ttgaaaggct    7140
tctacttcct tatagtgctc ggcaaggctt tcgcgcgcca ctagcatggc atattcaggc    7200
cccgtcatag cgtccacccg aattgccgag ctgaagatct gacggagtag gctgccatcg    7260
ccccacattc agcgggaaga tcgggccttt gcagctcgct aatgtgtcgt ttgtctggca    7320
gccgctcaaa gcgacaacta ggcacagcag gcaatacttc atagaattct ccattggagc    7380 gaattttttgc gcgacctagc ctcgctcaac ctgagcgaag cgacggtaca agctgctggc    7440
agattgggtt gcgccgctcc agtaactgcc tccaatgttg ccggcgatcg ccggcaaagc    7500
gacaatgagc gcatcccctg tcagaaaaaa catatcgagt tcgtaaagac caatgatctt    7560
ggccgcggtc gtaccggcga aggtgattac accaagcata agggtgagcg cagtcgcttc    7620
ggttaggatg acgatcgttg ccacgaggtt taagaggaga agcaagagac cgtaggtgat    7680
aagttgcccg atccacttag ctgcgatgtc ccgcgtgcga tcaaaatat atccgacgag    7740 gatcagaggc ccgatcgcga gaagcacttt cgtgagaatt ccaacggcgt cgtaaactcc    7800
gaaggcagac cagagcgtgc cgtaaaggac ccactgtgcc ccttggaaag caaggatgtc    7860
ctggtcgttc atcggaccga tttcggatgc gattttctga aaaacggcct gggtcacggc    7920
gaacattgta tccaactgtg ccggaacagt ctgcagaggc aagccggtta cactaaactg    7980
```

```
ctgaacaaag tttgggaccg tcttttcgaa gatggaaacc acatagtctt ggtagttagc    8040
ctgcccaaca attagagcaa caacgatggt gaccgtgatc acccgagtga taccgctacg    8100
ggtatcgact tcgccgcgta tgactaaaat accctgaaca ataatccaaa gagtgacaca    8160
ggcgatcaat ggcgcactca ccgcctcctg gatagtctca agcatcgagt ccaagcctgt    8220
cgtgaaggct acatcgaaga tcgtatgaat ggccgtaaac ggcgccggaa tcgtgaaatt    8280
catcgattgg acctgaactt gactggtttg tcgcataatg ttggataaaa tgagctcgca    8340
ttcggcgagg atgcgggcgg atgaacaaat cgcccagcct taggggaggg caccaaagat    8400
gacagcggtc ttttgatgct ccttgcgttg agcggccgcc tcttccgcct cgtgaaggcc    8460
ggcctgcgcg gtagtcatcg ttaataggct tgtcgcctgt acattttgaa tcattgcgtc    8520
atggatctgc ttgagaagca aaccattggt cacggttgcc tgcatgatat tgcgagatcg    8580
ggaaagctga gcagacgtat cagcattcgc cgtcaagcgt ttgtccatcg tttccagatt    8640
gtcagccgca atgccagcgc tgtttgcgga accggtgatc tgcgatcgca acaggtccgc    8700
ttcagcatca ctacccacga ctgcacgatc tgtatcgctg gtgatcgcac gtgccgtggt    8760
cgacattggc attcgcggcg aaaacatttc attgtctagg tccttcgtcg aaggatactg    8820
attttctgg ttgagcgaag tcagtagtcc agtaacgccg taggccgacg tcaacatcgt    8880
aaccatcgct atagtctgag tgagattctc cgcagtcgcg agcgcagtcg cgagcgtctc    8940
agcctccgtt gccgggtcgc taacaacaaa ctgcgcccgc gcgggctgaa tatatagaaa    9000
gctgcaggtc aaaactgttg caataagttg cgtcgtcttc atcgtttcct accttatcaa    9060
tcttctgcct cgtggtgacg ggccatgaat tcgctgagcc agccagatga gttgccttct    9120
tgtgcctcgc gtagtcgagt tgcaaagcgc accgtgttgg cacgccccga agcacggcg    9180
acatattcac gcatatcccg cagatcaaat tcgcagatga cgcttccact ttctcgttta    9240
agaagaaact tacggctgcc gaccgtcatg tcttcacgga tcgcctgaaa ttccttttcg    9300
gtacatttca gtccatcgac ataagccgat cgatctgcgg ttggtgatgg atagaaaatc    9360
ttcgtcatac attgcgcaac caagctggct cctagcggcg attccagaac atgctctggt    9420
tgctgcgttg ccagtattag catcccgttg ttttttcgaa cggtcaggag gaatttgtcg    9480
acgacagtcg aaaatttagg gtttaacaaa taggcgcgaa actcatcgca gctcatcaca    9540
aaacggcggc cgtcgatcat ggctccaatc cgatgcagga gatatgctgc agcgggagcg    9600
catacttcct cgtattcgag aagatgcgtc atgtcgaagc cggtaatcga cggatctaac    9660
tttacttcgt caacttcgcc gtcaaatgcc cagccaagcg catggccccg gcaccagcgt    9720
tggagccgcg ctcctgcgcc ttcggcgggc ccatgcaaca aaaattcacg taaccccgcg    9780
attgaacgca tttgtggatc aaacgagagc tgacgatgga taccacggac cagacggcgg    9840
ttctcttccg gagaaatccc accccgacca tcactctcga tgagagccac gatccattcg    9900
cgcagaaaat cgtgtgaggc tgctgtgttt tctaggccac gcaacggcgc caacccgctg    9960
ggtgtgcctc tgtgaagtgc caaatatgtt cctcctgtgg cgcgaaccag caattcgcca   10020
ccccggtcct tgtcaaagaa cacgaccgta cctgcacggt cgaccatgct ctgttcgagc   10080
atggctagaa caaacatcat gagcgtcgtc ttacccctcc cgataggccc gaatattgcc   10140
gtcatgccaa catcgtgctc atgcgggata tagtcgaaag gcgttccgcc attggtacga   10200
aatcgggcaa tcgcgttgcc ccagtggcct gagctggcgc cctctggaaa gttttcgaaa   10260
gagacaaacc ctgcgaaatt gcgtgaagtg attgcgccag ggcgtgtgcg ccacttaaaa   10320
ttccccggca attgggacca ataggccgct tccataccaa taccttcttg gacaaccacg   10380
```

```
gcacctgcat ccgccattcg tgtccgagcc cgcgcgcccc tgtccccaag actattgaga    10440
tcgtctgcat agacgcaaag gctcaaatga tgtgagccca taacgaattc gttgctcgca    10500
agtgcgtcct cagcctcgga taatttgccg atttgagtca cggctttatc gccggaactc    10560
agcatctggc tcgatttgag gctaagtttc gcgtgcgctt gcgggcgagt caggaacgaa    10620
aaactctgcg tgagaacaag tggaaaatcg agggatagca gcgcgttgag catgcccggc    10680 cgtgttttg cagggtattc gcgaaacgaa tagatggatc caacgtaact gtcttttggc     10740
gttctgatct cgagtcctcg cttgccgcaa atgactctgt cggtataaat cgaagcgccg    10800
agtgagccgc tgacgaccgg aaccggtgtg aaccgaccag tcatgatcaa ccgtagcgct    10860
tcgccaattt cggtgaagag cacaccctgc ttctcgcgga tgccaagacg atgcaggcca    10920
tacgctttaa gagagccagc gacaacatgc caaagatctt ccatgttcct gatctggccc    10980
gtgagatcgt tttccctttt tccgcttagc ttggtgaacc tcctctttac cttccctaaa    11040
gccgcctgtg ggtagacaat caacgtaagg aagtgttcat tgcggaggag ttggccggag    11100
agcacgcgct gttcaaaagc ttcgttcagg ctagcggcga aaacactacg gaagtgtcgc    11160
ggcgccgatg atggcacgtc ggcatgacgt acgaggtgag catatattga cacatgatca    11220
tcagcgatat tgcgcaacag cgtgttgaac gcacgacaac gcgcattgcg catttcagtt    11280
tcctcaagct cgaatgcaac gccatcaatt ctcgcaatgg tcatgatcga tccgtcttca    11340
agaaggacga tatggtcgct gaggtggcca atataaggga gatagatctc accggatctt    11400
tcggtcgttc cactcgcgcc gagcatcaca ccattcctct ccctcgtggg ggaaccctaa    11460
ttggatttgg gctaacagta gcgccccccc aaactgcact atcaatgctt cttcccgcgg    11520
tccgcaaaaa tagcaggacg acgctcgccg cattgtagtc tcgctccacg atgagccggg    11580
ctgcaaacca taacggcacg agaacgactt cgtagagcgg gttctgaacg ataacgatga    11640
caaagccggc gaacatcatg aataaccctg ccaatgtcag tggcaccca agaaacaatg     11700 cgggccgtgt ggctgcgagg taaagggtcg attcttccaa acgatcagcc atcaactacc    11760
gccagtgagc gtttggccga ggaagctcgc cccaaacatg ataacaatgc cgccgacgac    11820
gccggcaacc agcccaagcg aagcccgccc gaacatccag gagatcccga tagcgacaat    11880
gccgagaaca gcgagtgact ggccgaacgg accaaggata aacgtgcata tattgttaac    11940
cattgtggcg gggtcagtgc cgccacccgc agattgcgct gcggcgggtc cggatgagga    12000
aatgctccat gcaattgcac cgcacaagct tggggcgcag ctcgatatca cgcgcatcat    12060
cgcattcgag agcgagaggc gatttagatg taaacggtat ctctcaaagc atcgcatcaa    12120
tgcgcacctc cttagtataa gtcgaataag acttgattgt cgtctgcgga tttgccgttg    12180
tcctggtgtg gcggtggcgg agcgattaaa ccgccagcgc catcctcctg cgagcggcgc    12240
tgatatgacc cccaaacatc ccacgtctct tcggatttta gcgcctcgtg atcgtctttt    12300
ggaggctcga ttaacgcggg caccagcgat tgagcagctg tttcaacttt tcgcactag     12360 ccgtttgcaa aaccgccgat gaaattaccg gtgttgtaag cggagatcgc ccgacgaagc    12420
gcaaattgct tctcgtcaat cgtttcgccg cctgcataac gacttttcag catgtttgca    12480
gcggcagata atgatgtgca cgcctggagc gcaccgtcag gtgtcagacc gagcatagaa    12540
aaatttcgag agtttatttg catgaggcca acatccagcg aatgccgtgc atcgagacgg    12600
tgcctgacga cttgggttgc ttggctgtga tcttgccagt gaagcgtttc gccggtcgtg    12660
ttgtcatgaa tcgctaaagg atcaaagcga ctctccacct tagctatcgc cgcaagcgta    12720
```

```
gatgtcgcaa ctgatggggc acacttgcga gcaacatggt caaactcagc agatgagagt   12780
ggcgtggcaa ggctcgacga acagaaggag accatcaagg caagagaaag cgacccccgat  12840 ctcttaagca taccttatct ccttagctcg caactaacac cgcctctccc gttggaagaa   12900
gtgcgttgtt ttatgttgaa gattatcggg agggtcggtt actcgaaaat tttcaattgc   12960
ttctttatga tttcaattga agcgagaaac ctcgcccggc gtcttggaac gcaacatgga   13020
ccgagaaccg cgcatccatg actaagcaac cggatcgacc tattcaggcc gcagttggtc   13080
aggtcaggct cagaacgaaa atgctcggcg aggttacgct gtctgtaaac ccattcgatg   13140
aacgggaagc ttccttccga ttgctcttgg caggaatatt ggcccatgcc tgcttgcgct   13200
ttgcaaatgc tcttatcgcg ttggtatcat atgccttgtc cgccagcaga aacgcactct   13260
aagcgattat ttgtaaaaat gtttcggtca tgcggcggtc atgggcttga cccgctgtca   13320
gcgcaagacg gatcggtcaa ccgtcggcat cgacaacagc gtgaatcttg gtggtcaaac   13380
cgccacggga acgtcccata cagccatcgt cttgatcccg ctgtttcccg tcgccgcatg   13440
ttggtggacg cggacacagg aactgtcaat catgacgaca ttctatcgaa agccttggaa   13500
atcacactca gaatatgatc ccagacgtct gcctcacgcc atcgtacaaa gcgattgtag   13560
caggttgtac aggaaccgta tcgatcagga acgtctgccc agggcgggcc cgtccggaag   13620
cgccacaaga tgacattgat cacccgcgtc aacgcgcggc acgcgacgcg gcttatttgg   13680
gaacaaagga ctgaacaaca gtccattcga aatcggtgac atcaaagcgg ggacgggtta   13740
tcagtggcct ccaagtcaag cctcaatgaa tcaaaatcag accgatttgc aaacctgatt   13800
tatgagtgtg cggcctaaat gatgaaatcg tccttctaga tcgcctccgt ggtgtagcaa   13860
cacctcgcag tatcgccgtg ctgaccttgg ccagggaatt gactggcaag ggtgctttca   13920
catgaccgct ctttttggccg cgatagatga tttcgttgct gctttgggca cgtagaagga   13980
gagaagtcat atcggagaaa ttcctcctgg cgcgagagcc tgctctatcg cgacggcatc   14040
ccactgtcgg gaacagaccg gatcattcac gaggcgaaag tcgtcaacac atgcgttata   14100
ggcatcttcc cttgaaggat gatcttgttg ctgccaatct ggaggtgcgg cagccgcagg   14160
cagatgcgat ctcagcgcaa cttgcggcaa aacatctcac tcacctgaaa accactagcg   14220
agtctcgcga tcagacgaag gccttttact taacgacaca atatccgatg tctgcatcac   14280
aggcgtcgct atcccagtca atactaaagc ggtgcaggaa ctaaagatta ctgatgactt   14340
aggcgtgcca cgaggcctga gacgacgcgc gtagacagtt ttttgaaatc attatcaaag   14400
tgatggcctc cgctgaagcc tatcacctct gcgccggtct gtcggagaga tgggcaagca   14460
ttattacggt cttcgcgccc gtacatgcat tggacgattg cagggtcaat ggatctgaga   14520
tcatccagag gattgccgcc cttaccttcc gtttcgagtt ggagccagcc cctaaatgag   14580
acgacatagt cgacttgatg tgacaatgcc aagagagaga tttgcttaac ccgatttttt   14640
tgctcaagcg taagcctatt gaagcttgcc ggcatgacgt ccgcgccgaa agaatatcct   14700
acaagtaaaa cattctgcac accgaaatgc ttggtgtaga catcgattat gtgaccaaga   14760
tccttagcag tttcgcttgg ggaccgctcc gaccagaaat accgaagtga actgacgcca   14820
atgacaggaa tcccttccgt ctgcagatag gtaccatcga tagatctgct gcctcgcgcg   14880
tttcggtgat gacggtgaaa acctctgaca catgcagctc ccggagacgg tcacagcttg   14940
tctgtaagcg gatgccggga gcagacaagc ccgtcagggc gcgtcagcgg gtgttggcgg   15000
gtgtcggggc gcagccatga cccagtcacg tagcgatagc ggagtgtata ctggcttaac   15060
tatgcggcat cagagcagat tgtactgaga gtgcaccata tgcggtgtga ataccgcac    15120
```

```
agatgcgtaa ggagaaaata ccgcatcagg cgctcttccg cttcctcgct cactgactcg   15180
ctgcgctcgg tcgttcggct gcggcgagcg gtatcagctc actcaaaggc ggtaatacgg   15240
ttatccacag aatcagggga taacgcagga agaacatgt  gagcaaaagg ccagcaaaag   15300
gccaggaacc gtaaaaaggc gcgttgctg  gcgttttcc  ataggctccg ccccctgac    15360 gagcatcaca aaaatcgacg ctcaagtcag aggtggcgaa acccgacagg actataaaga   15420
taccaggcgt ttccccctgg aagctccctc gtgcgctctc ctgttccgac cctgccgctt   15480
accggatacc tgtccgcctt tctcccttcg ggaagcgtgg cgctttctca tagctcacgc   15540
tgtaggtatc tcagttcggt gtaggtcgtt cgctccaagc tgggctgtgt gcacgaaccc   15600
cccgttcagc ccgaccgctg cgccttatcc ggtaactatc gtcttgagtc caacccggta   15660
agacacgact tatcgccact ggcagcagcc actggtaaca ggattagcag agcgaggtat   15720
gtaggcggtg ctacagagtt cttgaagtgg tggcctaact acggctacac tagaaggaca   15780
gtatttggta tctgcgctct gctgaagcca gttaccttcg gaaaaagagt tggtagctct   15840
tgatccggca acaaaccac  cgctggtagc ggtggttttt  ttgtttgcaa gcagcagatt   15900
acgcgcagaa aaaaggatc  tcaagaagat cctttgatct tttctacggg gtctgacgct   15960
cagtggaacg aaaactcacg ttaagggatt ttggtcatga gattatcaaa aaggatcttc   16020
acctagatcc ttttaaatta aaaatgaagt tttaaatcaa tctaaagtat atatgagtaa   16080
acttggtctg acagttacca atgcttaatc agtgaggcac ctatctcagc gatctgtcta   16140
tttcgttcat ccatagttgc ctgactcccc gtcgtgtaga taactacgat acgggagggc   16200
ttaccatctg gccccagtgc tgcaatgata ccgcgagacc cacgctcacc ggctccagat   16260
ttatcagcaa taaccagcc  agccggaagg gccgagcgca gaagtggtcc tgcaacttta   16320
tccgcctcca tccagtctat taattgttgc cgggaagcta gagtaagtag ttcgccagtt   16380
aatagtttgc gcaacgttgt tgccattgct gcaggggggg ggggggggg  gttccattgt   16440 tcattccacg gacaaaaaca gagaaaggaa acgacagagg ccaaaaagct cgctttcagc   16500
acctgtcgtt tcctttcttt tcagagggta ttttaaataa aaacattaag ttatgacgaa   16560
gaagaacgga aacgccttaa accggaaaat tttcataaat agcgaaaacc cgcgaggtcg   16620
ccgccccgta acctgtcgga tcaccggaaa ggacccgtaa agtgataatg attatcatct   16680
acatatcaca acgtgcgtgg aggccatcaa accacgtcaa ataatcaatt atgacgcagg   16740
tatcgtatta attgatctgc atcaacttaa cgtaaaaaca acttcagaca atacaaatca   16800
gcgacactga atacggggca acctcatgtc cccccccccc cccccctgc  aggcatcgtg   16860 gtgtcacgct cgtcgtttgg tatggcttca ttcagctccg gttcccaacg atcaaggcga   16920
gttacatgat cccccatgtt gtgcaaaaaa gcggttagct ccttcggtcc tccgatcgtt   16980
gtcagaagta agttggccgc agtgttatca ctcatggtta tggcagcact gcataattct   17040
cttactgtca tgccatccgt aagatgcttt tctgtgactg gtgagtactc aaccaagtca   17100
ttctgagaat agtgtatgcg cgaccgagt  tgctcttgcc cggcgtcaac acgggataat   17160
accgcgccac atagcagaac tttaaaagtg ctcatcattg gaaaacgttc ttcggggcga   17220
aaactctcaa ggatcttacc gctgttgaga tccagttcga tgtaacccac tcgtgcaccc   17280
aactgatctt cagcatcttt tactttcacc agcgtttctg ggtgagcaaa aacaggaagg   17340
caaaatgccg caaaaaaggg aataagggcg acacggaaat gttgaatact catactcttc   17400 cttttttcaat attattgaag catttatcag ggttattgtc tcatgagcgg atacatattt   17460
```

```
gaatgtattt agaaaaataa acaaataggg gttccgcgca catttccccg aaaagtgcca   17520
cctgacgtct aagaaaccat tattatcatg acattaacct ataaaaatag gcgtatcacg   17580
aggccctttc gtcttcaaga attcggagct tttgccattc tcaccggatt cagtcgtcac   17640
tcatggtgat ttctcacttg ataaccttat ttttgacgag gggaaattaa taggttgtat   17700
tgatgttgga cgagtcggaa tcgcagaccg ataccaggat cttgccatcc tatggaactg   17760
cctcggtgag ttttctcctt cattacagaa acggctttt caaaaatatg gtattgataa   17820
tcctgatatg aataaattgc agtttcattt gatgctcgat gagtttttct aatcagaatt   17880
ggttaattgg ttgtaacact ggcagagcat tacgctgact tgacgggacg gcggcttttgt  17940 tgaataaatc gaacttttgc tgagttgaag gatcagatca cgcatcttcc cgacaacgca   18000
gaccgttccg tggcaaagca aaagttcaaa atcaccaact ggtccaccta caacaaagct   18060
ctcatcaacc gtggctccct cactttctgg ctggatgatg gggcgattca ggcctggtat   18120
gagtcagcaa caccttcttc acgaggcaga cctcagcgcc agaaggccgc cagagaggcc   18180
gagcgcggcc gtgaggcttg gacgctaggg cagggcatga aaaagcccgt agcgggctgc   18240
tacgggcgtc tgacgcggtg gaaaggggga ggggatgttg tctacatggc tctgctgtag   18300
tgagtgggtt gcgctccggc agcggtcctg atcaatcgtc acccttttctc ggtccttcaa   18360 cgttcctgac aacgagcctc ctttttcgcca atccatcgac aatcaccgcg agtccctgct   18420
cgaacgctgc gtccggaccg gcttcgtcga aggcgtctat cgcggcccgc aacagcggcg   18480
agagcggagc ctgttcaacg gtgccgccgc gctcgccggc atcgctgtcg ccggcctgct   18540
cctcaagcac ggccccaaca gtgaagtagc tgattgtcat cagcgcattg acggcgtccc   18600
cggccgaaaa accgcctcg cagaggaagc gaagctgcgc gtcggccgtt ccatctgcg    18660 gtgcgcccgg tcgcgtgccg gcatggatgc gcgcgccatc gcggtaggcg agcagcgcct   18720
gcctgaagct gcgggcattc ccgatcagaa atgagcgcca gtcgtcgtcg gctctcggca   18780
ccgaatgcgt atgattctcc gccagcatgg cttcggccag tgcgtcgagc agcgcccgct   18840
tgttcctgaa gtgccagtaa agcgccggct gctgaacccc caaccgttcc gccagtttgc   18900
gtgtcgtcag accgtctacg ccgacctcgt tcaacaggtc cagggcggca cggatcactg   18960
tattcggctg caactttgtc atgcttgaca ctttatcact gataaacata atatgtccac   19020
caacttatca gtgataaaga atccgcgcgt tcaatcggac cagcggaggc tggtccggag   19080
gccagacgtg aaacccaaca taccctgat cgtaattctg agcactgtcg cgctcgacgc    19140
tgtcggcatc ggcctgatta tgccggtgct gccgggcctc ctgcgcgatc tggttcactc   19200
gaacgacgtc accgcccact atggcattct gctggcgctg tatgcgttgg tgcaatttgc   19260
ctgcgcacct gtgctgggcg cgctgtcgga tcgtttcggg cggcggccaa tcttgctcgt   19320
ctcgctggcc ggcgccactg tcgactacgc catcatggcg acagcgcctt tccttgggt    19380 tctctatatc gggcggatcg tggccggcat caccggggcg actggggcgg tagccggcgc   19440
ttatattgcc gatatcactg atggcgatga gcgcgcgcgg cacttcggct tcatgagcgc   19500
ctgtttcggg ttcgggatgg tcgcgggacc tgtgctcggt gggctgatgg gcggtttctc   19560
cccccacgct ccgttcttcg ccgcggcagc cttgaacggc ctcaatttcc tgacgggctg   19620
tttccttttg ccggagtcgc acaaaggcga acgccggccg ttacgccggg aggctctcaa   19680
cccgctcgct tcgttccggt gggcccgggg catgaccgtc gtcgccgccc tgatggcggt   19740
cttcttcatc atgcaacttg tcggacaggt gccggccgcg ctttgggtca ttttcggcga   19800
ggatcgcttt cactgggacg cgaccacgat cggcatttcg cttgccgcat ttggcattct   19860
```

```
gcattcactc gcccaggcaa tgatcaccgg ccctgtagcc gcccggctcg gcgaaaggcg    19920
ggcactcatg ctcggaatga ttgccgacgg cacaggctac atcctgcttg ccttcgcgac    19980
acggggatgg atggcgttcc cgatcatggt cctgcttgct tcgggtggca tcggaatgcc    20040
ggcgctgcaa gcaatgttgt ccaggcaggt ggatgaggaa cgtcagggc agctgcaagg     20100 ctcactggcg gcgctcacca gcctgacctc gatcgtcgga cccctcctct tcacggcgat    20160
ctatgcggct tctataacaa cgtggaacgg gtgggcatgg attgcaggcg ctgccctcta    20220
cttgctctgc ctgccggcgc tgcgtcgcgg gcttttggagc ggcgcagggc aacgagccga   20280
tcgctgatcg tggaaacgat aggcctatgc catgcgggtc aaggcgactt ccggcaagct    20340
atacgcgccc taggagtgcg gttggaacgt tgcccagcc agatactccc gatcacgagc     20400
aggacgccga tgatttgaag cgcactcagc gtctgatcca agaacaacca tcctagcaac    20460
acggcggtcc ccgggctgag aaagcccagt aaggaaacaa ctgtaggttc gagtcgcgag    20520
atcccccgga accaaaggaa gtaggttaaa cccgctccga tcaggccgag ccacgccagg    20580
ccgagaacat tggttcctgt aggcatcggg attggcggat caaacactaa agctactgga    20640
acgagcagaa gtcctccggc cgccagttgc caggcggtaa aggtgagcag aggcacggga    20700
ggttgccact tgcgggtcag cacggttccg aacgccatgg aaaccgcccc cgccaggccc    20760
gctgcgacgc cgacaggatc tagcgctgcg tttggtgtca acaccaacag cgccacgccc    20820
gcagttccgc aaatagcccc caggaccgcc atcaatcgta tcgggctacc tagcagagcg    20880
gcagagatga acacgaccat cagcggctgc acagcgccta ccgtcgccgc gaccccgccc    20940
ggcaggcggt agaccgaaat aaacaacaag ctccagaata gcgaaatatt aagtgcgccg    21000
aggatgaaga tgcgcatcca ccagattccc gttggaatct gtcggacgat catcacgagc    21060
aataaacccg ccggcaacgc ccgcagcagc ataccggcga cccctcggcc tcgctgttcg    21120
ggctccacga aaacgccgga cagatgcgcc ttgtgagcgt ccttgggcc gtcctcctgt     21180 ttgaagaccg acagcccaat gatctcgccg tcgatgtagg cgccgaatgc cacggcatct    21240
cgcaaccgtt cagcgaacgc ctccatgggc tttttctcct cgtgctcgta acggacccg     21300 aacatctctg gagctttctt cagggccgac aatcggatct cgcggaaatc ctgcacgtcg    21360
gccgctccaa gccgtcgaat ctgagcctta atcacaattg tcaattttaa tcctctgttt    21420
atcggcagtt cgtagagcgc gccgtgcgtc ccgagcgata ctgagcgaag caagtgcgtc    21480
gagcagtgcc cgcttgttcc tgaaatgcca gtaaagcgct ggctgctgaa ccccagccg     21540 gaactgaccc cacaaggccc tagcgtttgc aatgcaccag gtcatcattg acccaggcgt    21600
gttccaccag gccgctgcct cgcaactctt cgcaggcttc gccgacctgc tcgcgccact    21660
tcttcacgcg ggtggaatcc gatccgcaca tgaggcggaa ggtttccagc ttgagcgggt    21720
acggctcccg gtgcgagctg aaatagtcga acatccgtcg ggccgtcggc gacagcttgc    21780
ggtacttctc ccatatgaat ttcgtgtagt ggtcgccagc aaacagcacg acgatttcct    21840
cgtcgatcag gacctggcaa cgggacgttt tcttgccacg gtccaggacg cggaagcggt    21900
gcagcagcga caccgattcc aggtgcccaa cgccggtcgga cgtgaagccc atcgccgtcg   21960
cctgtaggcg cgacaggcat tcctcggcct tcgtgtaata ccggccattg atcgaccagc    22020
ccaggtcctg gcaaagctcg tagaacgtga aggtgatcgg ctcgccgata ggggtgcgct    22080
tcgcgtactc caaacctgc tgccacacca gttcgtcatc gtcggcccgc agctcgacgc     22140
cggtgtaggt gatcttcacg tccttgttga cgtggaaaat gaccttgttt tgcagcgcct    22200
```

```
cgcgcgggat tttcttgttg cgcgtggtga acagggcaga gcgggccgtg tcgtttggca    22260
tcgctcgcat cgtgtccggc cacggcgcaa tatcgaacaa ggaaagctgc atttccttga    22320
tctgctgctt cgtgtgtttc agcaacgcgg cctgcttggc ctcgctgacc tgttttgcca    22380
ggtcctcgcc ggcggttttt cgcttcttgg tcgtcatagt tcctcgcgtg tcgatggtca    22440
tcgacttcgc caaacctgcc gcctcctgtt cgagacgacg cgaacgctcc acggcggccg    22500
atggcgcggg cagggcaggg ggagccagtt gcacgctgtc gcgctcgatc ttggccgtag    22560
cttgctggac catcgagccg acggactgga aggtttcgcg gggcgcacgc atgacggtgc    22620
ggcttgcgat ggtttcggca tcctcggcgg aaaaccccgc gtcgatcagt tcttgcctgt    22680
atgccttccg gtcaaacgtc cgattcattc accctccttg cgggattgcc ccgactcacg    22740
ccggggcaat gtgcccttat tcctgatttg acccgcctgg tgccttggtg tccagataat    22800
ccaccttatc ggcaatgaag tcggtcccgt agaccgtctg gccgtccttc tcgtacttgg    22860
tattccgaat cttgccctgc acgaatacca gcgaccccctt gcccaaatac ttgccgtggg    22920
cctcggcctg agagccaaaa cacttgatgc ggaagaagtc ggtgcgctcc tgcttgtcgc    22980
cggcatcgtt gcgccactct tcattaaccg ctatatcgaa aattgcttgc ggcttgttag    23040
aattgccatg acgtacctcg gtgtcacggg taagattacc gataaactgg aactgattat    23100
ggctcatatc gaaagtctcc ttgagaaagg agactctagt ttagctaaac attggttccg    23160
ctgtcaagaa ctttagcggc taaaattttg cgggccgcga ccaaaggtgc gaggggcggc    23220
ttccgctgtg tacaaccaga tattttcac caacatcctt cgtctgctcg atgagcgggg    23280
catgacgaaa catgagctgt cggagagggc aggggtttca atttcgtttt tatcagactt    23340
aaccaacggt aaggccaacc cctcgttgaa ggtgatggag gccattgccg acgccctgga    23400
aactccccta cctcttctcc tggagtccac cgaccttgac cgcgaggcac tcgcggagat    23460
tgcgggtcat cctttcaaga gcagcgtgcc gcccggatac gaacgcatca gtgtggtttt    23520
gccgtcacat aaggcgttta tcgtaaagaa atggggcgac gacacccgaa aaaagctgcg    23580
tggaaggctc tgacgccaag ggttagggct tgcacttcct tctttagccg ctaaaacggc    23640
cccttctctg cgggccgtcg gctcgcgcat catatcgaca tcctcaacgg aagccgtgcc    23700
gcgaatggca tcgggcgggt gcgctttgac agttgttttc tatcagaacc cctacgtcgt    23760
gcggttcgat tagctgtttg tcttgcaggc taaacacttt cggtatatcg tttgcctgtg    23820
cgataatgtt gctaatgatt tgttgcgtag gggttactga aaagtgagcg ggaaagaaga    23880
gtttcagacc atcaaggagc gggccaagcg caagctggaa cgcgacatgg gtgcggacct    23940
gttggccgcg ctcaacgacc cgaaaaccgt tgaagtcatg ctcaacgcgg acggcaaggt    24000
gtggcacgaa cgccttggcg agccgatgcg gtacatctgc gacatgcggc ccagccagtc    24060
gcaggcgatt atagaaacgg tggccggatt ccacggcaaa gaggtcacgc ggcattcgcc    24120
catcctggaa ggcgagttcc ccttggatgg cagccgcttt gccggccaat tgccgccggt    24180
cgtggccgcg ccaaccttg cgatccgcaa gcgcgcggtc gccatcttca cgctggaaca    24240
gtacgtcgag gcgggcatca tgacccgcga gcaatacgag gtcattaaaa gcgccgtcgc    24300
ggcgcatcga aacatcctcg tcattggcgg tactggctcg gcaagacca cgtcgtcaa    24360
cgcgatcatc aatgaaatgg tcgccttcaa cccgtctgag cgcgtcgtca tcatcgagga    24420
caccggcgaa atccagtgcg ccgcagagaa cgccgtccaa taccacacca gcatcgacgt    24480
ctcgatgacg ctgctgctca agacaacgct gcgtatgcgc cccgaccgca tcctggtcgg    24540
tgaggtacgt ggccccgaag cccttgatct gttgatggcc tggaacaccg gcatgaagg    24600
```

```
aggtgccgcc accctgcacg caaacaaccc caaagcgggc ctgagccggc tcgccatgct   24660
tatcagcatg cacccggatt caccgaaacc cattgagccg ctgattggcg aggcggttca   24720
tgtggtcgtc catatcgcca ggaccccfag cggccgtcga gtgcaagaaa ttctcgaagt   24780
tcttggttac gagaacggcc agtacatcac caaaaccctg taaggagtat ttccaatgac   24840
aacggctgtt ccgttccgtc tgaccatgaa tcgcggcatt ttgttctacc ttgccgtgtt   24900
cttcgttctc gctctcgcgt tatccgcgca tccggcgatg gcctcggaag caccggcgg    24960 cagcttgcca tatgagagct ggctgacgaa cctgcgcaac tccgtaaccg gcccggtggc   25020
cttcgcgctg tccatcatcg gcatcgtcgt cgccggcggc gtgctgatct tcggcggcga   25080
actcaacgcc ttcttccgaa ccctgatctt cctggttctg gtgatggcgc tgctggtcgg   25140
cgcgcagaac gtgatgagca ccttcttcgg tcgtggtgcc gaaatcgcgg ccctcggcaa   25200
cggggcgctg caccaggtgc aagtcgcggc ggcggatgcc gtgcgtgcgg tagcggctgg   25260
acggctcgcc taatcatggc tctgcgcacg atccccatcc gtcgcgcagg caaccgagaa   25320
aacctgttca tgggtggtga tcgtgaactg gtgatgttct cgggcctgat ggcgtttgcg   25380
ctgattttca gcgcccaaga gctgcgggcc accgtggtcg gtctgatcct gtggttcggg   25440
gcgctctatg cgttccgaat catggcgaag gccgatccga agatgcggtt cgtgtacctg   25500
cgtcaccgcc ggtacaagcc gtattacccg gcccgctcga ccccgttccg cgagaacacc   25560
aatagccaag ggaagcaata ccgatgatcc aagcaattgc gattgcaatc gcgggcctcg   25620
gcgcgcttct gttgttcatc ctctttgccc gcatccgcgc ggtcgatgcc gaactgaaac   25680
tgaaaaagca tcgttccaag gacgccggcc tggccgatct gctcaactac gccgctgtcg   25740
tcgatgacgg cgtaatcgtg ggcaagaacg gcagctttat ggctgcctgg ctgtacaagg   25800
gcgatgacaa cgcaagcagc accgaccagc agcgcgaagt agtgtccgcc cgcatcaacc   25860
aggccctcgc gggcctggga agtgggtgga tgatccatgt ggacgccgtg cggcgtcctg   25920
ctccgaacta cgcggagcgg ggcctgtcgg cgttccctga ccgtctgacg gcagcgattg   25980
aagaagagcg ctcggtcttg ccttgctcgt cggtgatgta cttcaccagc tccgcgaagt   26040
cgctcttctt gatggagcgc atgggacgt gcttggcaat cacgcgcacc ccccggccgt    26100
tttagcggct aaaaaagtca tggctctgcc ctcgggcgga ccacgcccat catgaccttg   26160
ccaagctcgt cctgcttctc ttcgatcttc gccagcaggg cgaggatcgt ggcatcaccg   26220
aaccgcgccg tgcgcgggtc gtcggtgagc cagagtttca gcaggccgcc caggcggccc   26280
aggtcgccat tgatgcgggc cagctcgcgg acgtgctcat agtccacgac gcccgtgatt   26340
ttgtagccct ggccgacggc cagcaggtag gccgacaggc tcatgccggc cgccgccgcc   26400
ttttcctcaa tcgctcttcg ttcgtctgga aggcagtaca ccttgatagg tgggctgccc   26460
ttcctggttg gcttggtttc atcagccatc cgcttgccct catctgttac gccggcggta   26520
gccggccagc ctcgcagagc aggattcccg ttgagcaccg ccaggtgcga ataagggaca   26580
gtgaagaagg aacacccgct cgcgggtggg cctacttcac ctatcctgcc cggctgacgc   26640
cgttggatac accaaggaaa gtctacacga acccttfggc aaaatcctgt atatcgtgcg   26700
aaaaaggatg gatataccga aaaaatcgct ataatgaccc cgaagcaggg ttatgcagcg   26760
gaaaagcgct gcttccctgc tgtttfgtgg aatatctacc gactggaaac aggcaaatgc   26820
aggaaattac tgaactgagg ggacaggcga gagacgatgc caaagagcta caccgacgag   26880
ctggccgagt gggttgaatc ccgcgcggcc aagaagcgcc ggcgtgatga ggctgcggtt   26940
```

```
gcgttcctgg cggtgagggc ggatgtcgag gcggcgttag cgtccggcta tgcgctcgtc   27000
accatttggg agcacatgcg ggaaacgggg aaggtcaagt tctcctacga gacgttccgc   27060
tcgcacgcca ggcggcacat caaggccaag cccgccgatg tgcccgcacc gcaggccaag   27120
gctgcggaac ccgcgccggc acccaagacg ccggagccac ggcggccgaa gcaggggggc   27180
aaggctgaaa agccggcccc cgctgcggcc ccgaccggct tcaccttcaa cccaacaccg   27240
gacaaaaagg atctactgta atggcgaaaa ttcacatggt tttgcagggc aagggcgggg   27300
tcggcaagtc ggccatcgcc gcgatcattg cgcagtacaa gatggacaag gggcagacac   27360
ccttgtgcat cgacaccgac ccggtgaacg cgacgttcga gggctacaag gccctgaacg   27420
tccgccggct gaacatcatg gccggcgacg aaattaactc gcgcaacttc gacaccctgg   27480
tcgagctgat tgcgccgacc aaggatgacg tggtgatcga caacggtgcc agctcgttcg   27540
tgcctctgtc gcattacctc atcagcaacc aggtgccggc tctgctgcaa gaaatggggc   27600
atgagctggt catccatacc gtcgtcaccg gcggccaggc tctcctggac acggtgagcg   27660
gcttcgccca gctcgccagc cagttcccgg ccgaagcgct tttcgtggtc tggctgaacc   27720
cgtattgggg gcctatcgag catgagggca agagctttga gcagatgaag gcgtacacgg   27780
ccaacaaggc ccgcgtgtcg tccatcatcc agattccggc cctcaaggaa gaaacctacg   27840
gccgcgattt cagcgacatg ctgcaagagc ggctgacgtt cgaccaggcg ctggccgatg   27900
aatcgctcac gatcatgacg cggcaacgcc tcaagatcgt gcggcgcggc ctgtttgaac   27960
agctcgacgc ggcggccgtg ctatgagcga ccagattgaa gagctgatcc gggagattgc   28020
ggccaagcac ggcatcgccg tcggccgcga cgacccggtg ctgatcctgc ataccatcaa   28080
cgcccggctc atggccgaca gtgcggccaa gcaagaggaa tccttgccg cgttcaagga   28140 agagctggaa gggatcgccc atcgttgggg cgaggacgcc aaggccaaag cggagcggat   28200
gctgaacgcg gccctggcgg ccagcaagga cgcaatggcg aaggtaatga aggacagcgc   28260
cgcgcaggcg gccgaagcga tccgcaggga aatcgacgac ggccttggcc gccagctcgc   28320
ggccaaggtc gcggacgcgc ggcgcgtggc gatgatgaac atgatcgccg gcggcatggt   28380
gttgttcgcg gccgccctgg tggtgtgggc ctcgttatga atcgcagagg cgcagatgaa   28440
aaagcccggc gttgccgggc tttgttttg cgttagctgg gcttgtttga caggcccaag   28500
ctctgactgc gcccgcgctc gcgctcctgg gcctgtttct tctcctgctc ctgcttgcgc   28560
atcagggcct ggtgccgtcg ggctgcttca cgcatcgaat cccagtcgcc ggccagctcg   28620
ggatgctccg cgcgcatctt gcgcgtcgcc agttcctcga tcttgggcgc gtgaatgccc   28680
atgccttcct tgatttcgcg caccatgtcc agccgcgtgt gcagggtctg caagcgggct   28740
tgctgttggg cctgctgctg ctgccaggcg gcctttgtac gcggcaggga cagcaagccg   28800
ggggcattgg actgtagctg ctgcaaacgc gcctgctgac ggtctacgag ctgttctagg   28860
cggtcctcga tgcgctccac ctggtcatgc tttgcctgca cgtagagcgc aagggtctgc   28920
tggtaggtct gctcgatggg cgcggattct aagagggcct gctgttccgt ctcggcctcc   28980
tgggccgcct gtagcaaatc ctcgccgctg ttgccgctgg actgctttac tgccggggac   29040
tgctgttgcc ctgctcgcgc cgtcgtcgca gttcggcttg cccccactcg attgactgct   29100
tcatttcgag ccgcagcgat gcgatctcgg attgcgtcaa cggacggggc agcgcggagg   29160
tgtccggctt ctccttgggt gagtcggtcg atgccatagc caaggttttc cttccaaaat   29220
gcgtccattg ctggaccgtg tttctcattg atgcccgcaa gcatcttcgg cttgaccgcc   29280
aggtcaagcg cgccttcatg ggcggtcatg acggacgccg ccatgacctt gccgccgttg   29340
```

```
ttctcgatgt agccgcgtaa tgaggcaatg gtgccgccca tcgtcagcgt gtcatcgaca   29400
acgatgtact tctggccggg gatcacctcc ccctcgaaag tcgggttgaa cgccaggcga   29460
tgatctgaac cggctccggt tcgggcgacc ttctcccgct gcacaatgtc cgtttcgacc   29520
tcaaggccaa ggcggtcggc cagaacgacc gccatcatgg ccggaatctt gttgttcccc   29580
gccgcctcga cggcgaggac tggaacgatg cggggcttgt cgtcgccgat cagcgtcttg   29640
agctgggcaa cagtgtcgtc cgaaatcagg cgctcgacca aattaagcgc cgcttccgcg   29700
tcgccctgct tcgcagcctg gtattcaggc tcgttggtca agaaccaag gtcgccgttg    29760 cgaaccacct tcgggaagtc tccccacggt gcgcgctcgg ctctgctgta gctgctcaag   29820
acgcctccct ttttagccgc taaaactcta acgagtgcgc ccgcgactca acttgacgct   29880 tcggcactt acctgtgcct tgccacttgc gtcataggtg atgcttttcg cactcccgat    29940
ttcaggtact ttatcgaaat ctgaccgggc gtgcattaca aagttcttcc ccacctgttg   30000
gtaaatgctg ccgctatctg cgtggacgat gctgccgtcg tggcgctgcg acttatcggc   30060
cttttgggcc atatagatgt tgtaaatgcc aggtttcagg gccccggctt tatctacctt   30120
ctggttcgtc catgcgcctt ggttctcggt ctggacaatt cttttgcccat tcatgaccag   30180 gaggcggtgt ttcattgggt gactcctgac ggttgcctct ggtgttaaac gtgtcctggt   30240
cgcttgccgg ctaaaaaaa gccgacctcg gcagttcgag gccggctttc cctagagccg   30300
ggcgcgtcaa ggttgttcca tctattttag tgaactgcgt tcgatttatc agttactttc   30360
ctcccgcttt gtgtttcctc ccactcgttt ccgcgtctag ccgacccctc aacatagcgg   30420
cctcttcttg ggctgccttt gcctcttgcc gcgcttcgtc acgctcggct tgcaccgtcg   30480
taaagcgctc ggcctgcctg gccgcctctt gcgccgccaa cttcctttgc tcctggtggg   30540
cctcggcgtc ggcctgcgcc ttcgctttca ccgctgccaa ctccgtgcgc aaactctccg   30600
cttcgcgcct ggtggcgtcg cgctcgccgc gaagcgcctg catttcctgg ttggccgcgt   30660
ccagggtctt gcggctctct tctttgaatg cgcgggcgtc ctggtgagcg tagtccagct   30720
cggcgcgcag ctcctgcgct cgacgctcca cctcgtcggc ccgctgcgtc gccagcgcgg   30780
cccgctgctc ggctcctgcc agggcggtgc gtgcttcggc cagggcttgc cgctggcgtg   30840
cggccagctc ggccgcctcg gcggcctgct gctctagcaa tgtaacgcgc gcctgggctt   30900
cttccagctc gcgggcctgc gcctcgaagg cgtcggccag ctccccgcgc acggcttcca   30960
actcgttgcg ctcacgatcc cagccggctt gcgctgcctg caacgattca ttggcaaggg   31020
cctgggcggc ttgccagagg gcggccacgg cctggttgcc ggcctgctgc accgcgtccg   31080
gcacctggac tgccagcggg gcggcctgcg ccgtgcgctg gcgtcgccat tcgcgcatgc   31140
cggcgctggc gtcgttcatg ttgacgcggg cggccttacg cactgcatcc acggtcggga   31200
agttctcccg gtcgccttgc tcgaacagct cgtccgcagc cgcaaaaatg cggtcgcgcg   31260
tctctttgtt cagttccatg ttggctccgg taattggtaa gaataataat actcttacct   31320
accttatcag cgcaagagtt tagctgaaca gttctcgact taacggcagg tttttagcg    31380 gctgaagggc aggcaaaaaa agccccgcac ggtcggcggg ggcaaagggt cagcgggaag   31440
gggattagcg ggcgtcgggc ttcttcatgc gtcgggccg cgcttcttgg gatgagcac     31500 gacgaagcgc gcacgcgcat cgtcctcggc cctatcggcc cgcgtcgcgg tcaggaactt   31560
gtcgcgcgct aggtcctccc tggtgggcac caggggcatg aactcggcct gctcgatgta   31620
ggtccactcc atgaccgcat cgcagtcgag gccgcgttcc ttcaccgtct cttgcaggtc   31680
```

```
gcggtacgcc cgctcgttga gcggctggta acgggccaat tggtcgtaaa tggctgtcgg   31740
ccatgagcgg cctttcctgt tgagccagca gccgacgacg aagccggcaa tgcaggcccc   31800
tggcacaacc aggccgacgc cggggggcagg ggatggcagc agctcgccaa ccaggaaccc   31860
cgccgcgatg atgccgatgc cggtcaacca gcccttgaaa ctatccggcc ccgaaacacc   31920
cctgcgcatt gcctggatgc tgcgccggat agcttgcaac atcaggagcc gtttcttttg   31980
ttcgtcagtc atggtccgcc ctcaccagtt gttcgtatcg gtgtcggacg aactgaaatc   32040
gcaagagctg ccggtatcgg tccagccgct gtccgtgtcg ctgctgccga agcacggcga   32100
ggggtccgcg aacgccgcag acggcgtatc cggccgcagc gcatcgccca gcatggcccc   32160
ggtcagcgag ccgccggcca ggtagcccag catggtgctg ttggtcgccc cggccaccag   32220
ggccgacgtg acgaaatcgc cgtcattccc tctggattgt tcgctgctcg gcggggcagt   32280
gcgccgcgcc ggcggcgtcg tggatggctc gggttggctg gcctgcgacg gccggcgaaa   32340
ggtgcgcagc agctcgttat cgaccggctg cggcgtcggg gccgccgcct tgcgctgcgg   32400
tcggtgttcc ttcttcggct cgcgcagctt gaacagcatg atcgcggaaa ccagcagcaa   32460
cgccgcgcct acgcctcccg cgatgtagaa cagcatcgga ttcattcttc ggtcctcctt   32520
gtagcggaac cgttgtctgt gcggcgcggg tggcccgcgc cgctgtcttt ggggatcagc   32580
cctcgatgag cgcgaccagt ttcacgtcgg caaggttcgc ctcgaactcc tggccgtcgt   32640
cctcgtactt caaccaggca tagccttccg ccggcggccg acggttgagg ataaggcggg   32700
cagggcgctc gtcgtgctcg acctggacga tggccttttt cagcttgtcc gggtccggct   32760
ccttcgcgcc cttttccttg gcgtccttac cgtcctggtc gccgtcctcg ccgtcctggc   32820
cgtcgccggc ctccgcgtca cgctcggcat cagtctggcc gttgaaggca tcgacggtgt   32880
tgggatcgcg gcccttctcg tccaggaact cgcgcagcag cttgaccgtg ccgcgcgtga   32940
tttcctgggt gtcgtcgtca agccacgcct cgacttcctc cgggcgcttc ttgaaggccg   33000
tcaccagctc gttcaccacg gtcacgtcgc gcacgcggcc ggtgttgaac gcatcggcga   33060
tcttctccgg caggtccagc agcgtgacgt gctgggtgat gaacgccggc gacttgccga   33120
tttccttggc gatatcgcct tcttcttgc ccttcgccag ctcgcggcca atgaagtcgg   33180
caatttcgcg cggggtcagc tcgttgcgtt gcaggttctc gataacctgg tcggcttcgt   33240
tgtagtcgtt gtcgatgaac gccgggatgg acttcttgcc ggcccacttc gagccacggt   33300
agcggcgggc gccgtgattg atgatatagc ggcccggctg ctcctggttc tcgcgcaccg   33360
aaatgggtga cttcaccccg cgctctttga tcgtggcacc gatttccgcg atgctctccg   33420
gggaaaagcc ggggttgtcg gccgtccgcg gctgatgcgg atcttcgtcg atcaggtcca   33480
ggtccagctc gatagggccg gaaccgcccct gagacgccgc aggagcgtcc aggaggctcg   33540
acaggtcgcc gatgctatcc aacccccaggc cggacggctg cgccgcgcct gcggcttcct   33600
gagcggccgc agcggtgttt ttcttggtgg tcttggcttg agccgcagtc attgggaaat   33660
ctccatcttc gtgaacacgt aatcagccag ggcgcgaacc tctttcgatg ccttgcgcgc   33720
ggccgttttc ttgatcttcc agaccggcac accggatgcg agggcatcgg cgatgctgct   33780
gcgcaggcca acgtggccg gaatcatcat cttggggtac gcggccagca gctcggcttg   33840
gtggcgcgcg tggcgcggat ccgcgcatc gaccttgctg gcaccatgc caaggaattg   33900 cagcttggcg ttcttctggc gcacgttcgc aatggtcgtg accatcttct tgatgccctg   33960
gatgctgtac gcctcaagct cgatgggggga cagcacatag tcggccgcga agagggcggc   34020
cgccaggccg acgccaaggg tcggggccgt gtcgatcagg cacacgtcga agccttggtt   34080
```

```
cgccagggcc ttgatgttcg ccccgaacag ctcgcgggcg tcgtccagcg acagccgttc   34140
ggcgttcgcc agtaccgggt tggactcgat gagggcgagg cgcgcggcct ggccgtcgcc   34200
ggctgcgggt gcggtttcgg tccagccgcc ggcagggaca gcgccgaaca gcttgcttgc   34260
atgcaggccg gtagcaaagt ccttgagcgt gtaggacgac ttgccctggg ggtccaggtc   34320
gatcacggca acccgcaagc cgcgctcgaa aaagtcgaag gcaagatgca caagggtcga   34380
agtcttgccg acgccgcctt tctggttggc cgtgaccaaa gttttcatcg tttggtttcc   34440
tgttttttct tggcgtccgc ttcccacttc cggacgatgt acgcctgatg ttccggcaga   34500
accgccgtta cccgcgcgta cccctcgggc aagttcttgt cctcgaacgc ggcccacacg   34560
cgatgcaccg cttgcgacac tgcgcccctg gtcagtccca gcgacgttgc gaacgtcgcc   34620
tgtggcttcc catcgactaa gacgccccgc gctatctcga tggtctgctg ccccacttcc   34680
agcccctgga tcgcctcctg gaactggctt tcggtaagcc gtttcttcat ggataacacc   34740
cataatttgc tccgcgcctt ggttgaacat agcggtgaca gccgccagca catgagagaa   34800
gtttagctaa acatttctcg cacgtcaaca cctttagccg ctaaaactcg tccttggcgt   34860
aacaaaacaa aagcccggaa accgggcttt cgtctcttgc cgcttatggc tctgcacccg   34920
gctccatcac caacaggtcg cgcacgcgct tcactcggtt gcggatcgac actgccagcc   34980
caacaaagcc ggttgccgcc gccgccagga tcgcgccgat gatgccggcc acaccggcca   35040
tcgcccacca ggtcgccgcc ttccggttcc attcctgctg gtactgcttc gcaatgctgg   35100
acctcggctc accataggct gaccgctcga tggcgtatgc cgcttctccc cttggcgtaa   35160
aacccagcgc cgcaggcggc attgccatgc tgcccgccgc tttcccgacc acgacgcgcg   35220
caccaggctt gcggtccaga ccttcggcca cggcagctg cgcaaggaca taatcagccg   35280
ccgacttggc tccacgcgcc tcgatcagct cttgcactcg cgcgaaatcc ttggcctcca   35340
cggccgccat gaatcgcgca cgcggcgaag gctccgcagg gccggcgtcg tgatcgccgc   35400
cgagaatgcc cttcaccaag ttcgacgaca cgaaaatcat gctgacggct atcaccatca   35460
tgcagacgga tcgcacgaac ccgctgaatt gaacacgagc acggcacccg cgaccactat   35520
gccaagaatg cccaaggtaa aaattgccgg ccccgccatg aagtccgtga atgccccgac   35580
ggccgaagtg aagggcaggc cgccacccag gccgccgccc tcactgcccg gcacctggtc   35640
gctgaatgtc gatgccagca cctgcggcac gtcaatgctt ccgggcgtcg cgctcgggct   35700
gatcgcccat cccgttactg ccccgatccc ggcaatggca aggactgcca gcgctgccat   35760
ttttggggtg aggccgttcg cggccgaggg gcgcagcccc tgggggatg ggaggcccgc   35820 gttagcgggc cgggagggtt cgagaagggg gggcaccccc cttcggcgtg cgcggtcacg   35880
cgcacagggc gcagccctgg ttaaaaacaa ggtttataaa tattggttta aaagcaggtt   35940
aaaagacagg ttagcggtgg ccgaaaaacg ggcggaaacc cttgcaaatg ctggattttc   36000
tgcctgtgga cagcccctca aatgtcaata ggtgcgcccc tcatctgtca gcactctgcc   36060
cctcaagtgt caaggatcgc gcccctcatc tgtcagtagt cgcgcccctc aagtgtcaat   36120
accgcagggc acttatcccc aggcttgtcc acatcatctg tgggaaactc gcgtaaaatc   36180
aggcgttttc gccgatttgc gaggctggcc agctccacgt cgccgccga aatcgagcct   36240 gcccctcatc tgtcaacgcc gcgccgggtg agtcggcccc tcaagtgtca acgtccgccc   36300
ctcatctgtc agtgagggcc aagttttccg cgaggtatcc acaacgccgg cggccgcggt   36360
gtctcgcaca cggcttcgac ggcgtttctg gcgcgtttgc agggccatag acggccgcca   36420
```

```
gcccagcggc gagggcaacc agcccggtga gcgtcggaaa ggcgctggaa gccccgtagc    36480
gacgcggaga ggggcgagac aagccaaggg cgcaggctcg atgcgcagca cgacatagcc    36540
ggttctcgca aggacgagaa tttccctgcg gtgcccctca agtgtcaatg aaagtttcca    36600
acgcgagcca ttcgcgagag ccttgagtcc acgctagatg agagctttgt tgtaggtgga    36660
ccagttggtg atttttgaact tttgctttgc cacggaacgg tctgcgttgt cgggaagatg    36720
cgtgatctga tccttcaact cagcaaaagt tcgatttatt caacaaagcc acgttgtgtc    36780
tcaaaatctc tgatgttaca ttgcacaaga taaaaatata tcatcatgaa caataaaact    36840
gtctgcttac ataaacagta atacaagggg tgttatgagc catattcaac gggaaacgtc    36900
ttgctcgac                                                           36909

<210> SEQ ID NO 8
<211> LENGTH: 13019
<212> TYPE: DNA
<213> ORGANISM: artificial sequence
<220> FEATURE:
<223> OTHER INFORMATION: vector used to construct PHP23236

<400> SEQUENCE: 8
gttacccgga ccgaagctta gcccgggcat gcctgcagtg cagcgtgacc cggtcgtgcc      60
cctctctaga gataatgagc attgcatgtc taagttataa aaaattacca catattttt     120 ttgtcacact tgtttgaagt gcagtttatc tatcttata catatattta aactttactc     180
tacgaataat ataatctata gtactacaat aatatcagtg ttttagagaa tcatataaat    240
gaacagttag acatggtcta aaggacaatt gagtattttg acaacaggac tctacagttt    300
tatcttttta gtgtgcatgt gttctccttt tttttttgcaa atagcttcac ctatataata    360
cttcatccat tttattagta catccattta gggtttaggg ttaatggttt ttatagacta    420
atttttttag tacatctatt ttattctatt ttagcctcta aattaagaaa actaaaactc    480
tattttagtt tttttattta ataatttaga tataaaaatag aataaaataa agtgactaaa    540
aattaaacaa atacccttta agaaattaaa aaaactaagg aaacatttt cttgtttcga    600 gtagataatg ccagcctgtt aaacgccgtc gacgagtcta acggacacca accagcgaac    660
cagcagcgtc gcgtcgggcc aagcgaagca gacggcacgg catctctgtc gctgcctctg    720 gaccctctc gagagttccg ctccaccgtt ggacttgctc cgctgtcggc atccagaaat    780
tgcgtggcgg agcggcagac gtgagccggc acggcaggcg gcctcctcct cctctcacgg    840
cacggcagct acgggggatt cctttcccac cgctccttcg cttttcccttc ctcgcccgcc    900 gtaataaata gacaccccct ccacaccctc tttccccaac ctcgtgttgt tcggagcgca    960
cacacacaca accagatctc ccccaaatcc acccgtcggc acctccgctt caaggtacgc   1020
cgctcgtcct cccccccccc ccctctctac cttctctaga tcggcgttcc ggtccatggt   1080
tagggcccgg tagttctact tctgttcatg tttgtgttag atccgtgttt gtgttagatc   1140
cgtgctgcta gcgttcgtac acggatgcga cctgtacgtc agacacgttc tgattgctaa   1200
cttgccagtg tttctctttg gggaatcctg ggatggctct agccgttccg cagacgggat   1260
cgatttcatg attttttttg tttcgttgca tagggtttgg tttgcccttt ccttttattt   1320
caatatatgc cgtgcacttg tttgtcgggt catctttca tgcttttttt tgtcttggtt   1380
gtgatgatgt ggtctggttg ggcggtcgtt ctagatcgga gtagaattct gtttcaaact   1440
acctggtgga tttattaatt ttggatctgt atgtgtgtgc catacatatt catagttacg   1500
aattgaagat gatggatgga aatatcgatc taggataggt atacatgttg atgcgggttt   1560
```

-continued

```
tactgatgca tatacagaga tgcttttgt tcgcttggtt gtgatgatgt ggtgtggttg    1620
ggcggtcgtt cattcgttct agatcggagt agaatactgt ttcaaactac ctggtgtatt   1680
tattaatttt ggaactgtat gtgtgtgtca tacatcttca tagttacgag tttaagatgg   1740
atggaaatat cgatctagga taggtataca tgttgatgtg ggttttactg atgcatatac   1800
atgatggcat atgcagcatc tattcatatg ctctaacctt gagtacctat ctattataat   1860
aaacaagtat gttttataat tattttgatc ttgatatact tggatgatgg catatgcagc   1920
agctatatgt ggattttttt agccctgcct tcatacgcta tttatttgct tggtactgtt   1980
tcttttgtcg atgctcaccc tgttgtttgg tgttacttct gcaggtcgac tctagaggat   2040
ccacaagttt gtacaaaaaa gctgaacgag aaacgtaaaa tgatataaat atcaatatat   2100
taaattagat tttgcataaa aaacagacta cataatactg taaaacacaa catatccagt   2160
cactatggcg gccgcattag gcaccccagg ctttacactt tatgcttccg gctcgtataa   2220
tgtgtggatt ttgagttagg atttaaatac gcgttgatcc ggcttactaa agccagata    2280 acagtatgcg tatttgcgcg ctgatttttg cggtataaga atatatactg atatgtatac   2340
ccgaagtatg tcaaaaagag gtatgctatg aagcagcgta ttacagtgac agttgacagc   2400
gacagctatc agttgctcaa ggcatatatg atgtcaatat ctccggtctg gtaagcacaa   2460
ccatgcagaa tgaagcccgt cgtctgcgtg ccgaacgctg gaaagcggaa atcaggaag   2520 ggatggctga ggtcgcccgg tttattgaaa tgaacggctc ttttgctgac gagaacaggg   2580
gctggtgaaa tgcagtttaa ggtttacacc tataaaagag agagccgtta tcgtctgttt   2640
gtggatgtac agagtgatat cattgacacg cccggtcgac ggatggtgat cccctggcc   2700 agtgcacgtc tgctgtcaga taaagtctcc cgtgaacttt accggtggt gcatatcggg   2760 gatgaaagct ggcgcatgat gaccaccgat atggccagtg tgccggtctc cgttatcggg   2820
gaagaagtgg ctgatctcag ccaccgcgaa aatgacatca aaaacgccat taacctgatg   2880
ttctggggaa tataaatgtc aggctccctt atacacagcc agtctgcagg tcgaccatag   2940
tgactggata tgttgtgttt tacagtatta tgtagtctgt tttttatgca aaatctaatt   3000
taatatattg atatttatat cattttacgt ttctcgttca gctttcttgt acaaagtggt   3060
gttaacctag acttgtccat cttctggatt ggccaactta attaatgtat gaaataaaag   3120
gatgcacaca tagtgacatg ctaatcacta taatgtgggc atcaaagttg tgtgttatgt   3180
gtaattacta gttatctgaa taaaagagaa agagatcatc catatttctt atcctaaatg   3240
aatgtcacgt gtctttataa ttctttgatg aaccagatgc atttcattaa ccaaatccat   3300
atacatataa atattaatca tatataatta atatcaattg ggttagcaaa acaaatctag   3360
tctaggtgtg ttttgcgaat tgcggccgcc accgcggtgg agctcgaatt ccggtccggg   3420
tcacctttgt ccaccaagat ggaactgcgg ccgctcatta attaagtcag gcgcgcctct   3480
agttgaagac acgttcatgt cttcatcgta agaagacact cagtagtctt cggccagaat   3540
ggccatctgg attcagcagg cctagaaggc catttaaatc ctgaggatct ggtcttccta   3600
aggacccggg atatcggacc gattaaactt taattcggtc cgaagcttgc atgcctgcag   3660
tgcagcgtga cccggtcgtg cccctctcta gagataatga gcattgcatg tctaagttat   3720
aaaaaattac cacatatttt ttttgtcaca cttgtttgaa gtgcagttta tctatcttta   3780
tacatatatt taaactttac tctacgaata atataatcta tagtactaca ataatatcag   3840
tgttttagag aatcatataa atgaacagtt agacatggtc taaaggacaa ttgagtattt   3900
```

```
tgacaacagg actctacagt tttatctttt tagtgtgcat gtgttctcct ttttttttgc    3960
aaatagcttc acctatataa tacttcatcc attttattag tacatccatt tagggtttag    4020
ggttaatggt ttttatagac taatttttt agtacatcta ttttattcta ttttagcctc    4080
taaattaaga aaactaaaac tctatttag tttttttatt taataattta gatataaaat    4140
agaataaaat aaagtgacta aaattaaac aaatacccctt taagaaatta aaaaaactaa    4200
ggaaacattt ttcttgtttc gagtagataa tgccagcctg ttaaacgccg tcgacgagtc    4260
taacggacac caaccagcga accagcagcg tcgcgtcggg ccaagcgaag cagacggcac    4320
ggcatctctg tcgctgcctc tggacccctc tcgagagttc cgctccaccg ttggacttgc    4380
tccgctgtcg gcatccagaa attgcgtggc ggagcggcag acgtgagccg gcacggcagg    4440
cggcctcctc ctcctctcac ggcaccggca gctacggggg attcctttcc caccgctcct    4500
tcgctttccc ttcctcgccc gccgtaataa atagacaccc cctccacacc ctctttcccc    4560
aacctcgtgt tgttcggagc gcacacacac acaaccagat ctcccccaaa tccacccgtc    4620
ggcacctccg cttcaaggta cgccgctcgt cctccccccc cccctctct accttctcta    4680 gatcggcgtt ccggtccatg catggttagg gcccggtagt tctacttctg ttcatgtttg    4740
tgttagatcc gtgtttgtgt tagatccgtg ctgctagcgt tcgtacacgg atgcgacctg    4800
tacgtcagac acgttctgat tgctaacttg ccagtgtttc tctttgggga atcctgggat    4860
ggctctagcc gttccgcaga cgggatcgat ttcatgattt tttttgtttc gttgcatagg    4920
gtttggtttg cccttttcct ttatttcaat atatgccgtg cacttgtttg tcgggtcatc    4980
ttttcatgct ttttttttgtc ttggttgtga tgatgtggtc tggttgggcg gtcgttctag    5040
atcggagtag aattctgttt caaactacct ggtggattta ttaattttgg atctgtatgt    5100
gtgtgccata catattcata gttacgaatt gaagatgatg gatggaaata tcgatctagg    5160
ataggtatac atgttgatgc gggttttact gatgcatata cagagatgct ttttgttcgc    5220
ttggttgtga tgatgtggtg tggttgggcg gtcgttcatt cgttctagat cggagtagaa    5280
tactgtttca aactacctgg tgtatttatt aattttggaa ctgtatgtgt gtgtcataca    5340
tcttcatagt tacgagttta agatggatgg aaatatcgat ctaggatagg tatacatgtt    5400
gatgtgggtt ttactgatgc atatacatga tggcatatgc agcatctatt catatgctct    5460
aaccttgagt acctatctat tataataaac aagtatgttt tataattatt ttgatcttga    5520
tatacttgga tgatggcata tgcagcagct atatgtggat ttttttagcc ctgccttcat    5580
acgctattta tttgcttggt actgtttctt ttgtcgatgc tcaccctgtt gtttggtgtt    5640
acttctgcag gtcgacttta acttagccta ggatccacac gacaccatgt cccccgagcg    5700
ccgccccgtc gagatccgcc cggccaccgc cgccgacatg gccgccgtgt gcgacatcgt    5760
gaaccactac atcgagacct ccaccgtgaa cttccgcacc gagccgcaga ccccgcagga    5820
gtggatcgac gacctggagc gcctccagga ccgctacccg tggctcgtgg ccgaggtgga    5880
gggcgtggtg gccggcatcg cctacgccgg cccgtggaag gccgcaacg cctacgactg    5940 gaccgtggag tccaccgtgt acgtgtccca ccgccaccag cgcctcggcc tcggctccac    6000
cctctacacc cacctcctca agagcatgga ggcccagggc ttcaagtccg tggtggccgt    6060
gatcggcctc ccgaacgacc cgtccgtgcg cctccacgag gccctcggct acaccgcccg    6120 cggcacccctc cgcgccgccg gctacaagca cggcggctgg cacgacgtcg gcttctggca    6180
gcgcgacttc gagctgccgg ccccgccgcg ccggtgcgc ccggtgacgc agatctgagt    6240
cgaaacctag acttgtccat cttctggatt ggccaactta attaatgtat gaaataaaag    6300
```

```
gatgcacaca tagtgacatg ctaatcacta taatgtgggc atcaaagttg tgtgttatgt   6360
gtaattacta gttatctgaa taaaagagaa agagatcatc catatttctt atcctaaatg   6420
aatgtcacgt gtctttataa ttctttgatg aaccagatgc atttcattaa ccaaatccat   6480
atacatataa atattaatca tatataatta atatcaattg ggttagcaaa acaaatctag   6540
tctaggtgtg ttttgcgaat tgcggccgcc accgcggtgg agctcgaatt cattccgatt   6600
aatcgtggcc tcttgctctt caggatgaag agctatgttt aaacgtgcaa gcgctactag   6660
acaattcagt acattaaaaa cgtccgcaat gtgttattaa gttgtctaag cgtcaatttg   6720
tttacaccac aatatatcct gccaccagcc agccaacagc tccccgaccg gcagctcggc   6780
acaaaatcac cactcgatac aggcagccca tcagtccggg acggcgtcag cgggagagcc   6840
gttgtaaggc ggcagacttt gctcatgtta ccgatgctat tcggaagaac ggcaactaag   6900
ctgccgggtt tgaaacacgg atgatctcgc ggagggtagc atgttgattg taacgatgac   6960
agagcgttgc tgcctgtgat caaatatcat ctccctcgca gagatccgaa ttatcagcct   7020
tcttattcat ttctcgctta accgtgacag gctgtcgatc ttgagaacta tgccgacata   7080
ataggaaatc gctggataaa gccgctgagg aagctgagtg gcgctatttc tttagaagtg   7140
aacgttgacg atcgtcgacc gtaccccgat gaattaattc ggacgtacgt tctgaacaca   7200
gctggatact tacttgggcg attgtcatac atgacatcaa caatgtaccc gtttgtgtaa   7260
ccgtctcttg gaggttcgta tgacactagt ggttcccctc agcttgcgac tagatgttga   7320
ggcctaacat tttattagag agcaggctag ttgcttagat acatgatctt caggccgtta   7380
tctgtcaggg caagcgaaaa ttggccattt atgacgacca atgccccgca gaagctccca   7440
tctttgccgc catagacgcc gcgccccct tttggggtgt agaacatcct tttgccagat   7500
gtggaaaaga agttcgttgt cccattgttg gcaatgacgt agtagccggc gaaagtgcga   7560
gacccatttg cgctatatat aagcctacga tttccgttgc gactattgtc gtaattggat   7620
gaactattat cgtagttgct ctcagagttg tcgtaatttg atggactatt gtcgtaattg   7680
cttatggagt tgtcgtagtt gcttggagaa atgtcgtagt tggatgggga gtagtcatag   7740
ggaagacgag cttcatccac taaaacaatt ggcaggtcag caagtgcctg ccccgatgcc   7800
atcgcaagta cgaggcttag aaccaccttc aacagatcgc gcatagtctt ccccagctct   7860
ctaacgcttg agttaagccg cgccgcgaag cggcgtcggc ttgaacgaat tgttagacat   7920
tatttgccga ctaccttggt gatctcgcct ttcacgtagt gaacaaattc ttccaactga   7980
tctgcgcgcg aggccaagcg atcttcttgt ccaagataag cctgcctagc ttcaagtatg   8040
acgggctgat actgggccgg caggcgctcc attgcccagt cggcagcgac atccttcggc   8100
gcgattttgc cggttactgc gctgtaccaa atgcgggaca acgtaagcac tacatttcgc   8160
tcatcgccag cccagtcggg cggcgagttc catagcgtta aggtttcatt tagcgcctca   8220
aatagatcct gttcaggaac cggatcaaag agttcctccg ccgctggacc taccaaggca   8280
acgctatgtt ctcttgcttt tgtcagcaag atagccagat caatgtcgat cgtggctggc   8340
tcgaagatac ctgcaagaat gtcattgcgc tgccattctc caaattgcag ttcgcgctta   8400
gctggataac gccacggaat gatgtcgtcg tgcacaacaa tggtgacttc tacagcgcgg   8460
agaatctcgc tctctccagg ggaagccgaa gtttccaaaa ggtcgttgat caaagctcgc   8520
cgcgttgttt catcaagcct tacagtcacc gtaaccagca aatcaatatc actgtgtggc   8580
ttcaggccgc catccactgc ggagccgtac aaatgtacgg ccagcaacgt cggttcgaga   8640
```

```
tggcgctcga tgacgccaac tacctctgat agttgagtcg atacttcggc gatcaccgct    8700
tccctcatga tgtttaactc ctgaattaag ccgcgccgcg aagcggtgtc ggcttgaatg    8760
aattgttagg cgtcatcctg tgctcccgag aaccagtacc agtacatcgc tgtttcgttc    8820
gagacttgag gtctagtttt atacgtgaac aggtcaatgc cgccgagagt aaagccacat    8880
tttgcgtaca aattgcaggc aggtacattg ttcgtttgtg tctctaatcg tatgccaagg    8940
agctgtctgc ttagtgccca cttttcgca aattcgatga gactgtgcgc gactcctttg    9000
cctcggtgcg tgtgcgacac aacaatgtgt tcgatagagg ctagatcgtt ccatgttgag    9060
ttgagttcaa tcttcccgac aagctcttgg tcgatgaatg cgccatagca agcagagtct    9120
tcatcagagt catcatccga gatgtaatcc ttccggtagg ggctcacact tctggtagat    9180
agttcaaagc cttggtcgga taggtgcaca tcgaacactt cacgaacaat gaaatggttc    9240
tcagcatcca atgtttccgc cacctgctca gggatcaccg aaatcttcat atgacgccta    9300
acgcctggca cagcggatcg caaacctggc gcggcttttg gcacaaaagg cgtgacaggt    9360
ttgcgaatcc gttgctgcca cttgttaacc cttttgccag atttggtaac tataatttat    9420
gttagaggcg aagtcttggg taaaaactgg cctaaaattg ctggggattt caggaaagta    9480
aacatcacct tccggctcga tgtctattgt agatatatgt agtgtatcta cttgatcggg    9540
ggatctgctg cctcgcgcgt ttcggtgatg acggtgaaaa cctctgacac atgcagctcc    9600
cggagacggt cacagcttgt ctgtaagcgg atgccgggag cagacaagcc cgtcagggcg    9660
cgtcagcggg tgttggcggg tgtcggggcg cagccatgac ccagtcacgt agcgatagcg    9720
gagtgtatac tggcttaact atgcggcatc agagcagatt gtactgagag tgcaccatat    9780
gcggtgtgaa ataccgcaca gatgcgtaag gagaaaatac cgcatcaggc gctcttccgc    9840
ttcctcgctc actgactcgc tgcgctcggt cgttcggctg cggcgagcgg tatcagctca    9900
ctcaaaggcg gtaatacggt tatccacaga atcagggat aacgcaggaa agaacatgtg    9960
agcaaaaggc cagcaaaagg ccaggaaccg taaaaaggcc gcgttgctgg cgttttccca   10020
taggctccgc cccctgacg agcatcacaa aaatcgacgc tcaagtcaga ggtggcgaaa   10080
cccgacagga ctataaagat accaggcgtt tccccctgga agctccctcg tgcgctctcc   10140
tgttccgacc ctgccgctta ccggatacct gtccgccttt ctcccttcgg gaagcgtggc   10200
gctttctcat agctcacgct gtaggtatct cagttcggtg taggtcgttc gctccaagct   10260
gggctgtgtg cacgaacccc ccgttcagcc cgaccgctgc gccttatccg gtaactatcg   10320
tcttgagtcc aacccggtaa gacacgactt atcgccactg gcagcagcca ctggtaacag   10380
gattagcaga gcgaggtatg taggcggtgc tacagagttc ttgaagtggt ggcctaacta   10440
cggctacact agaaggacag tatttggtat ctgcgctctg ctgaagccag ttaccttcgg   10500
aaaaagagtt ggtagctctt gatccggcaa acaaaccacc gctggtagcg gtggtttttt   10560
tgtttgcaag cagcagatta cgcgcagaaa aaaaggatct caagaagatc ctttgatctt   10620
ttctacgggg tctgacgctc agtggaacga aaactcacgt taagggattt tggtcatgag   10680
attatcaaaa aggatcttca cctagatcct tttaaattaa aaatgaagtt ttaaatcaat   10740
ctaaagtata tatgagtaaa cttggtctga cagttaccaa tgcttaatca gtgaggcacc   10800
tatctcagcg atctgtctat ttcgttcatc catagttgcc tgactccccg tcgtgtagat   10860
aactacgata cgggagggct taccatctgg ccccagtgct gcaatgatac cgcgagaccc   10920
acgctcaccg gctccagatt tatcagcaat aaaccagcca gccggaaggg ccgagcgcag   10980
aagtggtcct gcaactttat ccgcctccat ccagtctatt aattgttgcc gggaagctag   11040
```

```
agtaagtagt tcgccagtta atagtttgcg caacgttgtt gccattgctg caggggggggg    11100
gggggggggg gacttccatt gttcattcca cggacaaaaa cagagaaagg aaacgacaga    11160
ggccaaaaag cctcgctttc agcacctgtc gtttcctttc ttttcagagg gtattttaaa    11220
taaaaacatt aagttatgac gaagaagaac ggaaacgcct taaaccggaa aattttcata    11280
aatagcgaaa acccgcgagg tcgccgcccc gtaacctgtc ggatcaccgg aaaggacccg    11340
taaagtgata atgattatca tctacatatc acaacgtgcg tggaggccat caaaccacgt    11400
caaataatca attatgacgc aggtatcgta ttaattgatc tgcatcaact taacgtaaaa    11460
acaacttcag acaatacaaa tcagcgacac tgaatacggg gcaacctcat gtccccccc    11520
ccccccccc tgcaggcatc gtggtgtcac gctcgtcgtt tggtatggct tcattcagct    11580
ccggttccca acgatcaagg cgagttacat gatcccccat gttgtgcaaa aaagcggtta    11640
gctccttcgg tcctccgatc gttgtcagaa gtaagttggc cgcagtgtta tcactcatgg    11700
ttatggcagc actgcataat tctcttactg tcatgccatc cgtaagatgc ttttctgtga    11760
ctggtgagta ctcaaccaag tcattctgag aatagtgtat gcggcgaccg agttgctctt    11820
gcccggcgtc aacacgggat aataccgcgc cacatagcag aactttaaaa gtgctcatca    11880
ttggaaaacg ttcttcgggg cgaaaactct caaggatctt accgctgttg agatccagtt    11940
cgatgtaacc cactcgtgca cccaactgat cttcagcatc ttttactttc accagcgttt    12000
ctgggtgagc aaaaacagga aggcaaaatg ccgcaaaaaa gggaataagg gcgacacgga    12060
aatgttgaat actcatactc ttcctttttc aatattattg aagcatttat cagggttatt    12120
gtctcatgag cggatacata tttgaatgta tttagaaaaa taaacaaata ggggttccgc    12180
gcacatttcc ccgaaaagtg ccacctgacg tctaagaaac cattattatc atgacattaa    12240
cctataaaaa taggcgtatc acgaggccct ttcgtcttca agaattggtc gacgatcttg    12300
ctgcgttcgg atattttcgt ggagttcccg ccacagaccc ggattgaagg cgagatccag    12360
caactcgcgc cagatcatcc tgtgacggaa ctttggcgcg tgatgactgg ccaggacgtc    12420
ggccgaaaga gcgacaagca gatcacgctt ttcgacagcg tcggatttgc gatcgaggat    12480
ttttcggcgc tgcgctacgt ccgcgaccgc gttgagggat caagccacag cagcccactc    12540
gaccttctag ccgacccaga cgagccaagg gatctttttg gaatgctgct ccgtcgtcag    12600
gctttccgac gtttgggtgg ttgaacagaa gtcattatcg tacggaatgc caagcactcc    12660
cgagggaac cctgtggttg gcatgcacat acaaatggac gaacggataa accttttcac    12720
gccctttaa atatccgtta ttctaataaa cgctctttc tcttaggttt acccgccaat    12780
atatcctgtc aaacactgat agtttaaact gaaggcggga aacgacaatc tgatcatgag    12840
cggagaatta agggagtcac gttatgaccc ccgccgatga cgcgggacaa gccgttttac    12900
gtttggaact gacagaaccg caacgttgaa ggagccactc agcaagctgg tacgattgta    12960
atacgactca ctatagggcg aattgagcgc tgtttaaacg ctcttcaact ggaagagcg    13019
```

<210> SEQ ID NO 9
<211> LENGTH: 15663
<212> TYPE: DNA
<213> ORGANISM: Artificial Sequence
<220> FEATURE:
<223> OTHER INFORMATION: PHP28647 destination vector for use with maize inbred-derived lines

<400> SEQUENCE: 9

```
gtttacccgc caatatatcc tgtcaaacac tgatagttta aactgaaggc gggaaacgac    60
```

```
aatctgatca tgagcggaga attaagggag tcacgttatg accccgccg atgacgcggg       120 acaagccgtt ttacgtttgg aactgacaga accgcaacgt tgaaggagcc actcagcaag      180
ctggtacgat tgtaatacga ctcactatag ggcgaattga gcgctgttta acgctcttc       240 aactggaaga gcggttaccc ggaccgaagc ttgcatgcct gcagtgcagc gtgacccggt      300
cgtgcccctc tctagagata atgagcattg catgtctaag ttataaaaaa ttaccacata      360 tttttttgt cacacttgtt tgaagtgcag tttatctatc tttatacata tatttaaact       420
ttactctacg aataatataa tctatagtac tacaataata tcagtgtttt agagaatcat      480
ataaatgaac agttagacat ggtctaaagg acaattgagt attttgacaa caggactcta      540
cagttttatc ttttttagtgt gcatgtgttc tccttttttt ttgcaaatag cttcacctat     600
ataatacttc atccatttta ttagtacatc catttagggt ttagggttaa tggttttttat     660 agactaattt ttttagtaca tctattttat tctattttag cctctaaatt aagaaaacta      720
aaactctatt ttagtttttt tatttaataa tttagatata aaatagaata aaataaagtg      780
actaaaaatt aaacaaatac cctttaagaa attaaaaaaa ctaaggaaac attttttcttg     840 tttcgagtag ataatgccag cctgttaaac gccgtcgacg agtctaacgg acaccaacca     900
gcgaaccagc agcgtcgcgt cgggccaagc gaagcagacg gcacggcatc tctgtcgctg     960
cctctggacc cctctcgaga gttccgctcc accgttggac ttgctccgct gtcggcatcc    1020
agaaattgcg tggcggagcg gcagacgtga gccggcacgg caggcggcct cctcctcctc    1080
tcacggcacg gcagctacgg gggattcctt tcccaccgct ccttcgcttt cccttcctcg    1140
cccgccgtaa taaatagaca ccccctccac accctctttc cccaacctcg tgttgttcgg    1200
agcgcacaca cacacaacca gatctccccc aaatccaccc gtcggcacct ccgcttcaag    1260
gtacgccgct cgtcctcccc ccccccccct ctctaccttc tctagatcgg cgttccggtc    1320
catggttagg gcccggtagt tctacttctg ttcatgtttg tgttagatcc gtgtttgtgt    1380
tagatccgtg ctgctagcgt tcgtacacgg atgcgacctg tacgtcagac acgttctgat    1440
tgctaacttg ccagtgtttc tctttgggga atcctgggat ggctctagcc gttccgcaga    1500
cgggatcgat ttcatgattt tttttgtttc gttgcatagg gtttggtttg cccttttcct    1560
ttatttcaat atatgccgtg cacttgtttg tcgggtcatc ttttcatgct ttttttttgtc   1620 ttggttgtga tgatgtggtc tggttgggcg gtcgttctag atcggagtag aattctgttt    1680
caaactacct ggtggattta ttaattttgg atctgtatgt gtgtgccata catattcata    1740
gttacgaatt gaagatgatg gatggaaata tcgatctagg ataggtatac atgttgatgc    1800
gggttttact gatgcatata cagagatgct ttttgttcgc ttggttgtga tgatgtggtg    1860
tggttgggcg gtcgttcatt cgttctagat cggagtagaa tactgtttca aactacctgg    1920
tgtatttatt aattttggaa ctgtatgtgt gtgtcataca tcttcatagt tacgagttta    1980
agatggatgg aaatatcgat ctaggatagg tatacatgtt gatgtgggtt ttactgatgc    2040
atatacatga tggcatatgc agcatctatt catatgctct aaccttgagt acctatctat    2100
tataataaac aagtatgttt tataattatt ttgatcttga tatacttgga tgatggcata    2160
tgcagcagct atatgtggat tttttagcc ctgccttcat acgctattta tttgcttggt     2220
actgtttctt ttgtcgatgc tcaccctgtt gtttggtgtt acttctgcag gtcgactcta    2280
gaggatctac aagtttgtac aaaaaagctg aacgagaaac gtaaaatgat ataaatatca    2340
atatattaaa ttagattttg cataaaaaac agactacata atactgtaaa acacaacata    2400
```

```
tccagtcact atggcggccg cattaggcac cccaggcttt acactttatg cttccggctc    2460
gtataatgtg tggattttga gttaggatcc ggcgagattt tcaggagcta aggaagctaa    2520
aatggagaaa aaaatcactg gatataccac cgttgatata tcccaatggc atcgtaaaga    2580
acattttgag gcatttcagt cagttgctca atgtacctat aaccagaccg ttcagctgga    2640
tattacggcc ttttttaaaga ccgtaaagaa aaataagcac aagttttatc cggcctttat    2700
tcacattctt gcccgcctga tgaatgctca tccggaattc cgtatggcaa tgaaagacgg    2760
tgagctggtg atatgggata gtgttcaccc ttgttacacc gttttccatg agcaaactga    2820
aacgttttca tcgctctgga gtgaatacca cgacgatttc cggcagtttc tacacatata    2880
ttcgcaagat gtggcgtgtt acggtgaaaa cctggcctat ttccctaaag ggtttattga    2940
gaatatgttt ttcgtctcag ccaatccctg ggtgagtttc accagttttg atttaaacgt    3000
ggccaatatg gacaacttct tcgcccccgt tttcaccatg ggcaaatatt atacgcaagg    3060
cgacaaggtg ctgatgccgc tggcgattca ggttcatcat gccgtctgtg atggcttcca    3120
tgtcggcaga atgcttaatg aattacaaca gtactgcgat gagtggcagg gcggggcgta    3180
aacgcgtgga tccggcttac taaaaagcca gataacagtat gcgtatttgc gcgctgattt    3240
ttgcggtata agaatatata ctgatatgta tacccgaagt atgtcaaaaa gaggtatgct    3300
atgaagcagc gtattacagt gacagttgac agcgacagct atcagttgct caaggcatat    3360
atgatgtcaa tatctccggt ctggtaagca caaccatgca gaatgaagcc cgtcgtctgc    3420
gtgccgaacg ctggaaagcg gaaaatcagg aagggatggc tgaggtcgcc cggtttattg    3480
aaatgaacgg ctctttttgct gacgagaaca ggggctggtg aaatgcagtt taaggtttac    3540
acctataaaa gagagagccg ttatcgtctg tttgtggatg tacagagtga tattattgac    3600
acgcccgggc gacggatggt gatcccctg gccagtgcac gtctgctgtc agataaagtc    3660
tcccgtgaac tttacccggt ggtgcatatc ggggatgaaa gctggcgcat gatgaccacc    3720
gatatggcca gtgtgccggt ctccgttatc ggggaagaag tggctgatct cagccaccgc    3780
gaaaatgaca tcaaaaacgc cattaacctg atgttctggg gaatataaat gtcaggctcc    3840
cttatacaca gccagtctgc aggtcgacca tagtgactgg atatgttgtg ttttacagta    3900
ttatgtagtc tgttttttat gcaaaatcta atttaatata ttgatattta tatcatttta    3960
cgtttctcgt tcagctttct tgtacaaagt ggtgttaacc tagacttgtc catcttctgg    4020
attggccaac ttaattaatg tatgaaataa aaggatgcac acatagtgac atgctaatca    4080
ctataatgtg ggcatcaaag ttgtgtgtta tgtgtaatta ctagttatct gaataaaaga    4140
gaaagagatc atccatattt cttatcctaa atgaatgtca cgtgtcttta taattctttg    4200
atgaaccaga tgcatttcat taaccaaatc catatacata taaatattaa tcatatataa    4260
ttaatatcaa ttgggttagc aaaacaaatc tagtctaggt gtgttttgcg aattgcggcc    4320
gccaccgcgg tggagctcga attccggtcc gggtcacctt tgtccaccaa gatgaactg    4380
cggccgctca ttaattaagt caggcgcgcc tctagttgaa gacacgttca tgtcttcatc    4440
gtaagaagac actcagtagt cttcggccag aatgccatc tggattcagc aggcctagaa    4500
ggccatttaa atcctgagga tctggtcttc ctaaggaccc gggatatcgg accgaagctg    4560
gccgctctag aactagtgga tctcgatgtg tagtctacga aagggttaa ccgtctcttc    4620
gtgagaataa ccgtggccta aaataagcc gatgaggata aataaatgt ggtggtacag    4680
tacttcaaga ggtttactca tcaagaggat gcttttccga tgagctctag tagtacatcg    4740
gacctcacat acctccattg tggtgaaata ttttgtgctc atttagtgat gggtaaattt    4800
```

```
tgtttatgtc actctaggtt ttgacatttc agttttgcca ctcttaggtt ttgacaaata    4860
atttccattc cgcggcaaaa gcaaaacaat tttattttac ttttaccact cttagctttc    4920
acaatgtatc acaaatgcca ctctagaaat tctgtttatg ccacagaatg tgaaaaaaaa    4980
cactcactta tttgaagcca aggtgttcat ggcatgaaaa tgtgacataa agtaacgttc    5040
gtgtataaga aaaaattgta ctcctcgtaa caagagacgg aaacatcatg agacaatcgc    5100
gtttggaagg ctttgcatca cctttggatg atgcgcatga atggagtcgt ctgcttgcta    5160
gccttcgcct accgcccact gagtccgggc ggcaactacc atcggcgaac gacccagctg    5220
acctctaccg accggacttg aatgcgctac cttcgtcagc gacgatggcc gcgtacgctg    5280
gcgacgtgcc cccgcatgca tggcggcaca tggcgagctc agaccgtgcg tggctggcta    5340
caaatacgta ccccgtgagt gccctagcta gaaacttaca cctgcaactg cgagagcgag    5400
cgtgtgagtg tagccgagta gatccccgg gctgcaggtc gactctagag gatccaccgg    5460
tcgccaccat ggcctcctcc gagaacgtca tcaccgagtt catgcgcttc aaggtgcgca    5520
tggagggcac cgtgaacggc cacgagttcg agatcgaggg cgagggcgag ggccgcccct    5580
acgagggcca caacaccgtg aagctgaagg tgacgaaggg cggccccctg cccttcgcct    5640
gggacatcct gtcccccag ttccagtacg gctccaaggt gtacgtgaag caccccgccg    5700
acatccccga ctacaagaag ctgtccttcc ccgagggctt caagtgggag cgcgtgatga    5760
acttcgagga cggcggcgtg gcgaccgtga cccaggactc ctccctgcag gacggctgct    5820
tcatctacaa ggtgaagttc atcggcgtga acttcccctc cgacggcccc gtgatgcaga    5880
agaagaccat gggctgggag gcctccaccg agcgcctgta ccccgcgac ggcgtgctga    5940 agggcgagac ccacaaggcc ctgaagctga aggacggcgg ccactacctg gtggagttca    6000
agtccatcta catggccaag aagcccgtgc agctgcccgg ctactactac gtggacgcca    6060
agctggacat cacctcccac aacgaggact acaccatcgt ggagcagtac gagcgcaccg    6120
agggccgcca ccacctgttc ctgtagcggc ccatggatat tcgaacgcgt aggtaccaca    6180
tggttaacct agacttgtcc atcttctgga ttggccaact taattaatgt atgaaataaa    6240
aggatgcaca catagtgaca tgctaatcac tataatgtgg gcatcaaagt tgtgtgttat    6300
gtgtaattac tagttatctg aataaaagag aaagagatca tccatatttc ttatcctaaa    6360
tgaatgtcac gtgtctttat aattctttga tgaaccagat gcatttcatt aaccaaatcc    6420
atatacatat aaatattaat catatataat taatatcaat tgggttagca aaacaaatct    6480
agtctaggtg tgttttgcga atgcggccgc caccgcggtg gagctcgaat ccggtccga    6540 agcttgcatg cctgcagtgc agcgtgaccc ggtcgtgccc ctctctagag ataatgagca    6600
ttgcatgtct aagttataaa aaattaccac atattttttt tgtcacactt gtttgaagtg    6660
cagtttatct atctttatac atatatttaa actttactct acgaataata taatctatag    6720
tactacaata atatcagtgt tttagagaat catataaatg aacagttaga catggtctaa    6780
aggacaattg agtattttga caacaggact ctacagtttt atcttttag tgtgcatgtg    6840 ttctcctttt tttttgcaaa tagcttcacc tatataatac ttcatccatt ttattagtac    6900
atccatttag ggtttagggt taatggtttt tatagactaa ttttttttagt acatctattt    6960 tattctattt tagcctctaa attaagaaaa ctaaaactct attttagttt ttttatttaa    7020
taatttagat ataaaataga ataaaataaa gtgactaaaa attaaacaaa tacccttaa    7080 gaaattaaaa aaactaagga acatttttc ttgtttcgag tagataatgc cagcctgtta    7140
```

```
aacgccgtcg acgagtctaa cggacaccaa ccagcgaacc agcagcgtcg cgtcgggcca    7200
agcgaagcag acggcacggc atctctgtcg ctgcctctgg acccctctcg agagttccgc    7260
tccaccgttg gacttgctcc gctgtcggca tccagaaatt gcgtggcgga gcggcagacg    7320
tgagccggca cggcaggcgg cctcctcctc ctctcacggc accggcagct acggggggatt   7380
cctttcccac cgctccttcg ctttcccttc ctcgcccgcc gtaataaata dacacccct     7440
ccacaccctc tttccccaac ctcgtgttgt tcggagcgca cacacacaca accagatctc    7500
ccccaaatcc acccgtcggc acctccgctt caaggtacgc cgctcgtcct ccccccccccc   7560
cctctctacc ttctctagat cggcgttccg gtccatgcat ggttagggcc cggtagttct    7620
acttctgttc atgtttgtgt tagatccgtg tttgtgttag atccgtgctg ctagcgttcg    7680
tacacggatg cgacctgtac gtcagacacg ttctgattgc taacttgcca gtgtttctct    7740
ttggggaatc ctgggatggc tctagccgtt ccgcagacgg gatcgatttc atgattttt     7800
ttgtttcgtt gcatagggtt tggttttgcc ttttccttta tttcaatata tgccgtgcac    7860
ttgtttgtcg ggtcatcttt tcatgctttt ttttgtcttg gttgtgatga tgtggtctgg    7920
ttgggcggtc gttctagatc ggagtagaat tctgtttcaa actacctggt ggatttatta    7980
attttggatc tgtatgtgtg tgccatacat attcatagtt acgaattgaa gatgatggat    8040
ggaaatatcg atctaggata ggtatacatg ttgatgcggg ttttactgat gcatatacag    8100
agatgctttt tgttcgcttg gttgtgatga tgtggtgtgg ttgggcggtc gttcattcgt    8160
tctagatcgg agtagaatac tgtttcaaac tacctggtgt atttattaat tttggaactg    8220
tatgtgtgtg tcatacatct tcatagttac gagtttaaga tggatggaaa tatcgatcta    8280
ggataggtat acatgttgat gtgggtttta ctgatgcata tacatgatgg catatgcagc    8340
atctattcat atgctctaac cttgagtacc tatctattat aataaacaag tatgtttat     8400
aattattttg atcttgatat acttggatga tggcatatgc agcagctata tgtggattt     8460
tttagccctg ccttcatacg ctatttattt gcttggtact gtttcttttg tcgatgctca    8520
ccctgttgtt tggtgttact tctgcaggtc gactttaact tagcctagga tccacacgac    8580
accatgtccc ccgagcgccg ccccgtcgag atccgcccgg ccaccgccgc cgacatggcc    8640
gccgtgtgcg acatcgtgaa ccactacatc gagacctcca ccgtgaactt ccgcaccgag    8700
ccgcagaccc cgcaggagtg gatcgacgac ctggagcgcc tccaggaccg ctacccgtgg    8760
ctcgtggccg aggtggaggg cgtggtggcc ggcatcgcct acgccggccc gtggaaggcc    8820
cgcaacgcct acgactggac cgtggagtcc accgtgtacg tgtcccaccg ccaccagcgc    8880
ctcggcctcg gctccaccct ctacacccac ctcctcaaga gcatggaggc ccagggcttc    8940
aagtccgtgg tggccgtgat cggcctcccg aacgacccgt ccgtgcgcct ccacgaggcc    9000
ctcggctaca ccgcccgcgg caccctccgc gccgccggct acaagcacgg cggctggcac    9060
gacgtcggct tctggcagcg cgacttcgag ctgccggccc cgccgcgccc ggtgcgcccg    9120
gtgacgcaga tctgagtcga aacctagact tgtccatctt ctggattggc caacttaatt    9180
aatgtatgaa ataaaaggat gcacacatag tgacatgcta atcactataa tgtgggcatc    9240
aaagttgtgt gttatgtgta attactagtt atctgaataa aagagaaaga gatcatccat    9300
atttcttatc ctaaatgaat gtcacgtgtc tttataattc tttgatgaac cagatgcatt    9360
tcattaacca aatccatata catataaata ttaatcatat ataattaata tcaattgggt    9420
tagcaaaaca aatctagtct aggtgtgttt tgcgaattgc ggccgccacc gcggtggagc    9480
tcgaattcat tccgattaat cgtggcctct tgctcttcag gatgaagagc tatgtttaaa    9540
```

```
cgtgcaagcg ctactagaca attcagtaca ttaaaaacgt ccgcaatgtg ttattaagtt    9600
gtctaagcgt caatttgttt acaccacaat atatcctgcc accagccagc caacagctcc    9660
ccgaccggca gctcggcaca aaatcaccac tcgatacagg cagcccatca gtccgggacg    9720
gcgtcagcgg gagagccgtt gtaaggcggc agactttgct catgttaccg atgctattcg    9780
gaagaacggc aactaagctg ccgggtttga aacacggatg atctcgcgga gggtagcatg    9840
ttgattgtaa cgatgacaga gcgttgctgc ctgtgatcaa atatcatctc cctcgcagag    9900
atccgaatta tcagccttct tattcatttc tcgcttaacc gtgacaggct gtcgatcttg    9960
agaactatgc cgacataata ggaaatcgct ggataaagcc gctgaggaag ctgagtggcg   10020
ctatttcttt agaagtgaac gttgacgatc gtcgaccgta ccccgatgaa ttaattcgga   10080
cgtacgttct gaacacagct ggatacttac ttgggcgatt gtcatacatg acatcaacaa   10140
tgtacccgtt tgtgtaaccg tctcttggag gttcgtatga cactagtggt tcccctcagc   10200
ttgcgactag atgttgaggc ctaacatttt attagagagc aggctagttg cttagataca   10260
tgatcttcag gccgttatct gtcagggcaa gcgaaaattg gccatttatg acgaccaatg   10320
ccccgcagaa gctcccatct ttgccgccat agacgccgcg ccccccttt ggggtgtaga   10380 acatcctttt gccagatgtg gaaaagaagt tcgttgtccc attgttggca atgacgtagt   10440
agccggcgaa agtgcgagac ccatttgcgc tatatataag cctacgattt ccgttgcgac   10500
tattgtcgta attggatgaa ctattatcgt agttgctctc agagttgtcg taatttgatg   10560
gactattgtc gtaattgctt atggagttgt cgtagttgct tggagaaatg tcgtagttgg   10620
atggggagta gtcataggga agacgagctt catccactaa aacaattggc aggtcagcaa   10680
gtgcctgccc cgatgccatc gcaagtacga ggcttagaac caccttcaac agatcgcgca   10740
tagtcttccc cagctctcta acgcttgagt taagccgcgc cgcgaagcgg cgtcggcttg   10800
aacgaattgt tagacattat ttgccgacta ccttggtgat ctcgcctttc acgtagtgaa   10860
caaattcttc caactgatct gcgcgcgagg ccaagcgatc ttcttgtcca agataagcct   10920
gcctagcttc aagtatgacg ggctgatact gggccggcag gcgctccatt gcccagtcgg   10980
cagcgacatc cttcggcgcg attttgccgg ttactgcgct gtaccaaatg cgggacaacg   11040
taagcactac atttcgctca tcgccagccc agtcgggcgg cgagttccat agcgttaagg   11100
tttcatttag cgcctcaaat agatcctgtt caggaaccgg atcaaagagt tcctccgccg   11160
ctggacctac caaggcaacg ctatgttctc ttgcttttgt cagcaagata gccagatcaa   11220
tgtcgatcgt ggctggctcg aagatacctg caagaatgtc attgcgctgc cattctccaa   11280
attgcagttc gcgcttagct ggataacgcc acggaatgat gtcgtcgtgc acaacaatgg   11340
tgacttctac agcgcggaga atctcgctct ctccagggga agccgaagtt tccaaaaggt   11400
cgttgatcaa agctcgccgc gttgtttcat caagccttac agtcaccgta accagcaaat   11460
caatatcact gtgtggcttc aggccgccat ccactgcgga gccgtacaaa tgtacggcca   11520
gcaacgtcgg ttcgagatgg cgctcgatga cgccaactac ctctgatagt tgagtcgata   11580
cttcggcgat caccgcttcc ctcatgatgt ttaactcctg aattaagccg cgccgcgaag   11640
cggtgtcggc ttgaatgaat tgttaggcgt catcctgtgc tcccgagaac cagtaccagt   11700
acatcgctgt ttcgttcgag acttgaggtc tagttttata cgtgaacagg tcaatgccgc   11760
cgagagtaaa gccacatttt gcgtacaaat tgcaggcagg tacattgttc gtttgtgtct   11820
ctaatcgtat gccaaggagc tgtctgctta gtgcccactt tttcgcaaat tcgatgagac   11880
```

-continued

```
tgtgcgcgac tcctttgcct cggtgcgtgt gcgacacaac aatgtgttcg atagaggcta    11940
gatcgttcca tgttgagttg agttcaatct tcccgacaag ctcttggtcg atgaatgcgc    12000
catagcaagc agagtcttca tcagagtcat catccgagat gtaatccttc cggtagggc     12060 tcacacttct ggtagatagt tcaaagcctt ggtcggatag gtgcacatcg aacacttcac    12120
gaacaatgaa atggttctca gcatccaatg tttccgccac ctgctcaggg atcaccgaaa    12180
tcttcatatg acgcctaacg cctggcacag cggatcgcaa acctggcgcg gcttttggca    12240
caaaaggcgt gacaggtttg cgaatccgtt gctgccactt gttaaccctt ttgccagatt    12300
tggtaactat aatttatgtt agaggcgaag tcttgggtaa aaactggcct aaaattgctg    12360
gggatttcag gaaagtaaac atcaccttcc ggctcgatgt ctattgtaga tatatgtagt    12420
gtatctactt gatcggggga tctgctgcct cgcgcgtttc ggtgatgacg gtgaaaacct    12480
ctgacacatg cagctcccgg agacggtcac agcttgtctg taagcggatg ccgggagcag    12540
acaagcccgt cagggcgcgt cagcgggtgt tggcgggtgt cggggcgcag ccatgaccca    12600
gtcacgtagc gatagcggag tgtatactgg cttaactatg cggcatcaga gcagattgta    12660
ctgagagtgc accatatgcg gtgtgaaata ccgcacagat gcgtaaggag aaaataccgc    12720
atcaggcgct cttccgcttc ctcgctcact gactcgctgc gctcggtcgt tcggctgcgg    12780
cgagcggtat cagctcactc aaaggcggta atacggttat ccacagaatc aggggataac    12840
gcaggaaaga acatgtgagc aaaaggccag caaaaggcca ggaaccgtaa aaaggccgcg    12900
ttgctggcgt ttttccatag gctccgcccc cctgacgagc atcacaaaaa tcgacgctca    12960
agtcagaggt ggcgaaaccc gacaggacta taaagatacc aggcgtttcc ccctggaagc    13020
tccctcgtgc gctctcctgt tccgaccctg ccgcttaccg gatacctgtc gcctttctc     13080 ccttcgggaa gcgtggcgct ttctcatagc tcacgctgta ggtatctcag ttcggtgtag    13140
gtcgttcgct ccaagctggg ctgtgtgcac gaaccccccg ttcagcccga ccgctgcgcc    13200
ttatccggta actatcgtct tgagtccaac ccggtaagac acgacttatc gccactggca    13260
gcagccactg gtaacaggat tagcagagcg aggtatgtag gcggtgctac agagttcttg    13320
aagtggtggc ctaactacgg ctacactaga aggacagtat ttggtatctg cgctctgctg    13380
aagccagtta ccttcggaaa aagagttggt agctcttgat ccggcaaaca aaccaccgct    13440
ggtagcggtg ttttttgt ttgcaagcag cagattacgc gcagaaaaaa aggatctcaa      13500
gaagatcctt tgatcttttc tacggggtct gacgctcagt ggaacgaaaa ctcacgttaa    13560
gggattttgg tcatgagatt atcaaaaagg atcttcacct agatcctttt aaattaaaaa    13620
tgaagtttta aatcaatcta agtatatat gagtaaactt ggtctgacag ttaccaatgc     13680
ttaatcagtg aggcacctat ctcagcgatc tgtctatttc gttcatccat agttgcctga    13740
ctccccgtcg tgtagataac tacgatacgg gagggcttac catctggccc cagtgctgca    13800
atgataccgc gagacccacg ctcaccggct ccagatttat cagcaataaa ccagccagcc    13860
ggaagggccg agcgcagaag tggtcctgca actttatccg cctccatcca gtctattaat    13920
tgttgccggg aagctagagt aagtagttcg ccagttaata gtttgcgcaa cgttgttgcc    13980
attgctgcag ggggggggg ggggggggac ttccattgtt cattccacgg acaaaaacag     14040
agaaaggaaa cgacagaggc caaaaagcct cgctttcagc acctgtcgtt tcctttcttt    14100
tcagggggta ttttaaataa aaacattaag ttatgacgaa gaagaacgga aacgccttaa    14160
accggaaaat tttcataaat agcgaaaacc cgcgaggtcg ccgccccgta acctgtcgga    14220
tcaccggaaa ggacccgtaa agtgataatg attatcatct acatatcaca acgtgcgtgg    14280
```

```
aggccatcaa accacgtcaa ataatcaatt atgacgcagg tatcgtatta attgatctgc  14340
atcaacttaa cgtaaaaaca acttcagaca atacaaatca gcgacactga atacggggca  14400
acctcatgtc cccccccccc cccccctgc aggcatcgtg gtgtcacgct cgtcgtttgg  14460
tatggcttca ttcagctccg gttcccaacg atcaaggcga gttacatgat cccccatgtt  14520
gtgcaaaaaa gcggttagct ccttcggtcc tccgatcgtt gtcagaagta agttggccgc  14580
agtgttatca ctcatggtta tggcagcact gcataattct cttactgtca tgccatccgt  14640
aagatgcttt tctgtgactg gtgagtactc aaccaagtca ttctgagaat agtgtatgcg  14700
gcgaccgagt tgctcttgcc cggcgtcaac acgggataat accgcgccac atagcagaac  14760
tttaaaagtg ctcatcattg gaaaacgttc ttcggggcga aaactctcaa ggatcttacc  14820
gctgttgaga tccagttcga tgtaacccac tcgtgcaccc aactgatctt cagcatcttt  14880
tactttcacc agcgtttctg ggtgagcaaa aacaggaagg caaaatgccg caaaaaaggg  14940
aataagggcg acacggaaat gttgaatact catactcttc cttttcaat attattgaag  15000
catttatcag ggttattgtc tcatgagcgg atacatattt gaatgtattt agaaaaataa  15060
acaaataggg gttccgcgca catttccccg aaaagtgcca cctgacgtct aagaaaccat  15120
tattatcatg acattaacct ataaaaatag gcgtatcacg aggccctttc gtcttcaaga  15180
attggtcgac gatcttgctg cgttcggata ttttcgtgga gttcccgcca cagacccgga  15240
ttgaaggcga gatccagcaa ctcgcgccag atcatcctgt gacggaactt tggcgcgtga  15300
tgactggcca ggacgtcggc cgaaagagcg acaagcagat cacgcttttc gacagcgtcg  15360
gatttgcgat cgaggatttt tcggcgctgc gctacgtccg cgaccgcgtt gagggatcaa  15420
gccacagcag cccactcgac cttctagccg acccagacga gccaagggat cttttggaa  15480
tgctgctccg tcgtcaggct ttccgacgtt tgggtggttg aacagaagtc attatcgtac  15540
ggaatgccaa gcactcccga ggggaaccct gtggttggca tgcacataca aatggacgaa  15600
cggataaacc ttttcacgcc cttttaaata tccgttattc taataaacgc tcttttctct  15660
tag                                                                15663
```

<210> SEQ ID NO 10
<211> LENGTH: 25
<212> TYPE: DNA
<213> ORGANISM: Artificial Sequence
<220> FEATURE:
<223> OTHER INFORMATION: attB1 site

<400> SEQUENCE: 10
acaagtttgt acaaaaaagc aggct                                        25

<210> SEQ ID NO 11
<211> LENGTH: 25
<212> TYPE: DNA
<213> ORGANISM: Artificial Sequence
<220> FEATURE:
<223> OTHER INFORMATION: attB2 site

<400> SEQUENCE: 11
accactttgt acaagaaagc tgggt                                        25

<210> SEQ ID NO 12
<211> LENGTH: 55
<212> TYPE: DNA
<213> ORGANISM: Artificial Sequence
<220> FEATURE:

-continued

<223> OTHER INFORMATION: At1g68490 5'attB forward primer

<400> SEQUENCE: 12
ggggacaagt ttgtacaaaa aagcaggctc gaagaaaaga tgaatcactt tgcgg          55

<210> SEQ ID NO 13
<211> LENGTH: 54
<212> TYPE: DNA
<213> ORGANISM: Artificial Sequence
<220> FEATURE:
<223> OTHER INFORMATION: At1g68490 3'attB reverse primer

<400> SEQUENCE: 13
ggggaccact ttgtacaaga aagctgggtc caaaagggtt cgtttcgggt ttcg           54

<210> SEQ ID NO 14
<211> LENGTH: 54
<212> TYPE: DNA
<213> ORGANISM: Artificial Sequence
<220> FEATURE:
<223> OTHER INFORMATION: VC062 primer

<400> SEQUENCE: 14
ttaaacaagt ttgtacaaaa aagcaggctg caattaaccc tcactaaagg gaac           54

<210> SEQ ID NO 15
<211> LENGTH: 53
<212> TYPE: DNA
<213> ORGANISM: Artificial Sequence
<220> FEATURE:
<223> OTHER INFORMATION: VC063 primer

<400> SEQUENCE: 15
ttaaaccact ttgtacaaga aagctgggtg cgtaatacga ctcactatag ggc            53

<210> SEQ ID NO 16
<211> LENGTH: 50905
<212> TYPE: DNA
<213> ORGANISM: Artificial Sequence
<220> FEATURE:
<223> OTHER INFORMATION: destination vector for use with Gaspe-flint
      derived maize lines

<400> SEQUENCE: 16
gggggggggg ggggggggtt ccattgttca ttccacggac aaaaacagag aaaggaaacg     60
acagaggcca aaaagctcgc tttcagcacc tgtcgtttcc tttcttttca gagggtattt    120
taaataaaaa cattaagtta tgacgaagaa gaacggaaac gccttaaacc ggaaaatttt    180
cataaatagc gaaaacccgc gaggtcgccg ccccgtaacc tgtcggatca ccggaaagga    240
cccgtaaagt gataatgatt atcatctaca tatcacaacg tgcgtggagg ccatcaaacc    300
acgtcaaata atcaattatg acgcaggtat cgtattaatt gatctgcatc aacttaacgt    360
aaaaacaact tcagacaata caaatcagcg acactgaata cggggcaacc tcatgtcccc    420
cccccccccc cccctgcagg catcgtggtg tcacgctcgt cgtttggtat ggcttcattc    480
agctccggtt cccaacgatc aaggcgagtt acatgatccc ccatgttgtg caaaaaagcg    540
gttagctcct tcggtcctcc gatcgttgtc agaagtaagt tggccgcagt gttatcactc    600
atggttatgg cagcactgca taattctctt actgtcatgc catccgtaag atgcttttct    660
gtgactggtg agtactcaac caagtcattc tgagaatagt gtatgcggcg accgagttgc    720
tcttgcccgg cgtcaacacg ggataatacc gcgccacata gcagaacttt aaaagtgctc    780

```
atcattggaa aacgttcttc ggggcgaaaa ctctcaagga tcttaccgct gttgagatcc    840
agttcgatgt aacccactcg tgcacccaac tgatcttcag catcttttac tttcaccagc    900
gtttctgggt gagcaaaaac aggaaggcaa aatgccgcaa aaagggaat aagggcgaca     960
cggaaatgtt gaatactcat actcttcctt tttcaatatt attgaagcat ttatcagggt   1020
tattgtctca tgagcggata catatttgaa tgtatttaga aaataaaca aatagggggtt   1080
ccgcgcacat ttccccgaaa agtgccacct gacgtctaag aaaccattat tatcatgaca   1140
ttaacctata aaataggcg tatcacgagg ccctttcgtc ttcaagaatt cggagctttt    1200
gccattctca ccggattcag tcgtcactca tggtgatttc tcacttgata accttatttt   1260
tgacgagggg aaattaatag gttgtattga tgttggacga gtcggaatcg cagaccgata   1320
ccaggatctt gccatcctat ggaactgcct cggtgagttt tctccttcat tacagaaacg   1380
gcttttttcaa aaatatggta ttgataatcc tgatatgaat aaattgcagt ttcatttgat  1440
gctcgatgag ttttttctaat cagaattggt taattggttg taacactggc agagcattac  1500
gctgacttga cgggacggcg gctttgttga ataaatcgaa cttttgctga gttgaaggat   1560
cagatcacgc atcttcccga caacgcagac cgttccgtgg caaagcaaaa gttcaaaatc   1620
accaactggt ccacctacaa caaagctctc atcaaccgtg ctccctcac tttctggctg    1680
gatgatgggg cgattcaggc ctggtatgag tcagcaacac cttcttcacg aggcagacct   1740
cagcgccaga aggccgccag agaggccgag gcgggccgtg aggcttggac gctagggcag   1800
ggcatgaaaa agcccgtagc gggctgctac gggcgtctga cgcggtggaa aggggagggg   1860
gatgttgtct acatggctct gctgtagtga gtgggttgcg ctccggcagc ggtcctgatc   1920
aatcgtcacc ctttctcggt ccttcaacgt tcctgacaac gagcctcctt ttcgccaatc   1980
catcgacaat caccgcgagt ccctgctcga acgctgcgtc cggaccggct tcgtcgaagg   2040
cgtctatcgc ggcccgcaac agcggcgaga gcggagcctg ttcaacggtg ccgccgcgct   2100
cgccggcatc gctgtcgccg gcctgctcct caagcacggc cccaacagtg aagtagctga   2160
ttgtcatcag cgcattgacg gcgtccccgg ccgaaaaacc cgcctcgcag aggaagcgaa   2220
gctgcgcgtc ggccgtttcc atctgcggtg cgcccgggtcg cgtgccggca tggatgcgcg   2280
cgccatcgcg gtaggcgagc agcgcctgcc tgaagctgcg ggcattcccg atcagaaatg   2340
agcgccagtc gtcgtcggct ctcggcaccg aatgcgtatg attctccgcc agcatggctt   2400
cggccagtgc gtcgagcagc gcccgcttgt tcctgaagtg ccagtaaagc gccggctgct   2460
gaaccccccaa ccgttccgcc agtttgcgtg tcgtcagacc gtctacgccg acctcgttca   2520
acaggtccag ggcggcacgg atcactgtat tcggctgcaa cttttgtcatg cttgacactt   2580
tatcactgat aaacataata tgtccaccaa cttatcagtg ataaagaatc cgcgcgttca   2640
atcggaccag cggaggctgg tccggaggcc agacgtgaaa cccaacatac ccctgatcgt   2700
aattctgagc actgtcgcgc tcgacgctgt cggcatcggc ctgattatgc cggtgctgcc   2760
gggcctcctg cgcgatctgg ttcactcgaa cgacgtcacc gcccactatg gcattctgct   2820
ggcgctgtat gcgttggtgc aatttgcctg cgcacctgtg ctgggcgcgc tgtcggatcg   2880
tttcgggcgg cggccaatct tgctcgtctc gctggccggc gccactgtcg actacgccat   2940
catggcgaca gcgcctttcc tttgggttct ctatatcggg cggatcgtgg ccggcatcac   3000
cggggcgact ggggcggtag ccggcgctta tattgccgat atcactgatg gcgatgagcg   3060
cgcgcggcac ttcggcttca tgagcgcctg tttcggttc gggatggtcg cgggacctgt    3120
gctcggtggg ctgatgggcg gtttctcccc ccacgctccg ttcttcgccg cggcagcctt    3180
```

```
gaacggcctc aatttcctga cgggctgttt ccttttgccg gagtcgcaca aaggcgaacg    3240
ccggccgtta cgccgggagg ctctcaaccc gctcgcttcg ttccggtggg cccggggcat    3300
gaccgtcgtc gccgccctga tggcggtctt cttcatcatg caacttgtcg gacaggtgcc    3360
ggccgcgctt tgggtcattt tcggcgagga tcgctttcac tgggacgcga ccacgatcgg    3420
catttcgctt gccgcatttg gcattctgca ttcactcgcc caggcaatga tcaccggccc    3480
tgtagccgcc cggctcggcg aaaggcgggc actcatgctc ggaatgattg ccgacggcac    3540
aggctacatc ctgcttgcct tcgcgacacg gggatggatg gcgttcccga tcatggtcct    3600
gcttgcttcg ggtggcatcg gaatgccggc gctgcaagca atgttgtcca ggcaggtgga    3660
tgaggaacgt caggggcagc tgcaaggctc actggcggcg ctcaccagcc tgacctcgat    3720
cgtcggaccc ctcctcttca cggcgatcta tgcggcttct ataacaacgt ggaacgggtg    3780
ggcatggatt gcaggcgctg ccctctactt gctctgcctg ccggcgctgc gtcgcgggct    3840
ttggagcggc gcagggcaac gagccgatcg ctgatcgtgg aaacgatagg cctatgccat    3900
gcgggtcaag gcgacttccg gcaagctata cgcgccctag gagtgcggtt ggaacgttgg    3960
cccagccaga tactcccgat cacgagcagg acgccgatga tttgaagcgc actcagcgtc    4020
tgatccaaga acaaccatcc tagcaacacg gcggtccccg ggctgagaaa gcccagtaag    4080
gaaacaactg taggttcgag tcgcgagatc ccccggaacc aaaggaagta ggttaaaccc    4140
gctccgatca ggccgagcca cgccaggccg agaacattgg ttcctgtagg catcgggatt    4200
ggcggatcaa acactaaagc tactggaacg agcagaagtc ctccggccgc cagttgccag    4260
gcggtaaagg tgagcagagg cacgggaggt tgccacttgc gggtcagcac ggttccgaac    4320
gccatggaaa ccgcccccgc caggcccgct gcgacgccga caggatctag cgctgcgttt    4380
ggtgtcaaca ccaacagcgc cacgcccgca gttccgcaaa tagcccccag gaccgccatc    4440
aatcgtatcg ggctacctag cagagcggca gagatgaaca cgaccatcag cggctgcaca    4500
gcgcctaccg tcgccgcgac cccgcccggc aggcggtaga ccgaaataaa caacaagctc    4560
cagaatagcg aaatattaag tgcgccgagg atgaagatgc gcatccacca gattcccgtt    4620
ggaatctgtc ggacgatcat cacgagcaat aaacccgccg gcaacgcccg cagcagcata    4680
ccggcgaccc ctcggcctcg ctgttcgggc tccacgaaaa cgccggacag atgcgccttg    4740
tgagcgtcct tggggccgtc ctcctgtttg aagaccgaca gcccaatgat ctcgccgtcg    4800
atgtaggcgc cgaatgccac ggcatctcgc aaccgttcag cgaacgcctc catgggcttt    4860
ttctcctcgt gctcgtaaac ggacccgaac atctctggag cttttcttcag ggccgacaat    4920 cggatctcgc ggaaatcctg cacgtcggcc gctccaagcc gtcgaatctg agccttaatc    4980
acaattgtca attttaatcc tctgtttatc ggcagttcgt agagcgcgcc gtgcgtcccg    5040
agcgatactg agcgaagcaa gtgcgtcgag cagtgcccgc ttgttcctga aatgccagta    5100
aagcgctggc tgctgaaccc ccagccgaaa ctgaccccac aaggccctag cgtttgcaat    5160
gcaccaggtc atcattgacc caggcgtgtt ccaccaggcc gctgcctcgc aactcttcgc    5220
aggcttcgcc gacctgctcg cgccacttct tcacgcgggt ggaatccgat ccgcacatga    5280
ggcggaaggt ttccagcttg agcgggtacg gctcccggtg cgagctgaaa tagtcgaaca    5340
tccgtcgggc cgtcggcgac agcttgcggt acttctccca tatgaatttc gtgtagtggt    5400
cgccagcaaa cagcacgacg atttcctcgt cgatcaggac ctggcaacgg gacgttttct    5460
tgccacggtc caggacgcgg aagcggtgca gcagcgacac cgattccagg tgcccaacgc    5520
```

```
ggtcggacgt gaagcccatc gccgtcgcct gtaggcgcga caggcattcc tcggccttcg    5580
tgtaataccg gccattgatc gaccagccca ggtcctggca aagctcgtag aacgtgaagg    5640
tgatcggctc gccgataggg gtgcgcttcg cgtactccaa cacctgctgc cacaccagtt    5700
cgtcatcgtc ggcccgcagc tcgacgccgg tgtaggtgat cttcacgtcc ttgttgacgt    5760
ggaaaatgac cttgttttgc agcgcctcgc gcgggatttt cttgttgcgc gtggtgaaca    5820
gggcagagcg ggccgtgtcg tttggcatcg ctcgcatcgt gtccggccac ggcgcaatat    5880
cgaacaagga aagctgcatt tccttgatct gctgcttcgt gtgtttcagc aacgcggcct    5940
gcttggcctc gctgacctgt tttgccaggt cctcgccggc ggttttcgc ttcttggtcg    6000 tcatagttcc tcgcgtgtcg atggtcatcg acttcgccaa acctgccgcc tcctgttcga    6060
gacgacgcga acgctccacg gcggccgatg gcgcgggcag ggcaggggga gccagttgca    6120
cgctgtcgcg ctcgatcttg gccgtagctt gctggaccat cgagccgacg gactggaagg    6180
tttcgcgggg cgcacgcatg acggtgcggc ttgcgatggt ttcggcatcc tcggcggaaa    6240
accccgcgtc gatcagttct tgcctgtatg ccttccggtc aaacgtccga ttcattcacc    6300
ctccttgcgg gattgccccg actcacgccg gggcaatgtg cccttattcc tgatttgacc    6360
cgcctggtgc cttggtgtcc agataatcca ccttatcggc aatgaagtcg gtcccgtaga    6420
ccgtctggcc gtccttctcg tacttggtat tccgaatctt gccctgcacg aataccagcg    6480
accccttgcc caaatacttg ccgtgggcct cggcctgaga gccaaaacac ttgatgcgga    6540
agaagtcggt gcgctcctgc ttgtcgccgg catcgttgcg ccactcttca ttaaccgcta    6600
tatcgaaaat tgcttgcggc ttgttagaat tgccatgacg tacctcggtg tcacgggtaa    6660
gattaccgat aaactggaac tgattatggc tcatatcgaa agtctccttg agaaaggaga    6720
ctctagttta gctaaacatt ggttccgctg tcaagaactt tagcggctaa aattttgcgg    6780
gccgcgacca aggtgcgagg ggcggcttc cgctgtgtac aaccagatat ttttcaccaa    6840
catccttcgt ctgctcgatg agcggggcat gacgaaacat gagctgtcgg agagggcagg    6900
ggtttcaatt tcgtttttat cagacttaac caacggtaag gccaacccct cgttgaaggt    6960
gatggaggcc attgccgacg ccctggaaac tcccctacct cttctcctgg agtccaccga    7020
ccttgaccgc gaggcactcg cggagattgc gggtcatcct ttcaagagca gcgtgccgcc    7080
cggatacgaa cgcatcagtg tggttttgcc gtcacataag gcgtttatcg taaagaaatg    7140
gggcgacgac acccgaaaaa agctgcgtgg aaggctctga cgccaagggt tagggcttgc    7200
acttccttct ttagccgcta aaacggcccc ttctctgcgg gccgtcggct cgcgcatcat    7260
atcgacatcc tcaacggaag ccgtgccgcg aatggcatcg ggcgggtgcg ctttgacagt    7320
tgttttctat cagaaccccct acgtcgtgcg gttcgattag ctgtttgtct tgcaggctaa    7380
acactttcgg tatatcgttt gcctgtgcga taatgttgct aatgatttgt tgcgtagggg    7440
ttactgaaaa gtgagcggga aagaagagtt tcagaccatc aaggagcggg ccaagcgcaa    7500
gctggaacgc gacatgggtg cggacctgtt ggccgcgctc aacgacccga aaaccgttga    7560
agtcatgctc aacgcggacg gcaaggtgtg gcacgaacgc cttggcgagc cgatgcggta    7620
catctgcgac atgcggccca gccagtcgca ggcgattata gaaacggtgg ccggattcca    7680
cggcaaagag gtcacgcggc attcgcccat cctggaaggc gagttcccct ggatggcag    7740 ccgctttgcc ggccaattgc cgccggtcgt ggccgcgcca accttgcga tccgcaagcg    7800 cgcggtcgcc atcttcacgc tggaacagta cgtcgaggcg ggcatcatga cccgcgagca    7860
atacgaggtc attaaaagcg ccgtcgcggc gcatcgaaac atcctcgtca ttggcggtac    7920
```

```
tggctcgggc aagaccacgc tcgtcaacgc gatcatcaat gaaatggtcg ccttcaaccc    7980
gtctgagcgc gtcgtcatca tcgaggacac cggcgaaatc cagtgcgccg cagagaacgc    8040
cgtccaatac cacaccagca tcgacgtctc gatgacgctg ctgctcaaga caacgctgcg    8100
tatgcgcccc gaccgcatcc tggtcggtga ggtacgtggc cccgaagccc ttgatctgtt    8160
gatggcctgg aacaccgggc atgaaggagg tgccgccacc ctgcacgcaa acaaccccaa    8220
agcgggcctg agccggctcg ccatgcttat cagcatgcac ccggattcac cgaaacccat    8280
tgagccgctg attggcgagg cggttcatgt ggtcgtccat atcgccagga cccctagcgg    8340
ccgtcgagtg caagaaattc tcgaagttct tggttacgag aacggccagt acatcaccaa    8400
aaccctgtaa ggagtatttc caatgacaac ggctgttccg ttccgtctga ccatgaatcg    8460
cggcattttg ttctaccttg ccgtgttctt cgttctcgct ctcgcgttat ccgcgcatcc    8520
ggcgatggcc tcggaaggca ccggcggcag cttgccatat gagagctggc tgacgaacct    8580
gcgcaactcc gtaaccggcc cggtggcctt cgcgctgtcc atcatcggca tcgtcgtcgc    8640
cggcggcgtg ctgatcttcg gcggcgaact caacgccttc ttccgaaccc tgatcttcct    8700
ggttctggtg atgcgcgctgc tggtcggcgc gcagaacgtg atgagcacct tcttcggtcg    8760
tggtgccgaa atcgcggccc tcggcaacgg ggcgctgcac caggtgcaag tcgcggcggc    8820
ggatgccgtg cgtgcggtag cggctggacg gctcgcctaa tcatggctct gcgcacgatc    8880
cccatccgtc gcgcaggcaa ccgagaaaac ctgttcatgg gtggtgatcg tgaactggtg    8940
atgttctcgg gcctgatggc gtttgcgctg attttcagcg cccaagagct gcgggccacc    9000
gtggtcggtc tgatcctgtg gttcggggcg ctctatgcgt tccgaatcat ggcgaaggcc    9060
gatccgaaga tgcggttcgt gtacctgcgt caccgccggt acaagccgta ttacccggcc    9120
cgctcgaccc cgttccgcga gaacaccaat agccaaggga agcaataccg atgatccaag    9180
caattgcgat tgcaatcgcg ggcctcggcg cgcttctgtt gttcatcctc tttgcccgca    9240
tccgcgcggt cgatgccgaa ctgaaactga aaaagcatcg ttccaaggac gccggcctgg    9300
ccgatctgct caactacgcc gctgtcgtcg atgacggcgt aatcgtgggc aagaacggca    9360
gctttatggc tgcctggctg tacaagggcg atgacaacgc aagcagcacc gaccagcagc    9420
gcgaagtagt gtccgcccgc atcaaccagg ccctcgcggg cctgggaagt gggtggatga    9480
tccatgtgga cgccgtgcgg cgtcctgctc cgaactacgc ggagcggggc ctgtcggcgt    9540
tccctgaccg tctgacggca gcgattgaag aagagcgctc ggtcttgcct tgctcgtcgg    9600
tgatgtactt caccagctcc gcgaagtcgc tcttcttgat ggagcgcatg gggacgtgct    9660
tggcaatcac gcgcacccccc cggccgtttt agcggctaaa aaagtcatgg ctctgccctc    9720
gggcggacca cgcccatcat gaccttgcca agctcgtcct gcttctcttc gatcttcgcc    9780
agcagggcga ggatcgtggc atcaccgaac cgcgccgtgc gcgggtcgtc ggtgagccag    9840
agtttcagca ggccgcccag gcggcccagg tcgccattga tgcgggccag ctcgcggacg    9900
tgctcatagt ccacgacgcc cgtgattttg tagccctggc cgacggccag caggtaggcc    9960
gacaggctca tgccggccgc cgccgccttt tcctcaatcg ctcttcgttc gtctggaagg    10020
cagtacacct tgataggtgg gctgcccttc ctggttggct tggtttcatc agccatccgc    10080
ttgccctcat ctgttacgcc ggcggtagcc ggccagcctc gcagagcagg attcccgttg    10140
agcaccgcca ggtgcgaata agggacagtg aagaaggaac accgctcgc gggtgggcct    10200
acttcaccta tcctgcccgg ctgacgccgt tggatacacc aaggaaagtc tacacgaacc    10260
```

```
ctttggcaaa atcctgtata tcgtgcgaaa aaggatggat ataccgaaaa aatcgctata    10320
atgaccccga agcagggtta tgcagcggaa aagcgctgct tccctgctgt tttgtggaat    10380
atctaccgac tggaaacagg caaatgcagg aaattactga actgagggga caggcgagag    10440
acgatgccaa agagctacac cgacgagctg gccgagtggg ttgaatcccg cgcggccaag    10500
aagcgccggc gtgatgaggc tgcggttgcg ttcctggcgg tgagggcgga tgtcgaggcg    10560
gcgttagcgt ccggctatgc gctcgtcacc atttgggagc acatgcggga aacggggaag    10620
gtcaagttct cctacgagac gttccgctcg cacgccaggc ggcacatcaa ggccaagccc    10680
gccgatgtgc ccgcaccgca ggccaaggct gcggaacccg cgccggcacc caagacgccg    10740
gagccacggc ggccgaagca gggggggcaag gctgaaaagc cggcccccgc tgcggccccg    10800
accggcttca ccttcaaccc aacaccggac aaaaaggatc tactgtaatg gcgaaaattc    10860
acatggtttt gcagggcaag ggcggggtcg gcaagtcggc catcgccgcg atcattgcgc    10920
agtacaagat ggacaagggg cagacaccct tgtgcatcga caccgacccg gtgaacgcga    10980
cgttcgaggg ctacaaggcc ctgaacgtcc gccggctgaa catcatggcc ggcgacgaaa    11040
ttaactcgcg caacttcgac accctggtcg agctgattgc gccgaccaag gatgacgtgg    11100
tgatcgacaa cggtgccagc tcgttcgtgc ctctgtcgca ttacctcatc agcaaccagg    11160
tgccggctct gctgcaagaa atggggcatg agctggtcat ccataccgtc gtcaccggcg    11220
gccaggctct cctggacacg gtgagcggct tcgcccagct cgccagccag ttcccggccg    11280
aagcgctttt cgtggtctgg ctgaacccgt attgggggcc tatcgagcat gagggcaaga    11340
gctttgagca gatgaaggcg tacacggcca acaaggcccg cgtgtcgtcc atcatccaga    11400
ttccggccct caaggaagaa acctacggcc gcgatttcag cgacatgctg caagagcggc    11460
tgacgttcga ccaggcgctg gccgatgaat cgctcacgat catgacgcgg caacgcctca    11520
agatcgtgcg gcgcggcctg tttgaacagc tcgacgcggc ggccgtgcta tgagcgacca    11580
gattgaagag ctgatccggg agattgcggc caagcacggc atcgccgtcg ccgcgacga    11640 cccggtgctg atcctgcata ccatcaacgc ccggctcatg ccgacagtg cggccaagca    11700 agaggaaatc cttgccgcgt tcaaggaaga gctggaaggg atcgcccatc gttggggcga    11760
ggacgccaag gccaaagcgg agcggatgct gaacgcggcc ctggcggcca gcaaggacgc    11820
aatggcgaag gtaatgaagg acagcgccgc gcaggcggcc gaagcgatcc gcagggaaat    11880
cgacgacggc cttggccgcc agctcgcggc caaggtcgcg gacgcgcggc gcgtggcgat    11940
gatgaacatg atcgccggcg gcatggtgtt gttcgcggcc gccctggtgg tgtgggcctc    12000
gttatgaatc gcagaggcgc agatgaaaaa gcccggcgtt gccgggcttt gtttttgcgt    12060
tagctgggct tgtttgacag gcccaagctc tgactgcgcc cgcgctcgcg ctcctgggcc    12120
tgtttcttct cctgctcctg cttgcgcatc agggcctggt gccgtcgggc tgcttcacgc    12180
atcgaatccc agtcgccggc cagctcggga tgctccgcgc gcatcttgcg cgtcgccagt    12240
tcctcgatct tgggcgcgtg aatgccoatg ccttccttga tttcgcgcac catgtccagc    12300
cgcgtgtgca gggtctgcaa gcgggcttgc tgttgggcct gctgctgctg ccaggcggcc    12360
tttgtacgcg gcagggacag caagccgggg gcattggact gtagctgctg caaacgcgcc    12420
tgctgacggt ctacgagctg ttctaggcgg tcctcgatgc gctccacctg gtcatgcttt    12480
gcctgcacgt agagcgcaag ggtctgctgg taggtctgct cgatgggcgc ggattctaag    12540
agggcctgct gttccgtctc ggcctcctgg gccgcctgta gcaaatcctc gccgctgttg    12600
ccgctggact gctttactgc cggggactgc tgttgccctg ctcgcgccgt cgtcgcagtt    12660
```

```
cggcttgccc ccactcgatt gactgcttca tttcgagccg cagcgatgcg atctcggatt   12720
gcgtcaacgg acggggcagc gcggaggtgt ccggcttctc cttgggtgag tcggtcgatg   12780
ccatagccaa aggtttcctt ccaaaatgcg tccattgctg gaccgtgttt ctcattgatg   12840
cccgcaagca tcttcggctt gaccgccagg tcaagcgcgc cttcatgggc ggtcatgacg   12900
gacgccgcca tgaccttgcc gccgttgttc tcgatgtagc cgcgtaatga ggcaatggtg   12960
ccgcccatcg tcagcgtgtc atcgacaacg atgtacttct ggccggggat cacctccccc   13020
tcgaaagtcg ggttgaacgc caggcgatga tctgaaccgg ctccggttcg ggcgaccttc   13080
tcccgctgca caatgtccgt ttcgacctca aggccaaggc ggtcggccag aacgaccgcc   13140
atcatggccg gaatcttgtt gttccccgcc gcctcgacgg cgaggactgg aacgatgcgg   13200
ggcttgtcgt cgccgatcag cgtcttgagc tgggcaacag tgtcgtccga atcaggcgc    13260
tcgaccaaat taagcgccgc ttccgcgtcg ccctgcttcg cagcctggta ttcaggctcg   13320
ttggtcaaag aaccaaggtc gccgttgcga accaccttcg ggaagtctcc ccacggtgcg   13380
cgctcggctc tgctgtagct gctcaagacg cctccctttt tagccgctaa aactctaacg   13440
agtgcgcccg cgactcaact tgacgctttc ggcacttacc tgtgccttgc cacttgcgtc   13500
ataggtgatg ctttcgcac tcccgatttc aggtacttta tcgaaatctg accgggcgtg    13560
cattacaaag ttcttcccca cctgttggta aatgctgccg ctatctgcgt ggacgatgct   13620
gccgtcgtgg cgctgcgact tatcggcctt tgggccata tagatgttgt aaatgccagg    13680
tttcagggcc ccggctttat ctaccttctg gttcgtccat gcgccttggt tctcggtctg   13740
gacaattctt tgcccattca tgaccaggag gcggtgtttc attgggtgac tcctgacggt   13800
tgcctctggt gttaaacgtg tcctggtcgc ttgccggcta aaaaaaagcc gacctcggca   13860
gttcgaggcc ggctttccct agagccgggc gcgtcaaggt tgttccatct attttagtga   13920
actgcgttcg atttatcagt tactttcctc ccgctttgtg tttcctccca ctcgtttccg   13980
cgtctagccg acccctcaac atagcggcct cttcttgggc tgccttttgcc tcttgccgcg   14040
cttcgtcacg ctcggcttgc accgtcgtaa agcgctcggc ctgcctggcc gcctcttgcg   14100
ccgccaactt cctttgctcc tggtgggcct cggcgtcggc ctgcgccttc gctttcaccg   14160
ctgccaactc cgtgcgcaaa ctctccgctt cgcgcctggt ggcgtcgcgc tcgccgcgaa   14220
gcgcctgcat ttcctggttg gccgcgtcca gggtcttgcg gctctcttct ttgaatgcgc   14280
gggcgtcctg gtgagcgtag tccagctcgg cgcgcagctc ctgcgctcga cgctccacct   14340
cgtcggcccg ctgcgtcgcc agcgcggccc gctgctcggc tcctgccagg gcggtgcgtg   14400
cttcggccag ggcttgccgc tggcgtgcgg ccagctcggc cgcctcggcg gcctgctgct   14460
ctagcaatgt aacgcgcgcc tgggcttctt ccagctcgcg ggcctgcgcc tcgaaggcgt   14520
cggccagctc cccgcgcacg gcttccaact cgttgcgctc acgatcccag ccggcttgcg   14580
ctgcctgcaa cgattcattg gcaagggcct gggcggcttg ccagagggcg gccacggcct   14640
ggttgccggc ctgctgcacc gcgtccggca cctggactgc cagcggggcg gcctgcgccg   14700
tgcgctggcg tcgccattcg cgcatgccgg cgctggcgtc gttcatgttg acgcgggcgg   14760
ccttacgcac tgcatccacg gtcgggaagt tctcccggtc gccttgctcg aacagctcgt   14820
ccgcagccgc aaaaatgcgg tcgcgcgtct cttttgttcag ttccatgttg gctccggtaa   14880
ttggtaagaa taataatact cttacctacc ttatcgcgc aagagtttag ctgaacagtt    14940
ctcgacttaa cggcaggttt tttagcggct gaagggcagg caaaaaaagc cccgcacggt   15000
```

```
cggcgggggc aaagggtcag cgggaagggg attagcgggc gtcgggcttc ttcatgcgtc   15060
ggggccgcgc ttcttgggat ggagcacgac gaagcgcgca cgcgcatcgt cctcggccct   15120
atcggcccgc gtcgcggtca ggaacttgtc gcgcgctagg tcctccctgg tgggcaccag   15180
gggcatgaac tcggcctgct cgatgtaggt ccactccatg accgcatcgc agtcgaggcc   15240
gcgttccttc accgtctctt gcaggtcgcg gtacgcccgc tcgttgagcg gctggtaacg   15300
ggccaattgg tcgtaaatgg ctgtcggcca tgagcggcct ttcctgttga gccagcagcc   15360
gacgacgaag ccggcaatgc aggcccctgg cacaaccagg ccgacgccgg gggcagggga   15420
tggcagcagc tcgccaacca ggaacccgc cgcgatgatg ccgatgccgg tcaaccagcc   15480
cttgaaacta tccggccccg aaacacccct gcgcattgcc tggatgctgc gccggatagc   15540
ttgcaacatc aggagccgtt tcttttgttc gtcagtcatg gtccgccctc accagttgtt   15600
cgtatcggtg tcggacgaac tgaaatcgca agagctgccg gtatcggtcc agccgctgtc   15660
cgtgtcgctg ctgccgaagc acggcgaggg gtccgcgaac gccgcagacg gcgtatccgg   15720
ccgcagcgca tcgcccagca tggccccggt cagcgagccg ccggccaggt agcccagcat   15780
ggtgctgttg gtcgccccgg ccaccagggc cgacgtgacg aaatcgccgt cattccctct   15840
ggattgttcg ctgctcggcg gggcagtgcg ccgcgccggc ggcgtcgtgg atggctcggg   15900
ttggctggcc tgcgacggcc ggcgaaaggt gcgcagcagc tcgttatcga ccggctgcgg   15960
cgtcggggcc gccgccttgc gctgcggtcg gtgttccttc ttcggctcgc gcagcttgaa   16020
cagcatgatc gcggaaacca gcagcaacgc cgcgcctacg cctcccgcga tgtagaacag   16080
catcggattc attcttcggt cctccttgta gcggaaccgt tgtctgtgcg gcgcgggtgg   16140
cccgcgccgc tgtctttggg gatcagccct cgatgagcgc gaccagtttc acgtcggcaa   16200
ggttcgcctc gaactcctgg ccgtcgtcct cgtacttcaa ccaggcatag ccttccgccg   16260
gcggccgacg gttgaggata aggcgggcag ggcgctcgtc gtgctcgacc tggacgatgg   16320
cctttttcag cttgtccggg tccggctcct tcgcgccctt ttccttggcg tccttaccgt   16380
cctggtcgcc gtcctcgccg tcctggccgt cgccggcctc cgcgtcacgc tcggcatcag   16440
tctggccgtt gaaggcatcg acggtgttgg gatcgcggcc cttctcgtcc aggaactcgc   16500
gcagcagctt gaccgtgccg cgcgtgattt cctgggtgtc gtcgtcaagc cacgcctcga   16560
cttcctccgg gcgcttcttg aaggccgtca ccagctcgtt caccacggtc acgtcgcgca   16620
cgcggccggt gttgaacgca tcggcgatct tctccggcag gtccagcagc gtgacgtgct   16680
gggtgatgaa cgccggcgac ttgccgattt ccttggcgat atcgcctttc ttcttgccct   16740
tcgccagctc gcggccaatg aagtcggcaa tttcgcgcgg ggtcagctcg ttgcgttgca   16800
ggttctcgat aacctggtcg gcttcgttgt agtcgttgtc gatgaacgcc gggatggact   16860
tcttgccggc ccacttcgag ccacggtagc ggcgggcgcc gtgattgatg atatagcggc   16920
ccggctgctc ctggttctcg cgcaccgaaa tgggtgactt caccccgcgc tctttgatcg   16980
tggcaccgat ttccgcgatg ctctccgggg aaaagccggg gttgtcggcc gtccgcggct   17040
gatgcggatc ttcgtcgatc aggtccaggt ccagctcgat agggccggaa ccgccctgag   17100
acgccgcagg agcgtccagg aggctcgaca ggtcgccgat gctatccaac cccaggccgg   17160
acggctgcgc cgcgcctgcg gcttcctgag cggccgcagc ggtgtttttc ttggtggtct   17220
tggcttgagc cgcagtcatt gggaaatctc catcttcgtg aacacgtaat cagccagggc   17280
gcgaacctct ttcgatgcct tgcgcgcggc cgttttcttg atcttccaga ccggcacacc   17340
ggatgcgagg gcatcggcga tgctgctgcg caggccaacg gtggccggaa tcatcatctt   17400
```

-continued

```
ggggtacgcg gccagcagct cggcttggtg gcgcgcgtgg cgcggattcc gcgcatcgac    17460
cttgctgggc accatgccaa ggaattgcag cttggcgttc ttctggcgca cgttcgcaat    17520
ggtcgtgacc atcttcttga tgccctggat gctgtacgcc tcaagctcga tgggggacag    17580
cacatagtcg gccgcgaaga gggcggccgc caggccgacg ccaagggtcg gggccgtgtc    17640
gatcaggcac acgtcgaagc cttggttcgc cagggccttg atgttcgccc gaacagctc    17700
gcgggcgtcg tccagcgaca gccgttcggc gttcgccagt accgggttgg actcgatgag    17760
ggcgaggcgc gcggcctggc cgtcgccggc tgcgggtgcg gtttcggtcc agccgccggc    17820
agggacagcg ccgaacagct tgcttgcatg caggccggta gcaaagtcct tgagcgtgta    17880
ggacgcattg ccctgggggt ccaggtcgat cacggcaacc cgcaagccgc gctcgaaaaa    17940
gtcgaaggca agatgcacaa gggtcgaagt cttgccgacg ccgcctttct ggttggccgt    18000
gaccaaagtt ttcatcgttt ggtttcctgt tttttcttgg cgtccgcttc ccacttccgg    18060
acgatgtacg cctgatgttc cggcagaacc gccgttaccc gcgcgtaccc ctcgggcaag    18120
ttcttgtcct cgaacgcggc ccacacgcga tgcaccgctt gcgacactgc gccctggtc    18180
agtcccagcg acgttgcgaa cgtcgcctgt ggcttcccat cgactaagac gccccgcgct    18240
atctcgatgg tctgctgccc cacttccagc ccctggatcg cctcctggaa ctggctttcg    18300
gtaagccgtt tcttcatgga taacacccat aatttgctcc gcgccttggt tgaacatagc    18360
ggtgacagcc gccagcacat gagagaagtt tagctaaaca tttctcgcac gtcaacacct    18420
ttagccgcta aaactcgtcc ttggcgtaac aaaacaaaag cccggaaacc gggctttcgt    18480
ctcttgccgc ttatggctct gcacccggct ccatcaccaa caggtcgcgc acgcgcttca    18540
ctcggttgcg gatcgacact gccagcccaa caaagccggt tgccgccgcc gccaggatcg    18600
cgccgatgat gccggccaca ccggccatcg cccaccaggt cgccgccttc cggttccatt    18660
cctgctggta ctgcttcgca atgctggacc tcggctcacc ataggctgac cgctcgatgg    18720
cgtatgccgc ttctcccctt ggcgtaaaac ccagcgccgc aggcggcatt gccatgctgc    18780
ccgccgcttt cccgaccacg acgcgcgcac caggcttgcg gtccagacct tcggccacgg    18840
cgagctgcgc aaggacataa tcagccgccg acttggctcc acgcgcctcg atcagctctt    18900
gcactcgcgc gaaatccttg gcctccacgg ccgccatgaa tcgcgcacgc ggcgaaggct    18960
ccgcagggcc ggcgtcgtga tcgccgccga gaatgcccttc accaagttc gacgacacga    19020
aaatcatgct gacggctatc accatcatgc agacggatcg cacgaacccg ctgaattgaa    19080
cacgagcacg gcaccgcga ccactatgcc aagaatgccc aaggtaaaaa ttgccggccc    19140
cgccatgaag tccgtgaatg ccccgacggc cgaagtgaag ggcaggccgc cacccaggcc    19200
gccgccctca ctgccggca cctggtcgct gaatgtcgat gccagcacct gcggcacgtc    19260
aatgcttccg ggcgtcgcgc tcgggctgat cgcccatccc gttactgccc cgatcccggc    19320
aatggcaagg actgccagcg ctgccatttt tggggtgagg ccgttcgcgg ccgaggggcg    19380
cagcccctgg ggggatggga ggcccgcgtt agcgggccgg gagggttcga aaggggggg    19440
cacccccctt cggcgtgcgc ggtcacgcgc acagggcgca gccctggtta aaaacaaggt    19500
ttataaatat tggtttaaaa gcaggttaaa agacaggtta gcggtggccg aaaaacgggc    19560
ggaaacccctt gcaaatgctg gattttctgc ctgtggacag cccctcaaat gtcaataggt    19620
gcgcccctca tctgtcagca ctctgcccct caagtgtcaa ggatcgcgcc cctcatctgt    19680
cagtagtcgc gccccctcaag tgtcaatacc gcagggcact tatccccagg cttgtccaca    19740
```

```
tcatctgtgg gaaactcgcg taaaatcagg cgttttcgcc gatttgcgag gctggccagc    19800
tccacgtcgc cggccgaaat cgagcctgcc cctcatctgt caacgccgcg ccgggtgagt    19860
cggcccctca agtgtcaacg tccgcccctc atctgtcagt gagggccaag ttttccgcga    19920
ggtatccaca acgccggcgg ccgcggtgtc tcgcacacgg cttcgacggc gtttctggcg    19980
cgtttgcagg gccatagacg gccgccagcc cagcggcgag ggcaaccagc ccggtgagcg    20040
tcggaaaggc gctggaagcc ccgtagcgac gcggagaggg gcgagacaag ccaagggcgc    20100
aggctcgatg cgcagcacga catagccggt tctcgcaagg acgagaattt ccctgcggtg    20160
cccctcaagt gtcaatgaaa gtttccaacg cgagccattc gcgagagcct tgagtccacg    20220
ctagatgaga gctttgttgt aggtggacca gttggtgatt ttgaactttt gctttgccac    20280
ggaacggtct gcgttgtcgg gaagatgcgt gatctgatcc ttcaactcag caaaagttcg    20340
atttattcaa caaagccacg ttgtgtctca aaatctctga tgttacattg cacaagataa    20400
aaatatatca tcatgaacaa taaaactgtc tgcttacata aacagtaata caaggggtgt    20460
tatgagccat attcaacggg aaacgtcttg ctcgactcta gagctcgttc ctcgaggcct    20520
cgaggcctcg aggaacggta cctgcgggga agcttacaat aatgtgtgtt gttaagtctt    20580
gttgcctgtc atcgtctgac tgactttcgt cataaatccc ggcctccgta acccagcttt    20640
gggcaagctc acggatttga tccggcggaa cgggatatc gagatgccgg gctgaacgct    20700
gcagttccag ctttcccttt cgggacaggt actccagctg attgattatc tgctgaaggg    20760
tcttggttcc acctcctggc acaatgcgaa tgattacttg agcgcgatcg ggcatccaat    20820
tttctcccgt caggtgcgtg gtcaagtgct acaaggcacc tttcagtaac gagcgaccgt    20880
cgatccgtcg ccgggatacg gacaaaatgg agcgcagtag tccatcgagg gcggcgaaag    20940
cctcgccaaa agcaatacgt tcatctcgca cagcctccag atccgatcga gggtcttcgg    21000
cgtaggcaga tagaagcatg gatacattgc ttgagagtat tccgatggac tgaagtatgg    21060
cttccatctt ttctcgtgtg tctgcatcta tttcgagaaa gccccgatg cggcgcaccg    21120 caacgcgaat tgccatacta tccgaaagtc ccagcaggcg cgcttgatag gaaaaggttt    21180
catactcggc cgatcgcaga cgggcactca cgacccttgaa cccttcaact ttcagggatc    21240
gatgctggtt gatggtagtc tcactcgacg tggctctggt gtgttttgac atagcttcct    21300
ccaaagaaag cggaaggtct ggatactcca gcacgaaatg tgcccgggta gacggatgga    21360
agtctagccc tgctcaatat gaaatcaaca gtacatttac agtcaatact gaatatactt    21420
gctacatttg caattgtctt ataacgaatg tgaaataaaa atagtgtaac aacgcttta    21480 ctcatcgata atcacaaaaa catttatacg aacaaaaata caaatgcact ccggtttcac    21540
aggataggcg ggatcagaat atgcaacttt tgacgttttg ttctttcaaa ggggtgctg    21600 gcaaaaccac cgcactcatg ggcctttgcg ctgctttggc aaatgacggt aaacgagtgg    21660
ccctctttga tgccgacgaa aaccggcctc tgacgcgatg gagagaaaac gccttacaaa    21720
gcagtactgg gatcctcgct gtgaagtcta ttccgccgac gaaatgcccc ttcttgaagc    21780
agcctatgaa aatgccgagc tcgaaggatt tgattatgcg ttggccgata cgcgtggcgg    21840
ctcgagcgag ctcaacaaca caatcatcgc tagctcaaac ctgcttctga tccccaccat    21900
gctaacgccg ctcgacatcg atgaggcact atctacctac cgctacgtca tcgagctgct    21960
gttgagtgaa aatttggcaa ttcctacagc tgttttgcgc caacgcgtcc cggtcggccg    22020
attgacaaca tcgcaacgca ggatgtcaga gacgctagag agccttccag ttgtaccgtc    22080
tcccatgcat gaaagagatg catttgccgc gatgaaagaa cgcggcatgt tgcatcttac    22140
```

```
attactaaac acgggaactg atccgacgat gcgcctcata gagaggaatc ttcggattgc   22200
gatggaggaa gtcgtggtca tttcgaaact gatcagcaaa atcttggagg cttgaagatg   22260
gcaattcgca agcccgcatt gtcggtcggc gaagcacggc ggcttgctgg tgctcgaccc   22320
gagatccacc atcccaaccc gacacttgtt ccccagaagc tggacctcca gcacttgcct   22380
gaaaaagccg acgagaaaga ccagcaacgt gagcctctcg tcgccgatca catttacagt   22440
cccgatcgac aacttaagct aactgtggat gcccttagtc cacctccgtc cccgaaaaag   22500
ctccaggttt ttcttcagc gcgaccgccc gcgcctcaag tgtcgaaaac atatgacaac   22560 ctcgttcgg aatacagtcc ctcgaagtcg ctacaaatga ttttaaggcg cgcgttggac   22620
gatttcgaaa gcatgctggc agatggatca tttcgcgtgg ccccgaaaag ttatccgatc   22680
ccttcaacta cagaaaaatc cgttctcgtt cagacctcac gcatgttccc ggttgcgttg   22740
ctcgaggtcg ctcgaagtca ttttgatccg ttggggttgg agaccgctcg agctttcggc   22800
cacaagctgg ctaccgccgc gctcgcgtca ttctttgctg gagagaagcc atcgagcaat   22860
tggtgaagag ggacctatcg gaacccctca ccaaatattg agtgtaggtt tgaggccgct   22920
ggccgcgtcc tcagtcacct tttgagccag ataattaaga gccaaatgca attggctcag   22980
gctgccatcg tccccccgtg cgaaacctgc acgtccgcgt caaagaaata accggcacct   23040
cttgctgttt ttatcagttg agggcttgac ggatccgcct caagtttgcg gcgcagccgc   23100
aaaatgagaa catctatact cctgtcgtaa acctcctcgt cgcgtactcg actggcaatg   23160
agaagttgct cgcgcgatag aacgtcgcgg ggtttctcta aaaacgcgag gagaagattg   23220
aactcacctg ccgtaagttt cacctcaccg ccagcttcgg acatcaagcg acgttgcctg   23280
agattaagtg tccagtcagt aaaacaaaaa gaccgtcggt cttggagcg gacaacgttg   23340 gggcgcacgc gcaaggcaac ccgaatgcgt gcaagaaact ctctcgtact aaacggctta   23400
gcgataaaat cacttgctcc tagctcgagt gcaacaactt tatccgtctc ctcaaggcgg   23460
tcgccactga taattatgat tggaatatca gactttgccg ccagatttcg aacgatctca   23520
agcccatctt cacgacctaa atttagatca acaaccacga catcgaccgt cgcggaagag   23580
agtactctag tgaactgggt gctgtcggct accgcggtca ctttgaaggc gtggatcgta   23640
aggtattcga taataagatg ccgcatagcg acatcgtcat cgataagaag aacgtgtttc   23700
aacggctcac ctttcaatct aaaatctgaa cccttgttca cagcgcttga gaaattttca   23760
cgtgaaggat gtacaatcat ctccagctaa atgggcagtt cgtcagaatt gcggctgacc   23820
gcggatgacg aaaatgcgaa ccaagtattt caattttatg acaaaagttc tcaatcgttg   23880
ttacaagtga aacgcttcga ggttacagct actattgatt aaggagatcg cctatggtct   23940
cgccccggcg tcgtgcgtcc gccgcgagcc agatctcgcc tacttcataa acgtcctcat   24000
aggcacggaa tggaatgatg acatcgatcg ccgtagagag catgtcaatc agtgtgcgat   24060
cttccaagct agcaccttgg gcgctacttt tgacaaggga aaacagtttc ttgaatcctt   24120
ggattggatt cgcgccgtgt attgttgaaa tcgatcccgg atgtcccgag acgacttcac   24180
tcagataagc ccatgctgca tcgtcgcgca tctcgccaag caatatccgg tccggccgca   24240
tacgcagact tgcttggagc aagtgctcgg cgctcacagc acccagccca gcaccgttct   24300
tggagtagag tagtctaaca tgattatcgt gtggaatgac gagttcgagc gtatcttcta   24360
tggtgattag ccttcctgg gggggatgg cgctgatcaa ggtcttgctc attgttgtct   24420
tgccgcttcc ggtagggcca catagcaaca tcgtcagtcg gctgacgacg catgcgtgca   24480
```

```
gaaacgcttc caaatccccg ttgtcaaaat gctgaaggat agcttcatca tcctgatttt    24540
ggcgtttcct tcgtgtctgc cactggttcc acctcgaagc atcataacgg gaggagactt    24600
ctttaagacc agaaacacgc gagcttggcc gtcgaatggt caagctgacg gtgcccgagg    24660
gaacggtcgg cggcagacag atttgtagtc gttcaccacc aggaagttca gtggcgcaga    24720
gggggttacg tggtccgaca tcctgctttc tcagcgcgcc cgctaaaata gcgatatctt    24780
caagatcatc ataagagacg ggcaaaggca tcttggtaaa aatgccggct ggcgcacaa     24840
atgcctctcc aggtcgattg atcgcaattt cttcagtctt cgggtcatcg agccattcca    24900
aaatcggctt cagaagaaag cgtagttgcg gatccacttc catttacaat gtatcctatc    24960
tctaagcgga aatttgaatt cattaagagc ggcggttcct cccccgcgtg gcgccgccag    25020
tcaggcggag ctggtaaaca ccaaagaaat cgaggtcccg tgctacgaaa atggaaacgg    25080
tgtcaccctg attcttcttc agggttggcg gtatgttgat ggttgcctta agggctgtct    25140
cagttgtctg ctcaccgtta ttttgaaagc tgttgaagct catcccgcca cccgagctgc    25200
cggcgtaggt gctagctgcc tggaaggcgc cttgaacaac actcaagagc atagctccgc    25260
taaaacgctg ccagaagtgg ctgtcgaccg agcccggcaa tcctgagcga ccgagttcgt    25320
ccgcgcttgg cgatgttaac gagatcatcg catggtcagg tgtctcggcg cgatcccaca    25380
acacaaaaac gcgcccatct ccctgttgca agccacgctg tatttcgcca acaacggtgg    25440
tgccacgatc aagaagcacg atattgttcg ttgttccacg aatatcctga ggcaagacac    25500
actttacata gcctgccaaa tttgtgtcga ttgcggtttg caagatgcac ggaattattg    25560
tcccttgcgt taccataaaa tcggggtgcg gcaagagcgt ggcgctgctg ggctgcagct    25620
cggtgggttt catacgtatc gacaaatcgt tctcgccgga cacttcgcca ttcggcaagg    25680
agttgtcgtc acgcttgcct tcttgtcttc ggcccgtgtc gccctgaatg gcgcgtttgc    25740
tgaccccttg atcgccgctg ctatatgcaa aaatcggtgt tcttccggc cgtggctcat     25800
gccgctccgg ttcgcccctc ggcggtagag gagcagcagg ctgaacagcc tcttgaaccg    25860
ctggaggatc cggcggcacc tcaatcggag ctggatgaaa tggcttggtg tttgttgcga    25920
tcaaagttga cggcgatgcg ttctcattca ccttcttttg gcgcccacct agccaaatga    25980
ggcttaatga taacgcgaga acgacacctc cgacgatcaa tttctgagac cccgaaagac    26040
gccggcgatg tttgtcggag accagggatc cagatgcatc aacctcatgt gccgcttgct    26100
gactatcgtt attcatccct tcgcccccctt caggacgcgt ttcacatcgg gcctcaccgt    26160
gcccgttttgc ggccttttggc caacgggatc gtaagcggtg ttccagatac atagtactgt    26220
gtggccatcc ctcagacgcc aacctcggga aaccgaagaa atctcgacat cgctcccttt    26280
aactgaatag ttggcaacag cttccttgcc atcaggattg atggtgtaga tggagggtat    26340
gcgtacattg cccggaaagt ggaataccgt cgtaaatcca ttgtcgaaga cttcgagtgg    26400
caacagcgaa cgatcgcctt gggcgacgta gtgccaatta ctgtccgccg caccaagggc    26460
tgtgacaggc tgatccaata aattctcagc tttccgttga tattgtgctt ccgcgtgtag    26520
tctgtccaca acagccttct gttgtgcctc ccttcgccga gccgccgcat cgtcggcggg    26580
gtaggcgaat tggacgctgt aatagagatc gggctgctct ttatcgaggt gggacagagt    26640
cttgaacttt atactgaaaa cataacggcg catcccggag tcgcttgcgg ttagcacgat    26700
tactggctga ggcgtgagga cctggcttgc cttgaaaaat agataatttc cccgcggtag    26760
ggctgctaga tctttgctat ttgaaacggc aaccgctgtc accgtttcgt tcgtggcgaa    26820
tgttacgacc aaagtagctc caaccgccgt cgagaggcgc accacttgat cgggattgta    26880

```
agccaaataa cgcatgcgcg gatctagctt gcccgccatt ggagtgtctt cagcctccgc 26940
accagtcgca gcggcaaata aacatgctaa aatgaaaagt gcttttctga tcatggttcg 27000
ctgtggccta cgtttgaaac ggtatcttcc gatgtctgat aggaggtgac aaccagacct 27060
gccgggttgg ttagtctcaa tctgccgggc aagctggtca ccttttcgta gcgaactgtc 27120
gcggtccacg tactcaccac aggcattttg ccgtcaacga cgagggtcct tttatagcga 27180
atttgctgcg tgcttggagt tacatcattt gaagcgatgt gctcgacctc caccctgccg 27240
cgtttgccaa gaatgacttg aggcgaactg ggattgggat agttgaagaa ttgctggtaa 27300
tcctggcgca ctgttggggc actgaagttc gataccaggt cgtaggcgta ctgagcggtg 27360
tcggcatcat aactctcgcg caggcgaacg tactcccaca atgaggcgtt aacgacggcc 27420
tcctcttgag ttgcaggcaa tcgcgagaca gacacctcgc tgtcaacggt gccgtccggc 27480
cgtatccata gatatacggg cacaagcctg ctcaacggca ccattgtggc tatagcgaac 27540
gcttgagcaa catttcccaa aatcgcgata gctgcgacag ctgcaatgag tttggagaga 27600
cgtcgcgccg atttcgctcg cgcggtttga aaggcttcta cttccttata gtgctcggca 27660
aggctttcgc gcgccactag catggcatat tcaggccccg tcatagcgtc cacccgaatt 27720
gccgagctga agatctgacg gagtaggctg ccatcgcccc acattcagcg ggaagatcgg 27780
gcctttgcag ctcgctaatg tgtcgtttgt ctggcagccg ctcaaagcga caactaggca 27840
cagcaggcaa tacttcatag aattctccat tgaggcgaat ttttgcgcga cctagcctcg 27900
ctcaacctga gcgaagcgac ggtacaagct gctggcagat tgggttgcgc cgctccagta 27960
actgcctcca atgttgccgg cgatcgccgg caaagcgaca atgagcgcat cccctgtcag 28020
aaaaaacata tcgagttcgt aaagaccaat gatcttggcc gcggtcgtac cggcgaaggt 28080
gattacacca agcataaggg tgagcgcagt cgcttcggtt aggatgacga tcgttgccac 28140
gaggtttaag aggagaagca agagaccgta ggtgataagt tgcccgatcc acttagctgc 28200
gatgtcccgc gtgcgatcaa aaatatatcc gacgaggatc agaggcccga tcgcgagaag 28260
cactttcgtg agaattccaa cggcgtcgta aactccgaag gcagaccaga gcgtgccgta 28320
aaggacccac tgtgcccctt ggaaagcaag gatgtcctgg tcgttcatcg gaccgatttc 28380
ggatgcgatt ttctgaaaaa cggcctgggt cacggcgaac attgtatcca actgtgccgg 28440
aacagtctgc agaggcaagc cggttacact aaactgctga acaaagtttg ggaccgtctt 28500
ttcgaagatg gaaaccacat agtcttggta gttagcctgc ccaacaatta gagcaacaac 28560
gatggtgacc gtgatcaccc gagtgatacc gctacgggta tcgacttcgc cgcgtatgac 28620
taaaataccc tgaacaataa tccaaagagt gacacaggcg atcaatggcg cactcaccgc 28680
ctcctggata gtctcaagca tcgagtccaa gcctgtcgtg aaggctacat cgaagatcgt 28740
atgaatggcc gtaaacggcg ccggaatcgt gaaattcatc gattggacct gaacttgact 28800
ggtttgtcgc ataatgttgg ataaaatgag ctcgcattcg gcgaggatgc gggcggatga 28860
acaaatcgcc cagccttagg ggagggcacc aaagatgaca gcggtctttt gatgctcctt 28920
gcgttgagcg gccgcctctt ccgcctcgtg aaggccggcc tgcgcggtag tcatcgttaa 28980
taggcttgtc gcctgtacat tttgaatcat tgcgtcatgg atctgcttga gaagcaaacc 29040
attggtcacg gttgcctgca tgatattgcg agatcgggaa agctgagcag acgtatcagc 29100
attcgccgtc aagcgtttgt ccatcgtttc cagattgtca gccgcaatgc cagcgctgtt 29160
tgcggaaccg gtgatctgcg atcgcaacag gtccgcttca gcatcactac ccacgactgc 29220

```
acgatctgta tcgctggtga tcgcacgtgc cgtggtcgac attggcattc gcggcgaaaa    29280
catttcattg tctaggtcct tcgtcgaagg atactgattt ttctggttga gcgaagtcag    29340
tagtccagta acgccgtagg ccgacgtcaa catcgtaacc atcgctatag tctgagtgag    29400
attctccgca gtcgcgagcg cagtcgcgag cgtctcagcc tccgttgccg ggtcgctaac    29460
aacaaactgc gcccgcgcgg gctgaatata tagaaagctg caggtcaaaa ctgttgcaat    29520
aagttgcgtc gtcttcatcg tttcctacct tatcaatctt ctgcctcgtg gtgacgggcc    29580
atgaattcgc tgagccagcc agatgagttg ccttcttgtg cctcgcgtag tcgagttgca    29640
aagcgcaccg tgttggcacg ccccgaaagc acggcgacat attcacgcat atcccgcaga    29700
tcaaattcgc agatgacgct tccactttct cgtttaagaa gaaacttacg gctgccgacc    29760
gtcatgtctt cacggatcgc ctgaaattcc ttttcggtac atttcagtcc atcgacataa    29820
gccgatcgat ctgcggttgg tgatggatag aaaatcttcg tcatacattg cgcaaccaag    29880
ctggctccta gcggcgattc cagaacatgc tctggttgct gcgttgccag tattagcatc    29940
ccgttgtttt ttcgaacggt caggaggaat ttgtcgacga cagtcgaaaa tttagggttt    30000
aacaaatagg cgcgaaactc atcgcagctc atcacaaaac ggcggccgtc gatcatggct    30060
ccaatccgat gcaggagata tgctgcagcg ggagcgcata cttcctcgta ttcgagaaga    30120
tgcgtcatgt cgaagccggt aatcgacgga tctaacttta cttcgtcaac ttcgccgtca    30180
aatgcccagc caagcgcatg gccccggcac cagcgttgga gccgcgctcc tgcgccttcg    30240
gcgggcccat gcaacaaaaa ttcacgtaac cccgcgattg aacgcatttg tggatcaaac    30300
gagagctgac gatggatacc acggaccaga cggcggttct cttccggaga aatcccaccc    30360
cgaccatcac tctcgatgag agccacgatc cattcgcgca gaaaatcgtg tgaggctgct    30420
gtgttttcta ggccacgcaa cggcgccaac ccgctgggtg tgcctctgtg aagtgccaaa    30480
tatgttcctc ctgtggcgcg aaccagcaat tcgccacccc ggtccttgtc aaagaacacg    30540
accgtacctg cacggtcgac catgctctgt tcgagcatgg ctagaacaaa catcatgagc    30600
gtcgtcttac ccctcccgat aggcccgaat attgccgtca tgccaacatc gtgctcatgc    30660
gggatatagt cgaaaggcgt tccgccattg gtacgaaatc gggcaatcgc gttgccccag    30720
tggcctgagc tggcgccctc tggaaagttt tcgaaagaga caaaccctgc gaaattgcgt    30780
gaagtgattg cgccagggcg tgtgcgccac ttaaaattcc ccggcaattg ggaccaatag    30840
gccgcttcca taccaatacc ttcttggaca accacggcac ctgcatccgc cattcgtgtc    30900
cgagcccgcg cgccccctgtc cccaagacta ttgagatcgt ctgcatagac gcaaaggctc    30960
aaatgatgtg agcccataac gaattcgttg ctcgcaagtg cgtcctcagc ctcggataat    31020
ttgccgattt gagtcacggc tttatcgccg gaactcagca tctggctcga tttgaggcta    31080
agtttcgcgt gcgcttgcgg gcgagtcagg aacgaaaaac tctgcgtgag aacaagtgga    31140
aaatcgaggg atagcagcgc gttgagcatg cccggccgtg tttttgcagg gtattcgcga    31200
aacgaataga tggatccaac gtaactgtct tttggcgttc tgatctcgag tcctcgcttg    31260
ccgcaaatga ctctgtcggt ataaatcgaa gcgccgagtg agccgctgac gaccggaacc    31320
ggtgtgaacc gaccagtcat gatcaaccgt agcgcttcgc caatttcggt gaagagcaca    31380
ccctgcttct cgcggatgcc aagacgatgc aggccatacg ctttaagaga gccagcgaca    31440
acatgccaaa gatcttccat gttcctgatc tggcccgtga gatcgttttc ccttttccg    31500 cttagcttgg tgaacctcct ctttaccttc cctaaagccg cctgtgggta gacaatcaac    31560
gtaaggaagt gttcattgcg gaggagttgg ccggagagca cgcgctgttc aaaagcttcg    31620
```

```
ttcaggctag cggcgaaaac actacggaag tgtcgcggcg ccgatgatgg cacgtcggca   31680
tgacgtacga ggtgagcata tattgacaca tgatcatcag cgatattgcg caacagcgtg   31740
ttgaacgcac gacaacgcgc attgcgcatt tcagtttcct caagctcgaa tgcaacgcca   31800
tcaattctcg caatggtcat gatcgatccg tcttcaagaa ggacgatatg gtcgctgagg   31860
tggccaatat aagggagata gatctcaccg gatctttcgg tcgttccact cgcgccgagc   31920
atcacaccat tcctctccct cgtgggggaa ccctaattgg atttgggcta acagtagcgc   31980 cccccaaac tgcactatca atgcttcttc ccgcggtccg caaaaatagc aggacgacgc   32040
tcgccgcatt gtagtctcgc tccacgatga gccgggctgc aaaccataac ggcacgagaa   32100
cgacttcgta gagcgggttc tgaacgataa cgatgacaaa gccggcgaac atcatgaata   32160
accctgccaa tgtcagtggc accccaagaa acaatgcggg ccgtgtggct gcgaggtaaa   32220
gggtcgattc ttccaaacga tcagccatca actaccgcca gtgagcgttt ggccgaggaa   32280
gctcgcccca aacatgataa caatgccgcc gacgacgccg gcaaccagcc caagcgaagc   32340
ccgcccgaac atccaggaga tcccgatagc gacaatgccg agaacagcga gtgactggcc   32400
gaacggacca aggataaacg tgcatatatt gttaaccatt gtggcggggt cagtgccgcc   32460
acccgcagat tgcgctgcgg cgggtccgga tgaggaaatg ctccatgcaa ttgcaccgca   32520
caagcttggg gcgcagctcg atatcacgcg catcatcgca ttcgagagcg agaggcgatt   32580
tagatgtaaa cggtatctct caaagcatcg catcaatgcg cacctcctta gtataagtcg   32640
aataagactt gattgtcgtc tgcggatttg ccgttgtcct ggtgtggcgg tggcggagcg   32700
attaaaccgc cagcgccatc ctcctgcgag cggcgctgat atgaccccca acatcccac   32760 gtctcttcgg atttttagcgc ctcgtgatcg tcttttggag gctcgattaa cgcgggcacc   32820
agcgattgag cagctgtttc aacttttcgc acgtagccgt ttgcaaaacc gccgatgaaa   32880
ttaccggtgt tgtaagcgga gatcgcccga cgaagcgcaa attgcttctc gtcaatcgtt   32940
tcgccgcctg cataacgact tttcagcatg tttgcagcgg cagataatga tgtgcacgcc   33000
tggagcgcac cgtcaggtgt cagaccgagc atagaaaaat tcgagagtt tatttgcatg   33060 aggccaacat ccagcgaatg ccgtgcatcg agacggtgcc tgacgacttg ggttgcttgg   33120
ctgtgatctt gccagtgaag cgtttcgccg gtcgtgttgt catgaatcgc taaaggatca   33180
aagcgactct ccaccttagc tatcgccgca agcgtagatg tcgcaactga tggggcacac   33240
ttgcgagcaa catggtcaaa ctcagcagat gagagtggcg tggcaaggct cgacgaacag   33300
aaggagacca tcaaggcaag agaaagcgac cccgatctct taagcatacc ttatctcctt   33360
agctcgcaac taacaccgcc tctcccgttg gaagaagtgc gttgtttat gttgaagatt   33420 atcgggaggg tcggttactc gaaaattttc aattgcttct ttatgatttc aattgaagcg   33480
agaaacctcg cccggcgtct tggaacgcaa catggaccga gaaccgcgca tccatgacta   33540
agcaaccgga tcgacctatt caggccgcag ttggtcaggt caggctcaga acgaaaatgc   33600
tcggcgaggt tacgctgtct gtaaacccat tcgatgaacg ggaagcttcc ttccgattgc   33660
tcttggcagg aatattggcc catgcctgct tgcgctttgc aaatgctctt atcgcgttgg   33720
tatcatatgc cttgtccgcc agcagaaacg cactctaagc gattatttgt aaaaatgttt   33780
cggtcatgcg gcggtcatgg gcttgacccg ctgtcagcgc aagacggatc ggtcaaccgt   33840
cggcatcgac aacagcgtga atcttggtgg tcaaaccgcc acgggaacgt cccatacagc   33900
catcgtcttg atcccgctgt ttcccgtcgc cgcatgttgg tggacgcgga cacaggaact   33960
```

```
gtcaatcatg acgacattct atcgaaagcc ttggaaatca cactcagaat atgatcccag    34020
acgtctgcct cacgccatcg tacaaagcga ttgtagcagg ttgtacagga accgtatcga    34080
tcaggaacgt ctgcccaggg cgggcccgtc cggaagcgcc acaagatgac attgatcacc    34140
cgcgtcaacg cgcggcacgc gacgcggctt atttgggaac aaaggactga acaacagtcc    34200
attcgaaatc ggtgacatca aagcggggac gggttatcag tggcctccaa gtcaagcctc    34260
aatgaatcaa aatcagaccg atttgcaaac ctgatttatg agtgtgcggc ctaaatgatg    34320
aaatcgtcct tctagatcgc ctccgtggtg tagcaacacc tcgcagtatc gccgtgctga    34380
ccttggccag ggaattgact ggcaagggtg cttttcacatg accgctcttt tggccgcgat    34440
agatgatttc gttgctgctt tgggcacgta gaaggagaga agtcatatcg gagaaattcc    34500
tcctggcgcg agagcctgct ctatcgcgac ggcatcccac tgtcgggaac agaccggatc    34560
attcacgagg cgaaagtcgt caacacatgc gttataggca tcttcccttg aaggatgatc    34620
ttgttgctgc caatctggag gtgcggcagc cgcaggcaga tgcgatctca gcgcaacttg    34680
cggcaaaaca tctcactcac ctgaaaacca ctagcgagtc tcgcgatcag acgaaggcct    34740
tttacttaac gacacaatat ccgatgtctg catcacaggc gtcgctatcc cagtcaatac    34800
taaagcggtg caggaactaa agattactga tgacttaggc gtgccacgag gcctgagacg    34860
acgcgcgtag acagttttt gaaatcatta tcaaagtgat ggcctccgct gaagcctatc    34920
acctctcgcg cggtctgtcg gagagatggg caagcattat tacggtcttc gcgcccgtac    34980
atgcattgga cgattgcagg gtcaatggat ctgagatcat ccagaggatt gccgcccta    35040 ccttccgttt cgagttggag ccagcccta aatgagacga catagtcgac ttgatgtgac    35100
aatgccaaga gagagatttg cttaacccga tttttttgct caagcgtaag cctattgaag    35160
cttgccggca tgacgtccgc gccgaaagaa tatcctacaa gtaaaacatt ctgcacaccg    35220
aaatgcttgg tgtagacatc gattatgtga ccaagatcct tagcagtttc gcttggggac    35280
cgctccgacc agaaataccg aagtgaactg acgccaatga caggaatccc ttccgtctgc    35340
agataggtac catcgataga tctgctgcct cgcgcgtttc ggtgatgacg gtgaaaacct    35400
ctgacacatg cagctcccgg agacggtcac agcttgtctg taagcggatg ccgggagcag    35460
acaagcccgt cagggcgcgt cagcgggtgt tggcgggtgt cggggcgcag ccatgaccca    35520
gtcacgtagc gatagcggag tgtatactgg cttaactatg cggcatcaga gcagattgta    35580
ctgagagtgc accatatgcg gtgtgaaata ccgcacagat gcgtaaggag aaaataccgc    35640
atcaggcgct cttccgcttc ctcgctcact gactcgctgc gctcggtcgt tcggctgcgg    35700
cgagcggtat cagctcactc aaaggcggta atacggttat ccacagaatc aggggataac    35760
gcaggaaaga acatgtgagc aaaaggccag caaaaggcca ggaaccgtaa aaaggccgcg    35820
ttgctggcgt ttttccatag gctccgcccc cctgacgagc atcacaaaaa tcgacgctca    35880
agtcagaggt ggcgaaaccc gacaggacta taaagatacc aggcgtttcc ccctggaagc    35940
tccctcgtgc gctctcctgt tccgaccctg ccgcttaccg gatacctgtc cgcctttctc    36000
ccttcgggaa gcgtggcgct ttctcatagc tcacgctgta ggtatctcag ttcggtgtag    36060
gtcgttcgct ccaagctggg ctgtgtgcac gaaccccccg ttcagcccga ccgctgcgcc    36120
ttatccggta actatcgtct tgagtccaac ccggtaagac acgacttatc gccactggca    36180
gcagccactg gtaacaggat tagcagagcg aggtatgtag gcggtgctac agagttcttg    36240
aagtggtggc ctaactacgg ctacactaga aggacagtat ttggtatctg cgctctgctg    36300
aagccagtta ccttcggaaa aagagttggt agctcttgat ccggcaaaca aaccaccgct    36360
```

```
ggtagcggtg gttttttttgt ttgcaagcag cagattacgc gcagaaaaaa aggatctcaa   36420
gaagatcctt tgatcttttc tacggggtct gacgctcagt ggaacgaaaa ctcacgttaa   36480
gggattttgg tcatgagatt atcaaaaagg atcttcacct agatcctttt aaattaaaaa   36540
tgaagtttta aatcaatcta aagtatatat gagtaaactt ggtctgacag ttaccaatgc   36600
ttaatcagtg aggcacctat ctcagcgatc tgtctatttc gttcatccat agttgcctga   36660
ctccccgtcg tgtagataac tacgatacgg agggcttac catctggccc cagtgctgca   36720
atgataccgc gagacccacg ctcaccggct ccagatttat cagcaataaa ccagccagcc   36780
ggaagggccg agcgcagaag tggtcctgca actttatccg cctccatcca gtctattaat   36840
tgttgccggg aagctagagt aagtagttcg ccagttaata gtttgcgcaa cgttgttgcc   36900
attgctgcag gggggggggg ggggggggac ttccattgtt cattccacgg acaaaaacag   36960
agaaaggaaa cgacagaggc caaaaagcct cgctttcagc acctgtcgtt tcctttcttt   37020
tcagagggta ttttaaataa aaacattaag ttatgacgaa gaagaacgga aacgccttaa   37080
accggaaaat tttcataaat agcgaaaacc cgcgaggtcg ccgccccgta acctgtcgga   37140
tcaccggaaa ggacccgtaa agtgataatg attatcatct acatatcaca acgtgcgtgg   37200
aggccatcaa accacgtcaa ataatcaatt atgacgcagg tatcgtatta attgatctgc   37260
atcaacttaa cgtaaaaaca acttcagaca atacaaatca gcgacactga atacggggca   37320
acctcatgtc cccccccccc cccccctgc aggcatcgtg gtgtcacgct cgtcgtttgg   37380
tatggcttca ttcagctccg gttcccaacg atcaaggcga gttacatgat cccccatgtt   37440
gtgcaaaaaa gcggttagct ccttcggtcc tccgatcgtt gtcagaagta agttggccgc   37500
agtgttatca ctcatggtta tggcagcact gcataattct cttactgtca tgccatccgt   37560
aagatgcttt tctgtgactg gtgagtactc aaccaagtca ttctgagaat agtgtatgcg   37620
gcgaccgagt tgctcttgcc cggcgtcaac acgggataat accgcgccac atagcagaac   37680
tttaaaagtg ctcatcattg gaaaacgttc ttcgggggcga aaactctcaa ggatcttacc   37740
gctgttgaga tccagttcga tgtaacccac tcgtgcaccc aactgatctt cagcatcttt   37800
tactttcacc agcgtttctg ggtgagcaaa aacaggaagg caaaatgccg caaaaaaggg   37860
aataagggcg acacggaaat gttgaatact catactcttc ctttttcaat attattgaag   37920
catttatcag ggttattgtc tcatgagcgg atacatattt gaatgtattt agaaaaataa   37980
acaaataggg gttccgcgca catttccccg aaaagtgcca cctgacgtct aagaaaccat   38040
tattatcatg acattaacct ataaaaatag gcgtatcacg aggccctttc gtcttcaaga   38100
attggtcgac gatcttgctg cgttcggata ttttcgtgga gttcccgcca cagacccgga   38160
ttgaaggcga gatccagcaa ctcgcgccag atcatcctgt gacggaactt ggcgcgtga   38220 tgactggcca ggacgtcggc cgaaagagcg acaagcagat cacgcttttc gacagcgtcg   38280
gatttgcgat cgaggatttt tcggcgctgc gctacgtccg cgaccgcgtt gagggatcaa   38340
gccacagcag cccactcgac cttctagccg acccagacga gccaagggat ctttttggaa   38400
tgctgctccg tcgtcaggct ttccgacgtt tgggtggttg aacagaagtc attatcgtac   38460
ggaatgccaa gcactcccga ggggaaccct gtggttggca tgcacataca aatggacgaa   38520
cggataaacc ttttcacgcc cttttaaata tccgttattc taataaacgc tcttttctct   38580
taggtttacc cgccaatata tcctgtcaaa cactgatagt ttaaactgaa ggcgggaaac   38640
gacaatctga tcatgagcgg agaattaagg gagtcacgtt atgaccccg ccgatgacgc   38700
```

```
gggacaagcc gttttacgtt tggaactgac agaaccgcaa cgttgaagga gccactcagc   38760
aagctggtac gattgtaata cgactcacta tagggcgaat tgagcgctgt ttaaacgctc   38820
ttcaactgga agagcggtta cccggaccga agcttgaagt tcctattccg aagttcctat   38880
tctctagaaa gtataggaac ttcagatctc gatgctcacc ctgttgtttg gtgttacttc   38940
tgcaggtcga ctctagagga tccaccatga gcccagaacg acgcccggcc gacatccgcc   39000
gtgccaccga ggcggacatg ccggcggtct gcaccatcgt caaccactac atcgagacaa   39060
gcacggtcaa cttccgtacc gagccgcagg aaccgcagga ctggacggac gacctcgtcc   39120
gtctgcggga gcgctatccc tggctcgtcg ccgaggtgga cggcgaggtc gccggcatcg   39180
cctacgcggg ccccctggaag gcacgcaacg cctacgactg gacggccgag tcgaccgtgt   39240
acgtctcccc ccgccaccag cggacgggac tgggctccac gctctacacc cacctgctga   39300
agtccctgga ggcacagggc ttcaagagcg tggtcgctgt catcgggctg cccaacgacc   39360
cgagcgtgcg catgcacgag cgctcggat  atgcccccg  cggcatgctg cgggcggccg   39420
gcttcaagca cgggaactgg catgacgtgg gtttctggca gctggacttc agcctgccgg   39480
taccgccccg tccggtcctg cccgtcaccg agatctgatc cgtcgaccaa cctagacttg   39540
tccatcttct ggattggcca acttaattaa tgtatgaaat aaaaggatgc acacatagtg   39600
acatgctaat cactataatg tgggcatcaa agttgtgtgt tatgtgtaat tactagttat   39660
ctgaataaaa gagaaagaga tcatccatat ttcttatcct aaatgaatgt cacgtgtctt   39720
tataattctt tgatgaacca gatgcatttc attaaccaaa tccatataca tataaatatt   39780
aatcatatat aattaatatc aattgggtta gcaaaacaaa tctagtctag gtgtgttttg   39840
cgaattgcgg ccgcgatctg gggaattccc atggacaccg tgtgcagcg  tgacccggtc   39900 gtgccccctct ctagagataa tgagcattgc atgtctaagt tataaaaaat taccacatat   39960 ttttttttgtc acacttgttt gaagtgcagt ttatctatct ttatacatat atttaaactt   40020
tactctacga ataatataat ctatagtact acaataatat cagtgttta  gagaatcata   40080 taaatgaaca gttagacatg gtctaaagga caattgagta ttttgacaac aggactctac   40140
agttttatct ttttagtgtg catgtgttct cctttttttt tgcaaatagc ttcacctata   40200
taatacttca tccattttat tagtacatcc atttagggtt tagggttaat ggtttttata   40260
gactaatttt tttagtacat ctattttatt ctattttagc ctctaaatta agaaaactaa   40320
aactctattt tagtttttttt atttaataat ttagatataa aatagaataa aataaagtga   40380
ctaaaaatta aacaaatacc ctttaagaaa ttaaaaaaac taaggaaaca tttttcttgt   40440
ttcgagtaga taatgccagc ctgttaaacg ccgtcgacga gtctaacgga caccaaccag   40500
cgaaccagca gcgtcgcgtc gggccaagcg aagcagacgg cacggcatct ctgtcgctgc   40560
ctctggaccc ctctcgagag ttccgctcca ccgttggact tgctccgctg tcggcatcca   40620
gaaattgcgt ggcggagcgg cagacgtgag ccggcacggc aggcggcctc ctcctcctct   40680
cacggcaccg gcagctacgg gggattcctt tcccaccgct ccttcgcttt ccttcctcg    40740 cccgccgtaa taaatagaca ccccctccac accctctttc cccaacctcg tgttgttcgg   40800
agcgcacaca cacacaacca gatctccccc aaatccaccc gtcggcacct ccgcttcaag   40860
gtacgccgct cgtcctcccc ccccccctc  tctaccttct ctagatcggc gttccggtcc   40920
atgcatggtt agggcccggt agttctactt ctgttcatgt ttgtgttaga tccgtgtttg   40980
tgttagatcc gtgctgctag cgttcgtaca cggatgcgac ctgtacgtca gacacgttct   41040
gattgctaac ttgccagtgt ttctctttgg ggaatcctgg gatggctcta gccgttccgc   41100
```

```
agacgggatc gatttcatga ttttttttgt ttcgttgcat agggtttggt ttgcccttt   41160
cctttatttc aatatatgcc gtgcacttgt ttgtcgggtc atcttttcat gcttttttt   41220
gtcttggttg tgatgatgtg gtctggttgg gcggtcgttc tagatcggag tagaattctg   41280
tttcaaacta cctggtggat ttattaattt tggatcgtga tgtgtgtgcc atacatattc   41340
atagttacga attgaagatg atggatggaa atatcgatct aggataggta tacatgttga   41400
tgcgggtttt actgatgcat atacagagat gcttttttgtt cgcttggttg tgatgatgtg   41460
gtgtggttgg gcggtcgttc attcgttcta gatcggagta gaatactgtt tcaaactacc   41520
tggtgtattt attaattttg gaactgtatg tgtgtgtcat acatcttcat agttacgagt   41580
ttaagatgga tggaaatatc gatctaggat aggtatacat gttgatgtgg gttttactga   41640
tgcatataca tgatggcata tgcagcatct attcatatgc tctaaccttg agtacctatc   41700
tattataata aacaagtatg ttttataatt attttgatct tgatatactt ggatgatggc   41760
atatgcagca gctatatgtg gatttttta gccctgcctt catacgctat ttatttgctt   41820
ggtactgttt cttttgtcga tgctcaccct gttgtttggt gttacttctg caggtaccgg   41880
tctctacgta cagtccggac tggcgccttg gcgcgccgat catccacaag tttgtacaaa   41940
aaagctgaac gagaaacgta aaatgatata aatatcaata tattaaatta gattttgcat   42000
aaaaaacaga ctacataata ctgtaaaaca caacatatcc agtcactatg gcggccgcat   42060
taggcacccc aggctttaca ctttatgctt ccggctcgta taatgtgtgg attttgagtt   42120
aggatttaaa tacgcgttga tccggcttac taaaagccag ataacagtat gcgtatttgc   42180
gcgctgattt ttgcggtata agaatatata ctgatatgta tacccgaagt atgtcaaaaa   42240
gaggtatgct atgaagcagc gtattacagt gacagttgac agcgacagct atcagttgct   42300
caaggcatat atgatgtcaa tatctccggt ctggtaagca caaccatgca gaatgaagcc   42360
cgtcgtctgc gtgccgaacg ctggaaagcg gaaaatcagg aagggatggc tgaggtcgcc   42420
cggtttattg aaatgaacgg ctcttttgct gacgagaaca ggggctggtg aaatgcagtt   42480
taaggtttac acctataaaa gagagagccg ttatcgtctg tttgtggatg tacagagtga   42540
tatcattgac acgcccggtc gacggatggt gatcccctg gccagtgcac gtctgctgtc   42600
agataaagtc tcccgtgaac tttacccggt ggtgcatatc ggggatgaaa gctggcgcat   42660
gatgaccacc gatatggcca gtgtgccggt ctccgttatc ggggaagaag tggctgatct   42720
cagccaccgc gaaaatgaca tcaaaaacgc cattaacctg atgttctggg aatataaat   42780
gtcaggctcc cttatacaca gccagtctgc aggtcgacca tagtgactgg atatgttgtg   42840
ttttacagta ttatgtagtc tgttttttat gcaaaatcta atttaatata ttgatatta   42900
tatcatttta cgtttctcgt tcagctttct tgtacaaagt ggtgttaacc tagacttgtc   42960
catcttctgg attggccaac ttaattaatg tatgaaataa aaggatgcac acatagtgac   43020
atgctaatca ctataatgtg gcatcaaag ttgtgtgtta tgtgtaatta ctagttatct   43080
gaataaaaga gaaagagatc atccatattt cttatcctaa atgaatgtca cgtgtcttta   43140
taattctttg atgaaccaga tgcatttcat taaccaaatc catatacata taaatattaa   43200
tcatatataa ttaatatcaa ttgggttagc aaaacaaatc tagtctaggt gtgttttgcg   43260
aattgcggcc gccaccgcgg tggagctcga attccggtcc gggtcacctt tgtccaccaa   43320
gatgaaactg cggccgctca ttaattaagt caggcgcgcc tctagttgaa gacacgttca   43380
tgtcttcatc gtaagaagac actcagtagt cttcggccag aatggccatc tggattcagc   43440
```

```
aggcctagaa ggccatttaa atcctgagga tctggtcttc ctaaggaccc gggatatcgg   43500
accgattaaa ctttaattcg gtccgaagct tgaagttcct attccgaagt tcctattctc   43560
cagaaagtat aggaacttcg catgcctgca gtgcagcgtg acccggtcgt gcccctctct   43620
agagataatg agcattgcat gtctaagtta taaaaaatta ccacatattt tttttgtcac   43680
acttgtttga agtgcagttt atctatcttt atacatatat ttaaacttta ctctacgaat   43740
aatataatct atagtactac aataatatca gtgttttaga gaatcatata aatgaacagt   43800
tagacatggt ctaaaggaca attgagtatt ttgacaacag gactctacag ttttatcttt   43860
ttagtgtgca tgtgttctcc ttttttttg caaatagctt cacctatata atacttcatc   43920
cattttatta gtacatccat ttagggttta gggttaatgg ttttataga ctaattttt   43980 tagtacatct attttattct attttagcct ctaaattaag aaaactaaaa ctctatttta   44040 gttttttat ttaataattt agatataaaa tagaataaaa taaagtgact aaaaattaaa   44100 caaatccct ttaagaaatt aaaaaaacta aggaaacatt tttcttgttt cgagtagata   44160
atgccagcct gttaaacgcc gtcgacgagt ctaacgdaca ccaaccagcg aaccagcagc   44220
gtcgcgtcgg gccaagcgaa gcagacggca cggcatctct gtcgctgcct ctggacccct   44280
ctcgagagtt ccgctccacc gttggacttg ctccgctgtc ggcatccaga aattgcgtgg   44340
cggagcggca gacgtgagcc ggcacggcag gcggcctcct cctcctctca cggcaccggc   44400
agctacgggg gattccttc ccaccgctcc ttcgctttcc cttcctcgcc cgccgtaata   44460
aatagacacc ccctccacac cctctttccc caacctcgtg ttgttcggag cgcacacaca   44520
cacaaccaga tctcccccaa atccacccgt cggcacctcc gcttcaaggt acgccgctcg   44580 tcctccccc ccccctctc taccttctct agatcggcgt tccggtccat gcatggttag   44640
ggcccggtag ttctacttct gttcatgttt gtgttagatc cgtgtttgtg ttagatccgt   44700
gctgctagcg ttcgtacacg gatgcgacct gtacgtcaga cacgttctga ttgctaactt   44760
gccagtgttt ctctttgggg aatcctggga tggctctagc cgttccgcag acgggatcga   44820
tttcatgatt ttttttgttt cgttgcatag ggtttggttt gccctttcc tttatttcaa   44880 tatatgccgt gcacttgttt gtcgggtcat cttttcatgc ttttttttgt cttggttgtg   44940
atgatgtggt ctggttgggc ggtcgttcta gatcggagta gaattctgtt tcaaactacc   45000
tggtggattt attaattttg gatctgtatg tgtgtgccat acatattcat agttacgaat   45060
tgaagatgat ggatggaaat atcgatctag gataggtata catgttgatg cgggttttac   45120
tgatgcatat acagagatgc tttttgttcg cttggttgtg atgatgtggt gtggttgggc   45180
ggtcgttcat tcgttctaga tcggagtaga atactgtttc aaactacctg gtgtatttat   45240
taattttgga actgtatgtg tgtgtcatac atcttcatag ttacgagttt aagatggatg   45300
gaaatatcga tctaggatag gtatacatgt tgatgtgggt tttactgatg catatacatg   45360
atggcatatg cagcatctat tcatatgctc taaccttgag tacctatcta ttataataaa   45420
caagtatgtt ttataattat tttgatcttg atatacttgg atgatggcat atgcagcagc   45480
tatatgtgga tttttttagc cctgccttca tacgctattt attgcttgg tactgtttct   45540 tttgtcgatg ctcaccctgt tgtttggtgt tacttctgca ggtcgacttt aacttagcct   45600
aggatccaca cgacaccatg atagaggtga aaccgattaa cgcagaggat acctatgaac   45660
taaggcatag aatactcaga ccaaaccagc cgatagaagc gtgtatgttt gaaagcgatt   45720
tacttcgtgg tgcatttcac ttaggcggct attacggggg caaactgatt tccatagctt   45780
cattccacca ggccgagcac tcagaactcc aaggccagaa acagtaccag ctccgaggta   45840
```

```
tggctacctt ggaaggttat cgtgagcaga aggcgggatc gagtctaatt aaacacgctg   45900
aagaaattct tcgtaagagg ggggcggact tgctttggtg taatgcgcgg acatccgcct   45960
caggctacta caaaaagtta ggcttcagcg agcagggaga ggtattcgac acgccgccag   46020
taggacctca catcctgatg tataaaagga tcacataact agctagtcag ttaacctaga   46080
cttgtccatc ttctggattg gccaacttaa ttaatgtatg aaataaaagg atgcacacat   46140
agtgacatgc taatcactat aatgtgggca tcaaagttgt gtgttatgtg taattactag   46200
ttatctgaat aaaagagaaa gagatcatcc atatttctta tcctaaatga atgtcacgtg   46260
tctttataat tctttgatga accagatgca tttcattaac caaatccata tacatataaa   46320
tattaatcat atataattaa tatcaattgg gttagcaaaa caaatctagt ctaggtgtgt   46380
tttgcgaatt cagagctcga attcattccg attaatcgtg gcctcttgct cttcaggatg   46440
aagagctatg tttaaacgtg caagcgctac tagacaattc agtacattaa aaacgtccgc   46500
aatgtgttat taagttgtct aagcgtcaat ttgtttacac cacaatatat cctgccacca   46560
gccagccaac agctccccga ccggcagctc ggcacaaaat caccactcga tacaggcagc   46620
ccatcagtcc gggacggcgt cagcgggaga gccgttgtaa ggcggcagac tttgctcatg   46680
ttaccgatgc tattcggaag aacggcaact aagctgccgg gtttgaaaca cggatgatct   46740
cgcggagggt agcatgttga ttgtaacgat gacagagcgt tgctgcctgt gatcaaaatat   46800 catctccctc gcagagatcc gaattatcag ccttcttatt catttctcgc ttaaccgtga   46860
caggctgtcg atcttgagaa ctatgccgac ataataggaa atcgctggat aaagccgctg   46920
aggaagctga gtggcgctat ttctttagaa gtgaacgttg acgatcgtcg accgtacccc   46980
gatgaattaa ttcggacgta cgttctgaac acagctggat acttacttgg gcgattgtca   47040
tacatgacat caacaatgta cccgtttgtg taaccgtctc ttggaggttc gtatgacact   47100
agtggttccc ctcagcttgc gactagatgt tgaggcctaa catttttatta gagagcaggc   47160 tagttgctta gatacatgat cttcaggccg ttatctgtca gggcaagcga aaattggcca   47220
tttatgacga ccaatgcccc gcagaagctc ccatctttgc cgccatagac gccgcgcccc   47280 cctttttgggg tgtagaacat cctttttgcca gatgtggaaa agaagttcgt tgtcccattg   47340
ttggcaatga cgtagtagcc ggcgaaagtg cgagacccat ttgcgctata tataagccta   47400
cgatttccgt tgcgactatt gtcgtaattg gatgaactat tatcgtagtt gctctcagag   47460
ttgtcgtaat ttgatggact attgtcgtaa ttgcttatgg agttgtcgta gttgcttgga   47520
gaaatgtcgt agttggatgg ggagtagtca tagggaagac gagcttcatc cactaaaaca   47580
attggcaggt cagcaagtgc ctgccccgat gccatcgcaa gtacgaggct tagaaccacc   47640
ttcaacagat cgcgcatagt cttccccagc tctctaacgc ttgagttaag ccgcgccgcg   47700
aagcggcgtc ggcttgaacg aattgttaga cattatttgc cgactacctt ggtgatctcg   47760
cctttcacgt agtgaacaaa ttcttccaac tgatctgcgc gcgaggccaa gcgatcttct   47820
tgtccaagat aagcctgcct agcttcaagt atgacgggct gatactgggc cggcaggcgc   47880
tccattgccc agtcggcagc gacatccttc ggcgcgattt tgccggttac tgcgctgtac   47940
caaatgcggg acaacgtaag cactacattt cgctcatcgc cagcccagtc gggcggcgag   48000
ttccatagcg ttaaggtttc atttagcgcc tcaaatagat cctgttcagg aaccggatca   48060
aagagttcct ccgccgctgg acctaccaag gcaacgctat gttctcttgc ttttgtcagc   48120
aagatagcca gatcaatgtc gatcgtggct ggctcgaaga tacctgcaag aatgtcattg   48180
```

```
cgctgccatt ctccaaattg cagttcgcgc ttagctggat aacgccacgg aatgatgtcg   48240
tcgtgcacaa caatggtgac ttctacagcg cggagaatct cgctctctcc aggggaagcc   48300
gaagtttcca aaaggtcgtt gatcaaagct cgccgcgttg tttcatcaag ccttacagtc   48360
accgtaacca gcaaatcaat atcactgtgt ggcttcaggc cgccatccac tgcggagccg   48420
tacaaatgta cggccagcaa cgtcggttcg agatggcgct cgatgacgcc aactacctct   48480
gatagttgag tcgatacttc ggcgatcacc gcttccctca tgatgtttaa ctcctgaatt   48540
aagccgcgcc gcgaagcggt gtcggcttga atgaattgtt aggcgtcatc ctgtgctccc   48600
gagaaccagt accagtacat cgctgttccg ttcgagactt gaggtctagt tttatacgtg   48660
aacaggtcaa tgccgccgag agtaaagcca cattttgcgt acaaattgca ggcaggtaca   48720
ttgttcgttt gtgtctctaa tcgtatgcca aggagctgtc tgcttagtgc ccactttttc   48780
gcaaattcga tgagactgtg cgcgactcct ttgcctcggt gcgtgtgcga cacaacaatg   48840
tgttcgatag aggctagatc gttccatgtt gagttgagtt caatcttccc gacaagctct   48900
tggtcgatga atgcgccata gcaagcagag tcttcatcag agtcatcatc cgagatgtaa   48960
tccttccggt aggggctcac acttctggta gatagttcaa agccttggtc ggataggtgc   49020
acatcgaaca cttcacgaac aatgaaatgg ttctcagcat ccaatgtttc cgccacctgc   49080
tcagggatca ccgaaatctt catatgacgc ctaacgcctg gcacagcgga tcgcaaacct   49140
ggcgcggctt ttggcacaaa aggcgtgaca ggtttgcgaa tccgttgctg ccacttgtta   49200
acccttttgc cagatttggt aactataatt tatgttagag gcgaagtctt gggtaaaaac   49260
tggcctaaaa ttgctgggga tttcaggaaa gtaaacatca ccttccggct cgatgtctat   49320
tgtagatata tgtagtgtat ctacttgatc gggggatctg ctgcctcgcg cgtttcggtg   49380
atgacggtga aaacctctga cacatgcagc tcccggagac ggtcacagct tgtctgtaag   49440
cggatgccgg gagcagacaa gcccgtcagg gcgcgtcagc gggtgttggc gggtgtcggg   49500
gcgcagccat gacccagtca cgtagcgata gcggagtgta tactggctta actatgcggc   49560
atcagagcag attgtactga gagtgcacca tatgcggtgt gaaataccgc acagatgcgt   49620
aaggagaaaa taccgcatca ggcgctcttc cgcttcctcg ctcactgact cgctgcgctc   49680
ggtcgttcgg ctgcggcgag cggtatcagc tcactcaaag gcggtaatac ggttatccac   49740
agaatcaggg gataacgcag gaaagaacat gtgagcaaaa ggccagcaaa aggccaggaa   49800
ccgtaaaaag gccgcgttgc tggcgttttt ccataggctc cgcccccctg acgagcatca   49860
caaaaatcga cgctcaagtc agaggtggcg aaacccgaca ggactataaa gataccaggc   49920
gtttccccct ggaagctccc tcgtgcgctc tcctgttccg accctgccgc ttaccggata   49980
cctgtccgcc tttctccctt cgggaagcgt ggcgctttct catagctcac gctgtaggta   50040
tctcagttcg gtgtaggtcg ttcgctccaa gctgggctgt gtgcacgaac cccccgttca   50100
gcccgaccgc tgcgccttat ccggtaacta tcgtcttgag tccaacccgg taagacacga   50160
cttatcgcca ctggcagcag ccactggtaa caggattagc agagcgaggt atgtaggcgg   50220
tgctacagag ttcttgaagt ggtggcctaa ctacggctac actagaagga cagtatttgg   50280
tatctgcgct ctgctgaagc cagttacctt cggaaaaaga gttggtagct cttgatccgg   50340
caaacaaacc accgctggta gcggtggttt ttttgtttgc aagcagcaga ttacgcgcag   50400
aaaaaaagga tctcaagaag atcctttgat cttttctacg gggtctgacg ctcagtggaa   50460
cgaaaactca cgttaaggga ttttggtcat gagattatca aaaaggatct tcacctagat   50520
ccttttaaat taaaaatgaa gttttaaatc aatctaaagt atatatgagt aaacttggtc   50580
```

```
tgacagttac caatgcttaa tcagtgaggc acctatctca gcgatctgtc tatttcgttc    50640
atccatagtt gcctgactcc ccgtcgtgta gataactacg atacgggagg gcttaccatc    50700
tggccccagt gctgcaatga taccgcgaga cccacgctca ccggctccag atttatcagc    50760
aataaaccag ccagccggaa gggccgagcg cagaagtggt cctgcaactt tatccgcctc    50820
catccagtct attaattgtt gccgggaagc tagagtaagt agttcgccag ttaatagttt    50880
gcgcaacgtt gttgccattg ctgca                                          50905

<210> SEQ ID NO 17
<211> LENGTH: 552
<212> TYPE: DNA
<213> ORGANISM: Arabidopsis thaliana

<400> SEQUENCE: 17
atgaatcact ttgcggttca accaaacgcg ttcgctgccg gcggagattt gagaagcagc      60
tccgtttcag ttgttgaaag agatcaaacc accgtcgttt gtccaaaacc acgtcgtatt     120
ggtctccgta caaccatca ccatccttct cgatctctcc gttgttactt cagtcatcaa      180
ttggagcttt gtgaatccaa agcagagact gatatcttag atatcatact caccaaggat     240
ggttatggtg cagaacaagt taataagcag gtaatagact cgccgtcccc gtttttatgt     300
gggtcgccgc cgagcagagt cgctaaccca ttaacacagg atgctcgatt tcgagatgag     360
attgtatcgg tttcttcagt gattccgcct cagttgggtt tacctccttc ttcatctcct     420
tcttcttcct ctgggaggaa aggaggatgt gttgttagag caattttggg taacagccca     480
aaggttagag ttgaagggtt tgattgtctt gacagggata gcagaaactg cagcatccct     540
gccttggctt ag                                                        552

<210> SEQ ID NO 18
<211> LENGTH: 183
<212> TYPE: PRT
<213> ORGANISM: Arabidopsis thaliana

<400> SEQUENCE: 18

Met Asn His Phe Ala Val Gln Pro Asn Ala Phe Ala Ala Gly Gly Asp
1               5                   10                  15

Leu Arg Ser Ser Val Ser Val Val Glu Arg Asp Gln Thr Thr Val
            20                  25                  30

Val Cys Pro Lys Pro Arg Arg Ile Gly Leu Arg Asn Asn His His His
        35                  40                  45

Pro Ser Arg Ser Leu Arg Cys Tyr Phe Ser His Gln Leu Glu Leu Cys
    50                  55                  60

Glu Ser Lys Ala Glu Thr Asp Ile Leu Asp Ile Ile Leu Thr Lys Asp
65                  70                  75                  80

Gly Tyr Gly Ala Glu Gln Val Asn Lys Gln Val Ile Asp Ser Pro Ser
                85                  90                  95

Pro Phe Leu Cys Gly Ser Pro Ser Arg Val Ala Asn Pro Leu Thr
            100                 105                 110

Gln Asp Ala Arg Phe Arg Asp Glu Ile Val Ser Val Ser Ser Val Ile
        115                 120                 125

Pro Pro Gln Leu Gly Leu Pro Pro Ser Ser Pro Ser Ser Ser
    130                 135                 140

Gly Arg Lys Gly Gly Cys Val Val Arg Gly Asn Phe Gly Asn Ser Pro
145                 150                 155                 160
```

Lys Val Arg Val Glu Gly Phe Asp Cys Leu Asp Arg Asp Ser Arg Asn
              165                 170                 175

Cys Ser Ile Pro Ala Leu Ala
            180

<210> SEQ ID NO 19
<211> LENGTH: 1187
<212> TYPE: DNA
<213> ORGANISM: Zea mays

<400> SEQUENCE: 19

```
cgaatcggaa ggcagcggat cggctcggac cgggccgggc cggggcgtgt ggctgcgctg      60
cgtcgcctcg cctcgcgtcg gcgattcttc cggcgaacca acggcgccag ccacacctga     120
gcgagcggcg cagaaaggtg gcgcgtggac gccacgctcg cctcagcctt agggatcgag     180
ggccctttcc gtccgcgtgg ctgctgctcc tctcgtctct cctcccaccc gtccaaggca     240
tggagcactg ctatgtggga cagccgatct cgagggccga ggcaatgccc gagaggaggt     300
ccaggttctg gcagatggat gcgcctcctc cgccccgggc ggaggtcatc tgcccccagc     360
ctcgccgcgc cacccggatt cccctcaccg ctgtggaaac cctgaacaaa gccagcccca     420
agatgaacgg tgcatttccg ccgtacagat cggactccac ttgcgatata cttgatctta     480
tcctcagtaa gaatgactcg gatggagatt cgagcagcca ggtgggcttc ttatgcggct     540
cacctccgat acgcgctgac aaccctgtta tccatgatcc acagtttggt aaagactgc      600
catccttttc tcctccagga gggagctcct atggcaaaat gccagcagta cgagttgaag     660
taggctcgcc atcttgcggc gttagcagca gcccaaaagt aaggattgaa ggtttcgcct     720
gtggcaactc cgagacccac tatgcagtta cctttgtctg agcattttgt tggtatgttc     780
ctgattttgc ccttggaccg accgaccgct cgctccttgt gaatcaccgt ggtggtgtgc     840
aggatattaa gtagtgcatt taagctagcc tgattagagt tgccttttgc ccttctgact     900
ggcaatcgaa actgcacaat tgcagtgagt agtgagatgt atataagtga ggtccccgca     960
tatttacctt atgatgtatg tgtctagtaa atttagctgg agatctggtg tttcatggat    1020
aagagcctgt gaatagagtt gagttttttgc attcagaagt aagatgcaac atggagtttt    1080
cagttattat tatgaatgca tctttgtttt gtgtcaaaaa aaaaaaaaa aaaaaaaaa      1140
aaaaaaaaa aaaaaaaaa aaaaaaaaa aaaaaaaaa aaaaaaa                     1187
```

<210> SEQ ID NO 20
<211> LENGTH: 173
<212> TYPE: PRT
<213> ORGANISM: Zea mays

<400> SEQUENCE: 20

Met Glu His Cys Tyr Val Gly Gln Pro Ile Ser Arg Ala Glu Ala Met
1               5                  10                  15

Pro Glu Arg Arg Ser Arg Phe Trp Gln Met Asp Ala Pro Pro Pro
            20                  25                  30

Arg Ala Glu Val Ile Cys Pro Gln Pro Arg Arg Ala Thr Arg Ile Pro
        35                  40                  45

Leu Thr Ala Val Glu Thr Leu Asn Lys Ala Ser Pro Lys Met Asn Gly
    50                  55                  60

Ala Phe Pro Pro Tyr Arg Ser Asp Ser Thr Cys Asp Ile Leu Asp Leu
65                  70                  75                  80

Ile Leu Ser Lys Asn Asp Ser Asp Gly Asp Ser Ser Gln Val Gly
            85                  90                  95

```
Phe Leu Cys Gly Ser Pro Pro Ile Arg Ala Asp Asn Pro Val Ile His
                100                 105                 110

Asp Pro Gln Phe Gly Lys Arg Leu Pro Ser Phe Ser Pro Gly Gly
            115                 120                 125

Ser Ser Tyr Gly Lys Met Pro Ala Val Arg Val Glu Val Gly Ser Pro
    130                 135                 140

Ser Cys Gly Val Ser Ser Pro Lys Val Arg Ile Glu Gly Phe Ala
145                 150                 155                 160

Cys Gly Asn Ser Glu Thr His Tyr Ala Val Thr Phe Val
                165                 170
```

<210> SEQ ID NO 21
<211> LENGTH: 1021
<212> TYPE: DNA
<213> ORGANISM: Zea mays

<400> SEQUENCE: 21

```
ctctcttctc ctccctctct tccttttctc ttttcttttt ctcattgcga cgcctgcctg      60
ggcgaccgtc gccgctctac accaggtgcc caggtcttcg ccggcgccga gcagccacca     120
gccgctgtgc aacaaatcac gtctgtcgag ggcatggatc cctacatgac aaggctcggc     180
gccggagcca ctcaccagct ttccagggct gaagcaatgc ctgaccgaag gtctaggttt     240
tggcagacag atgtgcagct gcgcctcgg atagacatca tctgccctct gcctcgccgc     300
ccttctcgcc taccggttct caatagcccc aagctcaatg ggcactccc actgtataga     360
gcagaccca cttttgatat cgttgacctc atccttagca agaatgaccc tgatgtggat     420
actgattcaa gcagccaggc gggcttttc tgtggctcgc ctcctgcacg cactgacaac     480
cctgttatca atgacccaca gtttggaaag aaaacaccat ccttttctcc tttatttggt     540
ggaagctctt ccgggaaaat gacagctgga agagtcgaag taggttctcc gtcgtcttgc     600
ggggcgagca gcccgaaagt aaggatcgaa ggttttgctt gcgggaacaa agagcccct     660
cactgtttg cctgatgatc cggatcattg accctaccta accctgtttt gctaccccg     720
caacatgtac atttccctg ctagtttctt tggttaaaaa acctggtagt ttctttgagt     780
cggagtcgag taagagcgct tgttgttgcc ccttgtgatg accgtgggtg gcttttggtg     840
caagggagca gagcacagct ctcggatgta aatagggtgg cgtatgtagt gctagatgtt     900
tgtatgtgtc tgctaaaatg tagtagtaag gttgggtggg tccatgtgtc ggcgtctgta     960
aatagcgtca tgcatttgga tgtaaattga aatgcgtctt caattaaaaa aaaaaaaaa    1020
a                                                                    1021
```

<210> SEQ ID NO 22
<211> LENGTH: 173
<212> TYPE: PRT
<213> ORGANISM: Zea mays

<400> SEQUENCE: 22

```
Met Asp Pro Tyr Met Thr Arg Leu Gly Ala Gly Ala Thr His Gln Leu
1               5                   10                  15

Ser Arg Ala Glu Ala Met Pro Arg Arg Ser Arg Phe Trp Gln Thr
            20                  25                  30

Asp Val Gln Leu Ala Pro Arg Ile Asp Ile Ile Cys Pro Leu Pro Arg
        35                  40                  45

Arg Pro Ser Arg Leu Pro Val Leu Asn Ser Pro Lys Leu Asn Gly Ala
    50                  55                  60
```

Leu Pro Leu Tyr Arg Ala Asp Pro Thr Phe Asp Ile Val Asp Leu Ile
65                  70                  75                  80

Leu Ser Lys Asn Asp Pro Asp Val Asp Thr Asp Ser Ser Ser Gln Ala
                85                  90                  95

Gly Phe Phe Cys Gly Ser Pro Pro Ala Arg Thr Asp Asn Pro Val Ile
            100                 105                 110

Asn Asp Pro Gln Phe Gly Lys Lys Thr Pro Ser Phe Ser Pro Leu Phe
        115                 120                 125

Gly Gly Ser Ser Ser Gly Lys Met Thr Ala Gly Arg Val Glu Val Gly
    130                 135                 140

Ser Pro Ser Ser Cys Gly Ala Ser Ser Pro Lys Val Arg Ile Glu Gly
145                 150                 155                 160

Phe Ala Cys Gly Asn Lys Glu Pro Pro His Cys Phe Ala
                165                 170

<210> SEQ ID NO 23
<211> LENGTH: 1148
<212> TYPE: DNA
<213> ORGANISM: Zea mays

<400> SEQUENCE: 23

| | | | | | |
|---|---|---|---|---|---|
| ggtcgaggca | gtcaaaaccc | tcgacgcgga | ccgcggcggg | ctggaacgcg | aaccgggcgc | 60 |
| gggcgcaccc | gttgccgccg | cgcggcgaca | tgggcggcgc | cgccgacggc | cggtgcacgg | 120 |
| ccgccgccgc | caccggcatg | gcacgggca | ggggcgggca | gtccacgccg | aaccggctgt | 180 |
| cgtggaccac | cgggttcgac | gcccgccgcg | gcggcgagcc | gcagaacagc | ggggacgccg | 240 |
| ccgacaggcc | gctctcctct | ccctgccaag | accaagttcg | acacgtcag | cgccatgtac | 300 |
| taagtagaag | cgacgaaaag | accttcgaga | ggggcagatc | cggggacgag | gtagcaaaaa | 360 |
| aaaaagatgt | cccacctttg | acaggaggag | gtcgagcaga | tccatgccgg | cgtcgccgcc | 420 |
| ctggtggcac | cgcaggggcg | ccgcggggcg | ccgcggcttg | ggcagaaga | gcgggctctt | 480 |
| ggcgtcgccg | gcggcgggcg | cggccacggc | gaggggctc | ttcacggcgg | cggcggcgaa | 540 |
| gtggctcatg | ctttctcgcg | ttattttttg | ttttttttc | tctctggtta | gtcgattaga | 600 |
| tctagaatcc | ctttatacaa | accctgcagg | aacaaaagga | cgacgcaaga | actggttagg | 660 |
| tgcgtcagtt | gagcgggcag | gaagaagagt | aaagttgaga | tgtttcttca | gcagttgtgc | 720 |
| agatctgagt | ttggagagga | caaaacagga | ggaggggcaa | aaaaatgacg | aatcttcaga | 780 |
| cagatttgtg | cgagaaagca | tgttatttag | acatgagacc | agcgttgggg | agatctgtgg | 840 |
| ccactggcct | tgccaaaaaa | aaccaaatct | ttcagcaagg | cacaggcaca | ggcacgtaaa | 900 |
| taggtacgac | gaacccgtgc | aagaacaggg | acagatctga | gctacataag | gggtggagag | 960 |
| cacaggcgag | aggggcgtca | tgtttacctg | aagctttgcc | tccggatttc | tctcctctcc | 1020 |
| tctctcctcg | ggtagagagc | gaggaggaag | aaggctgcca | gaaactattg | ttactcctac | 1080 |
| caagaaaaca | aaacaaaaca | agaaaaaata | aagctcggag | cctcgagtgg | ggagggagct | 1140 |
| gtgctgcc | | | | | | 1148 |

<210> SEQ ID NO 24
<211> LENGTH: 159
<212> TYPE: PRT
<213> ORGANISM: Zea mays

<400> SEQUENCE: 24

Met Ser His Phe Ala Ala Ala Ala Val Lys Ser Pro Leu Ala Val Ala

```
    1               5                  10                 15
Ala Pro Ala Ala Gly Asp Ala Lys Ser Pro Leu Phe Cys Pro Lys Pro
                20                 25                 30

Arg Arg Pro Ala Ala Pro Leu Arg Cys His Gln Gly Gly Asp Ala Gly
            35                 40                 45

Met Asp Leu Leu Asp Leu Leu Leu Ser Lys Gly Glu Glu Ser Gly Leu
    50                 55                 60

Ser Ala Ala Ser Pro Leu Phe Cys Gly Ser Pro Pro Arg Arg Ala Ser
65                 70                 75                 80

Asn Pro Val Val His Asp Ser Arg Phe Gly Val Asp Cys Pro Pro Leu
                85                 90                 95

Pro Val Pro Met Pro Val Ala Ala Ala Val His Arg Pro Ser Ala
            100                105                110

Ala Pro Pro Met Ser Pro Arg Gly Gly Asn Gly Cys Ala Arg Ala Arg
                115                120                125

Phe Ala Phe Gln Pro Ala Ala Val Arg Val Glu Gly Phe Asp Cys Leu
            130                135                140

Asp Arg Gly Arg Gly Gly Arg Gly His Gly Ile Thr Ala Met Ala
145                150                155
```

<210> SEQ ID NO 25
<211> LENGTH: 477
<212> TYPE: DNA
<213> ORGANISM: Zea mays

<400> SEQUENCE: 25

```
atgaagagcc cccttgcggt cgccgtcgcc gcgcccgccg gcgccgccga cgctaagagc     60
ccgctcttct gccccaagcc gcggcgcccc gcggcgccgc tgcggtgcca tcagagcggc    120
ggcttctccg acgccggcac ggatctgctc gacctcctcc tctcgaaggg cgacgagagc    180
ggcctgtcgt cggcgtcccc gcagccgccg ctgttctgcg gctcgccgcc gcggcgagcg    240
tcgaacccgg tggtccacga cagcaggttc ggcgcggact gcccgcccat gcccgtgcca    300
gggctgcccg tgcaccggcc aagcccgcgc ccgtcgacgg cggcgccgtc catgtcgccg    360
cgcgggtgtg cccgcgcgcg gttcgcgttc cagcccgccg cggtccgcgt cgagggtttt    420
gactgcctcg accgcggccg cggcggccgt ggccatggca tcaccgccat ggcctag       477
```

<210> SEQ ID NO 26
<211> LENGTH: 158
<212> TYPE: PRT
<213> ORGANISM: Zea mays

<400> SEQUENCE: 26

```
Met Lys Ser Pro Leu Ala Val Ala Val Ala Ala Pro Ala Gly Ala Ala
1               5                  10                 15

Asp Ala Lys Ser Pro Leu Phe Cys Pro Lys Pro Arg Arg Pro Ala Ala
                20                 25                 30

Pro Leu Arg Cys His Gln Ser Gly Gly Phe Ser Asp Ala Gly Thr Asp
            35                 40                 45

Leu Leu Asp Leu Leu Leu Ser Lys Gly Asp Glu Ser Gly Leu Ser Ser
    50                 55                 60

Ala Ser Pro Gln Pro Pro Leu Phe Cys Gly Ser Pro Pro Arg Arg Ala
65                 70                 75                 80

Ser Asn Pro Val Val His Asp Ser Arg Phe Gly Ala Asp Cys Pro Pro
                85                 90                 95
```

```
Met Pro Val Pro Gly Leu Pro Val His Arg Pro Ser Pro Arg Pro Ser
            100                 105                 110

Thr Ala Ala Pro Ser Met Ser Pro Arg Gly Cys Ala Arg Ala Arg Phe
        115                 120                 125

Ala Phe Gln Pro Ala Ala Val Arg Val Glu Gly Phe Asp Cys Leu Asp
    130                 135                 140

Arg Gly Arg Gly Gly Arg Gly His Gly Ile Thr Ala Met Ala
145                 150                 155

<210> SEQ ID NO 27
<211> LENGTH: 877
<212> TYPE: DNA
<213> ORGANISM: Zea mays

<400> SEQUENCE: 27
ctttcttgtt gcacgcctgc ctgggcgaac cgtcgccgct atacaccagg cgcccagggc      60
ttcgccggcg ccgagtagcc accagctgcc gctcaacatt cacctctgcc aagggcatgg     120
accacatgac gatgctcggc gccggagccc ccaccagct ctccagggct gaaccaatgc      180
ctgaccgtag gtcaaggttc tggcagacgg atgtgcagcc tgtgcctcgg atagacatca    240
tctgtcctct gccttgtcgc ccttcccgct cactgctcct caataggccc agccccaagc    300
ctaatggggc actcccattt tatggagcaa accctactta tgatatcgtt gatctcatcc    360
ttagcaagaa tgaccctgat gtggatactg attcaagcag ccaggccgcc ttttctgtg     420 gctcgcctcc tgctcgcact aacaaccctg ttatccatga cccacagttt ggaaagaaag    480
caccatcctt ttctcctcta ggaagctctt ctggaaaaat ggcagctgga agagctgaag    540
taggttctcc gtcctgcagg tcgagcagcc caaaaatgag aatcgaaggt tttgcttgcg    600
ggaacaaaga gccccctcac tgctttgcct gatgatcccc attgaccctg cctaaccctg    660
ttttgctacc ctgcaacctg tacattttcg ctgcccagct gagagttcgt ttcgttataa    720
gctgttaaac tagctgagag tcccatgtga ttgtggcttt tgaaaattgc atgatccaag    780
gggacggatg taaataggtc gagttgtccg gtgtatgtac tagatgttgt atgcgtctgg    840
taaatgtagt catgctgggt gggtccatgg tcggcgt                              877

<210> SEQ ID NO 28
<211> LENGTH: 171
<212> TYPE: PRT
<213> ORGANISM: Zea mays

<400> SEQUENCE: 28

Met Asp His Met Thr Met Leu Gly Ala Gly Ala Pro His Gln Leu Ser
1               5                   10                  15

Arg Ala Glu Pro Met Pro Asp Arg Arg Ser Arg Phe Trp Gln Thr Asp
            20                  25                  30

Val Gln Pro Val Pro Arg Ile Asp Ile Cys Pro Leu Pro Cys Arg
        35                  40                  45

Pro Ser Arg Ser Leu Leu Asn Arg Pro Ser Lys Pro Asn Gly
    50                  55                  60

Ala Leu Pro Phe Tyr Gly Ala Asn Pro Thr Tyr Asp Ile Val Asp Leu
65                  70                  75                  80

Ile Leu Ser Lys Asn Asp Pro Asp Val Asp Thr Asp Ser Ser Gln
                85                  90                  95

Ala Ala Phe Phe Cys Gly Ser Pro Ala Arg Thr Asn Asn Pro Val
            100                 105                 110
```

-continued

```
Ile His Asp Pro Gln Phe Gly Lys Lys Ala Pro Ser Phe Ser Pro Leu
        115                 120                 125

Gly Ser Ser Ser Gly Lys Met Ala Ala Gly Arg Ala Glu Val Gly Ser
130                 135                 140

Pro Ser Cys Arg Ser Ser Pro Lys Met Arg Ile Glu Gly Phe Ala
145                 150                 155                 160

Cys Gly Asn Lys Glu Pro Pro His Cys Phe Ala
                165                 170
```

<210> SEQ ID NO 29
<211> LENGTH: 562
<212> TYPE: DNA
<213> ORGANISM: Eragrostis nindensis

<400> SEQUENCE: 29

```
aaaaaagaga ccatgagcca cttcgccgcc gccatgaaga gcccctgcc cgtcgccgcc      60
tccgccgccg ccggcgacgc gaagagcccg ctcttctgcc ccaagccgcg cgcccggtg    120
gcgcccctcc ggtgccagca gagcggcggc tactccgacg ccggcgccgg catggatctg   180
ctcgacctcc tcctctcaaa gggagaggag actggtctct cggcggcgtc cccgcagccg   240
ccgctgttct gcggctcgcc accgcggcga gcgtcgaacc cgctggtcca cgacagccgg   300
ttcggcatgg actgcccgcc catgccgacg ccgctgccgg tggtggccgc ccctgtggcg   360
gcacgggcct acgccacgcc gcgcccgtcg gcggcgccat ccatgtcgcc acgcggcggc   420
tccgggtgcg ctcgtgcccg gttctcgttc cagccggcgg cggtgcgcgt cgagggttttt   480
gactgcctcg acggcggccg ccgcggccgc ggcatggca tcaccgccat ggcctagatg   540
cacatacaac acccagtaac cc                                            562
```

<210> SEQ ID NO 30
<211> LENGTH: 174
<212> TYPE: PRT
<213> ORGANISM: Eragrostis nindensis

<400> SEQUENCE: 30

```
Met Ser His Phe Ala Ala Ala Met Lys Ser Pro Leu Pro Val Ala Ala
1               5                  10                  15

Ser Ala Ala Gly Asp Ala Lys Ser Pro Leu Phe Cys Pro Lys Pro
            20                  25                  30

Arg Arg Pro Val Ala Pro Leu Arg Cys Gln Gln Ser Gly Gly Tyr Ser
        35                  40                  45

Asp Ala Gly Ala Gly Met Asp Leu Leu Asp Leu Leu Ser Lys Gly
    50                  55                  60

Glu Glu Thr Gly Leu Ser Ala Ala Ser Pro Gln Pro Pro Leu Phe Cys
65                  70                  75                  80

Gly Ser Pro Pro Arg Arg Ala Ser Asn Pro Leu Val His Asp Ser Arg
                85                  90                  95

Phe Gly Met Asp Cys Pro Pro Met Pro Thr Pro Leu Pro Val Val Ala
            100                 105                 110

Ala Pro Val Ala Ala Arg Ala Tyr Ala Thr Pro Arg Pro Ser Ala Ala
        115                 120                 125

Pro Ser Met Ser Pro Arg Gly Gly Ser Gly Cys Ala Arg Ala Arg Phe
    130                 135                 140

Ser Phe Gln Pro Ala Ala Val Arg Val Glu Gly Phe Asp Cys Leu Asp
145                 150                 155                 160

Gly Gly Arg Arg Gly Arg Gly His Gly Ile Thr Ala Met Ala
```

<210> SEQ ID NO 31
<211> LENGTH: 925
<212> TYPE: DNA
<213> ORGANISM: Paspalum notatum

<400> SEQUENCE: 31

```
aaaaaaaaaa ccaaaagaaa gcaagagcga ccatgagcca cttcgccgcc atgaagagcc      60
cggtccccgt cgccgcgtcc gccgcgggcg acgccaagag cccgctcttc tgccccaagc     120
cgcggcgccc cgtggcgccc ctccggtgcc accagagcgg tagcggcggc gggttctccg     180
acgccgccgg catggacctg ctcgacctcc tcctgtcaaa gggagaggag accgggctgt     240
cggcggcgtc cccgcaggcg ccgctgttct gcggctcgcc gccgcggcgc cgtcgaacc      300
cggtggtcca cgacagccgg ttcggcctgg actgccggc gctgccgctg ccccgctgc      360
aggtgcaggt gccggcgcac cggcccacgc cgcggccgtc ggtggcggct gcgccgccca     420
tgtcgccgcg cggcgggtgc gccccgcgcg cccggttcgc gttccagccc gccgcggtcc     480
gcgtcgaggg ttttgactgc ctcgaccgct cccgcggcgg ccgcggccac ggcatcaccg     540
ccatggccta gacgatgcac ataccacacc aagtaacccc caacgggac ctctcctccc      600
tccaatccat ggtgcagaaa accttcttgg tacaacaagc acgcttgggt gttgggaggt     660
gagaggatca attcgtcctt aaatttaacc ccgcccttaa aaacctatat aatccatccc     720
atccacctgc cgcccttcca atccacccat cccaggtatc ccaccacaac tataatgagg     780
tttaggtaat tttccacaga tcttttttgta tgtaaataaa gttcgtcgca gggtccaggt     840
tcctcgtgta aaaattcggg agcactagct taagcttggg gagtgagtgt gagtgaagaa     900
accgggtaga gagaatcatt agagg                                           925
```

<210> SEQ ID NO 32
<211> LENGTH: 172
<212> TYPE: PRT
<213> ORGANISM: Paspalum notatum

<400> SEQUENCE: 32

```
Met Ser His Phe Ala Ala Met Lys Ser Pro Val Pro Val Ala Ala Ser
1               5                   10                  15

Ala Ala Gly Asp Ala Lys Ser Pro Leu Phe Cys Pro Lys Pro Arg Arg
            20                  25                  30

Pro Val Ala Pro Leu Arg Cys His Gln Ser Gly Ser Gly Gly Gly Phe
        35                  40                  45

Ser Asp Ala Ala Gly Met Asp Leu Leu Asp Leu Leu Leu Ser Lys Gly
    50                  55                  60

Glu Glu Thr Gly Leu Ser Ala Ala Ser Pro Gln Ala Pro Leu Phe Cys
65                  70                  75                  80

Gly Ser Pro Pro Arg Arg Ala Ser Asn Pro Val Val His Asp Ser Arg
                85                  90                  95

Phe Gly Leu Asp Cys Pro Ala Leu Pro Leu Pro Leu Gln Val Gln
            100                 105                 110

Val Pro Ala His Arg Pro Thr Pro Arg Pro Ser Val Ala Ala Pro
        115                 120                 125

Pro Met Ser Pro Arg Gly Gly Cys Ala Pro Arg Ala Arg Phe Ala Phe
    130                 135                 140

Gln Pro Ala Ala Val Arg Val Glu Gly Phe Asp Cys Leu Asp Arg Ser
145                 150                 155                 160
```

Arg Gly Gly Arg Gly His Gly Ile Thr Ala Met Ala
            165                 170

<210> SEQ ID NO 33
<211> LENGTH: 1023
<212> TYPE: DNA
<213> ORGANISM: Glycine max

<400> SEQUENCE: 33

```
gcacgaggat tcttcgttt ggaggatacc ctcaaggtg ttctactgtg aaagttagcc      60
gattttgaag atgaattatt ataatcttca gaagaatgcc ttcccagcct gtgaagagat   120
gagaggctct attcccattg ctgatcagaa tggtggacct gtcttttgcc ctaagccacg   180
ccgagctggg gttttaatga acttgcctat tcggccagta aaatggcatt taggtcaaca   240
aggtgagggg tctgattcaa aagctggggc agaactactt gacattgttc tcaagaggga   300
gagttatggg gaagaatttg caaatcagat accttcatct cctccatatt tctgtggttc   360
tcctccagtt cgggcttcta atcccttgat ccaagatgct cgatttggag atgaagtatc   420
aacaatttca tcgccttcag gtttactgtc tccatcttca gcatctcgca aagcaggatg   480
tgctaggatg aagtttggac ttaaaccggc tgctgttaga gtagaaggat ttgattgcct   540
cagcagggat tgccagaatt ccggcatccc ggctgttgct taaactccat tcatagaagt   600
gtatatagaa gaagtcaagt ggcattactt ataaaacgtg acttaactag agagagtttt   660
gaatgtttg gagggaagta agaaattcag ttagttgtgt atatagcaaa tgcttttttg   720
tatggtgagg tgaatcatct cattgtgagt atccgtggca agtttaggga gctgcagaaa   780
aagcaaacct tcggttcttg aggttttatg tgtagagagc atgtcttttt gtaatattag   840
gcggttgtat cggagtgtct tttaaacctt ttaggctatc accgtaagag tgtattattg   900
tataggaatt ggttattttg gtcatcgtcc ctgtaaatat atttagaggt gactttgcaa   960
ctatgtctat tatatttagt tattcaactt gttttctgtt cccataaaaa aaaaaaaaa  1020
aaa                                                               1023
```

<210> SEQ ID NO 34
<211> LENGTH: 170
<212> TYPE: PRT
<213> ORGANISM: Glycine max

<400> SEQUENCE: 34

Met Asn Tyr Tyr Asn Leu Gln Lys Asn Ala Phe Pro Ala Cys Glu Glu
1               5                   10                  15

Met Arg Gly Ser Ile Pro Ile Ala Asp Gln Asn Gly Gly Pro Val Phe
            20                  25                  30

Cys Pro Lys Pro Arg Arg Ala Gly Val Leu Met Asn Leu Pro Ile Arg
        35                  40                  45

Pro Val Lys Trp His Leu Gly Gln Gln Gly Glu Gly Ser Asp Ser Lys
    50                  55                  60

Ala Gly Ala Glu Leu Leu Asp Ile Val Leu Lys Arg Glu Ser Tyr Gly
65                  70                  75                  80

Glu Glu Phe Ala Asn Gln Ile Pro Ser Ser Pro Pro Tyr Phe Cys Gly
                85                  90                  95

Ser Pro Pro Val Arg Ala Ser Asn Pro Leu Ile Gln Asp Ala Arg Phe
            100                 105                 110

Gly Asp Glu Val Ser Thr Ile Ser Ser Pro Ser Gly Leu Leu Ser Pro
        115                 120                 125

```
Ser Ser Ala Ser Arg Lys Ala Gly Cys Ala Arg Met Lys Phe Gly Leu
    130                 135                 140

Lys Pro Ala Ala Val Arg Val Glu Gly Phe Asp Cys Leu Ser Arg Asp
145                 150                 155                 160

Cys Gln Asn Ser Gly Ile Pro Ala Val Ala
            165                 170
```

<210> SEQ ID NO 35
<211> LENGTH: 1294
<212> TYPE: DNA
<213> ORGANISM: Glycine max

<400> SEQUENCE: 35

```
cggccgccca tcaactttgt gtttctctct tcaccttcgt cttcttttca tttcaattct     60
ttgtggttca gaaactctgt acagttaatc aagcccaacc tcacctcacc tcacctcaca   120
ggttttagtt gttaattaaa tatatagata gaaatccaag gaagaagatg aagcagtttg   180
ccgtccaaaa cgtcgtcgct ccatcccacg atgagattag cgtggtttgc cccaagcccc   240
gccgcctcgg cctcttcaac ttccccgtga acgatccccc tgttagaccc ttctactggc   300
atctcagttg ccaggctgag ccatgtgatt caaactcgtc tggttcaaat cctttggaca   360
acttacttac caaggatggt gattttgatg tagagcaatc atggccagtg gtaacctcgt   420
cgcccccatt tttctgcggg tcgccgccga gtagagcagc taacccttg attcaggatg    480
ctcgatttgg ggatgagaat ttttccccgc tctccccacc gtcgtgggtg gtggttccgg   540
ctgctgcgtc gggtctgcca ccgtctccct cttcctctgc aaggaaggga gggtgtgtcc   600
gagccaattt tggtaacaat cctgctgtga gaattgaggg gttcgattgc cttgacaggg   660
acaggcgaaa ttgcagcatc ccggctctgg cttagaacac cctcctcaca cgccacacgt   720
ctctttgata ttaggattca gttcaacata taaacataac cacagaagat gagccttcat   780
acaatataat accctacgga gaagagtaat tttggatgct tgagagttga atctagagga   840
agagataaaa ttttatcttg tgtctgtttg taaatatgtt cagttaatcg gccagtgcat   900
gtaaatgtca atagtgtgtc ttgtgtagag aaatattgtc tagcctccaa ataatgatag   960
agggttgatt tgggtgttaa ttagatttcg cccgtgccct atgttagtag tgtctaagga  1020
aaaataccat tctctttttt gtaagtagaa gtcttttgag gatggagaat atttcatttt  1080
gattttcttt tatgatgggt ctctctcctt gaattgtaat tagtagcggc ttaagaagca  1140
aaatctgtac aaaggaatgg tttgttttga gaattctcag ttcatgggtc tttttgaaat  1200
gtgaaaagca tgagcaaagt tttactgcgt aaaagaaaa ggctggtttg tgtttcaaaa   1260
aaaaaaaaa aaaaaaaaa aaaaaaaaa aaga                                 1294
```

<210> SEQ ID NO 36
<211> LENGTH: 175
<212> TYPE: PRT
<213> ORGANISM: Glycine max

<400> SEQUENCE: 36

```
Met Lys Gln Phe Ala Val Gln Asn Val Val Ala Pro Ser His Asp Glu
1               5                   10                  15

Ile Ser Val Val Cys Pro Lys Pro Arg Arg Leu Gly Leu Phe Asn Phe
            20                  25                  30

Pro Val Asn Asp Pro Val Arg Pro Phe Tyr Trp His Leu Ser Cys
            35                  40                  45
```

```
Gln Ala Glu Pro Cys Asp Ser Asn Ser Ser Gly Ser Asn Pro Leu Asp
    50              55                  60
Asn Leu Leu Thr Lys Asp Gly Asp Phe Asp Val Glu Gln Ser Trp Pro
65              70                  75                  80
Val Val Thr Ser Pro Pro Phe Phe Cys Gly Ser Pro Pro Ser Arg
                85                  90                  95
Ala Ala Asn Pro Leu Ile Gln Asp Ala Arg Phe Gly Asp Glu Asn Phe
            100                 105                 110
Ser Pro Leu Ser Pro Ser Trp Val Val Pro Ala Ala Ala Ser
            115                 120                 125
Gly Leu Pro Pro Ser Pro Ser Ser Ala Arg Lys Gly Gly Cys Val
    130                 135                 140
Arg Ala Asn Phe Gly Asn Asn Pro Ala Val Arg Ile Glu Gly Phe Asp
145                 150                 155                 160
Cys Leu Asp Arg Asp Arg Arg Asn Cys Ser Ile Pro Ala Leu Ala
                165                 170                 175
```

<210> SEQ ID NO 37
<211> LENGTH: 531
<212> TYPE: DNA
<213> ORGANISM: Zea mays

<400> SEQUENCE: 37

```
atggagcact gctatttgag gcagccgatc tcgagggccg aggcagtgcc cgagaggagg    60
tccaggttgt ggcagatgga cgcgctgccg ctgccgcccc gggcggaggt cctctgcccc   120
cagcctcgcc gcgccgcccg gatcccctcc gccgtttcag taaacaaggc catccccagg   180
tcgaattgtg cgcttccgcc gtacagacca gcctccgcct gcgacatact cgatgatctt   240
atcctcagca agaatgactt ctcagatgga gcagattcga gcagcggcca ggcgggtttt   300
ttatgcggct cgcctccagt gcgcgctaac aaccctgtcg tccatgaccc gcagttcggt   360
aaaagagcgc tgccatccat gtctccccta gggagcagct cccacgtcaa gcttaaggtt   420
gaggcaggct cgccatcctg cggcgttagc agcagcccga agtgaggat cgaaggcttt    480
gcctgtggca actcggagac ccactacgca gttacgccgc tccttgtgtg a            531
```

<210> SEQ ID NO 38
<211> LENGTH: 176
<212> TYPE: PRT
<213> ORGANISM: Zea mays

<400> SEQUENCE: 38

```
Met Glu His Cys Tyr Leu Arg Gln Pro Ile Ser Arg Ala Glu Ala Val
1               5                   10                  15
Pro Glu Arg Arg Ser Arg Leu Trp Gln Met Asp Ala Leu Pro Leu Pro
            20                  25                  30
Pro Arg Ala Glu Val Leu Cys Pro Gln Pro Arg Arg Ala Ala Arg Ile
        35                  40                  45
Pro Phe Ala Val Ser Val Asn Lys Ala Ile Pro Arg Ser Asn Cys Ala
    50                  55                  60
Leu Pro Pro Tyr Arg Pro Ala Ser Ala Cys Asp Ile Leu Asp Asp Leu
65                  70                  75                  80
Ile Leu Ser Lys Asn Asp Phe Ser Asp Gly Ala Asp Ser Ser Ser Gly
                85                  90                  95
Gln Ala Gly Phe Leu Cys Gly Ser Pro Pro Val Arg Ala Asn Asn Pro
            100                 105                 110
```

```
Val Val His Asp Pro Gln Phe Gly Lys Arg Ala Leu Pro Ser Met Ser
            115                 120                 125

Pro Leu Gly Ser Ser His Val Lys Leu Lys Val Glu Ala Gly Ser
130                 135                 140

Pro Ser Cys Gly Val Ser Ser Pro Lys Val Arg Ile Glu Gly Phe
145                 150                 155                 160

Ala Cys Gly Asn Ser Glu Thr His Tyr Ala Val Thr Pro Leu Leu Val
                165                 170                 175

<210> SEQ ID NO 39
<211> LENGTH: 181
<212> TYPE: PRT
<213> ORGANISM: Manihot esculenta

<400> SEQUENCE: 39

Met Asn Gln Cys Ala Ile His Pro Ser Ala Phe Ser Thr Cys Glu Glu
1               5                   10                  15

Ile Arg Ser Pro Val Ser Asp Arg Arg Asp Ser Val Val Cys Pro Lys
                20                  25                  30

Pro Arg Arg Leu Gly Leu Leu Asn Val Thr Ala Asn Asp His Pro Val
            35                  40                  45

Arg Ser Leu Arg Trp Gln Ile Ser His Gln Ala Glu Leu Cys Asp Ser
    50                  55                  60

Lys Ala Gly Thr Asp Leu Leu Glu Ile Ile Leu Thr Lys Gly Gly Cys
65                  70                  75                  80

Gly Val Glu Gln Ser Tyr Thr Gln Val Ala Ser Ser Pro Pro Phe Phe
                85                  90                  95

Cys Gly Ser Pro Pro Ser Arg Val Ala Asn Pro Leu Ile Gln Asp Ala
            100                 105                 110

Arg Phe Gly Asp Glu Lys Phe Ser Pro Ile Ser Pro Leu Met Pro Met
        115                 120                 125

Pro Ile Leu Pro Pro Ser Gly Leu Ser Ser Ser Pro Thr Ser Ser Thr
    130                 135                 140

Arg Lys Gly Gly Cys Val Arg Ser Asn Phe Gly Asn Lys Pro Ala Val
145                 150                 155                 160

Arg Val Glu Gly Phe Asp Cys Leu Asp Arg Asp Ser Arg Asn Cys Ser
                165                 170                 175

Ile Pro Thr Leu Ala
            180

<210> SEQ ID NO 40
<211> LENGTH: 189
<212> TYPE: PRT
<213> ORGANISM: Ricinus communis

<400> SEQUENCE: 40

Met Lys Gln Cys Ala Ile Gln Thr Ser Ala Phe Ser Thr Arg Glu Glu
1               5                   10                  15

Ile Arg Ser Ser Val Ser Gly Thr Met Ser Glu Arg Arg Asp Pro Val
                20                  25                  30

Val Cys Pro Lys Pro Arg Arg Phe Gly Leu Phe Asn Ala Ser Val Asn
            35                  40                  45

Asp His Pro Val Arg Ser Leu Arg Trp His Leu Ser His Gln Thr Glu
        50                  55                  60

Ile Cys Glu Ser Lys Ala Gly Asn Asp Leu Leu Asp Ile Ile Leu Thr
65                  70                  75                  80
```

```
Lys Gly Gly Cys Tyr Gly Val Glu Gln Ser Cys Thr Gln Val Ala
                85                  90                  95

Ser Ser Pro Pro Pro Phe Phe Cys Gly Ser Pro Pro Arg Val Ala
            100                 105                 110

Asn Pro Leu Ile Gln Asp Ala Arg Phe Gly Glu Glu Leu Ser Pro
            115                 120                 125

Ile Ser Pro Leu Met Pro Met Pro Ile Gln Pro Pro Ser Ser Ser
130                 135                 140

Ser Ser Ser Pro Thr Ser Ser Gly Arg Lys Gly Gly Cys Val Arg Ala
145                 150                 155                 160

Asn Phe Gly Asn Lys Pro Ala Val Arg Val Glu Gly Phe Asp Cys Leu
            165                 170                 175

Asp Arg Asp Arg Arg Ser Cys Ser Ile Pro Ala Leu Ala
            180                 185

<210> SEQ ID NO 41
<211> LENGTH: 181
<212> TYPE: PRT
<213> ORGANISM: Populus balsamifera subsp. trichocarpa

<400> SEQUENCE: 41

Met Asn His Cys Ala Ile Gln Gln Asn Ala Phe Ser Thr Arg Glu Glu
1               5                   10                  15

Ile Arg Ser Ser Val Ser Val Pro Val Ser Asp Arg Arg Asp Pro Val
            20                  25                  30

Val Cys Pro Lys Pro Arg Arg Leu Gly Leu Leu Asn Asn Tyr Pro Ala
            35                  40                  45

Arg Ser Ile Arg Phe Gln Leu Ser His Gln Ser Glu Leu Cys Asp Ser
50                  55                  60

Lys Ala Gly Asn Glu Phe Leu Asp Ile Ile Leu Ala Lys Gly Gly Tyr
65                  70                  75                  80

Gly Val Asp Asn Gln Ser Phe Cys Lys Gln Val Ala Ser Ser Pro Pro
            85                  90                  95

Pro Phe Phe Cys Gly Ser Pro Ser Arg Val Ala Asn Pro Leu Ile
            100                 105                 110

Gln Asp Ala Arg Phe Gly Asp Glu Lys Phe Ser Pro Leu Ser Pro Val
            115                 120                 125

Thr Pro Ile Pro Pro Thr Met Asp Leu Ser Ser Ser Ser Ser Pro
            130                 135                 140

Arg Lys Gly Gly Leu Val Arg Ala Asn Phe Gly Asn Lys Pro Val Val
145                 150                 155                 160

Arg Ile Glu Gly Phe Asp Cys Leu Asp Arg Asp Cys Arg Asn Cys Ser
            165                 170                 175

Ile Pro Ala Leu Ala
            180

<210> SEQ ID NO 42
<211> LENGTH: 181
<212> TYPE: PRT
<213> ORGANISM: Populus balsamifera subsp. trichocarpa

<400> SEQUENCE: 42

Met Asn His Cys Ala Ile Gln Gln Asn Ala Phe Ser Thr Arg Glu Glu
1               5                   10                  15

Ile Arg Asn Ser Val Ser Ile Pro Ile Ser Glu Arg Arg Asp Pro Val
            20                  25                  30
```

```
Val Cys Pro Lys Pro Arg Arg Leu Gly Leu Leu Asn Asp His Pro Ala
        35                  40                  45

Arg Ser Leu Arg Phe Gln Leu Ser His Gln Ser Glu Leu Cys Asp Ser
 50                  55                  60

Ile Ala Gly Thr Asp Phe Leu Glu Ile Ile Leu Ala Lys Gly Cys Tyr
 65                  70                  75                  80

Gly Met Asp Asn Gln Ser Phe Cys Thr Gln Val Ser Ser Ser Pro Pro
                 85                  90                  95

Pro Phe Phe Cys Gly Ser Pro Ser Arg Val Ala Asn Pro Leu Ile
                100                 105                 110

Gln Asp Ala Arg Phe Gly Asn Glu Lys Phe Ser Pro Phe Ser Pro Val
            115                 120                 125

Thr Pro Ile Pro Pro Gln Met Asp Leu Ser Ser Ser Ser Ser Ser Pro
130                 135                 140

Arg Lys Gly Gly Leu Val Arg Ser Ser Phe Gly Ser Lys Pro Val Val
145                 150                 155                 160

Arg Ile Glu Gly Phe Asp Cys Leu Asp Arg Asp Cys Arg Asn Cys Ser
                165                 170                 175

Val Pro Ala Leu Ala
            180

<210> SEQ ID NO 43
<211> LENGTH: 183
<212> TYPE: PRT
<213> ORGANISM: Paeonia suffruticosa

<400> SEQUENCE: 43

Met Asn His Cys Ala Ile Gln Gln Gln Asn Val Tyr Ala Ala Arg Glu
 1               5                  10                  15

Glu Met Arg Ser Pro Val Ser Ile Pro Met Ser Asp Arg Arg Asp Ser
             20                  25                  30

Val Val Cys Pro Lys Pro Arg Arg Met Gly Leu Leu Asp Ser Thr Ile
        35                  40                  45

Ser Asp Pro Ile Arg Pro Leu Arg Trp His Leu Ser His His Gln Ser
 50                  55                  60

Glu Tyr Ser Asp Ser Arg Ala Gly Thr Asp Leu Leu Asp Ile Ile Leu
 65                  70                  75                  80

Ser Lys Gly Gly Tyr Ser Val Glu Gln Ser Gly Asn Gln Leu Ala Ser
                 85                  90                  95

Ser Pro Pro Phe Phe Ser Gly Ser Pro Pro Ser Arg Val Ala Asn Pro
                100                 105                 110

Val Val Leu Asp Ala Arg Phe Gly Asp Glu Lys Ile Thr Pro Ser Ala
            115                 120                 125

Pro Leu Gln Pro Leu Leu Ser Pro Gly Pro Ser Ser Pro Ser Ser
130                 135                 140

Ser Ala Arg Lys Gly Gly Cys Leu Arg Ala Asn Tyr Gly Ser Lys Pro
145                 150                 155                 160

Val Val Arg Ile Glu Gly Phe Asp Cys Leu Asp Arg Asp Arg Arg Asn
                165                 170                 175

Cys Ser Ile Pro Ala Leu Ala
            180

<210> SEQ ID NO 44
<211> LENGTH: 174
<212> TYPE: PRT
<213> ORGANISM: glycine max
```

-continued

```
<400> SEQUENCE: 44

Met Lys Gln Phe Ala Val Gln Asn Val Val Pro Ser His Asp Glu
1               5                   10                  15

Ile Ser Val Val Cys Pro Lys Pro Arg Arg Leu Gly Leu Phe Asn Phe
            20                  25                  30

Pro Val Asn Asp Pro Thr Val Arg Pro Phe Arg Trp His Leu Ser Tyr
        35                  40                  45

His Val Glu Pro Cys Asp Ser Asn Ser Ser Gly Ser Asn Pro Leu Asp
    50                  55                  60

Asn Leu Leu Thr Lys Asp Gly Asp Phe Asp Val Glu Gln Ser Trp Pro
65                  70                  75                  80

Val Val Ala Pro Ser Pro Leu Phe Phe Ser Gly Ser Pro Pro Ser Arg
                85                  90                  95

Ala Ala Asn Pro Leu Ile Gln Asp Ala Arg Phe Gly Asp Glu Asn Phe
            100                 105                 110

Ser Pro Leu Ser Pro Ser Trp Val Val Pro Ala Val Ser Gly
        115                 120                 125

Leu Pro Pro Ser Pro Ser Ser Ala Arg Lys Gly Gly Cys Val Arg
130                 135                 140

Ala Asn Phe Gly Asn Asn Pro Val Val Arg Ile Glu Gly Phe Asp Cys
145                 150                 155                 160

Leu Asp Arg Asp Arg Arg Asn Cys Ser Ile Pro Ala Leu Ala
                165                 170

<210> SEQ ID NO 45
<211> LENGTH: 162
<212> TYPE: PRT
<213> ORGANISM: Glycine max

<400> SEQUENCE: 45

Met Asn Gln Cys Gly Tyr Gln Gln Lys Lys Ala Leu Thr Ser Cys Glu
1               5                   10                  15

Glu Met Arg Met Glu Ser Val Val Cys Pro Lys Pro Arg Arg Leu Gly
            20                  25                  30

Leu Leu Asn His Ser Thr Phe Asp Asn His Ile Arg Pro Leu Arg Pro
        35                  40                  45

Pro Phe Ile Asn Tyr Gln Ser Glu Ile Glu Asp Ser Gly Val Gly Ala
    50                  55                  60

Glu Leu Met Asp Ile Ile Leu Pro Lys Arg Ser Gly Gly Gln Val Ala
65                  70                  75                  80

Ser Ser Pro Pro Phe Phe Cys Gly Ser Pro Pro Ser Arg Ala Ser Asn
                85                  90                  95

Pro Val Ile Gln Asp Glu Gln Phe Gly Ser Asn Gly Asn Glu Ser Phe
            100                 105                 110

Gly Ser Phe Ser Leu Ala Pro Pro Ser Pro Ser Ser Ala Arg Gly
        115                 120                 125

Cys Val Arg Met Lys Phe Gly His Thr Pro Ala Ala Val Arg Ile Glu
130                 135                 140

Gly Phe Asp Cys Leu Ser Arg Asp Arg Arg Asn Cys Ser Ile Ser Ala
145                 150                 155                 160

Val Ala

<210> SEQ ID NO 46
<211> LENGTH: 162
```

```
<212> TYPE: PRT
<213> ORGANISM: Glycine max

<400> SEQUENCE: 46

Met Asn Gln Cys Gly Tyr Gln Gln Lys Asn Ala Leu Thr Ser Cys Glu
1               5                   10                  15

Glu Met Arg Met Glu Ser Val Val Cys Pro Lys Pro Arg Arg Leu Gly
            20                  25                  30

Leu Leu Asn His Ser Thr Phe Asp Asp His Ile Arg Pro Leu Arg Pro
        35                  40                  45

Pro Phe Ile Asn Tyr Gln Ser Glu Ile Glu Asp Ser Gly Val Gly Ala
    50                  55                  60

Glu Leu Leu Asp Ile Ile Leu Pro Lys Arg Ser Gly Gly Gln Val Ala
65                  70                  75                  80

Ser Ser Pro Pro Phe Phe Cys Gly Ser Pro Pro Ser Arg Ala Ser Asn
                85                  90                  95

Pro Val Ile Gln Asp Glu Gln Phe Gly Ser Asn Gly Asn Glu Asn Phe
            100                 105                 110

Gly Ala Phe Ser Leu Ala Pro Pro Ser Pro Ser Ser Ala Arg Gly
        115                 120                 125

Cys Val Arg Met Lys Phe Gly His Thr Pro Ala Ala Val Arg Ile Glu
    130                 135                 140

Gly Phe Asn Cys Leu Ser Arg Asp Arg Arg Asn Cys Ser Ile Ser Ala
145                 150                 155                 160

Val Ala

<210> SEQ ID NO 47
<211> LENGTH: 174
<212> TYPE: PRT
<213> ORGANISM: Vitis vinifera

<400> SEQUENCE: 47

Met Asn Gln Tyr Cys Ala Leu Ala Ala Cys Glu Glu Met Arg Arg Ser
1               5                   10                  15

Val Pro Ala Ser Glu Arg Arg Ala Pro Val Val Cys Pro Lys Pro Arg
            20                  25                  30

Arg Leu Gly Leu Leu Asn Ala Thr Ile Val Asp Pro Leu Arg Pro Ile
        35                  40                  45

Arg Trp His Leu Ser Asn Gln Thr Glu Leu Ser Asp Ser Lys Ser Gly
    50                  55                  60

Thr Asp Leu Leu Asp Ile Ile Leu Ala Lys Gly Gly Tyr Gly Ala Glu
65                  70                  75                  80

Ser Cys Thr Gln Val Ala Ser Ser Pro Pro Phe Phe Ser Gly Ser Pro
                85                  90                  95

Pro Ser Arg Val Ala Asn Pro Leu Ile Gln Asp Ala Arg Phe Gly Asp
            100                 105                 110

Glu Lys Leu Asn Pro Ile Ser Pro Leu Val Ser Val Pro Ser Gly
        115                 120                 125

Leu Ser Ser Pro Ser Ser Ser Ala Arg Lys Gly Gly Cys Ile Arg
    130                 135                 140

Ala Asn Phe Gly Asn Asn Pro Ala Val Arg Ile Glu Gly Phe Asp Cys
145                 150                 155                 160

Leu Asp Arg Asp Arg Arg Asn Cys Ser Ile Pro Ala Leu Ala
            165                 170
```

```
<210> SEQ ID NO 48
<211> LENGTH: 179
<212> TYPE: PRT
<213> ORGANISM: Vitis vinifera

<400> SEQUENCE: 48

Met Asn His Phe Asn Leu Gln Gln Ile Ala Phe Ala Ala Gly Glu Glu
1               5                   10                  15

Met Arg Gly Ser Ala Ser Ile Ala Asp Arg Lys Glu Pro Val Val Cys
            20                  25                  30

Pro Arg Pro Arg Arg Val Ser Leu Leu Ser Asn Ser Gln Gly Arg Pro
        35                  40                  45

Phe Arg Trp His Thr Ser His Ala Glu Val Cys Asp Val Lys Ala Gly
    50                  55                  60

Ser Glu Leu Leu Asp Ile Ile Leu Met Lys Glu Gly Tyr Gly Ala Glu
65                  70                  75                  80

Pro Ser Thr Pro Gln Val Ala Ser Ser Pro Gly Phe Phe Cys Gly
            85                  90                  95

Ser Pro Pro Ser Arg Ala Ala Asn Pro Leu Thr Gln Asp Val Arg Phe
            100                 105                 110

Gly Asp Glu Arg Leu Thr His Leu Ser Met Leu Pro Ile Pro Pro Ser
            115                 120                 125

Pro Ser Pro Ser Gly Leu Ala Ser Pro Ser Ser Ala Arg Lys Gly
        130                 135                 140

Gly Cys Val Arg Met Lys Val Gly Phe Lys Pro Ala Ala Val Arg Val
145                 150                 155                 160

Glu Gly Phe Asp Cys Leu Asn Arg Asp Arg Gln Asn Ser Ser Ile Pro
                165                 170                 175

Ala Val Ala

<210> SEQ ID NO 49
<211> LENGTH: 178
<212> TYPE: PRT
<213> ORGANISM: Populus balsamifera subsp. trichocarpa

<400> SEQUENCE: 49

Met Asn Gln Val Ser Leu Gln Gln Asn Ala Ile Thr Phe Cys Asp Glu
1               5                   10                  15

Arg Arg Gly Leu Val Ser Ile Ser Asp Tyr Lys Gly Pro Val Val Cys
            20                  25                  30

Pro Lys Pro Arg Arg Val Gly Ile Leu Ala Asn Asn Pro Ile Arg Pro
        35                  40                  45

Leu Arg Trp Pro Val Ser His Gln Ala Glu Met Cys Asp Ser Lys Ala
    50                  55                  60

Gly Ala Glu Leu Leu Asp Ile Ile Leu Met Lys Glu Gly His Gly Ala
65                  70                  75                  80

Asp Tyr Pro Ala Asn Gln Ala Ala Ser Pro Pro Phe Cys
            85                  90                  95

Gly Ser Pro Pro Thr Arg Val Gly Asn Pro Leu Ile Gln Asp Ala Arg
            100                 105                 110

Phe Gly Asp Glu Lys Phe Thr Pro Ile Ser Pro Leu Ser Ile Pro Ser
            115                 120                 125

Pro Ser Gly Leu Ser Ser Pro Ser Thr Ser Ala Cys Lys Gly Gly Gly
        130                 135                 140

Cys Val Arg Met Lys Phe Gly Leu Lys Pro Ala Glu Val Arg Val Glu
145                 150                 155                 160
```

```
Gly Phe Asp Cys Leu Asn Arg Asp Arg Gln Asn Ser Ser Ile Pro Ala
                165                 170                 175
Val Ala

<210> SEQ ID NO 50
<211> LENGTH: 175
<212> TYPE: PRT
<213> ORGANISM: Ricinus communis

<400> SEQUENCE: 50

Met Asn His Phe Asn Leu Gln Lys Asn Ala Val Ala Ser Cys Asp Glu
1               5                   10                  15

Ser Arg Gly Leu Val Ser Ile Tyr Asp Pro Lys Gly Pro Val Val Cys
                20                  25                  30

Pro Lys Pro Arg Arg Val Gly Ile Leu Ala Asn Asn Pro Ile Arg Pro
            35                  40                  45

Leu Arg Trp His Met Ser His Gln Ala Glu Ile Tyr Glu Ser Lys Ala
        50                  55                  60

Gly Ala Asp Leu Leu Asp Ile Ile Leu Met Lys Glu Gly His Ala Val
65                  70                  75                  80

Glu Ser Ala Thr Gln Val Ala Ser Ser Pro Phe Phe Ser Gly Ser
                85                  90                  95

Pro Pro Thr Arg Ala Thr Asn Pro Leu Ile Gln Asp Ala Arg Phe Gly
            100                 105                 110

Asp Glu Lys Leu Thr Pro Ile Pro Pro Leu Ser Ile Pro Thr Pro Ser
        115                 120                 125

Gly Leu Ser Ser Pro Thr Pro Ser Arg Lys Gly Gly Cys Val Arg
            130                 135                 140

Met Asn Tyr Gly Leu Lys Pro Ala Ala Val Arg Val Glu Gly Phe Asp
145                 150                 155                 160

Cys Leu Asn Arg Asp Arg Gln Asn Ser Ser Ile Pro Ala Met Ala
                165                 170                 175

<210> SEQ ID NO 51
<211> LENGTH: 200
<212> TYPE: PRT
<213> ORGANISM: cleome spinosa

<400> SEQUENCE: 51

Met Gly Phe Asp Leu Ser Cys Asp Ala Gln Val Arg Arg Ser Ser Ala
1               5                   10                  15

Asp Gln Gly Gly Ser Lys Met Asn Arg Cys Ser Leu Gln Gln Asn Ala
                20                  25                  30

Phe Val Ser Arg Asp Glu Met Arg Gly Gly Phe Val Pro Ile Ser Asp
            35                  40                  45

Pro Lys Asp Pro Val Val Cys Pro Met Pro Arg Arg Val Gly Ile Leu
        50                  55                  60

Ala Asn Asn Val Ile Arg Pro Leu Arg Leu His Met Ser Gln Ala Ser
65                  70                  75                  80

Glu Val Cys Asp Ser Lys Ala Gly Ala Asp Leu Leu Asp Ile Ile Leu
                85                  90                  95

Arg Lys Glu Asp Tyr Gly Thr Gly Gln Ser Leu Leu Ser Val Ala Ser
            100                 105                 110

Ser Pro Pro Phe Phe Cys Gly Ser Pro Pro Ser Arg Ala Ser Asn Pro
        115                 120                 125
```

```
Gln Val Gln Asp Ala Arg Phe Gly Asp Glu Lys Leu Asn Pro Ile Ser
    130                 135                 140

Pro Ser Pro Leu Ser Ala Gly Phe Pro Ser Pro Thr Ser Val Val Ala
145                 150                 155                 160

Pro Arg Gly Lys Gly Gly Cys Val Arg Met Lys Phe Gly Leu Lys Pro
                165                 170                 175

Ala Ala Val Arg Val Glu Gly Phe Asp Cys Leu Asp Arg Asp Arg Gln
            180                 185                 190

Asn Ser Ser Ile Pro Ala Met Ala
        195                 200

<210> SEQ ID NO 52
<211> LENGTH: 198
<212> TYPE: PRT
<213> ORGANISM: cleome spinosa

<400> SEQUENCE: 52

Met Val Phe Asp Leu Phe Pro Asp Ala Gln Ile Arg Arg Ser Ser Ala
1               5                   10                  15

Asp Gln Gly Gly Ser Lys Met Asn His Cys Asn Leu Gln Gln Asn Ala
            20                  25                  30

Phe Val Ser Arg Asp Glu Met Arg Gly Phe Val Pro Ile Cys Asp Pro
        35                  40                  45

Lys Asp Leu Val Val Cys Pro Lys Pro Arg Arg Val Gly Ile Leu Ala
50                  55                  60

Asn Asn Gly Met Arg Pro Leu Arg Leu His Val Ser Gln Ala Ala Glu
65                  70                  75                  80

Val Cys Asp Ser Lys Ala Gly Ala Glu Leu Leu Asp Ile Ile Leu Arg
                85                  90                  95

Lys Glu Asp Tyr Gly Thr Gly Gln Ser Val Leu Ser Val Gly Ser Ser
            100                 105                 110

Pro Pro Phe Phe Cys Gly Ser Pro Ser Arg Ala Val Asn Pro Gln
        115                 120                 125

Val Gln Asp Ala Arg Phe Gly Asp Glu Lys Leu Asp Pro Ile Ser Pro
    130                 135                 140

Ser Pro Leu Ser Ser Gly Phe Pro Ser Pro Thr Ser Ala Ala Ser Arg
145                 150                 155                 160

Gly Lys Gly Gly Tyr Val Arg Met Lys Phe Gly Leu Lys Pro Ala Ala
                165                 170                 175

Val Arg Val Glu Gly Phe Asp Cys Leu Asn Arg Asp Arg Gln Asn Ser
            180                 185                 190

Ser Ile Pro Ala Met Ala
        195

<210> SEQ ID NO 53
<211> LENGTH: 160
<212> TYPE: PRT
<213> ORGANISM: Medicago truncatula

<400> SEQUENCE: 53

Met Asn Gly Arg Glu Ser Val Val Cys Pro Lys Pro Arg Arg Val Gly
1               5                   10                  15

Leu Leu Asn Phe Ala Val Asn Asp Tyr Pro Ser Arg Ser Phe Arg Trp
            20                  25                  30

His Leu Ser Cys Gln Val Glu Pro Cys Asp Ser Asn Ser Ser Ala Ser
        35                  40                  45
```

```
Asn Pro Leu Asp Thr Ile Leu Thr Lys Asp Asp Phe Asp Arg Glu
        50                  55                  60

Gln Leu Ser Pro Pro Val Ala Ser Ser Pro Pro Phe Phe Cys Gly
 65                  70                  75                  80

Ser Pro Pro Ser Arg Val Ala Asn Pro Leu Ile Gln Asp Ala Arg Phe
                 85                  90                  95

Gly Asp Glu Asn Phe Ser Pro Ser Ser Trp Val Val Pro Ala Pro
                100                 105                 110

Ser Gly Leu Pro Pro Ser Pro Ser Ser Ala Arg Lys Gly Gly Cys
            115                 120                 125

Val Arg Ala Asn Phe Gly Asn Asn Pro Ala Val Arg Val Glu Gly Phe
130                 135                 140

Asp Cys Leu Asp Arg Asp Ser Arg Asn Cys Gly Ile Ala Ala Leu Ala
145                 150                 155                 160

<210> SEQ ID NO 54
<211> LENGTH: 176
<212> TYPE: PRT
<213> ORGANISM: Arabidopsis thaliana

<400> SEQUENCE: 54

Met Met Asn Ser Cys Gly Ile Gln Gln Asn Ala Phe Glu Glu Met Arg
 1               5                  10                  15

Arg Asn Ala Ala Val Ser Asp Arg Arg Asp Ala Val Ile Cys Pro Lys
                20                  25                  30

Pro Arg Arg Val Gly Ala Leu Asn His His Ser Ser Arg Ser Leu Arg
                35                  40                  45

Trp Gln Leu Asn His Gln Met Glu Leu Cys Glu Ser Asn Ser Gly Ser
 50                  55                  60

Glu Ile Leu Asp Phe Ile Leu Thr Lys Gly Gly Gly Gly Gly Gly Glu
 65                  70                  75                  80

Gln Asp Gln Thr Arg Thr Val Met Thr Pro Pro Leu Phe Phe Thr Gly
                85                  90                  95

Ser Pro Pro Ser Arg Val Ser Asn Pro Leu Thr Lys Asp Ser Leu Phe
                100                 105                 110

Arg Glu Glu Leu Leu Met Val Ala Ser Pro Ser Pro Ser Thr Pro Arg
            115                 120                 125

Ala Thr Lys Pro Gln Pro Pro Ser Ser Pro Arg Asn Gly Ser Cys Val
130                 135                 140

Met Ala Ala Thr Ser Phe Gly Asn Asn Pro Val Val Arg Val Val Gly
145                 150                 155                 160

Phe Asp Cys Asp Arg Arg Ser Ser Asn Arg Ser Ile Ser Thr Leu Ala
                165                 170                 175

<210> SEQ ID NO 55
<211> LENGTH: 182
<212> TYPE: PRT
<213> ORGANISM: Brassica napus
<220> FEATURE:
<221> NAME/KEY: misc_feature
<222> LOCATION: (51)..(51)
<223> OTHER INFORMATION: Xaa can be any naturally occurring amino acid

<400> SEQUENCE: 55

Met Asn His Trp Ala Val Gln Pro Asn Ala Phe Ala Ala Gly Gly Asp
 1               5                  10                  15

Leu Arg Asn Ser Val Ser Val Val Glu Arg Asp Gln Thr Val Val Val
                20                  25                  30
```

-continued

Cys Pro Lys Pro Arg Arg Ile Gly Leu Arg Asn Pro Ser Leu His His
        35                  40                  45

His Pro Xaa Ser Leu Arg Cys Tyr Ile Ser His Gln Gln Val Glu Val
    50                  55                  60

Cys Glu Ser Lys Ala Glu Thr Asp Ile Leu Asp Ile Ile Leu Thr Lys
65                  70                  75                  80

Asp Gly Tyr Gly Thr Glu Gln Val His Gln Thr Gln Val Leu Asp Ser
                85                  90                  95

Pro Ser Pro Phe Leu Cys Gly Ser Pro Pro Ser Arg Val Ala Asn Pro
            100                 105                 110

Leu Thr Gln Asp Ala Arg Phe Arg Asp Glu Ile Ser Ser Ser Pro Ile
        115                 120                 125

Ser Thr Leu Leu Gly Gln Pro Pro Ser Ser Pro Ser Ser Ser Ser Ser
    130                 135                 140

Gly Arg Lys Gly Gly Cys Val Arg Gly Asn Phe Gly Asn Ser Pro Ala
145                 150                 155                 160

Val Arg Ile Glu Gly Phe Asp Cys Leu Asp Arg Asp Ser Arg Asn Cys
                165                 170                 175

Ser Ile Pro Ala Leu Ala
            180

<210> SEQ ID NO 56
<211> LENGTH: 183
<212> TYPE: PRT
<213> ORGANISM: Arabidopsis thaliana

<400> SEQUENCE: 56

Met Asn His Phe Ala Val Gln Pro Asn Ala Phe Ala Ala Gly Gly Asp
1               5                   10                  15

Leu Arg Ser Ser Ser Val Ser Val Val Glu Arg Asp Gln Thr Thr Val
            20                  25                  30

Val Cys Pro Lys Pro Arg Arg Ile Gly Leu Arg Asn Asn His His His
        35                  40                  45

Pro Ser Arg Ser Leu Arg Cys Tyr Phe Ser His Gln Leu Glu Leu Cys
    50                  55                  60

Glu Ser Lys Ala Glu Thr Asp Ile Leu Asp Ile Ile Leu Thr Lys Asp
65                  70                  75                  80

Gly Tyr Gly Ala Glu Gln Val Asn Lys Gln Val Ile Asp Ser Pro Ser
                85                  90                  95

Pro Phe Leu Cys Gly Ser Pro Ser Arg Val Ala Asn Pro Leu Thr
            100                 105                 110

Gln Asp Ala Arg Phe Arg Asp Glu Ile Val Ser Val Ser Ser Val Ile
        115                 120                 125

Pro Pro Gln Leu Gly Leu Pro Pro Ser Ser Pro Ser Ser Ser Ser Ser
    130                 135                 140

Gly Arg Lys Gly Gly Cys Val Arg Gly Asn Phe Gly Asn Ser Pro
145                 150                 155                 160

Lys Val Arg Val Glu Gly Phe Asp Cys Leu Asp Arg Asp Ser Arg Asn
                165                 170                 175

Cys Ser Ile Pro Ala Leu Ala
            180

<210> SEQ ID NO 57
<211> LENGTH: 173
<212> TYPE: PRT

<213> ORGANISM: Zea mays

<400> SEQUENCE: 57

```
Met Glu His Cys Tyr Val Gly Gln Pro Ile Ser Arg Ala Glu Ala Met
1               5                   10                  15

Pro Glu Arg Arg Ser Arg Phe Trp Gln Met Asp Ala Pro Pro Pro Pro
            20                  25                  30

Arg Ala Glu Val Ile Cys Pro Gln Pro Arg Arg Ala Thr Arg Ile Pro
        35                  40                  45

Leu Thr Ala Val Glu Thr Leu Asn Lys Ala Ser Pro Lys Met Asn Gly
    50                  55                  60

Ala Phe Pro Pro Tyr Arg Ser Asp Ser Thr Cys Asp Ile Leu Asp Leu
65                  70                  75                  80

Ile Leu Ser Lys Asn Asp Ser Asp Gly Asp Ser Ser Ser Gln Val Gly
                85                  90                  95

Phe Leu Cys Gly Ser Pro Pro Ile Arg Ala Asp Asn Pro Val Ile His
            100                 105                 110

Asp Pro Gln Phe Gly Lys Arg Leu Pro Ser Phe Ser Pro Leu Gly Gly
        115                 120                 125

Ser Ser Tyr Gly Lys Met Pro Ala Val Arg Val Glu Val Gly Ser Pro
    130                 135                 140

Ser Cys Gly Val Ser Ser Ser Pro Lys Val Arg Ile Glu Gly Phe Ala
145                 150                 155                 160

Cys Gly Asn Ser Glu Thr His Tyr Ala Val Thr Phe Val
                165                 170
```

<210> SEQ ID NO 58
<211> LENGTH: 174
<212> TYPE: PRT
<213> ORGANISM: Sorghum bicolor

<400> SEQUENCE: 58

```
Val Ser Gly Met Glu His Cys Tyr Leu Arg Gln Pro Ile Pro Arg Ala
1               5                   10                  15

Glu Ala Met Pro Glu Arg Arg Ser Arg Phe Trp Gln Met Asp Ala Pro
            20                  25                  30

Pro Pro Pro Arg Ala Glu Val Ile Cys Pro Gln Pro Arg Arg Ala Thr
        35                  40                  45

Arg Thr Pro Phe Ala Val Glu Thr Val Asn Lys Ala Ser Pro Lys Thr
    50                  55                  60

Asn Gly Ala Phe Pro Leu Tyr Arg Ser Asp Ser Thr Cys Asp Ile Leu
65                  70                  75                  80

Asp Leu Ile Leu Ser Lys Asn Asp Ser Asp Gly Asp Ser Ser Ser Gln
                85                  90                  95

Val Gly Phe Leu Cys Gly Ser Pro Pro Val Arg Thr Asn Asn Pro Val
            100                 105                 110

Ile His Asp Pro Gln Phe Gly Lys Lys Val Pro Ser Phe Ser Pro Leu
        115                 120                 125

Gly Ser Ser Tyr Gly Lys Ala Pro Thr Val Arg Val Glu Val Gly Ser
    130                 135                 140

Pro Ser Cys Gly Val Ser Ser Pro Lys Val Arg Ile Glu Gly Phe
145                 150                 155                 160

Ala Cys Gly Asn Ser Glu Thr His Tyr Ala Val Thr Phe Val
                165                 170
```

```
<210> SEQ ID NO 59
<211> LENGTH: 173
<212> TYPE: PRT
<213> ORGANISM: zea mays

<400> SEQUENCE: 59
```

| | | | | | | | | | | | | | | |
|---|---|---|---|---|---|---|---|---|---|---|---|---|---|---|
Met Asp Pro Tyr Met Thr Arg Leu Gly Ala Gly Ala Thr His Gln Leu
1               5                   10                  15

Ser Arg Ala Glu Ala Met Pro Asp Arg Arg Ser Arg Phe Trp Gln Thr
                20                  25                  30

Asp Val Gln Leu Ala Pro Arg Ile Asp Ile Ile Cys Pro Leu Pro Arg
            35                  40                  45

Arg Pro Ser Arg Leu Pro Val Leu Asn Ser Pro Lys Leu Asn Gly Ala
        50                  55                  60

Leu Pro Leu Tyr Arg Ala Asp Pro Thr Phe Asp Ile Val Asp Leu Ile
65                  70                  75                  80

Leu Ser Lys Asn Asp Pro Asp Val Asp Thr Asp Ser Ser Ser Gln Ala
                85                  90                  95

Gly Phe Phe Cys Gly Ser Pro Pro Ala Arg Thr Asp Asn Pro Val Ile
            100                 105                 110

Asn Asp Pro Gln Phe Gly Lys Lys Thr Pro Ser Phe Ser Pro Leu Phe
        115                 120                 125

Gly Gly Ser Ser Ser Gly Lys Met Thr Ala Gly Arg Val Glu Val Gly
    130                 135                 140

Ser Pro Ser Ser Cys Gly Ala Ser Ser Pro Lys Val Arg Ile Glu Gly
145                 150                 155                 160

Phe Ala Cys Gly Asn Lys Glu Pro Pro His Cys Phe Ala
                165                 170

```
<210> SEQ ID NO 60
<211> LENGTH: 173
<212> TYPE: PRT
<213> ORGANISM: zea mays

<400> SEQUENCE: 60
```

Met Asp Pro Tyr Met Thr Arg Leu Gly Ala Gly Ala Thr His Gln Leu
1               5                   10                  15

Ser Arg Ala Glu Ala Met Pro Asp Arg Arg Ser Arg Phe Trp Gln Thr
                20                  25                  30

Asp Val Gln Leu Ala Pro Arg Ile Asp Ile Ile Cys Pro Leu Pro Arg
            35                  40                  45

Arg Pro Ser Arg Leu Pro Val Leu Asn Ser Pro Lys Leu Asn Gly Ala
        50                  55                  60

Leu Pro Leu Tyr Arg Ala Asp Pro Thr Phe Asp Ile Val Asp Leu Ile
65                  70                  75                  80

Leu Ser Lys Asn Asp Pro Asp Val Asp Thr Asp Ser Ser Ser Gln Ala
                85                  90                  95

Gly Phe Phe Cys Gly Ser Pro Pro Ala Arg Thr Asp Asn Pro Val Ile
            100                 105                 110

Asn Asp Pro Gln Phe Gly Lys Lys Thr Pro Ser Phe Ser Pro Leu Phe
        115                 120                 125

Gly Gly Ser Ser Ser Gly Lys Met Thr Ala Gly Arg Val Glu Val Gly
    130                 135                 140

Ser Pro Ser Ser Cys Gly Ala Ser Ser Pro Lys Val Arg Ile Glu Gly
145                 150                 155                 160

Phe Ala Cys Gly Asn Lys Glu Pro Pro His Cys Phe Ala

<210> SEQ ID NO 61
<211> LENGTH: 183
<212> TYPE: PRT
<213> ORGANISM: sorghum bicolor

<400> SEQUENCE: 61

Met Ser His Phe Ala Ala Thr Met Lys Ser Pro Val Ala Val Ala Ala
1               5                   10                  15

Pro Val Ala Ala Ala Gly Asp Ala Lys Ser Pro Leu Phe Cys Pro
            20                  25                  30

Lys Pro Arg Arg Pro Val Ala Pro Leu Arg Cys His Gln Ser Gly Gly
        35                  40                  45

Phe Ser Asp Ala Gly Met Asp Leu Leu Asp Leu Leu Leu Ser Lys Gly
    50                  55                  60

Glu Glu Ser Gly Leu Ser Ala Ala Ser Pro Gln Pro Pro Leu Phe Cys
65                  70                  75                  80

Gly Ser Pro Pro Arg Arg Ala Ser Asn Pro Val Val His Asp Ser Arg
                85                  90                  95

Phe Gly Met Asp Cys Pro Ala Met Pro Met Pro Met Pro Met Pro Gly
            100                 105                 110

Leu Pro Val Val Ala Ala Ala Pro Val Ala Val Gln Arg Pro Thr
        115                 120                 125

Pro Arg Pro Ser Val Ala Ala Pro Ser Met Ser Pro Arg Gly Gly
    130                 135                 140

Ala Gly Gly Cys Ala Arg Ala Arg Phe Ala Phe Gln Pro Ala Ala Val
145                 150                 155                 160

Arg Val Glu Gly Phe Asp Cys Leu Asp Arg Ser Arg Gly Gly Arg Gly
                165                 170                 175

His Gly Ile Thr Ala Met Ala
            180

<210> SEQ ID NO 62
<211> LENGTH: 147
<212> TYPE: PRT
<213> ORGANISM: zea mays

<400> SEQUENCE: 62

Met Ser His Phe Ala Ala Ala Ala Val Lys Ser Pro Leu Val Ala
1               5                   10                  15

Ala Pro Ala Ala Gly Asp Ala Lys Ser Pro Leu Phe Cys Pro Lys Pro
            20                  25                  30

Arg Arg Pro Ala Ala Pro Leu Arg Cys His Gln Gly Gly Asp Ala Gly
        35                  40                  45

Met Asp Leu Leu Asp Leu Leu Leu Ser Lys Gly Glu Glu Ser Gly Leu
    50                  55                  60

Ser Ala Ala Ser Pro Leu Phe Cys Gly Ser Pro Pro Arg Arg Ala Ser
65                  70                  75                  80

Asn Pro Val Val His Asp Ser Arg Phe Gly Val Asp Cys Pro Pro Leu
                85                  90                  95

Pro Val Pro Met Pro Val Ala Ala Ala Val His Arg Pro Ser Ala
            100                 105                 110

Ala Pro Pro Met Ser Pro Arg Gly Gly Asn Gly Cys Ala Arg Ala Arg
        115                 120                 125

Phe Ala Phe Gln Pro Ala Ala Val Arg Val Glu Gly Phe Asp Cys Leu

```
                130                 135                 140

Asp Arg Gly
145

<210> SEQ ID NO 63
<211> LENGTH: 151
<212> TYPE: PRT
<213> ORGANISM: zea mays

<400> SEQUENCE: 63

Met Ser His Phe Ala Ala Ala Met Lys Ser Pro Leu Ala Val Ala Val
1               5                   10                  15

Ala Ala Pro Ala Ala Ala Asp Ala Lys Ser Pro Leu Phe Cys Pro
            20                  25                  30

Lys Pro Arg Arg Pro Ala Ala Pro Leu Arg Cys His Gln Ser Gly Gly
            35                  40                  45

Phe Ser Asp Ala Gly Thr Asp Leu Leu Asp Leu Leu Ser Lys Gly
        50                  55                  60

Asp Glu Ser Gly Leu Ser Ser Ala Ser Pro Gln Pro Pro Leu Phe Cys
65                  70                  75                  80

Gly Ser Pro Pro Arg Arg Ala Ser Asn Pro Val Val His Asp Ser Arg
                85                  90                  95

Phe Gly Ala Asp Cys Pro Pro Met Pro Val Pro Gly Leu Pro Val His
            100                 105                 110

Arg Pro Ser Pro Arg Pro Ser Ala Ala Pro Ser Met Ser Pro Arg
        115                 120                 125

Gly Cys Ala Arg Ala Arg Phe Ala Phe Gln Pro Ala Ala Val Arg Val
    130                 135                 140

Glu Gly Phe Asp Cys Leu Asp
145                 150

<210> SEQ ID NO 64
<211> LENGTH: 171
<212> TYPE: PRT
<213> ORGANISM: zea mays

<400> SEQUENCE: 64

Met Asp His Met Thr Met Leu Gly Ala Gly Ala Pro His Gln Leu Ser
1               5                   10                  15

Arg Ala Glu Pro Met Pro Asp Arg Arg Ser Arg Phe Trp Gln Thr Asp
            20                  25                  30

Val Gln Pro Val Pro Arg Ile Asp Ile Ile Cys Pro Leu Pro Cys Arg
        35                  40                  45

Pro Ser Arg Ser Leu Leu Leu Asn Arg Pro Ser Pro Lys Pro Asn Gly
    50                  55                  60

Ala Leu Pro Phe Tyr Gly Ala Asn Pro Thr Tyr Asp Ile Val Asp Leu
65                  70                  75                  80

Ile Leu Ser Lys Asn Asp Pro Asp Val Asp Thr Asp Ser Ser Ser Gln
                85                  90                  95

Ala Ala Phe Phe Cys Gly Ser Pro Ala Arg Thr Asn Asn Pro Val
            100                 105                 110

Ile His Asp Pro Gln Phe Gly Lys Lys Ala Pro Ser Phe Ser Pro Leu
        115                 120                 125

Gly Ser Ser Ser Gly Lys Met Ala Ala Gly Arg Ala Glu Val Gly Ser
    130                 135                 140

Pro Ser Cys Arg Ser Ser Ser Pro Lys Met Arg Ile Glu Gly Phe Ala
```

```
                145                 150                 155                 160
Cys Gly Asn Lys Glu Pro Pro His Cys Phe Ala
                165                 170
```

<210> SEQ ID NO 65
<211> LENGTH: 223
<212> TYPE: PRT
<213> ORGANISM: zea mays

<400> SEQUENCE: 65

```
Gly Arg Glu Ser Ser Pro Pro Pro Ser Leu Asp Leu Ser Phe Leu
1               5                   10                  15

Leu His Ala Cys Leu Gly Glu Pro Ser Pro Leu Tyr Thr Arg Arg Pro
                20                  25                  30

Gly Leu Arg Arg Arg Val Ala Thr Ser Cys Arg Ser Thr Phe Thr
            35                  40                  45

Ser Ala Lys Gly Met Asp His Met Thr Met Leu Gly Ala Gly Ala Pro
    50                  55                  60

His Gln Leu Ser Arg Ala Glu Pro Met Pro Asp Arg Arg Ser Arg Phe
65                  70                  75                  80

Trp Gln Thr Asp Val Gln Pro Val Pro Arg Ile Asp Ile Ile Cys Pro
                85                  90                  95

Leu Pro Cys Arg Pro Ser Arg Ser Leu Leu Asn Arg Pro Ser Pro
                100                 105                 110

Lys Pro Asn Gly Ala Leu Pro Leu Tyr Gly Ala Asn Pro Thr Tyr Asp
            115                 120                 125

Ile Val Asp Leu Ile Leu Ser Lys Asn Asp Pro Asp Val Asp Thr Asp
    130                 135                 140

Ser Ser Ser Gln Ala Ala Phe Phe Cys Gly Ser Pro Pro Ala Arg Thr
145                 150                 155                 160

Asn Asn Pro Val Ile His Asp Pro Gln Phe Gly Lys Lys Ala Pro Ser
                165                 170                 175

Phe Ser Pro Leu Gly Ser Ser Gly Lys Met Ala Ala Gly Arg Ala
                180                 185                 190

Glu Val Gly Ser Pro Ser Cys Arg Ser Ser Pro Lys Met Arg Ile
            195                 200                 205

Glu Gly Phe Ala Cys Gly Asn Lys Glu Pro Pro His Cys Phe Ala
    210                 215                 220
```

<210> SEQ ID NO 66
<211> LENGTH: 169
<212> TYPE: PRT
<213> ORGANISM: Triticum aestivum

<400> SEQUENCE: 66

```
Met Ser His Phe Ala Ala Met Lys Ser Pro Val Pro Val Ala Ala
1               5                   10                  15

Ala Ala Thr Asp Ala Lys Ser Pro Leu Phe Cys Pro Lys Pro Arg Arg
                20                  25                  30

Pro Val Ala Pro Leu Arg Cys His Gln Ser Ser His Ser Asp Ala Gly
            35                  40                  45

Ala Gly Met Asp Leu Leu Asp Leu Leu Leu Ser Lys Gly Asp Glu Ser
    50                  55                  60

Asn Leu Ser Ala Ala Ser Pro Gln Pro Pro Leu Phe Cys Gly Ser Pro
65                  70                  75                  80

Pro Arg Arg Ala Ser Asn Pro Val Val His Asp Ser Arg Phe Gly Met
```

```
                      85                  90                  95
Asp Cys Pro Ser Ser Pro Leu Pro Trp Trp Pro Val Met Ser Pro Val
            100                 105                 110

Thr Pro Ala Pro Val Val Arg Pro Thr Pro Arg Pro Ala Gly Pro
            115                 120             125

Pro Met Ser Pro Arg Ser Ala Gly Cys Ala Arg Val Phe Gln Pro
        130                 135                 140

Ala Val Arg Val Glu Gly Phe Asp Cys Leu Asp Gly Arg Ser Gly
145                 150                 155                 160

Arg Gly His Gly Ile Ala Ala Met Val
                165

<210> SEQ ID NO 67
<211> LENGTH: 179
<212> TYPE: PRT
<213> ORGANISM: glycine max

<400> SEQUENCE: 67

Met Asn Cys Tyr Asn Leu Gln Lys Asn Ala Phe Ser Ala Cys Glu Glu
1               5                   10                  15

Met Arg Gly Ser Leu Pro Ile Ala Asp Gln Asn Gly Pro Val Phe Cys
            20                  25                  30

Pro Lys Pro Arg Arg Ala Gly Val Leu Met Asn Leu Pro Ile Arg Pro
        35                  40                  45

Val Lys Trp His Leu Gly Gln Gln Ala Glu Gly Ser Asp Ser Lys Ala
    50                  55                  60

Gly Ala Glu Leu Leu Asp Ile Val Leu Lys Arg Asp Ile Val Leu Lys
65                  70                  75                  80

Arg Glu Ser Tyr Gly Glu Glu Phe Ala Asn Gln Ile Pro Ser Ser Pro
                85                  90                  95

Pro Tyr Phe Cys Gly Ser Pro Pro Val Arg Ala Ser Asn Pro Leu Ile
            100                 105                 110

Gln Asp Ala Arg Phe Gly Asp Glu Glu Tyr Ser Leu Ile Ser Thr Ile
        115                 120                 125

Ser Ser Pro Ser Gly Leu Leu Ser Pro Ser Ser Ala Ser Arg Lys Ala
    130                 135                 140

Gly Cys Ala Arg Met Lys Phe Gly Leu Lys Pro Ala Ala Val Arg Val
145                 150                 155                 160

Glu Gly Phe Asp Cys Leu Ser Arg Asp Cys Gln Asn Ser Gly Ile Pro
                165                 170                 175

Ala Val Ala

<210> SEQ ID NO 68
<211> LENGTH: 179
<212> TYPE: PRT
<213> ORGANISM: glycine max

<400> SEQUENCE: 68

Met Asn Cys Tyr Asn Leu Gln Lys Asn Ala Phe Ser Ala Cys Glu Glu
1               5                   10                  15

Met Arg Gly Ser Leu Pro Ile Ala Asp Gln Asn Gly Pro Val Phe Cys
            20                  25                  30

Pro Lys Pro Arg Arg Ala Gly Val Leu Met Asn Leu Pro Ile Arg Pro
        35                  40                  45

Val Lys Trp His Leu Gly Gln Gln Ala Glu Gly Ser Asp Ser Lys Val
    50                  55                  60
```

```
Gly Ala Glu Leu Leu Asp Ile Val Leu Lys Arg Asp Ile Val Leu Lys
 65                  70                  75                  80

Arg Glu Ser Tyr Gly Glu Phe Ala Asn Gln Ile Pro Ser Ser Pro
             85                  90                  95

Pro Tyr Phe Cys Gly Ser Pro Val Arg Ala Ser Asn Pro Leu Ile
            100                 105                 110

Gln Asp Ala Arg Phe Gly Asp Glu Tyr Ser Leu Ile Ser Thr Ile
            115                 120                 125

Ser Ser Pro Ser Gly Leu Leu Ser Pro Ser Ser Ala Ser Arg Lys Ala
130                 135                 140

Gly Cys Ala Arg Met Lys Phe Gly Leu Lys Pro Ala Ala Val Arg Val
145                 150                 155                 160

Glu Gly Phe Asp Cys Leu Ser Arg Asp Cys Gln Asn Ser Gly Ile Pro
                165                 170                 175

Ala Val Ala

<210> SEQ ID NO 69
<211> LENGTH: 175
<212> TYPE: PRT
<213> ORGANISM: glycine max

<400> SEQUENCE: 69

Met Lys Gln Phe Ala Val Gln Asn Val Val Ala Pro Ser His Asp Glu
  1               5                  10                  15

Ile Ser Val Val Cys Pro Lys Pro Arg Arg Leu Gly Leu Phe Asn Phe
             20                  25                  30

Pro Val Asn Asp Pro Pro Val Arg Pro Phe Tyr Trp His Leu Ser Cys
             35                  40                  45

Gln Ala Glu Pro Cys Asp Ser Asn Ser Ser Gly Ser Asn Pro Leu Asp
 50                  55                  60

Asn Leu Leu Thr Lys Asp Gly Asp Phe Asp Val Glu Gln Ser Trp Pro
 65                  70                  75                  80

Val Val Thr Ser Ser Pro Pro Phe Phe Cys Gly Ser Pro Pro Ser Arg
             85                  90                  95

Ala Ala Asn Pro Leu Ile Gln Asp Ala Arg Phe Gly Asp Glu Asn Phe
            100                 105                 110

Ser Pro Leu Ser Pro Pro Ser Trp Val Val Pro Ala Thr Ala Ser
            115                 120                 125

Gly Leu Pro Pro Ser Pro Ser Ser Ala Arg Lys Gly Gly Cys Val
130                 135                 140

Arg Ala Asn Phe Gly Asn Asn Pro Ala Val Arg Ile Glu Gly Phe Asp
145                 150                 155                 160

Cys Leu Asp Arg Asp Arg Arg Asn Cys Ser Ile Pro Ala Leu Ala
                165                 170                 175

<210> SEQ ID NO 70
<211> LENGTH: 175
<212> TYPE: PRT
<213> ORGANISM: glycine max

<400> SEQUENCE: 70

Met Lys Gln Phe Ala Val Gln Asn Val Val Pro Ser His Asp Glu
  1               5                  10                  15

Ile Ser Val Val Cys Pro Lys Pro Arg Arg Leu Gly Leu Phe Asn Phe
             20                  25                  30
```

```
Pro Val Asn Asp Pro Thr Val Arg Pro Phe Arg Trp His Leu Ser Tyr
         35                  40                  45

His Val Glu Pro Cys Asp Ser Asn Ser Ser Gly Ser Asn Pro Leu Asp
 50                  55                  60

Asn Leu Leu Thr Lys Asp Gly Asp Phe Asp Val Glu Gln Ser Trp Pro
 65                  70                  75                  80

Val Val Thr Ser Ser Pro Pro Phe Phe Cys Gly Ser Pro Pro Ser Arg
                 85                  90                  95

Ala Ala Asn Pro Leu Ile Gln Asp Ala Arg Phe Gly Asp Glu Asn Phe
                100                 105                 110

Ser Pro Leu Ser Pro Pro Ser Trp Val Val Val Pro Ala Ala Ala Ser
            115                 120                 125

Gly Leu Pro Pro Ser Pro Ser Ser Ala Arg Lys Gly Gly Cys Val
        130                 135                 140

Arg Ala Asn Phe Gly Asn Asn Pro Ala Val Arg Ile Glu Gly Phe Asp
145                 150                 155                 160

Cys Leu Asp Arg Asp Arg Arg Asn Cys Ser Ile Pro Ala Leu Ala
                165                 170                 175

<210> SEQ ID NO 71
<211> LENGTH: 6
<212> TYPE: PRT
<213> ORGANISM: Artificial Sequence
<220> FEATURE:
<223> OTHER INFORMATION: motif 1
<220> FEATURE:
<221> NAME/KEY: Xaa
<222> LOCATION: (3)..(3)
<223> OTHER INFORMATION: K or Q or L
<220> FEATURE:
<221> NAME/KEY: Xaa
<222> LOCATION: (5)..(5)
<223> OTHER INFORMATION: R or C

<400> SEQUENCE: 71

Cys Pro Xaa Pro Xaa Arg
1               5

<210> SEQ ID NO 72
<211> LENGTH: 9
<212> TYPE: PRT
<213> ORGANISM: Artificial Sequence
<220> FEATURE:
<223> OTHER INFORMATION: motif 2
<220> FEATURE:
<221> NAME/KEY: Xaa
<222> LOCATION: (1)..(1)
<223> OTHER INFORMATION: F or L or Y
<220> FEATURE:
<221> NAME/KEY: Xaa
<222> LOCATION: (2)..(2)
<223> OTHER INFORMATION: F or L
<220> FEATURE:
<221> NAME/KEY: Xaa
<222> LOCATION: (8)..(8)
<223> OTHER INFORMATION: S or I or A or V

<400> SEQUENCE: 72

Xaa Xaa Cys Gly Ser Pro Pro Xaa Arg
1               5

<210> SEQ ID NO 73
<211> LENGTH: 9
<212> TYPE: PRT
<213> ORGANISM: Artificial Sequence
<220> FEATURE:
```

```
<223> OTHER INFORMATION: motif 3
<220> FEATURE:
<221> NAME/KEY: Xaa
<222> LOCATION: (2)..(2)
<223> OTHER INFORMATION: V or I
<220> FEATURE:
<221> NAME/KEY: Xaa
<222> LOCATION: (6)..(6)
<223> OTHER INFORMATION: D or A
<220> FEATURE:
<221> NAME/KEY: Xaa
<222> LOCATION: (9)..(9)
<223> OTHER INFORMATION: D or S

<400> SEQUENCE: 73

Arg Xaa Glu Gly Phe Xaa Cys Leu Xaa
1               5

<210> SEQ ID NO 74
<211> LENGTH: 1307
<212> TYPE: DNA
<213> ORGANISM: zea mays

<400> SEQUENCE: 74
caccgcctcc ttccttcctt ctcacgaaaa ggcaggcaag ggaaaggcaa aggacaaccc      60
atcccctgcc tcctccgttg ctctgctgct cccctcctt atctaatcct ctggttcctg     120
gacaccggcc tgcaagctcc agcagcagcg gcgccggcga cgaaaggagg aggattgcta    180
ccatcctata tcatatcata catatacaca aggaggagga gaaggtgtgt agcgaggttg    240
aggtccggag gatgccttcc agtgccatga gttccgggct ggagccggtg ctctgcgcgc    300
ctcggccgcg cagggtccag cagctgcacc cctgcagcgc cgacctcatc cttggcgcac    360 cgccctttccc gcgcaacgcc aacagcaagg ccagcggcag cagcagcagg aaggaggca    420 ggaagacgac caggccggcg gcggaggacg aggactgccg ctgggcggcg ttcggcgggt    480
cgccgccggc gcgcgcggac aacccgctgg tgcacgaccc ccggttcctg cggaaccagc    540
gccacccggc gccgctggag ctcgggtcgc cgaaccaccg gcggccgacc tacagcagcg    600
gtggcgacgg cagcgggttt gcctcgtcgt cgttcgcgcc ggccgtgagg atccagggct    660
tcgacgtcgc cgcgtgccgc gcgtgagagc gagctccggc cgggcgggc tttggctttt     720 cgatctatta aattaaatta acagcaggtg aggtcaggtc agatcagatc atagtaggga    780
ggaaggcgag gagggcggga gggatgggat gagatctcct cttcctcctc ctcgcgaggg    840
aggcgatcca gtcgtatgag tgaagtaaag aagagtactc cagtcgtact ataggttgat    900
gttcgccgat accacaccac acagcagccg gtcaaaggga gtgaaaactg attttttgtt    960
tacggggttt tgtcagcaag gttattaggt tttgtgtttg tgctgtagcc tgtaagatgt   1020
aagctactac tagcacgggt ctcttgttcg ttgctgctgc tctgctctgg cctctggtg    1080 cccctgtatt gtagatataa atcagcaccc agttcgggcg gtcggccagc gttcgttttt   1140
cttctagttg acgaggagga agaagatgtc cgctcctcgc catgtaatgt aaccatggct   1200
gtactcctac atacatgcaa tcatgtataa agatgaaaac gtgtacatac acaagatgaa   1260
agttggcatg cagtgaatga tctatcagaa aaaaaaaaa aaaaaaa                  1307

<210> SEQ ID NO 75
<211> LENGTH: 144
<212> TYPE: PRT
<213> ORGANISM: zea mays

<400> SEQUENCE: 75
```

```
Met Pro Ser Ser Ala Met Ser Ser Gly Leu Glu Pro Val Leu Cys Ala
1               5                   10                  15

Pro Arg Pro Arg Val Gln Gln Leu His Pro Cys Ser Ala Asp Leu
            20                  25                  30

Ile Leu Gly Ala Pro Pro Phe Pro Arg Asn Ala Asn Ser Lys Ala Ser
            35                  40                  45

Gly Ser Ser Ser Arg Glu Gly Arg Lys Thr Thr Arg Pro Ala Ala
    50                  55                  60

Glu Asp Glu Asp Cys Arg Trp Ala Ala Phe Gly Ser Pro Pro Ala
65                  70                  75                  80

Arg Ala Asp Asn Pro Leu Val His Asp Pro Arg Phe Leu Arg Asn Gln
            85                  90                  95

Arg His Pro Ala Pro Leu Glu Leu Gly Ser Pro Asn His Arg Arg Pro
            100                 105                 110

Thr Tyr Ser Ser Gly Gly Asp Gly Ser Gly Phe Ala Ser Ser Ser Phe
            115                 120                 125

Ala Pro Ala Val Arg Ile Gln Gly Phe Asp Val Ala Ala Cys Arg Ala
            130                 135                 140
```

<210> SEQ ID NO 76
<211> LENGTH: 939
<212> TYPE: DNA
<213> ORGANISM: zea mays

<400> SEQUENCE: 76

```
ctttcttgtt gcacgcctgc ctgggcgaac cgtcgccgct atacaccagg cgcccagggc      60
ttcgccggcg ccgagtagcc accagctgcc gctcaacatt cacctctgcc aagggcatgg     120
accacatgac gatgctcggc gccggagccc ccaccagct  ctccagggct gaaccaatgc     180
ctgaccgtag gtcaaggttc tggcagacgg atgtgcagcc tgtgcctcgg atagacatca     240
tctgtcctct gccttgtcgc ccttcccgct cactgctcct caataggccc agccccaagc     300
ctaatggggc actcccattg tatggagcaa accctactta tgatatcgtt gatctcatcc     360
ttagcaagaa tgaccctgat gtggatactg attcaagcag ccaggcgcc  ttttctgtg      420
gctcgcctcc tgcccgcact aacaaccctg ttatccatga cccacagttt ggaaagaaag     480
caccatcctt ttctcctcta ggaagctctt ctggaaaaat ggcagctgga agagctgaag     540
taggttctcc gtcctgcagg tcgagcagcc caaaaatgag aatcgaaggt tttgcttgcg     600
ggaacaaaga gccccctcac tgctttgcct gatgatcccc attgaccctg cctaaccctg     660
ttttgctacc ctgcaacctg tacattttcg ctgcccagct gagagttcgt ttcgttataa     720
gctgttaaac tagctgagag tcccatgtga ttgtggcttt tgaaaattgc atgatccaag     780
gggacggatg taaataggtc gagttgtccg gtgtatgtac tagatgttgt atgcgtctgg     840
taaatgtagt catgctgggt gggtccatgt gtcggcgtct gtaaatacag ccatgcattt     900
ggatgtgaaa tttaaatgcg tcttcagtta aaaaaaaaa                            939
```

<210> SEQ ID NO 77
<211> LENGTH: 171
<212> TYPE: PRT
<213> ORGANISM: zea mays

<400> SEQUENCE: 77

```
Met Asp His Met Thr Met Leu Gly Ala Gly Ala Pro His Gln Leu Ser
1               5                   10                  15

Arg Ala Glu Pro Met Pro Asp Arg Arg Ser Arg Phe Trp Gln Thr Asp
```

```
                20                  25                  30
Val Gln Pro Val Pro Arg Ile Asp Ile Ile Cys Pro Leu Pro Cys Arg
            35                  40                  45

Pro Ser Arg Ser Leu Leu Leu Asn Arg Pro Ser Pro Lys Pro Asn Gly
        50                  55                  60

Ala Leu Pro Leu Tyr Gly Ala Asn Pro Thr Tyr Asp Ile Val Asp Leu
65                  70                  75                  80

Ile Leu Ser Lys Asn Asp Pro Asp Val Asp Thr Asp Ser Ser Ser Gln
                85                  90                  95

Ala Ala Phe Phe Cys Gly Ser Pro Pro Ala Arg Thr Asn Asn Pro Val
            100                 105                 110

Ile His Asp Pro Gln Phe Gly Lys Lys Ala Pro Ser Phe Ser Pro Leu
        115                 120                 125

Gly Ser Ser Ser Gly Lys Met Ala Ala Gly Arg Ala Glu Val Gly Ser
130                 135                 140

Pro Ser Cys Arg Ser Ser Ser Pro Lys Met Arg Ile Glu Gly Phe Ala
145                 150                 155                 160

Cys Gly Asn Lys Glu Pro Pro His Cys Phe Ala
                165                 170

<210> SEQ ID NO 78
<211> LENGTH: 968
<212> TYPE: DNA
<213> ORGANISM: zea mays

<400> SEQUENCE: 78
gccgtgtaga aaggcggcgc ctcttttggc acccagctga gcattgcatt tccttcctcc      60
ttttcccagt cggaggaatg caatgccgta aacgaaagtt tcccatcctt gtgttttggg     120
gggtgggcca tcgcggtgtt gataagaaaa aggcggactc cttgtaccag tttggttttg     180
ttttgtacgc gcattggttc ctggcttgct caataaattg caaccacttc cttccgaatt     240
ccgatctagc ggactaccag ttcctcccga tcttgggttt gaggaggccc cgagccgagc     300
gtcaggcatg gagcactgct atttgaggca gccgatctcg agggccgagg cagtgcccga     360
gaggaggtcc aggttgtggc agatggacgc gctgccgctg ccgccccgga cggaggtcct     420
ctgccccctg cctcgccgcg ccgcccggat ccccttcgcc gtttcagtaa acaaggccat     480
ccccaggtcg aattgtgcgc ttccgccgta cagaccagcc tccgcctgcg acatacttga     540
tcttatcctc agcaagaatg acttctcaga tggagcagat cgagcagcg gccaggtggg     600 cttttcgcct ccagtgcgcg ctaccaaccc tgtcgtccac gacccgcagt tcggtaaaag     660
agtgccgcca tccatgtctc ctctagggag cagctcctac ggcaagctta aggttgaggt     720
aggctcgcca tcctgcggcg ttagcagcag acagcccgaa agtgaggatc gaaggctttg     780
cctgtggcaa ctcggagacc cactacgcag ttacgccgct ccttgtgtga atcgaatcgc     840
cgtggtggcg tagcctgatc agagtcgcgt ttttttgccc ttctgaatct gctgccatct     900
gaagcttcac aattgcagtg agcagtatga tttatgtgtg tctagtaaat gtagctggag     960
ttgcatgg                                                             968

<210> SEQ ID NO 79
<211> LENGTH: 181
<212> TYPE: PRT
<213> ORGANISM: zea mays

<400> SEQUENCE: 79
```

Met Glu His Cys Tyr Leu Arg Gln Pro Ile Ser Arg Ala Glu Ala Val
1               5                   10                  15

Pro Glu Arg Arg Ser Arg Leu Trp Gln Met Asp Ala Leu Pro Leu Pro
                20                  25                  30

Pro Arg Thr Glu Val Leu Cys Pro Leu Pro Arg Arg Ala Ala Arg Ile
            35                  40                  45

Pro Phe Ala Val Ser Val Asn Lys Ala Ile Pro Arg Ser Asn Cys Ala
        50                  55                  60

Leu Pro Pro Tyr Arg Pro Ala Ser Ala Cys Asp Ile Leu Asp Leu Ile
65                  70                  75                  80

Leu Ser Lys Asn Asp Phe Ser Asp Gly Ala Asp Ser Ser Ser Gly Gln
                85                  90                  95

Val Gly Phe Ser Pro Pro Val Arg Ala Thr Asn Pro Val Val His Asp
                100                 105                 110

Pro Gln Phe Gly Lys Arg Val Pro Ser Met Ser Pro Leu Gly Ser
            115                 120                 125

Ser Ser Tyr Gly Lys Leu Lys Val Glu Val Ser Pro Ser Cys Gly
            130                 135                 140

Val Ser Arg Gln Pro Glu Ser Glu Asp Arg Arg Leu Cys Leu Trp
145                 150                 155                 160

Gln Leu Gly Asp Pro Leu Arg Ser Tyr Ala Ala Pro Cys Val Asn Arg
                165                 170                 175

Ile Ala Val Val Ala
            180

<210> SEQ ID NO 80
<211> LENGTH: 690
<212> TYPE: DNA
<213> ORGANISM: Paspalum notatum

<400> SEQUENCE: 80

```
gcaataatga ccctgatgtg catactgatt caagcagcca ggcgggcttt ttctgtggct    60
cgcctcctgc gcgcactaac aaccctgtta ttcatgaccc acagtttggt aagaaaatac   120
catccttttc tcctctaggg agctcttttg gcaagatggc aactggaaga gttgaggtag   180
gttctccgtc ctgcggggcg agcagcccaa aagtaagaat cgaaggtttt gcttgcggga   240
acaaagaggc ccccaaccgt gcagttacct ttgtctgagc attttgcgac cctggttgac   300
cctaactcta ttctgcgacc ccacacaatc tgtacatttt ctcgcccgcc ctgaggatga   360
aactagctag tgtcttttgt taagctggta gctgctcatt gaattgaaga gagtttatgt   420
ttgaggagtg gagcgctcga tgctcttgtg attgtggctt ttgaaactgc tcaatcgcgg   480
ggagcagagc ttttcgttgg gtgtacatag atggaggtgt cctgtgtata tagtatctac   540
tagagatgtc ggtatgtgtg tctgctaaat gtagcaagtc cattggtgtc ggcatgtgtc   600
tgtaaatacc atgttgcatc cggatgcaag ttaaataaaa tttatctcat ttctgttggc   660
atgcatatgc cggcagttca ttgtcaaaaa                                   690
```

<210> SEQ ID NO 81
<211> LENGTH: 89
<212> TYPE: PRT
<213> ORGANISM: Paspalum notatum

<400> SEQUENCE: 81

Asn Asp Pro Asp Val His Thr Asp Ser Ser Ser Gln Ala Gly Phe Phe
1               5                   10                  15

Cys Gly Ser Pro Pro Ala Arg Thr Asn Asn Pro Val Ile His Asp Pro
            20                  25                  30

Gln Phe Gly Lys Lys Ile Pro Ser Phe Ser Pro Leu Gly Ser Ser Phe
        35                  40                  45

Gly Lys Met Ala Thr Gly Arg Val Glu Val Gly Ser Pro Ser Cys Gly
    50                  55                  60

Ala Ser Ser Pro Lys Val Arg Ile Glu Gly Phe Ala Cys Gly Asn Lys
65                  70                  75                  80

Glu Ala Pro Asn Arg Ala Val Thr Phe
                85

<210> SEQ ID NO 82
<211> LENGTH: 508
<212> TYPE: DNA
<213> ORGANISM: Paspalum notatum

<400> SEQUENCE: 82
aagatcgaag caaattgaga tcaggaggag ctaggatgcc ttccagggcc atcatgaaca      60
ggctgttcgt cgagtcgtct tcgtcctcct ccggcagcgg cggctgcggc agggaggcgg     120
agccgggcgc ggcggtgctc tgcgcgcctc ggccgcgcag ggtccaggtc cacccctgca     180
gcgccgacct catcctcggc gtgcccccct tcctgctcac caacaacaag agcggcaagg     240
aaggaggcaa gaccaaggcg gcgccgcggg aggccgacgg cgacgaggcc ggcgggtggg     300
cgctgttcgg cgggtcgccg ccggcgcgcg cggacaaccc gctggtgcac gaccccact      360
tcctgctgaa ccagcgcctg caccccgtgg agtcgtcgtc gccttcgccg ctggagctcg     420
ggatttttga ccaccagagc cccgccgct acagccaccg cggccccacc ccaacgtata     480
ttaacagcaa tagcagcagc agcagcag                                        508

<210> SEQ ID NO 83
<211> LENGTH: 157
<212> TYPE: PRT
<213> ORGANISM: Paspalum notatum

<400> SEQUENCE: 83

Met Pro Ser Arg Ala Ile Met Asn Arg Leu Phe Val Glu Ser Ser Ser
1               5                   10                  15

Ser Ser Ser Gly Ser Gly Gly Cys Gly Arg Glu Ala Glu Pro Gly Ala
            20                  25                  30

Ala Val Leu Cys Ala Pro Arg Pro Arg Val Gln Val His Pro Cys
        35                  40                  45

Ser Ala Asp Leu Ile Leu Gly Val Pro Pro Phe Leu Leu Thr Asn Asn
    50                  55                  60

Lys Ser Gly Lys Glu Gly Gly Lys Thr Lys Ala Ala Pro Arg Glu Ala
65                  70                  75                  80

Asp Gly Asp Glu Ala Gly Gly Trp Ala Leu Phe Gly Gly Ser Pro Pro
                85                  90                  95

Ala Arg Ala Asp Asn Pro Leu Val His Asp Pro His Phe Leu Leu Asn
            100                 105                 110

Gln Arg Leu His Pro Val Glu Ser Ser Pro Ser Pro Leu Glu Leu
        115                 120                 125

Gly Ile Phe Asp His Gln Ser Pro Arg Arg Tyr Ser His Arg Gly Pro
    130                 135                 140

Thr Pro Thr Tyr Ile Asn Ser Asn Ser Ser Ser Ser
145                 150                 155

<210> SEQ ID NO 84
<211> LENGTH: 749
<212> TYPE: DNA
<213> ORGANISM: Dennstaedtia punctilobula

<400> SEQUENCE: 84

```
gctctctggc ttcgttttac acattgaggg atctcctcct cctcctgctc ctctaccgtg      60
gcgctgattc ggggcccaaa tcgtgggagg agcagggtgg gagtcatctc tcgatgctag     120
cctttgtggg cgattcttct ctgtttcgtc ttgcggcatc tcgtgaaggg gtctcttcac     180
agttatactt ctttgcctgc tgaaggagaa ccagggcgtg agatattgga gatccttctg     240
gataaggctt ctttgggaaa tgttggcagt ccaggtggtt tgacaccatt ctcatatggg     300
tcacctccaa gccgagctag caatcctctt atacatgatg tacatttcac acagaagaaa     360
gccttaccgt caccattgtt tctccctcaa aattttcct gcagatccgg aggcaattcg      420
ccatacaaga aatcaacatg tggcacgtca tatgggtcga acccttttgt gcgcattgag     480
ggctttgcat gttcaacccc tgatgctcgg ggagtaccca cttttgcgta agatgtatgg     540
ccgtacatac gccatacttt cggtttcacg agtttatgca aaaactgtag cgatatgaat     600
ggcaaagctg cctttgtaga tacctccaaa cttttttgcat tcacaagcag agggtgcttt     660
cccaagaggt tacctatttc cctctacttg taaatgggac ccctttccta cattttaggt    720
cacaagataa attgaaagat accgacttt                                       749
```

<210> SEQ ID NO 85
<211> LENGTH: 122
<212> TYPE: PRT
<213> ORGANISM: Dennstaedtia punctilobula

<400> SEQUENCE: 85

```
Val Lys Gly Ser Leu His Ser Tyr Thr Ser Leu Pro Ala Glu Gly Glu
1               5                   10                  15

Pro Gly Arg Glu Ile Leu Glu Ile Leu Leu Asp Lys Ala Ser Leu Gly
            20                  25                  30

Asn Val Gly Ser Pro Gly Gly Leu Thr Pro Phe Ser Tyr Gly Ser Pro
        35                  40                  45

Pro Ser Arg Ala Ser Asn Pro Leu Ile His Asp Val His Phe Thr Gln
    50                  55                  60

Lys Lys Ala Leu Pro Ser Pro Leu Phe Leu Pro Gln Asn Phe Ser Cys
65                  70                  75                  80

Arg Ser Gly Gly Asn Ser Pro Tyr Lys Lys Ser Thr Cys Gly Thr Ser
                85                  90                  95

Tyr Gly Ser Lys Pro Phe Val Arg Ile Glu Gly Phe Ala Cys Ser Thr
            100                 105                 110

Pro Asp Ala Arg Gly Val Pro Thr Phe Ala
        115                 120
```

<210> SEQ ID NO 86
<211> LENGTH: 1112
<212> TYPE: DNA
<213> ORGANISM: Triticum aestivum
<220> FEATURE:
<221> NAME/KEY: misc_feature
<222> LOCATION: (906)..(906)
<223> OTHER INFORMATION: n is a, c, g, or t

<400> SEQUENCE: 86

```
acccacgctt ccgccatcgg cacgcccatc ccgctcctct cataatcctg agagtttctt      60
```

-continued

```
cttttgtttt attttctt gcttggtagg agtaacaata gttttggctc tcctcctttc    120
tctctccctg tatccaagga gagaaatcca gaggcgaagc ttcagggttt gtaaattttc    180
cggatctaat caactaacca aaaaaaccca aaaaaggaac catgagccac ttcgccgcca    240
tgaagagccc cgtcccggtc gccgccgccg ccgccaccga cgcgaagagc ccgctcttct    300
gccccaagcc gcgccgcccg gtcgcgcccc tccggtgcca ccagagtagc cactccgacg    360
cgggcgccgg catggatctg ctcgacctcc tcctgtcaaa gggcgatgag agcaatcttt    420
cggcggcgtc cccgcagccg ccgttgttct gtggctcgcc tccgcggcgg gcctcgaacc    480
cggtggtcca cgacagccgg ttcggcatgg actgtccgtc cagtcccctg ccgtggtggc    540
cggtgatgtc gccggtcacg ccagcgccgg tggtggtccg tcctacccca cgcccggcgg    600
gaccaccgat gtcgccccgt tcctcggctg gtgcgctcg cgtgttccag ccagccgtcc    660
gcgttgaggg ttttgactgc ctcgacggtg gccgtagcgg ccgtgggcat ggcatcgccg    720
ccatggtcta gatgcacata caacatcgaa taacccagga atcttctccc ctcagtagtg    780
caaaagcttg gagggagaga gatgagagtg aggagatgag tgagaggagc tttagtccaa    840
aatttaaccc ctaaaactat gtaatccatc attcaaatcc cataagtata ttgagtctag    900
gtatcntacc acaaatcttt tggtatgtaa ttaaattcag gttcaaatgc cggtgccctt    960
ttgtaaattg gaaccctat tttgggggg atgggtaaaa agaattctgg ggttggggat    1020
tagggaaaag gggcaaagaa aaacaagtta acccccctgt ttgaatacat ttttcagaga    1080
gcccttggct tcccttttgga ataaacaatc aa                               1112
```

<210> SEQ ID NO 87
<211> LENGTH: 169
<212> TYPE: PRT
<213> ORGANISM: Triticum aestivum

<400> SEQUENCE: 87

```
Met Ser His Phe Ala Ala Met Lys Ser Pro Val Pro Val Ala Ala
1               5                   10                  15

Ala Ala Thr Asp Ala Lys Ser Pro Leu Phe Cys Pro Lys Pro Arg Arg
            20                  25                  30

Pro Val Ala Pro Leu Arg Cys His Gln Ser Ser His Ser Asp Ala Gly
        35                  40                  45

Ala Gly Met Asp Leu Leu Asp Leu Leu Leu Ser Lys Gly Asp Glu Ser
    50                  55                  60

Asn Leu Ser Ala Ala Ser Pro Gln Pro Pro Leu Phe Cys Gly Ser Pro
65                  70                  75                  80

Pro Arg Arg Ala Ser Asn Pro Val Val His Asp Ser Arg Phe Gly Met
                85                  90                  95

Asp Cys Pro Ser Ser Pro Leu Pro Trp Trp Pro Val Met Ser Pro Val
            100                 105                 110

Thr Pro Ala Pro Val Val Arg Pro Thr Pro Arg Pro Ala Gly Pro
        115                 120                 125

Pro Met Ser Pro Arg Ser Ser Ala Gly Cys Ala Arg Val Phe Gln Pro
    130                 135                 140

Ala Val Arg Val Glu Gly Phe Asp Cys Leu Asp Gly Gly Arg Ser Gly
145                 150                 155                 160

Arg Gly His Gly Ile Ala Ala Met Val
                165
```

-continued

<210> SEQ ID NO 88
<211> LENGTH: 893
<212> TYPE: DNA
<213> ORGANISM: Hordeum vulgare
<220> FEATURE:
<221> NAME/KEY: misc_feature
<222> LOCATION: (795)..(795)
<223> OTHER INFORMATION: n is a, c, g, or t

<400> SEQUENCE: 88

| | | |
|---|---|---|
| catcccgctc ctctcataat cttgagattt tcttcttttg ttttatttttt ctttcttggt | 60 |
| aggagtaaca atagttttgg ctctcctcct ttctctctcc ctgtatccaa ggagagaaat | 120 |
| ccagaggcga agcttcaggg tttgtaaatt ttccggatct aatcaactaa cccaaaaaag | 180 |
| caaaaaaga aaccatgagc cacttcgccg ccatgaagag ccccgtcccg gtcgccgccg | 240 |
| ccgccgccac cgacgcgaag agcccactct tctgccccaa gccgcgccgc cggtcgcac | 300 |
| ccctccggtg ccaccagagc agcaactccg acgcgggcgc cggcatggat ctgctcgacc | 360 |
| tactcctgtc aaagggcgac gagagcaatc tttcggcggc gtccccgcag ccgcctctgt | 420 |
| tctgcggctc gcctccgcgg cgggcctcga ccccggggt gcacgacagc cggttcggca | 480 |
| tggactgtcc gtccagtccc ctgccggggt ggccggtgat gtcgccagcc accccagcgc | 540 |
| cgggggggtgg tccgggctac cccacgcccg ggggaacgg ccggtgtcgc cccggtccag | 600 |
| aacaagggg ccctcgggtg gtgccaccaa ccgtgccggt gggggggtgt gacgccctca | 660 |
| acggcggcgg gacgggcggg ggcatggaaa tgcgccgggg ctaaatgcat acaagaggga | 720 |
| taccaggaat cttttccttg ggggggaaa agttgaggag gaaagtgggg tgggttggg | 780 |
| gaggcaagca gaccngatga cgccaacgtg agcgaagaag ccgaggagag acgggtccg | 840 |
| ccggctttgg tgaaaaatag gggaggggc ggtgagagg gccgcagggg agg | 893 |

<210> SEQ ID NO 89
<211> LENGTH: 169
<212> TYPE: PRT
<213> ORGANISM: Hordeum vulgare

<400> SEQUENCE: 89

Met Ser His Phe Ala Ala Met Lys Ser Pro Val Pro Val Ala Ala Ala
1               5                   10                  15

Ala Ala Thr Asp Ala Lys Ser Pro Leu Phe Cys Pro Lys Pro Arg Arg
            20                  25                  30

Pro Val Ala Pro Leu Arg Cys His Gln Ser Ser Asn Ser Asp Ala Gly
        35                  40                  45

Ala Gly Met Asp Leu Leu Asp Leu Leu Leu Ser Lys Gly Asp Glu Ser
    50                  55                  60

Asn Leu Ser Ala Ala Ser Pro Gln Pro Pro Leu Phe Cys Gly Ser Pro
65                  70                  75                  80

Pro Arg Arg Ala Ser Thr Pro Gly Val His Asp Ser Arg Phe Gly Met
                85                  90                  95

Asp Cys Pro Ser Ser Pro Leu Pro Gly Trp Pro Val Met Ser Pro Ala
            100                 105                 110

Thr Pro Ala Pro Gly Gly Gly Pro Gly Tyr Pro Thr Pro Gly Gly Asn
        115                 120                 125

Gly Arg Cys Arg Pro Gly Pro Glu Gln Gly Gly Pro Arg Val Val Pro
    130                 135                 140

Pro Thr Val Pro Val Gly Gly Cys Asp Gly Leu Asn Gly Gly Gly Thr
145                 150                 155                 160

```
Gly Gly Gly Met Glu Met Arg Arg Gly
                165
```

<210> SEQ ID NO 90
<211> LENGTH: 19
<212> TYPE: PRT
<213> ORGANISM: Arabidopsis thaliana

<400> SEQUENCE: 90

```
Met Asn His Phe Ala Val Gln Pro Asn Ala Phe Ala Ala Gly Gly Asp
1               5                   10                  15

Leu Arg Ser
```

<210> SEQ ID NO 91
<211> LENGTH: 164
<212> TYPE: PRT
<213> ORGANISM: Arabidopsis thaliana

<400> SEQUENCE: 91

```
Ser Ser Val Ser Val Val Glu Arg Asp Gln Thr Thr Val Val Cys Pro
1               5                   10                  15

Lys Pro Arg Arg Ile Gly Leu Arg Asn Asn His His His Pro Ser Arg
            20                  25                  30

Ser Leu Arg Cys Tyr Phe Ser His Gln Leu Glu Leu Cys Glu Ser Lys
        35                  40                  45

Ala Glu Thr Asp Ile Leu Asp Ile Ile Leu Thr Lys Asp Gly Tyr Gly
    50                  55                  60

Ala Glu Gln Val Asn Lys Gln Val Ile Asp Ser Pro Ser Pro Phe Leu
65                  70                  75                  80

Cys Gly Ser Pro Pro Ser Arg Val Ala Asn Pro Leu Thr Gln Asp Ala
                85                  90                  95

Arg Phe Arg Asp Glu Ile Val Ser Val Ser Ser Val Ile Pro Pro Gln
            100                 105                 110

Leu Gly Leu Pro Pro Ser Ser Pro Ser Ser Ser Gly Arg Lys
        115                 120                 125

Gly Gly Cys Val Val Arg Gly Asn Phe Gly Asn Ser Pro Lys Val Arg
130                 135                 140

Val Glu Gly Phe Asp Cys Leu Asp Arg Asp Ser Arg Asn Cys Ser Ile
145                 150                 155                 160

Pro Ala Leu Ala
```

<210> SEQ ID NO 92
<211> LENGTH: 144
<212> TYPE: PRT
<213> ORGANISM: Zea mays

<400> SEQUENCE: 92

```
Met Pro Ser Ser Ala Met Ser Ser Gly Leu Glu Pro Val Leu Cys Ala
1               5                   10                  15

Pro Arg Pro Arg Arg Val Gln Gln Leu His Pro Cys Ser Ala Asp Leu
            20                  25                  30

Ile Leu Gly Ala Pro Pro Phe Pro Arg Asn Ala Asn Ser Lys Ala Ser
        35                  40                  45

Gly Ser Ser Ser Arg Glu Gly Gly Arg Lys Thr Thr Arg Pro Ala Ala
    50                  55                  60

Glu Asp Glu Asp Cys Arg Trp Ala Ala Phe Gly Gly Ser Pro Pro Ala
65                  70                  75                  80
```

```
Arg Ala Asp Asn Pro Leu Val His Asp Pro Arg Phe Leu Arg Asn Gln
             85                  90                  95

Arg His Pro Ala Pro Leu Glu Leu Gly Ser Pro Asn His Arg Arg Pro
            100                 105                 110

Thr Tyr Ser Ser Gly Gly Asp Gly Ser Gly Phe Ala Ser Ser Ser Phe
        115                 120                 125

Ala Pro Ala Val Arg Ile Gln Gly Phe Asp Val Ala Ala Cys Arg Ala
130                 135                 140

<210> SEQ ID NO 93
<211> LENGTH: 144
<212> TYPE: PRT
<213> ORGANISM: Zea mays

<400> SEQUENCE: 93

Met Pro Ser Ser Ala Met Ser Ser Gly Leu Glu Pro Val Leu Cys Ala
1               5                   10                  15

Pro Arg Pro Arg Arg Val Gln Gln Leu His Pro Cys Ser Ala Asp Leu
            20                  25                  30

Ile Leu Gly Ala Pro Pro Phe Pro Arg Asn Ala Asn Ser Lys Ala Ser
        35                  40                  45

Gly Ser Ser Arg Glu Gly Gly Arg Lys Thr Thr Arg Pro Ala Ala
    50                  55                  60

Glu Asp Glu Asp Cys Arg Trp Ala Ala Phe Gly Gly Ser Pro Pro Ala
65                  70                  75                  80

Arg Ala Asp Asn Pro Leu Val His Asp Pro Arg Phe Leu Arg Asn Gln
             85                  90                  95

Arg His Pro Ala Pro Leu Glu Leu Gly Ser Pro Asn His Arg Arg Pro
            100                 105                 110

Thr Tyr Ser Ser Gly Gly Asp Gly Ser Gly Phe Ala Ser Ser Ser Phe
        115                 120                 125

Ala Pro Ala Val Arg Ile Gln Gly Phe Asp Val Ala Ala Cys Arg Ala
130                 135                 140

<210> SEQ ID NO 94
<211> LENGTH: 223
<212> TYPE: PRT
<213> ORGANISM: Zea mays

<400> SEQUENCE: 94

Gly Arg Glu Ser Ser Pro Pro Pro Ser Leu Asp Leu Ser Phe Leu
1               5                   10                  15

Leu His Ala Cys Leu Gly Glu Pro Ser Pro Leu Tyr Thr Arg Arg Pro
            20                  25                  30

Gly Leu Arg Arg Arg Val Ala Thr Ser Cys Arg Ser Thr Phe Thr
        35                  40                  45

Ser Ala Lys Gly Met Asp His Met Thr Met Leu Gly Ala Gly Ala Pro
50                  55                  60

His Gln Leu Ser Arg Ala Glu Pro Met Pro Asp Arg Arg Ser Arg Phe
65                  70                  75                  80

Trp Gln Thr Asp Val Gln Pro Val Pro Arg Ile Asp Ile Ile Cys Pro
            85                  90                  95

Leu Pro Cys Arg Pro Ser Arg Ser Leu Leu Leu Asn Arg Pro Ser Pro
            100                 105                 110

Lys Pro Asn Gly Ala Leu Pro Leu Tyr Gly Ala Asn Pro Thr Tyr Asp
            115                 120                 125
```

```
Ile Val Asp Leu Ile Leu Ser Lys Asn Asp Pro Val Asp Thr Asp
            130                 135                 140

Ser Ser Ser Gln Ala Ala Phe Phe Cys Gly Ser Pro Ala Arg Thr
145                 150                 155                 160

Asn Asn Pro Val Ile His Asp Pro Gln Phe Gly Lys Lys Ala Pro Ser
                165                 170                 175

Phe Ser Pro Leu Gly Ser Ser Gly Lys Met Ala Ala Gly Arg Ala
            180                 185                 190

Glu Val Gly Ser Pro Ser Cys Arg Ser Ser Pro Lys Met Arg Ile
            195                 200                 205

Glu Gly Phe Ala Cys Gly Asn Lys Glu Pro Pro His Cys Phe Ala
210                 215                 220
```

<210> SEQ ID NO 95
<211> LENGTH: 171
<212> TYPE: PRT
<213> ORGANISM: Zea mays

<400> SEQUENCE: 95

```
Met Asp His Met Thr Met Leu Gly Ala Gly Ala Pro His Gln Leu Ser
1               5                   10                  15

Arg Ala Glu Pro Met Pro Asp Arg Arg Ser Arg Phe Trp Gln Thr Asp
                20                  25                  30

Val Gln Pro Val Pro Arg Ile Asp Ile Ile Cys Pro Leu Pro Cys Arg
            35                  40                  45

Pro Ser Arg Ser Leu Leu Leu Asn Arg Pro Ser Pro Lys Pro Asn Gly
        50                  55                  60

Ala Leu Pro Leu Tyr Gly Ala Asn Pro Thr Tyr Asp Ile Val Asp Leu
65                  70                  75                  80

Ile Leu Ser Lys Asn Asp Pro Asp Val Asp Thr Asp Ser Ser Ser Gln
                85                  90                  95

Ala Ala Phe Phe Cys Gly Ser Pro Pro Ala Arg Thr Asn Asn Pro Val
            100                 105                 110

Ile His Asp Pro Gln Phe Gly Lys Lys Ala Pro Ser Phe Ser Pro Leu
        115                 120                 125

Gly Ser Ser Ser Gly Lys Met Ala Ala Gly Arg Ala Glu Val Gly Ser
130                 135                 140

Pro Ser Cys Arg Ser Ser Ser Pro Lys Met Arg Ile Glu Gly Phe Ala
145                 150                 155                 160

Cys Gly Asn Lys Glu Pro Pro His Cys Phe Ala
                165                 170
```

<210> SEQ ID NO 96
<211> LENGTH: 288
<212> TYPE: PRT
<213> ORGANISM: Zea mays

<400> SEQUENCE: 96

```
Met Ala Ala Leu Asp Ala Gly Leu Pro Ala Glu Ala Val Arg His Phe
1               5                   10                  15

Thr Lys Ile Leu Glu Ala Arg Arg Gly Val Leu Pro His Pro Phe Ala
                20                  25                  30

Ala Ala Phe Gln Ala Gly Gly Arg Pro Ala Asp Ala Ile Ala Asp Cys
            35                  40                  45

Asn Arg Ser Leu Ala Leu Asp Pro Ala Tyr Ile Pro Thr Leu His Ala
        50                  55                  60
```

Arg Ala Asp Leu Leu Gln Ser Val Gly Ala Val Ala Asp Tyr Leu Arg
65                  70                  75                  80

Asp Leu Asp His Leu Lys Leu Leu Gln Gly Gly Val Arg Gly Leu Pro
                85                  90                  95

Val Pro Pro Asp Leu Gly Phe Glu Glu Ala Pro Ser Arg Ala Ser Gly
            100                 105                 110

Met Glu His Cys Tyr Leu Arg Gln Pro Ile Ser Arg Ala Glu Ala Val
            115                 120                 125

Pro Glu Arg Arg Ser Arg Leu Trp Gln Met Asp Ala Leu Pro Leu Pro
            130                 135                 140

Pro Arg Ala Glu Val Leu Cys Pro Gln Pro Arg Arg Ala Ala Arg Ile
145                 150                 155                 160

Pro Phe Ala Val Ser Val Asn Lys Ala Ile Pro Arg Ser Asn Cys Ala
                165                 170                 175

Leu Pro Pro Tyr Arg Pro Ala Ser Ala Cys Asp Ile Leu Asp Asp Leu
            180                 185                 190

Ile Leu Ser Lys Asn Asp Phe Ser Asp Gly Ala Asp Ser Ser Ser Gly
            195                 200                 205

Gln Ala Gly Phe Leu Cys Gly Ser Pro Val Arg Ala Asn Asn Pro
210                 215                 220

Val Val His Asp Pro Gln Phe Gly Lys Arg Ala Leu Pro Ser Met Ser
225                 230                 235                 240

Pro Leu Gly Ser Ser Ser His Val Lys Leu Lys Val Glu Ala Gly Ser
                245                 250                 255

Pro Ser Cys Gly Val Ser Ser Ser Pro Lys Val Arg Ile Glu Gly Phe
            260                 265                 270

Ala Cys Gly Asn Ser Glu Thr His Tyr Ala Val Thr Pro Leu Leu Val
            275                 280                 285

<210> SEQ ID NO 97
<211> LENGTH: 173
<212> TYPE: PRT
<213> ORGANISM: Zea mays

<400> SEQUENCE: 97

Met Glu His Cys Tyr Val Gly Gln Pro Ile Ser Arg Ala Glu Ala Met
1               5                   10                  15

Pro Glu Arg Arg Ser Arg Phe Trp Gln Met Asp Ala Pro Pro Pro Pro
            20                  25                  30

Arg Ala Glu Val Ile Cys Pro Gln Pro Arg Arg Ala Thr Arg Ile Pro
            35                  40                  45

Leu Thr Ala Val Glu Thr Leu Asn Lys Ala Ser Pro Lys Met Asn Gly
50                  55                  60

Ala Phe Pro Pro Tyr Arg Ser Asp Ser Thr Cys Asp Ile Leu Asp Leu
65                  70                  75                  80

Ile Leu Ser Lys Asn Asp Ser Asp Gly Asp Ser Ser Gln Val Gly
                85                  90                  95

Phe Leu Cys Gly Ser Pro Ile Arg Ala Asp Asn Pro Val Ile His
            100                 105                 110

Asp Pro Gln Phe Gly Lys Arg Leu Pro Ser Phe Ser Pro Leu Gly Gly
            115                 120                 125

Ser Ser Tyr Gly Lys Met Pro Ala Val Arg Val Glu Val Gly Ser Pro
            130                 135                 140

Ser Cys Gly Val Ser Ser Ser Pro Lys Val Arg Ile Glu Gly Phe Ala
145                 150                 155                 160

```
Cys Gly Asn Ser Glu Thr His Tyr Ala Val Thr Phe Val
            165                 170
```

<210> SEQ ID NO 98
<211> LENGTH: 178
<212> TYPE: PRT
<213> ORGANISM: Setaria italica

<400> SEQUENCE: 98

```
Glu His Tyr Met Met Arg Leu Gly Ala Gly Gly Gln Gln Leu Ser
1               5                   10                  15

Arg Val Glu Pro Ile Pro Asp Leu Arg Ser Arg Phe Trp Gln Met Asp
            20                  25                  30

Val Gln Pro Gly Ala Arg Ile Asp Leu Ile Cys Pro Gln Pro Arg Arg
        35                  40                  45

Ala Ser Arg Pro Pro Leu Leu Val Asp Ser Leu Ser Arg Pro Ser Pro
    50                  55                  60

Lys Pro Asn Gly Ala Leu Pro Val Tyr Arg Ala Glu Ser Thr Cys Asp
65                  70                  75                  80

Ile Leu Asp Leu Ile Leu Ser Lys Asn Asp Pro Asp Val Asp Thr Asp
                85                  90                  95

Pro Ser Ser Gln Ala Gly Phe Phe Cys Gly Ser Pro Pro Val Arg Thr
            100                 105                 110

Asn Asn Pro Val Ile His Asp Pro Leu Phe Gly Lys Lys Thr Pro Ser
        115                 120                 125

Phe Ser Pro Leu Gly Ser Ser Phe Gly Lys Met Gly Ala Gly Arg Ala
    130                 135                 140

Glu Val Gly Ser Pro Ser Cys Gly Ala Ser Ser Pro Lys Val Arg Ile
145                 150                 155                 160

Glu Gly Phe Ala Cys Gly Asn Lys Glu Pro Ala His Cys Ala Val Thr
                165                 170                 175

Phe Ala
```

<210> SEQ ID NO 99
<211> LENGTH: 173
<212> TYPE: PRT
<213> ORGANISM: zea mays

<400> SEQUENCE: 99

```
Met Asp Pro Tyr Met Thr Arg Leu Gly Ala Gly Ala Thr His Gln Leu
1               5                   10                  15

Ser Arg Ala Glu Ala Met Pro Asp Arg Arg Ser Arg Phe Trp Gln Thr
            20                  25                  30

Asp Val Gln Leu Ala Pro Arg Ile Asp Ile Ile Cys Pro Leu Pro Arg
        35                  40                  45

Arg Pro Ser Arg Leu Pro Val Leu Asn Ser Pro Lys Leu Asn Gly Ala
    50                  55                  60

Leu Pro Leu Tyr Arg Ala Asp Pro Thr Phe Asp Ile Val Asp Leu Ile
65                  70                  75                  80

Leu Ser Lys Asn Asp Pro Asp Val Asp Thr Asp Ser Ser Ser Gln Ala
                85                  90                  95

Gly Phe Phe Cys Gly Ser Pro Pro Ala Arg Thr Asp Asn Pro Val Ile
            100                 105                 110

Asn Asp Pro Gln Phe Gly Lys Lys Thr Pro Ser Phe Ser Pro Leu Phe
        115                 120                 125
```

```
Gly Gly Ser Ser Ser Gly Lys Met Thr Ala Gly Arg Val Glu Val Gly
            130                 135                 140

Ser Pro Ser Ser Cys Gly Ala Ser Ser Pro Lys Val Arg Ile Glu Gly
145                 150                 155                 160

Phe Ala Cys Gly Asn Lys Glu Pro Pro His Cys Phe Ala
                165                 170

<210> SEQ ID NO 100
<211> LENGTH: 186
<212> TYPE: PRT
<213> ORGANISM: Setaria italica

<400> SEQUENCE: 100

Met Pro Ser Arg Ala Met Asn Arg Leu Phe Val Glu Ser Ser Ser Ser
1               5                   10                  15

Ser Ser Gly Ser Gly Gly Cys Arg Glu Ala Ala Pro Ala Ala Ala Val
            20                  25                  30

Leu Cys Ala Pro Arg Pro Arg Arg Ala Gln Val His Pro Cys Ser Ala
        35                  40                  45

Asp Leu Ile Leu Gly Pro Pro Pro Phe Leu Leu Ser Ser Lys Lys Ser
    50                  55                  60

Lys Glu Gly Gly Lys Thr Lys Ser Ala Glu Ala Glu Val Asp Gly Asp
65                  70                  75                  80

Glu Asp Gly Gly Trp Ala Leu Phe Gly Gly Ser Pro Pro Ala Arg Ala
                85                  90                  95

Asp Asn Pro Leu Val His Asp Pro His Phe Leu Leu Asn Gln Arg His
            100                 105                 110

Pro Val Asp Ser Ser Pro Leu Glu Leu Gly Ile Phe Asp His Gln Ser
        115                 120                 125

Arg Ser Asn Tyr Ser His His Arg Pro Thr Tyr Ile Ser Ser Ser Ser
    130                 135                 140

Ser Asn Ser Ser Ser Ser Ser Phe Ala Pro Ser Phe Ala Pro Thr Val
145                 150                 155                 160

Arg Ile Gln Gly Phe Asp Val Ala Ala Cys Arg Ser Ser His Ser Asn
                165                 170                 175

Gly Gly Gly Arg Val Leu Ser Ala Arg Ala
            180                 185

<210> SEQ ID NO 101
<211> LENGTH: 172
<212> TYPE: PRT
<213> ORGANISM: Oryza sativa

<400> SEQUENCE: 101

Met Pro Thr Gly Ala Met Lys Arg Leu Phe Val Glu Ser Ser Ser Ser
1               5                   10                  15

Ala Ala Ala Ser Asn Ser Gly Arg Glu Ala Ala Val Leu Cys Ala Pro
            20                  25                  30

Arg Pro Arg Arg Val Gln Val His Pro Cys Ser Ala Asp Leu Ile Leu
        35                  40                  45

Gly Pro Pro Pro Phe Leu Leu Ser Ser Asn Asn Thr Asn Lys Gln Arg
    50                  55                  60

Glu Gly Lys Ser Lys Glu Glu Glu Glu Gly Arg Trp Glu Met Phe
65                  70                  75                  80

Gly Gly Ser Pro Pro Ala Arg Ala Asp Asn Pro Leu Val His Asp Pro
                85                  90                  95
```

```
His Phe Leu Leu Asn Gln Arg Pro His Ala Ala Ala Ala Ala Ala
                100                 105                 110

Pro Glu Leu Ser Ile Phe Asp His Arg Ser Thr His His Gly His His
        115                 120                 125

Pro Ala Tyr Ser Ser Ser Ser Phe Ala Pro Ser Phe Ala Pro Ala
    130                 135                 140

Val Arg Ile Gln Gly Phe Asp Val Ala Ala Cys Arg Ser Ser His Gly
145                 150                 155                 160

Ser Gly Gly Gly Gly Arg Val Leu Ser Ala Arg Ala
                165                 170

<210> SEQ ID NO 102
<211> LENGTH: 147
<212> TYPE: PRT
<213> ORGANISM: Picea sitchensis

<400> SEQUENCE: 102

Met Tyr Ala Leu Ser Asn Met Asn Gly Ser Leu Arg Lys Asp Gln Leu
1               5                   10                  15

Ile Cys Pro Ile Pro Asp Arg Met Met Ala Ser Gly Pro Cys Thr Thr
            20                  25                  30

Arg Ala Ile His Lys Leu Tyr Ala Arg Asn His Ser Tyr Ala Val Ala
        35                  40                  45

Gly Asn Glu Gly Glu Pro Ser Tyr Glu Ile Leu Glu Ile Leu Leu Asn
    50                  55                  60

Lys Ser Gln Tyr Gly Asp Gln Thr Ser Val Lys Asn Ser His Pro Tyr
65                  70                  75                  80

Phe Tyr Gly Ser Pro Pro Asn Arg Ser Asp Asn Pro Leu Val Arg Asp
                85                  90                  95

Thr Gln Phe Ile Arg Lys Gly Val Pro Ser Ser Pro Val Asn Leu Ser
            100                 105                 110

Gln Asn Thr Ser Cys Gly Ala Ser Tyr Gly Ala Lys Pro Leu Val Arg
        115                 120                 125

Val Glu Gly Phe Ala Ser Lys Asn Gln Asp Thr Arg Cys Asn Leu Ser
    130                 135                 140

Ala Leu Ala
145

<210> SEQ ID NO 103
<211> LENGTH: 147
<212> TYPE: PRT
<213> ORGANISM: Picea sitchensis

<400> SEQUENCE: 103

Met Tyr Ala Leu Ser Asn Met Asn Gly Ser Leu Arg Lys Asp Gln Leu
1               5                   10                  15

Ile Cys Pro Ile Pro Asp Arg Met Met Ala Ser Gly Pro Cys Thr Thr
            20                  25                  30

Arg Ala Ile His Lys Leu Tyr Ala Arg Asn His Ser Tyr Ala Val Ala
        35                  40                  45

Gly Asn Glu Gly Glu Pro Ser Tyr Glu Ile Leu Glu Ile Leu Leu Asn
    50                  55                  60

Lys Ser Gln Tyr Gly Asp Gln Thr Ser Val Lys Asn Ser His Pro Tyr
65                  70                  75                  80

Phe Tyr Gly Ser Pro Pro Asn Arg Ser Asp Asn Pro Leu Val Arg Asp
                85                  90                  95
```

-continued

```
Thr Gln Phe Ile Arg Lys Gly Val Pro Ser Ser Pro Val Asn Leu Ser
                100                 105                 110

Gln Asn Thr Ser Cys Gly Ala Ser Tyr Gly Ala Lys Pro Leu Val Arg
        115                 120                 125

Val Glu Gly Phe Ala Ser Lys Asn Gln Asp Thr Arg Cys Asn Leu Ser
    130                 135                 140

Ala Leu Ala
145

<210> SEQ ID NO 104
<211> LENGTH: 50
<212> TYPE: DNA
<213> ORGANISM: Artificial Sequence
<220> FEATURE:
<223> OTHER INFORMATION: PacI linker used in making pSHbarENDs2

<400> SEQUENCE: 104
gatcactagt ggcgcgccta ggagatctcg agtagggata acagggtaat              50

<210> SEQ ID NO 105
<211> LENGTH: 224
<212> TYPE: PRT
<213> ORGANISM: Artificial Sequence
<220> FEATURE:
<223> OTHER INFORMATION: Majority consensus sequence from FIG. 11A-11E
<220> FEATURE:
<221> NAME/KEY: MISC_FEATURE
<222> LOCATION: (2)..(2)
<223> OTHER INFORMATION: Xaa is any naturally occurring amino acid or
      the absence thereof
<220> FEATURE:
<221> NAME/KEY: MISC_FEATURE
<222> LOCATION: (4)..(4)
<223> OTHER INFORMATION: Xaa is any naturally occurring amino acid or
      the absence thereof
<220> FEATURE:
<221> NAME/KEY: MISC_FEATURE
<222> LOCATION: (6)..(13)
<223> OTHER INFORMATION: Xaa is any naturally occurring amino acid or
      the absence thereof
<220> FEATURE:
<221> NAME/KEY: MISC_FEATURE
<222> LOCATION: (15)..(16)
<223> OTHER INFORMATION: Xaa is any naturally occurring amino acid or
      the absence thereof
<220> FEATURE:
<221> NAME/KEY: MISC_FEATURE
<222> LOCATION: (19)..(22)
<223> OTHER INFORMATION: Xaa is any naturally occurring amino acid or
      the absence thereof
<220> FEATURE:
<221> NAME/KEY: MISC_FEATURE
<222> LOCATION: (25)..(25)
<223> OTHER INFORMATION: Xaa is any naturally occurring amino acid or
      the absence thereof
<220> FEATURE:
<221> NAME/KEY: MISC_FEATURE
<222> LOCATION: (28)..(28)
<223> OTHER INFORMATION: Xaa is any naturally occurring amino acid or
      the absence thereof
<220> FEATURE:
<221> NAME/KEY: MISC_FEATURE
<222> LOCATION: (30)..(42)
<223> OTHER INFORMATION: Xaa is any naturally occurring amino acid or
      the absence thereof
<220> FEATURE:
<221> NAME/KEY: MISC_FEATURE
<222> LOCATION: (47)..(47)
<223> OTHER INFORMATION: Xaa is any naturally occurring amino acid or
      the absence thereof
<220> FEATURE:
<221> NAME/KEY: MISC_FEATURE
<222> LOCATION: (53)..(62)
```

```
<223> OTHER INFORMATION: Xaa is any naturally occurring amino acid or
      the absence thereof
<220> FEATURE:
<221> NAME/KEY: MISC_FEATURE
<222> LOCATION: (64)..(65)
<223> OTHER INFORMATION: Xaa is any naturally occurring amino acid or
      the absence thereof
<220> FEATURE:
<221> NAME/KEY: MISC_FEATURE
<222> LOCATION: (70)..(72)
<223> OTHER INFORMATION: Xaa is any naturally occurring amino acid or
      the absence thereof
<220> FEATURE:
<221> NAME/KEY: MISC_FEATURE
<222> LOCATION: (74)..(77)
<223> OTHER INFORMATION: Xaa is any naturally occurring amino acid or
      the absence thereof
<220> FEATURE:
<221> NAME/KEY: MISC_FEATURE
<222> LOCATION: (80)..(80)
<223> OTHER INFORMATION: Xaa is any naturally occurring amino acid or
      the absence thereof
<220> FEATURE:
<221> NAME/KEY: MISC_FEATURE
<222> LOCATION: (84)..(84)
<223> OTHER INFORMATION: Xaa is any naturally occurring amino acid or
      the absence thereof
<220> FEATURE:
<221> NAME/KEY: MISC_FEATURE
<222> LOCATION: (99)..(103)
<223> OTHER INFORMATION: Xaa is any naturally occurring amino acid or
      the absence thereof
<220> FEATURE:
<221> NAME/KEY: MISC_FEATURE
<222> LOCATION: (108)..(110)
<223> OTHER INFORMATION: Xaa is any naturally occurring amino acid or
      the absence thereof
<220> FEATURE:
<221> NAME/KEY: MISC_FEATURE
<222> LOCATION: (140)..(140)
<223> OTHER INFORMATION: Xaa is any naturally occurring amino acid or
      the absence thereof
<220> FEATURE:
<221> NAME/KEY: MISC_FEATURE
<222> LOCATION: (142)..(151)
<223> OTHER INFORMATION: Xaa is any naturally occurring amino acid or
      the absence thereof
<220> FEATURE:
<221> NAME/KEY: MISC_FEATURE
<222> LOCATION: (155)..(156)
<223> OTHER INFORMATION: Xaa is any naturally occurring amino acid or
      the absence thereof
<220> FEATURE:
<221> NAME/KEY: MISC_FEATURE
<222> LOCATION: (160)..(161)
<223> OTHER INFORMATION: Xaa is any naturally occurring amino acid or
      the absence thereof
<220> FEATURE:
<221> NAME/KEY: MISC_FEATURE
<222> LOCATION: (168)..(168)
<223> OTHER INFORMATION: Xaa is any naturally occurring amino acid or
      the absence thereof
<220> FEATURE:
<221> NAME/KEY: MISC_FEATURE
<222> LOCATION: (171)..(176)
<223> OTHER INFORMATION: Xaa is any naturally occurring amino acid or
      the absence thereof
<220> FEATURE:
<221> NAME/KEY: MISC_FEATURE
<222> LOCATION: (178)..(179)
<223> OTHER INFORMATION: Xaa is any naturally occurring amino acid or
      the absence thereof
<220> FEATURE:
<221> NAME/KEY: MISC_FEATURE
<222> LOCATION: (183)..(183)
<223> OTHER INFORMATION: Xaa is any naturally occurring amino acid or
      the absence thereof
<220> FEATURE:
<221> NAME/KEY: MISC_FEATURE
```

```
<222> LOCATION: (188)..(190)
<223> OTHER INFORMATION: Xaa is any naturally occurring amino acid or
      the absence thereof
<220> FEATURE:
<221> NAME/KEY: MISC_FEATURE
<222> LOCATION: (192)..(192)
<223> OTHER INFORMATION: Xaa is any naturally occurring amino acid or
      the absence thereof
<220> FEATURE:
<221> NAME/KEY: MISC_FEATURE
<222> LOCATION: (203)..(206)
<223> OTHER INFORMATION: Xaa is any naturally occurring amino acid or
      the absence thereof
<220> FEATURE:
<221> NAME/KEY: MISC_FEATURE
<222> LOCATION: (209)..(209)
<223> OTHER INFORMATION: Xaa is any naturally occurring amino acid or
      the absence thereof
<220> FEATURE:
<221> NAME/KEY: MISC_FEATURE
<222> LOCATION: (211)..(212)
<223> OTHER INFORMATION: Xaa is any naturally occurring amino acid or
      the absence thereof
<220> FEATURE:
<221> NAME/KEY: MISC_FEATURE
<222> LOCATION: (214)..(215)
<223> OTHER INFORMATION: Xaa is any naturally occurring amino acid or
      the absence thereof
<220> FEATURE:
<221> NAME/KEY: MISC_FEATURE
<222> LOCATION: (217)..(219)
<223> OTHER INFORMATION: Xaa is any naturally occurring amino acid or
      the absence thereof
<220> FEATURE:
<221> NAME/KEY: MISC_FEATURE
<222> LOCATION: (223)..(223)
<223> OTHER INFORMATION: Xaa is any naturally occurring amino acid or
      the absence thereof

<400> SEQUENCE: 105

Met Xaa His Xaa Ala Xaa Xaa Xaa Xaa Xaa Xaa Xaa Xaa Pro Xaa Xaa
1               5                   10                  15

Leu Ser Xaa Xaa Xaa Xaa Met Pro Xaa Arg Arg Xaa Arg Xaa Xaa Xaa
            20                  25                  30

Xaa Xaa Xaa Xaa Xaa Xaa Xaa Xaa Xaa Xaa Pro Val Phe Cys Xaa Pro
        35                  40                  45

Lys Pro Arg Arg Xaa Xaa Xaa Xaa Xaa Xaa Xaa Xaa Xaa Xaa Pro Xaa
    50                  55                  60

Xaa Pro Leu Arg Cys Xaa Xaa Xaa His Xaa Xaa Xaa Xaa Leu Pro Xaa
65                  70                  75                  80

Tyr Ser Ser Xaa Ala Pro Gly Met Asp Ile Leu Asp Leu Ile Leu Ser
                85                  90                  95

Lys Asn Xaa Xaa Xaa Xaa Xaa Glu Glu Thr Asp Xaa Xaa Xaa Ser Ser
            100                 105                 110

Ser Gln Ala Pro Phe Phe Cys Gly Ser Pro Ala Arg Ala Ser Asn
        115                 120                 125

Pro Val Ile His Asp Pro Arg Phe Gly Lys Lys Xaa Pro Xaa Xaa Xaa
    130                 135                 140

Xaa Xaa Xaa Xaa Xaa Xaa Xaa Ser Pro Leu Xaa Xaa Pro Ser Ser Xaa
145                 150                 155                 160

Xaa Lys Met Arg Pro Ser Arg Xaa Glu Val Xaa Xaa Xaa Xaa Xaa Xaa
                165                 170                 175

Gly Xaa Xaa Ser Cys Ala Xaa Arg Ser Ser Phe Xaa Xaa Xaa Pro Xaa
            180                 185                 190
```

```
Ala Val Arg Ile Glu Gly Phe Asp Cys Leu Xaa Xaa Xaa Xaa Asp Arg
        195                 200                 205

Xaa Arg Xaa Xaa Arg Xaa Xaa Gly Xaa Xaa Xaa Ile Pro Ala Xaa Ala
    210                 215                 220
```